US011166996B2

(12) United States Patent
Weinstein et al.

(10) Patent No.: US 11,166,996 B2
(45) Date of Patent: Nov. 9, 2021

(54) ANELLOVIRUS COMPOSITIONS AND METHODS OF USE

(71) Applicant: FLAGSHIP PIONEERING INNOVATIONS V, INC., Cambridge, MA (US)

(72) Inventors: Erica Gabrielle Weinstein, Boston, MA (US); Avak Kahvejian, Lexington, MA (US); Simon Delagrave, Sudbury, MA (US); Nathan Lawrence Yozwiak, Cambridge, MA (US); Kevin James Lebo, Weymouth, MA (US); Fernando Martin Diaz, Boston, MA (US); Dhananjay Maniklal Nawandar, Brookline, MA (US); Ryan D. Tedstone, Brookline, MA (US); Jared David Pitts, Jamaica Plain, MA (US)

(73) Assignee: FLAGSHIP PIONEERING INNOVATIONS V, INC., Cambridge, MA (US)

( * ) Notice: Subject to any disclaimer, the term of this patent is extended or adjusted under 35 U.S.C. 154(b) by 0 days.

(21) Appl. No.: 16/448,589

(22) Filed: Jun. 21, 2019

(65) Prior Publication Data

US 2020/0188456 A1 Jun. 18, 2020

Related U.S. Application Data

(60) Provisional application No. 62/778,841, filed on Dec. 12, 2018.

(51) Int. Cl.

| | |
|---|---|
| ***C12N 15/86*** | (2006.01) |
| ***A61K 48/00*** | (2006.01) |
| ***A61K 35/76*** | (2015.01) |
| ***C12N 7/00*** | (2006.01) |
| ***C12N 15/113*** | (2010.01) |

(52) U.S. Cl.

CPC ................ *A61K 35/76* (2013.01); *C12N 7/00* (2013.01); *C12N 15/113* (2013.01); *C12N 15/86* (2013.01); *C12N 2310/141* (2013.01); *C12N 2310/532* (2013.01); *C12N 2750/00021* (2013.01); *C12N 2750/00042* (2013.01)

(58) Field of Classification Search

None

See application file for complete search history.

(56) References Cited

U.S. PATENT DOCUMENTS

| | | | |
|---|---|---|---|
| 4,650,764 | A | 3/1987 | Temin et al. |
| 5,166,057 | A | 11/1992 | Palese et al. |
| 5,854,037 | A | 12/1998 | Palese et al. |
| 6,146,642 | A | 11/2000 | Garcia-Sastre et al. |
| 6,395,472 | B1 | 5/2002 | Leary et al. |
| 6,693,086 | B1 | 2/2004 | Dow et al. |
| 7,745,651 | B2 | 6/2010 | Heyes et al. |
| 7,799,565 | B2 | 9/2010 | MacLachlan et al. |
| 7,803,397 | B2 | 9/2010 | Heyes et al. |
| 7,838,658 | B2 | 11/2010 | MacLachlan et al. |
| 7,901,708 | B2 | 3/2011 | MacLachlan et al. |
| 7,915,399 | B2 | 3/2011 | MacLachlan et al. |
| 7,982,027 | B2 | 7/2011 | MacLachlan et al. |
| 8,058,069 | B2 | 11/2011 | Yaworski et al. |
| 8,101,741 | B2 | 1/2012 | MacLachlan et al. |
| 8,188,263 | B2 | 5/2012 | MacLachlan et al. |
| 8,236,943 | B2 | 8/2012 | Lee et al. |
| 8,283,333 | B2 | 10/2012 | Yaworski et al. |
| 8,603,966 | B2 | 12/2013 | Wimley et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,624,511 | B2 | 4/2017 | zur Hausen et al. |
| 9,676,828 | B2 | 6/2017 | De Villiers et al. |
| 9,706,270 | B2 | 7/2017 | Vuopionpera et al. |
| 2003/0044781 | A1 | 3/2003 | Korlach et al. |
| 2006/0078937 | A1 | 4/2006 | Korlach et al. |

(Continued)

FOREIGN PATENT DOCUMENTS

| | | | |
|---|---|---|---|
| DE | 10149786 | A1 | 7/2003 |
| DE | 10214395 | A1 | 10/2003 |

(Continued)

OTHER PUBLICATIONS

Hou et al., Virologica Sinica, 2011, 26: 181-189.*
Villiers et al., Current Topics in Microbiology and Immunology, 2009, vol. 331, pp. 91-107.*
Yu et al., J. Med. Virol., 2002, 66: 276-284.*
Kota et al., Cell, 2009, 137: 1005-1017.*
Vignolini et al., Virus Res., 2016, 217: 18-22.*
Gu et al., Cancer Res., 2000, 60: 5359-5364.*

(Continued)

*Primary Examiner* — Ileana Popa
(74) *Attorney, Agent, or Firm* — Lando & Anastasi, LLP

(57) ABSTRACT

This invention relates generally to viral vectors and viral particles based on *Anelloviruses*, which can be used to deliver an agent (e.g., an exogenous effector or an endogenous effector, e.g., a therapeutic effector) to a cell (e.g., a cell in a subject to be treated therapeutically). Described herein are anellosomes, anellovectors, and compositions and uses thereof.

66 Claims, 54 Drawing Sheets
(2 of 54 Drawing Sheet(s) Filed in Color)
Specification includes a Sequence Listing.

(56) References Cited

U.S. PATENT DOCUMENTS

| | | | |
|---|---|---|---|
| 2008/0014144 A1 | 1/2008 | Saltzman et al. |
| 2011/0318363 A1 | 12/2011 | zur Hausen et al. |
| 2015/0344912 A1 | 12/2015 | Kim et al. |
| 2016/0138008 A1 | 5/2016 | Doudna et al. |
| 2016/0160216 A1 | 6/2016 | Zur Hausen et al. |
| 2016/0208243 A1 | 7/2016 | Zhang et al. |

FOREIGN PATENT DOCUMENTS

| | | | |
|---|---|---|---|
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| DE | 102006012317 A1 | 1/2007 |
| EP | 0702085 A1 | 3/1996 |
| EP | 780475 A1 | 6/1997 |
| WO | WO-9634625 A1 | 11/1996 |
| WO | WO-9712032 A1 | 4/1997 |
| WO | WO-9802530 A1 | 1/1998 |
| WO | WO-9810088 A1 | 3/1998 |
| WO | WO-9813501 A2 | 4/1998 |
| WO | WO-9853078 A1 | 11/1998 |
| WO | WO-9902657 A1 | 1/1999 |
| WO | WO-9915672 A1 | 4/1999 |
| WO | 00/46407 A2 | 8/2000 |
| WO | WO-02088382 A2 | 11/2002 |
| WO | WO-03020968 A2 | 3/2003 |
| WO | WO-03031947 A2 | 4/2003 |
| WO | WO-2004002453 A1 | 1/2004 |
| WO | WO-2005026372 A1 | 3/2005 |
| WO | WO-2005044836 A2 | 5/2005 |
| WO | WO-2005120152 A2 | 12/2005 |
| WO | WO-2005121348 A1 | 12/2005 |
| WO | WO-2008138619 A2 | 11/2008 |
| WO | WO-2015073587 A2 | 5/2015 |
| WO | WO-2015153102 A1 | 10/2015 |
| WO | WO-2016183482 A1 | 11/2016 |
| WO | WO-2017123644 A1 | 7/2017 |
| WO | WO-2017123646 A1 | 7/2017 |
| WO | WO-2018009838 A1 | 1/2018 |
| WO | WO-2018102740 A1 | 6/2018 |
| WO | WO-2018151829 A1 | 8/2018 |
| WO | WO-2018208728 A1 | 11/2018 |
| WO | WO-2018232017 A1 | 12/2018 |

OTHER PUBLICATIONS

Maggi, TT Viruses: The Still Elusive Human Pathogens, 2009, p. 65-90.*

Galmes et al., Eur. Respir. J., 2013, 42: 470-479.*

Hino et al., TT Viruses: The Still Elusive Human Pathogens, 2009, p. 117-130.*

Evan-Browning, Thesis, 2009.*

Zhang et al., Endocrinology, 1998, 139: 601-608.*

Oldstone, FASEB J., 1998, 12: 1255-1265.*

Reif, Thesis, 2014.*

Naso et al., BioDrugs, Jul. 1, 2017, 31: 317-334.*

Bendinelli et al., Clin. Microbiol. Rev., 2001, 14: 98-113.*

Suzuki et al., J. Virol., 2004, 78: 10820-10824.*

Kanai et al., Cancer Res., 1997,57: 461-465.*

Liu et al., MPMI, 1999, 12: 894-900.*

Adams et al., "The genome sequence of *Drosophila melanogaster*," Science (2000) vol. 287, pp. 2185-2195.

Allen, "Ligand-targeted therapeutics in anticancer therapy," Nat Rev Cancer (2002) vol. 2, No. 10, pp. 750-763.

Andersen et al., "Herpesvirus-Mediated Gene Delivery into the Rat Brain: Specificity and Efficiency of the Neuron-Specific Enolase Promoter," Cell Mol Neurobiol (1993) vol. 13, Issue 5, pp. 503-515.

Arbuthnot et al., "In Vitro and In Vivo Hepatoma Cell-Specific Expression of a Gene Transferred with an Adenoviral Vector," Hum Gene Ther (1996) vol. 7, No. 13, pp. 1503-1514.

Bartel, "MicroRNAs: genomics, biogenesis, mechanism, and function," Cell (2004) vol. 116, No. 2, pp. 281-297.

Bershteyn et al., "Polymer-supported lipid shells, onions, and flowers," Soft Matter (2008) vol. 4, No. 1, pp. 1787-1787.

Biagini, "Human circoviruses," Vet Microbiol (2004) vol. 98, Issue 2, pp. 95-101.

Birmingham et al., "3' UTR seed matches, but not overall identity, are associated with RNAi off-targets," Nat Methods (2006) vol. 3, pp. 199-204.

Boshart et al., "A very strong enhancer is located upstream of an immediate early gene of human cytomegalovirus," Cell (1985) vol. 41, pp. 521-530.

Calcedo et al., "Humoral Immune Response to AAV," Front Immunol (2013) vol. 4, Article 341, pp. 1-7.

Chen et al., "Expression of rat bone sialoprotein promoter in transgenic mice," J Bone Miner Res (1996) vol. 11, Issue 5, pp. 654-664.

Cong et al., "Multiplex Genome Engineering Using CRISPR/Cas Systems," Science (2013) vol. 339, Issue 6121, pp. 819-823.

Databse GenBank Accession JX134045.1, Galmes et al. , "TTV-like mini virus isolate TTMV_LY2, complete genome," Eur Respir J (2012) retrieved from ncbi.nlm.nih.gov/nuccore/JX134045.

Davis et al., "Nanoparticle therapeutics: an emerging treatment modality for cancer," Nat Rev Drug Discovery (2008) vol. 7, pp. 771-782.

De Groote et al., "*Epigenetic Editing*: targeted rewriting of epigenetic marks to modulate expression of selected target genes," Nuc Acids Res (2012) vol. 40, No. 21, pp. 10596-10613.

De Villiers et al., "The Diversity of Torque Teno Viruses: In Vitro Replication Leads to the Formation of Additional Replication-Competent Subviral Molecules," Journal of Virology (2011) vol. 85, No. 14, pp. 7284-7295.

Doench et al., "siRNAs can function as miRNAs," Genes Dev ( 2003) vol. 17, No. 4, pp. 438-442.

Duncan, "Polymer conjugates as anticancer nanomedicines," Nat Rev Cancer (2006) vol. 6, No. 9, pp. 688-701.

Gaj et al., "ZFN, TALEN, and CRISPR/Cas-based methods for genome engineering," Trends Biotechnol (2013) vol. 31, No. 7, pp. 397-405.

Galmes et al., "Potential implication of new torque teno mini viruses in parapneumonic empyema in children," Eur Respir J (2013) vol. 8, No. 9, pp. 470-479.

Gerner et al., "Mother-to-infant transmission of TT virus: prevalence, extend and mechanism of vertical transmission," Ped Infect Dis J (2000) vol. 19, No. 11, pp. 1074-1077.

Gordillo-Galeano et al., "Solid lipid nanoparticles and nanostructured lipid carriers: a review emphasizing on particle structure and drug release," European Journal of Pharmaceuticals and Biopharmaceutics (2018) vol. 133, pp. 285-308.

Gossen et al., "Tight control of gene expression in mammalian cells by tetracycline-responsive promoters," Proc Natl Acad Sci USA (1992) vol. 89, Issue 12, pp. 5547-5551.

Gossen et al., "Transcriptional activation by tetracyclines in mammalian cells," Science (1995) vol. 268, pp. 1766-1769.

Guan et al., "Application of CRISPR-Cas system in gene therapy: Pre-clinical progress in animal model," DNA Repair (2016) vol. 46, pp. 1-8.

Ha et al., "Exosomes as therapeutic drug carriers and delivery vehicles across biologcal membranes: current perspectives and future challenges," Acta Pharmaceutica Sinica B (2016) vol. 6, No. 4, pp. 287-296.

Hansal et al., "Cutting Edge: Induction of Antigen-Specific Hyporesponsiveness by Transplantation of Hemopoietic Cells Containing an MHC Class I Transgene Regulated by a Lymphocyte-Specific Promoter," J Immunol (1998) vol. 161, pp. 1063-1068.

Harvey et al., "Inducible control of gne expression: prospects for gene therapy," Curr Opin Chern Biol (1998) vol. 2, Issue 4, pp. 512-518.

(56) References Cited

OTHER PUBLICATIONS

Hendel et al., "Chemically modified guide RNAs enhance CRISPR-Cas genome editing in human primary cells," Nature Biotechnol (2015) vol. 33, No. 9, pp. 985-989.
Hino et al., "Torque teno virus (TTV): current status," Rev Med Virol (2007) vol. 17, pp. 45-57.
Huang et al., "Genetically engineered red cells expressing single domain camelid antibodies confer long-term protection against botulinum neurotoxin," Nature Communications (2017) vol. 8, Article 423, 13 pages.
Huang et al., "Rescue of a Porcine Anellovirus (Torque Teno Sus Virus 2) from Cloned Genomic DNA in Pigs," Journal of Virology (2012) vol. 86, No. 11, pp. 6042-6054.
International Search Report and Written Opinion issued in PCT/US2018/037379, dated Sep. 25, 2018.
Jelcic et al., "Isolation of Multiple TT Virus Genotypes from Spleen Biopsy Tissue from a Hodgkin's Disease Patient: Genome Reorganization and Diversity in the Hypervariable Region," Journal of Virology (2004) vol. 78, No. 14, pp. 7498-7507.
Kakkola et al., "Expression of all six human Torque teno virus (TTV) proteins in bacteria and in insect cells, and analysis of their IgG responses," Virology (2008) vol. 382, No. 2, pp. 182-189.
Kikuchi et al., "Indirect evidence of TTV replication in bone marrow cells, but not in hepatocytes, of a subacute hepatitis/aplastic anemia patient," J Med Virol (2000) vol. 61, No. 1, pp. 165-170.
Kincaid et al., "A Human Torque Teno Virus Encodes a MicroRNA That Inhibits Interferon Signaling," PLOS Pathogens (2013) vol. 9, No. 12, Article e1003818, 14 pages.
Laganà et al., "Computational Design of Artificial RNA Molecules for Gene Regulation," Methods Mol Bio (2015) vol. 1269, pp. 393-412.
Levene et al., "Zero-Mode Waveguides for Single-Molecule Analysis at High Concentrations," Science (2003) vol. 299, pp. 682-686.
Li et al., "A Review of the Structure, Preparation, and Application of NLCs, PNPs, and PLNs," Nanomaterials (2017) vol. 7, No. 6, Article 122, 25 pages.
Li et al., "Synthetic muscle promoters: activities exceeding naturally occurring regulatory sequences," Nat Biotechnol (1999) vol. 17, pp. 241-245.
Lim et al., "Microarray analysis shows that some microRNAs downregulate large numbers of target mRNAs," Nature (2005) vol. 433, pp. 769-773.
Lu et al., "Perspectives on the Discovery of Small-Molecule Modulators for Epigenetic Processes," J Biomolecular Screening (2012) vol. 17, No. 5, pp. 555-571.
Magari et al., "Pharmacologic Control of a Humanized Gene Therapy System Implanted into Nude Mice," J Clin Invest (1997) vol. 100, pp. 2865-2872.
Miyatake et al., "Transcriptional targeting of herpes simplex virus for cell-specific replication," J Virol (1997) vol. 71, No. 7, pp. 5124-5132.
Ng et al., "Intracellular Delivery of Proteins via Fusion Peptides in Intact Plants," PLoS One (2016) vol. 11, No. 4, Article e0154081, 13 Pages.
Novobrantseva et al., "Systemic RNAi-mediated Gene Silencing in Nonhuman Primate and Rodent Myeloid Cells," Molecular Therapy—Nucleic Acids (2012) vol. 1, e4; doi:10.1038/mtna.2011.3, 13 pages.
Okamoto et al., "Replicative forms of TT virus DNA in bone marrow cells," Biochem Biophys Res Commun (2002) vol. 270, pp. 657-662.
Okamoto et al., "The entire nucleotide sequence of a TT virus isolate from the United States (TUS01): comparison with reported isolates and phylogenetic analysis," Virology (1999) vol. 259, No. 2, pp. 437-448.
Orme-Johnson, "Appendix 2. Direct and indirect inhibitors of mitochondrial ATP synthesis," Methods Cell Biol (2007) vol. 80, pp. 813-826.
Piccioli et al., "Neuroantibodies: Ectopic Expression of a Recombinant Anti-Substance P Antibody in the Central Nervous System of Transgenic Mice," Neuron (1995) vol. 15, No. 2, pp. 373-384.
Piccioli et al., "Neuroantibodies: Molecular cloning of a monoclonal antibody against substance P for expression in the central nervous system," Proc Natl Acad Sci USA (1991), vol. 88, No. 13, pp. 5611-5615.
Qiu et al., "Human Circovirus TT Virus Genotype 6 Expresses Six Proteins following Transfection of a Full-Length Clone," J Virol (2005) vol. 79, No. 10, pp. 6505-6510.
Rajewsky, "microRNA target predictions in animals," Nat Genet (2006) vol. 38 Suppl, pp. S8-S13.
Ran et al., "Double Nicking by RNA-Guided CRISPR Cas9 for Enhanced Genome Editing Specificity," Cell (2013) vol. 154, No. 6, pp. 1380-1389.
Ran et al., "Genome engineering using the CRISPR-Cas9 system," Nature Protocols (2013) vol. 8, pp. 2281-2308.
Rey et al., "Prevalence and Persistence of TT Virus DNA in HIV1-Infected Individuals," Infect (2003) vol. 31, Issue 4, pp. 226-231.
Rivera et al., "A humanized system for pharmacologic control of gene expression," Nat Med (1996) vol. 2, No. 9, pp. 1028-1032.
Rodríguez-Iñigo et al., "Detection of TT virus DNA in liver biopsies by in situ hybridization," Am J Pathol (2000) vol. 156, No. 4, pp. 1227-1234.
Saback et al., "Infection with Hepatitis A and TT Viruses and Socioeconomic Status in Rio de Janeiro, Brazil," Scand J Infect Dis (2001) vol. 33, pp. 121-125.
Sandig et al., "HBV-derived promoters direct liver-specific expression of an adenovirally transduced LDL receptor gene," Gene Ther (1996) vol. 3, No. 11, pp. 1002-1009, Abstract Only.
Shi et al., "Engineered red blood cells as carriers for systematic delivery of a wide array of functional probes," PNAS (2014) vol. 111, No. 28, p. 10131-10136.
Spuch and Navarro, "Liposomes for Targeted Delivery of Active Agents against Neurodegenerative Diseases (Alzheimer's Disease and Parkinson's Disease)," Journal of Drug Delivery (2011) vol. 2011, Article ID 469679, 12 pages.
Steeland et al., "Nanobodies as therapeutics: big opportunities for small antibodies," Drug Discov Today (2016) vol. 21, No. 7, pp. 1076-1113.
Stein et al., "The osteocalcin gene: a model for multiple parameters of skeletal-specific transcriptional control," Mol Biol Rep (1997) vol. 24, Issue 3, pp. 185-196.
Templeton et al., "Improved DNA: liposome complexes for increased systemic delivery and gene expression," Nature Biotech (1997) vol. 15, pp. 647-652.
Tsuda et al., "Determination of antibodies to TT virus (TTV) and application to blood donor and patients with post-transfusion non-A to G hepatitis in Japan," J Virol Methods (1999) vol. 77, No. 2., pp. 199-206.
Tung et al., "Arginine containing peptides as delivery vectors," Advanced Drug Delivery Reviews (2003) vol. 55, No. 2, pp. 281-294.
Ui-Tei et al., "Sensitive assay of RNA interference in *Drosphila* and Chinese hamster cultured cells using firefly luciferase gene as target," FEBS Letters (2000) vol. 479, pp. 79-82.
Venter et al., "The Sequence of the Human Genome," Science (2001) vol. 291, Issue 5507, pp. 1304-1351.
Wang et al., "Ligand-inducible and liver-specific target gene expression in transgenic mice," Nat Biotech (1997) vol. 15, pp. 239-243.
Wang et al., "Positive and negative regulation of gene expression in eukaryotic cells wit an inducible transcriptional regulator," Gene Ther (1997) vol. 4, pp. 432-441.
Wu et al., "MicroRNAs direct rapid deadenylation of mRNA," Proc Natl Acad Sci USA (2006) vol. 103, No. 11, pp. 4034-4039.
Yzèbe et al., "TT virus. A review of the literature," Panminerva Med (2002) vol. 44, No. 3, pp. 167-177.
Zeng et al., "Both Natural and Designed Micro RNAs Can Inhibit the Expression of Cognate mRNAs When Expressed in Human Cells," Mol Cell (2002) vol. 9, No. 6, pp. 1327-1333.
Zetsche et al., "Cpf1 is a single RNA-guided endonuclease of a class 2 CRISPR-Cas system," Cell (2015) vol. 163, No. 3, pp. 759-771.
Zheng et al., "Precise gene deletion and replacement using the CRISPR/Cas9 system in human cells," BioTechniques (2014) vol. 57, No. 3, pp. 115-124.

(56) References Cited

OTHER PUBLICATIONS

Zylberberg et al., "Pharmaceutical liposomal drug delivery: a review of new delivery systems and a look at the regulatory landscape," Drug Deliv (2016) vol. 23, No. 9, pp. 3319-3329.
[No Author Listed] Gen Bank: FR751473.1. Torque teno virus complete genome, isolate TV-HD15b (gbCsCt38.1). Jul. 7, 2011.
Bostan et al., "Current and Future Prospects of Torque Teno Virus," J Vaccines Vaccin (2013) S1:004, 9 pages.
GenBank: AGG91484.1 hypothetical protein [TTV-like mini virus]. Dated Mar. 16, 2013.
Kakkola et al., "Construction and biological activity of a full-length molecular clone of human Torque teno virus (TTV) genotype 6," FEBS Journal (2007) vol. 247, pp. 4719-4730.
Leppik et al., "In Vivo and In Vitro Intragenomic Rearrangement of TT Viruses," Journal of Virology (2007) vol. 81, No. 17, pp. 9346-9356.
Racz et al., "Towards Gene Therapy for Growth Hormone Deficiency via Salivary Gland Expression of Growth Hormone," Oral Dis (2015) vol. 21, No. 2, pp. 149-155.
Rohle et al., "An inhibitor of Mutant IDH1 Delays Growth and Promotes Differentiation of Glioma Cells," Science (2013) VI. 340, pp. 626-630.
Auricchio et al., "Noninvasive gene transfer to the lung for systemic delivery of therapeutic proteins," Journal of Clinical Investigation (2002) vol. 110, No. 4, pp. 499-504.
International Search Report and Written Opinion issued in PCT/US2019/065874, dated Aug. 4, 2020, 19 pages.
International Search Report and Written Opinion issued in PCT/US2019/065919, dated Aug. 4, 2020, 18 pages.
International Search Report and Written Opinion issued in PCT/US2019/065963, dated Jul. 7, 2020, 17 pages.
International Search Report and Written Opinion issued in PCT/US2019/065995, dated Jul. 7, 2020.
Manzin et al., "Global Impact of Torque Teno Virus Infection in Wild and Domesticated Animals" J Infect Dev Ctries (2015) vol. 9, No. 6, pp. 562-570.
Ninomiya et al., "Identification and genomic characterization of a novel human torque teno virus of 3.2 kb," Journal of General Virology (2007) vol. 88, No. 7, pp. 1939-1944.
Hamburgh et al., "Structural Determinants of Slippage-mediated Mutations by Human Immunodeficiency Virus Type 1 Reverse Trancriptase," J Biol Chem (2006) vol. 281, No. 11, pp. 7421-7428.
Kaczorowska et al., "Human anelloviruses: diverse, omnipresent and commensal members of the virome," FEMS Microbiology Reviews (2020) vol. 44, Issue 3, pp. 305-313.
Shulman and Davidson, "Viruses with Circular Single-Stranded DNA Genomes are Everywhere!" Ann Rev Virol (2017) vol. 4, pp. 159-180.

* cited by examiner

Schematic of the kanamycin vector encoding the LY1 strain of TTMiniV (Anellosome 1)

Schematic of the kanamycin vector encoding the LY2 strain of TTMiniV (Anellosome 2)

|         | DNA   | AA    |
|---------|-------|-------|
| ORF 1   | 49.6% | 34.8% |
| ORF 1/1 | 49.6% | 34.2% |
| ORF 1/2 | 49.4% | 30.2% |
| ORF 2   | 47.8% | 34.2% |
| ORF 2/2 | 48.9% | 32.0% |
| ORF 2/3 | 48.8% | 32.9% |
| ORF 2t/3* | 48.9% | 37.5% |

ORF 2

ORF 1/1

ANELLOVIRUS COMPOSITIONS AND METHODS OF USE

CROSS-REFERENCE TO RELATED APPLICATIONS

This application claims the benefit of U.S. Provisional Application No. 62/778,841, filed Dec. 12, 2018. The contents of the aforementioned application are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 13, 2019, is named V2057-700511FT_SL.txt and is 459,419 bytes in size.

BACKGROUND

The present disclosure relates to the field of virology. Existing viral systems for delivering therapeutic agents utilize viruses that can be associated with diseases or disorders, and which can be highly immunogenic. There exists a need in the art for improved viral delivery vehicles that are substantially non-immunogenic and non-pathogenic.

SUMMARY

Described herein are viral vectors and viral particles based on *Anelloviruses*, which can be used to deliver an agent (e.g., an exogenous effector or an endogenous effector, e.g., a therapeutic effector) to a cell (e.g., a cell in a subject to be treated therapeutically). The inventors have discovered that *Anelloviruses* can be used as effective delivery vehicles for introducing an agent, such as an effector described herein, to a target cell, e.g., a target cell in a subject to be treated therapeutically or prophylactically.

The present disclosure provides an anellosome, e.g., a synthetic anellosome, that can be used as a delivery vehicle, e.g., for delivering a therapeutic agent to a eukaryotic cell. In some embodiments, an anellosome comprises a viral particle (e.g., an *Anellovirus*) comprising a genetic element encapsulated in a proteinaceous exterior (e.g., comprising an *Anellovirus* ORF1, e.g., as described herein), which is capable of introducing the genetic element into a cell (e.g., a human cell). In some embodiments, the anellosome is an *Anellovirus* comprising a proteinaceous exterior comprising an *Anellovirus* ORF1 (e.g., an ORF1 of *Alphatorquevirus, Betatorquevirus*, or *Gammatorquevirus*, e.g., an ORF1 of *Alphatorquevirus* Glade 1, *Alphatorquevirus* Glade 2, *Alphatorquevirus* Glade 3, *Alphatorquevirus* Glade 4, *Alphatorquevirus* Glade 5, *Alphatorquevirus* Glade 6, or *Alphatorquevirus* Glade 7, e.g., as described herein). The genetic element of an anellosome of the present disclosure can be, in some instances, a circular and/or single-stranded DNA molecule, and generally includes a protein binding sequence that binds to the proteinaceous exterior, or a polypeptide attached thereto, which may facilitate enclosure of the genetic element within the proteinaceous exterior and/or enrichment of the genetic element, relative to other nucleic acids, within the proteinaceous exterior. In some instances, the genetic element is circular or linear. In some instances, the genetic element comprises or encodes an effector (e.g., a nucleic acid effector, such as a non-coding RNA, or a polypeptide effector, e.g., a protein), e.g., which can be expressed in the cell. In some instances, the effector is an endogenous effector or an exogenous effector. In some embodiments, the effector is exogenous to a wild-type *Anellovirus*. For example, the anellosome can deliver an effector into a cell by contacting the cell and introducing a genetic element encoding the effector into the cell, such that the effector is made or expressed by the cell. In certain instances, the effector is an endogenous effector. In other instances, the effector is an exogenous effector. The effector can, in some instances, modulate a function of the cell or modulate an activity or level of a target molecule in the cell. For example, the effector may decrease viability of a cancer cell (e.g., as described in Example 22) or decrease levels of a target protein, e.g., interferon, in the cell (e.g., as described in Examples 3 and 4). In another example, the effector may be a protein expressed by the cell (e.g., as described in Example 9). Anellosomes can be used for treatment of diseases and disorders, e.g., by delivering an effector that can operate as a therapeutic agent to a desired cell or tissue.

The invention further provides synthetic anellosomes. A synthetic anellosome has at least one structural difference compared to a wild-type virus (e.g., a wild-type *Anellovirus*, e.g., a described herein), e.g., a deletion, insertion, substitution, enzymatic modification, relative to the wild-type virus. Generally, synthetic anellosomes include an exogenous genetic element enclosed within a proteinaceous exterior, which can be used as substantially non-immunogenic vehicles for delivering the genetic element, or an effector (e.g., an exogenous effector or an endogenous effector) encoded therein (e.g., a polypeptide or nucleic acid effector), into eukaryotic cells.

In an aspect, the invention features an anellosome comprising: (i) a genetic element comprising a promoter element and a sequence encoding an effector (e.g., an endogenous or exogenous effector), and a protein binding sequence (e.g., an exterior protein binding sequence, e.g., a packaging signal); and (ii) a proteinaceous exterior; wherein the genetic element is enclosed within the proteinaceous exterior; and wherein the anellosome is capable of delivering the genetic element into a eukaryotic cell. In some embodiments, the genetic element is a single-stranded DNA. Alternatively or in combination, the genetic element has one or both of the following properties: is circular and/or integrates into the genome of a eukaryotic cell at a frequency of less than about 0.001%, 0.005%, 0.01%, 0.05%, 0.1%, 0.5%, 1%, 1.5%, or 2% of the genetic element that enters the cell; and (ii) a proteinaceous exterior. In some embodiments, the genetic element is enclosed within the proteinaceous exterior. In some embodiments, the anellosome is capable of delivering the genetic element into a eukaryotic cell. In some embodiments, the genetic element comprises a nucleic acid sequence (e.g., a nucleic acid sequence of between 300-4000 nucleotides, e.g., between 300-3500 nucleotides, between 300-3000 nucleotides, between 300-2500 nucleotides, between 300-2000 nucleotides, between 300-1500 nucleotides) having at least 75% (e.g., at least 75, 76, 77, 78, 79, 80, 90, 91, 92, 93, 94, 95, 96, 97, 98, 99, or 100%) sequence identity to a sequence of a wild-type *Anellovirus* (e.g., a wild-type Torque Teno virus (TTV), Torque Teno mini virus (TTMV), or TTMDV sequence, e.g., a wild-type *Anellovirus* sequence as listed in any of Tables 1, 3, 5, 7, 9, 11, 13, 15, or 17). In some embodiments, the genetic element comprises a nucleic acid sequence (e.g., a nucleic acid sequence of at least 300 nucleotides, 500 nucleotides, 1000 nucleotides, 1500 nucleotides, 2000 nucleotides, 2500 nucleotides, 3000 nucleotides or more) having at least 75% (e.g., at least 75, 76, 77, 78, 79, 80, 90, 91, 92, 93, 94, 95, 96, 97, 98, 99, or 100%) sequence identity to a sequence of a wild-type *Anellovirus* (e.g., a wild-type *Anellovirus* sequence as described herein, e.g., as listed in any of Tables 1, 3, 5, 7, 9, 11, 13, 15, or 17). In some embodiments, the nucleic acid sequence is codon-optimized, e.g., for a mammalian (e.g., human) cell. In some embodiments, at least 50%, 60%, 70%, 80%, 90%, 95%, 96%, 97%, 98%, 99%, or 100% of the codons in the nucleic acid sequence are codon-optimized, e.g., for a mammalian (e.g., human) cell.

In an aspect, the invention features a polypeptide (e.g., an ORF1 molecule) comprising a first region comprising an amino acid sequence having at least 70% (e.g., at least about 70, 80, 90, 95, 96, 97, 98, 99, or 100%) sequence identity to an arginine-rich region sequence described herein or a sequence of at least about 40 amino acids comprising at least 60%, 70%, or 80% basic residues (e.g., arginine, lysine, or a combination thereof), a second region comprising an amino acid sequence having at least 30% (e.g., at least about 30, 35, 40, 50, 60, 70, 80, 90, 95, 96, 97, 98, 99, or 100%) sequence identity to a jelly-roll region sequence described herein or a sequence comprising at least 6 beta strands, a third region comprising an amino acid sequence having at least 30% (e.g., at least about 30, 35, 40, 50, 60, 70, 80, 90, 95, 96, 97, 98, 99, or 100%) sequence identity to an N22 domain sequence described herein, and a fourth region comprising an amino acid sequence having at least 70% (e.g., at least about 70, 80, 90, 95, 96, 97, 98, 99, or 100%) sequence identity to an *Anellovirus* ORF1 C-terminal domain (CTD) sequence described herein. In some embodiments, the polypeptide comprises at least about 70, 80, 90, 95, 96, 97, 98, 99, or 100% sequence identity to an *Anellovirus* ORF1 molecule as described herein (e.g., as listed in any of Tables 2, 4, 6, 8, 10, 12, 14, 16, 18, or 20-37). In some embodiments, the polypeptide comprises at least about 70, 80, 90, 95, 96, 97, 98, 99, or 100% sequence identity to a subsequence (e.g., an arginine (Arg)-rich domain, a jelly-roll domain, a hypervariable region (HVR), an N22 domain, or a C-terminal domain (CTD)) of an *Anellovirus* ORF1 molecule as described herein (e.g., as listed in any of Tables 20-37).

In an aspect, the invention features a complex comprising a polypeptide as described herein (e.g., an *Anellovirus* ORF1 molecule as described herein) and a genetic element comprising a promoter element and a nucleic acid sequence (e.g., a DNA sequence) encoding an effector (e.g., an exogenous effector or an endogenous effector), and a protein binding sequence.

The present disclosure further provides nucleic acid molecules (e.g., a viral vector, e.g., an anellovector as described herein). In an aspect, the invention features an isolated nucleic acid molecule comprising a genetic element comprising a promoter element and a sequence encoding an effector, e.g., a payload, and an exterior protein binding sequence. In embodiments, the genetic element is a single-stranded DNA, and wherein the genetic element is circular and/or integrates at a frequency of less than about 0.001%, 0.005%, 0.01%, 0.05%, 0.1%, 0.5%, 1%, 1.5%, or 2% of the genetic element that enters the cell. In embodiments, the effector does not originate from TTV and is not an SV40-miR-S1. In embodiments, the nucleic acid molecule does not comprise the polynucleotide sequence of TTMV-LY2. In embodiments, the promoter element is capable of directing expression of the effector in a eukaryotic cell. In some embodiments, the nucleic acid molecule is circular. In some embodiments, the nucleic acid molecule is linear. In some embodiments, the nucleic acid molecule comprises an anellovector, e.g., as described herein. In some embodiments, a nucleic acid molecule described herein comprises one or more modified nucleotides (e.g., a base modification, sugar modification, or backbone modification). In some embodiments, the nucleic acid molecule comprises a sequence encoding an *Anellovirus* ORF1. In some embodiments, the nucleic acid molecule comprises a sequence encoding an *Anellovirus* ORF2. In some embodiments, the nucleic acid molecule comprises a sequence encoding an *Anellovirus* ORF3. In an aspect, the invention features a genetic element comprising one, two, or three of: (i) a promoter element and a sequence encoding an effector, e.g., an exogenous or endogenous effector; (ii) at least 72 contiguous nucleotides (e.g., at least 72, 73, 74, 75, 76, 77, 78, 79, 80, 90, 100, or 150 nucleotides) having at least 75% (e.g., at least 75, 76, 77, 78, 79, 80, 90, 91, 92, 93, 94, 95, 96, 97, 98, 99, or 100%) sequence identity to a wild-type *Anellovirus* sequence; or at least 100 (e.g., at least 300, 500, 1000, 1500) contiguous nucleotides having at least 72% (e.g., at least 72, 73, 74, 75, 76, 77, 78, 79, 80, 90, 91, 92, 93, 94, 95, 96, 97, 98, 99, or 100%) sequence identity to a wild-type *Anellovirus* sequence; and (iii) a protein binding sequence, e.g., an exterior protein binding sequence, and wherein the nucleic acid construct is a single-stranded DNA; and wherein the nucleic acid construct is circular and/or integrates at a frequency of less than about 0.001%, 0.005%, 0.01%, 0.05%, 0.1%, 0.5%, 1%, 1.5%, or 2% of the genetic element that enters the cell. In some embodiments, a genetic element encoding an effector (e.g., an exogenous or endogenous effector, e.g., as described herein) is codon optimized. In some embodiments, the genetic element is circular. In some embodiments, the genetic element is linear. In some embodiments, the genetic element comprises an anellovector, e.g., as described herein. In some embodiments, a genetic element described herein comprises one or more modified nucleotides (e.g., a base modification, sugar modification, or backbone modification). In some embodiments, the genetic element comprises a sequence encoding an *Anellovirus* ORF1. In some embodiments, the genetic element comprises a sequence encoding an *Anellovirus* ORF2. In some embodiments, the genetic element comprises a sequence encoding an *Anellovirus* ORF3.

In an aspect, the invention features a host cell or helper cell comprising a nucleic acid encoding a polypeptide of any of the preceding claims, wherein the nucleic acid is a plasmid, is a viral nucleic acid, or is integrated into a helper cell chromosome; and a genetic element, wherein the genetic element comprises a promoter element and a nucleic acid sequence (e.g., a DNA sequence) encoding an effector (e.g., an exogenous effector or an endogenous effector), and a protein binding sequence, wherein optionally the genetic element does not encode an ORF1 polypeptide. In some embodiments, the host cell or helper cell is adherent or in suspension, or both. In some embodiments, the host cell or helper cell is grown in a microcarrier. In some mbodiments, the host cell or helper cell is compatible with cGMP manufacturing practices. In some embodiments, the host cell or helper cell is grown in a medium suitable for promoting cell growth. In certain embodiments, once the host cell or helper cell has grown sufficiently (e.g., to an appropriate cell density), the medium may be exchanged with a medium suitable for production of anellosomes by the host cell or helper cell.

In an aspect, the invention features a pharmaceutical composition comprising an anellosome (e.g., a synthetic anellosome) as described herein. In embodiments, the pharmaceutical composition further comprises a pharmaceutically acceptable carrier or excipient. In embodiments, the pharmaceutical composition comprises a dose comprising about $10^5$-$10^{14}$ genome equivalents of the anellosome per kilogram. In some embodiments, the pharmaceutical composition comprising the preparation will be stable over an acceptable period of time and temperature, and/or be compatible with the desired route of administration and/or any devices this route of administration will require, e.g., needles or syringes. In some embodiments, the pharmaceutical composition is formulated for administration as a single dose or multiple doses. In some embodiments, the pharmaceutical composition is formulated at the site of administration, e.g., by a healthcare professional. In some embodiments, the pharmaceutical composition comprises a desired concentration of anellosome genomes or genomic equivalents (e.g., as defined by number of genomes per volume).

In an aspect, the invention features a method of treating a disease or disorder in a subject, the method comprising administering to the subject an anellosome, e.g., a synthetic anellosome, e.g., as described herein.

In an aspect, the invention features a method of delivering an effector (e.g., an endogenous or exogenous effector) to a cell, tissue or subject, the method comprising administering to the subject an anellosome, e.g., a synthetic anellosome, e.g., as described herein, wherein the anellosome comprises a nucleic acid sequence encoding the effector. In embodiments, the payload is a nucleic acid. In embodiments, the payload is a polypeptide.

In an aspect, the invention features a method of delivering an anellosome to a cell, comprising contacting the anellosome, e.g., a synthetic anellosome, e.g., as described herein, with a cell, e.g., a eukaryotic cell, e.g., a mammalian cell.

In an aspect, the invention features a method of manufacturing an anellosome composition, comprising:

a) providing a host cell comprising, e.g., expressing one or more components (e.g., all of the components) of an anellosome, e.g., a synthetic anellosome, e.g., as described herein;
b) producing a preparation of anellosomes from the host cell, wherein the anellosomes of the preparation comprise a proteinaceous exterior and a genetic element comprising a promoter element, a sequence encoding an effector, (e.g., an endogenous or exogenous effector), and a protein binding sequence (e.g., an exterior protein binding sequence, e.g., a packaging signal), thereby making a preparation of anellosomes; and
c) formulating the preparation of anellosomes, e.g., as a pharmaceutical composition suitable for administration to a subject.

In some embodiments, the components of the anellosome are introduced into the host cell at the time of production (e.g., by transient transfection). In some embodiments, the host cell stably expresses the components of the anellosome (e.g., wherein one or more nucleic acids encoding the components of the anellosome are introduced into the host cell, or a progenitor thereof, e.g., by stable transfection).

In some embodiments, formulating the preparation of anellosomes comprises one or more purification steps (e.g., purification by chromatography and/or ultrafiltration). In some ebodiments, the purification steps comprise removing serum, host cell DNA, host cell proteins, and/or phenol red from the preparation. In some embodiments, the resultant preparation or a pharmaceutical composition comprising the preparation will be stable over an acceptable period of time and temperature, and/or be compatible with the desired route of administration and/or any devices this route of administration will require, e.g., needles or syringes.

In an aspect, the invention features a method of manufacturing an anellosome composition, comprising: a) providing a plurality of anellosomes described herein, or a pharmaceutical composition described herein; and b) formulating the anellosomes, e.g., as a pharmaceutical composition suitable for administration to a subject.

In an aspect, the invention features a method of making a host cell, e.g., a first host cell or a producer cell (e.g., as shown in FIG. 12), e.g., a population of first host cells, comprising an anellosome, the method comprising introducing a genetic element, e.g., as described herein, to a host cell and culturing the host cell under conditions suitable for production of the anellosome. In embodiments, the method further comprises introducing a helper, e.g., a helper virus, to the host cell. In embodiments, the introducing comprises transfection (e.g., chemical transfection) or electroporation of the host cell with the anellosome.

In an aspect, the invention features a method of making an anellosome, comprising providing a host cell, e.g., a first host cell or producer cell (e.g., as shown in FIG. 12), comprising an anellosome, e.g., as described herein, and purifying the anellosome from the host cell. In some embodiments, the method further comprises, prior to the providing step, contacting the host cell with an anellosome, e.g., as described herein, and incubating the host cell under conditions suitable for production of the anellosome. In embodiments, the host cell is the first host cell or producer cell described in the above method of making a host cell. In embodiments, purifying the anellosome from the host cell comprises lysing the host cell.

In some embodiments, the method further comprises a second step of contacting the anellosome produced by the first host cell or producer cell with a second host cell, e.g., a permissive cell (e.g., as shown in FIG. 12), e.g., a population of second host cells. In some embodiments, the method further comprises incubating the second host cell under conditions suitable for production of the anellosome. In some embodiments, the method further comprises purifying an anellosome from the second host cell, e.g., thereby producing an anellosome seed population. In embodiments, at least about 2-100-fold more of the anellosome is produced from the population of second host cells than from the population of first host cells. In embodiments, purifying the anellosome from the second host cell comprises lysing the second host cell. In some embodiments, the method further comprises a second step of contacting the anellosome produced by the second host cell with a third host cell, e.g., permissive cells (e.g., as shown in FIG. 12), e.g., a population of third host cells. In some embodiments, the method further comprises incubating the third host cell under conditions suitable for production of the anellosome. In some embodiments, the method further comprises purifying a anellosome from the third host cell, e.g., thereby producing an anellosome stock population. In embodiments, purifying the anellosome from the third host cell comprises lysing the third host cell. In embodiments, at least about 2-100-fold more of the anellosome is produced from the population of third host cells than from the population of second host cells.

In some embodiments, the method further comprises evaluating one or more anellosomes from the anellosome seed population or the anellosome stock population for one or more quality control parameters, e.g., purity, titer, potency (e.g., in genomic equivalents per anellosome particle), and/or the nucleic acid sequence, e.g., from the genetic element comprised by the anellosome. In some embodiments, the evaluated nucleic acid sequence comprises the nucleic acid sequence encoding an effector (e.g., an endogenous effector or an exogenous effector).

In some embodiments, the host cell is grown in a medium suitable for promoting cell growth. In certain embodiments, once the host cell has grown sufficiently (e.g., to an appropriate cell density), the medium may be exchanged with a medium suitable for production of anellosomes by the host cell. In some embodiments, anellosomes produced by a host cell separated from the host cell (e.g., by lysing the host cell) prior to contact with a second host cell. In some embodiments, anellosomes produced by a host cell are contacted with a second host cell without an intervening purification step.

In an aspect, the invention comprises evaluating one or more anellosomes, e.g., from an anellosome seed population or an anellosome stock population, for one or more quality control parameters, e.g., purity, titer, potency, and/or the nucleic acid sequence, e.g., from the genetic element comprised by the synthetic anellosome. In some embodiments, the evaluated nucleic acid sequence comprises the nucleic acid sequence encoding an effector (e.g., an endogenous effector or an exogenous effector). In some embodiments, purity comprises a sufficiently high ratio of functional versus nonfunctional anellosomes (e.g., as evaluated by HPLC). In some embodiments, potency comprises a sufficiently high level of anellosome function (e.g., expression and/or function of an effector encoded therein) detectable in an anellosome preparation.

In some embodiments, multiple anellosomes can be produced in a single batch. In embodiments, the levels of the anellosomes produced in the batch can be evaluated (e.g., individually or together).

In an aspect, the invention features a reaction mixture comprising an anellosome described herein and a helper virus, wherein the helper virus comprises a polynucleotide, e.g., a polynucleotide encoding an exterior protein, (e.g., an exterior protein capable of binding to the exterior protein binding sequence and, optionally, a lipid envelope), a polynucleotide encoding a replication protein (e.g., a polymerase), or any combination thereof.

In some embodiments, an anellosome (e.g., a synthetic anellosome) is isolated, e.g., isolated from a host cell and/or isolated from other constituents in a solution (e.g., a supernatant). In some embodiments, an anellosome (e.g., a synthetic anellosome) is purified, e.g., from a solution (e.g., a supernatant). In some embodiments, an anellosome is enriched in a solution relative to other constituents in the solution.

In some embodiments of any of the aforesaid anellosomes, compositions or methods, providing an anellosome comprises separating (e.g., harvesting) an anellosome from a composition comprising an anellosome-producing cell, e.g., as described herein. In other embodiments, providing an anellosome comprises obtaining an anellosome or a preparation thereof, e.g., from a third party.

In some embodiments of any of the aforesaid anellosomes, compositions or methods, a jelly-roll domain or region, comprises (e.g., consists of) a polypeptide (e.g., a domain or region comprised in a larger polypeptide) comprising one or more (e.g., 1, 2, or 3) of the following characteristics:

(i) at least 30% (e.g., at least 30%, 35%, 40%, 45%, 50%, 55%, 60%, 65%, 70%, 75%, 80%, 90%, or more) of the amino acids of the jelly-roll domain are part of one or more β-sheets;

(ii) the secondary structure of the jelly-roll domain comprises at least four (e.g., at least 4, 5, 6, 7, 8, 9, 10, 11, or 12) β-strands; and/or (iii) the tertiary structure of the jelly-roll domain comprises at least two (e.g., at least 2, 3, or 4) β-sheets; and/or (iv) the jelly-roll domain comprises a ratio of β-sheets to α-helices of at least 2:1, 3:1, 4:1, 5:1, 6:1, 7:1, 8:1, 9:1, or 10:1.

In certain embodiments, a jelly-roll domain comprises two β-sheets.

In certain embodiments, one or more (e.g., 1, 2, 3, 4, 5, 6, 7, 8, 9, or 10) of the β-sheets comprises about eight (e.g., 4, 5, 6, 7, 8, 9, 10, 11, or 12) β-strands. In certain embodiments, one or more (e.g., 1, 2, 3, 4, 5, 6, 7, 8, 9, or 10) of the β-sheets comprises eight β-strands. In certain embodiments, one or more (e.g., 1, 2, 3, 4, 5, 6, 7, 8, 9, or 10) of the β-sheets comprises seven β-strands. In certain embodiments, one or more (e.g., 1, 2, 3, 4, 5, 6, 7, 8, 9, or 10) of the β-sheets comprises six β-strands. In certain embodiments, one or more (e.g., 1, 2, 3, 4, 5, 6, 7, 8, 9, or 10) of the β-sheets comprises five β-strands. In certain embodiments, one or more (e.g., 1, 2, 3, 4, 5, 6, 7, 8, 9, or 10) of the β-sheets comprises four β-strands.

In some embodiments, the jelly-roll domain comprises a first β-sheet in antiparallel orientation to a second β-sheet. In certain embodiments, the first β-sheet comprises about four (e.g., 3, 4, 5, or 6) β-strands. In certain embodiments, the second β-sheet comprises about four (e.g., 3, 4, 5, or 6) β-strands. In embodiments, the first and second β-sheet comprise, in total, about eight (e.g., 6, 7, 8, 9, 10, 11, or 12) β-strands.

In certain embodiments, a jelly-roll domain is a component of a capsid protein (e.g., an ORF1 molecule as described herein). In certain embodiments, a jelly-roll domain has self-assembly activity. In some embodiments, a polypeptide comprising a jelly-roll domain binds to another copy of the polypeptide comprising the jelly-roll domain. In some embodiments, a jelly-roll domain of a first polypeptide binds to a jelly-roll domain of a second copy of the polypeptide.

In some embodiments of any of the aforesaid anellosomes, anellovectors, compositions or methods, the genetic element comprises a minimal anellosome genome, e.g., as identified according to the method described in Example 9. In some embodiments, the minimal anellosome genome comprises a minimal *Anellovirus* genome sufficient for replication of the anellosome (e.g., in a host cell). In embodiments, the minimal anellosome genome comprises a TTV-tth8 nucleic acid sequence, e.g., a TTV-tth8 nucleic acid sequence shown in Table 5, having deletions of at least 10%, 20%, 30%, 40%, 50%, 60%, 70%, 80%, 90%, 95%, 99%, or 100% of nucleotides 3436-3707 of the TTV-tth8 nucleic acid sequence. In embodiments, the minimal anellosome genome comprises a TTMV-LY2 nucleic acid sequence, e.g., a TTMV-LY2 nucleic acid sequence shown in Table 15, having deletions of at least 10%, 20%, 30%, 40%, 50%, 60%, 70%, 80%, 90%, 95%, 99%, or 100% of nucleotides 574-1371, 1432-2210, 574-2210, and/or 2610-2809 of the TTMV-LY2 nucleic acid sequence. In embodiments, the minimal anellosome genome is a minimal anellosome genome capable of self-replication and/or self-amplification. In embodiments, the minimal anellosome genome is a minimal anellosome genome capable of replicating or being amplified in the presence of a helper, e.g., a helper virus.

Additional features of any of the aforesaid anellosomes, anellovectors, compositions or methods include one or more of the following enumerated embodiments.

Those skilled in the art will recognize, or be able to ascertain using no more than routine experimentation, many equivalents to the specific embodiments of the invention described herein. Such equivalents are intended to be encompassed by the following enumerated embodiments.

Enumerated Embodiments

1000. A polypeptide comprising one or more of:

(a) a first region comprising an amino acid sequence having at least 70% (e.g., at least about 70, 80, 90, 95, 96, 97, 98, 99, or 100%) sequence identity to an arginine-rich region sequence described herein (e.g., MPYYYRRRRYNYRRPRWYGRGWIRRPFRRRFRRKRRVR (SEQ ID NO: 216) or MAWGWWKRRRRWWFRKRWTRGRLRRRWPRSARRRPRRRRVRRRRRWRRGRRKTRTYRRRRRFRRRGRK (SEQ ID NO: 186), or as listed in any of Tables 20-37) or a sequence of at least about 40 amino acids comprising at least 60%, 70%, or 80% basic residues (e.g., arginine, lysine, or a combination thereof), (b) a second region comprising an amino acid sequence having at least 30% (e.g., at least about 30, 35, 40, 50, 60, 70, 80, 90, 95, 96, 97, 98, 99, or 100%) sequence identity to a jelly-roll region sequence described herein (e.g., PTYTTIPLKQWQPPYKRTCYIKGQDCLIYYSNLRLGMNSTMYEKSIVPVHWPGGGSFSVSMLTLDALYDIHKLCRNWWTSTNQDLPLVRYKGCKITFYQSTFTDYIVRIHTELPANSNKLTYPNTHPLMMMMSKYKHIIPSRQTRRKKKPYTKIFVKPPPQFENKWYFATDLYKIPLLQIHCTACNLQNPFVKPDKLSNNVTLWSLNT (SEQ ID NO: 217), or as listed in any of Tables 20-37) or a sequence comprising at least 6 (e.g., at least 6, 7, 8, 9, 10, 11, or 12) beta strands;

(c) a third region comprising an amino acid sequence having at least 30% (e.g., at least about 30, 35, 40, 50, 60, 70, 80, 90, 95, 96, 97, 98, 99, or 100%) sequence identity to an N22 domain sequence described herein (e.g.,

```
                                         (SEQ ID NO: 219)
TMALTPFNEPIFTQIQYNPDRDTGEDTQLYLLSNATGTGWDPPGIPELIL

EGFPLWLIYWGFADFQKNLKKVTNIDTNYMLVAKTKFTQKPGTFYLVILN

DTFVEGNSPYEKQPLPEDNIKWYPQVQYQLEAQNKLLQTGPFTPNIQGQL

SDNISMFYKFYFK,
or as listed in any of Tables 20-37);
```

and (d) a fourth region comprising an amino acid sequence having at least 30% (e.g., at least about 30, 35, 40, 50, 60, 70, 80, 90, 95, 96, 97, 98, 99, or 100%) sequence identity to an *Anellovirus* ORF1 C-terminal domain (CTD) sequence described herein (e.g.,

```
                                         (SEQ ID NO: 220)
WGGSPPKAINVENPAHQIQYPIPRNEHETTSLQSPGEAPESILYSFDYRH

GNYTTTALSRISQDWALKDTVSKITEPDRQQLLKQALECLQISEETQEKK

EKEVQQLISNLRQQQQLYRERIISLLKDQ,
or as listed in any of Tables 20-37);
```

wherein the ORF1 molecule comprises at least one difference (e.g., a mutation, chemical modification, or epigenetic alteration) relative to a wild-type ORF1 protein (e.g., as described herein), e.g., an insertion, substitution, chemical or enzymatic modification, and/or deletion, e.g., a deletion of a domain (e.g., one or more of an arginine-rich region, jelly-roll domain, HVR, N22, or CTD, e.g., as described herein).

1001. The polypeptide of embodiment 1000, wherein the polypeptide comprises:

(i) the first region and the second region;
(ii) the first region and the third region;
(iii) the first region and the fourth region;
(iv) the second region and the third region;
(v) the second region and the fourth region;
(vi) the third region and the fourth region;
(vii) the first region, the second region, and the third region;
(viii) the first region, the second region, and the fourth region;
(ix) the first region, the third region, and the fourth region; or
(x) the second region, the third region, and the fourth region.

1002. A polypeptide comprising:

(a) a first region comprising an amino acid sequence having at least 70% (e.g., at least about 70, 80, 90, 95, 96, 97, 98, 99, or 100%) sequence identity to an arginine-rich region sequence described herein (e.g., MPYYYRRRRYNYRRPRWYGRGWIRRPFRRRFRRKRRVR (SEQ ID NO: 216) or MAWGWWKRRRRWWFRKRWTRGRLRRRWPRSARRRPRRRRVRRRRRWRRGRRKTRTYRRRRRFRRRGRK (SEQ ID NO: 186), or as listed in any of Tables 20-37) or a sequence of at least about 40 amino acids comprising at least 60%, 70%, or 80% basic residues (e.g., arginine, lysine, or a combination thereof), (b) a second region comprising an amino acid sequence having at least 30% (e.g., at least about 30, 35, 40, 50, 60, 70, 80, 90, 95, 96, 97, 98, 99, or 100%) sequence identity to a jelly-roll region sequence described herein (e.g., PTYTTIPLKQWQPPYKRTCYIKGQDCLIYYSNLRLGMNSTMYEKSIVPVHWPGGGSFSVSMLTLDALYDIHKLCRNWWTSTNQDLPLVRYKGCKITFYQSTFTDYIVRIHTELPANSNKLTYPNTHPLMMMMSKYKHIIPSRQTRRKKKPYTKIFVKPPPQFENKWYFATDLYKIPLLQIHCTACNLQNPFVKPDKLSNNVTLWSLNT (SEQ ID NO: 217), or as listed in any of Tables 20-37) or a sequence comprising at least 6 beta strands;

(c) a third region comprising an amino acid sequence having at least 30% (e.g., at least about 30, 35, 40, 50, 60, 70, 80, 90, 95, 96, 97, 98, 99, or 100%) sequence identity to an N22 domain sequence described herein (e.g., (SEQ ID NO: 219)
TMALTPFNEPIFTQIQYNPDRDTGEDTQLYLLSNATGTGWDPPGIPELIL

EGFPLWLIYWGFADFQKNLKKVTNIDTNYMLVAKTKFTQKPGTFYLVILN

DTFVEGNSPYEKQPLPEDNIKWYPQVQYQLEAQNKLLQTGPFTPNIQGQL

SDNISMFYKFYFK,
or as listed in any of Tables 20-37;

and (d) a fourth region comprising an amino acid sequence having at least 30% (e.g., at least about 30, 35, 40, 50, 60, 70, 80, 90, 95, 96, 97, 98, 99, or 100%) sequence identity to an *Anellovirus* ORF1 C-terminal domain (CTD) sequence described herein (e.g., (SEQ ID NO: 220)
WGGSPPKAINVENPAHQIQYPIPRNEHETTSLQSPGEAPESILYSFDYRH

GNYTTTALSRISQDWALKDTVSKITEPDRQQLLKQALECLQISEETQEKK

EKEVQQLISNLRQQQQLYRERIISLLKDQ,
or as listed in any of Tables 20-37);

wherein the ORF1 molecule comprises at least one difference (e.g., a mutation, chemical modification, or epigenetic alteration) relative to a wild-type ORF1 protein (e.g., as described herein), e.g., an insertion, substitution, chemical or enzymatic modification, and/or deletion, e.g., a deletion of a domain (e.g., one or more of an arginine-rich region, jelly-roll domain, HVR, N22, or CTD, e.g., as described herein).

1003. The polypeptide of any of the preceding embodiments, wherein:

the first region comprises an amino acid sequence having at least 70% (e.g., at least about 70, 80, 90, 95, 96, 97, 98, 99, or 100%) sequence identity to amino acids 1-38 of the ORF1 sequence listed in Table 16;

the second region comprises an amino acid sequence having at least 70% (e.g., at least about 70, 80, 90, 95, 96, 97, 98, 99, or 100%) sequence identity to amino acids 39-246 of the ORF1 sequence listed in Table 16;

the third region comprises an amino acid sequence having at least 70% (e.g., at least about 70, 80, 90, 95, 96, 97, 98, 99, or 100%) sequence identity to amino acids 375-537 of the ORF1 sequence listed in Table 16; and/or the fourth region comprises an amino acid sequence having at least 70% (e.g., at least about 70, 80, 90, 95, 96, 97, 98, 99, or 100%) sequence identity to amino acids 538-666 of the ORF1 sequence listed in Table 16.

1004. The polypeptide of any of the preceding embodiments, wherein:

the first region comprises an amino acid sequence having at least 70% (e.g., at least about 70, 80, 90, 95, 96, 97, 98, 99, or 100%) sequence identity to an arginine-rich region sequence as listed in any of Tables 20-37;

the second region comprises an amino acid sequence having at least 70% (e.g., at least about 70, 80, 90, 95, 96, 97, 98, 99, or 100%) sequence identity to a jelly-roll region sequence as listed in any of Tables 20-37;

the third region comprises an amino acid sequence having at least 70% (e.g., at least about 70, 80, 90, 95, 96, 97, 98, 99, or 100%) sequence identity to an N22 domain sequence as listed in any of Tables 20-37; and/or the fourth region comprises an amino acid sequence having at least 70% (e.g., at least about 70, 80, 90, 95, 96, 97, 98, 99, or 100%) sequence identity to a CTD sequence as listed in any of Tables 20-37.

1005. The polypeptide of any of the preceding embodiments, wherein the polypeptide comprises, in N-terminal to C-terminal order, the first region, the second region, the third region, and the fourth region.

1006. The polypeptide of any of the preceding embodiments, wherein the at least one difference comprises at least one difference in the first region relative to the arginine-rich region of a wild-type ORF1 protein.

1007. The polypeptide of any of the preceding embodiments, wherein the first region comprises an arginine-rich region from the ORF1 protein of an *Anellovirus* other than the wild-type *Anellovirus* to which the polypeptide, or the portion thereof excluding the first region, has greatest sequence identity.

1008. The polypeptide of any of the preceding embodiments, wherein the first region comprises an amino acid sequence having at least 70% sequence identity to the arginine-rich region from an *Anellovirus* other than the wild-type *Anellovirus* to which the polypeptide has greatest sequence identity.

1009. The polypeptide of any of the preceding embodiments, wherein the first region comprises a polypeptide that has less than 15% (e.g., less than 15%, 14%, 13%, 12%, 11%, 10%, 9%, 8%, 7%, 6%, 5%, 4%, 3%, 2%, or 1%) sequence identity to an wild-type *Anellovirus* genome (e.g., as described herein), or a portion thereof having the same amino acid length as the first region.

1010. The polypeptide of any of the preceding embodiments, wherein the first region has DNA binding activity and/or nuclear localization activity.

1011. The polypeptide of any of the preceding embodiments, wherein the first region comprises a DNA-binding region and/or a nuclear localization sequence.

1012. The polypeptide of any of the preceding embodiments, wherein the at least one difference comprises at least one difference in the second region relative to the jelly-roll region of a wild-type ORF1 protein.

1013. The polypeptide of any of the preceding embodiments, wherein the second region comprises a jelly-roll region from the ORF1 protein of an *Anellovirus* other than the wild-type *Anellovirus* to which the polypeptide, or the portion thereof excluding the second region, has greatest sequence identity.

1014. The polypeptide of any of the preceding embodiments, wherein the second region comprises an amino acid sequence having at least 70% sequence identity to the jelly-roll region from an *Anellovirus* other than the wild-type *Anellovirus* to which the polypeptide has greatest sequence identity.

1015. The polypeptide of any of the preceding embodiments, wherein the second region comprises a polypeptide that has less than 15% (e.g., less than 15%, 14%, 13%, 12%, 11%, 10%, 9%, 8%, 7%, 6%, 5%, 4%, 3%, 2%, or 1%) sequence identity to an wild-type *Anellovirus* genome (e.g., as described herein), or a portion thereof having the same amino acid length as the second region.

1016. The polypeptide of any of the preceding embodiments, wherein the at least one difference comprises at least one difference in the third region relative to the N22 domain of a wild-type ORF1 protein.

1017. The polypeptide of any of the preceding embodiments, wherein the third region comprises an N22 domain from the ORF1 protein of an *Anellovirus* other than the wild-type *Anellovirus* to which the polypeptide, or the portion thereof excluding the third region, has greatest sequence identity.

1018. The polypeptide of any of the preceding embodiments, wherein the third region comprises an amino acid sequence having at least 70% sequence identity to the N22 region from an *Anellovirus* other than the wild-type *Anellovirus* to which the polypeptide has greatest sequence identity.

1019. The polypeptide of any of the preceding embodiments, wherein the third region comprises a polypeptide that has less than 15% (e.g., less than 15%, 14%, 13%, 12%, 11%, 10%, 9%, 8%, 7%, 6%, 5%, 4%, 3%, 2%, or 1%) sequence identity to an wild-type *Anellovirus* genome (e.g., as described herein), or a portion thereof having the same amino acid length as the third region.

1020. The polypeptide of any of the preceding embodiments, wherein the at least one difference comprises at least one difference in the fourth region relative to the CTD domain of a wild-type ORF1 protein.

1021. The polypeptide of any of the preceding embodiments, wherein the fourth region comprises a CTD domain from the ORF1 protein of an *Anellovirus* other than the wild-type *Anellovirus* to which the polypeptide, or the portion thereof excluding the fourth region, has greatest sequence identity.

1022. The polypeptide of any of the preceding embodiments, wherein the fourth region comprises an amino acid sequence having at least 70% sequence identity to the CTD region from an *Anellovirus* other than the wild-type *Anellovirus* to which the polypeptide has greatest sequence identity.

1023. The polypeptide of any of the preceding embodiments, wherein the fourth region comprises a polypeptide that has less than 15% (e.g., less than 15%, 14%, 13%, 12%, 11%, 10%, 9%, 8%, 7%, 6%, 5%, 4%, 3%, 2%, or 1%) sequence identity to an wild-type *Anellovirus* genome (e.g., as described herein), or a portion thereof having the same amino acid length as the fourth region.

1024. The polypeptide of any of the preceding embodiments, further comprising an amino acid sequence, e.g., a hypervariable region (HVR) sequence (e.g., the HVR sequence of an *Anellovirus* ORF1 molecule, e.g., as described herein), wherein the amino acid sequence comprises at least about 55 (e.g., at least about 45, 50, 51, 52, 53, 54, 55, 56, 57, 58, 59, 60, or 65) amino acids (e.g., about 45-160, 50-160, 55-160, 60-160, 45-150, 50-150, 55-150, 60-150, 45-140, 50-140, 55-140, or 60-140 amino acids).

1025. The polypeptide of embodiment 1024, wherein the HVR sequence is positioned between the second region and the third region.

1026. The polypeptide of embodiment 1024 or 1025, wherein the HVR sequence comprises an amino acid sequence having at least 70% (e.g., at least about 70, 80, 90, 95, 96, 97, 98, 99, or 100%) sequence identity to the HVR from an *Anellovirus* other than the wild-type *Anellovirus* to which the ORF1 protein has greatest sequence identity.

1027. The polypeptide of any of embodiments 1024-1026, wherein the HVR sequence is heterologous relative to one or more of the first region, second region, third region, and/or fourth region.

1028. The polypeptide of any of embodiments 1024-1027, wherein the at least one difference comprises at least one difference in the HVR sequence relative to the sequence of an HVR of a wild-type ORF1 protein (e.g., from a wild-type *Anellovirus* genome, e.g., as described herein).

1029. The polypeptide of any of embodiments 1024-1028, wherein the HVR sequence comprises an HVR from the ORF1 protein of an *Anellovirus* other than the wild-type *Anellovirus* to which the polypeptide, or the portion thereof excluding the HVR sequence, has greatest sequence identity.

1030. The polypeptide of any of embodiments 1024-1029, wherein the HVR sequence comprises an amino acid sequence having at least 70% sequence identity to the HVR from an *Anellovirus* other than the wild-type *Anellovirus* to which the polypeptide has greatest sequence identity.

1031. The polypeptide of any of embodiments 1024-1030, wherein the HVR comprises an amino acid sequence having at least 70% (e.g., at least about 70, 80, 90, 95, 96, 97, 98, 99, or 100%) sequence identity to HVR sequence as listed in any of Tables 20-37.

1032. The polypeptide of any of embodiments 1024-1031, wherein the HVR sequence comprises at least 70% (e.g., at least about 70, 80, 90, 95, 96, 97, 98, 99, or 100%) sequence identity to amino acids 247-374 of the ORF1 sequence listed in Table 16.

1033. The polypeptide of any of the preceding embodiments, further comprising a heterologous polypeptide, e.g., a polypeptide that is heterologous relative to one or more of the first region, second region, third region, and/or fourth region, and/or is exogenous relative to an anellosome comprising the polypeptide.

1034. The polypeptide of embodiment 1033, wherein the polypeptide lacks an *Anellovirus* HVR sequence.

1035. The polypeptide of embodiment 1033, wherein the heterologous polypeptide is present on the exterior of the anellosome.

1036. The polypeptide of embodiment 1033, wherein the heterologous polypeptide is present on the interior of the anellosome.

1037. The polypeptide of any of embodiments 1033-1036, wherein the heterologous polypeptide has a functionality that is exogenous to the anellosome or a wild-type *Anellovirus*.

1038. The polypeptide of any of embodiments 1033-1037, wherein the heterologous polypeptide consists of about 140 or fewer amino acids (e.g., 100, 110, 120, 125, 130, 135, 136, 137, 138, 139, 140, 145, 150, 155, or 160 or fewer amino acids).

1039. The polypeptide of any of embodiments 1033-1038, wherein the size of the heterologous polypeptide is between 50-150% relative to a wild-type HVR region of an *Anellovirus*, e.g., as described herein.

1039A. The polypeptide of any of embodiments 1033-1039, wherein the heterologous polypeptide is positioned between the second region and the third region.

1040. The polypeptide of any of the preceding embodiments, further comprising one or more amino acids between the first region and the second region, one or more amino acids between the second region and the third region, and/or one or more amino acids between the third region and the fourth region.

1041. The polypeptide of any of the preceding embodiments, further comprising one or more amino acids positioned N-terminal relative to the first region.

1042. The polypeptide of any of the preceding embodiments, further comprising one or more amino acids positioned C-terminal relative to the fourth region.

1043. The polypeptide of any of the preceding embodiments, comprising a plurality of subsequences of at least four (e.g., 4, 5, 6, 7, 8, 9, 10, 15, 20, 25, or 30) contiguous amino acids having 100% sequence identity to the corresponding subsequences of a wild-type *Anellovirus* ORF1 amino acid sequence, e.g., as listed in any of Tables 2, 4, 6, 8, 10, 12, 14, 16, 18, or 20-37.

1044. The polypeptide of any of the preceding embodiments, comprising a plurality of subsequences of at least ten (e.g., 10, 15, 20, 25, 30, 40, or 50) contiguous amino acids having at least 80% sequence identity to the corresponding subsequences of a wild-type *Anellovirus* ORF1 amino acid sequence, e.g., as listed in any of Tables 2, 4, 6, 8, 10, 12, 14, 16, 18, or 20-37.

1045. The polypeptide of any of the preceding embodiments, comprising a plurality of subsequences of at least twenty (e.g., 20, 25, 30, 40, 50, 60, 70, 80, 90, or 100) contiguous amino acids having at least 60% sequence identity to the corresponding subsequences of a wild-type *Anellovirus* ORF1 amino acid sequence, e.g., as listed in any of Tables 2, 4, 6, 8, 10, 12, 14, 16, 18, or 20-37.

1046. The polypeptide of any of embodiments 1043-1045, wherein the plurality of subsequences are positioned within the first region, second region, third region, and/or fourth region.

1047. The polypeptide of any of the preceding embodiments, wherein the first region comprises at least about 40 amino acids (e.g., at least about 50, 60, 70, 80, 90, or 100 amino acids, e.g., about 40-100, 40-90, 40-80, 40-70, 50-100, 50-70, 60-100, 60-90, 60-80, or 60-70 amino acids).

1048. The polypeptide of any of the preceding embodiments, wherein the first region comprises at least about 70% (e.g., at least about 70%, 75%, 80%, 85%, 90%, 95%, or 100%) basic residues (e.g., arginine, lysine, or a combination thereof).

1049. The polypeptide of any of the preceding embodiments, wherein the first region comprises at least about 70% (e.g., at least about 70%, 75%, 80%, 85%, 90%, 95%, or 100%) arginine residues.

1050. The polypeptide of any of the preceding embodiments, wherein the polypeptide forms homomultimers with additional copies of the polypeptide.

1051. The polypeptide of embodiment 1050, wherein the first region binds to corresponding first regions on additional copies of the polypeptide.

1052. The polypeptide of embodiment 1050, wherein the homomultimers form a capsid, e.g., encapsulating a nucleic acid, e.g., a genetic element or an *Anellovirus* genome or a portion thereof.

1053. The polypeptide of any of the preceding embodiments, wherein the polypeptide is a capsid protein or can form a portion of a capsid.

1054. The polypeptide of any of the preceding embodiments, wherein the polypeptide has replicase activity.

1055. The polypeptide of any of the preceding embodiments, wherein the polypeptide binds to a nucleic acid (e.g., DNA).

1056. A complex comprising:
- (a) the polypeptide of any of the preceding embodiments, and
- (b) a genetic element comprising a promoter element and a nucleic acid sequence (e.g., a DNA sequence) encoding an effector (e.g., an exogenous effector or an endogenous effector), and a protein binding sequence.

1057. A complex comprising:
- (a) an ORF1 molecule, and
- (b) a genetic element comprising a promoter element and a nucleic acid sequence (e.g., a DNA sequence) encoding an effector (e.g., an exogenous effector or an endogenous effector), and a protein binding sequence;

wherein the ORF1 molecule is bound to (e.g., non-covalently bound to) the genetic element, wherein the ORF1 molecule, the genetic element, or both of the ORF1 molecule and the genetic element comprise at least one difference (e.g., a mutation, chemical modification, or epigenetic alteration) relative to a wild-type ORF1 protein, wild-type *Anellovirus* genome, or both of the wild-type ORF1 protein and wild-type *Anellovirus* genome, respectively (e.g., as described herein), e.g., an insertion, substitution, chemical or enzymatic modification, and/or deletion, e.g., a deletion of a domain (e.g., one or more of an arginine-rich region, jelly-roll domain, HVR, N22, or CTD, e.g., as described herein) or genomic region (e.g., one or more of a TATA box, cap site, transcriptional start site, 5' UTR, open reading frame (ORF), poly(A) signal, or GC-rich region, e.g., as described herein).

1058. The complex of embodiment 1056 or 1057, wherein the complex is in vitro, e.g., wherein the complex is in a substantially cell-free composition.

1059. The complex of any of embodiments 1056-1058, wherein the complex is in a cell, e.g., a host cell, e.g., a helper cell, e.g., in the nucleus of the cell.

1060. The complex of any of embodiments 1056-1059, wherein the ORF1 molecule is part of a proteinaceous exterior.

1061. The complex of any of embodiments 1056-1060, wherein the genetic element is undergoing replication.

1062. The complex of any of embodiments 1056-1061, wherein the complex is in an anellosome.

1063. The complex of any of embodiments 1056-1062, wherein the genetic element further comprises a nucleic acid sequence encoding the polypeptide.

1064. The complex of any of embodiments 1056-1063, wherein the genetic element does not comprise a nucleic acid sequence encoding the polypeptide.

1065. The complex of any of embodiments 1056-1064, wherein the genetic element comprises a GC-rich region, e.g., as described herein.

1066. The complex of embodiment 1065, wherein the GC-rich region comprises at least 10, 15, 20, 25, 30, 31, 32, 33, 34, 35, or 36 consecutive nucleotides of the nucleic acid sequence of any of:

(SEQ ID NO: 160)
(i) CGCGCTGCGCGCGCCGCCCAGTAGGGGGAGCCATGC, (SEQ ID NO: 164)
(ii) GCGCT$X_1$CGCGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

(SEQ ID NO: 170)
(viii) GCGCTTCGCGCGCGCGCCGGGGGGCTGCGCCCCCCC;

-continued

```
                                     (SEQ ID NO: 171)
(ix) GCGCTACGCGCGCGCGCCGGGGGGCTGCGCCCCCCC;
or

                                     (SEQ ID NO: 172)
(x) GCGCTACGCGCGCGCGCCGGGGGGCTCTGCCCCCCC;
```

or a nucleic acid sequence having at least 75, 76, 77, 78, 79, 80, 85, 90, 91, 92, 93, 94, 95, 96, 97, 98, 99, or 100% sequence identity thereto.

1067. An anellosome comprising:

(a) a proteinaceous exterior;

(b) the polypeptide or complex of any of the preceding embodiments;

(c) a genetic element comprising a promoter element operably linked to a nucleic acid sequence (e.g., a DNA sequence) encoding an effector (e.g., an endogenous effector or an exogenous effector, e.g., as described herein); and wherein the genetic element is enclosed within the proteinaceous exterior.

1068. An anellosome comprising:

(a) a proteinaceous exterior;

(b) a genetic element comprising:

(i) a promoter element operably linked to a nucleic acid sequence (e.g., a DNA sequence) encoding an effector (e.g., an endogenous effector or an exogenous effector, e.g., as described herein), and (ii) a nucleic acid encoding the polypeptide of any of the preceding embodiments; and wherein the genetic element is enclosed within the proteinaceous exterior.

1069. An anellosome comprising:

(a) a proteinaceous exterior;

(b) an ORF1 molecule or a nucleic acid encoding the ORF1 molecule;

(c) a genetic element comprising a promoter element operably linked to a heterologous nucleic acid sequence (e.g., a DNA sequence) encoding an effector; and wherein the genetic element is enclosed within the proteinaceous exterior.

1070. An anellosome comprising:

(a) a proteinaceous exterior;

(b) an ORF1 molecule or a nucleic acid encoding the ORF1 molecule;

(c) a genetic element comprising a promoter element, a nucleic acid sequence (e.g., a DNA sequence) encoding an effector (e.g., an exogenous effector or an endogenous effector), and a region comprising at least 10, 15, 20, 25, 30, 31, 32, 33, 34, 35, or 36 consecutive nucleotides of the nucleic acid sequence:

```
                                     (SEQ ID NO: 160)
(i) CGCGCTGCGCGCGCCGCCCAGTAGGGGGAGCCATGC,

                                     (SEQ ID NO: 164)
(ii) GCGCTX1CGCGCGCGCGCCGGGGGGCTGCGCCCCCCC,
```

wherein $X_1$ is selected from T, G, or A;

```
                                     (SEQ ID NO: 165)
(iii) GCGCTTCGCGCGCCGCCCACTAGGGGGCGTTGCGCG;

                                     (SEQ ID NO: 166)
(iv) GCGCTGCGCGCGCCGCCCAGTAGGGGGCGCAATGCG;

                                     (SEQ ID NO: 167)
(v) GCGCTGCGCGCGCGGCCCCCGGGGGAGGCATTGCCT;

                                     (SEQ ID NO: 168)
(vi) GCGCTGCGCGCGCGCGCCGGGGGGGCGCCAGCGCCC;

                                     (SEQ ID NO: 169)
(vii) GCGCTTCGCGCGCGCGCCGGGGGGCTCCGCCCCCCC;

                                     (SEQ ID NO: 170)
(viii) GCGCTTCGCGCGCGCGCCGGGGGGCTGCGCCCCCCC;

                                     (SEQ ID NO: 171)
(ix) GCGCTACGCGCGCGCGCCGGGGGGCTGCGCCCCCCC;
or

                                     (SEQ ID NO: 172)
(x) GCGCTACGCGCGCGCGCCGGGGGGCTCTGCCCCCCC;
```

or a nucleic acid sequence having at least 75, 76, 77, 78, 79, 80, 85, 90, 91, 92, 93, 94, 95, 96, 97, 98, 99, or 100% sequence identity thereto; and wherein the genetic element comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);

wherein the genetic element is enclosed within the proteinaceous exterior; and wherein the anellosome is configured to deliver the genetic element into a eukaryotic cell; and optionally, wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein.

1071. An anellosome comprising:

(a) a proteinaceous exterior;

(b) an ORF1 molecule or a nucleic acid encoding the ORF1 molecule;

(c) a genetic element comprising a promoter element, a nucleic acid sequence (e.g., a DNA sequence) encoding an effector (e.g., an exogenous effector or an endogenous effector), and a sequence comprising at least 20 (e.g., at least 20, 25, 30, 31, 32, 33, 34, 35, or 36) consecutive nucleotides having a GC content of at least 70% (e.g., at least 70%, 71%, 72%, 73%, 74%, 75%, 76%, 77%, 78%, 79%, 80%, or 80.6%);

wherein the genetic element comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);

wherein the genetic element is enclosed within the proteinaceous exterior; and wherein the anellosome is configured to deliver the genetic element into a eukaryotic cell; and optionally wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein.

1072. An anellosome comprising:

(a) a proteinaceous exterior;

(b) an ORF1 molecule or a nucleic acid encoding the ORF1 molecule;

wherein:

(i) at least 30% (e.g., at least 30%, 35%, 40%, 45%, 50%, 55%, 60%, 65%, 70%, 75%, 80%, 90%, or more) of the amino acids of the ORF1 molecule are part of a β-strands;

(ii) the secondary structure of the ORF1 molecule comprises at least three (e.g., at least 3, 4, 5, 6, 7, 8, 9, 10, 11, 12, 13, 14, 15, 16, 17, 18, 19, or 20) β-strands;

(iii) the secondary structure of the ORF1 molecule comprises a ratio of β-strands to α-helices of at least 1:1, 2:1, 3:1, 4:1, 5:1, 6:1, 7:1, 8:1, 9:1, or 10:1; and (c) a genetic element comprising a promoter element, a nucleic acid sequence (e.g., a DNA sequence) encoding an effector (e.g., an exogenous effector or an endogenous effector), and a protein binding sequence;

wherein the genetic element comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);

wherein the genetic element is enclosed within the proteinaceous exterior; and wherein the anellosome is configured to deliver the genetic element into a eukaryotic cell; and optionally wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein.

1073. An anellosome comprising:

(a) a proteinaceous exterior;

(b) an ORF1 molecule or a nucleic acid encoding the ORF1 molecule;

(c) a genetic element comprising a promoter element and a nucleic acid sequence (e.g., a DNA sequence) encoding an effector (e.g., an exogenous effector or an endogenous effector), and a protein binding sequence;

wherein the genetic element comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);

wherein the genetic element is enclosed within the proteinaceous exterior; and wherein the anellosome is configured to deliver the genetic element into a eukaryotic cell; and optionally wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein.

1074. An anellosome comprising:

(a) a proteinaceous exterior;

(b) a genetic element comprising a promoter element, a nucleic acid sequence (e.g., a DNA sequence) encoding an effector (e.g., an exogenous effector or an endogenous effector), and a region comprising at least 10, 15, 20, 25, 30, 31, 32, 33, 34, 35, or 36 consecutive nucleotides of the nucleic acid sequence:

(SEQ ID NO: 160)
(i) CGCGCTGCGCGCGCCGCCCAGTAGGGGGAGCCATGC, (SEQ ID NO: 164)
(ii) GCGCT$X_1$CGCGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

(SEQ ID NO: 170)
(viii) GCGCTTCGCGCGCGCGCCGGGGGGCTGCGCCCCCCC;

(SEQ ID NO: 171)
(ix) GCGCTACGCGCGCGCGCCGGGGGGCTGCGCCCCCCC;
or (SEQ ID NO: 172)
(x) GCGCTACGCGCGCGCGCCGGGGGGCTCTGCCCCCCC;

or a nucleic acid sequence having at least 75, 76, 77, 78, 79, 80, 85, 90, 91, 92, 93, 94, 95, 96, 97, 98, 99, or 100% sequence identity thereto; and wherein the genetic element comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);

wherein the genetic element is enclosed within the proteinaceous exterior; and wherein the anellosome is configured to deliver the genetic element into a eukaryotic cell; and optionally, wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein.

1075. An anellosome comprising:

(a) a proteinaceous exterior;

(b) a genetic element comprising a promoter element, a nucleic acid sequence (e.g., a DNA sequence) encoding an effector (e.g., an exogenous effector or an endogenous effector), and a sequence comprising at least 20, 25, 30, 31, 32, 33, 34, 35, or 36 consecutive nucleotides having a GC content of at least 70%, 71%, 72%, 73%, 74%, 75%, 76%, 77%, 78%, 79%, 80%, or 80.6%; and wherein the genetic element comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);

wherein the genetic element is enclosed within the proteinaceous exterior; and wherein the anellosome is configured to deliver the genetic element into a eukaryotic cell; and optionally, wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein.

1076. An anellosome comprising:

(a) a proteinaceous exterior;

(b) a genetic element comprising a promoter element and a nucleic acid sequence (e.g., a DNA sequence) encoding an effector (e.g., an exogenous effector or an endogenous effector), wherein the genetic element comprises a region (e.g., a packaging region, e.g., positioned 3' relative to the nucleic acid sequence encoding the effector) having:

at least 95% (e.g., at least 95, 96, 97, 98, 99, or 100%) sequence identity to the nucleic acid (SEQ ID NO: 160)
sequence: CGCGCTGCGCGCGCCGCCCAGTAGGGGGAGCCATGC;

wherein the genetic element is enclosed within the proteinaceous exterior; and wherein the anellosome is configured to deliver the genetic element into a eukaryotic cell.

1077. The anellosome of any of the preceding embodiments, wherein the proteinaceous exterior comprises the ORF1 molecule.

1078. The anellosome of any of the preceding embodiments, wherein at least 60% (e.g., at least 60%, 65%, 70%, 75%, 80%, 85%, 90%, 95%, 96%, 97%, 98%, 99%, or 100%) of protein in the proteinaceous exterior comprises an ORF1 molecule.

1079. The anellosome of any of the preceding embodiments, wherein no more than 1% (e.g., no more than 1%, 2%, 3%, 4%, 5%, 10%, 15%, 20%, 25%, 30%, 35%, or 40%) of protein in the proteinaceous exterior comprises an ORF1/1, ORF1/2, ORF2, ORF2/2, ORF2/3, ORF2t/3, and/or ORF3 molecule.

1080. The anellosome of any of the preceding embodiments, wherein the ORF1 molecule comprises an amino acid sequence having at least 70% (e.g., at least 70%, 75%, 80%, 85%, 90%, 95%, 96%, 97%, 98%, 99%, or 100%) identity to an ORF1 protein listed in, or encoded by a sequence listed in any of Tables 1-18 or 20-37.

1081. The anellosome of any of the preceding embodiments, wherein the ORF1 molecule comprises a polypeptide of any of the preceding embodiments.

1082. The anellosome of any of the preceding embodiments, wherein the genetic element further comprises a nucleic acid sequence encoding the ORF1 molecule.

1083. The anellosome of any of the preceding embodiments, wherein the genetic element does not comprise a nucleic acid sequence encoding the ORF1 molecule.

1084. The anellosome of any of the preceding embodiments, wherein the genetic element comprises at least 20, 25, 30, 31, 32, 33, 34, 35, or 36 consecutive nucleotides having a GC content of at least 80%.

1085. The anellosome of any of the preceding embodiments, wherein the genetic element comprises at least 36 consecutive nucleotides having a GC content of at least 70%, 71%, 72%, 73%, 74%, 75%, 76%, 77%, 78%, 79%, 80%, or 80.6%.

1086. The anellosome of any of the preceding embodiments, wherein the genetic element comprises at least 36 consecutive nucleotides having a GC content of at least 80%.

1087. An isolated nucleic acid composition (e.g., comprising one, two, or more nucleic acid molecules) comprising a nucleic acid encoding the polypeptide of any of the preceding embodiments;

optionally wherein the isolated nucleic acid composition further comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region); and optionally wherein the nucleic acid molecule does not comprise:

(i) a deletion of nucleotides 3436 to 3607 relative to a wild-type TTV-tth8 genome sequence, e.g., as described herein;

(ii) a deletion of nucleotides 1432 to 2210 relative to a wild-type TTMV-LY2 genome sequence, e.g., as described herein; and/or (iii) a deletion of at least 101 nucleotides relative to a wild-type TTMV-LY2 genome sequence, e.g., as described herein.

1088. An isolated nucleic acid composition (e.g., comprising one, two, or more nucleic acid molecules), wherein the isolated nucleic acid composition comprises a genetic element encoding an ORF1 molecule;
  wherein:
    (i) at least 30% (e.g., at least 30%, 35%, 40%, 45%, 50%, 55%, 60%, 65%, 70%, 75%, 80%, 90%, or more) of the amino acids of the ORF1 molecule are part of a β-sheet;
    (ii) the tertiary structure of the ORF1 molecule comprises at least three (e.g., at least 3, 4, 5, 6, 7, 8, 9, 10, 11, 12, 13, 14, 15, 16, 17, 18, 19, or 20) β-sheets;
    (iii) the ORF1 molecule comprises a ratio of β-sheets to α-helices of at least 1:1, 2:1, 3:1, 4:1, 5:1, 6:1, 7:1, 8:1, 9:1, or 10:1; and
  wherein the genetic element comprises a promoter element, a nucleic acid sequence encoding an effector (e.g., an exogenous effector or an endogenous effector), and a protein binding sequence;
  wherein the genetic element comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region); and
  optionally wherein the nucleic acid molecule does not comprise:
    (i) a deletion of nucleotides 3436 to 3607 relative to a wild-type TTV-tth8 genome sequence, e.g., as described herein;
    (ii) a deletion of nucleotides 1432 to 2210 relative to a wild-type TTMV-LY2 genome sequence, e.g., as described herein; and/or
    (iii) a deletion of at least 101 nucleotides relative to a wild-type TTMV-LY2 genome sequence, e.g., as described herein.

1089. An isolated nucleic acid composition (e.g., comprising one, two, or more nucleic acid molecules) comprising:
  (a) a genetic element encoding an ORF1 molecule;
  (b) at least 10, 15, 20, 25, 30, 31, 32, 33, 34, 35, or 36 consecutive nucleotides of the nucleic acid sequence:

```
                                                 (SEQ ID NO: 160)
(i)   CGCGCTGCGCGCGCCGCCCAGTAGGGGGAGCCATGC,

                                                 (SEQ ID NO: 164)
(ii)  GCGCTX₁CGCGCGCGCGCCGGGGGGCTGCGCCCCCCC   ,
```
  wherein X₁ is selected from T, G, or A;

```
                                                 (SEQ ID NO: 165)
(iii) GCGCTTCGCGCGCCGCCCACTAGGGGGCGTTGCGCG;

                                                 (SEQ ID NO: 166)
(iv)  GCGCTGCGCGCGCCGCCCAGTAGGGGGCGCAATGCG;

                                                 (SEQ ID NO: 167)
(v)   GCGCTGCGCGCGCGGCCCCCGGGGGAGGCATTGCCT;

                                                 (SEQ ID NO: 168)
(vi)  GCGCTGCGCGCCGCGCCGGGGGGGCGCCAGCGCCC;

                                                 (SEQ ID NO: 169)
(vii) GCGCTTCGCGCGCGCGCCGGGGGGCTCCGCCCCCCC;

                                                 (SEQ ID NO: 170)
(viii) GCGCTTCGCGCGCGCGCCGGGGGGCTGCGCCCCCCC;

                                                 (SEQ ID NO: 171)
(ix)  GCGCTACGCGCGCGCGCCGGGGGGCTGCGCCCCCCC;
or

                                                 (SEQ ID NO: 172)
(x)   GCGCTACGCGCGCGCGCCGGGGGGCTCTGCCCCCCC;
```

or a nucleic acid sequence having at least 75, 76, 77, 78, 79, 80, 85, 90, 91, 92, 93, 94, 95, 96, 97, 98, 99, or 100% sequence identity thereto; and
  (c) at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);
  optionally wherein the nucleic acid molecule does not comprise:
    (i) a deletion of nucleotides 3436 to 3607 relative to a wild-type TTV-tth8 genome sequence, e.g., as described herein;
    (ii) a deletion of nucleotides 1432 to 2210 relative to a wild-type TTMV-LY2 genome sequence, e.g., as described herein; and/or
    (iii) a deletion of at least 101 nucleotides relative to a wild-type TTMV-LY2 genome sequence, e.g., as described herein.

1090. An isolated nucleic acid composition (e.g., comprising one, two, or more nucleic acid molecules), wherein the isolated nucleic acid composition comprises:
  (a) a genetic element encoding an ORF1 molecule;
  (b) at least 20, 25, 30, 31, 32, 33, 34, 35, or 36 consecutive nucleotides having a GC content of at least 70%, 71%, 72%, 73%, 74%, 75%, 76%, 77%, 78%, 79%, 80%, or 80.6%; and
  wherein the isolated nucleic acid composition comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region); and
  optionally wherein the nucleic acid molecule does not comprise:
    (i) a deletion of nucleotides 3436 to 3607 relative to a wild-type TTV-tth8 genome sequence, e.g., as described herein;
    (ii) a deletion of nucleotides 1432 to 2210 relative to a wild-type TTMV-LY2 genome sequence, e.g., as described herein; and/or
    (iii) a deletion of at least 101 nucleotides relative to a wild-type TTMV-LY2 genome sequence, e.g., as described herein.

1091. The isolated nucleic acid composition of any of embodiments 1089-1090, wherein (a) and (b) are part of the same nucleic acid.

1092. The isolated nucleic acid composition of any of embodiments 1089-1091, wherein (a) and (b) are part of different nucleic acids.

1093. The isolated nucleic acid composition of any of the preceding embodiments, wherein the genetic element further comprises one or more of: a TATA box, an initiator element, a cap site, a transcriptional start site, a 5' UTR conserved domain, an ORF1-encoding sequence, an ORF1/1-encoding sequence, an ORF1/2-encoding sequence, an ORF2-encoding sequence, an ORF2/2-encoding sequence, an ORF2/3-encoding sequence, an ORF2/3t-encoding sequence, a three open-reading frame region, a poly(A) signal, and/or a GC-rich region from an *Anellovirus* described herein (e.g., as listed in any of Tables 1, 3, 5, 7, 9, 11, 13, 15, or 17), or a sequence having at least 70%, 75%, 80%, 85%, 90%, 95%, 96%, 97%, 98%, 99%, or 100% sequence identity thereto.

1094. The isolated nucleic acid composition of any of the preceding embodiments, wherein the genetic element further comprises an *Anellovirus* genome sequence (e.g., as described herein, e.g., as listed in any of Tables 1, 3, 5, 7, 9, 11, 13, 15, or 17), or a sequence having at least 70%, 75%, 80%, 85%, 90%, 95%, 96%, 97%, 98%, 99%, or 100% sequence identity thereto.

1095. The isolated nucleic acid composition of embodiment 1094, further comprising at least one additional copy of the *Anellovirus* genome sequence or the sequence having at least 70%, 75%, 80%, 85%, 90%, 95%, 96%, 97%, 98%, 99%, or 100% sequence identity thereto (e.g., a total of 1, 2, 3, 4, 5, or 6 copies).

1096. The isolated nucleic acid composition of any of the preceding embodiments, further comprising at least one additional copy of the genetic element (e.g., a total of 1, 2, 3, 4, 5, or 6 copies).

1097. An isolated nucleic acid composition (e.g., comprising one, two, or more nucleic acid molecules) comprising at least 10, 15, 20, 25, 30, 31, 32, 33, 34, 35, or 36 consecutive nucleotides of the nucleic acid sequence:

(SEQ ID NO: 160)
(i) CGCGCTGCGCGCCGCCCAGTAGGGGGAGCCATGC, (SEQ ID NO: 164)
(ii) GCGCT$X_1$CGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

(SEQ ID NO: 170)
(viii) GCGCTTCGCGCGCGCGCCGGGGGGCTGCGCCCCCCC;

(SEQ ID NO: 171)
(ix) GCGCTACGCGCGCGCGCCGGGGGGCTGCGCCCCCCC;
or (SEQ ID NO: 172)
(x) GCGCTACGCGCGCGCGCCGGGGGGCTCTGCCCCCCC;

or a nucleic acid sequence having at least 75, 76, 77, 78, 79, 80, 85, 90, 91, 92, 93, 94, 95, 96, 97, 98, 99, or 100% sequence identity thereto; and at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region);

optionally wherein the nucleic acid molecule does not comprise:

(i) a deletion of nucleotides 3436 to 3607 relative to a wild-type TTV-tth8 genome sequence, e.g., as described herein;

(ii) a deletion of nucleotides 1432 to 2210 relative to a wild-type TTMV-LY2 genome sequence, e.g., as described herein; and/or (iii) a deletion of at least 101 nucleotides relative to a wild-type TTMV-LY2 genome sequence, e.g., as described herein.

1098. An isolated nucleic acid composition (e.g., comprising one, two, or more nucleic acid molecules), wherein the isolated nucleic acid composition comprises at least 20, 25, 30, 31, 32, 33, 34, 35, or 36 consecutive nucleotides having a GC content of at least 70%, 71%, 72%, 73%, 74%, 75%, 76%, 77%, 78%, 79%, 80%, or 80.6%; and wherein the isolated nucleic acid composition comprises at least one difference (e.g., a mutation, chemical modification, or epigenetic alteration) relative to a wild-type *Anellovirus* genome sequence (e.g., as described herein), e.g., an insertion, substitution, enzymatic modification, and/or deletion, e.g., a deletion of a domain (e.g., one or more of a TATA box, cap site, transcriptional start site, 5' UTR, open reading frame (ORF), poly(A) signal, or GC-rich region); and optionally wherein the nucleic acid molecule does not comprise:

(i) a deletion of nucleotides 3436 to 3607 relative to a wild-type TTV-tth8 genome sequence, e.g., as described herein;

(ii) a deletion of nucleotides 1432 to 2210 relative to a wild-type TTMV-LY2 genome sequence, e.g., as described herein; and/or (iii) a deletion of at least 101 nucleotides relative to a wild-type TTMV-LY2 genome sequence, e.g., as described herein.

1099. The isolated nucleic acid composition of any of the preceding embodiments, wherein the ORF1 molecule comprises a polypeptide of any of the preceding embodiments.

1100. The isolated nucleic acid composition of any of the preceding embodiments, comprising at least 20, 25, 30, 31, 32, 33, 34, 35, or 36 consecutive nucleotides having a GC content of at least 80%.

1101. The isolated nucleic acid composition of any of the preceding embodiments, comprising at least 36 consecutive nucleotides having a GC content of at least 70%, 71%, 72%, 73%, 74%, 75%, 76%, 77%, 78%, 79%, 80%, or 80.6%.

1102. The isolated nucleic acid composition of any of the preceding embodiments, comprising at least 36 consecutive nucleotides having a GC content of at least 80%.

1103. The isolated nucleic acid composition of any of the preceding embodiments, further comprising one or more of a promoter element, a nucleic acid sequence encoding an effector (e.g., an exogenous effector or an endogenous effector), and/or a protein binding sequence (e.g., an exterior protein binding sequence).

1104. The isolated nucleic acid composition of any of the preceding embodiments, comprising at least about 100, 150, 200, 250, 300, 350, 400, 450, or 500 consecutive nucleotides of a wild-type *Anellovirus* genome sequence, or a nucleic acid sequence having at least 75, 76, 77, 78, 79, 80, 85, 90, 91, 92, 93, 94, 95, 96, 97, 98, 99, or 100% sequence identity thereto.

1105. An isolated nucleic acid molecule (e.g., an expression vector) comprising a nucleic acid sequence having at least 95% (e.g., at least 95, 96, 97, 98, 99, or 100%) sequence identity to the nucleic acid sequence:

(SEQ ID NO: 160)
(i) CGCGCTGCGCGCGCCGCCCAGTAGGGGGAGCCATGC, (SEQ ID NO: 164)
(ii) GCGCT$X_1$CGCGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

(SEQ ID NO: 170)
(viii) GCGCTTCGCGCGCGCGCCGGGGGGCTGCGCCCCCCC;

(SEQ ID NO: 171)
(ix) GCGCTACGCGCGCGCGCCGGGGGGCTGCGCCCCCCC
or (SEQ ID NO: 172)
(x) GCGCTACGCGCGCGCGCCGGGGGGCTCTGCCCCCCC.

1106. The isolated nucleic acid composition of any of the preceding embodiments, wherein the isolated nucleic acid molecule is circular.

1107. An isolated cell comprising:
- (a) a nucleic acid encoding a polypeptide of any of the preceding embodiments, wherein the nucleic acid is a plasmid, is a viral nucleic acid, or is integrated into a cell chromosome, and
- (b) a genetic element, wherein the genetic element comprises a promoter element and a nucleic acid sequence (e.g., a DNA sequence) encoding an effector (e.g., an exogenous effector or an endogenous effector), and a protein binding sequence, wherein optionally the genetic element does not encode an ORF1 polypeptide.

1108. An isolated cell comprising:
- (a) a nucleic acid encoding an ORF1 molecule, wherein the nucleic acid is a plasmid, is a viral nucleic acid, or is integrated into a cell chromosome, and
- (b) a genetic element, wherein the genetic element comprises a promoter element and a nucleic acid sequence (e.g., a DNA sequence) encoding an effector (e.g., an exogenous effector or an endogenous effector), and a protein binding sequence.

1109. An isolated cell comprising:
- (a) a nucleic acid encoding an ORF1 molecule (e.g., wherein the nucleic acid is a plasmid, is a viral nucleic acid, or is integrated into a cell chromosome), and
- (b) a genetic element that does not encode an ORF1 molecule, wherein the genetic element comprises a promoter element and a nucleic acid sequence (e.g., a DNA sequence) encoding an effector (e.g., an exogenous effector or an endogenous effector), and a protein binding sequence.

1110. The isolated cell of any of the preceding embodiments, wherein the genetic element that does not encode an ORF1 molecule encodes a fragment of an ORF1 molecule, e.g., a fragment that does not form a capsid, e.g., a fragment of less than 1000, 900, 800, 700, 600, 500, 400, 300, 200, 100, 50, 20, or 10 nucleotides.

1111. An isolated cell comprising a nucleic acid encoding an ORF1 molecule (e.g., wherein the nucleic acid is a plasmid, is a viral nucleic acid, or is integrated into a cell chromosome), wherein the isolated cell does not comprise one or more of an ORF1/1, ORF1/2, ORF2, ORF2/2, ORF2/3, ORF2t/3, and/or ORF3 molecule.

1112. An isolated cell comprising the nucleic acid composition of any of the preceding embodiments.

1113. A helper nucleic acid (e.g., a plasmid or viral nucleic acid) encoding an ORF1 molecule, wherein the isolated cell does not comprise one or more of an ORF1/1, ORF1/2, ORF2, ORF2/2, ORF2/3, ORF2t/3, and/or ORF3 molecule.

1114. A composition comprising:
- (a) an isolated cell described herein, and
- (b) an anellosome described herein.

1115. A composition comprising:
- (a) a cell comprising a nucleic acid encoding an ORF1 molecule (e.g., wherein the nucleic acid is a plasmid, is a viral nucleic acid, or is integrated into a cell chromosome), and
- (b) a genetic element (e.g., inside the cell or outside the cell, e.g., in cell culture medium) that does not encode an ORF1 molecule, wherein the genetic element comprises a promoter element and a nucleic acid sequence (e.g., a DNA sequence) encoding an effector (e.g., an exogenous effector or an endogenous effector), and a protein binding sequence.

1116. A pharmaceutical composition comprising the polypeptide, complex, anellosome or isolated nucleic acid of any of the preceding embodiments and a pharmaceutically acceptable carrier and/or excipient.

1117. A method of manufacturing an ORF1 molecule, the method comprising:
- (a) providing a host cell (e.g., a host cell described herein) comprising a nucleic acid encoding the polypeptide of any of the preceding embodiments, and
- (b) maintaining the host cell under conditions that allow the cell to produce the polypeptide;

thereby manufacturing the ORF1 molecule.

1118. A method of manufacturing an ORF1 molecule, the method comprising:
- (a) providing a host cell (e.g., a host cell described herein) comprising the nucleic acid composition of any of the preceding embodiments, and
- (b) maintaining the host cell under conditions that allow the cell to produce the polypeptide;

thereby manufacturing the ORF1 molecule.

1119. The method of embodiment 1117 or 1118, wherein the host cell is a helper cell.

1120. The method of embodiment 1119, wherein the helper cell comprises one or more additional nucleic acids encoding one or more additional ORFs (e.g., one or more of ORF1/1, ORF1/2, ORF2, ORF2/2, ORF2/3, ORF2t/3, and/or ORF3) of a wild-type *Anellovirus*, e.g., as described herein.

1121. The method of any of embodiments 1117-1120, wherein the nucleic acid is integrated into the genome of the host cell.

1122. The method of any of embodiments 1117-1121, wherein the host cell produces at least about 10, 20, 30, 40, 50, 60, 70, 80, 90, 100, 200, 300, 400, 500, 1000, 10,000, 50,000, 100,000, 500,000, or 1,000,000 copies (e.g., at least about 60 copies) of the polypeptide per host cell.

1123. The method of any of embodiments 1117-1122, wherein the host cell produces at least about 1, 2, 3, 4, 5, 6, 7, 8, 9, 10, 20, 30, 40, 50, 60, 70, 80, 90, 100, 200, 300, 400, 500, 1000, 10,000, or 100,000 copies (e.g., at least about 60 copies) of the polypeptide per anellosome produced by the host cell.

1124. The method of any of embodiments 1117-1123, wherein the method comprises providing a plurality of host cells, and maintaining the host cells under conditions that allow the production of at least 1000 copies of the polypeptide per cell.

1125. The method of embodiment 1124, wherein the plurality of host cells produces at least about $1\times10^5$, $1\times10^6$, $1\times10^7$, $1\times10^8$, $9\times10^8$, $1\times10^9$, $1\times10^{10}$, $1\times10^{11}$, or $1\times10^{12}$ copies of the polypeptide.

1126. A method of manufacturing an anellosome composition, the method comprising:

(a) providing a helper cell, e.g., a helper cell described herein;

(b) introducing a genetic element into the helper cell under conditions that allow the cell to produce anellosomes, and (c) formulating the anellosomes, e.g., as a pharmaceutical composition suitable for administration to a subject, thereby making the anellosome composition.

1127. A method of manufacturing an anellosome composition, the method comprising:

(a) providing a host cell;

(b) introducing a helper nucleic acid into the host cell;

(c) introducing a genetic element into the host cell (e.g., before, after, or simultaneously with (b)), under conditions that allow the cell to produce anellosomes; and (d) formulating the anellosomes, e.g., as a pharmaceutical composition suitable for administration to a subject; thereby making the anellosome composition.

1128. A method of manufacturing an anellosome composition, the method comprising:

(a) providing a helper cell comprising a nucleic acid encoding an ORF1 molecule (e.g., wherein the nucleic acid is a plasmid, is a viral nucleic acid, or is integrated into a helper cell chromosome);

(b) introducing a genetic element into the helper cell under conditions that allow the cell to produce anellosomes, wherein the genetic element does not encode an ORF1 molecule, wherein the genetic element comprises a promoter element and a nucleic acid sequence (e.g., a DNA sequence) encoding an effector (e.g., an exogenous effector or an endogenous effector), and a protein binding sequence; and (c) formulating the anellosomes, e.g., as a pharmaceutical composition suitable for administration to a subject; thereby making the anellosome composition.

1129. A method of manufacturing an anellosome composition, the method comprising:

(a) providing a host cell;

(b) introducing a helper nucleic acid encoding an ORF1 molecule (e.g., wherein the nucleic acid is a plasmid, or a viral nucleic acid), into the host cell; and (c) introducing a genetic element into the host cell (e.g., before, after, or simultaneously with (b)), under conditions that allow the cell to produce an anellosome, wherein the genetic element does not encode an ORF1 molecule, wherein the genetic element comprises a promoter element and a nucleic acid sequence (e.g., a DNA sequence) encoding an effector (e.g., an exogenous effector or an endogenous effector), and a protein binding sequence, thereby making the anellosome.

1130. The method of any of the preceding embodiments, which further comprises separating the anellosome from the helper cell or host cell.

1131. The method of any of the preceding embodiments, wherein providing a helper cell comprises introducing a helper nucleic acid into the host cell, e.g., wherein the helper nucleic acid encodes an ORF1 molecule (e.g., wherein the nucleic acid is a plasmid, or a viral nucleic acid).

1132. The method of any of the preceding embodiments, wherein the helper cell comprises the ORF1 molecule.

1133. The method of any of the preceding embodiments, wherein the nucleic acid comprises one or more of: a TATA box, an initiator element, a cap site, a transcriptional start site, a 5' UTR conserved domain, an ORF1-encoding sequence, an ORF1/1-encoding sequence, an ORF1/2-encoding sequence, an ORF2-encoding sequence, an ORF2/2-encoding sequence, an ORF2/3-encoding sequence, an ORF2/3t-encoding sequence, a three open-reading frame region, a poly(A) signal, and/or a GC-rich region from an *Anellovirus* described herein (e.g., as listed in any of Tables 1, 3, 5, 7, 9, 11, 13, 15, or 17), or a sequence having at least 70%, 75%, 80%, 85%, 90%, 95%, 96%, 97%, 98%, 99%, or 100% sequence identity thereto.

1134. The method of any of the preceding embodiments, wherein the nucleic acid comprises an *Anellovirus* genome sequence (e.g., as described herein, e.g., as listed in any of Tables 1, 3, 5, 7, 9, 11, 13, 15, or 17), or a sequence having at least 70%, 75%, 80%, 85%, 90%, 95%, 96%, 97%, 98%, 99%, or 100% sequence identity thereto.

1135. The method of any of the preceding embodiments, wherein the nucleic acid comprises at least one additional copy of the *Anellovirus* genome sequence or the sequence having at least 70%, 75%, 80%, 85%, 90%, 95%, 96%, 97%, 98%, 99%, or 100% sequence identity thereto (e.g., a total of 1, 2, 3, 4, 5, or 6 copies).

1136. The method of any of the preceding embodiments, wherein the host cell or helper cell comprises at least one additional copy of the nucleic acid (e.g., a total of 1, 2, 3, 4, 5, or 6 copies).

1137. The method of any of the preceding embodiments, wherein the nucleic acid is circular.

1138. A method of delivering an effector to a subject, comprising administering to the subject an anellosome comprising:

(a) a proteinaceous exterior that comprises an ORF1 molecule;

(b) a genetic element comprising a promoter element and a nucleic acid sequence (e.g., a DNA sequence) encoding the effector (e.g., an exogenous effector or an endogenous effector), and a region comprising at least 10, 15, 20, 25, 30, 31, 32, 33, 34, 35, or 36 consecutive nucleotides of the nucleic acid sequence:

(SEQ ID NO: 160)
(i) CGCGCTGCGCGCGCCGCCCAGTAGGGGGAGCCATGC, (SEQ ID NO: 164)
(ii) GCGCT$X_1$CGCGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

(SEQ ID NO: 170)
(viii) GCGCTTCGCGCGCGCGCCGGGGGGCTGCGCCCCCCC;

(SEQ ID NO: 171)
(ix) GCGCTACGCGCGCGCGCCGGGGGGCTGCGCCCCCCC;
or (SEQ ID NO: 172)
(x) GCGCTACGCGCGCGCGCCGGGGGGCTCTGCCCCCCC;

or a nucleic acid sequence having at least 75, 76, 77, 78, 79, 80, 85, 90, 91, 92, 93, 94, 95, 96, 97, 98, 99, or 100% sequence identity thereto; and wherein the genetic element is enclosed within the proteinaceous exterior; and optionally wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein, thereby delivering the effector to a subject.

1139. A method of delivering an effector to a subject, comprising administering to the subject an anellosome comprising:

(a) a proteinaceous exterior that comprises an ORF1 molecule;

(b) a genetic element comprising a promoter element, a nucleic acid sequence (e.g., a DNA sequence) encoding the effector (e.g., an exogenous effector or an endogenous effector), and a sequence comprising at least 20, 25, 30, 31, 32, 33, 34, 35, or 36 consecutive nucleotides having a GC content of at least 70%, 71%, 72%, 73%, 74%, 75%, 76%, 77%, 78%, 79%, 80%, or 80.6%;

wherein the genetic element is enclosed within the proteinaceous exterior; and optionally wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein, thereby delivering the effector to a subject.

1140. A method of delivering an effector to a subject, comprising administering to the subject an anellosome comprising:

(a) a proteinaceous exterior that comprises an ORF1 molecule;

(b) a genetic element comprising a promoter element and a nucleic acid sequence (e.g., a DNA sequence) encoding the effector (e.g., an exogenous effector or an endogenous effector), and a protein binding sequence;

wherein the genetic element is enclosed within the proteinaceous exterior; and optionally wherein the genetic element:

(i) does not comprise a deletion of nucleotides 3436 to 3607 relative to a wild-type TTV-tth8 genome sequence, e.g., as described herein;

(ii) does not comprise a deletion of nucleotides 1432 to 2210 relative to a wild-type TTMV-LY2 genome sequence, e.g., as described herein; and/or (iii) does not comprise a deletion of at least 101 nucleotides relative to a wild-type TTMV-LY2 genome sequence, e.g., as described herein, thereby delivering the effector to a subject.

1141. A method of delivering an effector to a target cell, comprising contacting the target cell with an anellosome comprising:

(a) a proteinaceous exterior that comprises an ORF1 molecule;

(b) a genetic element comprising a promoter element and a nucleic acid sequence (e.g., a DNA sequence) encoding the effector (e.g., an exogenous effector or an endogenous effector), and a region comprising at least 10, 15, 20, 25, 30, 31, 32, 33, 34, 35, or 36 consecutive nucleotides of the nucleic acid sequence:

(SEQ ID NO: 160)
(i) CGCGCTGCGCGCGCCGCCCAGTAGGGGGAGCCATGC, (SEQ ID NO: 164)
(ii) GCGCT$X_1$CGCGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

(SEQ ID NO: 170)
(viii) GCGCTTCGCGCGCGCGCCGGGGGGCTGCGCCCCCCC;

(SEQ ID NO: 171)
(ix) GCGCTACGCGCGCGCGCCGGGGGGCTGCGCCCCCCC;
or (SEQ ID NO: 172)
(x) GCGCTACGCGCGCGCGCCGGGGGGCTCTGCCCCCCC;

or a nucleic acid sequence having at least 75, 76, 77, 78, 79, 80, 85, 90, 91, 92, 93, 94, 95, 96, 97, 98, 99, or 100% sequence identity thereto; and wherein the genetic element is enclosed within the proteinaceous exterior; and
optionally wherein the genetic element:
(i) does not comprise a deletion of nucleotides 3436 to 3607 relative to a wild-type TTV-tth8 genome sequence, e.g., as described herein;
(ii) does not comprise a deletion of nucleotides 1432 to 2210 relative to a wild-type TTMV-LY2 genome sequence, e.g., as described herein; and/or
(iii) does not comprise a deletion of at least 101 nucleotides relative to a wild-type TTMV-LY2 genome sequence, e.g., as described herein,
thereby delivering the effector to the target cell.

1142. A method of delivering an effector to a target cell, comprising contacting the target cell with an anellosome comprising:
(a) a proteinaceous exterior that comprises an ORF1 molecule;
(b) a genetic element comprising a promoter element, a nucleic acid sequence (e.g., a DNA sequence) encoding the effector (e.g., an exogenous effector or an endogenous effector), and a sequence comprising at least 20, 25, 30, 31, 32, 33, 34, 35, or 36 consecutive nucleotides having a GC content of at least 70%, 71%, 72%, 73%, 74%, 75%, 76%, 77%, 78%, 79%, 80%, or 80.6%;
wherein the genetic element is enclosed within the proteinaceous exterior; and
optionally wherein the genetic element:
(i) does not comprise a deletion of nucleotides 3436 to 3607 relative to a wild-type TTV-tth8 genome sequence, e.g., as described herein;
(ii) does not comprise a deletion of nucleotides 1432 to 2210 relative to a wild-type TTMV-LY2 genome sequence, e.g., as described herein; and/or
(iii) does not comprise a deletion of at least 101 nucleotides relative to a wild-type TTMV-LY2 genome sequence, e.g., as described herein,
thereby delivering the effector to the target cell.

1143. A method of delivering an effector to a target cell, comprising contacting the target cell with an anellosome comprising:
(a) a proteinaceous exterior that comprises an ORF1 molecule;
(b) a genetic element comprising a promoter element and a nucleic acid sequence (e.g., a DNA sequence) encoding the effector (e.g., an exogenous effector or an endogenous effector), and a protein binding sequence;
wherein the genetic element is enclosed within the proteinaceous exterior; and
optionally wherein the genetic element:
(i) does not comprise a deletion of nucleotides 3436 to 3607 relative to a wild-type TTV-tth8 genome sequence, e.g., as described herein;
(ii) does not comprise a deletion of nucleotides 1432 to 2210 relative to a wild-type TTMV-LY2 genome sequence, e.g., as described herein; and/or
(iii) does not comprise a deletion of at least 101 nucleotides relative to a wild-type TTMV-LY2 genome sequence, e.g., as described herein,
thereby delivering the effector to the target cell.

1144. The polypeptide, complex, anellosome, isolated nucleic acid, cell, composition, or method of any of the preceding embodiments, wherein the genetic element does not encode the amino acid sequence of NCBI Accession No. A7XCE8.1.

1145. The polypeptide, complex, anellosome, isolated nucleic acid, cell, composition, or method of any of the preceding embodiments, wherein the ORF1 molecule comprises an amino acid sequence having at least 70% (e.g., at least 70%, 75%, 80%, 85%, 90%, 95%, 96%, 97%, 98%, 99%, or 100%) sequence identity to an ORF1 sequence listed in any of Tables 2, 4, 6, 8, 10, 12, 14, 16, 18, or 20-37.

1146. The polypeptide, complex, anellosome, isolated nucleic acid, cell, composition, or method of any of the preceding embodiments, wherein at least 30% (e.g., at least 30%, 35%, 40%, 45%, 50%, 55%, 60%, 65%, 70%, 75%, 80%, 90%, or more) of the amino acids of the ORF1 molecule are part of a β-sheet.

1147. The polypeptide, complex, anellosome, isolated nucleic acid, cell, composition, or method of any of the preceding embodiments, wherein the tertiary structure of the ORF1 molecule comprises at least three (e.g., at least 3, 4, 5, 6, 7, 8, 9, 10, 11, 12, 13, 14, 15, 16, 17, 18, 19, or 20) β-sheets.

1148. The polypeptide, complex, anellosome, isolated nucleic acid, cell, composition, or method of any of the preceding embodiments, wherein the ORF1 molecule comprises a ratio of β-sheets to α-helices of at least 1:1, 2:1, 3:1, 4:1, 5:1, 6:1, 7:1, 8:1, 9:1, or 10:1.

1149. The polypeptide, complex, anellosome, isolated nucleic acid, cell, composition, or method of any of the preceding embodiments, wherein the ORF1 molecule comprises an arginine-rich region (e.g., having at least 70%, 80%, 85%, 90%, 95%, 96%, 97%, 98%, 99%, or 100% identity to an arginine-rich region sequence listed in any of Tables 20-37).

1150. The polypeptide, complex, anellosome, isolated nucleic acid, cell, composition, or method of embodiment 1149, wherein the arginine-rich region comprises at least 15, 20, 25, 26, 27, 28, 29, 30, 31, 32, 33, 34, 35, 36, 37, 38, 39, 40, 45, or 50 consecutive nucleotides comprising at least 40% (e.g., at least 40%, 41%, 42%, 43%, 44%, 45%, 46%, 47%, 48%, 49%, 50%, 55%, 60%, 65%, 66%, 67%, 68%, 69%, 70%, 75%, 80%, 85%, 90%, or 95%) arginine residues.

1151. The polypeptide, complex, anellosome, isolated nucleic acid, cell, composition, or method of embodiment 1149 or 1150, wherein the arginine-rich region is located at the N-terminal or C-terminal end of the ORF1 molecule.

1152. The polypeptide, complex, anellosome, isolated nucleic acid, cell, composition, or method of any of embodiments 1149-1151, wherein the arginine-rich region has at least 70% (e.g., at least 70%, 75%, 80%, 85%, 90%, 95%, 96%, 97%, 98%, 99%, or 100%) sequence identity to the amino acid sequence

```
                                          (SEQ ID NO: 808)
TVVRRRGRSPRRRTPSPRRRRSQSPRRRRSQSRESQC,

                                          (SEQ ID NO: 809)
RRRYARPYRRRHIRRYRRRRRHFRRRR,

                                          (SEQ ID NO: 216)
MPYYYRRRRYNYRRPRWYGRGWIRRPFRRRFRRKRRVR,
or
                                          (SEQ ID NO: 186)
MAWGWWKRRRRWWFRKRWTRGRLRRRWPRSARRRPRRRRVRRRRRWRRGR

RKTRTYRRRRRFRRRGRK.
```

1153. The polypeptide, complex, anellosome, isolated nucleic acid, cell, composition, or method of any of embodiments 1149-1152, wherein the arginine-rich region has at least 70%, 80%, 85%, 90%, 95%, 96%, 97%, 98%, 99%, or 100% identity to an arginine-rich region sequence listed in any of Tables 20-37.

1154. The polypeptide, complex, anellosome, isolated nucleic acid, cell, composition, or method of any of the preceding embodiments, wherein the ORF1 molecule comprises a jelly-roll domain, e.g., having at least at least 30% (e.g., at least about 30, 35, 40, 50, 60, 70, 80, 90, 95, 96, 97, 98, 99, or 100%) sequence identity to the amino acid sequence of the jelly-roll domain of an ORF1 molecule described herein, e.g., a jelly-roll domain having the amino acid sequence

```
                                     (SEQ ID NO: 217)
PTYTTIPLKQWQPPYKRTCYIKGQDCLIYYSNLRLGMNSTMYEKSIVPVH

WPGGGSFSVSMLTLDALYDIHKLCRNWWTSTNQDLPLVRYKGCKITFYQS

TFTDYIVRIHTELPANSNKLTYPNTHPLMMMMSKYKHIIPSRQTRRKKKP

YTKIFVKPPPQFENKWYFATDLYKIPLLQIHCTACNLQNPFVKPDKLSNN

VTLWSLNT,
or a jelly-roll domain sequence listed in any of
Tables 20-37.
```

1155. The polypeptide, complex, anellosome, isolated nucleic acid, cell, composition, or method of any of the preceding embodiments, wherein the ORF1 molecule comprises an N22 domain, e.g., having at least 30% (e.g., at least about 30, 35, 40, 50, 60, 70, 80, 90, 95, 96, 97, 98, 99, or 100%) sequence identity to the amino acid sequence of an N22 domain of an ORF1 molecule described herein, e.g., an N22 domain having the amino acid sequence

```
                                     (SEQ ID NO: 219)
TMALTPFNEPIFTQIQYNPDRDTGEDTQLYLLSNATGTGWDPPGIPELI

LEGFPLWLIYWGFADFQKNLKKVTNIDTNYMLVAKTKFTQKPGTFYLVI

LNDTFVEGNSPYEKQPLPEDNIKWYPQVQYQLEAQNKLLQTGPFTPNIQ

GQLSDNISMFYKFYFK,
or an N22 domain sequence listed in any of Tables
20-37.
```

1156. The polypeptide, complex, anellosome, isolated nucleic acid, cell, composition, or method of any of the preceding embodiments, wherein the ORF1 molecule localizes to the nucleus of a cell.

1157. The polypeptide, complex, anellosome, isolated nucleic acid, cell, composition, or method of any of the preceding embodiments, wherein the genetic element or isolated nucleic acid molecule comprises no more than 50%, 60%, 70%, 80%, 90%, 95%, 96%, 97%, 98%, 99%, or 100% sequence identity relative to about 500, 1000, 1100, 1200, 1210, or 1219 consecutive nucleotides of a wild-type *Anellovirus* genome sequence, e.g., as described herein.

1158. The polypeptide, complex, anellosome, isolated nucleic acid, cell, composition, or method of any of the preceding embodiments, wherein the genetic element or isolated nucleic acid molecule comprises no more than 50%, 60%, 70%, 80%, 90%, 95%, 96%, 97%, 98%, 99%, or 100% sequence identity relative to about 500, 1000, 1500, 2000, 2100, 2200, 2300, 2400, 2500, 2600, 2700, 2800, 2900, 3000, 3100, 3200, 3300, 3400, 3450, 3460, 3470, 3480, 3490, 3500, 3510, 3520, 3530, 3540, 3550, 3560, 3570, or 3580 consecutive nucleotides of a wild-type *Alphatorquevirus* (e.g., a Glade 1, 2, or 3 *Alphatorquevirus*) genome sequence, e.g., as described herein.

1159. The polypeptide, complex, anellosome, isolated nucleic acid, cell, composition, or method of any of the preceding embodiments, wherein the genetic element or isolated nucleic acid molecule comprises no more than 50%, 60%, 70%, 80%, 90%, 95%, 96%, 97%, 98%, 99%, or 100% sequence identity relative to about 500, 1000, 1100, 1200, 1210, or 1219 consecutive nucleotides of a wild-type *Betatorquevirus* genome sequence, e.g., as described herein.

1160. The polypeptide, complex, anellosome, isolated nucleic acid, cell, composition, or method of any of the preceding embodiments, wherein the genetic element or isolated nucleic acid molecule comprises no more than 50%, 60%, 70%, 80%, 90%, 95%, 96%, 97%, 98%, 99%, or 100% sequence identity relative to about 500, 1000, 1500, 2000, 2100, 2200, 2300, 2400, 2500, 2600, 2700, 2800, 2900, 3000, 3100, 3120, 3130, 3140, 3141, or 3142 consecutive nucleotides of a wild-type *Gammatorquevirus* genome sequence, e.g., as described herein.

1161. The polypeptide, complex, anellosome, isolated nucleic acid, cell, composition, or method of any of the preceding embodiments, wherein the genetic element or isolated nucleic acid molecule comprises at least 50%, 60%, 70%, 80%, 90%, 95%, 96%, 97%, 98%, 99%, or 100% sequence identity relative to at least about 500, 1000, 1500, 2000, 2100, 2200, 2300, 2400, 2500, 2600, 2700, 2800, 2900, 3000, 3100, 3200, 3300, 3400, 3450, 3460, 3470, 3480, 3490, 3500, 3510, 3520, 3530, 3540, 3550, 3560, 3570, or 3580 consecutive nucleotides (e.g., about 500-3580, 1000-3580, 1500-3580, 2000-3580, or 3000-3580 consecutive nucleotides) of a wild-type *Alphatorquevirus* (e.g., a Glade 1, 2, or 3 *Alphatorquevirus*) genome sequence, e.g., as described herein.

1162. The polypeptide, complex, anellosome, isolated nucleic acid, cell, composition, or method of any of the preceding embodiments, wherein the genetic element or isolated nucleic acid molecule comprises at least 50%, 60%, 70%, 80%, 90%, 95%, 96%, 97%, 98%, 99%, or 100% sequence identity relative to at least about 500, 1000, 1100, 1200, 1210, or 1219 consecutive nucleotides (e.g., about 500-1000, 500-1100, 500-1200, 500-1219, 1000-1100, 1000-1200, or 1000-1219 consecutive nucleotides) of a wild-type *Betatorquevirus* genome sequence, e.g., as described herein.

1163. The polypeptide, complex, anellosome, isolated nucleic acid, cell, composition, or method of any of the preceding embodiments, wherein the genetic element or isolated nucleic acid molecule comprises at least 50%, 60%, 70%, 80%, 90%, 95%, 96%, 97%, 98%, 99%, or 100% sequence identity relative to at least about 500, 1000, 1500, 2000, 2100, 2200, 2300, 2400, 2500, 2600, 2700, 2800, 2900, 3000, 3100, 3120, 3130, 3140, 3141, or 3142 consecutive nucleotides (e.g., about 500-3142, 1000-3142, 1500-3142, 2000-3142, or 2500-3142 consecutive nucleotides) of a wild-type *Gammatorquevirus* genome sequence, e.g., as described herein.

1164. The polypeptide, complex, anellosome, isolated nucleic acid, cell, composition, or method of any of the preceding embodiments, wherein the genetic element or isolated nucleic acid molecule comprises no more than 50%, 60%, 70%, 80%, 90%, 95%, 96%, 97%, 98%, or 99% sequence identity relative to about 500, 1000, 1100, 1200, 1210, or 1219 consecutive nucleotides of a wild-type TTMV-LY2 genome sequence, e.g., as described herein.

1165. The polypeptide, complex, anellosome, isolated nucleic acid, cell, composition, or method of any of the preceding embodiments, wherein the genetic element or isolated nucleic acid molecule comprises no more than 50%, 60%, 70%, 80%, 90%, 95%, 96%, 97%, 98%, or 99% sequence identity relative to about 500, 1000, 1500, 2000, 2100, 2200, 2300, 2400, 2500, 2600, 2700, 2800, 2900, 3000, 3100, 3200, 3300, 3400, 3500, 3550, 3560, 3570, 3580, or 3581 consecutive nucleotides of a wild-type TTV-tth8 genome sequence, e.g., as described herein.

1166. The polypeptide, complex, anellosome, isolated nucleic acid, cell, composition, or method of any of the preceding embodiments, wherein the genetic element or isolated nucleic acid molecule comprises a deletion of at least 1578, 1579, 1580, 1590, 1600, 1650, 1700, 1750, or 2000 nucleotides relative to a wild-type *Anellovirus* genome sequence, e.g., as described herein.

1167. The polypeptide, complex, anellosome, isolated nucleic acid, cell, composition, or method of any of the preceding embodiments, wherein the genetic element or isolated nucleic acid molecule comprises a deletion of between 1 and 99, 1 and 90, 1 and 80, 1 and 70, 1 and 60, 1 and 50, 10 and 99, 10 and 90, 10 and 80, 10 and 70, 10 and 60, 10 and 50, 20 and 99, 20 and 90, 20 and 80, 20 and 70, 20 and 60, 20 and 50, 30 and 99, 30 and 90, 30 and 80, 30 and 70, 30 and 60, 30 and 50, 40 and 99, 40 and 90, 40 and 80, 40 and 70, 40 and 60, or 40 and 50 nucleotides relative to a wild-type *Anellovirus* genome sequence, e.g., as described herein.

1168. The polypeptide, complex, anellosome, isolated nucleic acid, cell, composition, or method of any of the preceding embodiments, wherein the genetic element or isolated nucleic acid molecule does not have a 100 nucleotide deletion, a 172 nucleotide deletion, or a 1577 nucleotide deletion relative to a wild-type *Anellovirus* genome sequence, e.g., as described herein.

1169. The polypeptide, complex, anellosome, isolated nucleic acid, cell, composition, or method of any of the preceding embodiments, wherein the genetic element or isolated nucleic acid molecule comprises three or more deletions relative to a wild-type *Anellovirus* genome sequence, e.g., as described herein.

1170. The polypeptide, complex, anellosome, isolated nucleic acid, cell, composition, or method of any of the preceding embodiments, wherein the genetic element or isolated nucleic acid molecule comprises a region having at least 75% (e.g., at least 75, 76, 77, 78, 79, 80, 85, 90, 91, 92, 93, 94, 95, 96, 97, 98, 99, or 100%) sequence identity to the nucleic acid sequence:

(SEQ ID NO: 160)
(i) CGCGCTGCGCGCGCCGCCCAGTAGGGGGAGCCATGC, (SEQ ID NO: 164)
(ii) GCGCT$X_1$CGCGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

-continued (SEQ ID NO: 170)
(viii) GCGCTTCGCGCGCGCGCCGGGGGGCTGCGCCCCCCC;

(SEQ ID NO: 171)
(ix) GCGCTACGCGCGCGCGCCGGGGGGCTGCGCCCCCCC;
or (SEQ ID NO: 172)
(x) GCGCTACGCGCGCGCGCCGGGGGGCTCTGCCCCCCC.

1171. The polypeptide, complex, anellosome, isolated nucleic acid, cell, composition, or method of any of the preceding embodiments, wherein the genetic element or isolated nucleic acid molecule comprises a region having at least 95% (e.g., at least 95, 96, 97, 98, 99, or 100%) sequence identity to the nucleic acid sequence:

(SEQ ID NO: 160)
(i) CGCGCTGCGCGCGCCGCCCAGTAGGGGGAGCCATGC, (SEQ ID NO: 164)
(ii) GCGCT$X_1$CGCGCGCGCGCCGGGGGGCTGCGCCCCCCC, wherein $X_1$ is selected from T, G, or A;

(SEQ ID NO: 165)
(iii) GCGCTTCGCGCGCCGCCCACTAGGGGGCGTTGCGCG;

(SEQ ID NO: 166)
(iv) GCGCTGCGCGCGCCGCCCAGTAGGGGGCGCAATGCG;

(SEQ ID NO: 167)
(v) GCGCTGCGCGCGCGGCCCCCGGGGGAGGCATTGCCT;

(SEQ ID NO: 168)
(vi) GCGCTGCGCGCGCGCGCCGGGGGGGCGCCAGCGCCC;

(SEQ ID NO: 169)
(vii) GCGCTTCGCGCGCGCGCCGGGGGGCTCCGCCCCCCC;

(SEQ ID NO: 170)
(viii) GCGCTTCGCGCGCGCGCCGGGGGGCTGCGCCCCCCC;

(SEQ ID NO: 171)
(ix) GCGCTACGCGCGCGCGCCGGGGGGCTGCGCCCCCCC;
or (SEQ ID NO: 172)
(x) GCGCTACGCGCGCGCGCCGGGGGGCTCTGCCCCCCC.

1172. The polypeptide, complex, anellosome, isolated nucleic acid, cell, composition, or method of any of the preceding embodiments, wherein the genetic element or isolated nucleic acid molecule comprises a region having at least 75% (e.g., at least 75, 76, 77, 78, 79, 80, 85, 90, 91, 92, 93, 94, 95, 96, 97, 98, 99, or 100%) sequence identity to the nucleic acid sequence (SEQ ID NO: 161)
CCGCCATCTTAAGTAGTTGAGGCGGACGGTGGCGTGAGTTCAAAGGTCAC

CATCAGCCACACCTACTCAAAATGGTGG.

1173. The polypeptide, complex, anellosome, isolated nucleic acid, cell, composition, or method of any of the preceding embodiments, wherein the genetic element or isolated nucleic acid molecule comprises a region having at least 75% (e.g., at least 75, 76, 77, 78, 79, 80, 85, 90, 91, 92, 93, 94, 95, 96, 97, 98, 99, or 100%) sequence identity to the nucleic acid sequence (SEQ ID NO: 162)
CTTAAGTAGTTGAGGCGGACGGTGGCGTGAGTTCAAAGGTCACCATCAGC

CACACCTACTCAAAATGGTGGACAATTTCTTCCGGGTCAAAGGTTACAGC

CGCCATGTTAAAACACGTGACGTATGACGTCACGGCCGCCATTTTGTGAC

ACAAGATGGCCGACTTCCTTCC.

1174. The polypeptide, complex, anellosome, isolated nucleic acid, cell, composition, or method of any of the preceding embodiments, wherein the genetic element or isolated nucleic acid molecule comprises at least 20, 25, 30, 31, 32, 33, 34, 35, or 36 consecutive nucleotides having a GC content of at least 80%.

1175. The polypeptide, complex, anellosome, isolated nucleic acid, cell, composition, or method of any of the preceding embodiments, wherein the genetic element or isolated nucleic acid molecule comprises at least 36 consecutive nucleotides having a GC content of at least 70%, 71%, 72%, 73%, 74%, 75%, 76%, 77%, 78%, 79%, 80%, or 80.6%.

1176. The polypeptide, complex, anellosome, isolated nucleic acid, cell, composition, or method of any of the preceding embodiments, wherein the genetic element or isolated nucleic acid molecule comprises at least 36 consecutive nucleotides having a GC content of at least 80%.

1177. The polypeptide, complex, anellosome, isolated nucleic acid, cell, composition, or method of any of the preceding embodiments, further comprising a nucleic acid sequence encoding an ORF1, ORF1/1, ORF1/2, ORF2, ORF2/2, ORF2/3, ORF2t/3, and/or ORF3 of an *Anellovirus*, e.g., a wild-type *Anellovirus*, e.g., as described herein.

1178. The polypeptide, complex, anellosome, isolated nucleic acid, cell, composition, or method of any of the preceding embodiments, wherein the promoter element, nucleic acid sequence encoding the effector, or protein binding sequence have at least 75% (e.g., at least 75, 76, 77, 78, 79, 80, 85, 90, 91, 92, 93, 94, 95, 96, 97, 98, 99, or 100%) sequence identity to a promoter element, nucleic acid sequence encoding an effector, or protein binding sequence, respectively, of an *Anellovirus* of any of Tables 1-18, e.g., as described herein.

1179. The polypeptide, complex, anellosome, isolated nucleic acid, cell, composition, or method of any of the preceding embodiments, wherein the genetic element or isolated nucleic acid molecule comprises a packaging region positioned 3' relative to the nucleic acid sequence encoding the effector.

1180. The polypeptide, complex, anellosome, isolated nucleic acid, cell, composition, or method of any of the preceding embodiments, wherein the genetic element or isolated nucleic acid molecule comprises a packaging region positioned 5' relative to the nucleic acid sequence encoding the effector.

1181. The polypeptide, complex, anellosome, isolated nucleic acid, cell, composition, or method of any of the preceding embodiments, wherein the genetic element or isolated nucleic acid molecule comprises a nucleic acid sequence encoding an *Anellovirus* protein having at least 75% (e.g., at least 75, 76, 77, 78, 79, 80, 85, 90, 91, 92, 93, 94, 95, 96, 97, 98, 99, or 100%) sequence identity to the amino acid sequence of an ORF1, ORF1/1, ORF1/2, ORF2, ORF2/2, ORF2/3, ORF2t/3, and/or ORF3 of an *Anellovirus* described herein.

1182. The polypeptide, complex, anellosome, isolated nucleic acid, cell, composition, or method of any of the preceding embodiments, wherein the genetic element or isolated nucleic acid molecule comprises a single-stranded DNA.

1183. The polypeptide, complex, anellosome, isolated nucleic acid, cell, composition, or method of any of the preceding embodiments, wherein the genetic element or isolated nucleic acid molecule is circular and/or integrates into the genome of a eukaryotic cell at a frequency of less than about 0.001%, 0.005%, 0.01%, 0.05%, 0.1%, 0.5%, 1%, 1.5%, or 2% of the genetic element that enters the cell.

1184. The polypeptide, complex, anellosome, isolated nucleic acid, cell, composition, or method of any of the preceding embodiments, wherein the genetic element or isolated nucleic acid has at least 75% (e.g., at least 75, 76, 77, 78, 79, 80, 85, 90, 91, 92, 93, 94, 95, 96, 97, 98, 99, or 100%) sequence identity to a wild-type *Anellovirus* sequence (e.g., a wild-type Torque Teno virus (TTV), Torque Teno mini virus (TTMV), or TTMDV sequence, e.g., a wild-type *Anellovirus* sequence, e.g., as listed in any of Tables 1, 3, 5, 7, 9, 11, 13, 15, or 17), or a portion thereof consisting of about 50, 60, 70, 80, 90, 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 consecutive nucleotides therefrom.

1185. The polypeptide, complex, anellosome, isolated nucleic acid, cell, composition, or method of any of the preceding embodiments, wherein the protein binding sequence has at least 75% (e.g., at least 75, 76, 77, 78, 79, 80, 85, 90, 91, 92, 93, 94, 95, 96, 97, 98, 99, or 100%) sequence identity to the Consensus 5' UTR sequence shown in Table 20.

1186. The polypeptide, complex, anellosome, isolated nucleic acid, cell, composition, or method of any of the preceding embodiments, wherein the protein binding sequence has at least 75% (e.g., at least 75, 76, 77, 78, 79, 80, 85, 90, 91, 92, 93, 94, 95, 96, 97, 98, 99, or 100%) sequence identity to the Consensus GC-rich sequence shown in Table 21.

1187. The polypeptide, complex, anellosome, isolated nucleic acid, cell, composition, or method of any of the preceding embodiments, wherein the protein binding sequence has at least 75% (e.g., at least 75, 76, 77, 78, 79, 80, 85, 90, 91, 92, 93, 94, 95, 96, 97, 98, 99, or 100%) sequence identity to a 5' UTR sequence shown in Table 38 and to a GC-rich sequence shown in Table 39.

1188. The polypeptide, complex, anellosome, isolated nucleic acid, cell, composition, or method of any of the preceding embodiments, wherein the genetic element or isolated nucleic acid molecule comprises a sequence having at least 85% sequence identity to the *Anellovirus* 5' UTR conserved domain of the nucleic acid sequence of Table 1, 3, 5, 7, 9, 11, 13, 15, or 17.

1189. The polypeptide, complex, anellosome, isolated nucleic acid, cell, composition, or method of any of the preceding embodiments, wherein the genetic element or isolated nucleic acid molecule comprises a sequence having at least 85% sequence identity to the *Anellovirus* GC-rich region of the nucleic acid sequence of of Table 1, 3, 5, 7, 9, 11, 13, 15, or 17.

1190. The polypeptide, complex, anellosome, isolated nucleic acid, cell, composition, or method of any of the preceding embodiments, wherein the promoter element comprises an RNA polymerase II-dependent promoter, an RNA polymerase III-dependent promoter, a PGK promoter, a CMV promoter, an EF-1α promoter, an SV40 promoter, a CAGG promoter, or a UBC promoter, TTV viral promoters, Tissue specific, U6 (pollll), minimal CMV promoter with upstream DNA binding sites for activator proteins (TetR-VP16, Ga14-VP16, dCas9-VP16, etc).

1191. The polypeptide, complex, anellosome, isolated nucleic acid, cell, composition, or method of any of the preceding embodiments, wherein the effector encodes a therapeutic agent, e.g., a therapeutic peptide or polypeptide or a therapeutic nucleic acid.

1192. The polypeptide, complex, anellosome, isolated nucleic acid, cell, composition, or method of the any of the preceding embodiments, wherein the effector comprises a regulatory nucleic acid, e.g., an miRNA, siRNA, mRNA, lncRNA, RNA, DNA, an antisense RNA, gRNA; a fluorescent tag or marker, an antigen, a peptide, a synthetic or analog peptide from a naturally-bioactive peptide, an agonist or antagonist peptide, an anti-microbial peptide, a pore-forming peptide, a bicyclic peptide, a targeting or cytotoxic peptide, a degradation or self-destruction peptide, a small molecule, an immune effector (e.g., influences susceptibility to an immune response/signal), a death protein (e.g., an inducer of apoptosis or necrosis), a non-lytic inhibitor of a tumor (e.g., an inhibitor of an oncoprotein), an epigenetic modifying agent, an epigenetic enzyme, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis effector or inhibitor, a nuclease, a protein fragment or domain, a ligand, an antibody, a receptor, or a CRISPR system or component.

1193. The polypeptide, complex, anellosome, isolated nucleic acid, cell, composition, or method of any of the preceding embodiments, wherein the anellosome is capable of replicating autonomously.

1194. The isolated nucleic acid molecule of any of the preceding embodiments, wherein the expression vector is selected from the group consisting of a plasmid, a cosmid, an artificial chromosome, a phage and a virus.

1195. An isolated cell comprising the isolated nucleic acid or anellosome of any of the preceding embodiments.

1196. The isolated cell of embodiment 195, further comprising an ORF1/1, ORF1/2, ORF2, ORF2/2, ORF2/3, ORF2t/3, and/or ORF3 of an *Anellovirus*, e.g., a wild-type *Anellovirus*, e.g., as described herein.

1197. A method of delivering an effector to a subject, comprising administering the polypeptide, complex, anellosome, isolated nucleic acid, isolated cell, or composition of any of the preceding embodiments to the subject; wherein the genetic element or isolated nucleic acid molecule encodes an effector, and wherein the effector is expressed in the subject.

1198. A method of treating a disease or disorder in a subject in need thereof, comprising administering the polypeptide, complex, anellosome, isolated nucleic acid, isolated cell, or composition of any of the preceding embodiments to the subject; wherein the genetic element or isolated nucleic acid molecule encodes a therapeutic agent, and wherein the therapeutic agent is expressed in the subject.

1199. A method of delivering an effector to a cell or population of cells ex vivo (e.g., a cell or population of cells obtained from a subject), comprising introducing the polypeptide, complex, anellosome, isolated nucleic acid, isolated cell, or composition of any of the preceding embodiments to the cell or population of cells; wherein the genetic element or isolated nucleic acid molecule encodes an effector, and wherein the effector is expressed in the cell or population of cells.

1200. The anellosome of any of the preceding embodiments, wherein the genetic element is a single-stranded DNA, and has one or both of the following properties: is circular and/or integrates into the genome of a eukaryotic cell at a frequency of less than about 0.001%, 0.005%, 0.01%, 0.05%, 0.1%, 0.5%, 1%, 1.5%, or 2% of the genetic element that enters the cell.

1201. The anellosome of any of the preceding embodiments, wherein the genetic element has at least 75% (e.g., at least 75, 76, 77, 78, 79, 80, 85, 90, 91, 92, 93, 94, 95, 96, 97, 98, 99, or 100%) sequence identity to a wild-type *Anellovirus* sequence (e.g., a wild-type Torque Teno virus (TTV), Torque Teno mini virus (TTMV), or TTMDV sequence, e.g., a wild-type *Anellovirus* sequence, e.g., as listed in any of Tables 1, 3, 5, 7, 9, 11, 13, 15, or 17).

1202. The anellosome of any of the preceding embodiments, wherein the protein binding sequence has at least 75% (e.g., at least 75, 76, 77, 78, 79, 80, 85, 90, 91, 92, 93, 94, 95, 96, 97, 98, 99, or 100%) sequence identity to the Consensus 5' UTR sequence shown in Table 38, or to the Consensus GC-rich sequence shown in Table 39, or both of the Consensus 5' UTR sequence shown in Table 38 and to the Consensus GC-rich sequence shown in Table 39.

1203. The anellosome of any of the preceding embodiments, wherein the promoter element comprises an RNA polymerase II-dependent promoter, an RNA polymerase III-dependent promoter, a PGK promoter, a CMV promoter, an EF-1a promoter, an SV40 promoter, a CAGG promoter, or a UBC promoter, TTV viral promoters, Tissue specific, U6 (pollll), minimal CMV promoter with upstream DNA binding sites for activator proteins (TetR-VP16, Ga14-VP16, dCas9-VP16, etc).

1204. The anellosome of any of the preceding embodiments, wherein the promoter element comprises a TATA box.

1205. The anellosome of any of the preceding embodiments, wherein the promoter element is endogenous to a wild-type *Anellovirus*, e.g., a wild-type *Anellovirus* sequence as listed in any of Tables 1, 3, 5, 6, 9, 11, 13, 15, or 17.

1206. The anellosome of any of the preceding embodiments, wherein the promoter element is exogenous to wild-type *Anellovirus*, e.g., a wild-type *Anellovirus* sequence as listed in any of Tables 1, 3, 5, 6, 9, 11, 13, 15, or 17.

1207. The anellosome of any of the preceding embodiments, wherein the effector encodes a therapeutic agent, e.g., a therapeutic peptide or polypeptide or a therapeutic nucleic acid.

1208. The anellosome of any of the preceding embodiments, wherein the effector comprises a regulatory nucleic acid, e.g., an miRNA, siRNA, mRNA, lncRNA, RNA, DNA, an antisense RNA, gRNA; a fluorescent tag or marker, an antigen, a peptide, a synthetic or analog peptide from a naturally-bioactive peptide, an agonist or antagonist peptide, an anti-microbial peptide, a pore-forming peptide, a bicyclic peptide, a targeting or cytotoxic peptide, a degradation or self-destruction peptide, a small molecule, an immune effector (e.g., influences susceptibility to an immune response/signal), a death protein (e.g., an inducer of apoptosis or necrosis), a non-lytic inhibitor of a tumor (e.g., an inhibitor of an oncoprotein), an epigenetic modifying agent, an epigenetic enzyme, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis effector or inhibitor, a nuclease, a protein fragment or domain, a ligand, an antibody, a receptor, or a CRISPR system or component.

1209. The anellosome of any of the preceding embodiments, wherein the effector comprises a miRNA.

1210. The anellosome of any of the preceding embodiments, wherein the effector, e.g., miRNA, targets a host gene, e.g., modulates expression of the gene, e.g., increases or decreases expression of the gene.

1211. The anellosome of any of the preceding embodiments, wherein the effector comprises an miRNA, and decreases expression of a host gene.

1212. The anellosome of any of the preceding embodiments, wherein the effector comprises a nucleic acid sequence about 20-200, 30-180, 40-160, 50-140, or 60-120 nucleotides in length.

1213. The anellosome of any of the preceding embodiments, wherein the nucleic acid sequence encoding the effector is about 20-200, 30-180, 40-160, 50-140, or 60-120 nucleotides in length.

1214. The anellosome of any of the preceding embodiments, wherein the sequence encoding the effector has a size of at least about 100 nucleotides.

1215. The anellosome of any of the preceding embodiments, wherein the sequence encoding the effector has a size of about 100 to about 5000 nucleotides.

1216. The anellosome of any of the preceding embodiments, wherein the sequence encoding the effector has a size of about 100-200, 200-300, 300-400, 400-500, 500-600, 600-700, 700-800, 800-900, 900-1000, 1000-1500, or 1500-2000 nucleotides.

1217. The anellosome of any of the preceding embodiments, wherein the sequence encoding the effector is situated at, within, or adjacent to (e.g., 5' or 3' to) one or more of the ORF1 locus (e.g., at the C-terminus of the ORF1 locus), the miRNA locus, the 5' noncoding region upstream of the TATA box, the 5' UTR, the 3' noncoding region downstream of the poly-A region, or a noncoding region upstream of the GC-rich region of the genetic element.

1218. The anellosome of embodiment 1217, wherein the sequence encoding the effector is located between the poly-A region and the GC-rich region of the genetic element.

1219. The anellosome of any of the preceding embodiments, wherein the protein binding sequence comprises a nucleic acid sequence having at least 75% (e.g., at least 75, 76, 77, 78, 79, 80, 90, 91, 92, 93, 94, 95, 96, 97, 98, 99, or 100%) sequence identity to the 5' UTR conserved domain or the GC-rich domain of a wild-type *Anellovirus*, e.g., a wild-type *Anellovirus* sequence as listed in any of Tables 1, 3, 5, 6, 9, 11, 13, 15, or 17.

1220. The anellosome of any of the preceding embodiments, wherein the genetic element, e.g., protein binding sequence of the genetic element, comprises least about 75% (e.g., at least 75%, 80%, 85%, 90%, 95%, 96%, 97%, 98%, 99%, or 100%) identity to:

(i) the Consensus 5' UTR nucleic acid sequence shown in Table 38;

(ii) the exemplary TTV 5' UTR nucleic acid sequence shown in Table 38;

(iii) the TTV-CT30F 5' UTR nucleic acid sequence shown in Table 38;

(iv) the TTV-HD23a 5' UTR nucleic acid sequence shown in Table 38;

(v) the TTV-JA20 5' UTR nucleic acid sequence shown in Table 38;

(vi) the TTV-TJN02 5' UTR nucleic acid sequence shown in Table 38;

(vii) the TTV-tth8 5' UTR nucleic acid sequence shown in Table 38;

(viii) the Consensus GC-rich region shown in Table 39;

(ix) the exemplary TTV GC-rich region shown in Table 39;

(x) the TTV-CT30F GC-rich region shown in Table 39;

(xi) the TTV-JA20 GC-rich region shown in Table 39;

(xii) the TTV-TJN02 GC-rich region shown in Table 39;

(xiii) the TTV-HD23a GC-rich region shown in Table 39; or (xiv) the TTV-tth8 GC-rich region shown in Table 39.

1221. The anellosome of any of the preceding embodiments, wherein the proteinaceous exterior comprises an exterior protein capable of specifically binding to the protein binding sequence.

1222. The anellosome of any of the preceding embodiments, wherein the proteinaceous exterior comprises one or more of the following: one or more glycosylated proteins, a hydrophilic DNA-binding region, a threonine-rich region, a glutamine-rich region, a N-terminal polyarginine sequence, a variable region, a C-terminal polyglutamine/glutamate sequence, and one or more disulfide bridges.

1223. The anellosome of any of the preceding embodiments, wherein the proteinaceous exterior comprises one or more of the following characteristics: an icosahedral symmetry, recognizes and/or binds a molecule that interacts with one or more host cell molecules to mediate entry into the host cell, lacks lipid molecules, lacks carbohydrates, is pH and temperature stable, is detergent resistant, and is substantially non-immunogenic or substantially non-pathogenic in a host.

1224. The anellosome of any of the preceding embodiments, wherein the proteinaceous exterior comprises at least one functional domain that provides one or more functions, e.g., species and/or tissue and/or cell selectivity, genetic element binding and/or packaging, immune evasion (substantial non-immunogenicity and/or tolerance), pharmacokinetics, endocytosis and/or cell attachment, nuclear entry, intracellular modulation and localization, exocytosis modulation, propagation, and nucleic acid protection.

1225. The anellosome of any of the preceding embodiments, wherein the portions of the genetic element excluding the effector have a combined size of about 2.5-5 kb (e.g., about 2.8-4 kb, about 2.8-3.2 kb, about 3.6-3.9 kb, or about 2.8-2.9 kb), less than about 5 kb (e.g., less than about 2.9 kb, 3.2 kb, 3.6 kb, 3.9 kb, or 4 kb), or at least 100 nucleotides (e.g., at least 1 kb).

1226. The anellosome of any of the preceding embodiments, wherein the genetic element is single-stranded.

1227. The anellosome of any of the preceding embodiments, wherein the genetic element is circular.

1228. The anellosome of any of the preceding embodiments, wherein the genetic element is DNA.

1229. The anellosome of any of the preceding embodiments, wherein the genetic element is a negative strand DNA.

1230. The anellosome of any of the preceding embodiments, wherein the genetic element comprises an episome.

1231. The anellosome of any of the preceding embodiments, wherein the anellosome has a lipid content of less than 10%, 5%, 2%, or 1% by weight, e.g., does not comprise a lipid bilayer.

1232. The anellosome of any of the preceding embodiments, wherein the anellosome is resistant to degradation by a detergent (e.g., a mild detergent, e.g., a biliary salt, e.g., sodium deoxycholate) relative to a viral particle comprising an external lipid bilayer, e.g., a retrovirus.

1233. The anellosome of embodiment 1232, wherein at least about 50% (e.g., at least about 50%, 60%, 70%, 80%, 85%, 90%, 95%, 96%, 97%, 98%, 99%, 99.5%, or 99.9%) of the anellosome is not degraded after incubation the detergent (e.g., 0.5% by weight of the detergent) for 30 minutes at 37° C.

1234. The anellosome of any of the preceding embodiments, wherein the genetic element comprises a deletion of at least one element, e.g., an element as listed in any of Tables 1, 3, 5, 7, 9, 11, 13, 15, or 17, relative to a wild-type *Anellovirus* sequence, e.g., a wild-type TTV sequence or a wild-type TTMV sequence.

1235. The anellosome of embodiment 1234, wherein the genetic element comprises a deletion comprising a nucleic acid sequence corresponding to:

(i) nucleotides 3436-3607 of a TTV-tth8 sequence, e.g., the nucleic acid sequence shown in Table 5;

(ii) nucleotides 574-1371 and/or nucleotides 1432-2210 of a TTMV-LY2 sequence, e.g., the nucleic acid sequence shown in Table 15;

(iii) nucleotides 1372-1431 of a TTMV-LY2 sequence, e.g., the nucleic acid sequence shown in Table 15; or (iv) nucleotides 2610-2809 of a TTMV-LY2 sequence, e.g., the nucleic acid sequence shown in Table 15.

1236. The anellosome of any of the preceding embodiments, wherein the genetic element comprises at least 72 nucleotides (e.g., at least 73, 74, 75, etc. nt, optionally less than the full length of the genome) of a wild-type *Anellovirus* sequence, e.g., a wild-type Torque Teno virus (TTV), Torque Teno mini virus (TTMV), or TTMDV sequence, e.g., a sequence as listed in any of Tables 1, 3, 5, 7, 9, 11, 13, 15, or 17.

1237. The anellosome of any of the preceding embodiments, wherein the genetic element further comprises one or more of the following sequences: a sequence that encodes one or more miRNAs, a sequence that encodes one or more replication proteins, a sequence that encodes an exogenous gene, a sequence that encodes a therapeutic, a regulatory sequence (e.g., a promoter, enhancer), a sequence that encodes one or more regulatory sequences that targets endogenous genes (siRNA, lncRNAs, shRNA), a sequence that encodes a therapeutic mRNA or protein, and a sequence that encodes a cytolytic/cytotoxic RNA or protein.

1238. The anellosome of any of the preceding embodiments, wherein the anellosome further comprises a second genetic element, e.g., a second genetic element enclosed within the proteinaceous exterior.

1239. The anellosome of embodiment 1238, wherein the second genetic element comprises a protein binding sequence, e.g., an exterior protein binding sequence, e.g., a packaging signal, e.g., a 5' UTR conserved domain or GC-rich region, e.g., as described herein.

1240. The anellosome of any of the preceding embodiments, wherein the anellosome does not detectably infect bacterial cells, e.g., infects less than 1%, 0.5%, 0.1%, or 0.01% of bacterial cells.

1241. The anellosome of any of the preceding embodiments, wherein the anellosome is capable of infecting mammalian cells, e.g., human cells, e.g., immune cells, liver cells, epithelial cells, e.g., in vitro.

1242. The anellosome of any of the preceding embodiments, wherein the genetic element integrates at a frequency of less than 10%, 8%, 6%, 4%, 3%, 2%, 1%, 0.5%, 0.2%, 0.1% of the anellosomes that enters the cell, e.g., wherein the anellosome is non-integrating.

1243. The anellosome of any of the preceding embodiments, wherein the genetic element is capable of replicating, e.g., capable of generating at least $10^2$, $2\times10^2$, 5x10, $10^3$, $2\times10^3$, $5\times10^3$, or $10^4$ genomic equivalents of the genetic element per cell, e.g., as measured by a quantitative PCR assay.

1244. The anellosome of any of the preceding embodiments, wherein the genetic element is capable of replicating, e.g., capable of generating at least $10^2$, $2\times10^2$, $5\times10^2$, $10^3$, $2\times10^3$, $5\times10^3$, or $10^4$ more genomic equivalents of the genetic element in a cell, e.g., as measured by a quantitative PCR assay, than were present in the anellosome prior to delivery of the genetic element into the cell.

1245. The anellosome of any of the preceding embodiments, wherein the genetic element is not capable of replicating, e.g., wherein the genetic element is altered at a replication origin or lacks a replication origin.

1246. The anellosome of any of the preceding embodiments, wherein the genetic element is not capable of self-replicating, e.g., capable of being replicated without being integrated into a host cell genome.

1247. The anellosome of any of the preceding embodiments, wherein the anellosome is substantially non-pathogenic, e.g., does not induce a detectable deleterious symptom in a subject (e.g., elevated cell death or toxicity, e.g., relative to a subject not exposed to the anellosome).

1248. The anellosome of any of the preceding embodiments, wherein the anellosome is substantially non-immunogenic, e.g., does not induce a detectable and/or unwanted immune response, e.g., as detected according to the method described in Example 4.

1249. The anellosome of embodiment 1248, wherein the substantially non-immunogenic anellosome has an efficacy in a subject that is a least about 10%, 20%, 30%, 40%, 50%, 60%, 70%, 80%, 90%, 95%, or 100% of the efficacy in a reference subject lacking an immune response.

1250. The anellosome of embodiment 1248 or 1249, wherein the immune response comprises one or more of an antibody specific to the anellosome or a portion thereof, or a product encoded by a nucleic acid thereof; a cellular response (e.g., an immune effector cell (e.g., T cell- or NK cell) response) against the anellosome or cells comprising the anellosome; or macrophage engulfment of the anellosome or cells comprising the anellosome.

1251. The anellosome of any of the preceding embodiments, wherein the anellosome is less immunogenic than an AAV, elicits an immune response below that detected for a comparable quantity of AAV, e.g., as measured by an assay described herein, induces an antibody prevalence of less than 70% (e.g., less than about 60%, 50%, 40%, 30%, 20%, or 10% antibody prevalence) as measured by an assay described herein, or is substantially non-immunogenic.

1252. The anellosome of any of the preceding embodiments, wherein a population of at least 1000 of the anellosomes is capable of delivering at least 100 copies of the genetic element into one or more of the eukaryotic cells.

1253. The anellosome of any of the preceding embodiments, wherein a population of the anellosomes is capable of delivering the genetic element into at least 10%, 20%, 30%, 40%, 50%, 60%, 70%, 80%, 90%, 95%, 99%, or more of a population of the eukaryotic cells.

1254. The anellosome of any of the preceding embodiments, wherein a population of the anellosomes is capable of delivering at least 1, 2, 5, 10, 20, 50, 100, 200, 500, 1000, 2000, 5000, 8,000, $1\times10^4$, $1\times10^5$, $1\times10^6$, $1\times10^7$ or greater copies of the genetic element per cell to a population of the eukaryotic cells.

1255. The anellosome of any of the preceding embodiments, wherein a population of the anellosomes is capable of delivering $1\times10^4$-$1\times10^5$, $1\times10^4$-$1\times10^6$, $1\times10^4$-$1\times10^7$, $1\times10^5$-$1\times10^6$, $1\times10^5$-$1\times10^7$, or $1\times10^6$-$1\times10^7$ copies of the genetic element per cell to a population of the eukaryotic cells.

1256. The anellosome of any of the preceding embodiments, wherein the anellosome is present after at least two passages.

1257. The anellosome of any of the preceding embodiments, wherein the anellosome was produced by a process comprising at least two passages.

1258. The anellosome of any of the preceding embodiments, wherein the anellosome selectively delivers the effector to, or is present at higher levels in (e.g., preferentially accumulates in), a desired cell type, tissue, or organ (e.g., bone marrow, blood, heart, GI, skin, photoreceptors in the retina, epithelial linings, or pancreas).

1259. The anellosome of any of the preceding embodiments, wherein the eukaryotic cell is a mammalian cell, e.g., a human cell.

1260. The anellosome of any of the preceding embodiments, wherein the anellosome, or copies thereof, are detectable in a cell 24 hours (e.g., 1 day, 2 days, 3 days, 4 days, 5 days, 6 days, 1 week, 2 weeks, 3 weeks, 4 weeks, 30 days, or 1 month) after delivery into the cell.

1261. The anellosome of any of the preceding embodiments, wherein the anellosome is produced in the cell pellet and the supernatant at at least about $10^8$-fold (e.g., about $10^5$-fold, $10^6$-fold, $10^7$-fold, $10^8$-fold, $10^9$-fold, or $10^{10}$-fold) genomic equivalents/mL, e.g., relative to the quantity of the anellosome used to infect the cells, after 3-4 days post infection, e.g., using an infectivity assay, e.g., an assay according to Example 7.

1262. A composition comprising the anellosome of any of the preceding embodiments.

1263. A pharmaceutical composition comprising the anellosome of any of the preceding embodiments, and a pharmaceutically acceptable carrier or excipient.

1264. The composition or pharmaceutical composition of embodiment 1262 or 1263, which comprises at least 50%, 60%, 70%, 80%, 90%, 95%, 96%, 97%, 98%, 99%, or more anellosomes, e.g., synthetic anellosomes.

1265. The composition or pharmaceutical composition of any of embodiments 1262-1264, which comprises at least $10^3$, $10^4$, $10^5$, $10^6$, $10^7$, $10^8$, or $10^9$ synthetic anellosomes.

1266. The composition or pharmaceutical composition of any of embodiments 1262-1265, having one or more of the following characteristics:

a) the pharmaceutical composition meets a pharmaceutical or good manufacturing practices (GMP) standard;

b) the pharmaceutical composition was made according to good manufacturing practices (GMP);

c) the pharmaceutical composition has a pathogen level below a predetermined reference value, e.g., is substantially free of pathogens;

d) the pharmaceutical composition has a contaminant level below a predetermined reference value, e.g., is substantially free of contaminants;

e) the pharmaceutical composition has a predetermined level of non-infectious particles or a predetermined ratio of particles:infectious units (e.g., <300:1, <200:1, <100:1, or <50:1), or f) the pharmaceutical composition has low immunogenicity or is substantially non-immunogenic, e.g., as described herein.

1267. The composition or pharmaceutical composition of any of embodiments 1262-1266, wherein the pharmaceutical composition has a contaminant level below a predetermined reference value, e.g., is substantially free of contaminants.

1268. The composition or pharmaceutical composition of embodiment 1267, wherein the contaminant is selected from the group consisting of: *mycoplasma*, endotoxin, host cell nucleic acids (e.g., host cell DNA and/or host cell RNA), animal-derived process impurities (e.g., serum albumin or trypsin), replication-competent agents (RCA), e.g., replication-competent virus or unwanted anellosomes (e.g., an anellosome other than the desired anellosome, e.g., a synthetic anellosome as described herein), free viral capsid protein, adventitious agents, and aggregates.

1269. The composition or pharmaceutical composition of embodiment 1268, wherein the contaminant is host cell DNA and the threshold amount is about 10 ng of host cell DNA per dose of the pharmaceutical composition.

1270. The composition or pharmaceutical composition of any of embodiments 1262-1269, wherein the pharmaceutical composition comprises less than 10% (e.g., less than about 10%, 5%, 4%, 3%, 2%, 1%, 0.5%, or 0.1%) contaminant by weight.

1271. Use of the anellosome, composition, or pharmaceutical composition of any of the preceding embodiments for treating a disease or disorder (e.g., as described herein) in a subject.

1272. The anellosome, composition, or pharmaceutical composition of any of the preceding embodiments for use in treating a disease or disorder (e.g., as described herein) in a subject.

1273. A method of treating a disease or disorder (e.g., as described herein) in a subject, the method comprising administering the anellosome (e.g., a synthetic anellosome) or the pharmaceutical composition of any of the preceding embodiments to the subject.

1274. A method of modulating, e.g., enhancing or inhibiting, a biological function (e.g., as described herein) in a subject, the method comprising administering the anellosome (e.g., a synthetic anellosome) or the pharmaceutical composition of any of the preceding embodiments to the subject.

1275. The method of any of embodiments 1273-1274, wherein the anellosome does not comprise an exogenous effector.

1276. The method of any of embodiments 1273-1275, wherein the anellosome comprises a wild-type wild-type *Anellovirus*, e.g., as described herein.

1277. The method of any of embodiments 1273-1276, wherein the administration of the anellosome, e.g., synthetic anellosome, results in delivery of the genetic element into at least 10%, 20%, 30%, 40%, 50%, 60%, 70%, 80%, 90%, 95%, 99%, or more of a population of target cells in the subject.

1278. The method of any of embodiments 1273-1277, wherein the administration of the anellosome, e.g., synthetic anellosome, results in delivery of the effector into at least 10%, 20%, 30%, 40%, 50%, 60%, 70%, 80%, 90%, 95%, 99%, or more of a population of target cells in the subject.

1279. The method of embodiment 1277 or 1278, wherein the target cells comprise mammalian cells, e.g., human cells, e.g., immune cells, liver cells, lung epithelial cells, e.g., in vitro.

1280. The method of any of embodiments 1277-1279, wherein the target cells are present in the liver or lung.

1281. The method of any of embodiments 1277-1280, wherein the target cells into which the genetic element is delivered each receive at least 10, 50, 100, 500, 1000, 10,000, 50,000, 100,000, or more copies of the genetic element.

1282. The method of any of embodiments 1273-1281, wherein the effector comprises a miRNA and wherein the miRNA reduces the level of a target protein or RNA in a cell or in a population of cells, e.g., into which the anellosome is delivered, e.g., by at least 10%, 20%, 30%, 40%, or 50%.

1283. A method of delivering an anellosome, e.g., a synthetic anellosome, to a cell, comprising contacting the anellosome of any of the preceding embodiments with a cell, e.g., a eukaryotic cell, e.g., a mammalian cell.

1284. The method of embodiment 1283, further comprising contacting a helper virus with the cell, wherein the helper virus comprises a polynucleotide, e.g., a polynucleotide encoding an exterior protein, e.g., an exterior protein capable of binding to the exterior protein binding sequence and, optionally, a lipid envelope.

1285. The method of embodiment 1284, wherein the helper virus is contacted with the cell prior to, concurrently with, or after contacting the anellosome with the cell.

1286. The method of embodiment 1283, further comprising contacting a helper polynucleotide with the cell.

1287. The method of embodiment 1286, wherein the helper polynucleotide comprises a sequence polynucleotide encoding an exterior protein, e.g., an exterior protein capable of binding to the exterior protein binding sequence and a lipid envelope.

1288. The method of embodiment 1286, wherein the helper polynucleotide is an RNA (e.g., mRNA), DNA, plasmid, viral polynucleotide, or any combination thereof.

1289. The method of any of embodiments 1286-1288, wherein the helper polynucleotide is contacted with the cell prior to, concurrently with, or after contacting the anellosome with the cell.

1290. The method of any of embodiments 1283-1289, further comprising contacting a helper protein (e.g., a growth factor) with the cell.

1291. The method of embodiment 1290, wherein the helper protein comprises a viral replication protein or a capsid protein.

1292. A host cell comprising the anellosome of any of the preceding embodiments.

1293. A nucleic acid molecule comprising a promoter element, a sequence encoding an effector (e.g., a payload), and an exterior protein binding sequence, wherein the nucleic acid molecule is a single-stranded DNA, and wherein the nucleic acid molecule is circular and/or integrates at a frequency of less than about 0.001%, 0.005%, 0.01%, 0.05%, 0.1%, 0.5%, 1%, 1.5%, or 2% of the nucleic acid molecule that enters a cell;

wherein the effector does not originate from TTV and is not an SV40-miR-S1;

wherein the nucleic acid molecule does not comprise the polynucleotide sequence of TTMV-LY;

wherein the promoter element is capable of directing expression of the effector in a eukaryotic cell.

1294. A genetic element comprising:

(i) a promoter element and a sequence encoding an effector, e.g., a payload, optionally wherein the effector is exogenous relative to a wild-type *Anellovirus* sequence;

(ii) at least 72 contiguous nucleotides (e.g., at least 72, 73, 74, 75, 76, 77, 78, 79, 80, 90, 100, or 150 nucleotides) having at least 75% sequence identity to a wild-type *Anellovirus* sequence; or at least 100 contiguous nucleotides having at least 72% (e.g., at least 72, 73, 74, 75, 76, 77, 78, 79, 80, 90, 91, 92, 93, 94, 95, 96, 97, 98, 99, or 100%) sequence identity to a wild-type *Anellovirus* sequence; and (iii) a protein binding sequence, e.g., an exterior protein binding sequence, and wherein the nucleic acid construct is a single-stranded DNA; and wherein the nucleic acid construct is circular and/or integrates at a frequency of less than about 0.001%, 0.005%, 0.01%, 0.05%, 0.1%, 0.5%, 1%, 1.5%, or 2% of the genetic element that enters a cell.

1295. A method of manufacturing an anellosome composition, comprising:

a) providing a host cell comprising one or more nucleic acid molecules encoding the components of an anellosome, e.g., a synthetic anellosome described herein, e.g., wherein the anellosome comprises a proteinaceous exterior and a genetic element, e.g., a genetic element comprising a promoter element, a sequence encoding an effector, (e.g., an endogenous or exogenous effector), and a protein binding sequence (e.g., an exterior protein binding sequence, e.g., a packaging signal);

b) producing an anellosome from the host cell, thereby making an anellosome; and c) formulating the anellosomes, e.g., as a pharmaceutical composition suitable for administration to a subject.

1296. A method of manufacturing a synthetic anellosome composition, comprising:

a) providing a plurality of anellosomes, compositions, or pharmaceutical compositions according to any of the preceding embodiments;

b) optionally evaluating the plurality for one or more of: a contaminant described herein, an optical density measurement (e.g., OD 260), particle number (e.g., by HPLC), infectivity (e.g., particle:infectious unit ratio, e.g., as determined by fluorescence and/or ELISA); and c) formulating the plurality of anellosomes, e.g., as a pharmaceutical composition suitable for administration to a subject, e.g., if one or more of the paramaters of (b) meet a specified threshold.

1297. The method of embodiment 1296, wherein the anellosome composition comprises at least $10^5$, $10^6$, $10^7$, $10^8$, $10^9$, $10^{10}$, 10", $10^{12}$, 10", 10', or $10^{15}$ anellosomes, or wherein the anellosome composition comprises at least $10^5$, $10^6$, $10^7$, $10^8$, $10^9$, $10^{10}$, 10", $10^{12}$, 10", 10', or $10^{15}$ anellosome genomes per mL.

1298. The method of embodiment 1296 or 1297, wherein the anellosome composition comprises at least 10 ml, 20 ml, 50 ml, 100 ml, 200 ml, 500 ml, 1 L, 2 L, 5 L, 10 L, 20 L, or 50 L.

1299. A reaction mixture comprising the anellosome of any of the preceding embodiments and a helper virus, wherein the helper virus comprises a polynucleotide, e.g., a polynucleotide encoding an exterior protein, e.g., an exterior protein capable of binding to the exterior protein binding sequence and, optionally, a lipid envelope.

1300. A reaction mixture comprising the anellosome of any of the preceding embodiments and a second nucleic acid sequence encoding one or more of an amino acid sequence chosen from ORF2, ORF2/2, ORF2/3, ORF2t/3, ORF1, ORF1/1, or ORF1/2 of any of Tables 2, 4, 6, 8, 10, 12, 14, 16, or 18, or an amino acid sequence having at least 75% (e.g., 75%, 80%, 85%, 90%, 95%, 96%, 97%, 98%, 99%, or 100%) sequence identity thereto.

1301. The reaction mixture of embodiment 1300, wherein the second nucleic acid sequence is part of the genetic element.

1302. The reaction mixture of embodiment 1301, wherein the second nucleic acid sequence is not part of the genetic element, e.g., the second nucleic acid sequence is comprised by a helper cell or helper virus.

1303. A synthetic anellosome comprising:

a genetic element comprising (i) a sequence encoding a non-pathogenic exterior protein, (ii) an exterior protein binding sequence that binds the genetic element to the non-pathogenic exterior protein, and (iii) a sequence encoding an effector, e.g., a regulatory nucleic acid; and a proteinaceous exterior that is associated with, e.g., envelops or encloses, the genetic element.

1304. A pharmaceutical composition comprising
- a) an anellosome comprising:
  - a genetic element comprising (i) a sequence encoding a non-pathogenic exterior protein, (ii) an exterior protein binding sequence that binds the genetic element to the non-pathogenic exterior protein, and (iii) a sequence encoding an effector, e.g., a regulatory nucleic acid; and a proteinaceous exterior that is associated with, e.g., envelops or encloses, the genetic element; and
- b) a pharmaceutical excipient.

1305. A pharmaceutical composition comprising
- a) at least $10^3$, $10^4$, $10^5$, $10^6$, $10^7$, $10^8$, or $10^9$ anellosomes (e.g., synthetic anellosomes described herein) comprising:
  - a genetic element comprising (i) a sequence encoding a non-pathogenic exterior protein, (ii) an exterior protein binding sequence that binds the genetic element to the non-pathogenic exterior protein, and (iii) a sequence encoding an effector, e.g., a regulatory nucleic acid; and a proteinaceous exterior that is associated with, e.g., envelops or encloses, the genetic element;
- b) a pharmaceutical excipient, and, optionally,
- c) less than a pre-determined amount of: *mycoplasma*, endotoxin, host cell nucleic acids (e.g., host cell DNA and/or host cell RNA), animal-derived process impurities (e.g., serum albumin or trypsin), replication-competent agents (RCA), e.g., replication-competent virus or unwanted anellosomes, free viral capsid protein, adventitious agents, endogenous agents, and/or aggregates.

1306. The anellosome or composition of any one of the previous embodiments, further comprising at least one of the following characteristics: the genetic element is a single-stranded DNA; the genetic element is circular; the anellosome is non-integrating; the anellosome has a sequence, structure, and/or function based on an *anellovirus* or other non-pathogenic virus, and the anellosome is non-pathogenic.

1307. The anellosome or composition of any one of the previous embodiments, wherein the proteinaceous exterior comprises the non-pathogenic exterior protein.

1308. The anellosome or composition of any one of the previous embodiments, wherein the proteinaceous exterior comprises one or more of the following: one or more glycosylated proteins, a hydrophilic DNA-binding region, an arginine-rich region, a threonine-rich region, a glutamine-rich region, a N-terminal polyarginine sequence, a variable region, a C-terminal polyglutamine/glutamate sequence, and one or more disulfide bridges.

1309. The anellosome or composition of any one of the previous embodiments, wherein the proteinaceous exterior comprises one or more of the following characteristics: an icosahedral symmetry, recognizes and/or binds a molecule that interacts with one or more host cell molecules to mediate entry into the host cell, lacks lipid molecules, lacks carbohydrates, comprises one or more desired carbohydrates (e.g., glycosylations), is pH and temperature stable, is detergent resistant, and is non-immunogenic or non-pathogenic in a host.

1310. The anellosome or composition of any one of the previous embodiments, wherein the sequence encoding the non-pathogenic exterior protein comprise a sequence at least 70%, 80%, 85%, 90%, 95%, 96%, 97%, 98%, 99% identical to one or more sequences or a fragment thereof listed in Table 19.

1311. The anellosome or composition of any one of the previous embodiments, wherein the non-pathogenic exterior protein comprises at least one functional domain that provides one or more functions, e.g., species and/or tissue and/or cell tropism, viral genome binding and/or packaging, immune evasion (non-immunogenicity and/or tolerance), pharmacokinetics, endocytosis and/or cell attachment, nuclear entry, intracellular modulation and localization, exocytosis modulation, propagation, and nucleic acid protection.

1312. The anellosome or composition of any one of the previous embodiments, wherein the effector comprises a regulatory nucleic acid, e.g., an miRNA, siRNA, mRNA, lncRNA, RNA, DNA, an antisense RNA, gRNA; a therapeutic, e.g., fluorescent tag or marker, antigen, peptide therapeutic, synthetic or analog peptide from naturally-bioactive peptide, agonist or antagonist peptide, anti-microbial peptide, pore-forming peptide, a bicyclic peptide, a targeting or cytotoxic peptide, a degradation or self-destruction peptide, and degradation or self-destruction peptides, small molecule, immune effector (e.g., influences susceptibility to an immune response/signal), a death protein (e.g., an inducer of apoptosis or necrosis), a non-lytic inhibitor of a tumor (e.g., an inhibitor of an oncoprotein), an epigenetic modifying agent, epigenetic enzyme, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis effector or inhibitor, a nuclease, a protein fragment or domain, a ligand or a receptor, and a CRISPR system or component.

1313. The anellosome or composition of any one of the previous embodiments, wherein the effector comprises a sequence having at least 70%, 80%, 85%, 90%, 95%, 96%, 97%, 98%, 99%, or 100% identity to one or more of the miRNA sequences listed in Table 40.

1314. The anellosome or composition of the previous embodiment, wherein the effector, e.g., miRNA, targets a host gene, e.g., modulates expression of the gene.

1315. The anellosome or composition of the previous embodiment, wherein the miRNA comprises a sequence having at least 70%, 80%, 85%, 90%, 95%, 96%, 97%, 98%, 99%, or 100% identity to one or more of the miRNA sequences listed in Table 40.

1316. The anellosome or composition of any one of the previous embodiments, wherein the genetic element further comprises one or more of the following sequences: a sequence that encodes one or more miRNAs, a sequence that encodes one or more replication proteins, a sequence that encodes an exogenous gene, a sequence that encodes a therapeutic, a regulatory sequence (e.g., a promoter, enhancer), a sequence that encodes one or more regulatory sequences that targets endogenous genes (siRNA, lncRNAs, shRNA), a sequence that encodes a therapeutic mRNA or protein, and a sequence that encodes a cytolytic/cytotoxic RNA or protein.

1317. The anellosome or composition of any one of the previous embodiments, wherein the genetic element has one or more of the following characteristics: is non-integrating with a host cell's genome, is an episomal nucleic acid, is a single stranded DNA, is about 1 to 10 kb, exists within the nucleus of the cell, is capable of being bound by endogenous proteins, and produces a microRNA that targets host genes.

1318. The anellosome or composition of any one of the previous embodiments, wherein the genetic element comprises at least one viral sequence or at least 70%, 80%, 85%, 90%, 95%, 96%, 97%, 98%, 99% identity to one or more sequences listed in Table 23, or a fragment thereof (e.g., a fragment encoding an an ORF1/1, ORF1/2, ORF2, ORF2/2, ORF2/3, ORF2t/3, and/or ORF3 molecule, and/or a fragment comprising one or more of a TATA box, cap site, transcriptional start site, 5' UTR, open reading frame (ORF), poly(A) signal, or GC-rich region).

1319. The anellosome or composition of the previous embodiment, wherein the viral sequence is from at least one of a single stranded DNA virus (e.g., *Anellovirus*, Bidnavirus, Circovirus, Geminivirus, Genomovirus, Inovirus, Microvirus, Nanovirus, Parvovirus, and Spiravirus), a double stranded DNA virus (e.g., Adenovirus, Ampullavirus, Ascovirus, Asfarvirus, Baculovirus, Fusellovirus, Globulovirus, Guttavirus, Hytrosavirus, Herpesvirus, Iridovirus, Lipothrixvirus, Nimavirus, and Poxvirus), a RNA virus (e.g., Alphavirus, Furovirus, Hepatitis virus, Hordeivirus, Tobamovirus, Tobravirus, Tricornavirus, Rubivirus, Birnavirus, Cystovirus, Partitivirus, and Reovirus).

1320. The anellosome or composition of the previous embodiment, wherein the viral sequence is from one or more non-*anelloviruses*, e.g., adenovirus, herpes virus, pox virus, vaccinia virus, SV40, papilloma virus, an RNA virus such as a retrovirus, e.g., *lenti* virus, a single-stranded RNA virus, e.g., hepatitis virus, or a double-stranded RNA virus e.g., rotavirus.

1321. The anellosome or composition of any one of the previous embodiments, wherein the protein binding sequence interacts with the arginine-rich region of the proteinaceous exterior.

1322. The anellosome or composition of any one of the previous embodiments, wherein the anellosome is capable of replicating in a mammalian cell, e.g., human cell.

1323. The anellosome or composition of the previous embodiment, wherein the anellosome is non-pathogenic and/or non-integrating in a host cell.

1324. The anellosome or composition of any one of the previous embodiments, wherein the anellosome is non-immunogenic in a host.

1325. The anellosome or composition of any one of the previous embodiments, wherein the anellosome inhibits/enhances one or more viral properties, e.g., selectivity, e.g., infectivity, e.g., immunosuppression/activation, in a host or host cell.

1326. The anellosome or composition of the previous embodiment, wherein the anellosome is in an amount sufficient to modulate (e.g., phenotype, virus levels, gene expression, compete with other viruses, disease state, etc. at least about 5%, 10%, 15%, 20%, 25%, 30%, 35%, 40%, 45%, 50%, or more).

1327. The composition of any one of the previous embodiments further comprising at least one virus or vector comprising a genome of the virus, e.g., a variant of the anellosome, e.g., a commensal/native virus.

1328. The composition of any one of the previous embodiments further comprising a heterologous moiety, at least one small molecule, antibody, polypeptide, nucleic acid, targeting agent, imaging agent, nanoparticle, and a combination thereof.

1329. A vector comprising a genetic element comprising (i) a sequence encoding a non-pathogenic exterior protein, (ii) an exterior protein binding sequence that binds the genetic element to the non-pathogenic exterior protein, and (iii) a sequence encoding an effector, e.g., a regulatory nucleic acid.

1330. The vector of the previous embodiment, wherein the genetic element fails to integrate with a host cell's genome.

1331. The vector of any one of the previous embodiments, wherein the genetic element is capable of replicating in a mammalian cell, e.g., human cell.

1332. The vector of any one of the previous embodiments further comprising an exogenous nucleic acid sequence, e.g., selected to modulate expression of a gene, e.g., a human gene.

1333. A pharmaceutical composition comprising the vector of any one of the previous embodiments and a pharmaceutical excipient.

1334. The composition of the previous embodiment, wherein the vector is non-pathogenic and/or non-integrating in a host cell.

1335. The composition of any one of the previous embodiments, wherein the vector is non-immunogenic in a host.

1336. The composition of the previous embodiment, wherein the vector is in an amount sufficient to modulate (phenotype, virus levels, gene expression, compete with other viruses, disease state, etc. at least about 5%, 10%, 15%, 20%, 25%, 30%, 35%, 40%, 45%, 50%, or more).

1337. The composition of any one of the previous embodiments further comprising at least one virus or vector comprising a genome of the virus, e.g., a variant of the anellosome, a commensal/native virus, a helper virus, a non-*anellovirus*.

1338. The composition of any one of the previous embodiments further comprising a heterologous moiety, at least one small molecule, antibody, polypeptide, nucleic acid, targeting agent, imaging agent, nanoparticle, and a combination thereof.

1339. A method of producing, propagating, and harvesting the anellosome of any one of the previous embodiments.

1340. A method of designing and making the vector of any one of the previous embodiments.

1341. A method of administering to a subject an effective amount of the composition of any one of the previous embodiments.

1342. A method of delivering a nucleic acid or protein payload to a target cell, tissue or subject, the method comprising contacting the target cell, tissue or subject with a nucleic acid composition that comprises (a) a first DNA sequence derived from a virus wherein the first DNA sequence is suffient to enable the production of a particle capable of infecting the target cell, tissue or subject and (a) a second DNA sequence encoding the nucleic acid or protein payload, the improvement comprising:

- the first DNA sequence comprises at least 500 (at least 600, 700, 800, 900, 1000, 1200, 1400, 1500, 1600, 1800, 2000) nucleotides having at least 80% (at least 85%, 90%, 95%, 97%, 99%, 100%) sequence identity to a corresponding sequence listed in any of Tables 1, 3, 5, 7, 9, 11, 13, 15, or 17, or
- the first DNA sequence encodes a sequence having at least 80% (at least 85%, 90%, 95%, 97%, 99%, 100%) sequence identity to an ORF listed in Table 2, 4, 6, 8, 10, 12, 14, 16, or 18, or
- the first DNA sequence comprises a sequence having at least 90% (at least 95%, 97%, 99%, 100%) sequence identity to a consensus sequence listed in Table 19.

1343. A method of delivering a nucleic acid or protein effector to a target cell, tissue or subject, the method comprising contacting the target cell, tissue or subject with an anellosome of any of the preceding embodiments or a nucleic acid composition that comprises (a) a first DNA sequence derived from a virus wherein the first DNA sequence is sufficient to enable the production of an anellosome of any of the preceding embodiments that can infect the target cell, tissue or subject and (a) a second DNA sequence encoding the nucleic acid or protein effector.

1344. A codon-optimized nucleic acid molecule encoding an amino acid sequence having at least 70%, 75%, 80%, 85%, 90%, 95%, 96%, 97%, 98%, 99%, or 100% identity to a wild-type *Anellovirus* ORF1, ORF2, or ORF3 amino acid sequence.

1345. The codon-optimized nucleic acid molecule of embodiment 1344, encoding an amino acid sequence having at least 70%, 75%, 80%, 85%, 90%, 95%, 96%, 97%, 98%, 99%, or 100% identity to a wild-type *Anellovirus* ORF1 amino acid sequence, e.g., as listed in any of Tables 2, 4, 6, 8, 10, 12, 14, 16, 18, or 20-37.

1346. A pharmaceutical composition comprising:

(a) an anellosome, e.g., an anellosome of any of the preceding embodiments, and (b) a carrier chosen from a vesicle, lipid nanoparticle (LNP), red blood cell, or fusosome.

Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

BRIEF DESCRIPTION OF THE DRAWINGS

The following detailed description of the embodiments of the invention will be better understood when read in conjunction with the appended drawings. For the purpose of illustrating the invention, there are shown in the drawings embodiments that are presently exemplified. It should be understood, however, that the invention is not limited to the precise arrangement and instrumentalities of the embodiments shown in the drawings. The patent or application file contains at least one drawing executed in color. Copies of this patent or patent application publication with color drawing(s) will be provided by the Office upon request and payment of the necessary fee.

FIG. 35 is a diagram showing the consensus sequence (SEQ ID NO: 828) from alignment of 258 sequences of

*Alphatorqueviruses* with residues with high similarity scores highlighted dark gray (100%), medium gray (80-99.9%), light gray (60-80%). Putative domains are indicated in boxes. Percent identity is also indicated by the box graph below the consensus sequence, with medium-gray boxes indicating 100% identity, light gray boxes indicating 30-99% identity, and dark gray boxes indicating below 30% identity.

Figure 36:
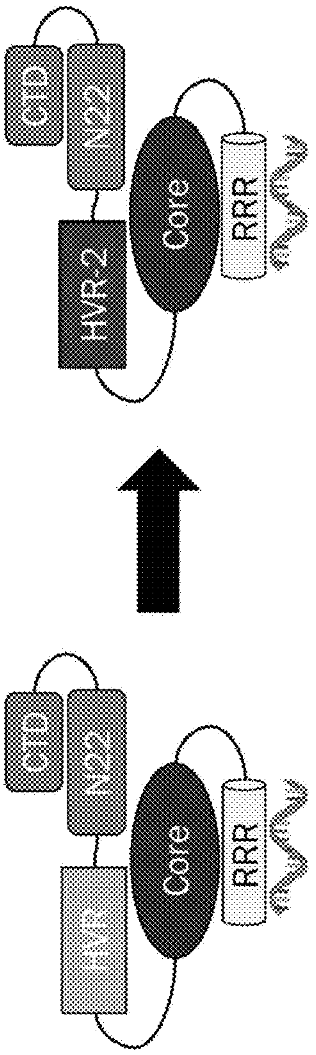

FIG. 36 is a schematic showing the domains of an *Anellovirus* ORF1 molecule and the hypervariable region to be replaced with a hypervariable domain from a different *Anellovirus*.

Figure 37:
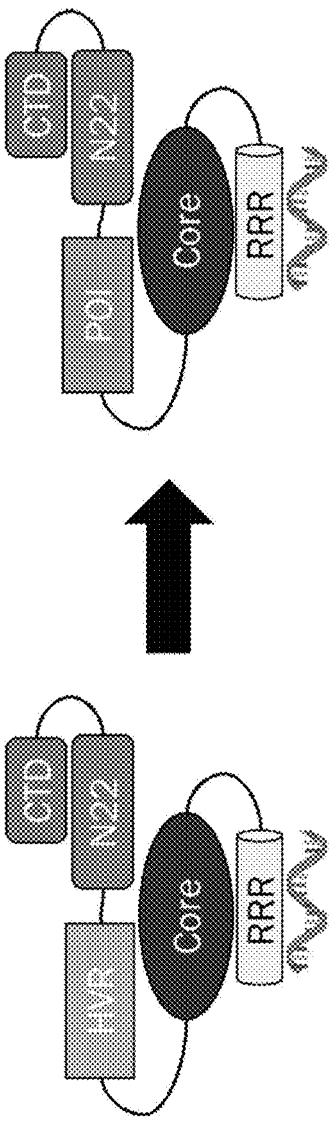

FIG. 37 is a schematic showing the domains of ORF1 and the hypervariable region that will be replaced with a protein or peptide of interest (POI) from a non-*anellovirus* source.

DETAILED DESCRIPTION OF CERTAIN EMBODIMENTS

Definitions

The wording "compound, composition, product, etc. for treating, modulating, etc." is to be understood to refer a compound, composition, product, etc. per se which is suitable for the indicated purposes of treating, modulating, etc. The wording "compound, composition, product, etc. for treating, modulating, etc." additionally discloses that, as an embodiment, such compound, composition, product, etc. is for use in treating, modulating, etc.

The wording "compound, composition, product, etc. for use in . . . " or "use of a compound, composition, product, etc in the manufacture of a medicament, pharmaceutical composition, veterinary composition, diagnostic composition, etc. for . . . " indicates that such compounds, compositions, products, etc. are to be used in therapeutic methods which may be practiced on the human or animal body. They are considered as an equivalent disclosure of embodiments and claims pertaining to methods of treatment, etc. If an embodiment or a claim thus refers to "a compound for use in treating a human or animal being suspected to suffer from a disease", this is considered to be also a disclosure of a "use of a compound in the manufacture of a medicament for treating a human or animal being suspected to suffer from a disease" or a "method of treatment by administering a compound to a human or animal being suspected to suffer from a disease". The wording "compound, composition, product, etc. for treating, modulating, etc." is to be understood to refer a compound, composition, product, etc. per se which is suitable for the indicated purposes of treating, modulating, etc.

If hereinafter examples of a term, value, number, etc. are provided in parentheses, this is to be understood as an indication that the examples mentioned in the parentheses can constitute an embodiment. For example, if it stated that "in embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1-encoding nucleotide sequence of Table 1 (e.g., nucleotides 571-2613 of the nucleic acid sequence of Table 1)", then some embodiments relate to nucleic acid molecules comprising a nucleic acid sequence having at least about 70%, 75%, 80%, 85%, 90%, 95%, 96%, 97%, 98%, 99%, or 100% sequence identity to nucleotides 571-2613 of the nucleic acid sequence of Table 1.

As used herein, the term "anellosome" refers to a vehicle comprising a genetic element, e.g., an episome, e.g., circular DNA, enclosed in a proteinaceous exterior. A "synthetic anellosome," as used herein, generally refers to an anellosome that is not naturally occurring, e.g., has a sequence that is different relative to a wild-type virus (e.g., a wild-type *Anellovirus* as described herein). In some embodiments, the synthetic anellosome is engineered or recombinant, e.g., comprises a genetic element that comprises a difference or modification relative to a wild-type viral genome (e.g., a wild-type *Anellovirus* genome as described herein). In some embodiments, enclosed within a proteinaceous exterior encompasses 100% coverage by a proteinaceous exterior, as well as less than 100% coverage, e.g., 95%, 90%, 85%, 80%, 70%, 60%, 50% or less. For example, gaps or discontinuities (e.g., that render the proteinaceous exterior permeable to water, ions, peptides, or small molecules) may be present in the proteinaceous exterior, so long as the genetic element is retained in the proteinaceous exterior, e.g., prior to entry into a host cell. In some embodiments, the anellosome is purified, e.g., it is separated from its original source and/or substantially free (>50%, >60%, >70%, >80%, >90%) of other components.

As used herein, the term "anellovector" refers to a vector that comprises sufficient nucleic acid sequence derived from or highly similar to (e.g., at least 85%, 90%, 95%, 96%, 97%, 98%, 99%, or 100% identical to) an *Anellovirus* genome sequence or a contiguous portion thereof to allow packaging into a proteinaceous exterior (e.g., a capsid), and further comprises a heterologous sequence. In some embodiments, the anellovector is a viral vector or a naked nucleic acid. In some embodiments, the anellovector comprises at least about 50, 60, 70, 71, 72, 73, 74, 75, 80, 90, 100, 150, 200, 300, 400, 500, 600, 700, 800, 900, 1000, 1100, 1200, 1300, 1400, 1500, 1600, 1700, 1800, 1900, 2000, 2500, 3000, or 3500 consecutive nucleotides of a native *Anellovirus* sequence or a sequence highly similar (e.g., at least 85%, 90%, 95%, 96%, 97%, 98%, 99%, or 100% identical) thereto. In some embodiments, the anellovector further comprises one or more of an *Anellovirus* ORF1, ORF2, or ORF3. In some embodiments, the heterologous sequence comprises a multiple cloning site, comprises a heterologous promoter, comprises a coding region for a therapeutic protein, or encodes a therapeutic nucleic acid. In some embodiments, the capsid is a wild-type *Anellovirus* capsid.

As used herein, the term "antibody molecule" refers to a protein, e.g., an immunoglobulin chain or fragment thereof, comprising at least one immunoglobulin variable domain sequence. The term "antibody molecule" encompasses full-length antibodies and antibody fragments (e.g., scFvs). In some embodiments, an antibody molecule is a multispecific antibody molecule, e.g., the antibody molecule comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In embodiments, the multispecific antibody molecule is a bispecific antibody molecule. A bispecific antibody molecule is generally characterized by a first immunoglobulin variable domain sequence which has binding specificity for a first epitope and a second immunoglobulin variable domain sequence that has binding specificity for a second epitope.

As used herein, a nucleic acid "encoding" refers to a nucleic acid sequence encoding an amino acid sequence or a functional polynucleotide (e.g., a non-coding RNA, e.g., an siRNA or miRNA).

An "exogenous" agent (e.g., an effector, a nucleic acid (e.g., RNA), a gene, payload, protein) as used herein refers to an agent that is either not comprised by, or not encoded by, a corresponding wild-type virus, e.g., an *Anellovirus* as described herein. In some embodiments, the exogenous agent does not naturally exist, such as a protein or nucleic acid that has a sequence that is altered (e.g., by insertion, deletion, or substitution) relative to a naturally occurring protein or nucleic acid. In some embodiments, the exogenous agent does not naturally exist in the host cell. In some embodiments, the exogenous agent exists naturally in the host cell but is exogenous to the virus. In some embodiments, the exogenous agent exists naturally in the host cell, but is not present at a desired level or at a desired time.

A "heterologous" agent or element (e.g., an effector, a nucleic acid sequence, an amino acid sequence), as used herein with respect to another agent or element (e.g., an effector, a nucleic acid sequence, an amino acid sequence), refers to agents or elements that are not naturally found together, e.g., in a wild-type virus, e.g., an *Anellovirus*. In some embodiments, a heterologous nucleic acid sequence may be present in the same nucleic acid as a naturally occurring nucleic acid sequence (e.g., a sequence that is naturally occurring in the *Anellovirus*). In some embodiments, a heterologous agent or element is exogenous relative to an *Anellovirus* from which other (e.g., the remainder of) elements of the anellosome are based.

As used herein, the term "genetic element" refers to a nucleic acid sequence, generally in an anellosome. It is understood that the genetic element can be produced as naked DNA and optionally further assembled into a proteinaceous exterior. It is also understood that an anellosome can insert its genetic element into a cell, resulting in the genetic element being present in the cell and the proteinaceous exterior not necessarily entering the cell.

As used herein, the term "ORF1 molecule" refers to a polypeptide having an activity and/or a structural feature of an *Anellovirus* ORF1 protein (e.g., an *Anellovirus* ORF1 protein as described herein, e.g., as listed in any of Tables 2, 4, 6, 8, 10, 12, 14, 16, 18, or 20-37), or a functional fragment thereof. An ORF1 molecule may, in some instances, comprise one or more of (e.g., 1, 2, 3 or 4 of): a first region comprising at least 60% basic residues (e.g., at least 60% arginine residues), a second region compising at least about six beta strands (e.g., at least 4, 5, 6, 7, 8, 9, 10, 11, or 12 beta strands), a third region comprising a structure or an activity of an *Anellovirus* N22 domain (e.g., as described herein, e.g., an N22 domain from an *Anellovirus* ORF1 protein as described herein), and/or a fourth region comprising a structure or an activity of an *Anellovirus* C-terminal domain (CTD) (e.g., as described herein, e.g., a CTD from an *Anellovirus* ORF1 protein as described herein). In some instances, the ORF1 molecule comprises, in N-terminal to C-terminal order, the first, second, third, and fourth regions. In some instances, an anellosome comprises an ORF1 molecule comprising, in N-terminal to C-terminal order, the first, second, third, and fourth regions. An ORF1 molecule may, in some instances, further comprise a heterologous sequence, e.g., a hypervariable region (HVR), e.g., an HVR from an *Anellovirus* ORF1 protein, e.g., as described herein. An "*Anellovirus* ORF1 protein," as used herein, refers to an ORF1 protein encoded by an *Anellovirus* genome (e.g., a wild-type *Anellovirus* genome, e.g., as described herein), e.g., an ORF1 protein having the amino acid sequence as listed in any of Tables 2, 4, 6, 8, 10, 12, 14, 16, 18, or 20-37, or as encoded by the ORF1 gene as listed in any of Tables 1, 3, 5, 7, 9, 11, 13, 15, or 17.

As used herein, the term "proteinaceous exterior" refers to an exterior component that is predominantly (e.g., >50%, >60%, >70%, >80%, >90%) protein.

As used herein, the term "regulatory nucleic acid" refers to a nucleic acid sequence that modifies expression, e.g., transcription and/or translation, of a DNA sequence that encodes an expression product. In embodiments, the expression product comprises RNA or protein.

As used herein, the term "regulatory sequence" refers to a nucleic acid sequence that modifies transcription of a target gene product. In some embodiments, the regulatory sequence is a promoter or an enhancer.

As used herein, the term "replication protein" refers to a protein, e.g., a viral protein, that is utilized during infection, viral genome replication/expression, viral protein synthesis, and/or assembly of the viral components.

As used herein, a "substantially non-pathogenic" organism, particle, or component, refers to an organism, particle (e.g., a virus or an anellosome, e.g., as described herein), or component thereof that does not cause or induce a detectable disease or pathogenic condition, e.g., in a host organism, e.g., a mammal, e.g., a human. In some embodiments, administration of an anellosome to a subject can result in minor reactions or side effects that are acceptable as part of standard of care.

As used herein, the term "non-pathogenic" refers to an organism or component thereof that does not cause or induce a detectable disease or pathogenic condition, e.g., in a host organism, e.g., a mammal, e.g., a human.

As used herein, a "substantially non-integrating" genetic element refers to a genetic element, e.g., a genetic element in a virus or anellosome, e.g., as described herein, wherein less than about 0.01%, 0.05%, 0.1%, 0.5%, or 1% of the genetic element that enter into a host cell (e.g., a eukaryotic cell) or organism (e.g., a mammal, e.g., a human) integrate into the genome. In some embodiments the genetic element does not detectably integrate into the genome of, e.g., a host cell. In some embodiments, integration of the genetic element into the genome can be detected using techniques as described herein, e.g., nucleic acid sequencing, PCR detection and/or nucleic acid hybridization.

As used herein, a "substantially non-immunogenic" organism, particle, or component, refers to an organism, particle (e.g., a virus or anellosome, e.g., as described herein), or component thereof, that does not cause or induce an undesired or untargeted immune response, e.g., in a host tissue or organism (e.g., a mammal, e.g., a human). In embodiments, the substantially non-immunogenic organism, particle, or component does not produce a detectable immune response. In embodiments, the substantially non-immunogenic anellosome does not produce a detectable immune response against a protein comprising an amino acid sequence or encoded by a nucleic acid sequence shown in any of Tables 1, 3, 5, 7, 9, 11, 13, 15, or 17. In embodiments, an immune response (e.g., an undesired or untargeted immune response) is detected by assaying antibody presence or level (e.g., presence or level of an anti-anellosome antibody, e.g., presence or level of an antibody against an anellosome as described herein) in a subject, e.g., according to the anti-TTV antibody detection method described in Tsuda et al. (1999*; J. Virol. Methods* 77: 199-206; incorporated herein by reference) and/or the method for determining anti-TTV IgG levels described in Kakkola et al. (2008*; Virology* 382: 182-189; incorporated herein by reference). Antibodies against an *Anellovirus* or an anellosome based thereon can also be detected by methods in the art for detecting anti-viral antibodies, e.g., methods of detecting anti-AAV antibodies, e.g., as described in Calcedo et al. (2013*; Front. Immunol.* 4(341): 1-7; incorporated herein by reference).

A "subsequence" as used herein refers to a nucleic acid sequence or an amino acid sequence that is comprised in a larger nucleic acid sequence or amino acid sequence, respectively. In some instances, a subsequence may comprise a domain or functional fragment of the larger sequence. In some instances, the subsequence may comprise a fragment of the larger sequence capable of forming secondary and/or tertiary structures when isolated from the larger sequence similar to the secondary and/or tertiary structures formed by the subsequence when present with the remainder of the larger sequence. In some instances, a subsequence can be replaced by another sequence (e.g., a subseqence comprising an exogenous sequence or a sequence heterologous to the remainder of the larger sequence, e.g., a corresponding subsequence from a different *Anellovirus*).

As used herein, "treatment", "treating" and cognates thereof refer to the medical management of a subject with the intent to improve, ameliorate, stabilize, prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to preventing, minimizing or partially or completely inhibiting the development of the associated disease, pathological condition, or disorder); and supportive treatment (treatment employed to supplement another therapy).

As used herein, the term "virome" refers to viruses in a particular environment, e.g., a part of a body, e.g., in an organism, e.g. in a cell, e.g. in a tissue.

This invention relates generally to anellosomes, e.g., synthetic anellosomes, and uses thereof. The present disclosure provides anellosomes, compositions comprising anellosomes, and methods of making or using anellosomes. Anellosomes are generally useful as delivery vehicles, e.g., for delivering a therapeutic agent to a eukaryotic cell. Generally, an anellosome will include a genetic element comprising a nucleic acid sequence (e.g., encoding an effector, e.g., an exogenous effector or an endogenous effector) enclosed within a proteinaceous exterior. An anellosome may include one or more deletions of sequences (e.g., regions or domains as described herein) relative to an *Anellovirus* sequence (e.g., as described herein). Anellosomes can be used as a substantially non-immunogenic vehicle for delivering the genetic element, or an effector encoded therein (e.g., a polypeptide or nucleic acid effector, e.g., as described herein), into eukaryotic cells, e.g., to treat a disease or disorder in a subject comprising the cells.

Anellosomes

In some aspects, the invention described herein comprises compositions and methods of using and making an anellosome, anellosome preparations, and therapeutic compositions. In some embodiments, the anellosome has a sequence, structure, and/or function that is based on an *Anellovirus* (e.g., an *Anellovirus* as described herein, e.g., an *Anellovirus* comprising a nucleic acid or polypeptide comprising a sequence as shown in any of Tables 1-18), or fragments or portions thereof, or other substantially non-pathogenic virus, e.g., a symbiotic virus, commensal virus, native virus. In some embodiments, an *Anellovirus*-based anellosome comprises at least one element exogenous to that *Anellovirus*, e.g., an exogenous effector or a nucleic acid sequence encoding an exogenous effector disposed within a genetic element of the anellosome. In some embodiments, an *Anellovirus*-based anellosome comprises at least one element heterologous to another element from that *Anellovirus*, e.g., an effector-encoding nucleic acid sequence that is heterologous to another linked nucleic acid sequence, such as a promoter element. In some embodiments, an anellosome comprises a genetic element (e.g., circular DNA, e.g., single stranded DNA), which comprise at least one element that is heterologous relative to the remainder of the genetic element and/or the proteinaceous exterior (e.g., an exogenous element encoding an effector, e.g., as described herein). An anellosome may be a delivery vehicle (e.g., a substantially non-pathogenic delivery vehicle) for a payload into a host, e.g., a human. In some embodiments, the anellosome is capable of replicating in a eukaryotic cell, e.g., a mammalian cell, e.g., a human cell. In some embodiments, the anellosome is substantially non-pathogenic and/or substantially non-integrating in the mammalian (e.g., human) cell. In some embodiments, the anellosome is substantially non-immunogenic in a mammal, e.g., a human. In some embodiments, the anellosome is replication-deficient. In some embodiments, the anellosome is replication-competent.

In some embodiments the anellosome comprises a curon, or a component thereof (e.g., a genetic element, e.g., comprising a sequence encoding an effector, and/or a proteinaceous exterior), e.g., as described in PCT Application No. PCT/US2018/037379, which is incorporated herein by reference in its entirety.

In an aspect, the invention includes an anellosome comprising (i) a genetic element comprising a promoter element, a sequence encoding an effector, (e.g., an endogenous effector or an exogenous effector, e.g., a payload), and a protein binding sequence (e.g., an exterior protein binding sequence, e.g., a packaging signal), wherein the genetic element is a single-stranded DNA, and has one or both of the following properties: is circular and/or integrates into the genome of a eukaryotic cell at a frequency of less than about 0.001%, 0.005%, 0.01%, 0.05%, 0.1%, 0.5%, 1%, 1.5%, or 2% of the genetic element that enters the cell; and (ii) a proteinaceous exterior; wherein the genetic element is enclosed within the proteinaceous exterior; and wherein the anellosome is capable of delivering the genetic element into a eukaryotic cell.

In some embodiments of the anellosome described herein, the genetic element integrates at a frequency of less than about 0.001%, 0.005%, 0.01%, 0.05%, 0.1%, 0.5%, 1%, 1.5%, or 2% of the genetic element that enters a cell. In some embodiments, less than about 0.01%, 0.05%, 0.1%, 0.5%, 1%, 2%, 3%, 4%, or 5% of the genetic elements from a plurality of the anellosomes administered to a subject will integrate into the genome of one or more host cells in the subject. In some embodiments, the genetic elements of a population of anellosomes, e.g., as described herein, integrate into the genome of a host cell at a frequency less than that of a comparable population of AAV viruses, e.g., at about a 50%, 60%, 70%, 75%, 80%, 85%, 90%, 95%, 100%, or more lower frequency than the comparable population of AAV viruses.

In an aspect, the invention includes an anellosome comprising: (i) a genetic element comprising a promoter element and a sequence encoding an effector (e.g., an endogenous effector or an exogenous effector, e.g., a payload), and a protein binding sequence (e.g., an exterior protein binding sequence), wherein the genetic element has at least 75% (e.g., at least 75, 76, 77, 78, 79, 80, 90, 91, 92, 93, 94, 95, 96, 97, 98, 99, or 100%) sequence identity to a wild-type *Anellovirus* sequence (e.g., a wild-type Torque Teno virus (TTV), Torque Teno mini virus (TTMV), or TTMDV sequence, e.g., a wild-type *Anellovirus* sequence as listed in any of Tables 1, 3, 5, 7, 9, 11, 13, 15, or 17); and (ii) a proteinaceous exterior; wherein the genetic element is enclosed within the proteinaceous exterior; and wherein the anellosome is capable of delivering the genetic element into a eukaryotic cell.

In one aspect, the invention includes an anellosome comprising:

a) a genetic element comprising (i) a sequence encoding an exterior protein (e.g., a non-pathogenic exterior protein), (ii) an exterior protein binding sequence that binds the genetic element to the non-pathogenic exterior protein, and (iii) a sequence encoding an effector (e.g., an endogenous or exogenous effector); and b) a proteinaceous exterior that is associated with, e.g., envelops or encloses, the genetic element.

In some embodiments, the anellosome includes sequences or expression products from (or having >70%, 75%, 80%, 85%, 90%, 95%, 97%, 98%, 99%, 100% homology to) a non-enveloped, circular, single-stranded DNA virus. Animal circular single-stranded DNA viruses generally refer to a subgroup of single strand DNA (ssDNA) viruses, which infect eukaryotic non-plant hosts, and have a circular genome. Thus, animal circular ssDNA viruses are distinguishable from ssDNA viruses that infect prokaryotes (i.e. Microviridae and Inoviridae) and from ssDNA viruses that infect plants (i.e. Geminiviridae and Nanoviridae). They are also distinguishable from linear ssDNA viruses that infect non-plant eukaryotes (i.e. Parvoviridiae).

In some embodiments, the anellosome modulates a host cellular function, e.g., transiently or long term. In certain embodiments, the cellular function is stably altered, such as a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the cellular function is transiently altered, e.g., such as a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, the genetic element comprises a promoter element. In embodiments, the promoter element is selected from an RNA polymerase II-dependent promoter, an RNA polymerase III-dependent promoter, a PGK promoter, a CMV promoter, an EF-1α promoter, an SV40 promoter, a CAGG promoter, or a UBC promoter, TTV viral promoters, Tissue specific, U6 (pollIII), minimal CMV promoter with upstream DNA binding sites for activator proteins (TetR-VP16, Ga14-VP16, dCas9-VP16, etc). In embodiments, the promoter element comprises a TATA box. In embodiments, the promoter element is endogenous to a wild-type *Anellovirus*, e.g., as described herein.

In some embodiments, the genetic element comprises one or more of the following characteristics: single-stranded, circular, negative strand, and/or DNA. In embodiments, the genetic element comprises an episome. In some embodiments, the portions of the genetic element excluding the effector have a combined size of about 2.5-5 kb (e.g., about 2.8-4 kb, about 2.8-3.2 kb, about 3.6-3.9 kb, or about 2.8-2.9 kb), less than about 5 kb (e.g., less than about 2.9 kb, 3.2 kb, 3.6 kb, 3.9 kb, or 4 kb), or at least 100 nucleotides (e.g., at least 1 kb).

The anellosomes, compositions comprising anellosomes, methods using such anellosomes, etc., as described herein are, in some instances, based in part on the examples which illustrate how different effectors, for example miRNAs (e.g. against IFN or miR-625), shRNA, etc and protein binding sequences, for example DNA sequences that bind to capsid protein such as Q99153, are combined with proteinaceious exteriors, for example a capsid disclosed in Arch Virol (2007) 152: 1961-1975, to produce anellosomes which can then be used to deliver an effector to cells (e.g., animal cells, e.g., human cells or non-human animal cells such as pig or mouse cells). In embodiments, the effector can silence expression of a factor such as an interferon. The examples further describe how anellosomes can be made by inserting effectors into sequences derived, e.g., from an *Anellovirus*. It is on the basis of these examples that the description hereinafter contemplates various variations of the specific findings and combinations considered in the examples. For example, the skilled person will understand from the examples that the specific miRNAs are used just as an example of an effector and that other effectors may be, e.g., other regulatory nucleic acids or therapeutic peptides. Similarly, the specific capsids used in the examples may be replaced by substantially non-pathogenic proteins described hereinafter. The specifc *Anellovirus* sequences described in the examples may also be replaced by the *Anellovirus* sequences described hereinafter. These considerations similarly apply to protein binding sequences, regulatory sequences such as promoters, and the like. Independent thereof, the person skilled in the art will in particular consider such embodiments which are closely related to the examples.

In some embodiments, an anellosome, or the genetic element comprised in the anellosome, is introduced into a cell (e.g., a human cell). In some embodiments, the effector (e.g., an RNA, e.g., an miRNA), e.g., encoded by the genetic element of an anellosome, is expressed in a cell (e.g., a human cell), e.g., once the anellosome or the genetic element has been introduced into the cell. In embodiments, introduction of the anellosome, or genetic element comprised therein, into a cell modulates (e.g., increases or decreases) the level of a target molecule (e.g., a target nucleic acid, e.g., RNA, or a target polypeptide) in the cell, e.g., by altering the expression level of the target molecule by the cell. In embodiments, introduction of the anellosome, or genetic element comprised therein, decreases level of interferon produced by the cell. In embodiments, introduction of the anellosome, or genetic element comprised therein, into a cell modulates (e.g., increases or decreases) a function of the cell. In embodiments, introduction of the anellosome, or genetic element comprised therein, into a cell modulates (e.g., increases or decreases) the viability of the cell. In embodiments, introduction of the anellosome, or genetic element comprised therein, into a cell decreases viability of a cell (e.g., a cancer cell).

In some embodiments, an anellosome (e.g., a synthetic anellosome) described herein induces an antibody prevalence of less than 70% (e.g., less than about 60%, 50%, 40%, 30%, 20%, or 10% antibody prevalence). In embodiments, antibody prevalence is determined according to methods known in the art. In embodiments, antibody prevalence is determined by detecting antibodies against an *Anellovirus* (e.g., as described herein), or an anellosome based thereon, in a biological sample, e.g., according to the anti-TTV antibody detection method described in Tsuda et al. (1999; *J. Virol. Methods* 77: 199-206; incorporated herein by reference) and/or the method for determining anti-TTV IgG seroprevalence described in Kakkola et al. (2008; *Virology* 382: 182-189; incorporated herein by reference). Antibodies against an *Anellovirus* or an anellosome based thereon can also be detected by methods in the art for detecting anti-viral antibodies, e.g., methods of detecting anti-AAV antibodies, e.g., as described in Calcedo et al. (2013; *Front. Immunol.* 4(341): 1-7; incorporated herein by reference).

*Anelloviruses*

In some embodiments, an anellosome, e.g., as described herein, comprises sequences or expression products derived from an *Anellovirus*. In some embodiments, an anellosome includes one or more sequences or expression products that are exogenous relative to the *Anellovirus*. In some embodiments, an anellosome includes one or more sequences or expression products that are endogenous relative to the *Anellovirus*. In some embodiments, an anellosome includes one or more sequences or expression products that are heterologous relative to one or more other sequences or expression products in the anellosome. *Anelloviruses* generally have single-stranded circular DNA genomes with negative polarity. *Anelloviruses* have not generally been linked to any human disease. However, attempts to link *Anellovirus* infection with human disease are confounded by the high incidence of asymptomatic *Anellovirus* viremia in control cohort population(s), the remarkable genomic diversity within the *anellovirus* viral family, the historical inability to propagate the agent in vitro, and the lack of animal model(s) of *Anellovirus* disease (Yzebe et al., Panminerva Med. (2002) 44:167-177; Biagini, P., Vet. Microbiol. (2004) 98:95-101).

*Anelloviruses* are generally transmitted by oronasal or fecal-oral infection, mother-to-infant and/or in utero transmission (Gerner et al., Ped. Infect. Dis. J. (2000) 19:1074-1077). Infected persons can, in some instances, be characterized by a prolonged (months to years) *Anellovirus* viremia. Humans may be co-infected with more than one genogroup or strain (Saback, et al., Scad. J. Infect. Dis. (2001) 33:121-125). There is a suggestion that these genogroups can recombine within infected humans (Rey et al., Infect. (2003) 31:226-233). The double stranded isoform (replicative) intermediates have been found in several tissues, such as liver, peripheral blood mononuclear cells and bone marrow (Kikuchi et al., J. Med. Virol. (2000) 61:165-170; Okamoto et al., Biochem. Biophys. Res. Commun. (2002) 270:657-662; Rodriguez-lnigo et al., Am. J. Pathol. (2000) 156:1227-1234).

In some embodiments, the genetic element comprises a nucleotide sequence encoding an amino acid sequence or a functional fragment thereof or a sequence having at least about 60%, 70% 80%, 85%, 90% 95%, 96%, 97%, 98%, 99%, or 100% sequence identity to any one of the amino acid sequences described herein, e.g., an *Anellovirus* amino acid sequence.

In some embodiments, an anellosome as described herein comprises one or more nucleic acid molecules (e.g., a genetic element as described herein) comprising a sequence having at least about 70%, 75%, 80%, 85%, 90%, 95%, 96%, 97%, 98%, 99%, or 100% sequence identity to an *Anellovirus* sequence, e.g., as described herein, or a fragment thereof. In embodiments, the anellosome comprises a nucleic acid sequence selected from a sequence as shown in any of Tables 1, 3, 5, 7, 9, 11, 13, 15, or 17, or a sequence having at least 70%, 75%, 80%, 85%, 90%, 95%, 96%, 97%, 98%, 99%, or 100% sequence identity thereto. In embodiments, the anellosome comprises a polypeptide comprising a sequence as shown in any of Tables 2, 4, 6, 8, 10, 12, 14, 16, or 18, or a sequence having at least 70%, 75%, 80%, 85%, 90%, 95%, 96%, 97%, 98%, 99%, or 100% sequence identity thereto.

In some embodiments, an anellosome as described herein comprises one or more nucleic acid molecules (e.g., a genetic element as described herein) comprising a sequence having at least about 70%, 75%, 80%, 85%, 90%, 95%, 96%, 97%, 98%, 99%, or 100% sequence identity to one or more of a TATA box, cap site, initiator element, transcriptional start site, 5' UTR conserved domain, ORF1, ORF1/1, ORF1/2, ORF2, ORF2/2, ORF2/3, ORF2t/3, three open-reading frame region, poly(A) signal, GC-rich region, or any combination thereof, of any of the *Anelloviruses* described herein (e.g., an *Anellovirus* sequence as annotated, or as encoded by a sequence listed, in any of Tables 1-18). In some embodiments, the nucleic acid molecule comprises a sequence encoding a capsid protein, e.g., an ORF1, ORF1/1, ORF1/2, ORF2, ORF2/2, ORF2/3, ORF2t/3 sequence of any of the *Anelloviruses* described herein (e.g., an *Anellovirus* sequence as annotated, or as encoded by a sequence listed, in any of Tables 1-18). In embodiments, the nucleic acid molecule comprises a sequence encoding a capsid protein comprising an amino acid sequence having at least about 70%, 75%, 80%, 85%, 90%, 95%, 96%, 97%, 98%, 99%, or 100% sequence identity to an *Anellovirus* ORF1 or ORF2 protein (e.g., an ORF1 or ORF2 amino acid sequence as shown in any of Tables 2, 4, 6, 8, 10, 12, 14, 16, or 18, or an ORF1 or ORF2 amino acid sequence encoded by a nucleic acid sequence as shown in any of Tables 1, 3, 5, 7, 9, 11, 13, 15, or 17). In embodiments, the nucleic acid molecule comprises a sequence encoding a capsid protein comprising an amino acid sequence having at least about 70%, 75%, 80%, 85%, 90%, 95%, 96%, 97%, 98%, 99%, or 100% sequence identity to an *Anellovirus* ORF1 protein (e.g., an ORF1 amino acid sequence as shown in any of Tables 2, 4, 6, 8, 10, 12, 14, 16, 18, or 20-37, or an ORF1 amino acid sequence encoded by a nucleic acid sequence as shown in any of Tables 1, 3, 5, 7, 9, 11, 13, 15, or 17).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 1 (e.g., nucleotides 571-2613 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 1 (e.g., nucleotides 571-587 and/or 2137-2613 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 1 (e.g., nucleotides 571-687 and/or 2339-2659 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 1 (e.g., nucleotides 299-691 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 1 (e.g., nucleotides 299-687 and/or 2137-2659 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 1 (e.g., nucleotides 299-687 and/or 2339-2831 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2t/3 nucleotide sequence of Table 1 (e.g., nucleotides 299-348 and/or 2339-2831 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 1 (e.g., nucleotides 84-90 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* Cap site nucleotide sequence of Table 1 (e.g., nucleotides 107-114 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 1 (e.g., nucleotide 114 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 1 (e.g., nucleotides 177-247 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 1 (e.g., nucleotides 2325-2610 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 1 (e.g., nucleotides 2813-2818 of the nucleic acid sequence of Table 1). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 1 (e.g., nucleotides 3415-3570 of the nucleic acid sequence of Table 1).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 3 (e.g., nucleotides 729-2972 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 3 (e.g., nucleotides 729-908 and/or 2490-2972 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 3 (e.g., nucleotides 729-908 and/or 2725-3039 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 3 (e.g., nucleotides 412-912 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 3 (e.g., nucleotides 412-908 and/or 2490-3039 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 3 (e.g., nucleotides 412-908 and/or 2725-3208 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 3 (e.g., nucleotides 112-119 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* initiator element nucleotide sequence of Table 3 (e.g., nucleotides 128-148 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 3 (e.g., nucleotide 148 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 3 (e.g., nucleotides 204-273 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 3 (e.g., nucleotides 2699-2969 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 3 (e.g., nucleotides 3220-3225 of the nucleic acid sequence of Table 3). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 3 (e.g., nucleotides 3302-3541 of the nucleic acid sequence of Table 3).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 5 (e.g., nucleotides 599-2830 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 5 (e.g., nucleotides 599-715 and/or 2363-2830 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 5 (e.g., nucleotides 599-715 and/or 2565-2789 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 5 (e.g., nucleotides 336-719 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 5 (e.g., nucleotides 336-715 and/or 2363-2789 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 5 (e.g., nucleotides 336-715 and/or 2565-3015 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2t/3 nucleotide sequence of Table 5 (e.g., nucleotides 336-388 and/or 2565-3015 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 5 (e.g., nucleotides 83-88 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* Cap site nucleotide sequence of Table 5 (e.g., nucleotides 104-111 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 5 (e.g., nucleotide 111 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 5 (e.g., nucleotides 170-240 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 5 (e.g., nucleotides 2551-2786 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 5 (e.g., nucleotides 3011-3016 of the nucleic acid sequence of Table 5). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 5 (e.g., nucleotides 3632-3753 of the nucleic acid sequence of Table 5).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 7 (e.g., nucleotides 586-2928 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 7 (e.g., nucleotides 586-717 and/or 2446-2928 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 7 (e.g., nucleotides 586-717 and/or 2675-2902 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 7 (e.g., nucleotides 335-721 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 7 (e.g., nucleotides 335-717 and/or 2446-2902 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 7 (e.g., nucleotides 335-717 and/or 2675-3109 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 7 (e.g., nucleotides 82-87 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* initiator element nucleotide sequence of Table 7 (e.g., nucleotides 95-115 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 7 (e.g., nucleotide 115 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 7 (e.g., nucleotides 170-238 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 7 (e.g., nucleotides 2640-2899 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 7 (e.g., nucleotides 3106-3114 of the nucleic acid sequence of Table 7). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 7 (e.g., nucleotides 3768-3878 of the nucleic acid sequence of Table 7).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 9 (e.g., nucleotides 588-2873 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 9 (e.g., nucleotides 588-722 and/or 2412-2873 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 9 (e.g., nucleotides 588-722 and/or 2638-2847 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 9 (e.g., nucleotides 331-726 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 9 (e.g., nucleotides 331-722 and/or 2412-2847 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 9 (e.g., nucleotides 331-722 and/or 2638-3058 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2t/3 nucleotide sequence of Table 9 (e.g., nucleotides 331-380 and/or 2638-3058 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 9 (e.g., nucleotides 82-86 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* initiator element nucleotide sequence of Table 9 (e.g., nucleotides 100-115 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 9 (e.g., nucleotide 115 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 9 (e.g., nucleotides 170-240 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 9 (e.g., nucleotides 2699-2969 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 9 (e.g., nucleotides 3220-3225 of the nucleic acid sequence of Table 9). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 9 (e.g., nucleotides 3302-3541 of the nucleic acid sequence of Table 9).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 11 (e.g., nucleotides 599-2839 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 11 (e.g., nucleotides 599-727 and/or 2381-2839 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 11 (e.g., nucleotides 599-727 and/or 2619-2813 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 11 (e.g., nucleotides 357-731 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 11 (e.g., nucleotides 357-727 and/or 2381-2813 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 11 (e.g., nucleotides 357-727 and/or 2619-3021 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2t/3 nucleotide sequence of Table 11 (e.g., nucleotides 357-406 and/or 2619-3021 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 11 (e.g., nucleotides 89-90 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* Cap site nucleotide sequence of Table 11 (e.g., nucleotides 107-114 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 11 (e.g., nucleotide 114 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 11 (e.g., nucleotides 174-244 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 11 (e.g., nucleotides 2596-2810 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 11 (e.g., nucleotides 3017-3022 of the nucleic acid sequence of Table 11). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 11 (e.g., nucleotides 3691-3794 of the nucleic acid sequence of Table 11).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 13 (e.g., nucleotides 599-2896 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 13 (e.g., nucleotides 599-724 and/or 2411-2896 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 13 (e.g., nucleotides 599-724 and/or 2646-2870 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 13 (e.g., nucleotides 357-728 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 13 (e.g., nucleotides 357-724 and/or 2411-2870 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 13 (e.g., nucleotides 357-724 and/or 2646-3081 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 13 (e.g., nucleotides 82-86 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* initiator element nucleotide sequence of Table 13 (e.g., nucleotides 94-115 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 13 (e.g., nucleotide 115 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 13 (e.g., nucleotides 170-240 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 13 (e.g., nucleotides 2629-2867 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 13 (e.g., nucleotides 3076-3086 of the nucleic acid sequence of Table 13). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 13 (e.g., nucleotides 3759-3866 of the nucleic acid sequence of Table 13).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 15 (e.g., nucleotides 612-2612 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 15 (e.g., nucleotides 612-719 and/or 2274-2612 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 15 (e.g., nucleotides 612-719 and/or 2449-2589 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 15 (e.g., nucleotides 424-723 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 15 (e.g., nucleotides 424-719 and/or 2274-2589 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the

*Anellovirus* ORF2/3 nucleotide sequence of Table 15 (e.g., nucleotides 424-719 and/or 2449-2812 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 15 (e.g., nucleotides 237-243 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* Cap site nucleotide sequence of Table 15 (e.g., nucleotides 260-267 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 15 (e.g., nucleotide 267 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 15 (e.g., nucleotides 323-393 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 15 (e.g., nucleotides 2441-2586 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 15 (e.g., nucleotides 2808-2813 of the nucleic acid sequence of Table 15). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 15 (e.g., nucleotides 2868-2929 of the nucleic acid sequence of Table 15).

In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1 nucleotide sequence of Table 17 (e.g., nucleotides 432-2453 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/1 nucleotide sequence of Table 17 (e.g., nucleotides 432-584 and/or 1977-2453 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF1/2 nucleotide sequence of Table 17 (e.g., nucleotides 432-584 and/or 2197-2388 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2 nucleotide sequence of Table 17 (e.g., nucleotides 283-588 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/2 nucleotide sequence of Table 17 (e.g., nucleotides 283-584 and/or 1977-2388 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* ORF2/3 nucleotide sequence of Table 17 (e.g., nucleotides 283-584 and/or 2197-2614 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* TATA box nucleotide sequence of Table 17 (e.g., nucleotides 21-25 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* Cap site nucleotide sequence of Table 17 (e.g., nucleotides 42-49 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* transcriptional start site nucleotide sequence of Table 17 (e.g., nucleotide 49 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* 5' UTR conserved domain nucleotide sequence of Table 17 (e.g., nucleotides 117-187 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* three open-reading frame region nucleotide sequence of Table 17 (e.g., nucleotides 2186-2385 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* poly(A) signal nucleotide sequence of Table 17 (e.g., nucleotides 2676-2681 of the nucleic acid sequence of Table 17). In embodiments, the nucleic acid molecule comprises a nucleic acid sequence having at least about 70%, 75%, 80%, 85%, 90%, 95%, 96%, 97%, 98%, 99%, or 100% sequence identity to the *Anellovirus* GC-rich nucleotide sequence of Table 17 (e.g., nucleotides 3054-3172 of the nucleic acid sequence of Table 17).

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 2. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 2. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 2. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 2. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 2. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 2. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 2.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 4. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 4. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 4. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 4. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 4. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 4.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 6. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 6. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 6. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 6. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 6. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 6. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 6.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 8. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 8. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 8. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 8. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 8. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 8.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 10. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 10. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 10. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 10. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 10. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus*

ORF2/3 amino acid sequence of Table 10. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 10.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 12. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 12. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 12. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 12. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 12. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 12. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 12.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 14. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 14. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 14. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 14. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 14. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 14.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 16. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 16. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 16. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 16. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 16. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 16.

In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1 amino acid sequence of Table 18. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/1 amino acid sequence of Table 18. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF1/2 amino acid sequence of Table 18. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2 amino acid sequence of Table 18. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/2 amino acid sequence of Table 18. In embodiments, the nucleic acid molecule comprises a nucleic acid sequence encoding an amino acid sequence having at least about 70%, 75%, 80%, 85%, 90%, 95%, 96%, 97%, 98%, 99%, or 100% sequence identity to the *Anellovirus* ORF2/3 amino acid sequence of Table 18.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 2. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 2. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 2. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 2. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 2. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 2. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 2.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 4. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 4. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 4. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 4. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 4. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 4.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 6. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 6. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 6. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 6. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 6. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 6. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 6.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 8. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 8. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 8. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 8. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 8. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 8.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 10. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 10. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 10. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 10. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 10. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 10. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 10.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 12. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 12. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 12. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 12. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 12. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 12. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2t/3 amino acid sequence of Table 12.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 14. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 14. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 14. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 14. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 14. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 14.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 16. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 16. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 16. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 16. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 16. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 16.

In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1 amino acid sequence of Table 18. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/1 amino acid sequence of Table 18. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF1/2 amino acid sequence of Table 18. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2 amino acid sequence of Table 18. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/2 amino acid sequence of Table 18. In embodiments, the anellosome described herein comprises a protein having an amino acid sequence having at least about 70%, 75%, 80%, 85%, 90%, 95%, 96%, 97%, 98%, 99%, or 100% sequence identity to the *Anellovirus* ORF2/3 amino acid sequence of Table 18.

In some embodiments, the polypeptide described herein comprises an amino acid sequence having at least about 70%, 75%, 80%, 85%, 90%, 95%, 96%, 97%, 98%, 99%, or 100% sequence identity to an *Anellovirus* ORF1 amino acid sequence described herein. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 2. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 4. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 6. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 8. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 10. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 12. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 14. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 16. In embodiments, the polypeptide described herein comprises an amino acid sequence having at least about 70%, 75%, 80%, 85%, 90%, 95%, 96%, 97%, 98%, 99%, or 100% sequence identity to the *Anellovirus* ORF1 amino acid sequence of Table 18.

In some embodiments, the polypeptide comprises an amino acid sequence (e.g., an ORF1, ORF1/1, ORF1/2, ORF2, ORF2/2, ORF2/3, ORF2t/3 sequence) as shown in any of Tables 2, 4, 6, 8, 10, 12, 14, 16, or 18, or a sequence having at least 70%, 75%, 80%, 85%, 90%, 95%, 96%, 97%, 98%, 99%, or 100% sequence identity thereto.

TABLE 1

Exemplary *Anellovirus* nucleic acid sequence (*Alphatorquevirus*, Clade 1)

Name TTV-CT30F
Genus/Clade *Alphatorquevirus*, Clade 1
Accession Number AB064597.1
Full Sequence: 3570 bp

```
1        10        20        30        40        50
|         |         |         |         |         |
ATTTTGTGCAGCCCGCCAATTCTCGTTCAAACAGGCCAATCAGGAGGCTC
TACGTACACTTCCTGGGGTGTGTCTTCGAAGAGTATATAAGCAGAGGCGG
TGACGAATGGTAGAGTTTTTCCTGGCCCGTCCGCGGCGAGAGCGCGAGCG
GAGCGAGCGATCGAGCGTCCCGTGGGCGGGTGCCGTAGGTGAGTTTACAC
ACCGCAGTCAAGGGGCAATTCGGGCTCGGGACTGGCCGGGCTATGGGCAA
GATTCTTAAAAAATTCCCCCGATCCCTCTGTCGCCAGGACATAAAAACAT
GCCGTGGAGACCGCCGGTGCATAGTGTCCAGGGGCGAGAGGATCAGTGGT
TCGCGAGCTTTTTTCACGGCCACGCTTCATTTTGCGGTTGCGGTGACGCT
GTTGGCCATCTTAATAGCATTGCTCCTCGCTTTCCTCGCGCCGGTCCACC
AAGGCCCCCTCCGGGGCTAGAGCAGCCTAACCCCCCGCAGCAGGGCCCGG
CCGGGCCCGGAGGGCCGCCCGCCATCTTGGCGCTGCCGGCTCCGCCCGCG
GAGCCTGACGACCCGCAGCCACGGCGTGGTGGTGGGGACGGTGGCGCCGC
CGCTGGCGCCGCAGGCGACCGTGGAGACCGAGACTACGACGAAGAAGAGC
TAGACGAGCTTTTCCGCGCCGCCGCCGAAGACGATTTGTAAGTAGGAGAT
GGCGCCGGCCTTACAGGCGCAGGAGGAGACGCGGGCGACGCAGACGCAGA
CGCAGACGCAGACATAAGCCCACCCTAGTACTCAGACAGTGGCAACCTGA
```

TABLE 1 -continued

Exemplary *Anellovirus* nucleic acid sequence (*Alphatorquevirus*, Clade 1)

```
CGTTATCAGACACTGTAAGATAACAGGACGGATGCCCCTCATTATCTGTG
GAAAGGGGTCCACCCAGTTCAACTACATCACCCACGCGGACGACATCACC
CCCAGGGGAGCCTCCTACGGGGGCAACTTCACAAACATGACTTTCTCCCT
GGAGGCAATATACGAACAGTTTCTGTACCACAGAAACAGGTGGTCAGCCT
CCAACCACGACCTCGAACTCTGCAGATACAAGGGTACCACCCTAAAACTG
TACAGGCACCCAGATGTAGACTACATAGTCACCTACAGCAGAACGGGACC
CTTTGAGATCAGCCACATGACCTACCTCAGCACTCACCCCCTTCTCATGC
TGCTAAACAAACACCACATAGTGGTGCCCAGCCTAAAGACTAAGCCCAGG
GGCAGAAAGGCCATAAAAGTCAGAATAAGACCCCCCAAACTCATGAACAA
CAAGTGGTACTTCACCAGAGACTTCTGTAACATAGGCCTCTTCCAGCTCT
GGGCCACAGGCTTAGAACTCAGAAACCCCTGGCTCAGAATGAGCACCCTG
AGCCCCTGCATAGGCTTCAATGTCCTTAAAAACAGCATTTACACAAACCT
CAGCAACCTACCTCAGCACAGAGAAGACAGACTTAACATTATTAACAACA
CATTACACCCACATGACATAACAGGACCAAACAATAAAAAATGGCAGTAC
ACATATACCAAACTCATGGCCCCCATTTACTATTCAGCAAACAGGGCCAG
CACCTATGACTTACTACGAGAGTATGGCCTCTACAGTCCATACTACCTAA
ACCCCACAAGGATAAACCTTGACTGGATGACCCCCTACACACACGTCAGG
TACAATCCACTAGTAGACAAGGGCTTCGGAAACAGAATATACATACAGTG
GTGCTCAGAGGCAGATGTAAGCTACAACAGGACTAAATCCAAGTGTCTCT
TACAAGACATGCCCCTGTTTTTCATGTGCTATGGCTACATAGACTGGGCA
ATTAAAAACACAGGGGTCTCCTCACTAGCGAGAGACGCCAGAATCTGCAT
CAGGTGTCCCTACACAGAGCCACAGCTGGTGGGCTCCACAGAAGACATAG
GGTTCGTACCCATCACAGAGACCTTCATGAGGGGCGACATGCCGGTACTT
GCACCATACATACCGTTGAGCTGGTTTTGCAAGTGGTATCCCAACATAGC
TCACCAGAAGGAAGTACTTGAGGCAATCATTTCCTGCAGCCCCTTCATGC
CCCGTGACCAGGGCATGAACGGTTGGGATATTACAATAGGTTACAAAATG
GACTTCTTATGGGGCGGTTCCCCTCTCCCCTCACAGCCAATCGACGACCC
CTGCCAGCAGGGAACCCACCCGATTCCCGACCCCGATAAGCACCCTCGCC
TCCTACAAGTGTCGAACCCGAAACTGCTCGGACCGAGGACAGTGTTCCAC
AAGTGGGACATCAGACGTGGGCAGTTTAGCAAAAGAAGTATTAAAAGAGT
GTCAGAATACTCATCGGATGATGAATCTCTTGCGCCAGGTCTCCCATCAA
AGCGAAACAAGCTCGACTCGGCCTTCAGAGGAGAAAACCCAGAGCAAAAA
GAATGCTATTCTCTCCTCAAAGCACTCGAGGAAGAAGAGACCCCAGAAGA
AGAAGAACCAGCACCCCAAGAAAAAGCCCAGAAAGAGGAGCTACTCCACC
AGCTCCAGCTCCAGAGACGCCACCAGCGAGTCCTCAGACGAGGGCTCAAG
CTCGTCTTTACAGACATCCTCCGACTCCGCCAGGGAGTCCACTGGAACCC
CGAGCTCACATAGAGCCCCCACCTTACATACCAGACCTACTTTTTCCCAA
TACTGGTAAAAAAAAAAAATTCTCTCCCTTCGACTGGGAAACGGAGGCCC
AGCTAGCAGGGATATTCAAGCGTCCTATGCGCTTCTATCCCTCAGACACC
CCTCACTACCCGTGGTTACCCCCCAAGCGCGATATCCCGAAAATATGTAA
CATAAACTTCAAAATAAAGCTGCAAGAGTGAGTGATTCGAGGCCCTCCTC
TGTTCACTTAGCGGTGTCTACCTCTTAAAGTCACCAAGCACTCCGAGCGT
CAGCGAGGAGTGCGACCCTCCACCAAGGGGCAACTTCCTCGGGGTCCGGC
GCTACGCGCTTCGCGCTGCGCCGGACGCCTCGGACCCCCCCCCGACCCGA
ATCGCTCGCGCGATTCGGACCTGCGGCCTCGGGGGGGGTCGGGGGCTTTA
CTAAACAGACTCCGAGTTGCCACTGGACTCAGGAGCTGTGAATCAGTAAC
GAAAGTGAGTGGGGCCAGACTTCGCCATAGGGCCTTTAACTTGGGGTCGT
CTGTCGGTGGCTTCCGGGTCCGCCTGGGCGCCGCCATTTTAGCTTTAGAC
GCCATTTTAGGCCCTCGCGGGCACCCGTAGGCGCGTTTTAATGACGTCAC
GGCAGCCATTTTGTCGTGACGTTTGAGACACGTGATGGGGGCGTGCCTAA
ACCCGGAAGCATCCCTGGTCACGTGACTCTGACGTCACGGCGGCCATTTT
GTGCTGTCCGCCATCTTGTGACTTCCTTCCGCTTTTTCAAAAAAAAAGAG
GAAGTATGACAGTAGCGGCGGGGGGGCGGCCGCGTTCGCGCGCCGCCCAC
CAGGGGGTGCTGCGCGCCCCCCCCCGCGCATGCGCGGGGCCCCCCCCCGG
GGGGGCTCCGCCCCCCCGGCCCCCCCCCGTGCTAAACCCACCGCGCATGC
GCGACCACGCCCCCGCCGCC (SEQ ID NO: 1)
```

Annotations:
Putative Domain Base range
TATA Box 84-90
Cap Site 107-114
Transcriptional Start Site 114
5' UTR Conserved Domain 177-247
ORF2 299-691
ORF2/2 299-687; 2137-2659
ORF2/3 299-687; 2339-2831
ORF2t/3 299-348; 2339-2831
ORF1 571-2613
ORF1/1 571-687; 2137-2613
ORF1/2 571-687; 2339-2659
Three open-reading frame region 2325-2610
Poly(A) Signal 2813-2818
GC-rich region 3415-3570

TABLE 2

| Exemplary *Anellovirus* amino acid sequences (*Alphatorquevirus*, Clade 1)<br>TTV-CT30F (*Alphatorquevirus* Clade 1) | |
|---|---|
| ORF2 | MPWRPPVHSVQGREDQWFASFFHGHASFCGCGDAVGHLNSIAPRFPRAGPPRPPPG<br>LEQPNPPQQGPAGPGGPPAILALPAPPAEPDDPQPRRGGGDGGAAAGAAGDRGDRD<br>YDEEELDELFRAAAEDDL (SEQ ID NO: 2) |
| ORF2/2 | MPWRPPVHSVQGREDQWFASFFHGHASFCGCGDAVGHLNSIAPRFPRAGPPRPPPG<br>LEQPNPPQQGPAGPGGPPAILALPAPPAEPDDPQPRRGGGDGGAAAGAAGDRGDRD<br>YDEEELDELFRAAAEDDFQSTTPASREPTRFPTPISTLASYKCRTRNCSDRGQCSTSG<br>TSDVGSLAKEVLKECQNTHRMMNLLRQVSHQSETSSTRPSEEKTQSKKNAILSSKH<br>SRKKRPQKKKNQHPKKKPRKRSYSTSSSSRDATSESSDEGSSSSLQTSSDSARESTGT<br>PSSHRAPTLHTRPTFSQYW (SEQ ID NO: 3) |
| ORF2/3 | MPWRPPVHSVQGREDQWFASFFHGHASFCGCGDAVGHLNSIAPRFPRAGPPRPPPG<br>LEQPNPPQQGPAGPGGPPAILALPAPPAEPDDPQPRRGGGDGGAAAGAAGDRGDRD<br>YDEEELDELFRAAAEDDLSPIKAKQARLGLQRRKPRAKRMLFSPQSTRGRRDPRRR<br>RTSTPRKSPERGATPPAPAPETPPASPQTRAQARLYRHPPTPPGSPLEPRAHIEPPPYIP<br>DLLFPNTGKKKKFSPFDWETEAQLAGIFKRPMRFYPSDTPHYPWLPPKRDIPKICNIN<br>FKIKLQE (SEQ ID NO: 4) |
| ORF2t/3 | MPWRPPVHSVQGREDQWSPIKAKQARLGLQRRKPRAKRMLFSPQSTRGRRDPRRR<br>RTSTPRKSPERGATPPAPAPETPPASPQTRAQARLYRHPPTPPGSPLEPRAHIEPPPYIP<br>DLLFPNTGKKKKFSPFDWETEAQLAGIFKRPMRFYPSDTPHYPWLPPKRDIPKICNIN<br>FKIKLQE (SEQ ID NO: 5) |
| ORF1 | TAWWWGRWRRRWRRRRPWRPRLRRRRARRAFPRRRRRRFVSRRWRRPYRRRRR<br>RGRRRRRRRRRHKPTLVLRQWQPDVIRHCKITGRMPLIICGKGSTQFNYITHADDIT<br>PRGASYGGNFTNMTFSLEAIYEQFLYHRNRWSASNHDLELCRYKGTTLKLYRHPD<br>VDYIVTYSRTGPFEISHMTYLSTHPLLMLLNKHHIVVPSLKTKPRGRKAIKVRIRPPK<br>LMNNKWYFTRDFCNIGLFQLWATGLELRNPWLRMSTLSPCIGFNVLKNSIYTNLSN<br>LPQHREDRLNIINNTLHPHDITGPNNKKWQYTYTKLMAPIYYSANRASTYDLLREY<br>GLYSPYYLNPTRINLDWMTPYTHVRYNPLVDKGFGNRIYIQWCSEADVSYNRTKSK<br>CLLQDMPLFFMCYGYIDWAIKNTGVSSLARDARICIRCPYTEPQLVGSTEDIGFVPIT<br>ETFMRGDMPVLAPYIPLSWFCKWYPNIAHQKEVLEAIISCSPFMPRDQGMNGWDITI<br>GYKMDFLWGGSPLPSQPIDDPCQQGTHPIPDPDKHPRLLQVSNPKLLGPRTVFHKW<br>DIRRGQFSKRSIKRVSEYSSDDESLAPGLPSKRNKLDSAFRGENPEQKECYSLLKALE<br>EEETPEEEEPAPQEKAQKEELLHQLQLQRRHQRVLRRGLKLVFTDILRLRQGVHWN<br>PELT (SEQ ID NO: 6) |
| ORF1/1 | TAWWWGRWRRRWRRRRPWRPRLRRRRARRAFPRRRRRRFPIDDPCQQGTHPIPDP<br>DKHPRLLQVSNPKLLGPRTVFHKWDIRRGQFSKRSIKRVSEYSSDDESLAPGLPSKR<br>NKLDSAFRGENPEQKECYSLLKALEEEETPEEEEPAPQEKAQKEELLHQLQLQRRH<br>QRVLRRGLKLVFTDILRLRQGVHWNPELT (SEQ ID NO: 7) |
| ORF1/2 | TAWWWGRWRRRWRRRRPWRPRLRRRRARRAFPRRRRRRFVSHQSETSSTRPSEE<br>KTQSKKNAILSSKHSRKKRPQKKKNQHPKKKPRKRSYSTSSSSRDATSESSDEGSSS<br>SLQTSSDSARESTGTPSSHRAPTLHTRPTFSQYW (SEQ ID NO: 8) |

TABLE 3

Exemplary *Anellovirus* nucleic acid sequence (*Alphatorquevirus*, Clade 2)

Name TTV-P13-1
Genus/Clade *Alphatorquevirus*, Clade 2
Accession Number KT163896.1
Full Sequence: 3451 bp

```
1        10        20        30        40        50
|        |         |         |         |         |
AATTTTGCTAAACAGACTCCGAGGTGCTCTTGGACACTGAGTGGGCGTAC
AGCAACGAAAGTGAGTGGGGCCAGACTTCGCCATAAGGCCTTTATCTTCG
GGTCTACATCATAATATAAAGATGTGCACTTCCGAATGGCTGAGTTTTTC
ACGCCATTCCGCAGCGGTGGAGCAGCGCAGCCACGACCCCCGCGTCCCGA
GGGCGGGTGCCGGAGGTGAGTTTACACACCGCAGTCAAGGGGCAATTCGG
GCTCGGGACTGGCCGGGCCCGGGCAAGGCTCTTAAAGCGAAACCATGTTC
CTCGGCAGGCCCTACCGCCACAGAAAGCGGCACCAGGCCGGCAAGAAAGG
GCCACTGCCACTGCCAAATCTGCAACCTGCACAGGAGAAACGGGCTGGTG
GTCCGTCCTTGATGGCCTCCGGACGCAGGGGATGGATGCCCCCGGACCTG
ACGGTCCAGGAGAGGGAGGATGCCTGGTGGACCAGCTTCTGCGCTAGCCA
CCGCAGCTTTTGTAGCTGCGACGATCCTGTGGGCCATATTAATACTCTCG
CCCGCGATAATAGTCCTCTGGCCCAGACTCCTACTACAACTTCAGGCCAG
GGGCCGCCGCCGCCGCCTACGCCTCCGCGGACGCCGGGGCCGCGCCCTGG
GTCTGCTCCGGACCAGGGGGGAAGGATCAGGGCCTCCTGGACCTACCCCC
TAGCCCCCGGAGGTCCCGGTAGCACGCCATGGCCTACTGGTGGGGCCGGA
GACGCCGGTGGCGCCGCTGGAGGAGGCGCCGGCGTCCTCTCCGCCGCCGC
CGGCGGTGGCGGAGAAGGCGACGCTGGCCCAGAAGGCGCCGGTGGAGGCG
```

TABLE 3 -continued

Exemplary *Anellovirus* nucleic acid sequence (*Alphatorquevirus*, Clade 2)

```
AAGGAGACGACGTGCGAGACCTGCTCGCCGCTATCGAAGGAGACGTGGGC
GCAGACGGGTAAGGAGACGCCGTCGCCCCCAGAAACTAGTACTGACTCAG
TGGAATCCCCAGACTGTGAGAAAGTGTGTTATTAGGGGGTTTCTGCCCCT
GTTCTTCTGCGGACAGGGGGCCTACCACAGAAACTTTACAGACCACTATG
ACGATGTGTTCCCCAAGGGACCCAGCGGAGGTGGGCACGGGAGCATGGTG
TTCAACCTGTCCTTTCTGTACCAAGAGTTTAAGAAGCACCACAATAAGTG
GTCGCGCAGCAACCTGGACTTTGACTTAGTGAGATACAAGGGCACAGTGA
TAAAGCTGTACAGACACCAGGACTTTGACTACATAGTGTGGATAAGCAGG
ACCCCTCCCTTCCAGGAGAGCCTGCTCACAGTAATGACCCACCAGCCCAG
CGTCATGCTGCAGGCAAAAAAGTGCATAATAGTAAAGAGCTACAGGACCC
ACCCGGGGGGCAAACCCTATGTAACTGCAAAAGTTAGGCCCCCCAGACTC
CTAACTGACAAGTGGTACTTCCAGTCAGACTTCTGCAACGTTCCGCTTTT
TAGCCTACAGTTTGCCCTTGCGGAACTGCGGTTTCCGATCTGCTCACCAC
AAACTGACACCAATTGCATTAACTTCCTGGTGTTAGATGACATCTACTAC
AAGTTTCTAGATAATAAGCCTAAACAGAGTTCAGACCCTAATGACGAAAA
CAGAATAAAATTCTGGCACGGCCTATGGTCCACTATGAGATATTTAAACA
CCACCTACATAAACACACTGTTTCCAGGCACAGACAGTCTAGTGGCCGCC
AAAGATACTGACAATAGTGTAAATAAATACCCCAGCACAGCCACTAAACA
GCCCTACAAAGACAGTCAGTACATGCAAAATATATGGAATACATCAAAAA
TACATGCCTTATATACGTGGGTAGCAGAGACAAACTACAAAAGACTGCAG
GCCTACTACACACAGACCTACGGAGGCTACCAGAGACAATTTTTCACAGG
AAAACAGTACTGGGACTACAGAGTAGGCATGTTTAGTCCAGCCTTCCTGA
GTCCCAGCAGACTAAATCCCCAGAACCCAGGGGCATACACAGAGGTCTCC
```

TABLE 3 -continued

| Exemplary *Anellovirus* nucleic acid sequence (*Alphatorquevirus*, Clade 2) |
|---|
| TACAACCCCTGGACAGACGAGGGCACGGGCAACGTAGTGTGCCTGCAGTA<br>TCTGACTAAAGAGACCTCAGACTACAAACCAGGTGGTGGGAGCAAGTTCT<br>GCATAGAAGGTGTGCCTCTATGGGCAGCGCTGGTGGGATACGTAGACATG<br>TGTAAAAAAGAGGGCAAGGACCCGGGCATCAGACTAAACTGTCTCCTGTT<br>AGTCAAGTGTCCCTATACAAAGCCTCAGCTGTATGACAAAAAAAACCCCG<br>AGAAACTGTTTGTACCTTACTCCTATAACTTTGGGCACGGCAAGATGCCG<br>GGGGGAGACAAATACATACCCATAGAGTTCAAAGACAGGTGGTACCCCTG<br>CCTGCTCCACCAAGAGGAGTGGATAGAGGACATTGTCAGGTCGGGACCCT<br>TCGTTCCAAAAGACATGCCCAGCAGCGTCACCTGCATGATGAGGTACAGC<br>TCTCTTTTTAACTGGGGCGGTAATATAATCCAAGAACAGGCCGTGGAAGA<br>CCCCTGTAAGAAAGGCACCTTCGTCGTTCCCGGAACCAGTGGCATCGCTC<br>GCATACTACAAGTCAGCAACCCGGCCAAGCAGACCCCCACGACAACCTGG<br>CACTCGTGGGACTGGAGACGATCCCTCTTTACAGAGACGGGTCTTAAAAG<br>AATGCGCGAACAACAACCATATGATGAACTGTCTTATACGGGCCCTAAAA<br>AGCCAAAACTGTCCCTTCCCGCAGGGCCCGCCGTCCCCGGTGCCGCCGTC<br>GCCTCCTCCTGGTGGGAAACAAAACAGGTCACCTCGCCAGACGTCAGCGA<br>GACGGAGACCGAAGCAGAAGCCCACCAAGAGGAAGAGACGGAGCCGGAGG<br>AGGGAGTCCAGCTCCAGCAGCTGTGGGAGCAGCAACTCCTGCAAAAGCGA<br>CAGCTGGGAGTCGTGTTCCAGCAACTCCTCCGACTCAGACAGGGGGCGGA<br>GATCCACCCGGGCCTCGTATAATTCCTGGGCCCCAGAACCCGTACCTGCT<br>TTTCCCGGAGCAGGCCCCTCCAAAAGTGCCTATTTTTGACCCCTTTGGTC<br>AGAAAACAGAGCTAGAGCTGTGCGGCTGCTTCGACAGGCCGCCCAGGAAC<br>AACCCCTACGACCACCCCTTCTACCCCTGGCTGCCCAAAGAGCCTCCCTC |

TABLE 3 -continued

| Exemplary *Anellovirus* nucleic acid sequence (*Alphatorquevirus*, Clade 2) |
|---|
| CTACTACCAGGGCTACAAAGTGTCTTTCAAACTAGGGTTCCACCCAGACA<br>AGCATGTGTGAACCCCGCCAATAAACCACTGCTGCTACACTGATTCTTAG<br>GCCGTGGGAGTCTCACTGGTCGGTGTCTACCTCTTAAGGTCACTAAGCAC<br>TCCGAGCGTTAGCGAGGAGTGCGACCCTACCCCCTGGGCCCACTTCTTCG<br>GAGCCGCGCGCTACGCCTTCGGCTGCGCGCGGCACCTCAGACCCCCGCTC<br>GTGCTGACACGCTTGCGCGTGTCAGACCACTTCGGGCTCGCGGGGGTCGG<br>G (SEQ ID NO: 9) |

Annotations:
Putative Domain Base range
TATA Box 112-119
Initiator Element 128-148
Transcriptional Start Site 148
5' UTR Conserved Domain 204-273
ORF2 412-912
ORF2/2 412-908; 2490-3039
ORF2/3 412-908; 2725-3208
ORF1 729-2972
ORF1/1 729-908; 2490-2972
ORF1/2 729-908; 2725-3039
Three open-reading frame region 2699-2969
Poly(A) Signal 3220-3225
GC-rich region 3302-3541

TABLE 4

| Exemplary *Anellovirus* amino acid sequences (*Alphatorquevirus*, Clade 2) TTV-P13-1 (*Alphatorquevirus* Clade 2) | |
|---|---|
| ORF2 | MASGRRGWMPPDLTVQEREDAWWTSFCASHRSFCSCDDPVGHINTLARDN<br>SPLAQTPTTTSGQGPPPPPTPPRTPGPRPGSAPDQGGRIRASWTYPLAPGGPG<br>STPWPTGGAGDAGGAAGGGAGVLSAAAGGGGEGDAGPEGAGGGEGDDV<br>RDLLAAIEGDVGADG (SEQ ID NO: 10) |
| ORF2/2 | MASGRRGWMPPDLTVQEREDAWWTSFCASHRSFCSCDDPVGHINTLARDN<br>SPLAQTPTTTSGQGPPPPPTPPRTPGPRPGSAPDQGGRIRASWTYPLAPGGPG<br>STPWPTGGAGDAGGAAGGGAGVLSAAAGGGGEGDAGPEGAGGGEGDDV<br>RDLLAAIEGDVGADGPWKTPVRKAPSSFPEPVASLAYYKSATRPSRPPRQPG<br>TRGTGDDPSLQRRVLKECANNNHMMNCLIRALKSQNCPFPQGPPSPVPPSPP<br>PGGKQNRSPRQTSARRRPKQKPTKRKRRSRRRESSSSSCGSSNSCKSDSWES<br>CSSNSSDSDRGRRSTRASYNSWAPEPVPAFPGAGPSKSAYF (SEQ ID NO: 11) |
| ORF2/3 | MASGRRGWMPPDLTVQEREDAWWTSFCASHRSFCSCDDPVGHINTLARDN<br>SPLAQTPTTTSGQGPPPPPTPPRTPGPRPGSAPDQGGRIRASWTYPLAPGGPG<br>STPWPTGGAGDAGGAAGGGAGVLSAAAGGGGEGDAGPEGAGGGEGDDV<br>RDLLAAIEGDVGADGARRPRCRRRLLLVGNKTGHLARRQRDGDRSRSPPRG<br>RDGAGGGSPAPAAVGAATPAKATAGSRVPATPPTQTGGGDPPGPRIIPGPQN<br>PYLLFPEQAPPKVPIFDPFGQKTELELCGCFDRPPRNNPYDHPFYPWLPKEPP<br>SYYQGYKVSFKLGFHPDKHV (SEQ ID NO: 12) |
| ORF1 | MAYWWGRRRRWRRWRRRRRPLRRRRRWRRRRRWPRRRRWRRRRRRARP<br>ARRYRRRRGRRRVRRRRRPQKLVLTQWNPQTVRKCVIRGFLPLFFCGQGAY<br>HRNFTDHYDDVFPKGPSGGGHGSMVFNLSFLYQEFKKHHNKWSRSNLDFD<br>LVRYKGTVIKLYRHQDFDYIVWISRTPPFQESLLTVMTHQPSVMLQAKKCII<br>VKSYRTHPGGKPYVTAKVRPPRLLTDKWYFQSDFCNVPLFSLQFALAELRF<br>PICSPQTDTNCINFLVLDDIYYKFLDNKPKQSSDPNDENRIKFWHGLWSTMR<br>YLNTTYINTLFPGTDSLVAAKDTDNSVNKYPSTATKQPYKDSQYMQNIWNT<br>SKIHALYTWVAETNYKRLQAYYTQTYGGYQRQFFTGKQYWDYRVGMFSP<br>AFLSPSRLNPQNPGAYTEVSYNPWTDEGTGNVVCLQYLTKETSDYKPGGGS<br>KFCIEGVPLWAALVGYVDMCKKEGKDPGIRLNCLLLVKCPYTKPQLYDKK<br>NPEKLFVPYSYNFGHGKMPGGDKYIPIEFKDRWYPCLLHQEEWIEDIVRSGP<br>FVPKDMPSSVTCMMRYSSLFNWGGNIIQEQAVEDPCKKGTFVVPGTSGIARI<br>LQVSNPAKQTPTTTWHSWDWRRSLFTETGLKRMREQQPYDELSYTGPKKP<br>KLSLPAGPAVPGAAVASSWWETKQVTSPDVSETETEAEAHQEEETEPEEGV<br>QLQQLWEQQLLQKRQLGVVFQQLLRLRQGAEIHPGLV (SEQ ID NO: 13) |

TABLE 4-continued

Exemplary *Anellovirus* amino acid sequences
(*Alphatorquevirus*, Clade 2)
TTV-P13-1 (*Alphatorquevirus* Clade 2)

| | |
|---|---|
| ORF1/1 | MAYWWGRRRRWRRWRRRRRPLRRRRRWRRRRRWPRRRRWRRRRRRARP<br>ARRYRRRRGRRRAVEDPCKKGTFVVPGTSGIARILQVSNPAKQTPTTTWHS<br>WDWRRSLFTETGLKRMREQQPYDELSYTGPKKPKLSLPAGPAVPGAAVASS<br>WWETKQVTSPDVSETETEAEAHQEEETEPEEGVQLQQLWEQQLLQKRQLG<br>VVFQQLLRLRQGAEIHPGLV (SEQ ID NO: 14) |
| ORF1/2 | MAYWWGRRRRWRRWRRRRRPLRRRRRWRRRRRWPRRRRWRRRRRRARP<br>ARRYRRRRGRRRGPPSPVPPSPPPGGKQNRSPRQTSARRRPKQKPTKRKRRS<br>RRRESSSSSCGSSNSCKSDSWESCSSNSSDSDRGRRSTRASYNSWAPEPVPAF<br>PGAGPSKSAYF (SEQ ID NO: 15) |

TABLE 5

Exemplary *Anellovirus* nucleic acid sequence
(*Alphatorquevirus*, Clade 3)

Name TTV-tth8
Genus/Clade *Alphatorquevirus*, Clade 3
Accession Number AJ620231.1
Full Sequence: 3753 bp

```
1        10        20        30        40        50
|         |         |         |         |         |
TGCTACGTCACTAACCCACGTGTCCTCTACAGGCCAATCGCAGTCTATGT
CGTGCACTTCCTGGGCATGGTCTACATAATTATATAAATGCTTGCACTTC
CGAATGGCTGAGTTTTTGCTGCCCGTCCGCGGAGAGGAGCCACGGCAGGG
GATCCGAACGTCCTGAGGGCGGGTGCCGGAGGTGAGTTTACACACCGAAG
TCAAGGGGCAATTCGGGCTCAGGACTGGCCGGGCTTTGGGCAAGGCTCTT
AAAAATGCACTTTTCTCGAATAAGCAGAAAGAAAAGGAAAGTGCTACTGC
TTTGCGTGCCAGCAGCTAAGAAAAAACCAACTGCTATGAGCTTCTGGAAA
CCTCCGGTACACAATGTCACGGGGATCCAACGCATGTGGTATGAGTCCTT
TCACCGTGGCCACGCTTCTTTTTGTGGTTGTGGGAATCCTATACTTCACA
TTACTGCACTTGCTGAAACATATGGCCATCCAACAGGCCCGAGACCTTCT
GGGCCACCGGGAGTAGACCCCAACCCCCACATCCGTAGAGCCAGGCCTGC
CCCGGCCGCTCCGGAGCCCTCACAGGTTGATTCGAGACCAGCCCTGACAT
GGCATGGGGATGGTGGAAGCGACGGAGGCGCTGGTGGTTCCGGAAGCGGT
GGACCCGTGGCAGACTTCGCAGACGATGGCCTCGATCAGCTCGTCGCCGC
CCTAGACGACGAAGAGTAAGGAGGCGCAGACGGTGGAGGAGGGGGAGACG
AAAAACAAGGACTTACAGACGCAGGAGACGCTTTAGACGCAGGGGACGAA
AAGCAAAACTTATAATAAAACTGTGGCAACCTGCAGTAATTAAAAGATGC
AGAATAAAGGGATACATACCACTGATTATAAGTGGGAACGGTACCTTTGC
CACAAACTTTACCAGTCACATAAATGACAGAATAATGAAAGGCCCCTTCG
GGGGAGGACACAGCACTATGAGGTTCAGCCTCTACATTTTGTTTGAGGAG
CACCTCAGACACATGAACTTCTGGACCAGAAGCAACGATAACCTAGAGCT
AACCAGATACTTGGGGGCTTCAGTAAAAATATACAGGCACCCAGACCAAG
ACTTTATAGTAATATACAACAGAAGAACCCCTCTAGGAGGCAACATCTAC
ACAGCACCCTCTCTACACCCAGGCAATGCCATTTTAGCAAAACACAAAAT
ATTAGTACCAAGTTTACAGACAAGACCAAAGGGTAGAAAAGCAATTAGAC
TAAGAATAGCACCCCCCACACTCTTTACAGACAAGTGGTACTTTCAAAAG
GACATAGCCGACCTCACCCTTTTCAACATCATGGCAGTTGAGGCTGACTT
GCGGTTTCCGTTCTGCTCACCACAAACTGACAACACTTGCATCAGCTTCC
AGGTCCTTAGTTCCGTTTACAACAACTACCTCAGTATTAATACCTTTAAT
AATGACAACTCAGACTCAAAGTTAAAAGAATTTTTAAATAAAGCATTTCC
AACAACAGGCACAAAAGGAACAAGTTTAAATGCACTAAATACATTTAGAA
CAGAAGGATGCATAAGTCACCCACAACTAAAAAAACCAAACCCACAAATA
AACAAACCATTAGAGTCACAATACTTTGCACCTTTAGATGCCCTCTGGGG
AGACCCCATATACTATAATGATCTAAATGAAAACAAAAGTTTGAACGATA
TCATTGAGAAAATACTAATAAAAAACATGATTACATACCATGCAAAACTA
AGAGAATTTCCAAATTCATACCAAGGAAACAAGGCCTTTTGCCACCTAAC
AGGCATATACAGCCCACCATACCTAAACCAAGGCAGAATATCTCCAGAAA
TATTTGGACTGTACACAGAAATAATTTACAACCCTTACACAGACAAAGGA
ACTGGAAACAAAGTATGGATGGACCCACTAACTAAAGAGAACAACATATA
TAAAGAAGGACAGAGCAAATGCCTACTGACTGACATGCCCCTATGGACTT
TACTTTTTGGATATACAGACTGGTGTAAAAAGGACACTAATAACTGGGAC
TTACCACTAAACTACAGACTAGTACTAATATGCCCTTATACCTTTCCAAA
ATTGTACAATGAAAAAGTAAAAGACTATGGGTACATCCCGTACTCCTACA
AATTCGGAGCGGGTCAGATGCCAGACGGCAGCAACTACATACCCTTTCAG
TTTAGAGCAAAGTGGTACCCCACAGTACTACACCAGCAACAGGTAATGGA
GGACATAAGCAGGAGCGGGCCCTTTGCACCTAAGGTAGAAAAACCAAGCA
CTCAGCTGGTAATGAAGTACTGTTTTAACTTTAACTGGGGCGGTAACCCT
ATCATTGAACAGATTGTTAAAGACCCCAGCTTCCAGCCCACCTATGAAAT
ACCCGGTACCGGTAACATCCCTAGAAGAATACAAGTCATCGACCCGCGGG
TCCTGGGACCGCACTACTCGTTCCGGTCATGGGACATGCGCAGACACACA
```

TABLE 5 -continued

Exemplary *Anellovirus* nucleic acid sequence
(*Alphatorquevirus*, Clade 3)

```
TTTAGCAGAGCAAGTATTAAGAGAGTGTCAGAACAACAAGAAACTTCTGA
CCTTGTATTCTCAGGCCCAAAAAAGCCTCGGGTCGACATCCCAAAACAAG
AAACCCAAGAAGAAAGCTCACATTCACTCCAAAGAGAATCGAGACCGTGG
GAGACCGAGGAAGAAAGCGAGACAGAAGCCCTCTCGCAAGAGAGCCAAGA
GGTCCCCTTCCAACAGCAGTTGCAGCAGCAGTACCAAGAGCAGCTCAAGC
TCAGACAGGGAATCAAAGTCCTCTTCGAGCAGCTCATAAGGACCCAACAA
GGGGTCCATGTAAACCCATGCCTACGGTAGGTCCCAGGCAGTGGCTGTTT
CCAGAGAGAAAGCCAGCCCCAGCTCCTAGCAGTGGAGACTGGGCCATGGA
GTTTCTCGCAGCAAAAATATTTGATAGGCCAGTTAGAAGCAACCTTAAAG
ATACCCCTTACTACCCATATGTTAAAAACCAATACAATGTCTACTTTGAC
CTTAAATTTGAATAAACAGCAGCTTCAAACTTGCAAGGCCGTGGGAGTTT
CACTGGTCGGTGTCTACCTCTAAAGGTCACTAAGCACTCCGAGCGTAAGC
GAGGAGTGCGACCCTCCCCCCTGGAACAACTTCTTCGGAGTCCGGCGCTA
CGCCTTCGGCTGCGCCGGACACCTCAGACCCCCCCTCCACCCGAAACGCT
TGCGCGTTTCGGACCTTCGGCGTCGGGGGGGTCGGGAGCTTTATTAAACG
GACTCCGAAGTGCTCTTGGACACTGAGGGGGTGAACAGCAACGAAAGTGA
GTGGGGCCAGACTTCGCCATAAGGCCTTTATCTTCTTGCCATTTGTCAGT
GTCCGGGGTCGCCATAGGCTTCGGGCTCGTTTTTAGGCCTTCCGGACTAC
AAAAATCGCCATTTTGGTGACGTCACGGCCGCCATCTTAAGTAGTTGAGG
CGGACGGTGGCGTGAGTTCAAAGGTCACCATCAGCCACACCTACTCAAAA
TGGTGGACAATTTCTTCCGGGTCAAAGGTTACAGCCGCCATGTTAAAACA
CGTGACGTATGACGTCACGGCCGCCATTTTGTGACACAAGATGGCCGACT
TCCTTCCTCTTTTTCAAAAAAAAGCGGAAGTGCCGCCGCGGCGGCGGGGG
GCGGCGCGCTGCGCGCGCCGCCCAGTAGGGGGAGCCATGCGCCCCCCCCC
GCGCATGCGCGGGGCCCCCCCCCGCGGGGGGCTCCGCCCCCCGGCCCCCC
CCG (SEQ ID NO: 16)
```

Annotations:

Putative Domain Base range
TATA Box 83-88
Cap Site 104-111
Transcriptional Start Site 111
5' UTR Conserved Domain 170-240
ORF2 336-719
ORF2/2 336-715; 2363-2789
ORF2/3 336-715; 2565-3015
ORF2t/3 336-388; 2565-3015
ORF1 599-2830
ORF1/1 599-715; 2363-2830
ORF1/2 599-715; 2565-2789
Three open-reading frame region 2551-2786
Poly(A) Signal 3011-3016
GC-rich region 3632-3753

TABLE 6

| Exemplary *Anellovirus* amino acid sequences (*Alphatorquevirus*, Clade 3) TTV-tth8 (*Alphatorquevirus* Clade 3) | |
|---|---|
| ORF2 | MSFWKPPVHNVTGIQRMWYESFHRGHASFCGCGNPILHITALAETYGHPTGPRPSG PPGVDPNPHIRRARPAPAAPEPSQVDSRPALTWHGDGGSDGGAGGSGSGGPVADFA DDGLDQLVAALDDEE (SEQ ID NO: 17) |
| ORF2/2 | MSFWKPPVHNVTGIQRMWYESFHRGHASFCGCGNPILHITALAETYGHPTGPRPSG PPGVDPNPHIRRARPAPAAPEPSQVDSRPALTWHGDGGSDGGAGGSGSGGPVADFA DDGLDQLVAALDDEELLKTPASSPPMKYPVPVTSLEEYKSSTRGSWDRTTRSGHGT CADTHLAEQVLRECQNNKKLLTLYSQAQKSLGSTSQNKKPKKKAHIHSKENRDRG RPRKKARQKPSRKRAKRSPSNSSCSSSTKSSSSSDRESKSSSSSS (SEQ ID NO: 18) |
| ORF2/3 | MSFWKPPVHNVTGIQRMWYESFHRGHASFCGCGNPILHITALAETYGHPTGPRPSG PPGVDPNPHIRRARPAPAAPEPSQVDSRPALTWHGDGGSDGGAGGSGSGGPVADFA DDGLDQLVAALDDEEPKKASGRHPKTRNPRRKLTFTPKRIETVGDRGRKRDRSPLA REPRGPLPTAVAAAVPRAAQAQTGNQSPLRAAHKDPTRGPCKPMPTVGPRQWLFP ERKPAPAPSSGDWAMEFLAAKIFDRPVRSNLKDTPYYPYVKNQYNVYFDLKFE (SEQ ID NO: 19) |
| ORF2t/3 | MSFWKPPVHNVTGIQRMWPKKASGRHPKTRNPRRKLTFTPKRIETVGDRGRKRDR SPLAREPRGPLPTAVAAAVPRAAQAQTGNQSPLRAAHKDPTRGPCKPMPTVGPRQ WLFPERKPAPAPSSGDWAMEFLAAKIFDRPVRSNLKDTPYYPYVKNQYNVYFDLK FE (SEQ ID NO: 20) |
| ORF1 | MAWGWWKRRRRWWFRKRWTRGRLRRRWPRSARRRPRRRRVRRRRRWRRGRRK TRTYRRRRRFRRRGRKAKLIIKLWQPAVIKRCRIKGYIPLIISGNGTFATNFTSHINDR IMKGPFGGGHSTMRFSLYILFEEHLRHMNFWTRSNDNLELTRYLGASVKIYRHPDQ DFIVIYNRRTPLGGNIYTAPSLHPGNAILAKHKILVPSLQTRPKGRKAIRLRIAPPTLFT DKWYFQKDIADLTLFNIMAVEADLRFPFCSPQTDNTCISFQVLSSVYNNYLSINTFN NDNSDSKLKEFLNKAFPTTGTKGTSLNALNTFRTEGCISHPQLKKPNPQINKPLESQ YFAPLDALWGDPIYYNDLNENKSLNDIIEKILIKNMITYHAKLREFPNSYQGNKAFC HLTGIYSPPYLNQGRISPEIFGLYTEIIYNPYTDKGTGNKVWMDPLTKENNIYKEGQS KCLLTDMPLWTLLFGYTDWCKKDTNNWDLPLNYRLVLICPYTFPKLYNEKVKDY GYIPYSYKFGAGQMPDGSNYIPFQFRAKWYPTVLHQQQVMEDISRSGPFAPKVEKP STQLVMKYCFNFNWGGNPIIEQIVKDPSFQPTYEIPGTGNIPRRIQVIDPRVLGPHYSF RSWDMRRHTFSRASIKRVSEQQETSDLVFSGPKKPRVDIPKQETQEESSHSLQRESR PWETEEESETEALSQESQEVPFQQQLQQQYQEQLKLRQGIKVLFEQLIRTQQGVHV NPCLR (SEQ ID NO: 21) |
| ORF1/1 | MAWGWWKRRRRWWFRKRWTRGRLRRRWPRSARRRPRRRRIVKDPSFQPTYEIPG TGNIPRRIQVIDPRVLGPHYSFRSWDMRRHTFSRASIKRVSEQQETSDLVFSGPKKPR VDIPKQETQEESSHSLQRESRPWETEEESETEALSQESQEVPFQQQLQQQYQEQLKL RQGIKVLFEQLIRTQQGVHVNPCLR (SEQ ID NO: 22) |
| ORF1/2 | MAWGWWKRRRRWWFRKRWTRGRLRRRWPRSARRRPRRRRAQKSLGSTSQNKK PKKKAHIHSKENRDRGRPRKKARQKPSRKRAKRSPSNSSCSSSTKSSSSSDRESKSSS SSS (SEQ ID NO: 23) |

TABLE 7

Exemplary *Anellovirus* nucleic acid sequence (*Alphatorquevirus*, Clade 4)

| | |
|---|---|
| Name | TTV-HD20a |
| Genus/Clade | *Alphatorquevirus*, Clade 4 |
| Accession Number | FR751492.1 |
| Full Sequence: 3878 bp | |

```
1         10        20        30        40        50
|         |         |         |         |         |
AAATACGTCACTAACCACGTGACTCCCACAGGCCAACCACAGTCTATGTC

GTGCACTTCCTGGGCATGGTCTACGTGATAATATAAAGCGGTGCACTTCC

GAATGGCTGAGTTTTCCACGCCCGTCCGCAGCGAGATCGCGACGTAGGAG

CGATCGAGCGTCCCGAGGGCGGGTGCCGGAGGTGAGTTTACACACCGCAG

TCAAGGGGCAATTCGGGCTCGGGAGGCCGGGCCATGGGCAAGGCTCTTAA

AAAGCTATGTTTCTCGGTAAAATCTACAGGAAGAAAAGGAAACTGCTTCT

GCAGGCTGTGCGTGCTCCGCAGACGCCATCTTCCATGAGCCGCTGCTGGT

GTCCCCCTCGGGGTGATGTCTCCTCCCGCGAGTCTCGATGGTACGAGGCG
```

TABLE 7-continued

Exemplary *Anellovirus* nucleic acid sequence (*Alphatorquevirus*, Clade 4)

```
GTTCGAGGAAGCCACGATGCTTTTTGTGGCTGTAGTGATCCTATTCTTCA

TCTTTCTCGTCTGGCTGCACGTTTTAACCATCAGGGACCTCCGACGCCCC

CCACGGACGACCGTGCGCCGCAGAATACCCCAGTGAGACGCCTGCTGCCT

CTCCCCAGCTACCCCGGCGAGGGTCCCCAGGCTAGATGGCCTGGTGGGGA

TGGAGGCGCCGCTGGTGGCGACCGAAGAGAAGGTGGAGATGGCGGCGCGC

GCGCCGCCGAAGACGAGTACCAGCCCGAAGACCTAGACGAGCTTTTCGGC

GCTATCGAACAAGAACAGTAAGGAGGAGGCGAAGGGGGAGGCGGAGGGGC

TACCGGCGCCGTTACAGACTGAGACGCTATGCCAGACGCAGGTTCCGACG

CAAAAAGATAGTACTGACTCAGTGGAACCCCCAGACTACCAGAAAATGTA

TAATAAGGGGCATGATGCCAGTACTGTGGGCCGGCATGGGTACGGGGGGC

AGAAACTATGCAGTGAGGTCAGATGACTATGTGGTGAACAAAGGGTTCGG

GGGCTCCTTCGCCACGGAGACCTTCTCCCTGAAGGTTCTCTATGACCAGT
```

TABLE 7-continued

| Exemplary *Anellovirus* nucleic acid sequence (*Alphatorquevirus*, Clade 4) |
|---|
| TTCAAAGGGGCTTCAACAGGTGGTCCCACACTAACGAGGACCTAGACCTG |
| GCCCGCTACAGGGGCTGCAGGTGGACTTTTTACAGACATAAAGACACAGA |
| CTTTATAGTGTACTTTACAAACAATCCTCCCATGAAGACCAACCAGTTCT |
| CCGCGCCCCTGACGACCCCCGGCATGCTCATGCGCAGTAAATACAAAGTC |
| CTCATTCCCAGCTTCCAGACCAGACCCAAGGGTCGCAAAACAGTAACCGT |
| TAAAATAAGACCCCCCAAACTATTTCAAGACAAGTGGTACACCCAGCAGG |
| ACCTGTGTTCAGTTCCTCTTGTCCAACTGAACGTGACCGCAGCTGATTTC |
| ACACATCCGTTCGGCTCACCACTAACTGAAACTCCTTGCGTAGAGTTCCA |
| GGTGCTGGGTGACTTGTACAATACATGTCTCAATATCGACCTTCCGCAAT |
| TTAGTGAATTAGGAGAAATAACTAGTGCCTACTCAAAACCAAACTCAAAT |
| AACCTAAAAGAATTATACAAAGAATTGTTCACAAAAGCCACATCAGGACA |
| CTACTGGCAGACATTCATAACCAACAGCATGGTCAGAGCACACATAGATG |
| CAGACAAAGCTAAAGAAGCACAAAGAGCATCCACCACACCCTCATACAAC |
| AATGACCCCTTCCCCACAATACCTGTTAAATCAGAGTTTGCACAGTGGAA |
| AAAGAAATTCACAGACACTAGAGACAGCCCCTTTCTTTTTGCCACTTACC |
| ATCCCGAAGCTATAAAAGACACAATTATGAAAATGAGAGAGAACAACTTT |
| AAGCTAGAGACAGGACCCAATGACAAGTATGGAGACTACACAGCACAGTA |
| CCAAGGAAACACACACATGCTAGACTACTACCTTGGCTTTTACAGCCCCA |
| TATTCCTCTCAGATGGAAGGTCTAACGTAGAATTCTTCACTGCCTACAGA |
| GACATAGTATACAATCCCTTCTTAGACAAGGCCCAGGGCAACATGGTGTG |
| GTTTCAGTACCACACAAAGACAGACAACAAGTTTAAAAAACCAGAGTGCC |
| ACTGGGAAATCAAAGACATGCCCCTGTGGGCCCTCCTAAACGGATATGTA |
| GACTACTTAGAGACTCAAATACAGTATGGTGACCTCAGTAAAGAAGGGAA |
| AGTCCTCATCAGGTGTCCCTACACCAAGCCAGCACTAGTAGACCCCAGAG |
| ACGACACTGCAGGATATGTAGTCTACAACAGAAACTTTGGCAGAGGCAAG |
| TGGATAGACGGAGGGGGCTACATCCCCCTGCACGAGAGGACAAAATGGTA |
| CGTGATGCTCAGATACCAGACGGACGTCTTCCATGACATAGTGACCTGTG |
| GGCCCTGGCAGTACAGAGACGACAACAAAAACAGCCAGCTAGTGGCCAAA |
| TACCGCTTCAGCTTTATATGGGGAGGTAACACTGTCCACTCTCAGGTCAT |
| CAGAAACCCGTGCAAAGACAACCAAGTATCCGGTCCCCGTCGACAGCCTA |
| GGGATATACAAGTCGTTGACCCGCAACGCATCACGCCGCCGTGGGTCCTC |
| CACAGCTTCGACCAGCGAAGAGGCCTCTTTACTGAAACAGCTCTCAGGCG |
| CCTGCTCCAGGAACCACTACCTGGCGAGTATGCTGTTAGCACCCTCAGGA |
| CACCCCTCCTCTTTCTACCCTCAGAATACCAGCGAGAAGACGGCGCTGCA |
| GAAAGCGCCTCAGGTTCACCGGCCAAAAGACCCCGTATCTGGTCAGAAGA |
| GAGTCAGACGGAGACGATCTCCTCGGAGGAGAACCCGGCGGAGACGACGA |
| GGGAGCTCCTCCAGCGAAAGCTCCGAGAGCAGCGAGCACTCCAGTTCCAA |
| CTCCAGCACTTCGCGGTCCAACTCGCCAAGACCCAGGCGAATCTCCACGT |
| AAACCCCCTGTTATCTTTCCCGCAATGAATAAGGTCTTTCTGTTTCCCCC |
| AGAGGGTCCCAAGCCCATCCTGGGCAAAGAGGCCTGGCAGGACGAGTACG |
| AGACCTGCAGGGTCTGGAACAGACCTGCCAGAACCCACCACACAGACACC |
| CCCTTCTATCCCTGGGCCCCCCACAAGTTCCATGTAAGCTTCAAACTTGG |
| CTTCCAATAAAATTACTAGGCCGTGGAACTCTCACTGGTCGGTGTCTACC |
| TCTTAAGGTCACTAAGCACTCCGAGCGTCAGCGAGGAGTGCGACCCTCTA |
| CCCTGGTGCAACGCCCTCGGCGGCCGCGCGCTACGCCTTCGGCTGCGCGC |
| GGCACCTCGGACCCCCGCTCGTGCTGACGCGCTCGCGCGCGTCAGACCAC |
| TTCGGGCTCGCGGGGGTCGGGAATTTTGCTAAACAGACTCCGAGTTGCCA |
| TTGGACACTGTAGCTGTGAATCAGTAACGAAAGTGAGTGGGGCCAGACTT |
| CGCCATAGGGCCTTTATCTTCTTGCCATTGGTCCGTGTAGGGGGTCGCCA |
| TAGGCTTCGACCTCCCTTTTAGGCCTTCCGGACTACAAAAATGGCGGATT |
| CAGTGACGTCACGGCCGCCATTTTAAGTAGGTGCCGTCCAGGACTGCAGT |
| TCCGGGTCAGAGTGCATCCTCGGCGGAACCTGCACAAAATGGCGGTCAAT |
| ATCTTCCGGGTCAAAGGTCACACCTACGTCATAAGTCACGTGACTGGGTC |
| CTGCTACGTCATATGCGGAAGTAGGCCCCGCCACGTGACTCGTCACGTGG |
| GCGCTGCGTCACGGCGGCCATTTTGTATCACAAAATGGCGGACTTCCTTC |
| CTCTTTTTTAAAAATAACGGCCCAGCGGCGGCGCGCGCGCTTCGCGCGCG |
| CGCCGGGGGGCTCCGCCCCCCCCCGCGCATGCGCGGGGCCCCCCCCCGCG |
| GGGGGCTCCGCCCCCCGGTCCCCCCCCG (SEQ ID NO: 24) |

Annotations:

| Putative Domain | Base range |
|---|---|
| TATA Box | 82-87 |
| Initiator Element | 95-115 |
| Transcriptional Start Site | 115 |
| 5' UTR Conserved Domain | 170-238 |
| ORF2 | 335-721 |
| ORF2/2 | 335-717; 2446-2902 |
| ORF2/3 | 335-717; 2675-3109 |
| ORF1 | 586-2928 |
| ORF1/1 | 586-717; 2446-2928 |
| ORF1/2 | 586-717; 2675-2902 |
| Three open-reading frame region | 2640-2899 |
| Poly(A) Signal | 3106-3114 |
| GC-rich region | 3768-3878 |

TABLE 8

| Exemplary *Anellovirus* amino acid sequences (*Alphatorquevirus*, Clade 4) TTV-HD20a (*Alphatorquevirus* Clade 4) | |
|---|---|
| ORF2 | MSRCWCPPRGDVSSRESRWYEAVRGSHDAFCGCSDPILHLS RLAARFNHQGPPTPPTDDRAPQNTPVRRLLPLPSYPGEGPQ ARWPGGDGGAAGGDRREGGDGGARAAEDEYQPEDLDELFGA IEQEQ (SEQ ID NO: 25) |
| ORF2/2 | MSRCWCPPRGDVSSRESRWYEAVRGSHDAFCGCSDPILHLS RLAARFNHQGPPTPPTDDRAPQNTPVRRLLPLPSYPGEGPQ ARWPGGDGGAAGGDRREGGDGGARAAEDEYQPEDLDELFGA |

TABLE 8-continued

Exemplary *Anellovirus* amino acid sequences (*Alphatorquevirus*, Clade 4)
TTV-HD20a (*Alphatorquevirus* Clade 4)

| | |
|---|---|
| | IEQEQSSETRAKTTKYPVPVDSLGIYKSLTRNASRRRGSST ASTSEEASLLKQLSGACSRNHYLASMLLAPSGHPSSFYPQN TSEKTALQKAPQVHRPKDPVSGQKRVRRRRSPRRRTRRRRR GSSSSESSESSEHSSSNSSTSRSNSPRPRRIST (SEQ ID NO: 26) |
| ORF2/3 | MSRCWCPPRGDVSSRESRWYEAVRGSHDAFCGCSDPILHLS RLAARFNHQGPPTPPTDDRAPQNTPVRRLLPLPSYPGEGPQ ARWPGGDGGAAGGDRREGGDGGARAAEDEYQPEDLDELFGA IEQEQIPARRRRCRKRLRFTGQKTPYLVRRESDGDDLLGGE PGGDDEGAPPAKAPRAASTPVPTPALRGPTRQDPGESPRKP PVIFPAMNKVFLFPPEGPKPILGKEAWQDEYETCRVWNRPA RTHHTDTPFYPWAPHKFHVSFKLGFQ (SEQ ID NO: 27) |
| ORF1 | MAWWGWRRRWWRPKRRWRWRRARRRRRVPARRPRRAFRRYR TRTVRRRRRGRRRGYRRRYRLRRYARRRFRRKKIVLTQWNP QTTRKCIIRGMMPVLWAGMGTGGRNYAVRSDDYVVNKGFGG SFATETFSLKVLYDQFQRGFNRWSHTNEDLDLARYRGCRWT FYRHKDTDFIVYFTNNPPMKTNQFSAPLTTPGMLMRSKYKV LIPSFQTRPKGRKTVTVKIRPPKLFQDKWYTQQDLCSVPLV QLNVTAADFTHPFGSPLTETPCVEFQVLGDLYNTCLNIDLP QFSELGEITSAYSKPNSNNLKELYKELFTKATSGHYWQTFI TNSMVRAHIDADKAKEAQRASTTPSYNNDPFPTIPVKSEFA QWKKKFTDTRDSPFLFATYHPEAIKDTIMKMRENNFKLETG PNDKYGDYTAQYQGNTHMLDYYLGFYSPIFLSDGRSNVEFF TAYRDIVYNPFLDKAQGNMVWFQYHTKTDNKFKKPECHWEI KDMPLWALLNGYVDYLETQIQYGDLSKEGKVLIRCPYTKPA LVDPRDDTAGYVVYNRNFGRGKWIDGGGYIPLHERTKWYVM LRYQTDVFHDIVTCGPWQYRDDNKNSQLVAKYRFSFIWGGN TVHSQVIRNPCKDNQVSGPRRQPRDIQVVDPQRITPPWVLH SFDQRRGLFTETALRRLLQEPLPGEYAVSTLRTPLLFLPSE YQREDGAAESASGSPAKRPRIWSEESQTETISSEENPAETT RELLQRKLREQRALQFQLQHFAVQLAKTQANLHVNPLLSFP Q (SEQ ID NO: 28) |
| ORF1/1 | MAWWGWRRRWWRPKRRWRWRRARRRRRVPARRPRRAFRRYR TRTVIRNPCKDNQVSGPRRQPRDIQVVDPQRITPPWVLHSF DQRRGLFTETALRRLLQEPLPGEYAVSTLRTPLLFLPSEYQ REDGAAESASGSPAKRPRIWSEESQTETISSEENPAETTRE LLQRKLREQRALQFQLQHFAVQLAKTQANLHVNPLLSFPQ (SEQ ID NO: 29) |
| ORF1/2 | MAWWGWRRRWWRPKRRWRWRRARRRRRVPARRPRRAFRRYR TRTNTSEKTALQKAPQVHRPKDPVSGQKRVRRRRSPRRRTR RRRRGSSSSESSESSEHSSSNSSTSRSNSPRPRRIST (SEQ ID NO: 30) |

TABLE 9

Exemplary *Anellovirus* nucleic acid sequence (*Alphatorquevirus*, Clade 5)

| | |
|---|---|
| Name | TTV-16 (TUS01) |
| Genus/Clade | *Alphatorquevirus*, Clade 5 |
| Accession Number | AB017613.1 |
| Full Sequence: 3818 bp | |

```
1        10        20        30        40        50
|         |         |         |         |         |
AAGTCCGCCACTAACCACGTGACTCCCGCAGGCCAACCCAGTACTATGTC

GTCCACTTCCTGGGACGAGTCTACGTCCTGATATAAGTAAGTGCACTTCC

GAATGGCTGAGTTTTCCACGCCCGTCCGCAGCGAGAACGCCACGGAGGGG

AGTCCGCGCGTCCCGAGGGCGGGTGCCGGAGGTGAGTTTACACACCGCAG

TCAAGGGGCAATTCGGGCTCGGGACTGGCCGGGCCCCGGGCAAGGCTCTT

AAAAAATGCACTTTCGCAGAGTGCGAGCGAAAAGGAAACTGCTACTGCAA

GCTGTGCGAGCTCCACCGAAGGCACCTGCCATGAGCTTCACCACACCTAC
```

TABLE 9-continued

Exemplary *Anellovirus* nucleic acid sequence (*Alphatorquevirus*, Clade 5)

```
TATTAATGCCGGGATCCGAGAGCAGCAATGGTTCGAGTCCACCCTTAGAT

CCCACCACTCGTTCTGTGGCTGTGGTGATCCCGTGCTTCATTTTACTAAC

CTTGCTACTCGCTTTAACTATCTGCCTGCTACCTCTTCGCCTCTGGACCC

TCCCGGCCCAGCGCCGCGAGGCCGCCCGGCGCTCCGCCGCCTCCCGGCAC

TCCCTTCAGCCCCCGCGACCCCTTCTAGAGAACTAGCATGGCCTACTGGT

TCAGAAGGTGGGGCTGGAGGCCGAGGCGCCGGTGGAGAAGGTGGCGCCGC

CGTCGAAGGAGACTACCGAGAAGAAGAACTAGACGAGCTGTTCGCGGCCT

TGGAAGAAGACGCAAACCAAGGGTAAGGAGGCGCCGCAGAACTCGCAGAC

GTACCTACAGACGGGGGTGGAGACGCAGGAGGTACATAAGACGGGGGCGA

CGCAAAAAGAAACTCATACTGACTCAGTGGAACCCGGCAATAGTTAAGAG

GTGCAACATTAAGGGCGGACTTCCAATAATTATATGCGGAGAGCCCAGGG

CAGCCTTTAACTATGGCTACCACATGGAGGACTACACTCCTCAACCTTTC

CCCTTCGGAGGGGGAATGAGCACAGTGACTTTCTCTCTGAAAGCCTTGTA

TGACCAGTACCTAAAACACCAAAACAGGTGGACTTTCTCAAACGACCAGC

TAGACCTCGCCAGATACAGGGGCTGTAAACTAAGGTTCTACAGAAGCCCC

GTCTGTGACTTTATAGTACACTACAACCTAATACCTCCACTAAAAATGAA

CCAGTTCACAAGTCCCAACACGCACCCGGGACTACTCATGCTCAGCAAAC

ACAAGATAATAATTCCCAGCTTTCAAACAAGACCTGGGGGCAGACGCTTT

GTTAAAATAAGACTTAATCCCCCCAAACTATTTGAAGACAAGTGGTACAC

TCAGCAAGACCTGTGCAAGGTTCCGCTCGTTAGTATTACAGCAACTGCGG

CTGACTTGCGGTATCCGTTCTGCTCACCACAAACGAACAACCCTTGCACC

ACCTTCCAGGTACTGCGCAAGAACTACAATACAGTTATAGGAACTTCCGT

AAAAGACCAAGAGTCCACACAAGACTTTGAAAATTGGCTTTATAAAACAG

ACTCACACTATCAAACATTTGCCACAGAGGCTCAACTAGGCAGAATTCCT

GCATTTAATCCTGATGGCACTAAAAACACTAAACAGCAGTCGTGGCAAGA

TAACTGGAGCAAAAAAAATTCACCATGGACAGGTAACTCAGGTACATACC

CACAAACAACCAGTGAAATGTACAAAATTCCATATGACAGTAACTTCGGC

TTTCCCACATACAGAGCCCAAAAAGACTACATTTTAGAAAGAAGACAGTG

CAACTTTAACTATGAAGTTAATAATCCAGTTAGCAAAAAAGTATGGCCAC

AACCTAGTACAACAACACCCACAGTAGACTACTATGAATACCACTGTGGA

TGGTTCAGCAACATATTCATAGGCCCCAACAGATACAACCTACAGTTTCA

AACAGCATATGTAGACACCACATACAACCCACTAATGGACAAGGGCAAAG

GCAACAAAATATGGTTTCAATATCTGTCTAAAAAGGGCACAGACTACAAT

GAAAAACAATGCTACTGCACCCTAGAAGACATGCCCCTATGGGCAATATG

CTTTGGATACACTGACTATGTAGAGACTCAACTAGGACCCAATGTGGACC

ATGAAACAGCAGGCTTAATAATTATGATCTGTCCATACACTCAACCACCT

ATGTATGACAAAAACAGACCTAACTGGGGATACGTAGTCTATGACACAAA

CTTTGGCAATGGAAAAATGCCCTCAGGAAGTGGCCAAGTCCCAGTATACT
```

TABLE 9-continued

| Exemplary *Anellovirus* nucleic acid sequence (*Alphatorquevirus*, Clade 5) |
|---|
| GGCAATGCCGATGGAGGCCCATGCTGTGGTTCCAACAACAAGTACTCAAT |
| GACATCTCAAAGACTGGACCGTACGCCTACAGAGACGAATATAAAAATGT |
| ACAACTGACTCTCTACTACAACTTTATTTTTAACTGGGGGGGCGACATGT |
| ATTACCCACAGGTCGTTAAAAACCCCTGTGGAGACTCCGGAATCGTTCCC |
| GGTTCCGGTAGATTCACTCGAGAAGTACAAGTCGTTAGCCCGCTTTCCAT |
| GGGACCGGCCTACATCTTCCACTACTTCGACTCCAGACGCGGGTTCTTTA |
| GTGAAAAAGCTCTTAAAAGAATGCAACAACAACAAGAATTTGATGAATCT |
| TTTACATTCAAACCTAAGAGACCCAAACTTTCTACAGCAGCCGCAGAAAT |
| CCTCCAGCTCGAAGAAGACTCGACTTCAGGGGAAGGAAAATCGCCACTAC |
| AGCAAGAAGAGAAAGAAGTCGAAGTCCTCCAAACGCCGACAGTACAGCTC |
| CAGCTCCAGCGAAACATCCAGGAGCAGCTCGCAATCAAGCAGCAGCTCCA |
| ATTCCTCTTGCTCCAACTCCTCAAAACCCAATCCAATTTGCATTTAAACC |
| CACAATTTTTAAGCCCTTCATAAAATATGACATGTTTGGGGACCCCCTTC |
| CTCACCCCCCAACAGCCGAAGAGTGGGAAACAGAGTACCAGTGCTGTAAG |
| GCCTTTAACAGACCACCTAGAACCAACCTAAAAGACACCCCCTTCTACCC |
| CTGGGTACCTAAACCTAAACCTCAATTCCGTGTATCTTTTAAACTTGGTT |
| TTCAATAAACAAGGCCGTGGGAGTTTCACTTGTCGGTGTCAACCTCTTAA |
| GGTCACTAAGCACTCCGAGCGTAAGCGAGGAGTGCGACCCTCCCCCCTGG |
| GGCAACTCCCTCGAAGTCCGGCGCTACGCGCTTCGCGCTGCGCCGGACAT |
| CTCGGACCCCCCCTCCACCCGAAACGCTTGCGCGTTTCGGACCTTCGGCG |
| TCGGGGGGGTCGGGGGCTTTACTAAACAGACTCCGAGGTGCCATTGGACA |
| CTGAGGGGATGAACAGCAACGAAAGTGAGTGGGGCCAGACTTCGCCATAA |
| GGCCTTTATCTTCTTGCCATTTGTCAGTATAGAGGGTCGCCATAGGCTTC |
| GGCCTCCATTTTAACCTCTAAAAACTACCAAAATGGCCGTTCCAGTGACG |
| TCACAGCCGCCATTTTAAGTAGCTGACGTCAAGGATTGACGTGAAGGTTA |
| AAGGTCATCCTCGGCGGAAGCTACACAAAATGGTGGACAACATCTTCCGG |
| GTCAAAGGTCGTGCACACGTCATAAGTCACGTGGTGGGGACCCGCTGTAA |
| CCCGGAAGTAGGCCCCGTCACGTGATTTGTCACGTGTGTACACGTCACAA |
| CCGCCATTTTGTTTTACAAAATGGCTGACTTCCTTCCTCTTTTTTAAAAA |
| AAACGGCCGTGCGGCGGCGCGCGCGCTTCGCGCGCGCGCCGGGGGCTGCC |
| GCCCCCCCCCGCGCATGCGCGCGGGGCCCCCCCCCGCGGGGGGCTCCGCC |
| CCCCGGCCCCCCCCCCCG (SEQ ID NO: 31) |

| Annotations: | |
|---|---|
| Putative Domain | Base range |
| TATA Box | 82-86 |
| Initiator Element | 100-115 |
| Transcriptional Start Site | 115 |
| 5' UTR Conserved Domain | 170-240 |
| ORF2 | 331-726 |
| ORF2/2 | 331-722; 2412-2847 |
| ORF2/3 | 331-722; 2638-3058 |
| ORF2t/3 | 331-380; 2638-3058 |

TABLE 9-continued

| Exemplary *Anellovirus* nucleic acid sequence (*Alphatorquevirus*, Clade 5) | |
|---|---|
| ORF1 | 588-2873 |
| ORF1/1 | 588-722; 2412-2873 |
| ORF1/2 | 588-722; 2638-2847 |
| Three open-reading frame region | 2699-2969 |
| Poly(A) Signal | 3220-3225 |
| GC-rich region | 3302-3541 |

TABLE 10

| Exemplary *Anellovirus* amino acid sequences (*Alphatorquevirus*, Clade 5) TTV-16-TUS01 (*Alphatorquevirus* Clade 5) | |
|---|---|
| ORF2 | MSFTTPTINAGIREQQWFESTLRSHHSFCGCGDPVLHFTNLATRFNYLPATSSPLDPPGPAPRGRPALRRLPALPSAPATPSRELAWPTGSEGGAGGRGAGGEGGAAVEGDYREEELDELFAALEEDANQG (SEQ ID NO: 32) |
| ORF2/2 | MSFTTPTINAGIREQQWFESTLRSHHSFCGCGDPVLHFTNLATRFNYLPATSSPLDPPGPAPRGRPALRRLPALPSAPATPSRELAWPTGSEGGAGGRGAGGEGGAAVEGDYREEELDELFAALEEDANQGSLKTPVETPESFPVPVDSLEKYKSLARFPWDRPTSSTTSTPDAGSLVKKLLKECNNNKNLMNLLHSNLRDPNFLQQPQKSSSSKKTRLQGKENRHYSKKRKKSKSSKRRQYSSSSSETSRSSSQSSSSSNSSCSNSSKPNPICI (SEQ ID NO: 33) |
| ORF2/3 | MSFTTPTINAGIREQQWFESTLRSHHSFCGCGDPVLHFTNLATRFNYLPATSSPLDPPGPAPRGRPALRRLPALPSAPATPSRELAWPTGSEGGAGGRGAGGEGGAAVEGDYREEELDELFAALEEDANQGSRRNPPARRRLDFRGRKIATTARRERSRSPPNADSTAPAPAKHPGAARNQAAAPIPLAPTPQNPIQFAFKPTIFKPFIKYDMFGDPLPHPPTAEEWETEYQCCKAFNRPPRTNLKDTPFYPWVPKPKPQFRVSFKLGFQ (SEQ ID NO: 34) |
| ORF2t/3 | MSFTTPTINAGIREQQCSRRNPPARRRLDFRGRKIATTARRERSRSPPNADSTAPAPAKHPGAARNQAAAPIPLAPTPQNPIQFAFKPTIFKPFIKYDMFGDPLPHPPTAEEWETEYQCCKAFNRPPRTNLKDTPFYPWVPKPKPQFRVSFKLGFQ (SEQ ID NO: 35) |
| ORF1 | MAYWFRRWGWRPRRRWRRWRRRRRRLPRRRTRRAVRGLGRRRKPRVRRRRRTRRRTYRRGWRRRRYIRRGRRKKKLILTQWNPAIVKRCNIKGGLPIIICGEPRAAFNYGYHMEDYTPQPFPFGGGMSTVTFSLKALYDQYLKHQNRWTFSNDQLDLARYRGCKLRFYRSPVCDFIVHYNLIPPLKMNQFTSPNTHPGLLMLSKHKIIIPSFQTRPGGRRFVKIRLNPPKLFEDKWYTQQDLCKVPLVSITATAADLRYPFCSPQTNNPCTTFQVLRKNYNTVIGTSVKDQESTQDFENWLYKTDSHYQTFATEAQLGRIPAFNPDGTKNTKQQSWQDNWSKKNSPWTGNSGTYPQTTSEMYKIPYDSNFGFPTYRAQKDYILERRQCNFNYEVNNPVSKKVWPQPSTTTPTVDYYEYHCGWFSNIFIGPNRYNLQFQTAYVDTTYNPLMDKGKGNKIWFQYLSKKGTDYNEKQCYCTLEDMPLWAICFGYTDYVETQLGPNVDHETAGLIIMICPYTQPPMYDKNRPNWGYVVYDTNFGNGKMPSGSGQVPVYWQCRWRPMLWFQQQVLNDISKTGPYAYRDEYKNVQLTLYYNFIFNWGGDMYYPQVVKNPCGDSGIVPGSGRFTREVQVVSPLSMGPAYIFHYFDSRRGFFSEKALKRMQQQQEFDESFTFKPKRPKLSTAAAEILQLEEDSTSGEGKSPLQQEEKEVEVLQTPTVQLQLQRNIQEQLAIKQQLQFLLLQLLKTQSNLHLNPQFLSPS (SEQ ID NO: 36) |
| ORF1/1 | MAYWFRRWGWRPRRRWRRWRRRRRRLPRRRTRRAVRGLGRRRKPRVVKNPCGDSGIVPGSGRFTREVQVVSPLSMGPAYIFHYFDSRRGFFSEKALKRMQQQQEFDESFTFKPKRPKLSTAAAEILQLEEDSTSGEGKSPLQQEEKEVEVLQTPTVQLQLQRNIQEQLAIKQQLQFLLLQLLKTQSNLHLNPQFLSPS (SEQ ID NO: 37) |
| ORF1/2 | MAYWFRRWGWRPRRRWRRWRRRRRRLPRRRTRRAVRGLGRRRKPRQPQKSSSSKKTRLQGKENRHYSKKRKKSKSSKRRQYSSSSSETSRSSSQSSSSSNSSCSNSSKPNPICI (SEQ ID NO: 38) |

TABLE 11

Exemplary *Anellovirus* nucleic acid sequence
(*Alphatorquevirus*, Clade 6)

| | |
|---|---|
| Name | TTV-TJN02 |
| Genus/Clade | *Alphatorquevirus*, Clade 6 |
| Accession Number | AB028669.1 |
| Full Sequence: 3794 bp | |

```
1         10        20        30        40        50
|         |         |         |         |         |
CCCGAAGTCCGTCACTAACCACGTGACTCCTGTCGCCCAATCAGAGTGTA
TGTCGTGCATTTCCTGGGCATGGTCTACATCCTGATATAACTAAGTGCAC
TTCCGAATGGCTGAGTTTTCCACGCCCGTCCGCAGCGAGGGAGCGACGGA
GGAGCTCCCGAGCGTCCCGAGGGCGGGTGCCGGAGGTGAGTTTACACACC
GCAGTCAAGGGGCAATTCGGGCTCGGGACTGGCCGGGCTATGGGCAAGGC
TCTTAGGGTCTTCATTCTTAATATGTTTCTTGGCAGAGTTTACCGCCACA
AGAAAAGGAAAGTGCTACTGTCCACACTGCGAGCTCCACAGGCGTCTCGC
AGGGCTATGAGTTGGCGACCCCCGGTACACGATGCACCCGGCATCGAGCG
CAATTGGTACGAGGCCTGTTTCAGAGCCCACGCTGGAGCTTGTGGCTGTG
GCAATTTTATTATGCACCTTAATCTTTTGGCTGGGCGTTATGGTTTTACT
CCGGGGTCAGCGCCGCCAGGTGGTCCTCCTCCGGGCACCCCGCAGATAAG
GAGAGCCAGGCCTAGTCCCGCCGCACCAGAGCAGCCCGCTGCCCTACCAT
GGCATGGGGATGGTGGAGATGGCGGCGCCGCTGGCCCGCCAGACGCTGGA
GGAGACGCCGTCGCCGGCGCCCCGTACGGAGAACAAGAGCTCGCCGACCT
GCTCGACGCTATAGAAGACGACGAACAGTAAGAACCAGGCGAAGGCGGTG
GGGGCGCAGACGGTACAGACGGGGCTGGAGACGCAGGACTTATGTGAGAA
AGGGGCGACACAGAAAAAAGAAAAAGAGACTGATACTGAGACAGTGGCAA
CCAGCCACAAGACGCAGATGTACCATAACTGGGTACCTGCCCATAGTGTT
CTGCGGCCACACTAGGGGCAATAAAAACTATGCACTACACTCTGACGACT
ACACCCCCCAAGGACAACCATTTGGAGGGGCTCTAAGCACTACCTCATTC
TCTTTAAAAGTACTATTTGACCAGCATCAGAGAGGACTAAACAAGTGGTC
TTTTCCAAACGACCAACTAGACCTCGCCAGATATAGAGGCTGCAAATTTA
TATTTTATAGAACAAAACAAACTGACTGGGTGGGCCAGTATGACATATCA
GAACCCTACAAGCTAGACAAATACAGCTGCCCCAACTATCACCCTGGAAA
CATGATTAAGGCAAAGCACAAATTTTTAATACCAAGCTATGACACTAATC
CTAGAGGCAGACAAAAAATTATAGTTAAAATTCCCCCCCCAGACCTCTTT
GTAGACAAGTGGTACACTCAAGAGGATCTGTGTTCCGTTAATCTTGTGTC
ACTTGCGGTTTCTGCGGCTTCCTTTCTCCACCCATTCGGCTCACCACAAA
CTGACAACCCTTGCTACACCTTCCAGGTGTTGAAAGAGTTCTACTATCAG
GCAATAGGCTTCTCTGCAAGCACACAAGCAATGACATCAGTATTAGACAC
GCTATACACACAAAACAGTTATTGGGAATCTAATCTAACTCAGTTTTATG
TACTTAATGCAAAAAAAGGCAGTGATACAACACAGCCTTTAACTAGCAAT
ATGCCAACTCGTGAAGAGTTTATGGCAAAAAAAAATACCAATTACAACTG
GTATACATACAAGGCCGCGTCAGTAAAAAATAAACTACATCAAATGAGAC
AAACCTATTTTGAGGAGTTAACCTCTAAGGGGCCACAAACAACAAAAAGT
```

TABLE 11-continued

Exemplary *Anellovirus* nucleic acid sequence
(*Alphatorquevirus*, Clade 6)

```
GAGGAAGGCTACAGTCAGCACTGGACCACCCCCTCCACAAACGCCTACGA
ATATCACTTAGGAATGTTTAGTGCAATATTTCTAGCCCCAGACAGGCCAG
TACCTAGATTTCCATGCGCCTACCAAGATGTAACTTACAACCCCTTAATG
GACAAAGGGGTGGGAAACCACATTTGGTTTCAGTACAACACAAAGGCAGA
CACTCAGCTAATAGTCACAGGAGGGTCCTGCAAAGCACACATACAAGACA
TACCACTGTGGGCGGCCTTCTATGGATACAGTGACTTTATAGAGTCAGAA
CTAGGCCCCTTTGTAGATGCAGAGACGGTAGGCTTAGTGTGTGTAATATG
CCCTTATACAAAACCCCCCATGTACAACAAGACAAACCCCGCCATGGGCT
ACGTGTTCTATGACAGAAACTTTGGTGACGGAAAATGGACTGACGGACGG
GGCAAAATAGAGCCCTACTGGCAAGTTAGGTGGAGGCCCGAAATGCTTTT
CCAAGAAACTGTAATGGCAGACCTAGTTCAGACTGGGCCCTTTAGCTACA
AAGACGAACTTAAAAACAGCACCCTAGTGTGCAAGTACAAATTCTATTTC
ACCTGGGGAGGTAACATGATGTTCCAACAGACGATCAAAAACCCGTGCAA
GACGGACGGACAACCCACCGACTCCAGTAGACACCCTAGAGGAATACAAG
TGGCGGACCCGGAACAAATGGGACCCCGCTGGGTGTTCCACTCCTTTGAC
TGGCGAAGGGGCTATCTTAGCGAGAAAGCTCTCAAACGCCTGCAAGAAAA
ACCTCTTGACTATGACGAATATTTTACACAACCAAAAAGACCTAGAATCT
TTCCTCCAACAGAATCAGCAGAGGGAGAGTTCCGAGAGCCCGAAAAAGGC
TCGTATTCAGAGGAAGAAAGGTCGCAAGCCTCTGCCGAAGAGCAGACGCA
GGAGGCGACAGTACTCCTCCTCAAGCGACGACTCAGAGAGCAACAGCAGC
TCCAGCAGCAGCTCCAATTCCTCACCCGAGAAATGTTCAAAACGCAAGCG
GGTCTCCACCTAAACCCTATGTTATTAAACCAGCGATAAACCAAGTGTAC
CTGTTTCCAGAGAGGGCCCCAAAACCCCCTCCTAGCAGCCAAGACTGGCA
GCAGGAGTACGAGGCCTGCGCAGCCTGGGACAGGCCCCCTAGATACAATC
TGTCCTCTCCTCCTTTCTACCCCAGCTGCCCTTCAAAATTCTGTGTAAAA
TTCAGCCTTGGCTTTAAATAAATGGCAACTTTACTGTGCAAGGCCGTGGG
AGTTTCACTGGTCGGTGTCTACCTCTAAAGGTCACTAAGCACTCCGAGCG
TTAGCGAGGAGTGCGACCCTTCCCCCTGACTCAACTTCTTCGGAGCCGCG
CGCTACGCCTTCGGCTGCGCGCGGCACCTCAGACCCCCGCTCGTGCTGAC
ACGCTCGCGCGTGTCAGACCACTTCGGGCTCGCGGGGGTCGGGAATTTTG
CTAAACAGACTCCGAGTTGCTCTTGGACACTGAGGGGGCATATCAGTAAC
GAAAGTGAGTGGGGCCAGACTTCGCCATAAGGCCTTTATCTTCTTGCCAT
TGGATAGTATCGAGGGTTGCCATAGGCTTCGACCTCCATTTTAGGCCTTC
CGGACTACAAAAATGGCCGTTTTAGTGACGTCACGGCCGCCATTTTAAGT
AAGGCGGAAGCAGCTCGGCGTACACAAAATGGCGGCGGAGCACTTCCGGC
TTGCCCAAAATGGTGGGCAACTTCTTCCGGGTCAAAGGTCACAGCTACGT
CACAAGTCACGTGGGGAGGGTTGGCGTTTAACCCGGAAGCCAATCCTCTT
ACGTGGCCTGTCACGTGACTTGTACGTCACGACCACCATTTTGTTTTACA
AAATGGCCGACTTCCTTCCTCTTTTTTAAAAATAACGGTTCGGCGGCGGC
```

TABLE 11-continued

Exemplary *Anellovirus* nucleic acid sequence (*Alphatorquevirus*, Clade 6)

GCGCGCGCTACGCGCGCGCGCCGGGGGGCTGCCGCCCCCCCCCCGCGCAT

GCGCGGGGCCCCCCCCCGCGGGGGGCTCCGCCCCCCGGCCCCCC (SEQ ID NO: 39)

Annotations:

| Putative Domain | Base range |
|---|---|
| TATA Box | 89-90 |
| Cap Site | 107-114 |
| Transcriptional Start Site | 114 |
| 5' UTR Conserved Domain | 174-244 |
| ORF2 | 357-731 |
| ORF2/2 | 357-727; 2381-2813 |
| ORF2/3 | 357-727; 2619-3021 |
| ORF2t/3 | 357-406; 2619-3021 |
| ORF1 | 599-2839 |
| ORF1/1 | 599-727; 2381-2839 |
| ORF1/2 | 599-727; 2619-2813 |
| Three open-reading frame region | 2596-2810 |
| Poly(A) Signal | 3017-3022 |
| GC-rich region | 3691-3794 |

TABLE 12

Exemplary *Anellovirus* amino acid sequences (*Alphatorquevirus*, Clade 6)
TTV-TJN02 (*Alphatorquevirus* Clade 6)

| | |
|---|---|
| ORF2 | MSWRPPVHDAPGIERNWYEACFRAHAGACGCGNFIMHLNLLAGRYGFTPGSAPPGGPPPGTPQIRRARPSPAAPEQPAALPWHGDGGDGGAAGPPDAGGDAVAGAPYGEQELADLLDAIEDDEQ (SEQ ID NO: 40) |
| ORF2/2 | MSWRPPVHDAPGIERNWYEACFRAHAGACGCGNFIMHLNLLAGRYGFTPGSAPPGGPPPGTPQIRRARPSPAAPEQPAALPWHGDGGDGGAAGPPDAGGDAVAGAPYGEQELADLLDAIEDDEQRSKTRARRTDNPPTPVDTLEEYKWRTRNKWDPAGCSTPLTGEGAILARKLSNACKKNLLTMTNILHNQKDLESFLQQNQQRESSESPKKARIQRKKGRKPLPKSRRRRRQYSSSSDDSESNSSSSSSNSSPEKCSKRKRVST (SEQ ID NO: 41) |
| ORF2/3 | MSWRPPVHDAPGIERNWYEACFRAHAGACGCGNFIMHLNLLAGRYGFTPGSAPPGGPPPGTPQIRRARPSPAAPEQPAALPWHGDGGDGGAAGPPDAGGDAVAGAPYGEQELADLLDAIEDDEHRGRVPRARKRLVFRGRKVASLCRRADAGGDSTPPQATTQRATAAPAAAPIPHPRNVQNASGSPPKPYVIKPAINQVYLFPERAPKPPPSSQDWQQEYEACAAWDRPPRYNLSSPPFYPSCPSKFCVKFSLGFK (SEQ ID NO: 42) |
| ORF2t/3 | MSWRPPVHDAPGIERNCRGRVPRARKRLVFRGRKVASLCRRADAGGDSTPPQATTQRATAAPAAAPIPHPRNVQNASGSPPKPYVIKPAINQVYLFPERAPKPPPSSQDWQQEYEACAAWDRPPRYNLSSPPFYPSCPSKFCVKFSLGFK (SEQ ID NO: 43) |
| ORF1 | MAWGWWRWRRRWPARRWRRRRRRRPVRRTRARRPARRYRRRRTVRTRRRRWGRRRYRRGWRRRTYVRKGRHRKKKKRLILRQWQPATRRRCTITGYLPIVFCGHTRGNKNYALHSDDYTPQGQPFGGALSTTSFSLKVLFDQHQRGLNKWSFPNDQLDLARYRGCKFIFYRTKQTDWVGQYDISEPYKLDKYSCPNYHPGNMIKAKHKFLIPSYDTNPRGRQKIIVKIPPPDLFVDKWYTQEDLCSVNLVSLAVSAASFLHPFGSPQTDNPCYTFQVLKEFYYQAIGFSASTQAMTSVLDTLYTQNSYWESNLTQFYVLNAKKGSDTTQPLTSNMPTREEFMAKKNTNYNWYTYKAASVKNKLHQMRQTYFEELTSKGPQTTKSEEGYSQHWTTPSTNAYEYHLGMFSAIFLAPDRPVPRFPCAYQDVTYNPLMDKGVGNHIWFQYNTKADTQLIVTGGSCKAHIQDIPLWAAFYGYSDFIESELGPFVDAETVGLVCVICPYTKPPMYNKTNPAMGYVFYDRNFGDGKWTDG |

TABLE 12-continued

Exemplary *Anellovirus* amino acid sequences (*Alphatorquevirus*, Clade 6)
TTV-TJN02 (*Alphatorquevirus* Clade 6)

| | |
|---|---|
| | RGKIEPYWQVRWRPEMLFQETVMADLVQTGPFSYKDELKNSTLVCKYKFYFTWGGNMMFQQTIKNPCKTDGQPTDSSRHPRGIQVADPEQMGPRWVFHSFDWRRGYLSEKALKRLQEKPLDYDEYFTQPKRPRIFPPTESAEGEFREPEKGSYSEEERSQASAEEQTQEATVLLLKRRLREQQQLQQQLQFLTREMFKTQAGLHLNPMLLNQR (SEQ ID NO: 44) |
| ORF1/1 | MAWGWWRWRRRWPARRWRRRRRRRPVRRTRARRPARRYRRRRTTIKNPCKTDGQPTDSSRHPRGIQVADPEQMGPRWVFHSFDWRRGYLSEKALKRLQEKPLDYDEYFTQPKRPRIFPPTESAEGEFREPEKGSYSEEERSQASAEEQTQEATVLLLKRRLREQQQLQQQLQFLTREMFKTQAGLHLNPMLLNQR (SEQ ID NO: 45) |
| ORF1/2 | MAWGWWRWRRRWPARRWRRRRRRRPVRRTRARRPARRYRRRRTQRESSESPKKARIQRKKGRKPLPKSRRRRRQYSSSSDDSESNSSSSSSNSSPEKCSKRKRVST (SEQ ID NO: 46) |

TABLE 13

Exemplary *Anellovirus* nucleic acid sequence (*Alphatorquevirus*, Clade 7)

| | |
|---|---|
| Name | TTV-HD16d |
| Genus/Clade | *Alphatorquevirus*, Clade 7 |
| Accession Number | FR751479.1 |
| Full Sequence: 3866 bp | |

```
1         10        20        30        40        50
|         |         |         |         |         |
AAGTCCGTCACTAACCACGTGACTCCCGCAGGCCAATCAGAGTCTATGTC

GTGCACTTCCTGGGCATGGTCTACGTTCTCATATAACTAACTGCACTTCC

GAATGGCTGAGTTTTCCACGCCCGTCCGCAGCGGCAGCACCACGGAGGGT

GATCCCCGCGTCCCGAGGGCGGGTGCCGAAGGTGAGTTTACACACCGCAG

TCAAGGGGCAATTCGGGCTCGGGACTGGCCGGGCTATGGGCAAGGCTCTT

AGGGCTTTCATTGTTAAAAATGTTTCTCGGCAGGCCTTACAGGAGAAAGA

AAAGGGCGCTGTCACTGCCTGGCGTGCGAGCTGCACAGGCGAAACAACCT

GGTGATATGAGCTGGAGCCGTCCAGTACATAATGCCGCCGGGATCGAAAG

GCAGTGGTTCGAATCCACCTTTAGATCCCACGCTAGTTGCTGTGGCTGCG

GCAATTTTGTTAATCATATTAATGTACTGGCTGCTCGCTACGGCTTTACT

GGGGGGCCGACGCCGCCAGGTGGTCCTGGGCCGCGTCCACAACTGAGGCC

CGCGCTTCCCGCGCCGGACCCCGACCCCCAGGCGCCCAACCGTGAGCCAT

GGCGTGGAGCTGGTGGTGGCAACGATGGAGAAGGCGCCGCTGGAAACCCA

GGAGGCGCCGCTGGAGACGTCTACGATGGAGAAGACCTAGACGCGCTGTT

CGCCGCCGTCGTCGAGGACGTAGAGTAAGGAGGCGGAGGTGGGCGCGTAG

ACGGGGGCGACGCAGACGGTACGCCACCAGACGAAAGAGACGTTATAGGG

GTCGCCGCTTTAAAAAGAAACTAGTACTGACTCAGTGGCACCCTAATACC

ATGAGACGCTGCTTAATCAAGGGCATAGTCCCCCTGGTAATATGCGGCCA

CACCAGGTGGAACTACAACTACGCCCTCCATAGCAAGGACTACACAGAGG

AGGGTCGCTACCCTCACGGGGGGGCCCTCAGCACCACTACGTGGTCCCTT

AAGGTGCTGTATGACGAGCACCTCAAACACCACGACTTCTGGGGCTATCC

CAACAACCAGCTAGACCTGGCCAGGTACAAGGGGGCCAAGTTCACCTTCT
```

TABLE 13-continued

| Exemplary *Anellovirus* nucleic acid sequence (*Alphatorquevirus*, Clade 7) |
|---|
| ACAGACACAAAAAGACTGACTTTATAATATTCTTTAACAGAAAGCCTCCC |
| TTTAAGCTAAACAAGTACAGCTGTGCCTCCTATCACCCAGGCATGCTGAT |
| GCAGCAGAGACACAAGATCCTGCTACCCAGCTACGAAACTAAACCCAAGG |
| GCAGGCCAAAGATAACAGTTAGAATAAAGCCCCCCACTCTGTTAGAGGAC |
| AAGTGGTACACCCAGCAGGACCTGTGCGACGTTAACCTGTTGCAACTTGT |
| GGTCACTGCGGCTGACTTTCGACATCCACTCTGCTCACCACAAACGAACA |
| CTCCAACCACAACCTTCCAGGTGTTGAAAGACATCTATTATGACACTATG |
| AGCATATCTGAACCCACAGACTCCTACACTAGTGTTAACAATAAAAGTAC |
| AACACAAACTTTTACTAACTACTCAAACACCTTAGAAAACATTCTGTACA |
| CACGAGCCTCCTACTGGAACTCGTTCCACGCCACTGAATACCTAAACCCC |
| AACATCATATACAAAAACGGTGAAAAACTATTCAAAGAACATGAAGACTT |
| AATAACCTGGATGACCCAAACTAACAATACCGGGTTTCTAACTAAAAACA |
| ACACAGCTTTTGGCAACAACAGCTACAGGCCCAATGCAGACAAAATTAAA |
| AAAGCCAGAAAGACATACTGGAACGCCCTAATAGGCACCAACGACCTGGC |
| CACTAATATAGGCCAGGCCAGAGCAGAAAGGTTCGAGTACCACCTAGGCT |
| GGTACTCCCCCATATTTCTCAGCAGACACAGGAGCAACATGAACTTTGCC |
| AGGGCCTACCAAGACGTCACATACAACCCCAACTGTGACAGGGGAGTTAA |
| CAACAGGGTGTGGGTTCAGCCTCTAACTAAACCCACCACAGAGTTCGACG |
| AGAAAAGGTGTAAGTGCGTAGTGCAGCACCTGCCTCTGTGGGCGGCTCTG |
| TACTGCTACCAAGACTTTGTAGAGGAGGAGCTGGGGTCCTCCTCAGAGAT |
| ATTAAATTCATGCCTACTGGTATTACAGTGCCCTTACACCTTTCCCCCAA |
| TGTATGACAAAAAGCTACCAGACAAGGGATTCGTGTTTTATGACTCCCTT |
| TTTGGAGACGGCAAAATGTCTGACGGACGCGGACAGGTGGACATTTTCTG |
| GCAACAGCGATGGTACCCTCGCTTAGCCACTCAGATGCAAGTCATGCACG |
| ACATCACCATGACGGGCCCCTTCTCCTACCGAGACGAGCTAGTTAGCACC |
| CAACTGACTGCCAAGTACACCTTTGACTTTATGTGGGGCGGAAATATGAT |
| CTCCACACAGATCATCAAGAACCCCTGCAAAGACAGTGGACTGGAACCCG |
| CCTACCCCGGTAGACAGCGTCGCGACTTACAAATTGTTGACCCATACTCC |
| ATGGGCCCCCAATTCTCGTTCCACAACTGGGACTACAGACATGGCCTTTT |
| TGGCCAAGACGCTATCGACAGAGTGTCTAAACAACCAAAAGATGATGCAG |
| ACTATCCTAACCCATACAAAAGGCCTAGATATTTTCCACCCACAGACCAA |
| GCCGCCCAAGAGCAAGAAAAAGACTTCAGTTTCCTCAAAACAGCACCGTC |
| GAACTCAGAAGAGAGCGATCAAGAAGTCCTCCAAGAAACGCAAGTACTCC |
| GATTCCAGCCAGAGCAGCACAAGCAACTCCACCTGCAGCTCGCAGAGCGG |
| CAGCGAATCGGAGAGCAACTCCGATACCTACTCCAACAGATGTTCAAAAC |
| TCAGGCCAATCTCCACCTAAACCCATATACATTTACCCAGCTGTAAAGCA |
| GGTGTTTATGTTTGACCCCCCGGGCCCTAAGGCTATCTCGGGCGCCAAGG |
| CCTGGGAGGACGAGTTCCTCACCGCAAAAGTGTGGAACCGCCCGGTACGC |

TABLE 13-continued

| Exemplary *Anellovirus* nucleic acid sequence (*Alphatorquevirus*, Clade 7) |
|---|
| AAGTACTACTCAGACACCCCCTACTACCCCTGGGCCCCCAAACCCCAGTA |
| CTCTGTCAGTTTCAAACTCGGCTGGAAATAAAAAAAGCCTGCTCCACTGT |
| ACTAGGCCGTGGGAGTTTCACTCGTCGGTGTCTACCTCTTAAGGTCACCA |
| AGCACTCCGAGCGTCAGCGAGGAGTGCGACCCTTGGGGGTGGGTGCAACG |
| CCCTCGGCGGCCGCGCGCTACGCCTTCGGCTGCGCGCGGCACCTCGGACC |
| CCCGCTCGTGCTGACGCGCTTGCGCGCGTCAGACCACTTCGGGCTCGCGG |
| GGGTCGGAAATTTTGCTAAACAGACTCCGAGTTGCCATTGGACACTGGAG |
| CCGTGAATCAGTAACGAAAGTGAGTGGGGCCAGACTTCGCCATAAGGCCT |
| TTATCTTTTTGCCATTTGTCCGTGGGGAAGGGTCGCTGCAAGCGCGGACC |
| CCGTTTTCACCCCTTCCGGACTACAAAAATAGCGCATTAGTGACGTCACG |
| GCCGCCATTTTAAGTAAGGCGGAAGCAACTCCACTTTCTCACAAAATGGC |
| GGCGGAGCACTTCCGGCTTGCCCAAAATGGCCGCCAAAAACATCCGGGTC |
| AAAGTTCGCCGCTACGTCATAAGTCACGTGACTGGGGAGGTACTTAAACA |
| CGGAAGTATCCTCAACCACGTAACTGGTCACGTGGTGCGCACGTCACGGC |
| AACCATTTTGTTTTACAAAATGGCGCATTTCCTTCCTCTTTTTTAAAAAT |
| TAACCGTTGGCGGCGGCGCGCGCGCTACGCGCGCGCGCCGGGGAGCTCTG |
| CCCCCCCCCGCGCATGCGCGCGGGTCCCCCCCCCGCGGGGGGCTCCGCCC |
| CCCGGTCCCCCCCCCG (SEQ ID NO: 47) |

Annotations:

| Putative Domain | Base range |
|---|---|
| TATA Box | 82-86 |
| Initiator Element | 94-115 |
| Transcriptional Start Site | 115 |
| 5' UTR Conserved Domain | 170-240 |
| ORF2 | 357-728 |
| ORF2/2 | 357-724; 2411-2870 |
| ORF2/3 | 357-724; 2646-3081 |
| ORF1 | 599-2896 |
| ORF1/1 | 599-724; 2411-2896 |
| ORF1/2 | 599-724; 2646-2870 |
| Three open-reading frame region | 2629-2867 |
| Poly(A) Signal | 3076-3086 |
| GC-rich region | 3759-3866 |

TABLE 14

| Exemplary *Anellovirus* amino acid sequences (*Alphatorquevirus*, Clade 7) TTV-HD16d (*Alphatorquevirus* Clade 7) | |
|---|---|
| ORF2 | MSWSRPVHNAAGIERQWFESTFRSHASCCGCGNFVNHINVL AARYGFTGGPTPPGGPGPRPQLRPALPAPDPDPQAPNREPW RGAGGGNDGEGAAGNPGGAAGDVYDGEDLDALFAAVVEDVE (SEQ ID NO: 48) |
| ORF2/2 | MSWSRPVHNAAGIERQWFESTFRSHASCCGCGNFVNHINVL AARYGFTGGPTPPGGPGPRPQLRPALPAPDPDPQAPNREPW RGAGGGNDGEGAAGNPGGAAGDVYDGEDLDALFAAVVEDVE |

TABLE 14-continued

Exemplary *Anellovirus* amino acid sequences (*Alphatorquevirus*, Clade 7)
TTV-HD16d (*Alphatorquevirus* Clade 7)

| | |
|---|---|
| | SSRTPAKTVDWNPPTPVDSVATYKLLTHTPWAPNSRSTTGT TDMAFLAKTLSTECLNNQKMMQTILTHTKGLDIFHPQTKPP KSKKKTSVSSKQHRRTQKRAIKKSSKKRKYSDSSQSSTSNS TCSSQSGSESESNSDTYSNRCSKLRPIST (SEQ ID NO: 49) |
| ORF2/3 | MSWSRPVHNAAGIERQWFESTFRSHASCCGCGNFVNHINVL AARYGFTGGPTPPGGPGPRPQLRPALPAPDPDPQAPNREPW RGAGGGNDGEGAAGNPGGAAGDVYDGEDLDALFAAVVEDVE PSRPRARKRLQFPQNSTVELRRERSRSPPRNASTPIPARAA QATPPAARRAAANRRATPIPTPTDVQNSGQSPPKPIYIYPA VKQVFMFDPPGPKAISGAKAWEDEFLTAKVWNRPVRKYYSD TPYYPWAPKPQYSVSFKLGWK (SEQ ID NO: 50) |
| ORF1 | MAWSWWWQRWRRRRWKPRRRRWRRLRWRRPRRAVRRRRRGR RVRRRRWARRRGRRRRYATRRKRRYRGRRFKKKLVLTQWHP NTMRRCLIKGIVPLVICGHTRWNYNYALHSKDYTEEGRYPH GGALSTTTWSLKVLYDEHLKHHDFWGYPNNQLDLARYKGAK FTFYRHKKTDFIIFFNRKPPFKLNKYSCASYHPGMLMQQRH KILLPSYETKPKGRPKITVRIKPPTLLEDKWYTQQDLCDVN LLQLVVTAADFRHPLCSPQTNTPTTTFQVLKDIYYDTMSIS EPTDSYTSVNNKSTTQTFTNYSNTLENILYTRASYWNSFHA TEYLNPNIIYKNGEKLFKEHEDLITWMTQTNNTGFLTKNNT AFGNNSYRPNADKIKKARKTYWNALIGTNDLATNIGQARAE RFEYHLGWYSPIFLSRHRSNMNFARAYQDVTYNPNCDRGVN NRVWVQPLTKPTTEFDEKRCKCVVQHLPLWAALYCYQDFVE EELGSSSEILNSCLLVLQCPYTFPPMYDKKLPDKGFVFYDS LFGDGKMSDGRGQVDIFWQQRWYPRLATQMQVMHDITMTGP FSYRDELVSTQLTAKYTFDFMWGGNMISTQIIKNPCKDSGL EPAYPGRQRRDLQIVDPYSMGPQFSFHNWDYRHGLFGQDAI DRVSKQPKDDADYPNPYKRPRYFPPTDQAAQEQEKDFSFLK TAPSNSEESDQEVLQETQVLRFQPEQHKQLHLQLAERQRIG EQLRYLLQQMFKTQANLHLNPYTFTQL (SEQ ID NO: 51) |
| ORF1/1 | MAWSWWWQRWRRRRWKPRRRRWRRLRWRRPRRAVRRRRRGR RIIKNPCKDSGLEPAYPGRQRRDLQIVDPYSMGPQFSFHNW DYRHGLFGQDAIDRVSKQPKDDADYPNPYKRPRYFPPTDQA AQEQEKDFSFLKTAPSNSEESDQEVLQETQVLRFQPEQHKQ LHLQLAERQRIGEQLRYLLQQMFKTQANLHLNPYTFTQL (SEQ ID NO: 52) |
| ORF1/2 | MAWSWWWQRWRRRRWKPRRRRWRRLRWRRPRRAVRRRRRGR RTKPPKSKKKTSVSSKQHRRTQKRAIKKSSKKRKYSDSSQS STSNSTCSSQSGSESESNSDTYSNRCSKLRPIST (SEQ ID NO: 53) |

TABLE 15

Exemplary *Anellovirus* nucleic acid sequence (*Betatorquevirus*)

| | |
|---|---|
| Name | TTMV-LY2 |
| Genus/Clade | *Betatorquevirus* |
| Accession Number | JX134045.1 |
| Full Sequence: 2797 bp | |

```
1         10         20         30         40         50
|          |          |          |          |          |
TAATAAATATTCAACAGGAAAACCACCTAATTTAAATTGCCGACCACAAA
CCGTCACTTAGTTCCCCTTTTTGCAACAACTTCTGCTTTTTTCCAACTGC
CGGAAAACCACATAATTTGCATGGCTAACCACAAACTGATATGCTAATTA
ACTTCCACAAAACAACTTCCCCTTTTAAAACCACACCTACAAATTAATTA
TTAAACACAGTCACATCCTGGGAGGTACTACCACACTATAATACCAAGTG
CACTTCCGAATGGCTGAGTTTATGCCGCTAGACGGAGAACGCATCAGTTA
CTGACTGCGGACTGAACTTGGGCGGGTGCCGAAGGTGAGTGAAACCACCG
```

TABLE 15-continued

Exemplary *Anellovirus* nucleic acid sequence (*Betatorquevirus*)

```
AAGTCAAGGGGCAATTCGGGCTAGTTCAGTCTAGCGGAACGGGCAAGAAA
CTTAAAATTATTTTATTTTTCAGATGAGCGACTGCTTTAAACCAACATGC
TACAACAACAAAACAAAGCAAACTCACTGGATTAATAACCTGCATTTAAC
CCACGACCTGATCTGCTTCTGCCCAACACCAACTAGACACTTATTACTAG
CTTTAGCAGAACAACAAGAAACAATTGAAGTGTCTAAACAAGAAAAAGAA
AAAATAACAAGATGCCTTATTACTACAGAAGAAGACGGTACAACTACAGA
CGTCCTAGATGGTATGGACGAGGTTGGATTAGACGCCCTTTTCGCAGAAG
ATTTCGAAGAAAAAGAAGGGTAAGACCTACTTATACTACTATTCCTCTAA
AGCAATGGCAACCGCCATATAAAAGAACATGCTATATAAAAGGACAAGAC
TGTTTAATATACTATAGCAACTTAAGACTGGGAATGAATAGTACAATGTA
TGAAAAAAGTATTGTACCTGTACATTGGCCGGGAGGGGGTTCTTTTTCTG
TAAGCATGTTAACTTTAGATGCCTTGTATGATATACATAAACTTTGTAGA
AACTGGTGGACATCCACAAACCAAGACTTACCACTAGTAAGATATAAAGG
ATGCAAAATAACATTTTATCAAAGCACATTTACAGACTACATAGTAAGAA
TACATACAGAACTACCAGCTAACAGTAACAAACTAACATACCCAAACACA
CATCCACTAATGATGATGATGTCTAAGTACAAACACATTATACCTAGTAG
ACAAACAAGAAGAAAAAAGAAACCATACACAAAAATATTTGTAAAACCAC
CTCCGCAATTTGAAAACAAATGGTACTTTGCTACAGACCTCTACAAAATT
CCATTACTACAAATACACTGCACAGCATGCAACTTACAAAACCCATTTGT
AAAACCAGACAAATTATCAAACAATGTTACATTATGGTCACTAAACACCA
TAAGCATACAAAATAGAAACATGTCAGTGGATCAAGGACAATCATGGCCA
TTTAAAATACTAGGAACACAAAGCTTTTATTTTTACTTTTACACCGGAGC
AAACCTACCAGGTGACACAACACAAATACCAGTAGCAGACCTATTACCAC
TAACAAACCCAAGAATAAACAGACCAGGACAATCACTAAATGAGGCAAAA
ATTACAGACCATATTACTTTCACAGAATACAAAAACAAATTTACAAATTA
TTGGGGTAACCCATTTAATAAACACATTCAAGAACACCTAGATATGATAC
TATACTCACTAAAAAGTCCAGAAGCAATAAAAAACGAATGGACAACAGAA
AACATGAAATGGAACCAATTAAACAATGCAGGAACAATGGCATTAACACC
ATTTAACGAGCCAATATTCACACAAATACAATATAACCCAGATAGAGACA
CAGGAGAAGACACTCAATTATACCTACTCTCTAACGCTACAGGAACAGGA
TGGGACCCACCAGGAATTCCAGAATTAATACTAGAAGGATTTCCACTATG
GTTAATATATTGGGGATTTGCAGACTTTCAAAAAAACCTAAAAAAAGTAA
CAAACATAGACACAAATTACATGTTAGTAGCAAAAACAAAATTTACACAA
AAACCTGGCACATTCTACTTAGTAATACTAAATGACACCTTTGTAGAAGG
CAATAGCCCATATGAAAAACAACCTTTACCTGAAGACAACATTAAATGGT
ACCCACAAGTACAATACCAATTAGAAGCACAAAACAAACTACTACAAACT
GGGCCATTTACACCAAACATACAAGGACAACTATCAGACAATATATCAAT
GTTTTATAAATTTTACTTTAAATGGGGAGGAAGCCCACCAAAAGCAATTA
ATGTTGAAAATCCTGCCCACCAGATTCAATATCCCATACCCCGTAACGAG
```

TABLE 15-continued

Exemplary *Anellovirus* nucleic acid sequence (*Betatorquevirus*)

CATGAAACAACTTCGTTACAGAGTCCAGGGGAAGCCCCAGAATCCATCTT

ATACTCCTTCGACTATAGACACGGGAACTACACAACAACAGCTTTGTCAC

GAATTAGCCAAGACTGGGCACTTAAAGACACTGTTTCTAAAATTACAGAG

CCAGATCGACAGCAACTGCTCAAACAAGCCCTCGAATGCCTGCAAATCTC

GGAAGAAACGCAGGAGAAAAAAGAAAAAGAAGTACAGCAGCTCATCAGCA

ACCTCAGACAGCAGCAGCAGCTGTACAGAGAGCGAATAATATCATTATTA

AAGGACCAATAACTTTTAACTGTGTAAAAAAGGTGAAATTGTTTGATGAT

AAACCAAAAAACCGTAGATTTACACCTGAGGAATTTGAAACTGAGTTACA

AATAGCAAAATGGTTAAAGAGACCCCCAAGATCCTTTGTAAATGATCCTC

CCTTTTACCCATGGTTACCACCTGAACCTGTTGTAAACTTTAAGCTTAAT

TTTACTGAATAAAGGCCAGCATTAATTCACTTAAGGAGTCTGTTTATTTA

AGTTAAACCTTAATAAACGGTCACCGCCTCCCTAATACGCAGGCGCAGAA

AGGGGGCTCCGCCCCCCTTTAACCCCCAGGGGGCTCCGCCCCCCTGAAACCC

CCAAGGGGGCTACGCCCCCTTACACCCCC (SEQ ID NO: 54)

Annotations:

| Putative Domain | Base range |
|---|---|
| TATA Box | 237-243 |
| Cap Site | 260-267 |
| Transcriptional Start Site | 267 |
| 5' UTR Conserved Domain | 323-393 |
| ORF2 | 424-723 |
| ORF2/2 | 424-719; 2274-2589 |
| ORF2/3 | 424-719; 2449-2812 |
| ORF1 | 612-2612 |
| ORF1/1 | 612-719; 2274-2612 |
| ORF1/2 | 612-719; 2449-2589 |
| Three open-reading frame region | 2441-2586 |
| Poly(A) Signal | 2808-2813 |
| GC-rich region | 2868-2929 |

TABLE 16

Exemplary *Anellovirus* amino acid sequences (*Betatorquevirus*) TTMV-LY2 (*Betatorquevirus*)

| | |
|---|---|
| ORF2 | MSDCFKPTCYNNKTKQTHWINNLHLTHDLICFCPTPTRHLL LALAEQQETIEVSKQEKEKITRCLITTEEDGTTTDVLDGMD EVGLDALFAEDFEEKEG (SEQ ID NO: 55) |
| ORF2/2 | MSDCFKPTCYNNKTKQTHWINNLHLTHDLICFCPTPTRHLL LALAEQQETIEVSKQEKEKITRCLITTEEDGTTTDVLDGMD EVGLDALFAEDFEEKEGFNIPYPVTSMKQLRYRVQGKPQNP SYTPSTIDTGTTQQQLCHELAKTGHLKTLFLKLQSQIDSNC SNKPSNACKSRKKRRRKKKKKYSSSSATSDSSSSCTESE (SEQ ID NO: 56) |
| ORF2/3 | MSDCFKPTCYNNKTKQTHWINNLHLTHDLICFCPTPTRHLL LALAEQQETIEVSKQEKEKITRCLITTEEDGTTTDVLDGMD EVGLDALFAEDFEEKEGARSTATAQTSPRMPANLGRNAGEK RKRSTAAHQQPQTAAAAVQRANNIIIKGPITFNCVKKVKLF DDKPKNRRFTPEEFETELQIAKWLKRPPRSFVNDPPFYPWL PPEPVVNFKLNFTE (SEQ ID NO: 57) |
| ORF1 | MPYYYRRRRYNYRRPRWYGRGWIRRPFRRRFRRKRRVRPTY TTIPLKQWQPPYKRTCYIKGQDCLIYYSNLRLGMNSTMYEK |

TABLE 16-continued

Exemplary *Anellovirus* amino acid sequences (*Betatorquevirus*) TTMV-LY2 (*Betatorquevirus*)

| | |
|---|---|
| | SIVPVHWPGGGSFSVSMLTLDALYDIHKLCRNWWTSTNQDL PLVRYKGCKITFYQSTFTDYIVRIHTELPANSNKLTYPNTH PLMMMMSKYKHIIPSRQTRRKKKPYTKIFVKPPPQFENKWY FATDLYKIPLLQIHCTACNLQNPFVKPDKLSNNVTLWSLNT ISIQNRNMSVDQGQSWPFKILGTQSFYFYFYTGANLPGDTT QIPVADLLPLTNPRINRPGQSLNEAKITDHITFTEYKNKFT NYWGNPFNKHIQEHLDMILYSLKSPEAIKNEWTTENMKWNQ LNNAGTMALTPFNEPIFTQIQYNPDRDTGEDTQLYLLSNAT GTGWDPPGIPELILEGFPLWLIYWGFADFQKNLKKVTNIDT NYMLVAKTKFTQKPGTFYLVILNDTFVEGNSPYEKQPLPED NIKWYPQVQYQLEAQNKLLQTGPFTPNIQGQLSDNISMFYK FYFKWGGSPPKAINVENPAHQIQYPIPRNEHETTSLQSPGE APESILYSFDYRHGNYTTTALSRISQDWALKDTVSKITEPD RQQLLKQALECLQISEETQEKKEKEVQQLISNLRQQQQLYR ERIISLLKDQ (SEQ ID NO: 58) |
| ORF1/1 | MPYYYRRRRYNYRRPRWYGRGWIRRPFRRRFRRKRRIQYPI PRNEHETTSLQSPGEAPESILYSFDYRHGNYTTTALSRISQ DWALKDTVSKITEPDRQQLLKQALECLQISEETQEKKEKEV QQLISNLRQQQQLYRERIISLLKDQ (SEQ ID NO: 59) |
| ORF1/2 | MPYYYRRRRYNYRRPRWYGRGWIRRPFRRRFRRKRRSQIDS NCSNKPSNACKSRKKRRRKKKKKYSSSSATSDSSSSCTESE (SEQ ID NO: 60) |

TABLE 17

Exemplary *Anellovirus* nucleic acid sequence (*Gammatorquevirus*)

| | |
|---|---|
| Name | TTMDV-MD1-073 |
| Genus/Clade | *Gammatorquevirus* |
| Accession Number | AB290918.1 |
| Full Sequence: 3242 bp | |

1 10 20 30 40 50
| | | | | |

AGGTGGAGACTCTTAAGCTATATAACCAAGTGGGGTGGCGAATGGCTGAG

TTTACCCCGCTAGACGGTGCAGGGACCGGATCGAGCGCAGCGAGGAGGTC

CCCGGCTGCCCGTGGGCGGGAGCCCGAGGTGAGTGAAACCACCGAGGTCT

AGGGGCAATTCGGGCTAGGGCAGTCTAGCGGAACGGGCAAGAAACTTAAA

AATATTTCTTTTACAGATGCAAAACCTATCAGCCAAAGACTTCTACAAAC

CATGCAGATACAACTGTGAAACTAAAAACCAAATGTGGATGTCTGGCATT

GCTGACTCCCATGACAGTTGGTGTGACTGTGATACTCCTTTTGCTCACCT

CCTGGCTAGTATTTTTCCTCCTGGTCACACAGATCGCACACGAACCATCC

AAGAAATACTTACCAGAGATTTTAGGAAAACATGCCTTTCTGGTGGGGCC

GACGCAACAAATTCTGGTATGGCCGAAACTATAGAAGAAAAAAGAGAAGA

TTTCCAAAAAGAAGAAAAAGAAGATTTTACAGAAGAACAAAATATAGAAG

ACCTGCTCGCCGCCGTCGCAGACGCAGAAGGAAGGTAAGAAGAAAAAAAA

AAACTCTTATAGTAAGACAATGGCAGCCAGACTCTATTGTACTCTGTAAA

ATTAAAGGGTATGACTCTATAATATGGGGAGCTGAAGGCACACAGTTTCA

ATGTTCTACACATGAAATGTATGAATATACAAGACAAAAGTACCCTGGGG

GAGGAGGATTTGGTGTACAACTTTACAGCTTAGAGTATTTGTATGACCAA

TGGAAACTTAGAAATAATATATGGACTAAAACAAATCAACTCAAAGATTT

GTGTAGATACTTAAAATGTGTTATGACCTTTTACAGACACCAACACATAG

TABLE 17-continued

| Exemplary *Anellovirus* nucleic acid sequence (*Gammatorquevirus*) |
|---|
| ATTTTGTAATTGTATATGAAAGACAACCCCCATTTGAAATAGATAAACTA |
| ACATACATGAAATATCATCCATATATGTTATTACAAAGAAAGCATAAAAT |
| AATTTTACCTAGTCAAACAACTAATCCTAGAGGTAAATTAAAAAAAAAGA |
| AAACTATTAAACCTCCCAAACAAATGCTCAGCAAATGGTTTTTTCAACAA |
| CAATTTGCTAAATATGATCTACTACTTATTGCTGCAGCAGCATGTAGTTT |
| AAGATACCCTAGAATAGGCTGCTGCAATGAAAATAGAATGATAACCTTAT |
| ACTGTTTAAATACTAAATTTTATCAAGATACAGAATGGGGAACTACAAAA |
| CAGGCCCCCCACTACTTTAAACCATATGCAACAATTAATAAATCCATGAT |
| ATTTGTCTCTAACTATGGAGGTAAAAAAACAGAATATAACATAGGCCAAT |
| GGATAGAAACAGATATACCTGGAGAAGGTAATCTAGCAAGATACTACAGA |
| TCAATAAGTAAAGAAGGAGGTTACTTTTCACCTAAAATACTGCAAGCATA |
| TCAAACAAAAGTAAAGTCTGTAGACTACAAACCTTTACCAATTGTTTTAG |
| GTAGATATAACCCAGCAATAGATGATGGAAAAGGCAACAAAATTTACTTA |
| CAAACTATAATGAATGGCCATTGGGGCCTACCTCAAAAAACACCAGATTA |
| TATAATAGAAGAGGTCCCTCTTTGGCTAGGCTTCTGGGGATACTATAACT |
| ACTTAAAACAAACAAGAACTGAAGCTATATTTCCACTACACATGTTTGTA |
| GTGCAAAGCAAATACATTCAAACACAACAAACAGAAACACCTAACAATTT |
| TTGGGCATTTATAGACAACAGCTTTATACAGGGCAAAAACCCATGGGACT |
| CAGTTATTACTTACTCAGAACAAAAGCTATGGTTTCCTACAGTTGCATGG |
| CAACTAAAAACCATAAATGCTATTTGTGAAAGTGGACCATATGTACCTAA |
| ACTAGACAATCAAACATATAGTACCTGGGAACTAGCAACTCATTACTCAT |
| TTCACTTTAAATGGGGTGGTCCACAGATATCAGACCAACCAGTTGAAGAC |
| CCAGGAAACAAAAACAAATATGATGTGCCCGATACAATCAAAGAAGCATT |
| ACAAATTGTTAACCCAGCAAAAAACATTGCTGCCACGATGTTCCATGACT |
| GGGACTACAGACGGGGTTGCATTACATCAACAGCTATTAAAAGAATGCAA |
| CAAAACCTCCCAACTGATTCATCTCTCGAATCTGATTCAGACTCAGAACC |
| AGCACCCAAGAAAAAAAGACTACTACCAGTCCTCCACGACCCACAAAAGA |
| AAACGGAAAAGATCAACCAATGTCTCCTCTCTCTCTGCGAAGAAAGTACA |
| TGCCAGGAGCAGGAAACGGAGGAAAACATCCTCAAGCTCATCCAGCAGCA |
| GCAGCAGCAGCAGCAGAAACTCAAGCACAACCTCTTAGTACTAATCAAGG |
| ACTTAAAAGTGAAACAAAGATTATTACAACTACAAACGGGGGTACTAGAA |
| TAACCCTTACCAGATTTAAACCAGGATTTGAGCAAGAAACTGAAAAAGAG |
| TTAGCACAAGCATTTAACAGACCCCCTAGACTGTTCAAAGAAGATAAACC |
| CTTTTACCCCTGGCTACCCAGATTTACACCCCTTGTAAACTTTCACCTTA |
| ATTTTAAAGGCTAGGCCTACACTGCTCACTTAGTGGTGTATGTTTATTAA |
| AGTTTGCACCCCAGAAAAATTGTAAAATAAAAAAAAAAAAAAAAAATAAA |
| AAATTGCAAAAATTCGGCGCTCGCGCGCGCTGCGCGCGCGAGCGCCGTCA |
| CGCGCCGGCGCTCGCGCGCCGCGCGTATGTGCTAACACACCACGCACCTA |
| GATTGGGGTGCGCGCGTAGCGCGCGCACCCCAATGCGCCCCGCCCTCGTT |
| CCGACCCGCTTGCGCGGGTCGGACCACTTCGGGCTCGGGGGGGCGCGCCT |
| GCGGCGCTTATTTACTAAACAGACTCCGAGTCGCCATTGGGCCCCCCCTA |
| AGCTCCGCCCCCCTCATGAATATTCATAAAGGAAACCACAAAATTAGAAT |
| TGCCGACCACAAACTGCCATATGCTAATTAGTTCCCCTTTTACACAGTAA |
| AAAGGGGAAGTGGGGGGGCAGAGCCCCCCCACACCCCCCGCGGGGGGGC |
| AGAGCCCCCCCCGCACCCCCCCTACGTCACAGGCCACGCCCCCGCCGCCA |
| TCTTGGGTGCGGCAGGGCGGGGACTAAAATGGCGGGACCCAATCATTTTA |
| TACTTTCACTTTCCAATTAAAACCCGCCACGTCACACAAAAG (SEQ ID NO: 61) |

| Annotations: | |
|---|---|
| Putative Domain | Base range |
| TATA Box | 21-25 |
| Cap Site | 42-49 |
| Transcriptional Start Site | 49 |
| 5' UTR Conserved Domain | 117-187 |
| ORF2 | 283-588 |
| ORF2/2 | 283-584; 1977-2388 |
| ORF2/3 | 283-584; 2197-2614 |
| ORF1 | 432-2453 |
| ORF1/1 | 432-584; 1977-2453 |
| ORF1/2 | 432-584; 2197-2388 |
| Three open-reading frame region | 2186-2385 |
| Poly(A) Signal | 2676-2681 |
| GC-rich region | 3054-3172 |

TABLE 18

| Exemplary *Anellovirus* amino acid sequences (*Gammatorquevirus*) TTMDV-MD1-073 (*Gammatorquevirus*) | |
|---|---|
| ORF2 | MWMSGIADSHDSWCDCDTPFAHLLASIFPPGHTDRTRTIQEILTRDFRKTCLSGGADATNSGMAETIEEKREDFQKEEKEDFTEEQNIEDLLAAVADAEGR (SEQ ID NO: 62) |
| ORF2/2 | MWMSGIADSHDSWCDCDTPFAHLLASIFPPGHTDRTRTIQEILTRDFRKTCLSGGADATNSGMAETIEEKREDFQKEEKEDFTEEQNIEDLLAAVADAEGRYQTNQLKTQETKTNMMCPIQSKKHYKLLTQQKTLLPRCSMTGTTDGVALHQQLLKECNKTSQLIHLSNLIQTQNQHPRKKDYYQSSTTHKRKRKRSTNVSSLSAKKVHARSRKRRKTSSSSSSSSSSSSRNSSTTS (SEQ ID NO: 63) |
| ORF2/3 | MWMSGIADSHDSWCDCDTPFAHLLASIFPPGHTDRTRTIQEILTRDFRKTCLSGGADATNSGMAETIEEKREDFQKEEKEDFTEEQNIEDLLAAVADAEGRTSTQEKKTTTSPPRPTKENGKDQPMSPLSLRRKYMPGAGNGGKHPQAHPAAAAAAAETQAQPLSTNQGLKSETKIITTTNGGTRITLTRFKPGFEQETEKELAQAFNRPPRLFKEDKPFYPWLPRFTPLVNFHLNFKG (SEQ ID NO: 64) |
| ORF1 | MPFWWGRRNKFWYGRNYRRKKRRFPKRRKRRFYRRTKYRRPARRRRRRRRKVRRKKKTLIVRQWQPDSIVLCKIKGYDSIIWGAEGTQFQCSTHEMYEYTRQKYPGGGGFGVQLYSLEYLYDQWKLRNNIWTKTNQLKDLCRYLKCVMTFYRHQHIDFVIVYERQPPFEIDKLTYMKYHPYMLLQRKHKIILPSQTTNPRGKLKKKKTIKPPKQMLSKWFFQQQFAKYDLLLIAAAACSLRYPRIGCCNENRMITLYCLNTKFYQDTEWGTTKQAPHYFKPYATINKSMIFVSNYGGKKTEYNIGQWIETDIPGEGNLARYYRSISKEGGYFSPKILQAYQTKVKSVDYKPLPIVLGRYNPAIDDGKGNKIYLQTIMNGHWGLPQKTPDYIIEEVPLWLGFWGYYNYLKQ |

TABLE 18-continued

| Exemplary *Anellovirus* amino acid sequences (*Gammatorquevirus*) TTMDV-MD1-073 (*Gammatorquevirus*) | |
|---|---|
| | TRTEAIFPLHMFVVQSKYIQTQQTETPNNFWAFIDNSFIQGKNPWDSVITYSEQKLWFPTVAWQLKTINAICESGPYVPKLDNQTYSTWELATHYSFHFKWGGPQISDQPVEDPGNKNKYDVPDTIKEALQIVNPAKNIAATMFHDWDYRRGCITSTAIKRMQQNLPTDSSLESDSDSEPAPKKKRLLPVLHDPQKKTEKINQCLLSLCEESTCQEQETEENILKLIQQQQQQQKLKHNLLVLIKDLKVKQRLLQLQTGVLE (SEQ ID NO: 65) |
| ORF1/1 | MPFWWGRRNKFWYGRNYRRKKRRFPKRRKRRFYRRTKYRRPARRRRRRRRKISDQPVEDPGNKNKYDVPDTIKEALQIVNPAKNIAATMFHDWDYRRGCITSTAIKRMQQNLPTDSSLESDSDSEPAPKKKRLLPVLHDPQKKTEKINQCLLSLCEESTCQEQETEENILKLIQQQQQQQKLKHNLLVLIKDLKVKQRLLQLQTGVLE (SEQ ID NO: 66) |
| ORF1/2 | MPFWWGRRNKFWYGRNYRRKKRRFPKRRKRRFYRRTKYRRPARRRRRRRRKISDQPVEDPGNKNKYDVPDTIKEALQIVNPAKNIAATMFHDWDYRRGCITSTAIKRMQQNLPTDSSLESDSDSEPAPKKKRLLPVLHDPQKKTEKINQCLLSLCEESTCQEQETEENILKLIQQQQQQQKLKHNLLVLIKDLKVKQRLLQLQTGVLE (SEQ ID NO: 67) |

In some embodiments, an anellosome comprises a nucleic acid comprising a sequence listed in PCT Application No. PCT/US2018/037379, incorporated herein by reference in its entirety. In some embodiments, an anellosome comprises a polypeptide comprising a sequence listed in PCT Application No. PCT/US2018/037379, incorporated herein by reference in its entirety.

In some embodiments, an anellosome comprises a minimal *Anellovirus* genome, e.g., as identified according to the method described in Example 9. In some embodiments, an anellosome comprises an *Anellovirus* sequence, or a portion thereof, as described in Example 13.

In some embodiments, an anellosome comprises a genetic element comprising a consensus *Anellovirus* motif, e.g., as shown in Table 19. In some embodiments, an anellosome comprises a genetic element comprising a consensus *Anellovirus* ORF1 motif, e.g., as shown in Table 19. In some embodiments, an anellosome comprises a genetic element comprising a consensus *Anellovirus* ORF1/1 motif, e.g., as shown in Table 19. In some embodiments, an anellosome comprises a genetic element comprising a consensus *Anellovirus* ORF1/2 motif, e.g., as shown in Table 19. In some embodiments, an anellosome comprises a genetic element comprising a consensus *Anellovirus* ORF2/2 motif, e.g., as shown in Table 19. In some embodiments, an anellosome comprises a genetic element comprising a consensus *Anellovirus* ORF2/3 motif, e.g., as shown in Table 19. In some embodiments, an anellosome comprises a genetic element comprising a consensus *Anellovirus* ORF2t/3 motif, e.g., as shown in Table 19. In some embodiments, X, as shown in Table 19, indicates any amino acid. In some embodiments, Z, as shown in Table 19, indicates glutamic acid or glutamine. In some embodiments, B, as shown in Table 19, indicates aspartic acid or asparagine. In some embodiments, J, as shown in Table 19, indicates leucine or isoleucine.

TABLE 19

Consensus motifs in open reading frames (ORFs) of *Anelloviruses*

| Consensus Threshold | Open Reading Frame | Position | Motif | SEQ ID NO: |
|---|---|---|---|---|
| 50 | ORF1 | 79 | LIJRQWQPXXIRRCXIXGYXPLIXC | 68 |
| 50 | ORF1 | 111 | NYXXHXD | 69 |
| 50 | ORF1 | 135 | FSLXXLYDZ | 70 |
| 50 | ORF1 | 149 | NXWTXSNXDLDLCRYXGC | 71 |
| 50 | ORF1 | 194 | TXPSXHPGXMXLXKHK | 72 |
| 50 | ORF1 | 212 | IPSLXTRPXG | 73 |
| 50 | ORF1 | 228 | RIXPPXLFXDKWYFQXDL | 74 |
| 50 | ORF1 | 250 | LLXIXATA | 75 |
| 50 | ORF1 | 260 | LXXPFXSPXTD | 76 |
| 50 | ORF1 | 448 | YNPXXDKGXGNXIW | 77 |
| 50 | ORF1 | 519 | CPYTZPXL | 78 |
| 50 | ORF1 | 542 | XFGXGXMP | 79 |
| 50 | ORF1 | 569 | HQXEVXEX | 80 |
| 50 | ORF1 | 600 | KYXFXFXWGGNP | 81 |
| 50 | ORF1 | 653 | HSWDXRRG | 82 |
| 50 | ORF1 | 666 | AIKRXQQ | 83 |
| 50 | ORF1 | 750 | XQZQXXLR | 84 |
| 50 | ORF1/1 | 73 | PRXJQXXDP | 85 |
| 50 | ORF1/1 | 91 | HSWDXRRG | 86 |
| 50 | ORF1/1 | 105 | AIKRXQQ | 87 |
| 50 | ORF1/1 | 187 | QZQXXLR | 88 |
| 50 | ORF1/2 | 97 | KXKRRRR | 89 |
| 50 | ORF2/2 | 158 | PIXSLXXYKXXTR | 90 |
| 50 | ORF2/2 | 189 | LAXQLLKECXKN | 91 |
| 50 | ORF2/3 | 39 | HLNXLA | 92 |
| 50 | ORF2/3 | 272 | DRPPR | 93 |
| 50 | ORF2/3 | 281 | DXPFYPWXP | 94 |
| 50 | ORF2/3 | 300 | VXFKLXF | 95 |
| 50 | ORF2t/3 | 4 | WXPPVHBVXGIERXW | 96 |
| 50 | ORF2t/3 | 37 | AKRKLX | 97 |
| 50 | ORF2t/3 | 140 | PSSXDWXXEY | 98 |
| 50 | ORF2t/3 | 156 | DRPPR | 99 |
| 50 | ORF2t/3 | 167 | PFYPW | 100 |
| 50 | ORF2t/3 | 183 | NVXFKLXF | 101 |
| 50 | ORF1 | 84 | JXXXXWQPXXXXXCXIXGXXXJWQP | 102 |

TABLE 19-continued

Consensus motifs in open reading frames (ORFs) of *Anelloviruses*

| Consensus Threshold | Open Reading Frame | Position | Motif | SEQ ID NO: |
|---|---|---|---|---|
| 50 | ORF1 | 149 | NXWXXXNXXXXLXRY | 103 |
| 50 | ORF1 | 448 | YNPXXDXG | 104 |

ORF1 Molecules

In some embodiments, the anellosome comprises an ORF1 molecule and/or a nucleic acid encoding an ORF1 molecule. Generally, an ORF1 molecule comprises a polypeptide having the structural features and/or activity of an *Anellovirus* ORF1 protein (e.g., an *Anellovirus* ORF1 protein as described herein, e.g., as listed in any of Tables 2, 4, 6, 8, 10, 12, 14, 16, 18, or 20-37), or a functional fragment thereof. In some embodiments, an ORF1 molecule comprises an amino acid sequence having at least 70%, 75%, 80%, 85%, 90%, 95%, 96%, 97%, 98%, 99%, or 100% sequence identity to a sequence as shown in any of Tables 2, 4, 6, 8, 10, 12, 14, 16, 18, or 20-37. An ORF1 molecule can generally bind to a nucleic acid molecule, such as DNA (e.g., a genetic element, e.g., as described herein). In some embodiments, an ORF1 molecule localizes to the nucleus of a cell. In certain embodiments, an ORF1 molecule localizes to the nucleolus of a cell.

Without wishing to be bound by theory, an ORF1 molecule may be capable of binding to other ORF1 molecules, e.g., to form a proteinaceous exterior (e.g., as described herein). Such an ORF1 molecule may be described as having the capacity to form a capsid. In some embodiments, the proteinaceous exterior may encapsidate a nucleic acid molecule (e.g., a genetic element as described herein). In some embodiments, a plurality of ORF1 molecules may form a multimer, e.g., to produce a proteinaceous exterior. In some embodiments, the multimer may be a homomultimer. In other embodiments, the multimer may be a heteromultimer (e.g., comprising a plurality of distinct ORF1 molecules). It is also contemplated that an ORF1 molecule may have replicase activity.

An ORF1 molecule may, in some embodiments, comprise one or more of: a first region comprising at least 60% basic residues (e.g., at least 60%, 65%, 70%, 75%, 80%, 85%, 90%, 95%, or 100% basic residues; e.g., between 60%-90%, 60%-80%, 70%-90%, or 70-80% basic residues), a second region comprising at least six beta strands (e.g., 4, 5, 6, 7, 8, 9, 10, 11, or 12 beta strands), a third region comprising the structure or activity of an *Anellovirus* N22 domain (e.g., as described herein, e.g., an N22 domain from an *Anellovirus* ORF1 protein as described herein), and/or a fourth region comprising the structure or activity of an *Anellovirus* C-terminal domain (CTD) (e.g., as described herein, e.g., a CTD from an *Anellovirus* ORF1 protein as described herein). In some embodiments, the ORF1 molecule comprises, in N-terminal to C-terminal order, the first, second, third, and fourth regions.

The ORF1 molecule may, in some embodiments, further comprise a hypervariable region (HVR), e.g., an HVR from an *Anellovirus* ORF1 protein, e.g., as described herein. In some embodiments, the HVR is positioned between the second region and the third region. In some embodiments, the HVR comprises comprises at least about 55 (e.g., at least about 45, 50, 51, 52, 53, 54, 55, 56, 57, 58, 59, 60, or 65) amino acids (e.g., about 45-160, 50-160, 55-160, 60-160, 45-150, 50-150, 55-150, 60-150, 45-140, 50-140, 55-140, or 60-140 amino acids).

In some embodiments, the first region can bind to a nucleic acid molecule (e.g., DNA). In some embodiments, the basic residues are selected from arginine, histidine, or lysine, or a combination thereof. In some embodiments, the first region comprises at least 60%, 65%, 70%, 75%, 80%, 85%, 90%, 95%, or 100% arginine residues (e.g., between 60%-90%, 60%-80%, 70%-90%, or 70-80% arginine residues). In some embodiments, the first region comprises about 30-120 amino acids (e.g., about 40-120, 40-100, 40-90, 40-80, 40-70, 50-100, 50-90, 50-80, 50-70, 60-100, 60-90, or 60-80 amino acids). In some embodiments, the first region comprises the structure or activity of a viral ORF1 arginine-rich region (e.g., an arginine-rich region from an *Anellovirus* ORF1 protein, e.g., as described herein). In some embodiments, the first region comprises a nuclear localization sigal.

In some embodiments, the second region comprises the structure or activity of a viral ORF1 jelly-roll domain (e.g., a jelly-roll domain from an *Anellovirus* ORF1 protein, e.g., as described herein). In some embodiments, the second region is capable of binding to the second region of another ORF1 molecule, e.g., to form a proteinaceous exterior (e.g., capsid) or a portion thereof.

In some embodiments, the fourth region is exposed on the surface of a proteinaceous exterior (e.g., a proteinaceous exterior comprising a multimer of ORF1 molecules, e.g., as described herein).

In some embodiments, the first region, second region, third region, fourth region, and/or HVR each comprise fewer than four (e.g., 0, 1, 2, or 3) beta sheets.

In some embodiments, one or more of the first region, second region, third region, fourth region, and/or HVR may be replaced by a heterologous amino acid sequence (e.g., the corresponding region from a heterologous ORF1 molecule). In some embodiments, the heterologous amino acid sequence has a desired functionality, e.g., as described herein.

Figure 34:
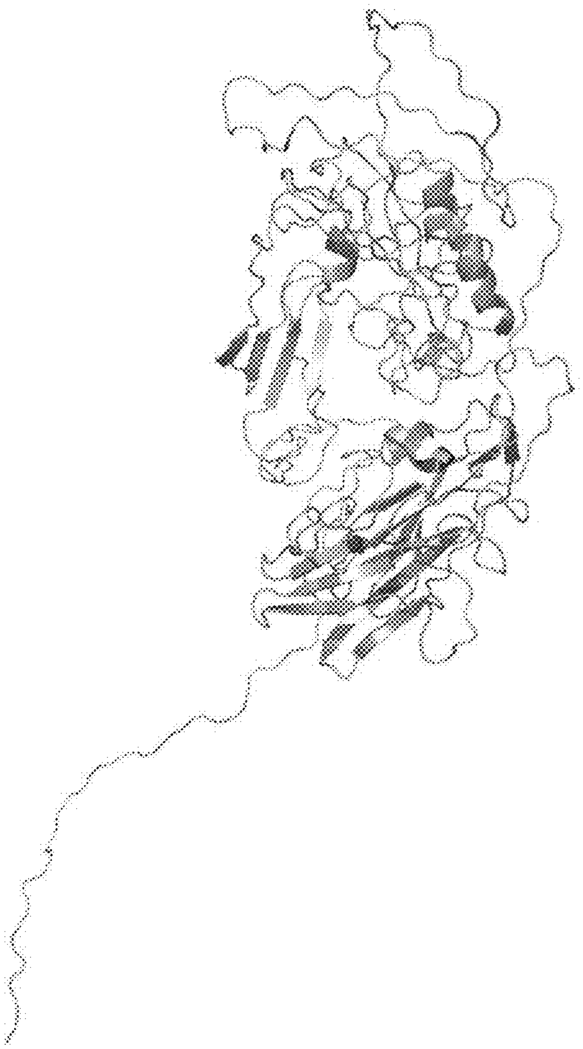
FIG. 34 is a diagram showing an ORF1 structure from *Betatorquevirus* strain CBS203. Residues showing high similarity among a set of 110 betatorqueviruses are indicated with highlighting. Green indicates residues of 60-79.9% similarity, orange indicates residues of 80-99.9% similarity, and red indicates 100% similarity among all strains evaluated.

In some embodiments, the ORF1 molecule comprises a plurality of conserved motifs (e.g., motifs comprising about 5, 6, 7, 8, 9, 10, 11, 12, 13, 14, 15, 16, 17, 18, 19, 20, 25, 30, 35, 40, 45, 50, 60, 70, 80, 90, 100, or more amino acids) (e.g., as shown in FIG. 34). In some embodiments, the conserved motifs may show 60, 70, 80, 85, 90, 95, or 100% sequence identity to an ORF1 protein of one or more wild-type *Anellovirus* clades (e.g., *Alphatorquevirus*, Glade 1; *Alphatorquevirus*, Glade 2; *Alphatorquevirus*, Glade 3; *Alphatorquevirus*, Glade 4; *Alphatorquevirus*, Glade 5; *Alphatorquevirus*, Glade 6; *Alphatorquevirus*, Glade 7; *Betatorquevirus*; and/or *Gammatorquevirus*). In embodiments, the conserved motifs each have a length between 1-1000 (e.g., between 5-10, 5-15, 5-20, 10-15, 10-20, 15-20, 5-50, 5-100, 10-50, 10-100, 10-1000, 50-100, 50-1000, or 100-1000) amino acids. In certain embodiments, the conserved motifs consist of about 2-4% (e.g., about 1-8%, 1-6%, 1-5%, 1-4%, 2-8%, 2-6%, 2-5%, or 2-4%) of the sequence of the ORF1 molecule, and each show 100% sequence identity to the corresponding motifs in an ORF1 protein of the wild-type *Anellovirus* Glade. In certain embodiments, the conserved motifs consist of about 5-10% (e.g., about 1-20%, 1-10%, 5-20%, or 5-10%) of the sequence of the ORF1 molecule, and each show 80% sequence identity to the corresponding motifs in an ORF1 protein of the wild-type *Anellovirus* Glade. In certain embodiments, the conserved motifs consist of about 10-50% (e.g., about 10-20%, 10-30%, 10-40%, 10-50%, 20-40%, 20-50%, or 30-50%) of the sequence of the ORF1 molecule, and each show 60% sequence identity to the corresponding motifs in an ORF1 protein of the wild-type *Anellovirus* Glade. In some embodiments, the conserved motifs comprise one or more amino acid sequences as listed in Table 19.

Exemplary ORF1 Sequences

In some embodiments, a polypeptide (e.g., an ORF1 molecule) described herein comprises an amino acid sequence having at least about 70%, 75%, 80%, 85%, 90%, 95%, 96%, 97%, 98%, 99%, or 100% sequence identity to one or more *Anellovirus* ORF1 subsequences, e.g., as described in any of Tables 20-37). In some embodiments, an anellosome described herein comprises an ORF1 molecule comprising an amino acid sequence having at least about 70%, 75%, 80%, 85%, 90%, 95%, 96%, 97%, 98%, 99%, or 100% sequence identity to one or more *Anellovirus* ORF1 subsequences, e.g., as described in any of Tables 20-37. In some embodiments, an anellosome described herein comprises a nucleic acid molecule (e.g., a genetic element) encoding an ORF1 molecule comprising an amino acid sequence having at least about 70%, 75%, 80%, 85%, 90%, 95%, 96%, 97%, 98%, 99%, or 100% sequence identity to one or more *Anellovirus* ORF1 subsequences, e.g., as described in any of Tables 20-37.

In some embodiments, the one or more *Anellovirus* ORF1 subsequences comprises one or more of an arginine (Arg)-rich domain, a jelly-roll domain, a hypervariable region (HVR), an N22 domain, or a C-terminal domain (CTD) (e.g., as listed in any of Tables 20-37), or sequences having at least about 70%, 75%, 80%, 85%, 90%, 95%, 96%, 97%, 98%, 99%, or 100% sequence identity thereto. In some embodiments, the ORF1 molecule comprises a plurality of subsequences from different *Anelloviruses* (e.g., any combination of ORF1 subsequences selected from the *Alphatorquevirus* Clade 1-7 subsequences listed in Tables 20-37). In embodiments, the ORF1 molecule comprises one or more of an Arg-rich domain, a jelly-roll domain, an N22 domain, and a CTD from one *Anellovirus*, and an HVR from another. In embodiments, the ORF1 molecule comprises one or more of a jelly-roll domain, an HVR, an N22 domain, and a CTD from one *Anellovirus*, and an Arg-rich domain from another. In embodiments, the ORF1 molecule comprises one or more of an Arg-rich domain, an HVR, an N22 domain, and a CTD from one *Anellovirus*, and a jelly-roll domain from another. In embodiments, the ORF1 molecule comprises one or more of an Arg-rich domain, a jelly-roll domain, an HVR, and a CTD from one *Anellovirus*, and an N22 domain from another. In embodiments, the ORF1 molecule comprises one or more of an Arg-rich domain, a jelly-roll domain, an HVR, and an N22 domain from one *Anellovirus*, and a CTD from another.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 20 (e.g., amino acids 1-66 of Table 20). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 21. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 20 (e.g., amino acids 67-277 of Table 20). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 21. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 20 (e.g., amino acids 278-347 of Table 20). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 21. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 20 (e.g., amino acids 348-513 of Table 20). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 21. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 20 (e.g., amino acids 513-680 of Table 20). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 21.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 22 (e.g., amino acids 1-69 of Table 22). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 23. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 22 (e.g., amino acids 70-279 of Table 22). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 23. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 22 (e.g., amino acids 280-411 of Table 22). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 23. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 22 (e.g., amino acids 412-578 of Table 22). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 23. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 22 (e.g., amino acids 579-747 of Table 22). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 23.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 24 (e.g., amino acids 1-68 of Table 24). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 25. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 24 (e.g., amino acids 69-280 of Table 24). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 25. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 24 (e.g., amino acids 281-413 of Table 24). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 25. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 24 (e.g., amino acids 414-479 of Table 24). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 25. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 24 (e.g., amino acids 580-743 of Table 24). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 25.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 26 (e.g., amino acids 1-74 of Table 26). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 27. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 26 (e.g., amino acids 75-284 of Table 26). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 27. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 26 (e.g., amino acids 285-445 of Table 26). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 27. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 26 (e.g., amino acids 446-611 of Table 26). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 27. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 26 (e.g., amino acids 612-780 of Table 26). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 27.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 28 (e.g., amino acids 1-75 of Table 28). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 29. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 28 (e.g., amino acids 75-284 of Table 28). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 29. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 28 (e.g., amino acids 285-432 of Table 28). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 29. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 28 (e.g., amino acids 433-599 of Table 28). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 29. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 28 (e.g., amino acids 600-780 of Table 28). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 29.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 30 (e.g., amino acids 1-77 of Table 30). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 31. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 30 (e.g., amino acids 78-286 of Table 30). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 31. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 30 (e.g., amino acids 287-416 of Table 30). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 31. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 30 (e.g., amino acids 417-585 of Table 30). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 31. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 30 (e.g., amino acids 586-746 of Table 30). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 31.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 32 (e.g., amino acids 1-74 of Table 32). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 33. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 32 (e.g., amino acids 75-286 of Table 32). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 33. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 32 (e.g., amino acids 287-428 of Table 32). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 33. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 32 (e.g., amino acids 429-595 of Table 32). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 33. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 32 (e.g., amino acids 596-765 of Table 32). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 33.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 34 (e.g., amino acids 1-38 of Table 34). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 35. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 34 (e.g., amino acids 39-246 of Table 34). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 35. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 34 (e.g., amino acids 247-374 of Table 34). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 35. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 34 (e.g., amino acids 375-537 of Table 34). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 35. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 34 (e.g., amino acids 538-666 of Table 34). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 35.

In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 36 (e.g., amino acids 1-57 of Table 36). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the Arg-rich region amino acid sequence of Table 37. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 36 (e.g., amino acids 58-259 of Table 36). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the jelly-roll region amino acid sequence of Table 37. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 36 (e.g., amino acids 260-351 of Table 36). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the HVR amino acid sequence of Table 37. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 36 (e.g., amino acids 352-510 of Table 36). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the N22 domain amino acid sequence of Table 37. In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD amino acid sequence of Table 36 (e.g., amino acids 511-673 of Table 36). In embodiments, the one or more *Anellovirus* ORF1 subsequences comprises an amino acid sequence having at least about 70%, 75%, 80%, 85%, 90%, 95%, 96%, 97%, 98%, 99%, or 100% sequence identity to the CTD region amino acid sequence of Table 37.

TABLE 20

Exemplary *Anellovirus* ORF1 amino acid subsequence (*Alphatorquevirus*, Clade 1)

| | |
|---|---|
| Name | CT30F |
| Genus/Clade | *Alphatorquevirus*, Clade 1 |
| Strain Accesion Number | AB064597.1 |
| Protein Accession Number | ANQ39351.1 |
| Full Sequence: 680 AA | |

```
1         10        20        30        40        50
|         |         |         |         |         |
TAWWWGRWRRRWRRRRPWRPRLRRRRARRAFPRRRRRRFVSRRWRRPYRR

RRRRGRRRRRRRRRHKPTLVLRQWQPDVIRHCKITGRMPLIICGKGSTQF

NYITHADDITPRGASYGGNFTNMTFSLEAIYEQFLYHRNRWSASNHDLEL

CRYKGTTLKLYRHPDVDYIVTYSRTGPFEISHMTYLSTHPLLMLLNKHHI

VVPSLKTKPRGRKAIKVRIRPPKLMNNKWYFTRDFCNIGLFQLWATGLEL

RNPWLRMSTLSPCIGFNVLKNSIYTNLSNLPQHREDRLNIINNTLHPHDI

TGPNNKKWQYTYTKLMAPIYYSANRASTYDLLREYGLYSPYYLNPTRINL

DWMTPYTHVRYNPLVDKGFGNRIYIQWCSEADVSYNRTKSKCLLQDMPLF

FMCYGYIDWAIKNTGVSSLARDARICIRCPYTEPQLVGSTEDIGFVPITE

TFMRGDMPVLAPYIPLSWFCKWYPNIAHQKEVLEAIISCSPFMPRDQGMN

GWDITIGYKMDFLWGGSPLPSQPIDDPCQQGTHPIPDPDKHPRLLQVSNP

KLLGPRTVFHKWDIRRGQFSKRSIKRVSEYSSDDESLAPGLPSKRNKLDS

AFRGENPEQKECYSLLKALEEEETPEEEEPAPQEKAQKEELLHQLQLQRR

HQRVLRRGLKLVFTDILRLRQGVHWNPELT (SEQ ID NO: 173)
```

Annotations:

| Putative Domain | AA range |
|---|---|
| Arg-Rich Region | 1-66 |
| Jelly-roll domain | 67-277 |
| Hypervariable Region | 278-347 |

TABLE 20-continued

| Exemplary *Anellovirus* ORF1 amino acid subsequence (*Alphatorquevirus*, Clade 1) | |
|---|---|
| N22 | 348-513 |
| C-terminal Domain | 513-680 |

TABLE 21

Exemplary *Anellovirus* ORF1 amino acid subsequence (*Alphatorquevirus*, Clade 1)
TTV-CT30F-ORF1 (*Alphatorquevirus* Clade 1)

| | |
|---|---|
| Arg-Rich Region | TAWWWGRWRRRWRRRRPWRPRLRRRRARRAFPRRRRRRFVSRRWRRPYRRRRRRGRRRRRRRRRHK (SEQ ID NO: 174) |
| Jelly-roll Domain | PTLVLRQWQPDVIRHCKITGRMPLIICGKGSTQFNYITHADDITPRGASYGGNFTNMTFSLEAIYEQFLYHRNRWSASNHDLELCRYKGTTLKLYRHPDVDYIVTYSRTGPFEISHMTYLSTHPLLMLLNKHHIVVPSLKTKPRGRKAIKVRIRPPKLMNNKWYFTRDFCNIGLFQLWATGLELRNPWLRMSTLSPCIGFNVLKNSIYTNL (SEQ ID NO: 175) |
| Hyper-variable domain | SNLPQHREDRLNIINNTLHPHDITGPNNKKWQYTYTKLMAPIYYSANRASTYDLLREYGLYSPYYLNPTR (SEQ ID NO: 176) |
| N22 | INLDWMTPYTHVRYNPLVDKGFGNRIYIQWCSEADVSYNRTKSKCLLQDMPLFFMCYGYIDWAIKNTGVSSLARDARICIRCPYTEPQLVGSTEDIGFVPITETFMRGDMPVLAPYIPLSWFCKWYPNIAHQKEVLEAIISCSPFMPRDQGMNGWDITIGYKMDFL (SEQ ID NO: 177) |
| C-terminal domain | WGGSPLPSQPIDDPCQQGTHPIPDPDKHPRLLQVSNPKLLGPRTVFHKWDIRRGQFSKRSIKRVSEYSSDDESLAPGLPSKRNKLDSAFRGENPEQKECYSLLKALEEEETPEEEEPAPQEKAQKEELLHQLQLQRRHQRVLRRGLKLVFTDILRLRQGVHWNPELT (SEQ ID NO: 178) |

TABLE 22

Exemplary *Anellovirus* ORF1 amino acid subsequence (*Alphatorquevirus*, Clade 2)

| | |
|---|---|
| Name | TTV-P13-1 |
| Genus/Clade | *Alphatorquevirus*, Clade 2 |
| Accession Number | KT163896.1 |
| Protein Accession Number | ANQ39351.1 |
| Full Sequence: 747 AA | |

```
1         10         20         30         40         50
|          |          |          |          |          |
MAYWWGRRRRWRRWRRRRRPLRRRRRWRRRRRWPRRRRWRRRRRRARPAR

RYRRRRGRRRVRRRRRPQKLVLTQWNPQTVRKCVIRGFLPLPFFCGQGAYH

RNFTDHYDDVFPKGPSGGGHGSMVFNLSFLYQEFKKHHNKWSRSNLDFDL

VRYKGTVIKLYRHQDFDYIVWISRTPPFQESLLTVMTHQPSVMLQAKKCI

IVKSYRTHPGGKPYVTAKVRPPRLLTDKWYFQSDFCNVPLFSLQFALAEL

RFPICSPQTDTNCINFLVLDDIYYKFLDNKPKQSSDPNDENRIKFWHGLW

STMRYLNTTYINTLFPGTDSLVAAKDTDNSVNKYPSTATKQPYKDSQYMQ

NIWNTSKIHALYTWVAETNYKRLQAYYTQTYGGYQRQFFTGKQYWDYRVG

MFSPAFLSPSRLNPQNPGAYTEVSYNPWTDEGTGNVVCLQYLTKETSDYK

PGGGSKFCIEGVPLWAALVGYVDMCKKEGKDPGIRLNCLLLVKCPYTKPQ

LYDKKNPEKLFVPYSYNFGHGKMPGGDKYIPIEFKDRWYPCLLHQEEWIE

DIVRSGPFVPKDMPSSVTCMMRYSSLFNWGGNIIQEQAVEDPCKKGTFVV
```

TABLE 22-continued

Exemplary *Anellovirus* ORF1 amino acid subsequence (*Alphatorquevirus*, Clade 2)

```
PGTSGIARILQVSNPAKQTPTTTWHSWDWRRSLFTETGLKRMREQQPYDE

LSYTGPKKPKLSLPAGPAVPGAAVASSWWETKQVTSPDVSETETEAEAHQ

EEETEPEEGVQLQQLWEQQLLQKRQLGVVFQQLLRLRQGAEIHPGLV

(SEQ ID NO: 179)
```

Annotations:

| Putative Domain | AA range |
|---|---|
| Arg-Rich Region | 1-69 |
| Jelly-roll domain | 70-279 |
| Hypervariable Region | 280-411 |
| N22 | 412-578 |
| C-terminal Domain | 579-747 |

TABLE 23

Exemplary *Anellovirus* ORF1 amino acid subsequence (*Alphatorquevirus*, Clade 2)
TTV-P13-1-ORF1 (*Alphatorquevirus* Clade 2)

| | |
|---|---|
| Arg-Rich Region | MAYWWGRRRRWRRWRRRRRPLRRRRRWRRRRRWPRRRRWRRRRRRARPARRYRRRRGRRRVRRRRRPQK (SEQ ID NO: 180) |
| Jelly-roll Domain | LVLT QWNPQTVRKCVIRGFLPLPFFCGQGAYHRNFTDHYDDVFPKGPSGGGHGSMVFNLSFLYQEFKKHHNKWSRSNLDFDLVRYKGTVIKLYRHQDFDYIVWISRTPPFQESLLTVMTHQPSVMLQAKKCIIVKSYRTHPGGKPYVTAKVRPPRLLTDKWYFQSDFCNVPLFSLQFALAELRFPICSPQTDTNCINFLVLDDIYYKFLDN (SEQ ID NO: 181) |
| Hyper-variable domain | KPKQSSDPNDENRIKFWHGLWSTMRYLNTTYINTLFPGTDSLVAAKDTDNSVNKYPSTATKQPYKDSQYMQNIWNTSKIHALYTWVAETNYKRLQAYYTQTYGGYQRQFFTGKQYWDYRVGMFSPAFLSPSR (SEQ ID NO: 182) |
| N22 | LNPQNPGAYTEVSYNPWTDEGTGNVVCLQYLTKETSDYKPGGGSKFCIEGVPLWAALVGYVDMCKKEGKDPGIRLNCLLLVKCPYTKPQLYDKKNPEKLFVPYSYNFGHGKMPGGDKYIPIEFKDRWYPCLLHQEEWIEDIVRSGPFVPKDMPSSVTCMMRYSSLFN (SEQ ID NO: 183) |
| C-terminal domain | WGGNIIQEQAVEDPCKKGTFVVPGTSGIARILQVSNPAKQTPTTTWHSWDWRRSLFTETGLKRMREQQPYDELSYTGPKKPKLSLPAGPAVPGAAVASSWWETKQVTSPDVSETETEAEAHQEEETEPEEGVQLQQLWEQQLLQKRQLGVVFQQLLRLRQGAEIHPGLV (SEQ ID NO: 184) |

TABLE 24

Exemplary *Anellovirus* ORF1 amino acid subsequence (*Alphatorquevirus*, Clade 3)

| | |
|---|---|
| Name | TTV-tth8 |
| Genus/Clade | *Alphatorquevirus*, Clade 3 |
| Accession Number | AJ620231.1 |
| Protein Accession Number | CAF05750.1 |
| Full Sequence: 743 AA | |

```
1         10         20         30         40         50
|          |          |          |          |          |
MAWGWWKRRRRWWFRKRWTRGRLRRRWPRSARRRPRRRRVRRRRRWRRGR

RKTRTYRRRRRFRRRGRKAKLIIKLWQPAVIKRCRIKGYIPLIISGNGTF

ATNFTSHINDRIMKGPFGGGHSTMRFSLYILFEEHLRHMNFWTRSNDNLE
```

TABLE 24-continued

Exemplary *Anellovirus* ORF1 amino acid subsequence
(*Alphatorquevirus*, Clade 3)

LTRYLGASVKIYRHPDQDFIVIYNRRTPLGGNIYTAPSLHPGNAILAKHK

ILVPSLQTRPKGRKAIRLRIAPPTLFTDKWYFQKDIADLTLFNIMAVEAD

LRFPFCSPQTDNTCISFQVLSSVYNNYLSINTFNNDNSDSKLKEFLNKAF

PTTGTKGTSLNALNTFRTEGCISHPQLKKPNPQINKPLESQYFAPLDALW

GDPIYYNDLNENKSLNDIIEKILIKNMITYHAKLREFPNSYQGNKAFCHL

TGIYSPPYLNQGRISPEIFGLYTEIIYNPYTDKGTGNKVWMDPLTKENNI

YKEGQSKCLLTDMPLWTLLFGYTDWCKKDTNNWDLPLNYRLVLICPYTFP

KLYNEKVKDYGYIPYSYKFGAGQMPDGSNYIPFQFRAKWYPTVLHQQQVM

EDISRSGPFAPKVEKPSTQLVMKYCFNFNWGGNPIIEQIVKDPSFQPTYE

IPGTGNIPRRIQVIDPRVLGPHYSFRSWDMRRHTFSRASIKRVSEQQETS

DLVFSGPKKPRVDIPKQETQEESSHSLQRESRPWETEEESETEALSQESQ

EVPFQQQLQQQYQEQLKLRQGIKVLFEQLIRTQQGVHVNPCLR (SEQ ID NO: 185)

| Annotations: | |
|---|---|
| Putative Domain | AA range |
| Arg-Rich Region | 1-68 |
| Jelly-roll domain | 69-280 |
| Hypervariable Region | 281-413 |
| N22 | 414-579 |
| C-terminal Domain | 580-743 |

TABLE 25

Exemplary *Anellovirus* ORF1 amino acid subsequence
(*Alphatorquevirus*, Clade 3)
TTV-tth8-ORF1 (*Alphatorquevirus* Clade 3)

| | |
|---|---|
| Arg-Rich Region | MAWGWWKRRRRWWFRKRWTRGRLRRRWPRSARRRPRRRR VRRRRRWRRGRRKTRTYRRRRRFRRRGRK (SEQ ID NO: 186) |
| Jelly-roll Domain | AKLIIKLWQPAVIKRCRIKGYIPLIISGNGTFATNFTSH INDRIMKGPFGGGHSTMRFSLYILFEEHLRHMNFWTRSN DNLELTRYLGASVKIYRHPDQDFIVIYNRRTPLGGNIYT APSLHPGNAILAKHKILVPSLQTRPKGRKAIRLRIAPPT LFTDKWYFQKDIADLTLFNIMAVEADLRFPFCSPQTDNT CISFQVLSSVYNNYLSI (SEQ ID NO: 187) |
| Hyper-variable domain | NTFNNDNSDSKLKEFLNKAFPTTGTKGTSLNALNTFRTE GCISHPQLKKPNPQ1NKPLESQYFAPLDALWGDPIYYND LNENKSLNDIIEKILIKNMITYHAKLREFPNSYQGNKAF CHLTGIYSPPYLNQGR (SEQ ID NO: 188) |
| N22 | ISPEIFGLYTEIIYNPYTDKGTGNKVWMDPLTKENNIYK EGQSKCLLTDMPLWTLLFGYTDWCKKDTNNWDLPLNYRL VLICPYTFPKLYNEKVKDYGYIPYSYKFGAGQMPDGSNY IPFQFRAKWYPTVLHQQQVMEDISRSGPFAPKVEKPSTQ LVMKYCFNFN (SEQ ID NO: 189) |
| C-terminal domain | WGGNPIIEQIVKDPSFQPTYEIPGTGNIPRRIQVIDPRV LGPHYSFRSWDMRRHTFSRASIKRVSEQQETSDLVFSGP KKPRVDIPKQETQEESSHSLQRESRPWETEEESETEALS QESQEVPFQQQLQQQYQEQLKLRQGIKVLFEQLIRTQQG VHVNPCLR (SEQ ID NO: 190) |

TABLE 26

Exemplary *Anellovirus* ORF1 amino acid subsequence
(*Alphatorquevirus*, Clade 4)

| | |
|---|---|
| Name | TTV-HD20a |
| Genus/Clade | *Alphatorquevirus*, Clade 4 |
| Accession Number | FR751492.1 |
| Protein Accession Number | NA |
| Full Sequence: 780 AA | |

```
         1        10        20        30        40        50
         |         |         |         |         |         |
```

MAWWGWRRRWWRPKRRWRWRRARRRRRVPARRPRRAFRRYRTRTVRRRRR

GRRRGYRRRYRLRRYARRRFRRKKIVLTQWNPQTTRKCIIRGMMPVLWAG

MGTGGRNYAVRSDDYVVNKGFGGSFATETFSLKVLYDQFQRGFNRWSHTN

EDLDLARYRGCRWTFYRHKDTDFIVYFTNNPPMKTNQFSAPLTTPGMLMR

SKYKVLIPSFQTRPKGRKTVTVKIRPPKLFQDKWYTQQDLCSVPLVQLNV

TAADFTHPFGSPLTETPCVEFQVLGDLYNTCLNIDLPQFSELGEITSAYS

KPNSNNLKELYKELFTKATSGHYWQTFITNSMVRAHIDADKAKEAQRAST

TPSYNNDPFPTIPVKSEFAQWKKKFTDTRDSPFLFATYHPEAIKDTIMKM

RENNFKLETGPNDKYGDYTAQYQGNTHMLDYYLGFYSPIFLSDGRSNVEF

FTAYRDIVYNPFLDKAQGNMVWFQYHTKTDNKFKKPECHWEIKDMPLWAL

LNGYVDYLETQIQYGDLSKEGKVLIRCPYTKPALVDPRDDTAGYVVYNRN

FGRGKWIDGGGYIPLHERTKWYVMLRYQTDVFHDIVTCGPWQYRDDNKNS

QLVAKYRFSFIWGGNTVHSQVIRNPCKDNQVSGPRRQPRDIQVVDPQRIT

PPWVLHSFDQRRGLFTETALRRLLQEPLPGEYAVSTLRTPLLFLPSEYQR

EDGAAESASGSPAKRPRIWSEESQTETISSEENPAETTRELLQRKLREQR

ALQFQLQHFAVQLAKTQANLHVNPLLSFPQ (SEQ ID NO: 191)

| Annotations: | |
|---|---|
| Putative Domain | AA range |
| Arg-Rich Region | 1-74 |
| Jelly-roll domain | 75-284 |
| Hypervariable Region | 285-445 |
| N22 | 446-611 |
| C-terminal Domain | 612-780 |

TABLE 27

Exemplary *Anellovirus* ORF1 amino acid subsequence
(*Alphatorquevirus*, Clade 4)
TTV-HD20a-ORF1 (*Alphatorquevirus* Clade 4)

| | |
|---|---|
| Arg-Rich Region | MAWWGWRRRWWRPKRRWRWRRARRRRRVPARRPRRAFRR YRTRTVRRRRGRRRGYRRRYRLRRYARRRFRRKK (SEQ ID NO: 192) |
| Jelly-roll Domain | IVLTQWNPQTTRKCIIRGMMPVLWAGMGTGGRNYAVRSD DYVVNKGFGGSFATETFSLKVLYDQFQRGFNRWSHTNED LDLARYRGCRWTFYRHKDTDFIVYFTNNPPMKTNQFSAP LTTPGMLMRSKYKVLIPSFQTRPKGRKTVTVKIRPPKLF QDKWYTQQDLCSVPLVQLNVTAADFTHPFGSPLTETPCV EFQVLGDLYNTCLNI (SEQ ID NO: 193) |
| Hyper-variable domain | DLPQFSELGEITSAYSKPNSNNLKELYKELFTKATSGHY WQTFITNSMVRAHIDADKAKEAQRASTTPSYNNDPFPTI PVKSEFAQWKKKFTDTRDSPFLFATYHPEAIKDTIMKMR ENNFKLETGPNDKYGDYTAQYQGNTHMLDYYLGFYSPIF LSDGR (SEQ ID NO: 194) |

TABLE 27-continued

| Exemplary *Anellovirus* ORF1 amino acid subsequence (*Alphatorquevirus*, Clade 4) TTV-HD20a-ORF1 (*Alphatorquevirus* Clade 4) | |
|---|---|
| N22 | SNVEFFTAYRDIVYNPFLDKAQGNMVWFQYHTKTDNKFKKPECHWEIKDMPLWALLNGYVDYLETQIQYGDLSKEGKVLIRCPYTKPALVDPRDDTAGYVVYNRNFGRGKWIDGGGYIPLHERTKWYVMLRYQTDVFHDIVTCGPWQYRDDNKNSQLVAKYRFSFI (SEQ ID NO: 195) |
| C-terminal domain | WGGNTVHSQVIRNPCKDNQVSGPRRQPRDIQVVDPQRITPPWVLHSFDQRRGLFTETALRRLLQEPLPGEYAVSTLRTPLLFLPSEYQREDGAAESASGSPAKRPRIWSEESQTETISSEENPAETTRELLQRKLREQRALQFQLQHFAVQLAKTQANLHVNPLLSFPQ (SEQ ID NO: 196) |

TABLE 28

Exemplary *Anellovirus* ORF1 amino acid subsequence (*Alphatorquevirus*, Clade 5)

| | |
|---|---|
| Name | TTV-16 (TUS01) |
| Genus/Clade | *Alphatorquevirus*, Clade 5 |
| Accession Number | AB017613.1 |
| Protein Accession Number | BAA82454.1 |
| Full Sequence: 761 AA | |

```
1         10         20         30         40         50
|         |          |          |          |          |
MAYWFRRWGWRPRRRWRRWRRRRRRLPRRRTRRAVRGLGRRRKPRVRRRR

RTRRRTYRRGWRRRRYIRRGRRKKKLILTQWNPAIVKRCNIKGGLPIIIC

GEPRAAFNYGYHMEDYTPQPFPFGGGMSTVTFSLKALYDQYLKHQNRWTF

SNDQLDLARYRGCKLRFYRSPVCDFIVHYNLIPPLKMNQFTSPNTHPGLL

MLSKHKIIIPSFQTRPGGRRFVKIRLNPPKLFEDKWYTQQDLCKVPLVSI

TATAADLRYPFCSPQTNNPCTTFQVLRKNYNTVIGTSVKDQESTQDFENW

LYKTDSHYQTFATEAQLGRIPAFNPDGTKNTKQQSWQDNWSKKNSPWTGN

SGTYPQTTSEMYKIPYDSNFGFPTYRAQKDYILERRQCNFNYEVNNPVSK

KVWPQPSTTTPTVDYYEYHCGWFSNIFIGPNRYNLQFQTAYVDTTYNPLM

DKGKGNKIWFQYLSKKGTDYNEKQCYCTLEDMPLWAICFGYTDYVETQLG

PNVDHETAGLIIMICPYTQPPMYDKNRPNWGYVVYDTNFGNGKMPSGSGQ

VPVYWQCRWRPMLWFQQQVLNDISKTGPYAYRDEYKNVQLTLYYNFIFNW

GGDMYYPQVVKNPCGDSGIVPGSGRFTREVQVVSPLSMGPAYIFHYFDSR

RGFFSEKALKRMQQQQEFDESFTFKPKRPKLSTAAAEILQLEEDSTSGEG

KSPLQQEEKEVEVLQTPTVQLQLQRNIQEQLAIKQQLQFLLLQLLKTQSN

LHLNPQFLSPS (SEQ ID NO: 197)
```

Annotations:

| Putative Domain | AA range |
|---|---|
| Arg-Rich Region | 1-75 |
| Jelly-roll domain | 75-284 |
| Hypervariable Region | 285-432 |
| N22 | 433-599 |
| C-terminal Domain | 600-780 |

TABLE 29

| Exemplary *Anellovirus* ORF1 amino acid subsequence (*Alphatorquevirus*, Clade 5) TTV-16(TUS01)-ORF1 (*Alphatorquevirus* Clade 5) | |
|---|---|
| Arg-Rich Region | MAYWFRRWGWRPRRRWRRWRRRRRRLPRRRTRRAVRGLGRRRKPRVRRRRRTRRRTYRRGWRRRRYIRRGRRKKK (SEQ ID NO: 198) |
| Jelly-roll Domain | LILTQWNPAIVKRCNIKGGLPIIICGEPRAAFNYGYHMEDYTPQPFPFGGGMSTVTFSLKALYDQYLKHQNRWTFSNDQLDLARYRGCKLRFYRSPVCDFIVHYNLIPPLKMNQFTSPNTHPGLLMLSKHKIIIPSFQTRPGGRRFVKIRLNPPKLFEDKWYTQQDLCKVPLVSITATAADLRYPFCSPQTNNPCTTFQVLRKNYNTVI (SEQ ID NO: 199) |
| Hyper-variable domain | GTSVKDQESTQDFENWLYKTDSHYQTFATEAQLGRIPAFNPDGTKNTKQQSWQDNWSKKNSPWTGNSGTYPQTTSEMYKIPYDSNFGFPTYRAQKDYILERRQCNFNYEVNNPVSKKVWPQPSTTTPTVDYYEYHCGWFSNIFIGPNR (SEQ ID NO: 200) |
| N22 | YNLQFQTAYVDTTYNPLMDKGKGNKIWFQYLSKKGTDYNEKQCYCTLEDMPLWAICFGYTDYVETQLGPNVDHETAGLIIMICPYTQPPMYDKNRPNWGYVVYDTNFGNGKMPSGSGQVPVYWQCRWRPMLWFQQQVLNDISKTGPYAYRDEYKNVQLTLYYNFIFN (SEQ ID NO: 201) |
| C-terminal domain | WGGDMYYPQVVKNPCGDSGIVPGSGRFTREVQVVSPLSMGPAYIFHYFDSRRGFFSEKALKRMQQQQEFDESFTFKPKRPKLSTAAAEILQLEEDSTSGEGKSPLQQEEKEVEVLQTPTVQLQLQRNIQEQLAIKQQLQFLLLQLLKTQSNLHLNPQFLSPS (SEQ ID NO: 202) |

TABLE 30

Exemplary *Anellovirus* ORF1 amino acid subsequence (*Alphatorquevirus*, Clade 6)

| | |
|---|---|
| Name | TTV-TJN02 |
| Genus/Clade | *Alphatorquevirus*, Clade 6 |
| Accession Number | AB028669.1 |
| Protein Accession Number | BAA94878.1 |
| Full Sequence: 746 AA | |

```
1         10         20         30         40         50
|         |          |          |          |          |
MAWGWWRWRRRWPARRWRRRRRRRPVRRTRARRPARRYRRRRTVRTRRRR
WGRRRYRRGWRRRTYVRKGRHRKKKKRLILRQWQPATRRRCTITGYLPIV
FCGHTRGNKNYALHSDDYTPQGQPFGGALSTTSFSLKVLFDQHQRGLNKW
SFPNDQLDLARYRGCKFIFYRTKQTDWVGQYDISEPYKLDKYSCPNYHPG
NMIKAKHKFLIPSYDTNPRGRQKIIVKIPPPDLFVDKWYTQEDLCSVNLV
SLAVSAASFLHPFGSPQTDNPCYTFQVLKEFYYQAIGFSASTQAMTSVLD
TLYTQNSYWESNLTQFYVLNAKKGSDTTQPLTSNMPTREEFMAKKNTNYN
WYTYKAASVKNKLHQMRQTYFEELTSKGPQTTKSEEGYSQHWTTPSTNAY
EYHLGMFSAIFLAPDRPVPRFPCAYQDVTYNPLMDKGVGNHIWFQYNTKA
DTQLIVTGGSCKAHIQDIPLWAAFYGYSDFIESELGPFVDAETVGLVCVI
CPYTKPPMYNKTNPAMGYVFYDRNFGDGKWTDGRGKIEPYWQVRWRPEML
FQETVMADLVQTGPFSYKDELKNSTLVCKYKFYFTWGGNMMFQQTIKNPC
KTDGQPTDSSRHPRGIQVADPEQMGPRWVFHSFDWRRGYLSEKALKRLQE
KPLDYDEYFTQPKRPRIFPPTESAEGEFREPEKGSYSEEERSQASAEEQT
QEATVLLLKRRLREQQQLQQQLQFLTREMFKTQAGLHLNPMLLNQR
(SEQ ID NO: 203)
```

Annotations:

| Putative Domain | AA range |
|---|---|
| Arg-Rich Region | 1-77 |
| Jelly-roll domain | 78-286 |
| Hypervariable Region | 287-416 |
| N22 | 417-585 |
| C-terminal Domain | 586-746 |

TABLE 31

| Exemplary *Anellovirus* ORF1 amino acid subsequence (*Alphatorquevirus*, Clade 6) TTV-TJNO2-ORF1 (*Alphatorquevirus* Clade 6) | |
|---|---|
| Arg-Rich Region | MAWGWWRWRRRWPARRWRRRRRRPVRRTRARR PARRYRRRRTVRTRRRRWGRRRYRRGWRRRTYV RKGRHRKKKKR (SEQ ID NO: 204) |
| Jelly-roll Domain | LILRQWQPATRRRCTITGYLPIVFCGHTRGNKN YALHSDDYTPQGQPFGGALSTTSFSLKVLFDQH QRGLNKWSFPNDQLDLARYRGCKFIFYRTKQTD WVGQYDISEPYKLDKYSCPNYHPGNMIKAKHKF LIPSYDTNPRGRQKIIVKIPPPDLFVDKWYTQE DLCSVNLVSLAVSAASFLHPFGSPQTDNPCYTF QVLKEFYYQAI (SEQ ID NO: 205) |
| Hypervariable domain | GFSASTQAMTSVLDTLYTQNSYWESNLTQFYVL NAKKGSDTTQPLTSNMPTREEFMAKKNTNYNWY TYKAASVKNKLHQMRQTYFEELTSKGPQTTKSE EGYSQHWTTPSTNAYEYHLGMFSAIFLAPDR (SEQ ID NO: 206) |
| N22 | PVPRFPCAYQDVTYNPLMDKGVGNHIWFQYNTK ADTQLIVTGGSCKAHIQDIPLWAAFYGYSDFIE SELGPFVDAETVGLVCVICPYTKPPMYNKTNPA MGYVFYDRNFGDGKWTDGRGKIEPYWQVRWRPE MLFQETVMADLVQTGPFSYKDELKNSTLVCKYK FYFT (SEQ ID NO: 207) |
| C-terminal domain | WGGNMMFQQTIKNPCKTDGQPTDSSRHPRGIQV ADPEQMGPRWVFHSFDWRRGYLSEKALKRLQEK PLDYDEYFTQPKRPRIFPPTESAEGEFREPEKG SYSEEERSQASAEEQTQEATVLLLKRRLREQQQ LQQQLQFLTREMFKTQAGLHLNPMLLNQR (SEQ ID NO: 208) |

TABLE 32

Exemplary *Anellovirus* ORF1 amino acid subsequence (*Alphatorquevirus*, Clade 7)

| | |
|---|---|
| Name | TTV-HD16d |
| Genus/Clade | *Alphatorquevirus*, Clade 7 |
| Accession Number | FR751479.1 |
| Protein Accession Number | NA |
| Full Sequence: 765 AA | |

```
1        10        20        30        40        50
|        |         |         |         |         |
MAWSWWWQRWRRRRWKPRRRRWRRLRWRRPRRAVRRRRRGRRVRRRRWAR
RRGRRRRYATRRKRRYRGRRFKKKLVLTQWHPNTMRRCLIKGIVPLVICG
HTRWNYNYALHSKDYTEEGRYPHGGALSTTTWSLKVLYDEHLKHHDFWGY
PNNQLDLARYKGAKFTFYRHKKTDFIIFFNRKPPFKLNKYSCASYHPGML
MQQRHKILLPSYETKPKGRPKITVRIKPPTLLEDKWYTQQDLCDVNLLQL
VVTAADFRHPLCSPQTNTPTTTFQVLKDIYYDTMSISEPTDSYTSVNNKS
TTQTFTNYSNTLENILYTRASYWNSFHATEYLNPNIIYKNGEKLFKEHED
LITWMTQTNNTGFLTKNNTAFGNNSYRPNADKIKKARKTYWNALIGTNDL
ATNIGQARAERFEYHLGWYSPIFLSRHRSNMNFARAYQDVTYNPNCDRGV
NNRVWVQPLTKPTTEFDEKRCKCVVQHLPLWAALYCYQDFVEEELGSSSE
ILNSCLLVLQCPYTFPPMYDKKLPDKGFVFYDSLFGDGKMSDGRGQVDIF
WQQRWYPRLATQMQVMHDITMTGPFSYRDELVSTQLTAKYTFDFMWGGNM
ISTQIIKNPCKDSGLEPAYPGRQRRDLQIVDPYSMGPQFSFHNWDYRHGL
FGQDAIDRVSKQPKDDADYPNPYKRPRYFPPTDQAAQEQEKDFSFLKTAP
```

TABLE 32-continued

Exemplary *Anellovirus* ORF1 amino acid subsequence (*Alphatorquevirus*, Clade 7)

```
SNSEESDQEVLQETQVLRFQPEQHKQLHLQLAERQRIGEQLRYLLQQMFK
TQANLHLNPYTFTQL
(SEQ ID NO: 209)
```

Annotations:

| Putative Domain | AA range |
|---|---|
| Arg-Rich Region | 1-74 |
| Jelly-roll domain | 75-286 |
| Hypervariable Region | 287-428 |
| N22 | 429-595 |
| C-terminal Domain | 596-765 |

TABLE 33

| Exemplary *Anellovirus* ORF1 amino acid subsequence (*Alphatorquevirus*, Clade 7) TTV-HD16d-ORF1 (*Alphatorquevirus* Clade 7) | |
|---|---|
| Arg-Rich Region | MAWSWWWQRWRRRRWKPRRRRWRRLRWRRPRRA VRRRRRGRRVRRRRWARRRGRRRRYATRRKRRY RGRRFKKK (SEQ ID NO: 210) |
| Jelly-roll Domain | LVLTQWHPNTMRRCLIKGIVPLVICGHTRWNYN YALHSKDYTEEGRYPHGGALSTTTWSLKVLYDE HLKHHDFWGYPNNQLDLARYKGAKFTFYRHKKT DFIIFFNRKPPFKLNKYSCASYHPGMLMQQRHK ILLPSYETKPKGRPKITVRIKPPTLLEDKWYTQ QDLCDVNLLQLVVTAADFRHPLCSPQTNTPTTT FQVLKDIYYDTMSI (SEQ ID NO: 211) |
| Hypervariable domain | SEPTDSYTSVNNKSTTQTFTNYSNTLENILYTR ASYWNSFHATEYLNPN IIYKNGEKLFKEHEDL ITWMTQTNNTGFLTKNNTAFGNNSYRPNADKIK KARKTYWNALIGTNDLATNIGQARAERFEYHLG WYSPIFLSRHR (SEQ ID NO: 212) |
| N22 | SNMNFARAYQDVTYNPNCDRGVNNRVWVQPLTK PTTEFDEKRCKCVVQHLPLWAALYCYQDFVEEE LGSSSEILNSCLLVLQCPYTFPPMYDKKLPDKG FVFYDSLFGDGKMSDGRGQVDIFWQQRWYPRLA TQMQVMHDITMTGPFSYRDELVSTQLTAKYTFD FM (SEQ ID NO: 213) |
| C-terminal domain | WGGNMISTQIIKNPCKDSGLEPAYPGRQRRDLQ IVDPYSMGPQFSFHNWDYRHGLFGQDAIDRVS KQPKDDADYPNPYKRPRYFPPTDQAAQEQEKDF SFLKTAPSNSEESDQEVLQETQVLRFQPEQHKQ LHLQLAERQRIGEQLRYLLQQMFKTQANLHLNP YTFTQL (SEQ ID NO: 214) |

TABLE 34

Exemplary *Anellovirus* ORF1 amino acid subsequence (*Betatorquevirus*)

| | |
|---|---|
| Name | TTMV-LY2 |
| Genus/Clade | *Betatorquevirus* |
| Accession Number | JX134045.1 |
| Protein Accession Number | AGG91484.1 |
| Full Sequence: 666 AA | |

```
1        10        20        30        40        50
|        |         |         |         |         |
MPYYYRRRRYNYRRPRWYGRGWIRRPFRRRFRRKRRVRPTYTTIPLKQWQ
PPYKRTCYIKGQDCLIYYSNLRLGMNSTMYEKSIVPVHWPGGGSFSVSML
TLDALYDIHKLCRNWWTSTNQDLPLVRYKGCKITFYQSTFTDYIVRIHTE
LPANSNKLTYPNTHPLMMMMSKYKHIIPSRQTRRKKKPYTKIFVKPPPQF
```

TABLE 34-continued

Exemplary *Anellovirus* ORF1 amino acid subsequence (*Betatorquevirus*)

ENKWYFATDLYKIPLLQIHCTACNLQNPFVKPDKLSNNVTLWSLNTISIQ
NRNMSVDQGQSWPFKILGTQSFYFYFYTGANLPGDTTQIPVADLLPLTNP
RINRPGQSLNEAKITDHITFTEYKNKFTNYWGNPFNKHIQEHLDMILYSL
KSPEAIKNEWTTENMKWNQLNNAGTMALTPFNEPIFTQIQYNPDRDTGED
TQLYLLSNATGTGWDPPGIPELILEGFPLWLIYWGFADFQKNLKKVTNID
TNYMLVAKTKFTQKPGTFYLVILNDTFVEGNSPYEKQPLPEDNIKWYPQV
QYQLEAQNKLLQTGPFTPNIQGQLSDNISMFYKFYFKWGGSPPKAINVEN
PAHQIQYPIPRNEHETTSLQSPGEAPESILYSFDYRHGNYTTTALSRISQ
DWALKDTVSKITEPDRQQLLKQALECLQISEETQEKKEKEVQQLISNLRQ
QQQLYRERIISLLKDQ
(SEQ ID NO: 215)

Annotations:

| Putative Domain | AA range |
|---|---|
| Arg-Rich Region | 1-38 |
| Jelly-roll domain | 39-246 |
| Hypervariable Region | 247-374 |
| N22 | 375-537 |
| C-terminal Domain | 538-666 |

TABLE 35

Exemplary *Anellovirus* ORF1 amino acid subsequence (*Betatorquevirus*)
TTV-HD16d-ORF1 (*Betatorquevirus*)

| | |
|---|---|
| Arg-Rich Region | MPYYYRRRRYNYRRPRWYGRGWIRRPFRRRFRR KRRVR (SEQ ID NO: 216) |
| Jelly-roll Domain | PTYTTIPLKQWQPPYKRTCYIKGQDCLIYYSNL RLGMNSTMYEKSIVPVHWPGGGSFSVSMLTLDA LYDIHKLCRNWWTSTNQDLPLVRYKGCKITFYQ STFTDYIVRIHTELPANSNKLTYPNTHPLMMMM SKYKHIIPSRQTRRKKKPYTKIFVKPPPQFENK WYFATDLYKIPLLQIHCTACNLQNPFVKPDKLS NNVTLWSLNT (SEQ ID NO: 217) |
| Hypervariable domain | ISIQNRNMSVDQGQSWPFKILGTQSFYFYFYTG ANLPGDTTQIPVADLLPLTNPRINRPGQSLNEA KITDHITFTEYKNKFTNYWGNPFNKHIQEHLDM ILYSLKSPEAIKNEWTTENMKWNQLNNAG (SEQ ID NO: 218) |
| N22 | TMALTPFNEPIFTQIQYNPDRDTGEDTQLYLLS NATGTGWDPPGIPELILEGFPLWLIYWGFADFQ KNLKKVTNIDTNYMLVAKTKFTQKPGTFYLVIL NDTFVEGNSPYEKQPLPEDNIKWYPQVQYQLEA QNKLLQTGPFTPNIQGQLSDNISMFYKFYFK (SEQ ID NO: 219) |
| C-terminal domain | WGGSPPKAINVENPAHQIQYPIPRNEHETTSLQ SPGEAPESILYSFDYRH GNYTTTALSRISQDW ALKDTVSKITEPDRQQLLKQALECLQISEETQE KKEKEVQQLISNLRQQQQLYRERIISLLKDQ (SEQ ID NO: 220) |

TABLE 36

Exemplary *Anellovirus* ORF1 amino acid subsequence (*Gammatorquevirus*)

| | |
|---|---|
| Name | TTMDV-MD1-073 |
| Genus/Clade | *Gammatorquevirus* |
| Accession Number | AB290918.1 |
| Protein Accession Number | BAG49427.1 |
| Full Sequence: 673 AA | |

1 10 20 30 40 50
| | | | | |
MPFWWGRRNKFWYGRNYRRKKRRFPKRRKRRFYRRTKYRRPARRRRRRRR
KVRRKKKTLIVRQWQPDSIVLCKIKGYDSIIWGAEGTQFQCSTHEMYEYT

TABLE 36-continued

Exemplary *Anellovirus* ORF1 amino acid subsequence (*Gammatorquevirus*)

RQKYPGGGGFGVQLYSLEYLYDQWKLRNNIWTKTNQLKDLCRYLKCVMTF
YRHQHIDFVIVYERQPPFEIDKLTYMKYHPYMLLQRKHKIILPSQTTNPR
GKLKKKKTIKPPKQMLSKWFFQQQFAKYDLLLIAAAACSLRYPRIGCCNE
NRMITLYCLNTKFYQDTEWGTTKQAPHYFKPYATINKSMIFVSNYGGKKT
EYNIGQWIETDIPGEGNLARYYRSISKEGGYFSPKILQAYQTKVKSVDYK
PLPIVLGRYNPAIDDGKGNKIYLQTIMNGHWGLPQKTPDYIIEEVPLWLG
FWGYYNYLKQTRTEAIFPLHMFVVQSKYIQTQQTETPNNFWAFIDNSFIQ
GKNPWDSVITYSEQKLWFPTVAWQLKTINAICESGPYVPKLDNQTYSTWE
LATHYSFHFKWGGPQISDQPVEDPGNKNKYDVPDTIKEALQIVNPAKNIA
ATMFHDWDYRRGCITSTAIKRMQQNLPTDSSLESDSDSEPAPKKKRLLPV
LHDPQKKTEKINQCLLSLCEESTCQEQETEENILKLIQQQQQQQQKLKHN
LLVLIKDLKVKQRLLQLQTGVLE
(SEQ ID NO: 221)

Annotations:

| Putative Domain | AA range |
|---|---|
| Arg-Rich Region | 1-57 |
| Jelly-roll domain | 58-259 |
| Hypervariable Region | 260-351 |
| N22 | 352-510 |
| C-terminal Domain | 511-673 |

TABLE 37

Exemplary *Anellovirus* ORF1 amino acid subsequence (*Gammatorquevirus*)
TTV-HD16d-ORF1 (*Gammatorquevirus*)

| | |
|---|---|
| Arg-Rich Region | MPFWWGRRNKFWYGRNYRRKKRRFPKRRKRRFY RRTKYRRPARRRRRRRRKVRRKKK (SEQ ID NO: 222) |
| Jelly-roll Domain | TLIVRQWQPDSIVLCKIKGYDSIIWGAEGTQFQ CSTHEMYEYTRQKYPGGGGFGVQLYSLEYLYDQ WKLRNNIWTKTNQLKDLCRYLKCVMTFYRHQHI DFVIVYERQPPFEIDKLTYMKYHPYMLLQRKHK IILPSQTTNPRGKLKKKKTIKPPKQMLSKWFFQ QQFAKYDLLLIAAAACSLRYPRIGCCNENRMIT LYCL (SEQ ID NO: 223) |
| Hypervariable domain | NTKFYQDTEWGTTKQAPHYFKPYATINKSMIFV SNYGGKKTEYNIGQWIETDIPGEGNLARYYRSI SKEGGYFSPKILQAYQTKVKSVDYKP (SEQ ID NO: 224) |
| N22 | LPIVLGRYNPAIDDGKGNKIYLQTIMNGHWGLP QKTPDYIIEEVPLWLGFWGYYNYLKQTRTEAIF PLHMFVVQSKYIQTQQTETPNNFWAFIDNSFIQ GKNPWDSVITYSEQKLWFPTVAWQLKTINAICE SGPYVPKLDNQTYSTWELATHYSFHFK (SEQ ID NO: 225) |
| C-terminal domain | WGGPQISDQPVEDPGNKNKYDVPDTIKEALQIV NPAKNIAATMFHDWDYRRGCITSTAIKRMQQNL PTDSSLESDSDSEPAPKKKRLLPVLHDPQKKTE KINQCLLSLCEESTCQEQETEENILKLIQQQQQ QQQKLKHNLLVLIKDLKVKQRLLQLQTGVLE (SEQ ID NO: 226) |

Consensus ORF1 Domain Sequences

In some embodiments, an ORF1 molecule, e.g., as described herein, comprises one or more of a jelly-roll domain, N22 domain, and/or C-terminal domain (CTD). In some embodiments, the jelly-roll domain comprises an amino acid sequence having a jelly-roll domain consensus sequence as described herein (e.g., as listed in any of Tables 37A-37C). In some embodiments, the N22 domain comprises an amino acid sequence having a N22 domain consensus sequence as described herein (e.g., as listed in any of Tables 37A-37C). In some embodiments, the CTD domain comprises an amino acid sequence having a CTD domain consensus sequence as described herein (e.g., as listed in any of Tables 37A-37C). In some embodiments, the amino acids listed in any of Tables 37A-37C in the format "($X_{a-b}$)" comprise a contiguous series of amino acids, in which the series comprises at least a, and at most b, amino acids. In certain embodiments, all of the amino acids in the series are identical. In other embodiments, the series comprises at least two (e.g., at least 2, 3, 4, 5, 6, 7, 8, 9, 10, 11, 12, 13, 14, 15, 16, 17, 18, 19, 20, or 21) different amino acids.

TABLE 37A

*Alphatorquevius* ORF1 domain consensus sequences

| Domain | Sequence | SEQ ID NO: |
|---|---|---|
| Jelly-Roll | LVLTQWQPNTVRRCYIRGYLPLIICGEN($X_{0-3}$)TTSRNYA THSDDTIQKGPFGGGMSTTTFSLRVLYDEYQRFMNRW TYSNEDLDLARYLGCKFTFYRHPDXDFIVQYNTNPPFK DTKLTAPSIHP($X_{1-5}$)GMLMLSKRKILIPSLKTRPKGKHY VKVRIGPPKLFEDKWYTQSDLCDVPLVXLYATAADLQ HPFGSPQTDNPCVTFQVLGSXYNKHLSISP; wherein X = any amino acid. | 227 |
| N22 | SNFEFPGAYTDITYNPLTDKGVGNMVWIQYLTKPDTIX DKTQS($X_{0-3}$)KCLIEDLPLWAALYGYVDFCEKETGDSAII XNXGRVLIRCPYTKPPLYDKT($X_{0-4}$)NKGFVPYSTNFGN GKMPGGSGYVPIYWRARWYPTLFHQKEVLEDIVQSGP FAYKDEKPSTQLVMKYCFNFN; wherein X = any amino acid. | 228 |
| CTD | WGGNPISQQVVRNPCKDSG($X_{0-3}$)SGXGRQPRSVQVVD PKYMGPEYTFHSWDWRRGLFGEKAIKRMSEQPTDDEI FTGGXPKRPRRDPPTXQXPEE($X_{1-4}$)QKESSSFR($X_{2-14}$) PW ESSSQEXESESQEEEE($X_{0-30}$)EQTVQQQLRQQLREQRRL RVQLQLLFQQLLKT($X_{0-4}$)QAGLHINPLLLSQA($X_{0-40}$)*; wherein X = any amino acid. | 229 |

TABLE 37B

*Betatorquevius* ORF1 domain consensus sequences

| Domain | Sequence | SEQ ID NO: |
|---|---|---|
| Jelly-Roll | LKQWQPSTIRKCKIKGYLPLFQCGKGRISNNYTQYKESI VPHHEPGGGGWSIQQFTLGALYEEHLKLRNWWTKSN DGLPLVRYLGCTIKLYRSEDTDYIVTYQRCYPMTATKL TYLSTQPSRMLMNKHKIIVPSKXT($X_{1-4}$)NKKKKPYKKIF IKPPSQMQNKWYFQQDIANTPLLQLTXTACSLDRMYL SSDSISNNITFTSLNTNFFQNPNFQ; wherein X = any amino acid. | 230 |
| N22 | ($X_{4-10}$)TPLYFECRYNPFKDKGTGNKVYLVSNN($X_{1-8}$)TG WDPPTDPDLIIEGFPLWLLLWGWLDWQKKLGKIQNID TDYILVIQSXYYIPP($X_{1-3}$)KLPYYVPLDXD($X_{0-2}$)FLHGRS PY($X_{3-16}$)PSDKQHWHPKVRFQXETINNIALTGPGTPKLP NQKSIQAHMKYKFYFK; wherein X = any amino acid. | 231 |
| CTD | WGGCPAPMETITDPCKQPKYPIPNNLLQTTSLQXPTTPI ETYLYKFDERRGLLTKKAAKRIKKDXTTETTLFTDTGX XTSTTLPTXXQTETTQEEXTSEEE($X_{0-5}$)ETLLQQLQQLR RKQKQLRXRILQLLQLLXLL($X_{0-26}$)*; wherein X = any amino acid. | 232 |

TABLE 37C

*Gammatorquevius* ORF1 domain consensus sequences

| Domain | Sequence | SEQ ID NO: |
|---|---|---|
| Jelly-Roll | TIPLKQWQPESIRKCKIKGYGTLVLGAEGRQFYCYTNE KDEYTPPKAPGGGGFGVELFSLEYLYEQWKARNNIWT KSNXYKDLCRYTGCKITFYRHPTTDFIVXYSRQPPFEID KXTYMXXHPQXLLLRKHKKIILSKATNPKGKLKKKIKI | 233 |

TABLE 37C-continued

*Gammatorquevius* ORF1 domain consensus sequences

| Domain | Sequence | SEQ ID NO: |
|---|---|---|
| | KPPKQMLNKWFFQKQFAXYGLVQLQAAACBLRYPRL GCCNENRLITLYYLN; wherein X = any amino acid. | |
| N22 | LPIVVARYNPAXDTGKGNKXWLXSTLNGSXWAPPTTD KDLIIEGLPLWLALYGYWSYJKKVKKDKGILQSHMFV VKSPAIQPLXTATTQXTFYPXIDNSFIQGKXPYDEPJTX NQKKLWYPTLEHQQETINAIVESGPYVPKLDNQKNST WELXYXYTFYFK; wherein X = any amino acid. | 234 |
| CTD | WGGPQIPDQPVEDPKXQGTYPVPDTXQQTIQIXNPLKQ KPETMFHDWDYRRGIITSTALKRMQENLETDSSFXSDS EETP($X_{0-2}$)KKKKRLTXELPXPQEETEEIQSCLLSLCEEST CQEE($X_{1-6}$)ENLQQLIHQQQQQQQLKHNILKLLSDLKZ KQRLLQLQTGILE($X_{1-10}$)*; wherein X = any amino acid. | 235 |

In some embodiments, the jelly-roll domain comprises a jelly-roll domain amino acid sequence as listed in any of Tables 21, 23, 25, 27, 29, 31, 33, 35, or 37A-37C, or an amino acid sequence having at least 70%, 75%, 80%, 8%, 90%, 95%, 96%, 97%, 98%, 99%, or 100% sequence identity thereto. In some embodiments, the N22 domain comprises a N22 domain amino acid sequence as listed in any of Tables 21, 23, 25, 27, 29, 31, 33, 35, or 37A-37C, or an amino acid sequence having at least 70%, 75%, 80%, 8%, 90%, 95%, 96%, 97%, 98%, 99%, or 100% sequence identity thereto. In some embodiments, the CTD domain comprises a CTD domain amino acid sequence as listed in any of Tables 21, 23, 25, 27, 29, 31, 33, 35, or 37A-37C, or an amino acid sequence having at least 70%, 75%, 80%, 8%, 90%, 95%, 96%, 97%, 98%, 99%, or 100% sequence identity thereto.

Genetic Element

In some embodiments, the anellosome comprises a genetic element. In some embodiments, the genetic element has one or more of the following characteristics: is substantially non-integrating with a host cell's genome, an episomal nucleic acid, a single stranded DNA, is circular, is about 1 to 10 kb, exists within the nucleus of the cell, can be bound by endogenous proteins, and produces a microRNA that targets host genes. In one embodiment, the genetic element is a substantially non-integrating DNA. In some embodiments, the genetic element has at least about 70%, 75%, 80%, 8%, 90%, 95%, 96%, 97%, 98%, 99%, or 100% sequence identity to an *Anellovirus* nucleic acid sequence, e.g., as described herein (e.g., as described in any of Tables 1, 3, 5, 7, 9, 11, 13, 15, or 17), or a fragment thereof, or encodes an amino acid sequence having at least about 70%, 75%, 80%, 8%, 90%, 95%, 96%, 97%, 98%, 99%, or 100% sequence identity to an *Anellovirus* amino acid sequence (e.g., as described in any of Tables 2, 4, 6, 8, 10, 12, 14, 16, or 18), or a fragment thereof. In embodiments, the genetic element comprises a sequence encoding an effector (e.g., an endogenous effector or an exogenous effector, e.g., a payload), e.g., a polypeptide effector (e.g., a protein) or nucleic acid effector (e.g., a non-coding RNA, e.g., a miRNA, siRNA, mRNA, lncRNA, RNA, DNA, an antisense RNA, gRNA).

In some embodiments, the genetic element has a length less than 20 kb (e.g., less than about 19 kb, 18 kb, 17 kb, 16 kb, 15 kb, 14 kb, 13 kb, 12 kb, 11 kb, 10 kb, 9 kb, 8 kb, 7 kb, 6 kb, 5 kb, 4 kb, 3 kb, 2 kb, 1 kb, or less). In some embodiments, the genetic element has, independently or in addition to, a length greater than 1000b (e.g., at least about 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4 kb, 4.1 kb, 4.2 kb, 4.3 kb, 4.4 kb, 4.5 kb, 4.6 kb, 4.7 kb, 4.8 kb, 4.9 kb, 5 kb, or greater). In some embodiments, the genetic element has a length of about 2.5-4.6, 2.8-4.0, 3.0-3.8, or 3.2-3.7 kb.

In some embodiments, the genetic element comprises one or more of the features described herein, e.g., a sequence encoding a substantially non-pathogenic protein, a protein binding sequence, one or more sequences encoding a regulatory nucleic acid, one or more regulatory sequences, one or more sequences encoding a replication protein, and other sequences. In some embodiments, the substantially non-pathogenic protein comprises an amino acid sequence or a functional fragment thereof or a sequence having at least about 60%, 65%, 70%, 75%, 80%, 85%, 90% 95%, 96%, 97%, 98%, 99%, or 100% sequence identity to any one of the amino acid sequences described herein, an *Anellovirus* amino acid sequence, e.g., as listed in any of Tables 2, 4, 6, 8, 10, 12, 14, 16, or 18.

In one embodiment, the invention includes a genetic element comprising a nucleic acid sequence (e.g., a DNA sequence) encoding (i) a substantially non-pathogenic exterior protein, (ii) an exterior protein binding sequence that binds the genetic element to the substantially non-pathogenic exterior protein, and (iii) a regulatory nucleic acid. In such an embodiment, the genetic element may comprise one or more sequences with at least about 60%, 70% 80%, 85%, 90% 95%, 96%, 97%, 98% and 99% nucleotide sequence identity to any one of the nucleotide sequences to a native viral sequence (e.g., a native *Anellovirus* sequence, e.g., as described herein).

Proteins, e.g., Substantially Non-Pathogenic Protein

In some embodiments, the genetic element comprises a sequence that encodes a protein, e.g., a substantially non-pathogenic protein. In embodiments, the substantially non-pathogenic protein is a major component of the proteinaceous exterior of the anellosome. Multiple substantially non-pathogenic protein molecules may self-assemble into an icosahedral formation that makes up the proteinaceous exterior. In embodiments, the protein is present in the proteinaceous exterior.

In some embodiments, the protein, e.g., substantially non-pathogenic protein and/or proteinaceous exterior protein, comprises one or more glycosylated amino acids, e.g., 2, 3, 4, 5, 6, 7, 8, 9, 10, or more.

In some embodiments, the protein, e.g., substantially non-pathogenic protein and/or proteinaceous exterior protein comprises at least one hydrophilic DNA-binding region, an arginine-rich region, a threonine-rich region, a glutamine-rich region, a N-terminal polyarginine sequence, a variable region, a C-terminal polyglutamine/glutamate sequence, and one or more disulfide bridges.

In some embodiments, the genetic element comprises a nucleotide sequence encoding a capsid protein or a fragment of a capsid protein or a sequence having at least about 60%, 65%, 70%, 75%, 80%, 85%, 90% 95%, 96%, 97%, 98%, 99%, or 100% nucleotide sequence identity to any one of the nucleotide sequences encoding a capsid protein described herein, e.g., an *Anellovirus* capsid sequence or a capsid protein sequence as listed in any of Tables 1-18. In some embodiments, the genetic element comprises a nucleotide sequence encoding a capsid protein or a functional fragment of a capsid protein or a nucleotide sequence having at least about 60%, 70% 80%, 85%, 90% 95%, 96%, 97%, 98%, 99%, or 100% sequence identity to any one of the nucleotide sequences described herein, e.g., an *Anellovirus* capsid sequence or a capsid protein sequence as listed in any of Tables 1-18. In some embodiments, the substantially non-pathogenic protein comprises a capsid protein or a functional fragment of a capsid protein that is encoded by a capsid nucleotide sequence or a sequence having at least about 60%, 65%, 70%, 75%, 80%, 85%, 90% 95%, 96%, 97%, 98%, 99%, or 100% nucleotide sequence identity to any one of the nucleotide sequences described herein, e.g., an *Anellovirus* capsid sequence or a capsid protein sequence as listed in any of Tables 1, 3, 5, 7, 9, 11, 13, 15, or 17.

In some embodiments, the genetic element comprises a nucleotide sequence encoding a capsid protein or a functional fragment of a capsid protein or a sequence having at least about 60%, 70% 80%, 85%, 90% 95%, 96%, 97%, 98%, 99%, or 100% sequence identity to any one of the amino acid sequences described herein, e.g., an *Anellovirus* capsid sequence or a capsid protein sequence in any of Tables 2, 4, 6, 8, 10, 12, 14, 16, or 18. In some embodiments, the substantially non-pathogenic protein comprises a capsid protein or a functional fragment of a capsid protein or a sequence having at least about 60%, 65%, 70%, 75%, 80%, 85%, 90% 95%, 96%, 97%, 98%, 99%, or 100% sequence identity to any one of the amino acid sequences described herein, e.g., an *Anellovirus* capsid sequence or a capsid protein sequence in any of Tables 2, 4, 6, 8, 10, 12, 14, 16, or 18.

Figure 1A:
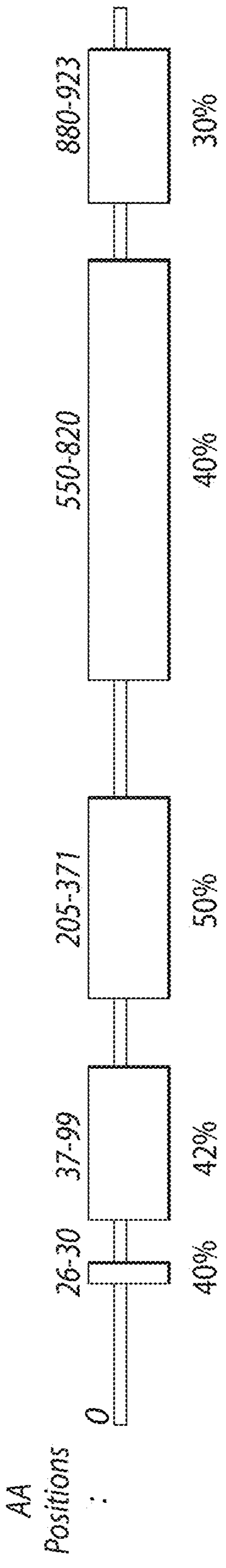
FIG. 1A is an illustration showing percent sequence similarity of amino acid regions of capsid protein sequences.
Figure 1B:
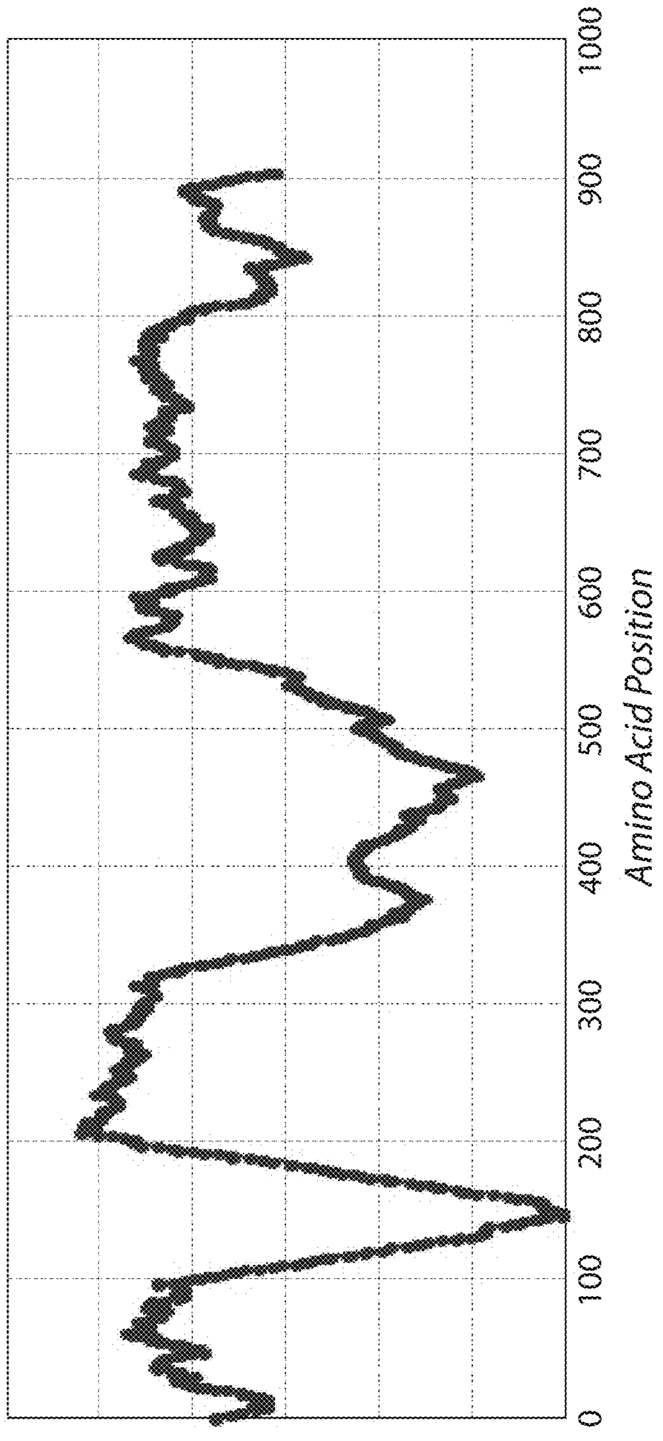
FIG. 1B is an illustration showing percent sequence similarity of capsid protein sequences.

In some embodiments, the genetic element comprises a nucleotide sequence encoding an amino acid sequence having about position 1 to about position 150 (e.g., or any subset of amino acids within each range, e.g., about position 20 to about position 35, about position 25 to about position 30, about position 26 to about 30), about position 150 to about position 390 (e.g., or any subset of amino acids within each range, e.g., about position 200 to about position 380, about position 205 to about position 375, about position 205 to about 371), about 390 to about position 525, about position 525 to about position 850 (e.g., or any subset of amino acids within each range, e.g., about position 530 to about position 840, about position 545 to about position 830, about position 550 to about 820), about 850 to about position 950 (e.g., or any subset of amino acids within each range, e.g., about position 860 to about position 940, about position 870 to about position 930, about position 880 to about 923) of the amino acid sequences described herein, an *Anellovirus* amino acid sequence, e.g., as listed in any of Tables 2, 4, 6, 8, 10, 12, 14, 16, or 18, or shown in FIG. 1, or a functional fragment thereof. In some embodiments, the substantially non-pathogenic protein comprises an amino acid sequence or a functional fragment thereof or a sequence having at least about 60%, 65%, 70%, 75%, 80%, 85%, 90% 95%, 96%, 97%, 98%, 99%, or 100% sequence identity to about position 1 to about position 150 (e.g., or any subset of amino acids within each range as described herein), about position 150 to about position 390, about position 390 to about position 525, about position 525 to about position 850, about position 850 to about position 950 of the amino acid sequences described herein, an *Anellovirus* amino acid sequence, e.g., as listed in any of Tables 2, 4, 6, 8, 10, 12, 14, 16, or 18, or as shown in FIG. 1.

In some embodiments, the substantially non-pathogenic protein comprises an amino acid sequence or a functional fragment thereof or a sequence having at least about 60%, 65%, 70%, 75%, 80%, 85%, 90% 95%, 96%, 97%, 98%, 99%, or 100% sequence identity to any one of the amino acid sequences or ranges of amino acids described herein, an *Anellovirus* amino acid sequence, e.g., as listed in any of Tables 2, 4, 6, 8, 10, 12, 14, 16, or 18, or shown in FIG. 1, where the sequence is a functional domain or provides a function, e.g., species and/or tissue and/or cell tropism, viral genome binding and/or packaging, immune evasion (non-immunogenicity and/or tolerance), pharmacokinetics, endocytosis and/or cell attachment, nuclear entry, intracellular modulation and localization, exocytosis modulation, propagation, nucleic acid protection, and a combination thereof. In some embodiments, the ranges of amino acids with less sequence identity may provide one or more of the properties described herein and differences in cell/tissue/species specificity (e.g. tropism).

Protein Binding Sequence

A strategy employed by many viruses is that the viral capsid protein recognizes a specific protein binding sequence in its genome. For example, in viruses with unsegmented genomes, such as the L-A virus of yeast, there is a secondary structure (stem-loop) and a specific sequence at the 5' end of the genome that are both used to bind the viral capsid protein. However, viruses with segmented genomes, such as Reoviridae, Orthomyxoviridae (influenza), Bunyaviruses and Arenaviruses, need to package each of the genomic segments. Some viruses utilize a complementarity region of the segments to aid the virus in including one of each of the genomic molecules. Other viruses have specific binding sites for each of the different segments. See for example, Curr Opin Struct Biol. 2010 February; 20(1): 114-120; and Journal of Virology (2003), 77(24), 13036-13041.

In some embodiments, the genetic element encodes a protein binding sequence that binds to the substantially non-pathogenic protein. In some embodiments, the protein binding sequence facilitates packaging the genetic element into the proteinaceous exterior. In some embodiments, the protein binding sequence specifically binds an arginine-rich region of the substantially non-pathogenic protein. In some embodiments, the genetic element comprises a protein binding sequence as described in Example 8. In some embodiments, the genetic element comprises a protein binding sequence having at least 70%, 80%, 85%, 90%, 95%, 96%, 97%, 98%, 99%, or 100% sequence identity to a 5' UTR conserved domain or GC-rich domain of an *Anellovirus* sequence (e.g., as shown in any of Tables 1, 3, 5, 7, 9, 11, 13, 15, or 17). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 1 (e.g., nucleotides 177-247 of the nucleic acid sequence of Table 1). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 1 (e.g., nucleotides 3415-3570 of the nucleic acid sequence of Table 1). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 3 (e.g., nucleotides 204-273 of the nucleic acid sequence of Table 3). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 3 (e.g., nucleotides 3302-3541 of the nucleic acid sequence of Table 3). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 5 (e.g., nucleotides 170-240 of the nucleic acid sequence of Table 5). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 5 (e.g., nucleotides 3632-3753 of the nucleic acid sequence of Table 5). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 7 (e.g., nucleotides 170-238 of the nucleic acid sequence of Table 7). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 7 (e.g., nucleotides 3768-3878 of the nucleic acid sequence of Table 7). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 9 (e.g., nucleotides 170-240 of the nucleic acid sequence of Table 9). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 9 (e.g., nucleotides 3302-3541 of the nucleic acid sequence of Table 9). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 11 (e.g., nucleotides 174-244 of the nucleic acid sequence of Table 11). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 11 (e.g., nucleotides 3691-3794 of the nucleic acid sequence of Table 11). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 13 (e.g., nucleotides 170-240 of the nucleic acid sequence of Table 13). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 13 (e.g., nucleotides 3759-3866 of the nucleic acid sequence of Table 13). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 15 (e.g., nucleotides 323-393 of the nucleic acid sequence of Table 15). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 15 (e.g., nucleotides 2868-2929 of the nucleic acid sequence of Table 15). In embodiments, the protein binding sequence has at least about 70%, 75%, 80%, 85%, 90%, 95%, 96%, 97%, 98%, 99%, or 100% sequence identity to the *Anellovirus* 5' UTR conserved domain nucleotide sequence of Table 17 (e.g., nucleotides 117-187 of the nucleic acid sequence of Table 17). In embodiments, the protein binding sequence has at least about 70%, 75%, 80%, 85%, 90%, 95%, 96%, 97%, 98%, 99%, or 100% sequence identity to the *Anellovirus* GC-rich nucleotide sequence of Table 17 (e.g., nucleotides 3054-3172 of the nucleic acid sequence of Table 17).

5' UTR Regions

Figure 20:
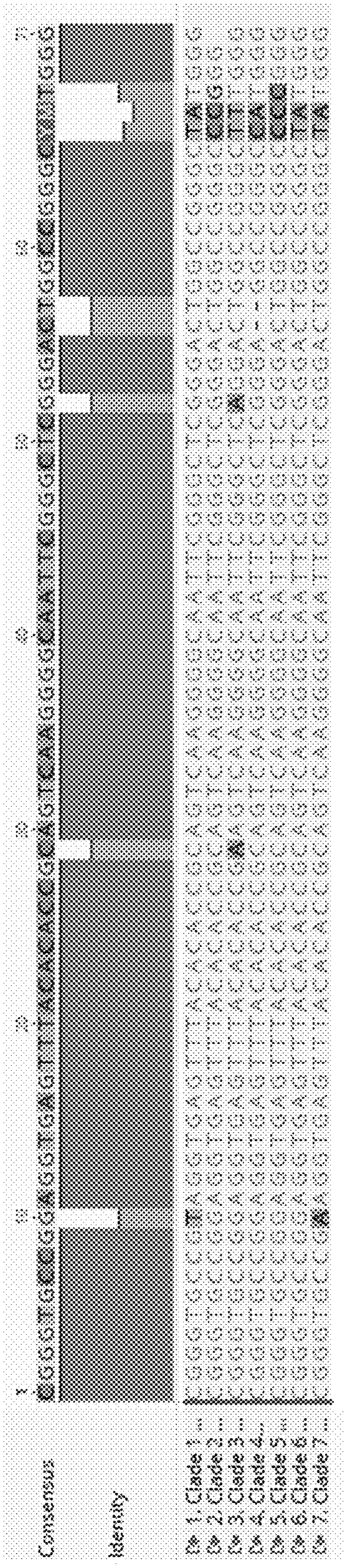
FIG. 20 is a diagram showing that a domain within the 5' UTR is highly conserved across the seven *Alphatorquevirus* clades (SEQ ID NOS 810-817, respectively, in order of appearance). The 71-bp 5'UTR conserved domain sequences for each representative *Alphatorquevirus* were aligned. The sequence has 95.2% pairwise identity between the seven clades.

In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a nucleic acid sequence shown in Table 38 and/or FIG. 20. In some embodiments, the genetic element (e.g., protein-binding sequence of the genetic element) comprises a nucleic acid sequence of the Consensus 5' UTR sequence shown in Table 38, wherein $X_1$, $X_2$, $X_3$, $X_4$, and $X_5$ are each independently any nucleotide, e.g., wherein $X_1$=G or T, $X_2$=C or A, $X_3$=G or A, $X_4$=T or C, and $X_5$=A, C, or T). In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the Consensus 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the exemplary TTV 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-CT30F 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-HD23a 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-JA20 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-TJN02 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the TTV-tth8 5' UTR sequence shown in Table 38.

In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Consensus 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Clade 1 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Clade 2 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Clade 3 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Clade 4 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Clade 5 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Clade 6 5' UTR sequence shown in Table 38. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to the *Alphatorquevirus* Clade 7 5' UTR sequence shown in Table 38.

TABLE 38

Exemplary 5' UTR sequences from *Anelloviruses*

| Source | Sequence | SEQ ID NO: |
|---|---|---|
| Consensus | CGGGTGCCG$X_1$AGGTGAGTTTACACACCG$X_2$AGT CAAGGGGCAATTCGGGCTC$X_3$GGACTGGCCGGG C$X_4X_5$TGGG<br>$X_1$ = G or T<br>$X_2$ = C or A<br>$X_3$ = G or A<br>$X_4$ = T or C<br>$X_5$ = A, C, or T | 105 |
| Exemplary TTV Sequence | CGGGTGCCGGAGGTGAGTTTACACACCGCAGTC AAGGGGCAATTCGGGCTCGGGACTGGCCGGGCT WTGGG | 106 |
| TTV-CT30F | CGGGTGCCGTAGGTGAGTTTACACACCGCAGTC AAGGGGCAATTCGGGCTCGGGACTGGCCGGGCT ATGGG | 107 |
| TTV-HD23a | CGGGTGCCGGAGGTGAGTTTACACACCGCAGTC AAGGGGCAATTCGGGCTCGGGACTGGCCGGGCC CTGGG | 108 |
| TTV-JA20 | CGGGTGCCGGAGGTGAGTTTACACACCGCAGTC AAGGGGCAATTCGGGCTCGGGACTGGCCGGGCT TTGGG | 109 |
| TTV-TJN02 | CGGGTGCCGGAGGTGAGTTTACACACCGCAGTC AAGGGGCAATTCGGGCTCGGGACTGGCCGGGCT ATGGG | 110 |
| TTV-tth8 | CGGGTGCCGGAGGTGAGTTTACACACCGAAGTC AAGGGGCAATTCGGGCTCAGGACTGGCCGGGCT TTGGG | 111 |
| *Alphatorquevirus* Consensus 5' UTR | CGGGTGCCGGAGGTGAGTTTACACACCGCAGTC AAGGGGCAATTCGGGCTCGGGACTGGCCGGGC $X_1X_2$TGGG; wherein $X_1$ comprises T or C, and wherein $X_2$ comprises A, C, or T. | 112 |
| *Alphatorquevirus* Clade 1 5' UTR (e.g., TTV-CT30F) | CGGGTGCCGTAGGTGAGTTTACACACCGCAGTC AAGGGGCAATTCGGGCTCGGGACTGGCCGGGCT ATGGG | 113 |

TABLE 38-continued

| Exemplary 5' UTR sequences from *Anelloviruses* | | |
|---|---|---|
| Source | Sequence | SEQ ID NO: |
| *Alphatorquevirus* Clade 2 5' UTR (e.g., TTV-P13-1) | CGGGTGCCGGAGGTGAGTTTACACACCGCAGTC AAGGGGCAATTCGGGCTCGGGACTGGCCGGGCC CGGG | 114 |
| *Alphatorquevirus* Clade 3 5' UTR (e.g., TTV-tth8) | CGGGTGCCGGAGGTGAGTTTACACACCGAAGTC AAGGGGCAATTCGGGCTCAGGACTGGCCGGGCT TTGGG | 115 |
| *Alphatorquevirus* Clade 4 5' UTR (e.g., TTV-HD20a) | CGGGTGCCGGAGGTGAGTTTACACACCGCAGTC AAGGGGCAATTCGGGCTCGGGAGGCCGGGCCAT GGG | 116 |
| *Alphatorquevirus* Clade 5 5' UTR (e.g., TTV-16) | CGGGTGCCGGAGGTGAGTTTACACACCGCAGTC AAGGGGCAATTCGGGCTCGGGACTGGCCGGGCC CCGGG | 117 |
| *Alphatorquevirus* Clade 6 5' UTR (e.g., TTV-TJN02) | CGGGTGCCGGAGGTGAGTTTACACACCGCAGTC AAGGGGCAATTCGGGCTCGGGACTGGCCGGGCT ATGGG | 118 |
| *Alphatorquevirus* Clade 7 5' UTR (e.g., TTV-HD16d) | CGGGTGCCGAAGGTGAGTTTACACACCGCAGTC AAGGGGCAATTCGGGCTCGGGACTGGCCGGGCT ATGGG | 119 |

GC-Rich Regions

Figure 32:
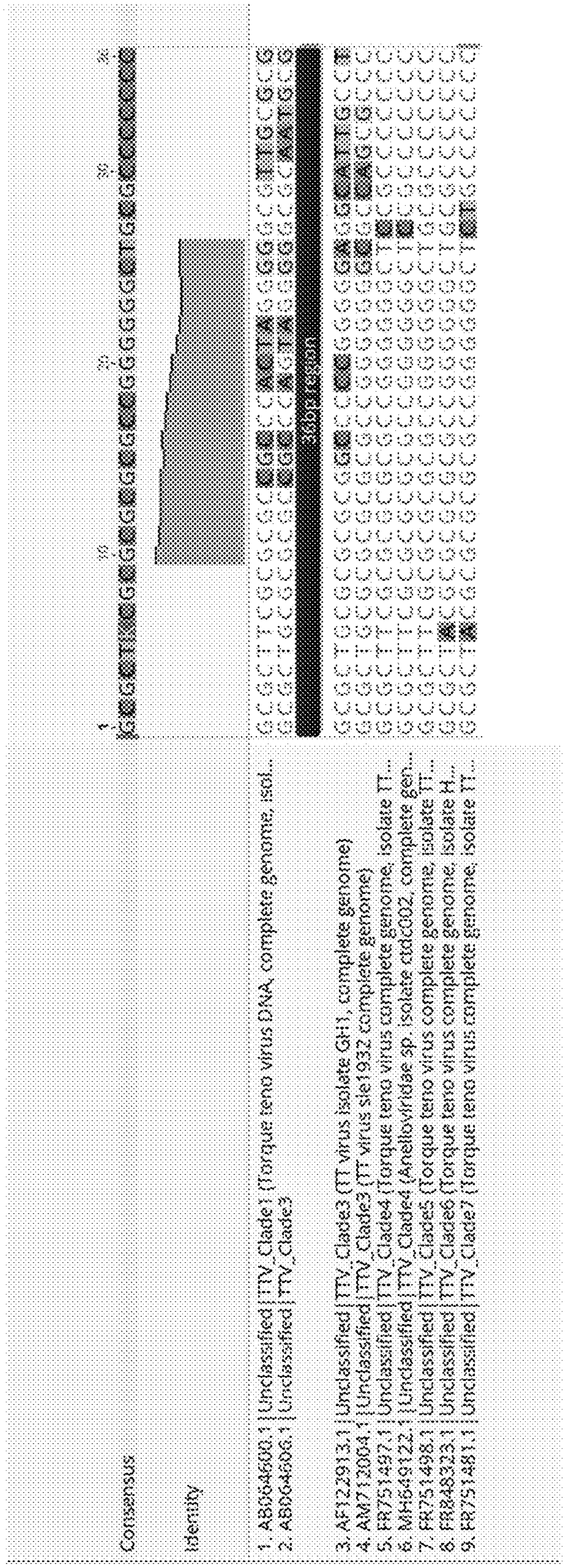
FIG. 32 is a diagram showing an alignment of 36-nucleotide GC-rich regions from nine *Anellovirus* genome sequences, and a consensus sequence based thereon (SEQ ID NOS 818-827, respectively, in order of appearance).

In some embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a nucleic acid sequence shown in any of Table 39 and/or FIGS. 20 and 32. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a GC-rich sequence shown in Table 39.

In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a 36-nucleotide GC-rich sequence as shown in Table 39 (e.g., 36-nucleotide consensus GC-rich region sequence 1, 36-nucleotide consensus GC-rich region sequence 2, TTV Clade 1 36-nucleotide region, TTV Clade 3 36-nucleotide region, TTV Clade 3 isolate GH1 36-nucleotide region, TTV Clade 3 sle1932 36-nucleotide region, TTV Clade 4 ctdc002 36-nucleotide region, TTV Clade 5 36-nucleotide region, TTV Clade 6 36-nucleotide region, or TTV Clade 7 36-nucleotide region). In embodiments, the genetic element (e.g., protein-binding sequence of the genetic element) comprises a nucleic acid sequence comprising at least 10, 15, 20, 25, 30, 31, 32, 33, 34, 35, or 36 consecutive nucleotides of a 36-nucleotide GC-rich sequence as shown in Table 39 (e.g., 36-nucleotide consensus GC-rich region sequence 1, 36-nucleotide consensus GC-rich region sequence 2, TTV Clade 1 36-nucleotide region, TTV Clade 3 36-nucleotide region, TTV Clade 3 isolate GH1 36-nucleotide region, TTV Clade 3 s1e1932 36-nucleotide region, TTV Clade 4 ctdc002 36-nucleotide region, TTV Clade 5 36-nucleotide region, TTV Clade 6 36-nucleotide region, or TTV Clade 7 36-nucleotide region).

In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to an *Alphatorquevirus* GC-rich region sequence, e.g., selected from TTV-CT30F, TTV-P13-1, TTV-tth8, TTV-HD20a, TTV-16, TTV-TJN02, or TTV-HD16d, e.g., as listed in Table 39. In embodiments, the genetic element (e.g., protein-binding sequence of the genetic element) comprises a nucleic acid sequence comprising at least 10, 15, 20, 25, 30, 35, 40, 45, 50, 60, 70, 80, 90, 100, 104, 105, 108, 110, 111, 115, 120, 122, 130, 140, 145, 150, 155, or 156 consecutive nucleotides of an *Alphatorquevirus* GC-rich region sequence, e.g., selected from TTV-CT30F, TTV-P13-1, TTV-tth8, TTV-HD20a, TTV-16, TTV-TJN02, or TTV-HD16d, e.g., as listed in Table 39.

In embodiments, the 36-nucleotide GC-rich sequence is selected from:

(i) (SEQ ID NO: 160)
CGCGCTGCGCGCGCCGCCCAGTAGGGGGAGCCATGC, (ii) (SEQ ID NO: 164)
GCGCT$X_1$CGCGCGCGCGCCGGGGGGCTGCGCCCCCCC, wherein $X_1$ is selected from T, G, or A;

(iii) (SEQ ID NO: 165)
GCGCTTCGCGCGCCGCCCACTAGGGGGCGTTGCGCG;

(iv) (SEQ ID NO: 166)
GCGCTGCGCGCGCCGCCCAGTAGGGGGCGCAATGCG;

(v) (SEQ ID NO: 167)
GCGCTGCGCGCGCGGCCCCCGGGGGAGGCATTGCCT;

(vi) (SEQ ID NO: 168)
GCGCTGCGCGCGCGCGCCGGGGGGGCGCCAGCGCCC;

-continued (vii)
(SEQ ID NO: 169)
GCGCTTCGCGCGCGCGCCGGGGGGCTCCGCCCCCCC;

(viii)
(SEQ ID NO: 170)
GCGCTTCGCGCGCGCGCCGGGGGGCTGCGCCCCCCC;

(ix)
(SEQ ID NO: 171)
GCGCTACGCGCGCGCGCCGGGGGGCTGCGCCCCCCC;
or (x)
(SEQ ID NO: 172)
GCGCTACGCGCGCGCGCCGGGGGGCTCTGCCCCCCC.

In embodiments, the genetic element (e.g., protein-binding sequence of the genetic element) comprises the nucleic acid sequence CGCGCTGCGCGCGCCGCCCAGTAGGGGGAGCCATGC (SEQ ID NO: 160).

In embodiments, the genetic element (e.g., protein-binding sequence of the genetic element) comprises a nucleic acid sequence of the Consensus GC-rich sequence shown in Table 39, wherein $X_1$, $X_4$, $X_5$, $X_6$, $X_7$, $X_{12}$, $X_{13}$, $X_{14}$, $X_{15}$, $X_{20}$, $X_{21}$, $X_{22}$, $X_{26}$, $X_{29}$, $X_{30}$, and $X_{33}$ are each independently any nucleotide and wherein $X_2$, $X_3$, $X_8$, $X_9$, $X_{10}$, $X_{11}$, $X_{16}$, $X_{17}$, $X_{18}$, $X_{19}$, $X_{23}$, $X_{24}$, $X_{25}$, $X_{27}$, $X_{28}$, $X_{31}$, $X_{32}$, and $X_{34}$ are each independently absent or any nucleotide. In some embodiments, one or more of (e.g., all of) $X_1$ through $X_{34}$ are each independently the nucleotide (or absent) specified in Table 39. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to an exemplary TTV GC-rich sequence shown in Table 39 (e.g., the full sequence, Fragment 1, Fragment 2, Fragment 3, or any combination thereof, e.g., Fragments 1-3 in order). In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-CT30F GC-rich sequence shown in Table 39 (e.g., the full sequence, Fragment 1, Fragment 2, Fragment 3, Fragment 4, Fragment 5, Fragment 6, Fragment 7, Fragment 8, or any combination thereof, e.g., Fragments 1-7 in order). In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-HD23a GC-rich sequence shown in Table 39 (e.g., the full sequence, Fragment 1, Fragment 2, Fragment 3, Fragment 4, Fragment 5, Fragment 6, or any combination thereof, e.g., Fragments 1-6 in order). In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-JA20 GC-rich sequence shown in Table 39 (e.g., the full sequence, Fragment 1, Fragment 2, or any combination thereof, e.g., Fragments 1 and 2 in order). In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-TJN02 GC-rich sequence shown in Table 39 (e.g., the full sequence, Fragment 1, Fragment 2, Fragment 3, Fragment 4, Fragment 5, Fragment 6, Fragment 7, Fragment 8, or any combination thereof, e.g., Fragments 1-8 in order). In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to a TTV-tth8 GC-rich sequence shown in Table 39 (e.g., the full sequence, Fragment 1, Fragment 2, Fragment 3, Fragment 4, Fragment 5, Fragment 6, Fragment 7, Fragment 8, Fragment 9, or any combination thereof, e.g., Fragments 1-6 in order). In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to Fragment 7 shown in Table 39. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to Fragment 8 shown in Table 39. In embodiments, the genetic element (e.g., protein-binding sequence of the genetic element) comprises a nucleic acid sequence having at least about 75% (e.g., at least 75%, 80%, 85%, 90%, 95%, 96%, 97%, 98%, 99%, or 100%) identity to Fragment 9 shown in Table 39.

TABLE 39

Exemplary GC-rich sequences from *Anelloviruses*

| Source | Sequence | SEQ ID NO: |
|---|---|---|
| Consensus | $CGGCGGX_1GGX_2GX_3X_4X_5CGCGCTX_6CGCGC$<br>$GCX_7X_8X_9X_{10}CX_{11}X_{12}X_{13}X_{14}GGGGX_{15}X_{16}X_{17}X_{18}$<br>$X_{19}X_{20}X_{21}GCX_{22}X_{23}X_{24}X_{25}CCCCCCCX_{26}CGCGC$<br>$ATX_{27}X_{28}GCX_{29}CGGGX_{30}CCCCCCCCCX_{31}X_{32}X_{33}$<br>GGGGGGCTCCGX34CCCCCCGGCCCCCC<br>$X_1$ = G or C<br>$X_2$ = G, C, or absent<br>$X_3$ = C or absent<br>$X_4$ = G or C<br>$X_5$ = G or C<br>$X_6$ = T, G, or A<br>$X_7$ = G or C<br>$X_8$ = G or absent<br>$X_9$ = C or absent<br>$X_{10}$ = C or absent<br>$X_{11}$ = G, A, or absent<br>$X_{12}$ = G or C<br>$X_{13}$ = C or T | 120 |

TABLE 39-continued

| Exemplary GC-rich sequences from *Anelloviruses* | | | |
|---|---|---|---|
| Source | Sequence | | SEQ ID NO: |
| | $X_{14}$ = G or A<br>$X_{15}$ = G or A<br>$X_{16}$ = A, G, T, or absent<br>$X_{17}$ = G, C, or absent<br>$X_{18}$ = G, C, or absent<br>$X_{19}$ = C, A, or absent<br>$X_{20}$ = C or A<br>$X_{21}$ = T or A<br>$X_{22}$ = G or C<br>$X_{23}$ = G, T, or absent<br>$X_{24}$ = C or absent<br>$X_{25}$ = G, C, or absent<br>$X_{26}$ = G or C<br>$X_{27}$ = G or absent<br>$X_{28}$ = C or absent<br>$X_{29}$ = G Or A<br>$X_{30}$ = G or T<br>$X_{31}$ = C, T, or absent<br>$X_{32}$ = G, C, A, or absent<br>$X_{33}$ = G or C<br>$X_{34}$ = C or absent | | |
| Exemplary TTV Sequence | Full sequence | GCCGCCGCGGCGGCGGSGGNGNSGCGCGCT<br>DCGCGCGCSNNNCRCCRGGGGGNNNNCWG<br>CSNCNCCCCCCCCCGCGCATGCGCGGGKCC<br>CCCCCCCNNCGGGGGGCTCCGCCCCCCGGC<br>CCCCCCCCGTGCTAAACCCACCGCGCATGC<br>GCGACCACGCCCCCGCCGCC | 121 |
| | Fragment 1 | GCCGCCGCGGCGGCGGSGGNGNSGCGCGCT<br>DCGCGCGCSNNNCRCCRGGGGGNNNNCWG<br>CSNCNCCCCCCCCCGCGCAT | 122 |
| | Fragment 2 | GCGCGGGKCCCCCCCCCNNCGGGGGGCTC<br>CG | 123 |
| | Fragment 3 | CCCCCCGGCCCCCCCCCGTGCTAAACCCAC<br>CGCGCATGCGCGACCACGCCCCCGCCGCC | 124 |
| TTV-CT30F | Full sequence | GCGGCGG-GGGGGCG-GCCGCG-<br>TTCGCGCGCCGCCCACCAGGGGGTG--<br>CTGCG-CGCCCCCCCCCGCGCAT<br>GCGCGGGGCCCCCCCCC--<br>GGGGGGGCTCCGCCCCCCCGGCCCCCCCCC<br>GTGCTAAACCCACCGCGCATGCGCGACCAC<br>GCCCCCGCCGCC | 125 |
| | Fragment 1 | GCGGCGG | 126 |
| | Fragment 2 | GGGGGCG | 127 |
| | Fragment 3 | GCCGCG | 128 |
| | Fragment 4 | TTCGCGCGCCGCCCACCAGGGGGTG | 129 |
| | Fragment 5 | CTGCG | 130 |
| | Fragment 6 | CGCCCCCCCCCGCGCAT | 131 |
| | Fragment 7 | GCGCGGGGCCCCCCCCC | 132 |
| | Fragment 8 | GGGGGGGCTCCGCCCCCCCGGCCCCCCCCC<br>GTGCTAAACCCACCGCGCATGCGCGACCAC<br>GCCCCCGCCGCC | 133 |
| TTV-HD23a | Full sequence | CGGCGGCGGCGGCG-<br>CGCGCGCTGCGCGCGCG---<br>CGCCGGGGGGGCGCCAGCG-<br>CCCCCCCCCCCGCGCAT<br>GCACGGGTCCCCCCCCCCACGGGGGGCTCC<br>G CCCCCCGGCCCCCCCCC | 134 |
| | Fragment 1 | CGGCGGCGGCGGCG | 135 |
| | Fragment 2 | CGCGCGCTGCGCGCGCG | 136 |

TABLE 39-continued

| Exemplary GC-rich sequences from *Anelloviruses* | | | |
|---|---|---|---|
| Source | Sequence | | SEQ ID NO: |
| | Fragment 3 | CGCCGGGGGGGCGCCAGCG | 137 |
| | Fragment 4 | CCCCCCCCCCCGCGCAT | 138 |
| | Fragment 5 | GCACGGGTCCCCCCCCCACGGGGGGCTCC G | 139 |
| | Fragment 6 | CCCCCCGGCCCCCCCCC | 140 |
| TTV-JA20 | Full sequence | CCGTCGGCGGGGGGGCCGCGCGCTGCGCG CGCGGCCC- CCGGGGGAGGCACAGCCTCCCCCCCCCGCG CGCATGCGCGCGGGTCCCCCCCCCTCCGGG GGGCTCCGCCCCCCGGCCCCCCCC | 141 |
| | Fragment 1 | CCGTCGGCGGGGGGGCCGCGCGCTGCGCG CGCGGCCC | 142 |
| | Fragment 2 | CCGGGGGAGGCACAGCCTCCCCCCCCCGCG CGCATGCGCGCGGGTCCCCCCCCCTCCGGG GGGCTCCGCCCCCCGGCCCCCCCC | 143 |
| TTV-TJN02 | Full sequence | CGGCGGCGGCG-CGCGCGCTACGCGCGCG-- -CGCCGGGGGG----CTGCCGC- CCCCCCCCCGCGCAT GCGCGGGGCCCCCCCCC- GCGGGGGGCTCCG CCCCCCGGCCCCCC | 144 |
| | Fragment 1 | CGGCGGCGGCG | 145 |
| | Fragment 2 | CGCGCGCTACGCGCGCG | 146 |
| | Fragment 3 | CGCCGGGGGG | 147 |
| | Fragment 4 | CTGCCGC | 148 |
| | Fragment 5 | CCCCCCCCCGCGCAT | 149 |
| | Fragment 6 | GCGCGGGGCCCCCCCCC | 150 |
| | Fragment 7 | GCGGGGGGCTCCG | 151 |
| | Fragment 8 | CCCCCCGGCCCCCC | 152 |
| TTV-tth8 | Full sequence | GCCGCCGCGGCGGCGGGGG- GCGGCGCGCTGCGCGCGCCGCCCAGTAGG GGGAGCCATGCG---CCCCCCCCCGCGCAT GCGCGGGGCCCCCCCCC- GCGGGGGGCTCCG CCCCCCGGCCCCCCCCG | 153 |
| | Fragment 1 | GCCGCCGCGGCGGCGGGGG | 154 |
| | Fragment 2 | GCGGCGCGCTGCGCGCGCCGCCCAGTAGG GGGAGCCATGCG | 155 |
| | Fragment 3 | CCCCCCCCCGCGCAT | 156 |
| | Fragment 4 | GCGCGGGGCCCCCCCCC | 157 |
| | Fragment 5 | GCGGGGGGCTCCG | 158 |
| | Fragment 6 | CCCCCCGGCCCCCCCCG | 159 |
| | Fragment 7 | CGCGCTGCGCGCGCCGCCCAGTAGGGGGA GCCATGC | 160 |
| | Fragment 8 | CCGCCATCTTAAGTAGTTGAGGCGGACGGT GGCGTGAGTTCAAAGGTCACCATCAGCCAC ACCTACTCAAAATGGTGG | 161 |
| | Fragment 9 | CTTAAGTAGTTGAGGCGGACGGTGGCGTGA GTTCAAAGGTCACCATCAGCCACACCTACT CAAAATGGTGGACAATTTCTTCCGGGTCAA | 162 |

TABLE 39-continued

Exemplary GC-rich sequences from *Anelloviruses*

| Source | Sequence | | SEQ ID NO: |
|---|---|---|---|
| | | AGGTTACAGCCGCCATGTTAAAACACGTGA CGTATGACGTCACGGCCGCCATTTTGTGAC ACAAGATGGCCGACTTCCTTCC | |
| Additional GC-rich Sequences (as shown in FIG. 32) | 36-nucleotide consensus GC-rich region sequence 1 | CGCGCTGCGCGCGCCGCCCAGTAGGGGGA GCCATGC | 163 |
| | 36-nucleotide region consensus sequence 2 | GCGCTX$_1$CGCGCGCGCGCCGGGGGGCTGCG CCCCCCC, wherein X$_1$ is selected from T, G, or A | 164 |
| | TTV Clade 1 36-nucleotide region | GCGCTTCGCGCGCCGCCCACTAGGGGGCGT TGCGCG | 165 |
| | TTV Clade 3 36-nucleotide region | GCGCTGCGCGCGCCGCCCAGTAGGGGGCG CAATGCG | 166 |
| | TTV Clade 3 isolate GH1 36-nucleotide region | GCGCTGCGCGCGCGGCCCCCGGGGGAGGC ATTGCCT | 167 |
| | TTV Clade 3 sle1932 36-nucleotide region | GCGCTGCGCGCGCGCGCCGGGGGGGCGCC AGCGCCC | 168 |
| | TTV Clade 4 ctdc002 36-nucleotide region | GCGCTTCGCGCGCGCGCCGGGGGGCTCCGC CCCCCC | 169 |
| | TTV Clade 5 36-nucleotide region | GCGCTTCGCGCGCGCGCCGGGGGGCTGCGC CCCCCC | 170 |
| | TTV Clade 6 36-nucleotide region | GCGCTACGCGCGCGCGCCGGGGGGCTGCG CCCCCCC | 171 |
| | TTV Clade 7 36-nucleotide region | GCGCTACGCGCGCGCGCCGGGGGGCTCTGC CCCCCC | 172 |
| Additional *Alphatorquevirus* GC-rich region sequences | TTV-CT30F | GCGGCGGGGGGGCGGCCGCGTTCGCGCGC CGCCCACCAGGGGGTGCTGCGCGCCCCCCC CCGCGCATGCGCGGGGCCCCCCCCCGGGG GGGCTCCGCCCCCCCCGGCCCCCCCCCGTGC TAAACCCACCGCGCATGCGCGACCACGCCC CCGCCGCC | 801 |
| | TTV-P13-1 | CCGAGCGTTAGCGAGGAGTGCGACCCTACC CCCTGGGCCCACTTCTTCGGAGCCGCGCGC TACGCCTTCGGCTGCGCGCGGCACCTCAGA CCCCCGCTCGTGCTGACACGCTTGCGCGTG TCAGACCACTTCGGGCTCGCGGGGGTCGGG | 802 |
| | TTV-tth8 | GCCGCCGCGGCGGCGGGGGGCGGCGCGCT GCGCGCGCCGCCCAGTAGGGGGAGCCATG CGCCCCCCCCCGCGCATGCGCGGGGCCCCC CCCCGCGGGGGGCTCCGCCCCCCGGCCCCC CCCG | 803 |
| | TTV-HD20a | CGGCCCAGCGGCGGCGCGCGCGCTTCGCGC GCGCGCCGGGGGGCTCCGCCCCCCCCCGCG CATGCGCGGGGCCCCCCCCCGCGGGGGGCT CCGCCCCCCGGTCCCCCCCCG | 804 |
| | TTV-16 | CGGCCGTGCGGCGGCGCGCGCGCTTCGCGC GCGCGCCGGGGGCTGCCGCCCCCCCCCGCG | 805 |

TABLE 39-continued

Exemplary GC-rich sequences from *Anelloviruses*

| Source | Sequence | | SEQ ID NO: |
|---|---|---|---|
| | | CATGCGCGCGGGGCCCCCCCCCGCGGGGG GCTCCGCCCCCCGGCCCCCCCCCCCG | |
| | TTV-TJN02 | CGGCGGCGGCGCGCGCGCTACGCGCGCGC GCCGGGGGGCTGCCGCCCCCCCCCCGCGCA TGCGCGGGGCCCCCCCCCGCGGGGGGCTCC GCCCCCCGGCCCCCC | 806 |
| | TTV-HD16d | GGCGGCGGCGCGCGCGCTACGCGCGCGCG CCGGGGAGCTCTGCCCCCCCCCCGCGCATGC GCGCGGGTCCCCCCCCCGCGGGGGGCTCCG CCCCCCGGTCCCCCCCCCG | 807 |

Effector

In some embodiments, the genetic element may include one or more sequences that encode a functional nucleic acid, e.g., an effector, e.g., an endogenous effector or an exogenous effector, e.g., a therapeutic, e.g., a regulatory nucleic acid, e.g., cytotoxic or cytolytic RNA or protein. In some embodiments, the functional nucleic acid is a non-coding RNA.

In some embodiments, the sequence encoding an effector is inserted into the genetic element, e.g., at an insert site as described in Example 10, 12, or 22. In embodiments, the sequence encoding an effector is inserted into the genetic element at a noncoding region, e.g., a noncoding region disposed 3' of the open reading frames and 5' of the GC-rich region of the genetic element, in the 5' noncoding region upstream of the TATA box, in the 5' UTR, in the 3' noncoding region downstream of the poly-A signal, or upstream of the GC-rich region. In embodiments, the sequence encoding an effector is inserted into the genetic element at about nucleotide 3588 of a TTV-tth8 plasmid, e.g., as described herein or at about nucleotide 2843 of a TTMV-LY2 plasmid, e.g., as described herein. In embodiments, the sequence encoding an effector is inserted into the genetic element at or within nucleotides 336-3015 of a TTV-tth8 plasmid, e.g., as described herein, or at or within nucleotides 242-2812 of a TTV-LY2 plasmid, e.g., as described herein. In some embodiments, the sequence encoding an effector replaces part or all of an open reading frame (e.g., an ORF as described herein, e.g., an ORF1, ORF1/1, ORF1/2, ORF2, ORF2/2, ORF2/3, and/or ORF2t/3 as shown in any of Tables 1-18).

In some embodiments, the sequence encoding an effector comprises 100-2000, 100-1000, 100-500, 100-200, 200-2000, 200-1000, 200-500, 500-1000, 500-2000, or 1000-2000 nucleotides. In some embodiments, the effector is a nucleic acid or protein payload, e.g., as described in Example 11.

Regulatory Nucleic Acid

In some embodiments, the regulatory nucleic acids modify expression of an endogenous gene and/or an exogenous gene. In one embodiment, the regulatory nucleic acid targets a host gene. The regulatory nucleic acids may include, but are not limited to, a nucleic acid that hybridizes to an endogenous gene (e.g., miRNA, siRNA, mRNA, lncRNA, RNA, DNA, an antisense RNA, gRNA as described herein elsewhere), nucleic acid that hybridizes to an exogenous nucleic acid such as a viral DNA or RNA, nucleic acid that hybridizes to an RNA, nucleic acid that interferes with gene transcription, nucleic acid that interferes with RNA translation, nucleic acid that stabilizes RNA or destabilizes RNA such as through targeting for degradation, and nucleic acid that modulates a DNA or RNA binding factor. In embodiments, the regulatory nucleic acid encodes an miRNA.

In some embodiments, the regulatory nucleic acid comprises RNA or RNA-like structures typically containing 5-500 base pairs (depending on the specific RNA structure, e.g., miRNA 5-30 bps, lncRNA 200-500 bps) and may have a nucleobase sequence identical (or complementary) or nearly identical (or substantially complementary) to a coding sequence in an expressed target gene within the cell, or a sequence encoding an expressed target gene within the cell.

In some embodiments, the regulatory nucleic acid comprises a nucleic acid sequence, e.g., a guide RNA (gRNA). In some embodiments, the DNA targeting moiety comprises a guide RNA or nucleic acid encoding the guide RNA. A gRNA short synthetic RNA can be composed of a "scaffold" sequence necessary for binding to the incomplete effector moiety and a user-defined ~20 nucleotide targeting sequence for a genomic target. In practice, guide RNA sequences are generally designed to have a length of between 17-24 nucleotides (e.g., 19, 20, or 21 nucleotides) and complementary to the targeted nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991.

The regulatory nucleic acid comprises a gRNA that recognizes specific DNA sequences (e.g., sequences adjacent to or within a promoter, enhancer, silencer, or repressor of a gene).

Certain regulatory nucleic acids can inhibit gene expression through the biological process of RNA interference (RNAi). RNAi molecules comprise RNA or RNA-like structures typically containing 15-50 base pairs (such as aboutl8-25 base pairs) and having a nucleobase sequence identical (complementary) or nearly identical (substantially complementary) to a coding sequence in an expressed target gene within the cell. RNAi molecules include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599, 8,349,809 and 8,513,207).

Long non-coding RNAs (lncRNA) are defined as non-protein coding transcripts longer than 100 nucleotides. This somewhat arbitrary limit distinguishes lncRNAs from small regulatory RNAs such as microRNAs (miRNAs), short interfering RNAs (siRNAs), and other short RNAs. In general, the majority (~78%) of lncRNAs are characterized as tissue-specific. Divergent lncRNAs that are transcribed in the opposite direction to nearby protein-coding genes (comprise a significant proportion ~20% of total lncRNAs in mammalian genomes) may possibly regulate the transcription of the nearby gene.

The genetic element may encode regulatory nucleic acids with a sequence substantially complementary, or fully complementary, to all or a fragment of an endogenous gene or gene product (e.g., mRNA). The regulatory nucleic acids may complement sequences at the boundary between introns and exons to prevent the maturation of newly-generated nuclear RNA transcripts of specific genes into mRNA for transcription. The regulatory nucleic acids that are complementary to specific genes can hybridize with the mRNA for that gene and prevent its translation. The antisense regulatory nucleic acid can be DNA, RNA, or a derivative or hybrid thereof.

The length of the regulatory nucleic acid that hybridizes to the transcript of interest may be between 5 to 30 nucleotides, between about 10 to 30 nucleotides, or about 11, 12, 13, 14, 15, 16, 17, 18, 19, 20, 21, 22, 23, 24, 25, 26, 27, 28, 29, 30 or more nucleotides. The degree of identity of the regulatory nucleic acid to the targeted transcript should be at least 75%, at least 80%, at least 85%, at least 90%, or at least 95%.

The genetic element may encode a regulatory nucleic acid, e.g., a micro RNA (miRNA) molecule identical to about 5 to about 25 contiguous nucleotides of a target gene. In some embodiments, the miRNA sequence targets a mRNA and commences with the dinucleotide AA, comprises a GC-content of about 30-70% (about 30-60%, about 40-60%, or about 45%-55%), and does not have a high percentage identity to any nucleotide sequence other than the target in the genome of the mammal in which it is to be introduced, for example as determined by standard BLAST search.

In some embodiments, the regulatory nucleic acid is at least one miRNA, e.g., 2, 3, 4, 5, 6, or more. In some embodiments, the genetic element comprises a sequence that encodes an miRNA at least about 75%, 80%, 85%, 90% 95%, 96%, 97%, 98%, 99% or 100% nucleotide sequence identity to any one of the nucleotide sequences or a sequence that is complementary to a sequence described herein, e.g., in Table 40.

TABLE 40

Examples of regulatory nucleic acids e.g., miRNAs.

| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
|---|---|---|---|---|---|---|---|
| AB008394.1 | AB008394_3475_ 3551 | GCCAUUUUAAGUA GCUGACGUCAAGG AUUGACGUAAAGG UUAAAGGUCAUCC UCGGCGGAAGCUA CACAAAAUGGU | 300 | AGUAGCUGAC GUCAAGGAUU GAC(5') | 395 | CAUCCUCGGC GGAAGCUACA CAA(3') | 490 |
| AB008394.1 | AB008394_3579_ 3657 | GCGUACGUCACAA GUCACGUGGAGGG GACCCGCUGUAAC CCGGAAGUAGGCC CCGUCACGUGACU UACCACGUGUGUA | 301 | CAAGUCACGU GGAGGGGACC CG(5') | 396 | GGCCCCGUCA CGUGACUUAC CAC(3') | 491 |
| AB017613.1 | AB017613_3462_ 3539 | GCCAUUUUAAGUA GCUGACGUCAAGG AUUGACGUGAAGG UUAAAGGUCAUCC UCGGCGGAAGCUA CACAAAAUGGUG | 302 | AAGUAGCUGA CGUCAAGGAU UGACG(5') | 397 | UCAUCCUCGG CGGAAGCUAC ACAA(3') | 492 |
| AB017613.1 | AB017613_3566_ 3644 | GCACACGUCAUAA GUCACGUGGUGGG GACCCGCUGUAAC CCGGAAGUAGGCC CCGUCACGUGAUU UGUCACGUGUGUA | 303 | AUAAGUCACG UGGUGGGGAC CCG(5') | 398 | GGCCCCGUCA CGUGAUUUGU CAC(3') | 493 |
| AB025946.1 | AB025946_3534_ 3600 | CUUCCGGGUCAUA GGUCACACCUACG UCACAAGUCACGU GGGGAGGGUUGGC GUAUAGCCCGGAA G | 304 | UGGGGAGGGU UGGCGUAUAG CCCGGA(3') | 399 | CCGGGUCAUA GGUCACACCU ACGUCAC(5') | 494 |

TABLE 40-continued

Examples of regulatory nucleic acids e.g., miRNAs.

| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
|---|---|---|---|---|---|---|---|
| AB025946.1 | AB025946_3730_ 3798 | GCCGGGGGGCUGC CGCCCCCCCCGGG GAAAGGGGGGGGC CCCCCCCGGGGGG GGGUUUGCCCCCC GGC | 305 | CCCCCCCCGG GGGGGGGUUU GCCC(3') | 400 | GGCUGCCGCC CCCCCCGGGG AAAGGGGG(5') | 495 |
| AB028668.1 | AB028668_3537_ 3615 | AUACGUCAUCAGU CACGUGGGGGAAG GCGUGCCUAAACC CGGAAGCAUCCUC GUCCACGUGACUG UGACGUGUGUGGC | 306 | AUCAGUCACG UGGGGGAAGG CGUGC(5') | 401 | AUCCUCGUCC ACGUGACUGU GA(3') | 496 |
| AB028669.1 | AB028669_3440_ 3513 | CAUUUUAAGUAAG GCGGAAGCAGCUC GGCGUACACAAAA UGGCGGCGGAGCA CUUCCGGCUUGCC CAAAAUGG | 307 | AAGUAAGGCG GAAGCAGCUC GG(5') | 402 | GAGCACUUCC GGCUUGCCCA A(3') | 497 |
| AB028669.1 | AB028669_3548_ 3619 | GUCACAAGUCACG UGGGGAGGGUUGG CGUUUAACCCGGA AGCCAAUCCUCUU ACGUGGCCUGUCA CGUGAC | 308 | AGUCACGUGG GGAGGGUUGG C(5') | 403 | CAAUCCUCUU ACGUGGCCUG (3') | 498 |
| AB037926.1 | AB037926_162_ 232 | CGACCGCGUCCCG AAGGCGGGUACCC GAGGUGAGUUUAC ACACCGAGGUUAA GGGCCAAUUCGGG CUUGG | 309 | CCCGAAGGCG GGUACCCGAG GU(5') | 404 | CGAGGUUAAG GGCCAAUUCG GGCU(3') | 499 |
| AB037926.1 | AB037926_3454_ 3513 | CGCGGUAUCGUAG CCGACGCGGACCC CGUUUUCGGGGCC CCCGCGGGGCUCU CGGCGCG | 310 | UAUCGUAGCC GACGCGGACC CCG(5') | 405 | GGGCCCCCGC GGGGCUCUCG GCG(3') | 500 |
| AB037926.1 | AB037926_3531_ 3609 | CGCCAUUUUGUGA UACGCGCGUCCCC UCCCGGCUUCCGU ACAACGUCAGGCG GGGCGUGGCCGUA UCAGAAAAUGGCG | 311 | AUUUUGUGAU ACGCGCGUCC CCUCCC(5') | 406 | GCGGGGCGUG GCCGUAUCAG AAAAUGG(3') | 501 |
| AB037926.1 | AB037926_3637_ 3714 | GCUACGUCAUAAG UCACGUGACUGGG CAGGUACUAAACC CGGAAGUAUCCUC GGUCACGUGGCCU GUCACGUAGUUG | 312 | AAGUCACGUG ACUGGGCAGGU(5') | 407 | CCUCGGUCAC GUGGCCUGU(3') | 502 |
| AB038621.1 | AB038621_3511_ 3591 | GGCUSUGACGUCA AAGUCACGUGGGR AGGGUGGCGUUAA ACCCGGAAGUCAU CCUCGUCACGUGA CCUGACGUCACAG CC | 313 | UGACGUCAAA GUCACGUGGG RAGGGU(5') | 408 | CCUCGUCACG UGACCUGACG UCACAG(3') | 503 |
| AB038622.1 | AB038622_227_ 293 | GCCCGUCCGCGGC GAGAGCGCGAGCG AAGCGAGCGAUCG AGCGUCCCGUGGG CGGGUGCCGAAGG U | 314 | GAUCGAGCGU CCCGUGGGCG GGU(3') | 409 | CCGUCCGCGG CGAGAGCGCG AGCGA(5') | 504 |
| AB038622.1 | AB038622_3510_ 3591 | GGUUGUGACGUCA AAGUCACGUGGGG AGGGCGGCGUUAA | 315 | UGACGUCAAA GUCACGUGGG GAGGGCGG(5') | 410 | AUCCUCGUCA CGUGACCUGA CGUCACG(3') | 505 |

TABLE 40-continued

| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
|---|---|---|---|---|---|---|---|
| Examples of regulatory nucleic acids e.g., miRNAs. | | | | | | | |
| | | ACCCGGAAGUCAU CCUCGUCACGUGA CCUGACGUCACGG CC | | | | | |
| AB038623.1 | AB038623_228_ 295 | GCCCGUCCGCGGC GAGAGCGCGAGCG AAGCGAGCGAUCG AGCGUCCCGUGGG CGGGUGCCGUAGG UG | 316 | GAUCGAGCGU CCCGUGGGCG GGU(3') | 411 | CCGUCCGCGG CGAGAGCGCG AGCGA(5') | 506 |
| AB038624.1 | AB038624_228_ 295 | GCCCGUCCGCGGC GAGAGCGCGAGCG AAGCGAGCGAUCG AGCGUCCCGUGGG CGGGUGCCGUAGG UG | 317 | GAUCGAGCGU CCCGUGGGCG GGU(3') | 412 | CCGUCCGCGG CGAGAGCGCG AGCGA(5') | 507 |
| AB038624.1 | AB038624_3511_ 3592 | GGCUGUGACGUCA AAGUCACGUGGGG AGGGCGGCGUUAA ACCCGGAAGUCAU CCUCGUCACGUGA CCUGACGUCACGG CC | 318 | UGACGUCAAA GUCACGUGGG GAGGGCGG(5') | 413 | AUCCUCGUCA CGUGACCUGA CGUCACG(3') | 508 |
| AB041957.1 | AB041957_3414_ 3493 | AGACCACGUGGUA AGUCACGUGGGGG CAGCUGCUGUAAA CCCGGAAGUAGCU GACCCGCGUGACU GGUCACGUGACCU G | 319 | ACGUGGUAAG UCACGUGGGG GCAGCU(5') | 414 | CUGACCCGCG UGACUGGUCA CGUGA(3') | 509 |
| AB049608.1 | AB049608_3199_ 3277 | CGCCAUUUUAUAA UACGCGCGUCCCC UCCCGGCUUCCGU ACUACGUCAGGCG GGGCGUGGCCGUA UUAGAAAAUGGUG | 320 | AUUUUAUAAU ACGCGCGUCC CCUCC(5') | 415 | CGGGGCGUGG CCGUAUUAGA AAAUGG(3') | 510 |
| AB050448.1 | AB050448_3393_ 3465 | UAAGUAAGGCGGA ACCAGGCUGUCAC CCUGUGUCAAAGG UCAAGGGACAGCC UUCCGGCUUGCAC AAAAUGG | 321 | AAGGGACAGC CUUCCGGCUU GC(3') | 416 | AGUAAGGCGG AACCAGGCUG UCACCCUGU(5') | 511 |
| AB054647.1 | AB054647_3537_ 3615 | UGCCUACGUCAUA AGUCACGUGGGGA CGGCUGCUGUAAA CACGGAAGUAGCU GACCCGCGUGACU UGUCACGUGAGCA | 322 | CAUAAGUCAC GUGGGGACGG CUGCU(5') | 417 | UAGCUGACCC GCGUGACUUG UCAC(3') | 512 |
| AB054648.1 | AB054648_3439_ 3511 | UUGUGUAAGGCGG AACAGGCUGACAC CCCGUGUCAAAGG UCAGGGGUCAGCC UCCGCUUUGCACC AAAUGGU | 323 | UAAGGCGGAA CAGGCUGACA CCCC(5') | 418 | GGUCAGCCUC CGCUUUGCA(3') | 513 |
| AB054648.1 | AB054648_3538_ 3617 | UACCUACGUCAUAA GUCACGUGGGAAG AGCUGCUGUGAAC CUGGAAGUAGCUG ACCCGCGUGGCUU GUCACGUGAGUGC | 324 | UACGUCAUAA GUCACGUGGG AAGAGCUG(5') | 419 | GCUGACCCGC GUGGCUUGUC ACGUGAGU(3') | 514 |
| AB064595.1 | AB064595_116_ 191 | UUUUCCUGGCCCG UCCGCGGCGAGAG CGCGAGCGAAGCG AGCGAUCGGGCGU | 325 | UCGGGCGUCC CGAGGGCGGG UG(3') | 420 | GGCCCGUCCG CGGCGAGAGC GCGAG(5') | 515 |

TABLE 40-continued

| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
|---|---|---|---|---|---|---|---|
| Examples of regulatory nucleic acids e.g., miRNAs. | | | | | | | |
| | | CCCGAGGGCGGGU GCCGGAGGUG | | | | | |
| AB064595.1 | AB064595_3283_ 3351 | AAAGUGAGUGGGG CCAGACUUCGCCA UAGGGCCUUUAAC UUCCGGGUGCGUC UGGGGGCCGCCAU UUU | 326 | AAAGUGAGUG GGGCCAGACU UCGCC(5') | 421 | UCCGGGUGCG UCUGGGGGCC GCCAUUU(3') | 516 |
| AB064595.1 | AB064595_3427_ 3500 | GUGACGUUACUCU CACGUGAUGGGGG CGUGCUCUAACCC GGAAGCAUCCUCG ACCACGUGACUGU GACGUCAC | 327 | CUCUCACGUG AUGGGGGCGU GC(5') | 422 | AUCCUCGACC ACGUGACUGU G(3') | 517 |
| AB064595.1 | AB064595_41_ 116 | AGCGUCUACUACG UACACUUCCUGGG GUGUGUCCUGCCA CUGUAUAUAAACCA GAGGGGUGACGAA UGGUAGAGU | 328 | UCUACUACGU ACACUUCCUG GGGUGUGU(5') | 423 | AUAAACCAGA GGGGUGACGA AUGGUAGAGU(3') | 518 |
| AB064596.1 | AB064596_3424_ 3497 | GUGACGUCAAAGU CACGUGGUGACGG CCAUUUUAACCCG GAAGUGGCUGUUG UCACGUGACUUGA CGUCACGG | 329 | UGGCUGUUGU CACGUGACUU GA(3') | 424 | CAAAGUCACG UGGUGACGGC CAU(5') | 519 |
| AB064597.1 | AB064597_3191_ 3253 | GCUUUAGACGCCA UUUUAGGCCCUCG CGGGCACCCGUAG GCGCGUUUUAAUG ACGUCACGGC | 330 | AGACGCCAUU UUAGGCCCUC GCGG(5') | 425 | GUAGGCGCGU UUUAAUGACG UCACGG(3') | 520 |
| AB064597.1 | AB064597_3221_ 3294 | CACCCGUAGGCGC GUUUUAAUGACGU CACGGCAGCCAUU UUGUCGUGACGUU UGAGACACGUGAU GGGGGCGU | 331 | UGUCGUGACG UUUGAGACAC GUGAU(3') | 426 | UAGGCGCGUU UUAAUGACGU CACGGCAG(5') | 521 |
| AB064597.1 | AB064597_3262_ 3342 | GUCGUGACGUUUG AGACACGUGAUGG GGGCGUGCCUAAA CCCGGAAGCAUCC CUGGUCACGUGAC UCUGACGUCACGG CG | 332 | UGACGUUUGA GACACGUGAU GGGGGCGUGC (5') | 427 | AUCCCUGGUC ACGUGACUCU GACGUCACG(3') | 522 |
| AB064598.1 | AB064598_3179_ 3256 | CGAAAGUGAGUGG GGCCAGACUUCGC CAUAAGGCCUUUA ACUUCCGGGUGCG UGUGGGGGCCGCC AUUUUAGCUUCG | 333 | AGUGAGUGGG GCCAGACUUC GC(5') | 428 | GCGUGUGGGG GCCGCCAUUU UAGCUU(3') | 523 |
| AB064598.1 | AB064598_3323_ 3399 | CUGUGACGUCAAA GUCACGUGGGGAG GGCGGCGUGUAAC CCGGAAGUCAUCC UCGUCACGUGACC UGACGUCACGG | 334 | UGUGACGUCA AAGUCACGUG GGGAGGGCGG (5') | 429 | UCAUCCUCGU CACGUGACCU GACGUCACG(3') | 524 |
| AB064598.1 | AB064598_3412_ 3485 | CUGUCCGCCAUCU UGUGACUUCCUUC CGCUUUUUCAAAAA AAAAGAGGAAGUAU GACGUAGCGGCGG GGGGGC | 335 | AAAAGAGGAA GUAUGACGUA GCGGCGG(3') | 430 | CGCCAUCUUG UGACUUCCUU CCGCUUUUU(5') | 525 |

TABLE 40-continued

| Examples of regulatory nucleic acids e.g., miRNAs. | | | | | | | |
|---|---|---|---|---|---|---|---|
| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
| AB064599.1 | AB064599_108_ 175 | GGUAGAGUUUUUU CCGCCCGUCCGCA GCGAGGACGCGAG CGCAGCGAGCGGC CGAGCGACCCGUG GG | 336 | AGCGAGCGGC CGAGCGACCC G(3') | 431 | UAGAGUUUUU UCCGCCCGUC CG(5') | 526 |
| AB064599.1 | AB064599_3389_ 3469 | GCUGUGACGUUUC AGUCACGUGGGGA GGGAACGCCUAAA CCCGGAAGCGUCC CUGGUCACGUGAU UGUGACGUCACGG CC | 337 | UUCAGUCACG UGGGGAGGGA ACGC(5') | 432 | GUCCCUGGUC ACGUGAUUGU GAC(3') | 527 |
| AB064599.1 | AB064599_3483_ 3546 | CCGCCAUUUUGUG ACUUCCUUCCGCU UUUUCAAAAAAAAA GAGGAAGUGUGAC GUAGCGGCGG | 338 | AAAAGAGGAA GUGUGACGUA GCGG(3') | 433 | CAUUUUGUGA CUUCCUUCCG CUUUUU(5') | 528 |
| AB064600.1 | AB064600_3378_ 3456 | GACUGUGACGUCA AAGUCACGUGGGG AGGGCGGCGUGUA ACCCGGAAGUCAU CCUCGUCACGUGA CCUGACGUCACGG | 339 | UGUGACGUCA AAGUCACGUG GGGAGGGCGG (5') | 434 | UCAUCCUCGU CACGUGACCU GACGUCACG(3') | 529 |
| AB064600.1 | AB064600_3469_ 3542 | CUGUCCGCCAUCU UGUGACUUCCUUC CGCUUUUUCAAAAA AAAAGAGGAAGUAU GACGUGGCGGCGG GGGGGC | 340 | AAAAGAGGAA GUAUGACGUG GCGG(3′) | 435 | CCGCCAUCUU GUGACUUCCU UCCGCUUUUU(5') | 530 |
| AB064601.1 | AB064601_3318_ 3398 | GGUUGUGACGUCA AAGUCACGUGGGG AGGGCGGCGUGUA ACCCGGAAGUCAU CCUCGUCACGUGA CCUGACGUCACGG CC | 341 | UGACGUCAAA GUCACGUGGGG GAGGGCGG(5') | 436 | AUCCUCGUCA CGUGACCUGA CGUCACG(3') | 531 |
| AB064601.1 | AB064601_3412_ 3477 | CCCGCCAUCUUGU GACUUCCUUCCGC UUUUUCAAAAAAAA AGAGGAAGUGUGA CGUAGCGGCGGG | 342 | AAAAAAGAGG AAGUGUGACG UAGCGGCGG(3') | 437 | CGCCAUCUUG UGACUUCCUU CCGCUUUUUC(5') | 532 |
| AB064602.1 | AB064602_125_ 192 | GCCCGUCCGCGGC GAGAGCGCGAGCG AAGCGAGCGAUCG AGCGUCCCGUGGG CGGGUGCCGUAGG UG | 343 | GAUCGAGCGU CCCGUGGGCG GGU(3') | 438 | CCGUCCGCGG CGAGAGCGCG AGCGA(5') | 533 |
| AB064602.1 | AB064602_3368_ 3446 | GACUGUGACGUCA AAGUCACGUGGGG AGGAGGGCGUGUA ACCCGGAAGUCAU CCUCGUCACGUGA CCUGACGUCACGG | 344 | UGUGACGUCA AAGUCACGUG GGGAGGAGGG (5') | 439 | UCAUCCUCGU CACGUGACCU GACGUCACG(3') | 534 |
| AB064603.1 | AB064603_3385_ 3447 | UCGCGUCUUAGUG ACGUCACGGCAGC CAUCUUGGUCCUG ACGUCACUGUCAC GUGGGGAGGG | 345 | UUGGUCCUGA CGUCACUGUC A(3') | 440 | CUUAGUGACG UCACGGCAGC CAU(5') | 535 |
| AB064603.1 | AB064603_3422_ 3498 | UGACGUCACUGUC ACGUGGGGAGGGA ACACGUGAACCCG GAAGUGUCCCUGG | 346 | CGUCACUGUC ACGUGGGGAG GGAACAC(5') | 441 | GUCCCUGGUC ACGUGACAUG ACGUC(3') | 536 |

TABLE 40-continued

| Examples of regulatory nucleic acids e.g., miRNAs. | | | | | | | |
|---|---|---|---|---|---|---|---|
| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
| | | UCACGUGACAUGA CGUCACGGCCG | | | | | |
| AB064604.1 | AB064604_3436_ 3514 | CGCCAUUUUAAGU AAGCAUGGCGGGC GGUGAUGUCAAAU GUUAAAGGUCACA GCCGGUCAUGCUU GCACAAAAUGGCG | 347 | UAAGUAAGCA UGGCGGGCGG UGAU(5') | 442 | CAUGCUUGCA CACAGCCGGU CAAA(3') | 537 |
| AB064605.1 | AB064605_3440_ 3518 | CGCCAUUUUAAGU AAGCAUGGCGGGC GGUGACGUGCAAU GUCAAAGGUCACA GCCUGUCAUGCUU GCACAAAAUGGCG | 348 | AAGUAAGCAU GGCGGGCGGU GA(5') | 443 | ACAGCCUGUC AUGCUUGCAC AA(3') | 538 |
| AB064606.1 | AB064606_3377_ 3449 | CCAUCUUAAGUAG UUGAGGCGGACGG UGGCGUCGGUUCA AAGGUCACCAUCA GCCACACCUACUC AAAAUGG | 349 | UAAGUAGUUG AGGCGGACGG UGGC(5') | 444 | CACCAUCAGC CACACCUACU CAAA(3') | 539 |
| AB064607.1 | AB064607_3502_ 3569 | GCCUGUCAUGCUU GCACAAAAUGGCG GACUUCCGCUUCC GGGUCGCCGCCAU AUUUGGUCACGUG AC | 350 | UCAUGCUUGC ACAAAAUGGC GGACUUCCG(5') | 445 | CGGGUCGCCG CCAUAUUUGG UCACGUGA(3') | 540 |
| AF079173.1 | AF079173_3475_ 3551 | GCCAUUUUAAGUA GCUGACGUCAAGG AUUGACGUAAAGG UUAAAGGUCAUCC UCGGCGGAAGCUA CACAAAAUGGU | 351 | AGUAGCUGAC GUCAAGGAUU GAC(5') | 446 | CAUCCUCGGC GGAAGCUACA CAA(3') | 541 |
| AF116842.1 | AF116842_3475_ 3551 | GCCAUUUUAAGUA GCUGACGUCAAGG AUUGACGUAAAGG UUAAAGGUCAUCC UCGGCGGAAGCUA CACAAAAUGGU | 352 | AGUAGCUGAC GUCAAGGAUU GAC(5') | 447 | CAUCCUCGGC GGAAGCUACA CAA(3') | 542 |
| AF116842.1 | AF116842_3579_ 3657 | GCAUACGUCACAA GUCACGUGGGGGG GACCCGCUGUAAC CCGGAAGUAGGCC CCGUCACGUGACU UACCACGUGUGUA | 353 | ACAAGUCACG UGGGGGGGAC CCG(5') | 448 | GGCCCCGUCA CGUGACUUAC CAC(3') | 543 |
| AF122913.1 | AF122913_3475_ 3551 | GCCAUUUUAAGUA GCUGACGUCAAGG AUUGACGUGAAGG UUAAAGGUCAUCC UCGGCGGAAGCUA CACAAAAUGGU | 354 | AAGUAGCUGA CGUCAAGGAU UGACG(5') | 449 | UCAUCCUCGG CGGAAGCUAC ACAA(3') | 544 |
| AF122913.1 | AF122913_3579_ 3657 | GCACACGUCAUAA GUCACGUGGUGGG GACCCGCUGUAAC CCGGAAGUAGGCC CCGUCACGUGAUU UGUCACGUGUGUA | 355 | AUAAGUCACG UGGUGGGGAC CCG(5') | 450 | GGCCCCGUCA CGUGAUUUGU CAC(3') | 545 |
| AF122914.1 | AF122914_3476_ 3552 | GCCAUUUUAAGUC AGCUCUGGGGAGG CGUGACUUCCAGU UCAAAGGUCAUCC UCACCAUAACUGG CACAAAAUGGC | 356 | AAGUCAGCUC UGGGGAGGCG UGACUU(5') | 451 | GUCAUCCUCA CCAUAACUGG CACAA(3') | 546 |

TABLE 40-continued

Examples of regulatory nucleic acids e.g., miRNAs.

| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
|---|---|---|---|---|---|---|---|
| AF122915.1 | AF122915_3475_ 3551 | GCCAUUUUAAGUA GCUGACGUCAAGG AUUGACGUAAAGG UUAAAGGUCAUCC UCGGCGGAAGCUA CACAAAAUGGU | 357 | AGUAGCUGAC GUCAAGGAUU GAC(5') | 452 | CAUCCUCGGC GGAAGCUACA CAA(3') | 547 |
| AF122915.1 | AF122915_3579_ 3657 | GCAUACGUCACAA GUCACGUGGAGGG GACACGCUGUAAC CCGGAAGUAGGCC CCGUCACGUGACU UACCACGUGUGUA | 358 | CAAGUCACGU GGAGGGGACA CC(5') | 453 | GGCCCCGUCA CGUGACUUAC CAC(3') | 548 |
| AF122916.1 | AF122916_3458_ 3537 | GCGCCAUGUUAAG UGGCUGUCGCCGA GGAUUGACGUCAC AGUUCAAAGGUCA UCCUCGACGGUAA CCGCAAACAUGGC G | 359 | UGUUAAGUGG CUGUCGCCGA GGAUUGA(5') | 454 | AUCCUCGACG GUAACCGCAA ACAUG(3') | 549 |
| AF122916.1 | AF122916_3565_ 3641 | CAUGCGUCAUAAG UCACAUGACAGGG GUCCACUUAAACAC GGAAGUAGGCCCC GACAUGUGACUCG UCACGUGUGU | 360 | UAAGUCACAU GACAGGGGUC CA(5') | 455 | GGCCCCGACA UGUGACUCGU C(3') | 550 |
| AF122916.1 | AF122916_91_ 164 | UGGCAGCACUUCC GAAUGGCUGAGUU UUCCACGCCCGUC CGCGGAGAGGGAG CCACGGAGGUGAU CCCGAACG | 361 | CGGAGAGGGA GCCACGGAGG UG(3') | 456 | AGCACUUCCG AAUGGCUGAG UUUUCCA(5') | 551 |
| AF122917.1 | AF122917_3369_ 3447 | GCCAUUUUAAGUC AGCGCUGGGGAGG CAUGACUGUAAGU UCAAAGGUCAUCC UCACCGGAACUGA CACAAAAUGGCCG | 362 | AAGUCAGCGC UGGGGAGGCA UGA(5') | 457 | AUCCUCACCG GAACUGACAC AA(3') | 552 |
| AF122918.1 | AF122918_3460_ 3540 | GCCAUCUUAAGUG GCUGUCGCCGAGG AUUGACGUCACAG UUCAAAGGUCAUC CUCGGCGGUAACC GCAAAGAUGGCGG UC | 363 | UCUUAAGUGG CUGUCGCCGA GGAUUGAC(5') | 458 | CAUCCUCGGC GGUAACCGCA AAGAUG(3') | 553 |
| AF122918.1 | AF122918_3566_ 3642 | AUACGUCAUAAGU CACAUGUCUAGGG GUCCACUUAAACAC GGAAGUAGGCCCC GACAUGUGACUCG UCACGUGUGU | 364 | AAGUCACAUG UCUAGGGGUC CACU(5') | 459 | UAGGCCCCGA CAUGUGACUC GU(3') | 554 |
| AF122919.1 | AF122919_3370_ 3447 | CCAUUUUAAGUAA GGCGGAAGCAGCU GUCCCUGUAACAA AAUGGCGGCGACA GCCUUCCGCUUUG CACAAAAUGGAG | 365 | AAGUAAGGCG GAAGCAGCUG UCC(5') | 460 | ACAGCCUUCC GCUUUGCACA A(3') | 555 |
| AF122920.1 | AF122920_3460_ 3540 | GCCAUCUUAAGUG GCUGUCGCUGAGG AUUGACGUCACAG UUCAAAGGUCAUC CUCGGCGGUAACC GCAAAGAUGGCGG UC | 366 | AUCUUAAGUG GCUGUCGCUG AGGAUUGAC(5') | 461 | CAUCCUCGGC GGUAACCGCA AAGAUGG(3') | 556 |

TABLE 40-continued

Examples of regulatory nucleic acids e.g., miRNAs.

| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
|---|---|---|---|---|---|---|---|
| AF122920.1 | AF122920_3565_ 3641 | CAUACGUCAUAAG UCACAUGACAGGA GUCCACUUAAACAC GGAAGUAGGCCCC GACAUGUGACUCG UCACGUGUGU | 367 | UAAGUCACAU GACAGGAGUC CACU(5') | 462 | UAGGCCCCGA CAUGUGACUC GUC(3') | 557 |
| AF122921.1 | AF122921_3459_ 3540 | CGCCAUCUUAAGU GGCUGUCGCCGAG GAUUGGCGUCACA GUUCAAAGGUCAU CCUCGGCGGUAAC CGCAAAGAUGGCG GU | 368 | AAGUGGCUGU CGCCGAGGAU UG(5') | 463 | UCCUCGGCGG UAACCGCAAA (3') | 558 |
| AF122921.1 | AF122921_3565_ 3641 | CAUACGUCAUAAG UCACAUGACAGGG GUCCACUUAAACAC GGAAGUAGGCCCC GACAUGUGACUCG UCACGUGUGU | 369 | UAAGUCACAU GACAGGGGUC CA(S5' | 464 | GGCCCCGACA UGUGACUCGU C(3') | 559 |
| AF129887.1 | AF129887_3579_ 3657 | GCAUACGUCACAA GUCACGUGGGGGG GACCCGCUGUAAC CCGGAAGUAGGCC CCGUCACGUGACU UACCACGUGGUGU | 370 | ACAAGUCACG UGGGGGGGAC CCG(5') | 465 | GGCCCCGUCA CGUGACUUAC CAC(3') | 560 |
| AF247137.1 | AF247137_3453_ 3530 | CCGCCAUUUUAGG CUGUUGCCGGGCG UUUGACUUCCGUG UUAAAGGUCAAACA CCCAGCGACACCA AAAAAUGGCCG | 371 | AUUUUAGGCU GUUGCCGGGC GUUUGACU(5') | 466 | UCAAACACCC AGCGACACCA AAAAAUGG(3') | 561 |
| AF247137.1 | AF247137_3559_ 3636 | CUACGUCAUAAGU CACGUGACAGGGA GGGGCGACAAACC CGGAAGUCAUCCU CGCCCACGUGACU UACCACGUGGUG | 372 | AUAAGUCACG UGACAGGGAG GGG(5') | 467 | CCUCGCCCAC GUGACUUACC AC(3') | 562 |
| AF247138.1 | AF247138_3455_ 3532 | GCCAUUUUAAGUA GGUGACGUCCAGG ACUGACGUAAAGU UCAAAGGUCAUCC UCGGCGGAACCUA UACAAAAUGGCG | 373 | AAGUAGGUGA CGUCCAGGAC U(5') | 468 | CCUCGGCGGA ACCUAUACAA (3') | 563 |
| AF247138.1 | AF247138_3561_ 3637 | CUACGUCAUAAGU CACGUGGGGACGG CUGUACUUAAACAC GGAAGUAGGCCCC GUCACGUGAUUUA CCACGUGGUG | 374 | CAUAAGUCAC GUGGGGACGG CUGU(5') | 469 | GCCCCGUCAC GUGAUUUACC AC(3') | 564 |
| AF261761.1 | AF261761_3431_ 3504 | GCCAUUUUAAGUA AGGCGGAAGAGCU CUAGCUAUACAAAA UGGCGGCGGAGCA CUUCCGCUUUGCC CAAAAUG | 375 | UAAGUAAGGC GGAAGAGCUC UAGCUA(5') | 470 | GCGGCGGAGC ACUUCCGCUU UGCCCAAA(3') | 565 |
| AF351132.1 | AF351132_3475_ 3552 | GCCAUUUUAAGUA GCUGACGUCAAGG AUUGACGUAGAGG UUAAAGGUCAUCC UCGGCGGAAGCUA CACAAAAUGGUG | 376 | AGUAGCUGAC GUCAAGGAUU GAC(5') | 471 | CAUCCUCGGC GGAAGCUACA CAA(3') | 566 |
| AF351132.1 | AF351132_3579_ 3657 | GCAUACGUCACAA GUCACGUGGGGGG GACCCGCUGUAAC | 377 | ACAAGUCACG UGGGGGGGAC CCG(5') | 472 | GGCCCCGUCA CGUGACUUAC CAC(3') | 567 |

TABLE 40-continued

Examples of regulatory nucleic acids e.g., miRNAs.

| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
|---|---|---|---|---|---|---|---|
| | | CCGGAAGUAGGCC CCGUCACGUGACU UACCACGUGUGUA | | | | | |
| AF435014.1 | AF435014_3344_ 3426 | GGCGCCAUUUUAA GUAAGCAUGGCGG GCGGCGACGUCAC AUGUCAAAGGUCA CCGCACUUCCGUG CUUGCACAAAAUG GC | 378 | UAAGUAAGCA UGGCGGGCGG CGAC(5′) | 473 | CACCGCACUU CCGUGCUUGC ACAAA(3′) | 568 |
| AF435014.1 | AF435014_3453_ 3526 | UGCUACGUCAUCG AGACACGUGGUGC CAGCAGCUGUAAA CCCGGAAGUCGCU GACACACGUGUCU UGUCACGU | 379 | AUCGAGACAC GUGGUGCCAG CAGCU(5') | 474 | UCGCUGACAC ACGUGUCUUG UCAC(3') | 569 |
| AJ620212.1 | AJ620212_3360_ 3438 | GCCAUUUUAAGUA AGCACCGCCUAGG GAUGACGUAUAAG UUCAAAGGUCAUC CUCAGCCGGAACU UACACAAAAUGGU | 380 | UCAUCCUCAG CCGGAACUUA CACAAAAUGG(3') | 475 | CAUUUUAAGU AAGCACCGCC UAGGGAUGAC(5') | 570 |
| AJ620212.1 | AJ620212_3470_ 3542 | ACGUCAUAUGUCA CGUGGGGAGGCCC UGCUGCGCAAACG CGGAAGUAGGCCC CGUCACGUGUCAU ACCACGU | 381 | AUAUGUCACG UGGGGAGGCC CUGCUG(5') | 476 | GUAGGCCCCG UCACGUGUCA UACCAC(3') | 571 |
| AJ620218.1 | AJ620218_3381_ 3458 | CCAUUUUAAGUAA GGCGGAAGCAGCU CCACUUUCUCACAA AAUGGCGGCGGGG CACUUCCGGCUUG CCCAAAAUGGC | 382 | AAGUAAGGCG GAAGCAGCUC CACUUU(5') | 477 | GGCGGGGCAC UUCCGGCUUG CCCAA(3') | 572 |
| AJ620226.1 | AJ620226_3451_ 3523 | CCAUUUUAAGUAA GGCGGAAGUUUCU CCACUAUACAAAAU GGCGGCGGAGCAC UUCCGGCUUGCCC AAAAUG | 383 | AAGUAAGGCG GAAGUUUCUC CACU(5') | 478 | CGGCGGAGCA CUUCCGGCUU GCCCAA(3') | 573 |
| AJ620227.1 | AJ620227_3379_ 3451 | CCAUCUUAAGUAG UUGAGGCGGACGG UGGCGUGAGUUCA AAGGUCACCAUCA GCCACACCUACUC AAAAUGG | 384 | UAAGUAGUUG AGGCGGACGG UGGC(5') | 479 | CACCAUCAGC CACACCUACU CAAA(3') | 574 |
| AJ620231.1 | AJ620231_3429_ 3505 | CGCCAUCUUAAGU AGUUGAGGCGGAC GGUGGCGUGAGUU CAAAGGUCACCAU CAGCCACACCUAC UCAAAAUGGUG | 385 | UAAGUAGUUG AGGCGGACGG UGG(5') | 480 | ACCAUCAGCC ACACCUACUC AAA(3') | 575 |
| AY666122.1 | AY666122_3163_ 3236 | UUUCGGACCUUCG GCGUCGGGGGGGU CGGGGGCUUUACU AAACAGACUCCGA GAUGCCAUUGGAC ACUGAGGG | 386 | GACCUUCGGC GUCGGGGGG GUCGGGGG(5') | 481 | GACUCCGAGA UGCCAUUGGA CACUGAGG(3') | 576 |
| AY666122.1 | AY666122_3388_ 3464 | CCAUUUUAAGUAG GUGCCGUCCAGCA CUGCUGUUCCGGG UUAAAGGGCAUCC UCGGCGGAACCUA UACAAAAUGGC | 387 | AUCCUCGGCG GAACCUAUA(3') | 482 | AGUAGGUGCC GUCCAGCA(5') | 577 |

TABLE 40-continued

| Examples of regulatory nucleic acids e.g., miRNAs. | | | | | | | |
|---|---|---|---|---|---|---|---|
| Accession number of strain | Exemplary subsequence nucleotides | Pre_miRNA | SEQ ID NO: | miRNA_5prime_ per_MiRdup | SEQ ID NO: | miRNA_3prime_ per_MiRdup | SEQ ID NO: |
| AY666122.1 | AY666122_3494_ 3567 | CUACGUCAUCGAU GACGUGGGGAGGC GUACUAUGAAACG CGGAAGUAGGCCC CGCUACGUCAUCA UCACGUGG | 388 | AUCGAUGACG UGGGGAGGCG UACUAU(5') | 483 | AAGUAGGCCC CGCUACGUCA UCAUCAC(3') | 578 |
| AY823988.1 | AY823988_3452_ 3525 | CCAUUUUAAGUAA GGCGGAAGAGCUG CUCUAUAUACAAAA UGGCGGAGGAGCA CUUCCGGCUUGCC CAAAAUG | 389 | UGGCGGAGGA GCACUUCCGG CUUG(3') | 484 | AAGGCGGAAG AGCUGCUCUA UAU(5') | 579 |
| AY823988.1 | AY823988_3554_ 3629 | UGCCUACGUAACA AGUCACGUGGGGA GGGUUGGCGUAUA ACCCGGAAGUCAA UCCUCCCACGUGG CCUGUCACGU | 390 | AACAAGUCAC GUGGGGAGGG UUGGC(5') | 485 | CAAUCCUCCC ACGUGGCCUG UCAC(3') | 580 |
| AY823989.1 | AY823989_3551_ 3623 | UAAGUAAGGCGGA ACCAGGCUGUCAC CCCGUGUCAAAGG UCAGGGGUCAGCC UUCCGCUUUACAC AAAAUGG | 391 | AGGGGUCAGC CUUCCGCUUU A(3') | 486 | AAGGCGGAAC CAGGCUGUCA CCCCGU(5') | 581 |
| AY823989.1 | AY823989_3551_ 3623 | UAAGUAAGGCGGA ACCAGGCUGUCAC CCCGUGUCAAAGG UCAGGGGUCAGCC UUCCGCUUUACAC AAAAUGG | 392 | AGGGGUCAGC CUUCCGCUUU A(3') | 487 | AAGGCGGAAC CAGGCUGUCA CCCCGU(5') | 582 |
| DQ361268.1 | D0361268_3413_ 3494 | GCAGCCAUUUUAA GUCAGCUUCGGGG AGGGUCACGCAAA GUUCAAAGGUCAU CCUCACCGGAACU GGUACAAAAUGGC CG | 393 | UAAGUCAGCU UCGGGGAGGG UCAC(5') | 488 | CAUCCUCACC GGAACUGGUA CAAA(3') | 583 |
| DQ361268.1 | D0361268_3519_ 3593 | UGCUACGUCAUAA GUGACGUAGCUGG UGUCUGCUGUAAA CACGGAAGUAGGC CCCGCCACGUCAC UUGUCACGU | 394 | UCAUAAGUGA CGUAGCUGGU GUCUGCU(5') | 489 | UAGGCCCCGC CACGUCACUU GUCACG(3') | 584 |

siRNAs and shRNAs resemble intermediates in the processing pathway of the endogenous microRNA (miRNA) genes (Bartel, Cell 116:281-297, 2004). In some embodiments, siRNAs can function as miRNAs and vice versa (Zeng et al., Mol Cell 9:1327-1333, 2002; Doench et al., Genes Dev 17:438-442, 2003). MicroRNAs, like siRNAs, use RISC to downregulate target genes, but unlike siRNAs, most animal miRNAs do not cleave the mRNA. Instead, miRNAs reduce protein output through translational suppression or polyA removal and mRNA degradation (Wu et al., Proc Natl Acad Sci USA 103:4034-4039, 2006). Known miRNA binding sites are within mRNA 3' UTRs; miRNAs seem to target sites with near-perfect complementarity to nucleotides 2-8 from the miRNA's 5' end (Rajewsky, Nat Genet 38 Suppl:S8-13, 2006; Lim et al., Nature 433:769-773, 2005). This region is known as the seed region. Because siRNAs and miRNAs are interchangeable, exogenous siRNAs downregulate mRNAs with seed complementarity to the siRNA (Birmingham et al., Nat Methods 3:199-204, 2006. Multiple target sites within a 3' UTR give stronger downregulation (Doench et al., Genes Dev 17:438-442, 2003).

Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Lagana et al., Methods Mol. Bio., 2015, 1269:393-412).

The regulatory nucleic acid may modulate expression of RNA encoded by a gene. Because multiple genes can share some degree of sequence homology with each other, in some embodiments, the regulatory nucleic acid can be designed to target a class of genes with sufficient sequence homology. In some embodiments, the regulatory nucleic acid can contain a sequence that has complementarity to sequences that are shared amongst different gene targets or are unique for a specific gene target. In some embodiments, the regulatory nucleic acid can be designed to target conserved regions of an RNA sequence having homology between several genes thereby targeting several genes in a gene family (e.g., different gene isoforms, splice variants, mutant genes, etc.). In some embodiments, the regulatory nucleic acid can be designed to target a sequence that is unique to a specific RNA sequence of a single gene.

In some embodiments, the genetic element may include one or more sequences that encode regulatory nucleic acids that modulate expression of one or more genes.

In one embodiment, the gRNA described elsewhere herein are used as part of a CRISPR system for gene editing. For the purposes of gene editing, the anellosome may be designed to include one or multiple guide RNA sequences corresponding to a desired target DNA sequence; see, for example, Cong et al. (2013) Science, 339:819-823; Ran et al. (2013) Nature Protocols, 8:2281-2308. At least about 16 or 17 nucleotides of gRNA sequence generally allow for Cas9-mediated DNA cleavage to occur; for Cpf1 at least about 16 nucleotides of gRNA sequence is needed to achieve detectable DNA cleavage.

Therapeutic Peptides or Polypeptides

In some embodiments, the genetic element comprises a sequence that encodes a therapeutic peptide or polypeptide. Such therapeutics include, but are not limited to, small peptides, peptidomimetics (e.g., peptoids), amino acids, and amino acid analogs. Such therapeutics generally have a molecular weight less than about 5,000 grams per mole, a molecular weight less than about 2,000 grams per mole, a molecular weight less than about 1,000 grams per mole, a molecular weight less than about 500 grams per mole, and salts, esters, and other pharmaceutically acceptable forms of such compounds. Such therapeutics may include, but are not limited to, a neurotransmitter, a hormone, a drug, a toxin, a viral or microbial particle, a synthetic molecule, and agonists or antagonists thereof.

In some embodiments, the genetic element includes a sequence encoding a peptide e.g., a therapeutic peptide. The peptides may be linear or branched. The peptide has a length from about 5 to about 500 amino acids, about 15 to about 400 amino acids, about 20 to about 325 amino acids, about 25 to about 250 amino acids, about 50 to about 150 amino acids, or any range therebetween.

Some examples of peptides include, but are not limited to, fluorescent tag or marker, antigen, peptide therapeutic, synthetic or analog peptide from naturally-bioactive peptide, agonist or antagonist peptide, anti-microbial peptide, a targeting or cytotoxic peptide, a degradation or self-destruction peptide, and degradation or self-destruction peptides. Peptides useful in the invention described herein also include antigen-binding peptides, e.g., antigen binding antibody or antibody-like fragments, such as single chain antibodies, nanobodies (see, e.g., Steeland et al. 2016. Nanobodies as therapeutics: big opportunities for small antibodies. Drug Discov Today: 21(7):1076-113). Such antigen binding peptides may bind a cytosolic antigen, a nuclear antigen, or an intra-organellar antigen.

In some embodiments, the genetic element includes a sequence encoding a protein e.g., a therapeutic protein. Some examples of therapeutic proteins may include, but are not limited to, a hormone, a cytokine, an enzyme, an antibody, a transcription factor, a receptor (e.g., a membrane receptor), a ligand, a membrane transporter, a secreted protein, a peptide, a carrier protein, a structural protein, a nuclease, or a component thereof.

In some embodiments, the composition or anellosome described herein includes a polypeptide linked to a ligand that is capable of targeting a specific location, tissue, or cell.

Regulatory Sequences

In some embodiments, the genetic element comprises a regulatory sequence, e.g., a promoter or an enhancer.

In some embodiments, a promoter includes a DNA sequence that is located adjacent to a DNA sequence that encodes an expression product. A promoter may be linked operatively to the adjacent DNA sequence. A promoter typically increases an amount of product expressed from the DNA sequence as compared to an amount of the expressed product when no promoter exists. A promoter from one organism can be utilized to enhance product expression from the DNA sequence that originates from another organism. For example, a vertebrate promoter may be used for the expression of jellyfish GFP in vertebrates. In addition, one promoter element can increase an amount of products expressed for multiple DNA sequences attached in tandem. Hence, one promoter element can enhance the expression of one or more products. Multiple promoter elements are well-known to persons of ordinary skill in the art.

In one embodiment, high-level constitutive expression is desired. Examples of such promoters include, without limitation, the retroviral Rous sarcoma virus (RSV) long terminal repeat (LTR) promoter/enhancer, the cytomegalovirus (CMV) immediate early promoter/enhancer (see, e.g., Boshart et al, Cell, 41:521-530 (1985)), the SV40 promoter, the dihydrofolate reductase promoter, the cytoplasmic .beta.-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible sheep metallothionine (MT) promoter; the dexamethasone (Dex)-inducible mouse mammary tumor virus (MMTV) promoter; the T7 polymerase promoter system (WO 98/10088); the tetracycline-repressible system (Gossen et al, Proc. Natl. Acad. Sci. USA, 89:5547-5551 (1992)); the tetracycline-inducible system (Gossen et al., Science, 268:1766-1769 (1995); see also Harvey et al., Curr. Opin. Chem. Biol., 2:512-518 (1998)); the RU486-inducible system (Wang et al., Nat. Biotech., 15:239-243 (1997) and Wang et al., Gene Ther., 4:432-441 (1997)]; and the rapamycin-inducible system (Magari et al., J. Clin. Invest., 100:2865-2872 (1997); Rivera et al., Nat. Medicine. 2:1028-1032 (1996)). Other types of inducible promoters which may be useful in this context are those which are regulated by a specific physiological state, e.g., temperature, acute phase, or in replicating cells only.

In some embodiments, a native promoter for a gene or nucleic acid sequence of interest is used. The native promoter may be used when it is desired that expression of the gene or the nucleic acid sequence should mimic the native expression. The native promoter may be used when expression of the gene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the genetic element comprises a gene operably linked to a tissue-specific promoter. For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters. See Li et al., Nat. Biotech., 17:241-245 (1999). Examples of promoters that are tissue-specific are known for liver albumin, Miyatake et al. J. Virol., 71:5124-32 (1997); hepatitis B virus core promoter, Sandig et al., Gene Ther. 3:1002-9 (1996); alpha-fetoprotein (AFP), Arbuthnot et al., Hum. Gene Ther., 7:1503-14 (1996)], bone (osteocalcin, Stein et al., Mol. Biol. Rep., 24:185-96 (1997); bone sialoprotein, Chen et al., J. Bone Miner. Res. 11:654-64 (1996)), lymphocytes (CD2, Hansal et al., J. Immunol., 161:1063-8 (1998); immunoglobulin heavy chain; T cell receptor a chain), neuronal (neuron-specific enolase (NSE) promoter, Andersen et al. Cell. Mol. Neurobiol., 13:503-15 (1993); neurofilament light-chain gene, Piccioli et al., Proc. Natl. Acad. Sci. USA, 88:5611-5 (1991); the neuron-specific vgf gene, Piccioli et al., Neuron, 15:373-84 (1995)]; among others.

The genetic element may include an enhancer, e.g., a DNA sequence that is located adjacent to the DNA sequence that encodes a gene. Enhancer elements are typically located upstream of a promoter element or can be located downstream of or within a coding DNA sequence (e.g., a DNA sequence transcribed or translated into a product or products). Hence, an enhancer element can be located 100 base pairs, 200 base pairs, or 300 or more base pairs upstream or downstream of a DNA sequence that encodes the product. Enhancer elements can increase an amount of recombinant product expressed from a DNA sequence above increased expression afforded by a promoter element. Multiple enhancer elements are readily available to persons of ordinary skill in the art.

In some embodiments, the genetic element comprises one or more inverted terminal repeats (ITR) flanking the sequences encoding the expression products described herein. In some embodiments, the genetic element comprises one or more long terminal repeats (LTR) flanking the sequence encoding the expression products described herein. Examples of promoter sequences that may be used, include, but are not limited to, the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, and a Rous sarcoma virus promoter.

Replication Proteins

In some embodiments, the genetic element of the anellosome, e.g., synthetic anellosome, may include sequences that encode one or more replication proteins. In some embodiments, the anellosome may replicate by a rolling-circle replication method, e.g., synthesis of the leading strand and the lagging strand is uncoupled. In such embodiments, the anellosome comprises three elements additional elements: i) a gene encoding an initiator protein, ii) a double strand origin, and iii) a single strand origin. A rolling circle replication (RCR) protein complex comprising replication proteins binds to the leading strand and destabilizes the replication origin. The RCR complex cleaves the genome to generate a free 3'OH extremity. Cellular DNA polymerase initiates viral DNA replication from the free 3'OH extremity. After the genome has been replicated, the RCR complex closes the loop covalently. This leads to the release of a positive circular single-stranded parental DNA molecule and a circular double-stranded DNA molecule composed of the negative parental strand and the newly synthesized positive strand. The single-stranded DNA molecule can be either encapsidated or involved in a second round of replication. See for example, Virology Journal 2009, 6:60 doi:10.1186/1743-422X-6-60.

The genetic element may comprise a sequence encoding a polymerase, e.g., RNA polymerase or a DNA polymerase.

Other Sequences

In some embodiments, the genetic element further includes a nucleic acid encoding a product (e.g., a ribozyme, a therapeutic mRNA encoding a protein, an exogenous gene).

In some embodiments, the genetic element includes one or more sequences that affect species and/or tissue and/or cell tropism (e.g. capsid protein sequences), infectivity (e.g. capsid protein sequences), immunosuppression/activation (e.g. regulatory nucleic acids), viral genome binding and/or packaging, immune evasion (non-immunogenicity and/or tolerance), pharmacokinetics, endocytosis and/or cell attachment, nuclear entry, intracellular modulation and localization, exocytosis modulation, propagation, and nucleic acid protection of the anellosome in a host or host cell.

In some embodiments, the genetic element may comprise other sequences that include DNA, RNA, or artificial nucleic acids. The other sequences may include, but are not limited to, genomic DNA, cDNA, or sequences that encode tRNA, mRNA, rRNA, miRNA, gRNA, siRNA, or other RNAi molecules. In one embodiment, the genetic element includes a sequence encoding an siRNA to target a different loci of the same gene expression product as the regulatory nucleic acid. In one embodiment, the genetic element includes a sequence encoding an siRNA to target a different gene expression product as the regulatory nucleic acid.

In some embodiments, the genetic element further comprises one or more of the following sequences: a sequence that encodes one or more miRNAs, a sequence that encodes one or more replication proteins, a sequence that encodes an exogenous gene, a sequence that encodes a therapeutic, a regulatory sequence (e.g., a promoter, enhancer), a sequence that encodes one or more regulatory sequences that targets endogenous genes (siRNA, lncRNAs, shRNA), and a sequence that encodes a therapeutic mRNA or protein.

The other sequences may have a length from about 2 to about 5000 nts, about 10 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, or any range therebetween.

Encoded Genes

For example, the genetic element may include a gene associated with a signaling biochemical pathway, e.g., a signaling biochemical pathway-associated gene or polynucleotide. Examples include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.). Examples of disease-associated genes and polynucleotides are listed in Tables A and B of U.S. Pat. No. 8,697,359, which are herein incorporated by reference in their entirety. Disease specific information is available from McKusick-Nathans Institute of Genetic Medicine, Johns Hopkins University (Baltimore, Md.) and National Center for Biotechnology Information, National Library of Medicine (Bethesda, Md.). Examples of signaling biochemical pathway-associated genes and polynucleotides are listed in Tables A-C of U.S. Pat. No. 8,697,359, which are herein incorporated by reference in their entirety.

Moreover, the genetic elements can encode targeting moieties, as described elsewhere herein. This can be achieved, e.g., by inserting a polynucleotide encoding a sugar, a glycolipid, or a protein, such as an antibody. Those skilled in the art know additional methods for generating targeting moieties.

Viral Sequence

In some embodiments, the genetic element comprises at least one viral sequence. In some embodiments, the sequence has homology or identity to one or more sequence from a single stranded DNA virus, e.g., *Anellovirus*, Bidnavirus, Circovirus, Geminivirus, Genomovirus, Inovirus, Microvirus, Nanovirus, Parvovirus, and Spiravirus. In some embodiments, the sequence has homology or identity to one or more sequence from a double stranded DNA virus, e.g., Adenovirus, Ampullavirus, Ascovirus, Asfarvirus, Baculovirus, Fusellovirus, Globulovirus, Guttavirus, Hytrosavirus, Herpesvirus, Iridovirus, Lipothrixvirus, Nimavirus, and Poxvirus. In some embodiments, the sequence has homology or identity to one or more sequence from an RNA virus, e.g., Alphavirus, Furovirus, Hepatitis virus, Hordeivirus, Tobamovirus, Tobravirus, Tricornavirus, Rubivirus, Birnavirus, Cystovirus, Partitivirus, and Reovirus.

In some embodiments, the genetic element may comprise one or more sequences from a non-pathogenic virus, e.g., a symbiotic virus, e.g., a commensal virus, e.g., a native virus, e.g., an *Anellovirus*. Recent changes in nomenclature have classified the three *Anelloviruses* able to infect human cells into *Alphatorquevirus* (TT), *Betatorquevirus* (TTM), and *Gammatorquevirus* (TTMD) Genera of the Anelloviridae family of viruses. To date *Anelloviruses* have not been linked to any human disease. In some embodiments, the genetic element may comprise a sequence with homology or identity to a Torque Teno Virus (TT), a non-enveloped, single-stranded DNA virus with a circular, negative-sense genome. In some embodiments, the genetic element may comprise a sequence with homology or identity to a SEN virus, a Sentinel virus, a TTV-like mini virus, and a TT virus. Different types of TT viruses have been described including TT virus genotype 6, TT virus group, TTV-like virus DXL1, and TTV-like virus DXL2. In some embodiments, the genetic element may comprise a sequence with homology or identity to a smaller virus, Torque Teno-like Mini Virus (TTM), or a third virus with a genomic size in between that of TTV and TTMV, named Torque Teno-like Midi Virus (TTMD). In some embodiments, the genetic element may comprise one or more sequences or a fragment of a sequence from a non-pathogenic virus having at least about 60%, 70% 80%, 85%, 90% 95%, 96%, 97%, 98% and 99% nucleotide sequence identity to any one of the nucleotide sequences described herein.

In some embodiments, the genetic element may comprise one or more sequences or a fragment of a sequence from a substantially non-pathogenic virus having at least about 60%, 70% 80%, 85%, 90% 95%, 96%, 97%, 98% and 99% nucleotide sequence identity to any one of the nucleotide sequences described herein, e.g., Table 41.

TABLE 41

Examples of Anelloviruses and their sequences. Accessions numbers and related sequence information may be obtained at www.ncbi.nlm.nih.gov/genbank/, as referenced on Dec. 11, 2018.

| Accession # | Description |
|---|---|
| AB017613.1 | Torque teno virus 16 DNA, complete genome, isolate: TUS01 |
| AB026345.1 | TT virus genes for ORF1 and ORF2, complete cds, isolate: TRM1 |
| AB026346.1 | TT virus genes for ORF1 and ORF2, complete cds, isolate: TK16 |
| AB026347.1 | TT virus genes for ORF1 and ORF2, complete cds, isolate: TP1-3 |
| AB028669.1 | TT virus gene for ORF1 and ORF2, complete genome, isolate: TJN02 |
| AB030487.1 | TT virus gene for pORF2a, pORF2b, pORF1, complete cds, clone: JaCHCTC19 |
| AB030488.1 | TT virus gene for pORF2a, pORF2b, pORF1, complete cds, clone: JaBD89 |
| AB030489.1 | TT virus gene for pORF2a, pORF2b, pORF1, complete cds, clone: JaBD98 |
| AB038340.1 | TT virus genes for ORF2s, ORF1, ORF3, complete cds |
| AB038622.1 | TT virus genes for ORF2, ORF1, ORF3, complete cds, isolate: TTVyon-LC011 |
| AB038623.1 | TT virus genes for ORF2, ORF1, ORF3, complete cds, isolate: TTVyon-KC186 |
| AB038624.1 | TT virus genes for ORF2, ORF1, ORF3, complete cds, isolate: TTVyon-KC197 |
| AB041821.1 | TT virus mRNA for VP1, complete cds |
| AB050448.1 | Torque teno virus genes for ORF1, ORF2, ORF3, ORF4, complete cds, isolate: TYM9 |
| AB060592.1 | Torque teno virus gene for ORF1, ORF2, ORF3, ORF4, clone: SAa-39 |
| AB060593.1 | Torque teno virus gene for ORF1, ORF2, ORF3, ORF4, complete cds, clone: SAa-38 |
| AB060595.1 | TT virus gene for ORF1, ORF2, ORF3, ORF4, complete cds, clone: SAj-30 |
| AB060596.1 | TT virus gene for ORF1, ORF2, ORF3, ORF4, complete cds, clone: SAf-09 |
| AB064596.1 | Torque teno virus DNA, complete genome, isolate: CT25F |
| AB064597.1 | Torque teno virus DNA, complete genome, isolate: CT30F |
| AB064599.1 | Torque teno virus DNA, complete genome, isolate: JT03F |
| AB064600.1 | Torque teno virus DNA, complete genome, isolate: JT05F |
| AB064601.1 | Torque teno virus DNA, complete genome, isolate: JT14F |
| AB064602.1 | Torque teno virus DNA, complete genome, isolate: JT19F |
| AB064603.1 | Torque teno virus DNA, complete genome, isolate: JT41F |

TABLE 41-continued

Examples of Anelloviruses and their sequences. Accessions numbers and related sequence information may be obtained at www.ncbi.nlm.nih.gov/genbank/, as referenced on Dec. 11, 2018.

| Accession # | Description |
|---|---|
| AB064604.1 | Torque teno virus DNA, complete genome, isolate: CT39F |
| AB064606.1 | Torque teno virus DNA, complete genome, isolate: JT33F |
| AB290918.1 | Torque teno midi virus 1 DNA, complete genome, isolate: MD1-073 |
| AF079173.1 | TT virus strain TTVCHN1, complete genome |
| AF116842.1 | TT virus strain BDH1, complete genome |
| AF122914.3 | TT virus isolate JA20, complete genome |
| AF122917.1 | TT virus isolate JA4, complete genome |
| AF122919.1 | TT virus isolate JA10 unknown genes |
| AF129887.1 | TT virus TTVCHN2, complete genome |
| AF247137.1 | TT virus isolate TUPB, complete genome |
| AF254410.1 | TT virus ORF2 protein and ORF1 protein genes, complete cds |
| AF298585.1 | TT virus Polish isolate P/1C1, complete genome |
| AF315076.1 | TTV-like virus DXL1 unknown genes |
| AF315077.1 | TTV-like virus DXL2 unknown genes |
| AF345521.1 | TT virus isolate TCHN-G1 Orf2 and Orf1 genes, complete cds |
| AF345522.1 | TT virus isolate TCHN-E Orf2 and Orf1 genes, complete cds |
| AF345525.1 | TT virus isolate TCHN-D2 Orf2 and Orf1 genes, complete cds |
| AF345527.1 | TT virus isolate TCHN-C2 Orf2 and Orf1 genes, complete cds |
| AF345528.1 | TT virus isolate TCHN-F Orf2 and Orf1 genes, complete cds |
| AF345529.1 | TT virus isolate TCHN-G2 Orf2 and Orf1 genes, complete cds |
| AF371370.1 | TT virus ORF1, ORF3, and ORF2 genes, complete cds |
| AJ620212.1 | Torque teno virus, isolate tth6, complete genome |
| AJ620213.1 | Torque teno virus, isolate tth10, complete genome |
| AJ620214.1 | Torque teno virus, isolate tth11g2, complete genome |
| AJ620215.1 | Torque teno virus, isolate tth18, complete genome |
| AJ620216.1 | Torque teno virus, isolate tth20, complete genome |
| AJ620217.1 | Torque teno virus, isolate tth21, complete genome |
| AJ620218.1 | Torque teno virus, isolate tth3, complete genome |
| AJ620219.1 | Torque teno virus, isolate tth9, complete genome |
| AJ620220.1 | Torque teno virus, isolate tth16, complete genome |
| AJ620221.1 | Torque teno virus, isolate tth17, complete genome |
| AJ620222.1 | Torque teno virus, isolate tth25, complete genome |
| AJ620223.1 | Torque teno virus, isolate tth26, complete genome |
| AJ620224.1 | Torque teno virus, isolate tth27, complete genome |
| AJ620225.1 | Torque teno virus, isolate tth31, complete genome |
| AJ620226.1 | Torque teno virus, isolate tth4, complete genome |
| AJ620227.1 | Torque teno virus, isolate tth5, complete genome |
| AJ620228.1 | Torque teno virus, isolate tth14, complete genome |
| AJ620229.1 | Torque teno virus, isolate tth29, complete genome |
| AJ620230.1 | Torque teno virus, isolate tth7, complete genome |
| AJ620231.1 | Torque teno virus, isolate tth8, complete genome |
| AJ620232.1 | Torque teno virus, isolate tth13, complete genome |
| AJ620233.1 | Torque teno virus, isolate tth19, complete genome |
| AJ620234.1 | Torque teno virus, isolate tth22g4, complete genome |
| AJ620235.1 | Torque teno virus, isolate tth23, complete genome |
| AM711976.1 | TT virus sle1957 complete genome |
| AM712003.1 | TT virus sle1931 complete genome |
| AM712004.1 | TT virus sle1932 complete genome |
| AM712030.1 | TT virus sle2057 complete genome |
| AM712031.1 | TT virus sle2058 complete genome |
| AM712032.1 | TT virus sle2072 complete genome |
| AM712033.1 | TT virus sle2061 complete genome |
| AM712034.1 | TT virus sle2065 complete genome |
| AY026465.1 | TT virus isolate L01 ORF2 and ORF1 genes, complete cds |
| AY026466.1 | TT virus isolate L02 ORF2 and ORF1 genes, complete cds |
| DQ003341.1 | Torque teno virus clone P2-9-02 ORF2 (ORF2), ORF1A (ORF1A), and ORF1B (ORF1B) genes, complete cds |
| DQ003342.1 | Torque teno virus clone P2-9-07 ORF2 (ORF2), ORF1A (ORF1A), and ORF1B (ORF1B) genes, complete cds |
| DQ003343.1 | Torque teno virus clone P2-9-08 ORF2 (ORF2), ORF1A (ORF1A), and ORF1B (ORF1B) genes, complete cds |
| DQ003344.1 | Torque teno virus clone P2-9-16 ORF2 (ORF2), ORF1A (ORF1A), and ORF1B (ORF1B) genes, complete cds |
| DQ186994.1 | Torque teno virus clone P601 ORF2 (ORF2) and ORF1 (ORF1) genes, complete cds |
| DQ186995.1 | Torque teno virus clone P605 ORF2 (ORF2) and ORF1 (ORF1) genes, complete cds |
| DQ186996.1 | Torque teno virus clone BM1A-02 ORF2 (ORF2) and ORF1 (ORF1) genes, complete cds |
| DQ186997.1 | Torque teno virus clone BM1A-09 ORF2 (ORF2) and ORF1 (ORF1) genes, complete cds |
| DQ186998.1 | Torque teno virus clone BM1A-13 ORF2 (ORF2) and ORF1 (ORF1) genes, complete cds |
| DQ186999.1 | Torque teno virus clone BM1B-05 ORF2 (ORF2) and ORF1 (ORF1) genes, complete cds |

TABLE 41-continued

Examples of Anelloviruses and their sequences. Accessions numbers and related sequence information may be obtained at www.ncbi.nlm.nih.gov/genbank/, as referenced on Dec. 11, 2018.

| Accession # | Description |
|---|---|
| DQ187000.1 | Torque teno virus clone BM1B-07 ORF2 (ORF2) and ORF1 (ORF1) genes, complete cds |
| DQ187001.1 | Torque teno virus clone BM1B-11 ORF2 (ORF2) and ORF1 (ORF1) genes, complete cds |
| DQ187002.1 | Torque teno virus clone BM1B-14 ORF2 (ORF2) and ORF1 (ORF1) genes, complete cds |
| DQ187003.1 | Torque teno virus clone BM1B-08 ORF2 (ORF2) gene, complete cds; and nonfunctional ORF1 (ORF1) gene, complete sequence |
| DQ187004.1 | Torque teno virus clone BM1C-16 ORF2 (ORF2) and ORF1 (ORF1) genes, complete cds |
| DQ187005.1 | Torque teno virus clone BM1C-10 ORF2 (ORF2) and ORF1 (ORF1) genes, complete cds |
| DQ187007.1 | Torque teno virus clone BM2C-25 ORF2 (ORF2) gene, complete cds; and nonfunctional ORF1 (ORF1) gene, complete sequence |
| DQ361268.1 | Torque teno virus isolate ViPi04 ORF1 gene, complete cds |
| EF538879.1 | Torque teno virus isolate CSC5 ORF2 and ORF1 genes, complete cds |
| EU305675.1 | Torque teno virus isolate LTT7 ORF1 gene, complete cds |
| EU305676.1 | Torque teno virus isolate LTT10 ORF1 gene, complete cds |
| EU889253.1 | Torque teno virus isolate ViPiO8 nonfunctional ORF1 gene, complete sequence |
| FJ392105.1 | Torque teno virus isolate TW53A25 ORF2 gene, partial cds; and ORF1 gene, complete cds |
| FJ392107.1 | Torque teno virus isolate TW53A27 ORF2 gene, partial cds; and ORF1 gene, complete cds |
| FJ392108.1 | Torque teno virus isolate TW53A29 ORF2 gene, partial cds; and ORF1 gene, complete cds |
| FJ392111.1 | Torque teno virus isolate TW53A35 ORF2 gene, partial cds; and ORF1 gene, complete cds |
| FJ392112.1 | Torque teno virus isolate TW53A39 ORF2 gene, partial cds; and ORF1 gene, complete cds |
| FJ392113.1 | Torque teno virus isolate TW53A26 ORF2 gene, complete cds; and nonfunctional ORF1 gene, complete sequence |
| FJ392114.1 | Torque teno virus isolate TW53A30 ORF2 and ORF1 genes, complete cds |
| FJ392115.1 | Torque teno virus isolate TW53A31 ORF2 and ORF1 genes, complete cds |
| FJ392117.1 | Torque teno virus isolate TW53A37 ORF1 gene, complete cds |
| FJ426280.1 | Torque teno virus strain SIA109, complete genome |
| FR751500.1 | Torque teno virus complete genome, isolate TTV-HD23a (rheu215) |
| GU797360.1 | Torque teno virus clone 8-17, complete genome |
| HC742700.1 | Sequence 7 from Patent WO2010044889 |
| HC742710.1 | Sequence 17 from Patent WO2010044889 |
| JX134044.1 | TTV-like mini virus isolate TTMV_LY1, complete genome |
| JX134045.1 | TTV-like mini virus isolate TTMV_LY2, complete genome |
| KU243129.1 | TTV-like mini virus isolate TTMV-204, complete genome |
| KY856742.1 | TTV-like mini virus isolate zhenjiang, complete genome |
| LC381845.1 | Torque teno virus Human/Japan/KS025/2016 DNA, complete genome |
| MH648892.1 | Anelloviridae sp. isolate ctdc048, complete genome |
| MH648893.1 | Anelloviridae sp. isolate ctdh007, complete genome |
| MH648897.1 | Anelloviridae sp. isolate ctcb038, complete genome |
| MH648900.1 | Anelloviridae sp. isolate ctfc019, complete genome |
| MH648901.1 | Anelloviridae sp. isolate ctbb022, complete genome |
| MH648907.1 | Anelloviridae sp. isolate ctcf040, complete genome |
| MH648911.1 | Anelloviridae sp. isolate cthi018, complete genome |
| MH648912.1 | Anelloviridae sp. isolate ctea38, complete genome |
| MH648913.1 | Anelloviridae sp. isolate ctbg006, complete genome |
| MH648916.1 | Anelloviridae sp. isolate ctbg020, complete genome |
| MH648925.1 | Anelloviridae sp. isolate ctci019, complete genome |
| MH648932.1 | Anelloviridae sp. isolate ctid031, complete genome |
| MH648946.1 | Anelloviridae sp. isolate ctdb017, complete genome |
| MH648957.1 | Anelloviridae sp. isolate ctch017, complete genome |
| MH648958.1 | Anelloviridae sp. isolate ctbh011, complete genome |
| MH648959.1 | Anelloviridae sp. isolate ctbc020, complete genome |
| MH648962.1 | Anelloviridae sp. isolate ctif015, complete genome |
| MH648966.1 | Anelloviridae sp. isolate ctei055, complete genome |
| MH648969.1 | Anelloviridae sp. isolate ctjg000, complete genome |
| MH648976.1 | Anelloviridae sp. isolate ctcj064, complete genome |
| MH648977.1 | Anelloviridae sp. isolate ctbj022, complete genome |
| MH648982.1 | Anelloviridae sp. isolate ctbf014, complete genome |
| MH648983.1 | Anelloviridae sp. isolate ctbd027, complete genome |
| MH648985.1 | Anelloviridae sp. isolate ctch016, complete genome |
| MH648986.1 | Anelloviridae sp. isolate ctbd020, complete genome |
| MH648989.1 | Anelloviridae sp. isolate ctga035, complete genome |
| MH648990.1 | Anelloviridae sp. isolate cthf001, complete genome |
| MH648995.1 | Anelloviridae sp. isolate ctbd067, complete genome |
| MH648997.1 | Anelloviridae sp. isolate ctce026, complete genome |
| MH648999.1 | Anelloviridae sp. isolate ctfb058, complete genome |
| MH649002.1 | Anelloviridae sp. isolate ctjj046, complete genome |

TABLE 41-continued

Examples of Anelloviruses and their sequences. Accessions numbers and related sequence information may be obtained at www.ncbi.nlm.nih.gov/genbank/, as referenced on Dec. 11, 2018.

| Accession # | Description |
|---|---|
| MH649006.1 | Anelloviridae sp. isolate ctcf030, complete genome |
| MH649008.1 | Anelloviridae sp. isolate ctbg025, complete genome |
| MH649011.1 | Anelloviridae sp. isolate ctbh052, complete genome |
| MH649014.1 | Anelloviridae sp. isolate ctba003, complete genome |
| MH649017.1 | Anelloviridae sp. isolate ctbb016, complete genome |
| MH649022.1 | Anelloviridae sp. isolate ctch023, complete genome |
| MH649023.1 | Anelloviridae sp. isolate ctbd051, complete genome |
| MH649028.1 | Anelloviridae sp. isolate ctbf9, complete genome |
| MH649038.1 | Anelloviridae sp. isolate ctbi030, complete genome |
| MH649039.1 | Anelloviridae sp. isolate ctca057, complete genome |
| MH649040.1 | Anelloviridae sp. isolate ctch033, complete genome |
| MH649042.1 | Anelloviridae sp. isolate ctjd005, complete genome |
| MH649045.1 | Anelloviridae sp. isolate ctdc021, complete genome |
| MH649051.1 | Anelloviridae sp. isolate ctdg044, complete genome |
| MH649056.1 | Anelloviridae sp. isolate ctcc062, complete genome |
| MH649061.1 | Anelloviridae sp. isolate ctid009, complete genome |
| MH649062.1 | Anelloviridae sp. isolate ctdc018, complete genome |
| MH649063.1 | Anelloviridae sp. isolate ctbf012, complete genome |
| MH649068.1 | Anelloviridae sp. isolate ctcc066, complete genome |
| MH649070.1 | Anelloviridae sp. isolate ctda011, complete genome |
| MH649077.1 | Anelloviridae sp. isolate ctbh034, complete genome |
| MH649083.1 | Anelloviridae sp. isolate ctdg028, complete genome |
| MH649084.1 | Anelloviridae sp. isolate ctii061, complete genome |
| MH649085.1 | Anelloviridae sp. isolate cteh021, complete genome |
| MH649092.1 | Anelloviridae sp. isolate ctbg012, complete genome |
| MH649101.1 | Anelloviridae sp. isolate ctif053, complete genome |
| MH649104.1 | Anelloviridae sp. isolate ctei657, complete genome |
| MH649106.1 | Anelloviridae sp. isolate ctca015, complete genome |
| MH649114.1 | Anelloviridae sp. isolate ctbf050, complete genome |
| MH649122.1 | Anelloviridae sp. isolate ctdc002, complete genome |
| MH649125.1 | Anelloviridae sp. isolate ctbb15, complete genome |
| MH649127.1 | Anelloviridae sp. isolate ctba013, complete genome |
| MH649137.1 | Anelloviridae sp. isolate ctbb000, complete genome |
| MH649141.1 | Anelloviridae sp. isolate ctbc019, complete genome |
| MH649142.1 | Anelloviridae sp. isolate ctid026, complete genome |
| MH649144.1 | Anelloviridae sp. isolate ctfj004, complete genome |
| MH649152.1 | Anelloviridae sp. isolate ctcj13, complete genome |
| MH649156.1 | Anelloviridae sp. isolate ctci006, complete genome |
| MH649157.1 | Anelloviridae sp. isolate ctbd025, complete genome |
| MH649158.1 | Anelloviridae sp. isolate ctbf005, complete genome |
| MH649161.1 | Anelloviridae sp. isolate ctcf045, complete genome |
| MH649165.1 | Anelloviridae sp. isolate ctcc29, complete genome |
| MH649169.1 | Anelloviridae sp. isolate ctib021, complete genome |
| MH649172.1 | Anelloviridae sp. isolate ctbh857, complete genome |
| MH649174.1 | Anelloviridae sp. isolate ctbj049, complete genome |
| MH649178.1 | Anelloviridae sp. isolate ctfc006, complete genome |
| MH649179.1 | Anelloviridae sp. isolate ctbe000, complete genome |
| MH649183.1 | Anelloviridae sp. isolate ctbb031, complete genome |
| MH649186.1 | Anelloviridae sp. isolate ctcb33, complete genome |
| MH649189.1 | Anelloviridae sp. isolate ctcc12, complete genome |
| MH649196.1 | Anelloviridae sp. isolate ctci060, complete genome |
| MH649199.1 | Anelloviridae sp. isolate ctbb017, complete genome |
| MH649203.1 | Anelloviridae sp. isolate cthc018, complete genome |
| MH649204.1 | Anelloviridae sp. isolate ctbj003, complete genome |
| MH649206.1 | Anelloviridae sp. isolate ctbg010, complete genome |
| MH649208.1 | Anelloviridae sp. isolate ctid008, complete genome |
| MH649209.1 | Anelloviridae sp. isolate ctbg056, complete genome |
| MH649210.1 | Anelloviridae sp. isolate ctda001, complete genome |
| MH649212.1 | Anelloviridae sp. isolate ctcf004, complete genome |
| MH649217.1 | Anelloviridae sp. isolate ctbe029, complete genome |
| MH649223.1 | Anelloviridae sp. isolate ctci016, complete genome |
| MH649224.1 | Anelloviridae sp. isolate ctce11, complete genome |
| MH649228.1 | Anelloviridae sp. isolate ctcf013, complete genome |
| MH649229.1 | Anelloviridae sp. isolate ctcb036, complete genome |
| MH649241.1 | Anelloviridae sp. isolate ctda027, complete genome |
| MH649242.1 | Anelloviridae sp. isolate ctbf003, complete genome |
| MH649254.1 | Anelloviridae sp. isolate ctjb007, complete genome |
| MH649255.1 | Anelloviridae sp. isolate ctbb023, complete genome |
| MH649256.1 | Anelloviridae sp. isolate ctca002, complete genome |
| MH649258.1 | Anelloviridae sp. isolate ctcg010, complete genome |
| MH649263.1 | Anelloviridae sp. isolate ctgh3, complete genome |
| MK012439.1 | Anelloviridae sp. isolate cthe000, complete genome |
| MK012440.1 | Anelloviridae sp. isolate ctjd008, complete genome |
| MK012448.1 | Anelloviridae sp. isolate ctch012, complete genome |
| MK012457.1 | Anelloviridae sp. isolate ctda009, complete genome |

TABLE 41-continued

Examples of Anelloviruses and their sequences. Accessions numbers and related sequence information may be obtained at www.ncbi.nlm.nih.gov/genbank/, as referenced on Dec. 11, 2018.

| Accession # | Description |
|---|---|
| MK012458.1 | Anelloviridae sp. isolate ctcd015, complete genome |
| MK012485.1 | Anelloviridae sp. isolate ctfd011, complete genome |
| MK012489.1 | Anelloviridae sp. isolate ctba003, complete genome |
| MK012492.1 | Anelloviridae sp. isolate ctbb005, complete genome |
| MK012493.1 | Anelloviridae sp. isolate ctcj014, complete genome |
| MK012500.1 | Anelloviridae sp. isolate ctcb001, complete genome |
| MK012504.1 | Anelloviridae sp. isolate ctcj010, complete genome |
| MK012516.1 | Anelloviridae sp. isolate ctcf003, complete genome |
| NC_038336.1 | Torque teno virus 5 isolate TCHN-C1 Orf2 and Orf1 genes, complete cds |
| NC_038338.1 | Torque teno virus 11 isolate TCHN-D1 Orf2 and Orf1 genes, complete cds |
| NC_038339.1 | Torque teno virus 13 isolate TCHN-A Orf2 and Orf1 genes, complete cds |
| NC_038340.1 | Torque teno virus 20 ORF4, ORF3, ORF2, ORF1 genes, complete cds, clone: SAa-10 |
| NC_038341.1 | Torque teno virus 21 isolate TCHN-B ORF2 and ORF1 genes, complete cds |
| NC_038342.1 | Torque teno virus 23 ORF2, ORF1 genes, complete cds, isolate: s-TTV CH65-2 |
| NC_038343.1 | Torque teno virus 24 ORF4, ORF3, ORF2, ORF1 genes, complete cds, clone: SAa-01 |
| NC_038344.1 | Torque teno virus 29 ORF2, ORF1, ORF3 genes, complete cds, isolate: TTVyon-KC009 |
| NC_038345.1 | Torque teno mini virus 10 isolate LIL-y1 ORF2, ORF1, ORF3, and ORF4 genes, complete cds |
| NC_038346.1 | Torque teno mini virus 11 isolate LIL-y2 ORF2, ORF1, and ORF3 genes, complete cds |
| NC_038347.1 | Torque teno mini virus 12 isolate LIL-y3 ORF2, ORF1, ORF3, and ORF4 genes, complete cds |
| NC_038350.1 | Torque teno midi virus 3 isolate 2PoSMA ORF2 and ORF1 genes, complete cds |
| NC_038351.1 | Torque teno midi virus 4 isolate 6PoSMA ORF2, ORF1, and ORF3 genes, complete cds |
| NC_038352.1 | Torque teno midi virus 5 DNA, complete genome, isolate: MDJHem2 |
| NC_038353.1 | Torque teno midi virus 6 DNA, complete genome, isolate: MDJHem3-1 |
| NC_038354.1 | Torque teno midi virus 7 DNA, complete genome, isolate: MDJHem3-2 |
| NC_038355.1 | Torque teno midi virus 8 DNA, complete genome, isolate: MDJN1 |
| NC_038356.1 | Torque teno midi virus 9 DNA, complete genome, isolate: MDJN2 |
| NC_038357.1 | Torque teno midi virus 10 DNA, complete genome, isolate: MDJN14 |
| NC_038358.1 | Torque teno midi virus 11 DNA, complete genome, isolate: MDJN47 |
| NC_038359.1 | Torque teno midi virus 12 DNA, complete genome, isolate: MDJN51 |
| NC_038360.1 | Torque teno midi virus 13 DNA, complete genome, isolate: MDJN69 |
| NC_038361.1 | Torque teno midi virus 14 DNA, complete genome, isolate: MDJN97 |
| NC_038362.1 | Torque teno midi virus 15 DNA, complete genome, isolate: Pt-TTMDV210 |

In some embodiments, the genetic element comprises one or more sequences with homology or identity to one or more sequences from one or more non-*Anelloviruses*, e.g., adenovirus, herpes virus, pox virus, vaccinia virus, SV40, papilloma virus, an RNA virus such as a retrovirus, e.g., lentivirus, a single-stranded RNA virus, e.g., hepatitis virus, or a double-stranded RNA virus e.g., rotavirus. Since, in some embodiments, recombinant retroviruses are defective, assistance may be provided order to produce infectious particles. Such assistance can be provided, e.g., by using helper cell lines that contain plasmids encoding all of the structural genes of the retrovirus under the control of regulatory sequences within the LTR. Suitable cell lines for replicating the anellosomes described herein include cell lines known in the art, e.g., A549 cells, which can be modified as described herein. Said genetic element can additionally contain a gene encoding a selectable marker so that the desired genetic elements can be identified.

In some embodiments, the genetic element includes non-silent mutations, e.g., base substitutions, deletions, or additions resulting in amino acid differences in the encoded polypeptide, so long as the sequence remains at least about 70%, 75%, 80%, 85%, 90%, 95%, 96%, 97%, 98%, or 99% identical to the polypeptide encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tryptophan and phenylalanine Amino acids can be classified according to physical properties and contribution to secondary and tertiary protein structure. A conservative substitution is recognized in the art as a substitution of one amino acid for another amino acid that has similar properties.

Identity of two or more nucleic acid or polypeptide sequences having the same or a specified percentage of nucleotides or amino acid residues that are the same (e.g., about 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) may be measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Identity may also refer to, or may be applied to, the compliment of a test sequence. Identity also includes sequences that have deletions and/or additions, as well as those that have substitutions. As described herein, the algorithms account for gaps and the like. Identity may exist over a region that is at least about 10 amino acids or nucleotides in length, about 15 amino acids or nucleotides in length, about 20 amino acids or nucleotides in length, about 25 amino acids or nucleotides in length, about 30 amino acids or nucleotides in length, about 35 amino acids or nucleotides in length, about 40 amino acids or nucleotides in length, about 45 amino acids or nucleotides in length, about 50 amino acids or nucleotides in length, or more.

In some embodiments, the genetic element comprises a nucleotide sequence with at least about 75% nucleotide sequence identity, at least about 80%, 85%, 90% 95%, 96%, 97%, 98%, 99% or 100% nucleotide sequence identity to any one of the nucleotide sequences described herein, e.g., as listed in any of Tables 1, 3, 5, 7, 9, 11, 13, 15, 17, or 41. Since the genetic code is degenerate, a homologous nucleotide sequence can include any number of silent base changes, i.e., nucleotide substitutions that nonetheless encode the same amino acid.

Gene Editing Component

The genetic element of the anellosome may include one or more genes that encode a component of a gene editing system. Exemplary gene editing systems include the clustered regulatory interspaced short palindromic repeat (CRISPR) system, zinc finger nucleases (ZFNs), and Transcription Activator-Like Effector-based Nucleases (TALEN). ZFNs, TALENs, and CRISPR-based methods are described, e.g., in Gaj et al. Trends Biotechnol. 31.7(2013): 397-405; CRISPR methods of gene editing are described, e.g., in Guan et al., Application of CRISPR-Cas system in gene therapy: Pre-clinical progress in animal model. DNA Repair 2016 October; 46:1-8. doi: 10.1016/j.dnarep.2016.07.004; Zheng et al., Precise gene deletion and replacement using the CRISPR/Cas9 system in human cells. BioTechniques, Vol. 57, No. 3, September 2014, pp. 115-124.

CRISPR systems are adaptive defense systems originally discovered in bacteria and archaea. CRISPR systems use RNA-guided nucleases termed CRISPR-associated or “Cas” endonucleases (e. g., Cas9 or Cpf1) to cleave foreign DNA. In a typical CRISPR/Cas system, an endonuclease is directed to a target nucleotide sequence (e. g., a site in the genome that is to be sequence-edited) by sequence-specific, non-coding “guide RNAs” that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA (“crRNA”), and a trans-activating crRNA (“tracrRNA”). The crRNA contains a “guide RNA”, typically about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence. The target DNA sequence must generally be adjacent to a “protospacer adjacent motif” (“PAM”) that is specific for a given Cas endonuclease; however, PAM sequences appear throughout a given genome.

In some embodiments, the anellosome includes a gene for a CRISPR endonuclease. For example, some CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningiditis*). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) Cell, 163:759-771.

A variety of CRISPR associated (Cas) genes may be included in the anellosome. Specific examples of genes are those that encode Cas proteins from class II systems including Cas1, Cas2, Cas3, Cas4, Cas5, Cas6, Cas7, Cas8, Cas9, Cas10, Cpf1, C2C1, or C2C3. In some embodiments, the anellosome includes a gene encoding a Cas protein, e.g., a Cas9 protein, may be from any of a variety of prokaryotic species. In some embodiments, the anellosome includes a gene encoding a particular Cas protein, e.g., a particular Cas9 protein, is selected to recognize a particular protospacer-adjacent motif (PAM) sequence. In some embodiments, the anellosome includes nucleic acids encoding two or more different Cas proteins, or two or more Cas proteins, may be introduced into a cell, zygote, embryo, or animal, e.g., to allow for recognition and modification of sites comprising the same, similar or different PAM motifs. In some embodiments, the anellosome includes a gene encoding a modified Cas protein with a deactivated nuclease, e.g., nuclease-deficient Cas9.

Whereas wild-type Cas9 protein generates double-strand breaks (DSBs) at specific DNA sequences targeted by a gRNA, a number of CRISPR endonucleases having modified functionalities are known, for example: a “nickase” version of Cas9 generates only a single-strand break; a catalytically inactive Cas9 (“dCas9”) does not cut the target DNA. A gene encoding a dCas9 can be fused with a gene encoding an effector domain to repress (CRISPRi) or activate (CRISPRa) expression of a target gene. For example, the gene may encode a Cas9 fusion with a transcriptional silencer (e.g., a KRAB domain) or a transcriptional activator (e.g., a dCas9-VP64 fusion). A gene encoding a catalytically inactive Cas9 (dCas9) fused to FokI nuclease (“dCas9-FokI”) can be included to generate DSBs at target sequences homologous to two gRNAs. See, e. g., the numerous CRISPR/Cas9 plasmids disclosed in and publicly available from the Addgene repository (Addgene, 75 Sidney St., Suite 550A, Cambridge, Mass. 02139; addgene.org/crispr/). A “double nickase” Cas9 that introduces two separate double-strand breaks, each directed by a separate guide RNA, is described as achieving more accurate genome editing by Ran et al. (2013) Cell, 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some embodiments, the anellosome comprises a gene encoding a polypeptide described herein, e.g., a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, and a gRNA. The choice of genes encoding the nuclease and gRNA(s) is determined by whether the targeted mutation is a deletion, substitution, or addition of nucleotides, e.g., a deletion, substitution, or addition of nucleotides to a targeted sequence. Genes that encode a catalytically inactive endonuclease e.g., a dead Cas9 (dCas9, e.g., D10A; H840A) tethered with all or a portion of (e.g., biologically active portion of) an (one or more) effector domain (e.g., VP64) create chimeric proteins that can modulate activity and/or expression of one or more target nucleic acids sequences.

As used herein, a "biologically active portion of an effector domain" is a portion that maintains the function (e.g. completely, partially, or minimally) of an effector domain (e.g., a "minimal" or "core" domain) In some embodiments, the anellosome includes a gene encoding a fusion of a dCas9 with all or a portion of one or more effector domains to create a chimeric protein useful in the methods described herein. Accordingly, in some embodiments, the anellosome includes a gene encoding a dCas9-methylase fusion. In other some embodiments, the anellosome includes a gene encoding a dCas9-enzyme fusion with a site-specific gRNA to target an endogenous gene.

In other aspects, the anellosome includes a gene encoding 1, 2, 3, 4, 5, 6, 7, 8, 9, 10, 11, 12, 13, 14, 15, 16, 17, 18, 19, 20, or more effector domains (all or a biologically active portion) fused with dCas9.

Proteinaceous Exterior

In some embodiments, the anellosome, e.g., synthetic anellosome, comprises a proteinaceous exterior that encloses the genetic element. The proteinaceous exterior can comprise a substantially non-pathogenic exterior protein that fails to elicit an immune response in a mammal. In some embodiments, the anellosome lacks lipids in the proteinaceous exterior. In some embodiments, the anellosome lacks a lipid bilayer, e.g., a viral envelope. In some embodiments, the interior of the anellosome is entirely covered (e.g., 100% coverage) by a proteinaceous exterior. In some embodiments, the interior of the anellosome is less than 100% covered by the proteinaceous exterior, e.g., 95%, 90%, 85%, 80%, 70%, 60%, 50% or less coverage. In some embodiments, the proteinaceous exterior comprises gaps or discontinuities, e.g., permitting permeability to water, ions, peptides, or small molecules, so long as the genetic element is retained in the anellosome.

In some embodiments, the proteinaceous exterior comprises one or more proteins or polypeptides that specifically recognize and/or bind a host cell, e.g., a complementary protein or polypeptide, to mediate entry of the genetic element into the host cell.

In some embodiments, the proteinaceous exterior comprises one or more of the following: one or more glycosylated proteins, a hydrophilic DNA-binding region, an arginine-rich region, a threonine-rich region, a glutamine-rich region, a N-terminal polyarginine sequence, a variable region, a C-terminal polyglutamine/glutamate sequence, and one or more disulfide bridges.

In some embodiments, the proteinaceous exterior comprises one or more of the following characteristics: an icosahedral symmetry, recognizes and/or binds a molecule that interacts with one or more host cell molecules to mediate entry into the host cell, lacks lipid molecules, lacks carbohydrates, is pH and temperature stable, is detergent resistant, and is substantially non-immunogenic or non-pathogenic in a host.

Vectors

The genetic element described herein may be included in a vector. Suitable vectors as well as methods for their manufacture and their use are well known in the prior art.

In one aspect, the invention includes a vector comprising a genetic element comprising (i) a sequence encoding a non-pathogenic exterior protein, (ii) an exterior protein binding sequence that binds the genetic element to the non-pathogenic exterior protein, and (iii) a sequence encoding a regulatory nucleic acid.

The genetic element or any of the sequences within the genetic element can be obtained using any suitable method. Various recombinant methods are known in the art, such as, for example screening libraries from cells harboring viral sequences, deriving the sequences from a vector known to include the same, or isolating directly from cells and tissues containing the same, using standard techniques. Alternatively or in combination, part or all of the genetic element can be produced synthetically, rather than cloned.

In some embodiments, the vector includes regulatory elements, nucleic acid sequences homologous to target genes, and various reporter constructs for causing the expression of reporter molecules within a viable cell and/or when an intracellular molecule is present within a target cell.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the vector is substantially non-pathogenic and/or substantially non-integrating in a host cell or is substantially non-immunogenic in a host.

In some embodiments, the vector is in an amount sufficient to modulate one or more of phenotype, virus levels, gene expression, compete with other viruses, disease state, etc. at least about 5%, 10%, 15%, 20%, 25%, 30%, 35%, 40%, 45%, 50%, or more.

Compositions

The anellosome or vector described herein may also be included in pharmaceutical compositions with a pharmaceutical excipient, e.g., as described herein. In some embodiments, the pharmaceutical composition comprises at least $10^5$, $10^6$, $10^7$, $10^8$, $10^9$, $10^{10}$, $10^{10}$, $10^{12}$, $10^{13}$, $10^{14}$, or $10^{15}$ anellosomes. In some embodiments, the pharmaceutical composition comprises about $10^5$-$10^{15}$, $10^5$-$10^{10}$, or $10^{10}$-$10^{15}$ anellosomes. In some embodiments, the pharmaceutical composition comprises about $10^8$ (e.g., about $10^5$, $10^6$, $10^7$, $10^8$, $10^9$, or $10^{10}$) genomic equivalents/mL of the anellosome. In some embodiments, the pharmaceutical composition comprises $10^5$-$10^{10}$, $10^6$-$10^{10}$, $10^7$-$10^{10}$, $10^8$-$10^{10}$, $10^9$-$10^{10}$, $10^5$-$10^6$, $10^5$-$10^7$, $10^5$-$10^8$, $10^5$-$10^9$, $10^5$-$10^{11}$, $10^5$-$10^{12}$, $10^5$-$10^{13}$, $10^5$-$10^{14}$, $10^5$-$10^{15}$, or $10^{10}$-$10^{15}$ genomic equivalents/mL of the anellosome, e.g., as determined according to the method of Example 18. In some embodiments, the pharmaceutical composition comprises sufficient anellosomes to deliver at least 1, 2, 5, or 10, 100, 500, 1000, 2000, 5000, 8,000, $1\times10^4$, $1\times10^5$, $1\times10^6$, $1\times10^7$ or greater copies of a genetic element comprised in the anellosomes per cell to a population of the eukaryotic cells. In some embodiments, the pharmaceutical composition comprises sufficient anellosomes to deliver at least about $1\times10^4$, $1\times10^5$, $1\times10^6$, 1× or $10^7$, or about $1\times10^4$-$1\times10^5$, $1\times10^4$-$1\times10^6$, $1\times10^4$-$1\times10^7$, $1\times10^5$-$1\times10^6$, $1\times10^5$-$1\times10^7$, or $1\times10^6$-$1\times10^7$ copies of a genetic element comprised in the anellosomes per cell to a population of the eukaryotic cells.

In some embodiments, the pharmaceutical composition has one or more of the following characteristics: the pharmaceutical composition meets a pharmaceutical or good manufacturing practices (GMP) standard; the pharmaceutical composition was made according to good manufacturing practices (GMP); the pharmaceutical composition has a pathogen level below a predetermined reference value, e.g., is substantially free of pathogens; the pharmaceutical composition has a contaminant level below a predetermined reference value, e.g., is substantially free of contaminants; or the pharmaceutical composition has low immunogenicity or is substantially non-immunogenic, e.g., as described herein.

In some embodiments, the pharmaceutical composition comprises below a threshold amount of one or more contaminants. Exemplary contaminants that are desirably excluded or minimized in the pharmaceutical composition include, without limitation, host cell nucleic acids (e.g., host cell DNA and/or host cell RNA), animal-derived components (e.g., serum albumin or trypsin), replication-competent viruses, non-infectious particles, free viral capsid protein, adventitious agents, and aggregates. In embodiments, the contaminant is host cell DNA. In embodiments, the composition comprises less than about 10 ng of host cell DNA per dose. In embodiments, the level of host cell DNA in the composition is reduced by filtration and/or enzymatic degradation of host cell DNA. In embodiments, the pharmaceutical composition consists of less than 10% (e.g., less than about 10%, 5%, 4%, 3%, 2%, 1%, 0.5%, or 0.1%) contaminant by weight.

In one aspect, the invention described herein includes a pharmaceutical composition comprising:

a) an anellosome comprising a genetic element comprising (i) a sequence encoding a non-pathogenic exterior protein, (ii) an exterior protein binding sequence that binds the genetic element to the non-pathogenic exterior protein, and (iii) a sequence encoding a regulatory nucleic acid; and a proteinaceous exterior that is associated with, e.g., envelops or encloses, the genetic element; and b) a pharmaceutical excipient.

Vesicles

In some embodiments, the composition further comprises a carrier component, e.g., a microparticle, liposome, vesicle, or exosome. In some embodiments, liposomes comprise spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are generally biocompatible, nontoxic, can deliver both hydrophilic and lipophilic drug molecules, protect their cargo from degradation by plasma enzymes, and transport their load across biological membranes (see, e.g., Spuch and Navarro, Journal of Drug Delivery, vol. 2011, Article ID 469679, 12 pages, 2011. doi:10.1155/2011/469679 for review).

Vesicles can be made from several different types of lipids; however, phospholipids are most commonly used to generate liposomes as drug carriers. Vesicles may comprise without limitation DOTMA, DOTAP, DOTIM, DDAB, alone or together with cholesterol to yield DOTMA and cholesterol, DOTAP and cholesterol, DOTIM and cholesterol, and DDAB and cholesterol. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

As described herein, additives may be added to vesicles to modify their structure and/or properties. For example, either cholesterol or sphingomyelin may be added to the mixture to help stabilize the structure and to prevent the leakage of the inner cargo. Further, vesicles can be prepared from hydrogenated egg phosphatidylcholine or egg phosphatidylcholine, cholesterol, and dicetyl phosphate. (see, e.g., Spuch and Navarro, Journal of Drug Delivery, vol. 2011, Article ID 469679, 12 pages, 2011. doi:10.1155/2011/469679 for review). Also, vesicles may be surface modified during or after synthesis to include reactive groups complementary to the reactive groups on the recipient cells. Such reactive groups include without limitation maleimide groups. As an example, vesicles may be synthesized to include maleimide conjugated phospholipids such as without limitation DSPE-MaL-PEG2000.

A vesicle formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Formulations made up of phospholipids only are less stable in plasma. However, manipulation of the lipid membrane with cholesterol reduces rapid release of the encapsulated cargo or 1,2-dioleoyl-sn-glycero-3-phosphoethanolamine (DOPE) increases stability (see, e.g., Spuch and Navarro, Journal of Drug Delivery, vol. 2011, Article ID 469679, 12 pages, 2011. doi:10.1155/2011/469679 for review).

In embodiments, lipids may be used to form lipid microparticles. Lipids include, but are not limited to, DLin-KC2-DMA4, C12-200 and colipids disteroylphosphatidyl choline, cholesterol, and PEG-DMG may be formulated (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). Tekmira has a portfolio of approximately 95 patent families, in the U.S. and abroad, that are directed to various aspects of lipid microparticles and lipid microparticles formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos. 1766035; 1519714; 1781593 and 1664316), all of which may be used and/or adapted to the present invention.

In some embodiments, microparticles comprise one or more solidified polymer(s) that is arranged in a random manner. The microparticles may be biodegradable. Biodegradable microparticles may be synthesized, e.g., using methods known in the art including without limitation solvent evaporation, hot melt microencapsulation, solvent removal, and spray drying. Exemplary methods for synthesizing microparticles are described by Bershteyn et al., Soft Matter 4:1787-1787, 2008 and in US 2008/0014144 A1, the specific teachings of which relating to microparticle synthesis are incorporated herein by reference.

Exemplary synthetic polymers which can be used to form biodegradable microparticles include without limitation aliphatic polyesters, poly (lactic acid) (PLA), poly (glycolic acid) (PGA), co-polymers of lactic acid and glycolic acid (PLGA), polycarprolactone (PCL), polyanhydrides, poly (ortho)esters, polyurethanes, poly(butyric acid), poly(valeric acid), and poly(lactide-co-caprolactone), and natural polymers such as albumin, alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water, by surface or bulk erosion.

The microparticles' diameter ranges from 0.1-1000 micrometers (μm). In some embodiments, their diameter ranges in size from 1-750 μm, or from 50-500 μm, or from 100-250 μm. In some embodiments, their diameter ranges in size from 50-1000 μm, from 50-750 μm, from 50-500 μm, or from 50-250 μm. In some embodiments, their diameter ranges in size from 0.05-1000 μm, from 10-1000 μm, from 100-1000 μm, or from 500-1000 μm. In some embodiments, their diameter is about 0.5 μm, about 10 μm, about 50 μm, about 100 μm, about 200 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, or about 1000 μm. As used in the context of microparticle diameters, the term "about" means+/−5% of the absolute value stated.

In some embodiments, a ligand is conjugated to the surface of the microparticle via a functional chemical group (carboxylic acids, aldehydes, amines, sulfhydryls and hydroxyls) present on the surface of the particle and present on the ligand to be attached. Functionality may be introduced into the microparticles by, for example, during the emulsion preparation of microparticles, incorporation of stabilizers with functional chemical groups.

Another example of introducing functional groups to the microparticle is during post-particle preparation, by direct crosslinking particles and ligands with homo- or heterobifunctional crosslinkers. This procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This also includes a process whereby amphiphilic molecules such as fatty acids, lipids or functional stabilizers may be passively adsorbed and adhered to the particle surface, thereby introducing functional end groups for tethering to ligands.

In some embodiments, the microparticles may be synthesized to comprise one or more targeting groups on their exterior surface to target a specific cell or tissue type (e.g., cardiomyocytes). These targeting groups include without limitation receptors, ligands, antibodies, and the like. These targeting groups bind their partner on the cells' surface. In some embodiments, the microparticles will integrate into a lipid bilayer that comprises the cell surface and the mitochondria are delivered to the cell.

The microparticles may also comprise a lipid bilayer on their outermost surface. This bilayer may be comprised of one or more lipids of the same or different type. Examples include without limitation phospholipids such as phosphocholines and phosphoinositols. Specific examples include without limitation DMPC, DOPC, DSPC, and various other lipids such as those described herein for liposomes.

In some embodiments, the carrier comprises nanoparticles, e.g., as described herein.

In some embodiments, the vesicles or microparticles described herein are functionalized with a diagnostic agent. Examples of diagnostic agents include, but are not limited to, commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium.

Carriers

A composition (e.g., pharmaceutical composition) described herein may comprise, be formulated with, and/or be delivered in, a carrier. In one aspect, the invention includes a composition, e.g., a pharmaceutical composition, comprising a carrier (e.g., a vesicle, a liposome, a lipid nanoparticle, an exosome, a red blood cell, a fusosome) comprising (e.g., encapsulating) a composition described herein (e.g., an anellosome, *Anellovirus*, anellovector, or genetic element described herein).

In some embodiments, the compositions and systems described herein can be formulated in liposomes or other similar vesicles. Generally, liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes generally have one or more (e.g., all) of the following characteristics: biocompatibility, nontoxicity, can deliver both hydrophilic and lipophilic drug molecules, can protect their cargo from degradation by plasma enzymes, and can transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679; and Zylberberg & Matosevic. 2016. Drug Delivery, 23:9, 3319-3329, doi: 10.1080/10717544.2016.1177136).

Vesicles can be made from several different types of lipids; however, phospholipids are most commonly used to generate liposomes as drug carriers. Methods for preparation of multilamellar vesicle lipids are known (see, for example, U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by, e.g., extruding through filters of decreasing size, as described in Templeton et al., Nature Biotech, 15:647-652, 1997.

Lipid nanoparticles (LNPs) are another example of a carrier that provides a biocompatible and biodegradable delivery system for the pharmaceutical compositions described herein. See, e.g., Gordillo-Galeano et al. European Journal of Pharmaceutics and Biopharmaceutics. Volume 133, December 2018, Pages 285-308. Nanostructured lipid carriers (NLCs) are modified solid lipid nanoparticles (SLNs) that retain the characteristics of the SLN, improve drug stability and loading capacity, and prevent drug leakage. Polymer nanoparticles (PNPs) are an important component of drug delivery. These nanoparticles can effectively direct drug delivery to specific targets and improve drug stability and controlled drug release. Lipid-polymer nanoparticles (PLNs), a new type of carrier that combines liposomes and polymers, may also be employed. These nanoparticles possess the complementary advantages of PNPs and liposomes. A PLN is composed of a core-shell structure; the polymer core provides a stable structure, and the phospholipid shell offers good biocompatibility. As such, the two components increase the drug encapsulation efficiency rate, facilitate surface modification, and prevent leakage of water-soluble drugs. For a review, see, e.g., Li et al. 2017, Nanomaterials 7, 122; doi:10.3390/nano7060122.

Exosomes can also be used as drug delivery vehicles for the compositions and systems described herein. For a review, see Ha et al. July 2016. Acta Pharmaceutica *Sinica* B. Volume 6, Issue 4, Pages 287-296; doi.org/10.1016/j.apsb.2016.02.001.

Ex vivo differentiated red blood cells can also be used as a carrier for a composition described herein. See, e.g., WO2015073587; WO2017123646; WO2017123644; WO2018102740; WO2016183482; WO2015153102; WO2018151829; WO2018009838; Shi et al. 2014. Proc Natl Acad Sci USA. 111(28): 10131-10136; U.S. Pat. No. 9,644,180; Huang et al. 2017. Nature Communications 8: 423; Shi et al. 2014. Proc Natl Acad Sci USA. 111(28): 10131-10136.

Fusosome compositions, e.g., as described in WO2018208728, can also be used as carriers to deliver a composition described herein.

Membrane Penetrating Polypeptides

In some embodiments, the composition further comprises a membrane penetrating polypeptide (MPP) to carry the components into cells or across a membrane, e.g., cell or nuclear membrane. Membrane penetrating polypeptides that are capable of facilitating transport of substances across a membrane include, but are not limited to, cell-penetrating peptides (CPPs)(see, e.g., U.S. Pat. No. 8,603,966), fusion peptides for plant intracellular delivery (see, e.g., Ng et al., PLoS One, 2016, 11:e0154081), protein transduction domains, Trojan peptides, and membrane translocation signals (MTS) (see, e.g., Tung et al., Advanced Drug Delivery Reviews 55:281-294 (2003)). Some MPP are rich in amino acids, such as arginine, with positively charged side chains.

Membrane penetrating polypeptides have the ability of inducing membrane penetration of a component and allow macromolecular translocation within cells of multiple tissues in vivo upon systemic administration. A membrane penetrating polypeptide may also refer to a peptide which, when brought into contact with a cell under appropriate conditions, passes from the external environment in the intracellular environment, including the cytoplasm, organelles such as mitochondria, or the nucleus of the cell, in amounts significantly greater than would be reached with passive diffusion.

Components transported across a membrane may be reversibly or irreversibly linked to the membrane penetrating polypeptide. A linker may be a chemical bond, e.g., one or more covalent bonds or non-covalent bonds. In some embodiments, the linker is a peptide linker. Such a linker may be between 2-30 amino acids, or longer. The linker includes flexible, rigid or cleavable linkers.

Combinations

In one aspect, the anellosome or composition comprising a anellosome described herein may also include one or more heterologous moiety. In one aspect, the anellosome or composition comprising a anellosome described herein may also include one or more heterologous moiety in a fusion. In some embodiments, a heterologous moiety may be linked with the genetic element. In some embodiments, a heterologous moiety may be enclosed in the proteinaceous exterior as part of the anellosome. In some embodiments, a heterologous moiety may be administered with the anellosome.

In one aspect, the invention includes a cell or tissue comprising any one of the anellosomes and heterologous moieties described herein.

In another aspect, the invention includes a pharmaceutical composition comprising a anellosome and the heterologous moiety described herein.

In some embodiments, the heterologous moiety may be a virus (e.g., an effector (e.g., a drug, small molecule), a targeting agent (e.g., a DNA targeting agent, antibody, receptor ligand), a tag (e.g., fluorophore, light sensitive agent such as KillerRed), or an editing or targeting moiety described herein. In some embodiments, a membrane translocating polypeptide described herein is linked to one or more heterologous moieties. In one embodiment, the heterologous moiety is a small molecule (e.g., a peptidomimetic or a small organic molecule with a molecular weight of less than 2000 daltons), a peptide or polypeptide (e.g., an antibody or antigen-binding fragment thereof), a nanoparticle, an aptamer, or pharmacoagent.

Viruses

In some embodiments, the composition may further comprise a virus as a heterologous moiety, e.g., a single stranded DNA virus, e.g., *Anellovirus*, Bidnavirus, Circovirus, Geminivirus, Genomovirus, Inovirus, Microvirus, Nanovirus, Parvovirus, and Spiravirus. In some embodiments, the composition may further comprise a double stranded DNA virus, e.g., Adenovirus, Ampullavirus, Ascovirus, Asfarvirus, Baculovirus, Fusellovirus, Globulovirus, Guttavirus, Hytrosavirus, Herpesvirus, Iridovirus, Lipothrixvirus, Nimavirus, and Poxvirus. In some embodiments, the composition may further comprise an RNA virus, e.g., Alphavirus, Furovirus, Hepatitis virus, Hordeivirus, Tobamovirus, Tobravirus, Tricornavirus, Rubivirus, Birnavirus, Cystovirus, Partitivirus, and Reovirus. In some embodiments, the anellosome is administered with a virus as a heterologous moiety.

In some embodiments, the heterologous moiety may comprise a non-pathogenic, e.g., symbiotic, commensal, native, virus. In some embodiments, the non-pathogenic virus is one or more *anelloviruses*, e.g., *Alphatorquevirus* (TT), *Betatorquevirus* (TTM), and *Gammatorquevirus* (TTMD). In some embodiments, the *anellovirus* may include a Torque Teno Virus (TT), a SEN virus, a Sentinel virus, a TTV-like mini virus, a TT virus, a TT virus genotype 6, a TT virus group, a TTV-like virus DXL1, a TTV-like virus DXL2, a Torque Teno-like Mini Virus (TTM), or a Torque Teno-like Midi Virus (TTMD). In some embodiments, the non-pathogenic virus comprises one or more sequences having at least at least about 60%, 70% 80%, 85%, 90% 95%, 96%, 97%, 98% and 99% nucleotide sequence identity to any one of the nucleotide sequences described herein, e.g., as listed in any of Tables 1, 3, 5, 7, 9, 11, 13, 15, 17, or 41.

In some embodiments, the heterologous moiety may comprise one or more viruses that are identified as lacking in the subject. For example, a subject identified as having dyvirosis may be administered a composition comprising an anellosome and one or more viral components or viruses that are imbalanced in the subject or having a ratio that differs from a reference value, e.g., a healthy subject.

In some embodiments, the heterologous moiety may comprise one or more non-*anelloviruses*, e.g., adenovirus, herpes virus, pox virus, vaccinia virus, SV40, papilloma virus, an RNA virus such as a retrovirus, e.g., *lenti* virus, a single-stranded RNA virus, e.g., hepatitis virus, or a double-stranded RNA virus e.g., rotavirus. In some embodiments, the anellosome or the virus is defective, or requires assistance in order to produce infectious particles. Such assistance can be provided, e.g., by using helper cell lines that contain a nucleic acid, e.g., plasmids or DNA integrated into the genome, encoding one or more of (e.g., all of) the structural genes of the replication defective anellosome or virus under the control of regulatory sequences within the LTR. Suitable cell lines for replicating the anellosomes described herein include cell lines known in the art, e.g., A549 cells, which can be modified as described herein.

Effector

In some embodiments, the composition or anellosome described herein may further comprise an effector that possesses effector activity. The effector may modulate a biological activity, for example increasing or decreasing enzymatic activity, gene expression, cell signaling, and cellular or organ function. Effector activities may also include binding regulatory proteins to modulate activity of the regulator, such as transcription or translation. Effector activities also may include activator or inhibitor functions. For example, the effector may induce enzymatic activity by triggering increased substrate affinity in an enzyme, e.g., fructose 2,6-bisphosphate activates phosphofructokinase 1 and increases the rate of glycolysis in response to the insulin. In another example, the effector may inhibit substrate binding to a receptor and inhibit its activation, e.g., naltrexone and naloxone bind opioid receptors without activating them and block the receptors' ability to bind opioids. Effector activities may also include modulating protein stability/degradation and/or transcript stability/degradation. For example, proteins may be targeted for degradation by the polypeptide co-factor, ubiquitin, onto proteins to mark them for degradation. In another example, the effector inhibits enzymatic activity by blocking the enzyme's active site, e.g., methotrexate is a structural analog of tetrahydrofolate, a coenzyme for the enzyme dihydrofolate reductase that binds to dihydrofolate reductase 1000-fold more tightly than the natural substrate and inhibits nucleotide base synthesis.

Targeting Moiety

In some embodiments, the composition or anellosome described herein may further comprise a targeting moiety, e.g., a targeting moiety that specifically binds to a molecule of interest present on a target cell. The targeting moiety may modulate a specific function of the molecule of interest or cell, modulate a specific molecule (e.g., enzyme, protein or nucleic acid), e.g., a specific molecule downstream of the molecule of interest in a pathway, or specifically bind to a target to localize the anellosome or genetic element. For example, a targeting moiety may include a therapeutic that interacts with a specific molecule of interest to increase, decrease or otherwise modulate its function.

Tagging or Monitoring Moiety

In some embodiments, the composition or anellosome described herein may further comprise a tag to label or monitor the anellosome or genetic element described herein. The tagging or monitoring moiety may be removable by chemical agents or enzymatic cleavage, such as proteolysis or intein splicing. An affinity tag may be useful to purify the tagged polypeptide using an affinity technique. Some examples include, chitin binding protein (CBP), maltose binding protein (MBP), glutathione-S-transferase (GST), and poly(His) tag. A solubilization tag may be useful to aid recombinant proteins expressed in chaperone-deficient species such as *E. coli* to assist in the proper folding in proteins and keep them from precipitating. Some examples include thioredoxin (TRX) and poly(NANP). The tagging or monitoring moiety may include a light sensitive tag, e.g., fluorescence. Fluorescent tags are useful for visualization. GFP and its variants are some examples commonly used as fluorescent tags. Protein tags may allow specific enzymatic modifications (such as biotinylation by biotin ligase) or chemical modifications (such as reaction with FlAsH-EDT2 for fluorescence imaging) to occur. Often tagging or monitoring moiety are combined, in order to connect proteins to multiple other components. The tagging or monitoring moiety may also be removed by specific proteolysis or enzymatic cleavage (e.g. by TEV protease, Thrombin, Factor Xa or Enteropeptidase).

Nanoparticles

In some embodiments, the composition or anellosome described herein may further comprise a nanoparticle. Nanoparticles include inorganic materials with a size between about 1 and about 1000 nanometers, between about 1 and about 500 nanometers in size, between about 1 and about 100 nm, between about 50 nm and about 300 nm, between about 75 nm and about 200 nm, between about 100 nm and about 200 nm, and any range therebetween. Nanoparticles generally have a composite structure of nanoscale dimensions. In some embodiments, nanoparticles are typically spherical although different morphologies are possible depending on the nanoparticle composition. The portion of the nanoparticle contacting an environment external to the nanoparticle is generally identified as the surface of the nanoparticle. In nanoparticles described herein, the size limitation can be restricted to two dimensions and so that nanoparticles include composite structure having a diameter from about 1 to about 1000 nm, where the specific diameter depends on the nanoparticle composition and on the intended use of the nanoparticle according to the experimental design. For example, nanoparticles used in therapeutic applications typically have a size of about 200 nm or below.

Additional desirable properties of the nanoparticle, such as surface charges and steric stabilization, can also vary in view of the specific application of interest. Exemplary properties that can be desirable in clinical applications such as cancer treatment are described in Davis et al, Nature 2008 vol. 7, pages 771-782; Duncan, Nature 2006 vol. 6, pages 688-701; and Allen, Nature 2002 vol. 2 pages 750-763, each incorporated herein by reference in its entirety. Additional properties are identifiable by a skilled person upon reading of the present disclosure. Nanoparticle dimensions and properties can be detected by techniques known in the art. Exemplary techniques to detect particles dimensions include but are not limited to dynamic light scattering (DLS) and a variety of microscopies such at transmission electron microscopy (TEM) and atomic force microscopy (AFM). Exemplary techniques to detect particle morphology include but are not limited to TEM and AFM. Exemplary techniques to detect surface charges of the nanoparticle include but are not limited to zeta potential method. Additional techniques suitable to detect other chemical properties comprise by $^{1}H$, $^{11}B$, and $^{13}C$ and $^{19}F$ NMR, UV/Vis and infrared/Raman spectroscopies and fluorescence spectroscopy (when nanoparticle is used in combination with fluorescent labels) and additional techniques identifiable by a skilled person.

Small Molecules

In some embodiments, the composition or anellosome described herein may further comprise a small molecule. Small molecule moieties include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organomettallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds. Small molecules may include, but are not limited to, a neurotransmitter, a hormone, a drug, a toxin, a viral or microbial particle, a synthetic molecule, and agonists or antagonists.

Examples of suitable small molecules include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Some examples of small molecules include, but are not limited to, prion drugs such as tacrolimus, ubiquitin ligase or HECT ligase inhibitors such as heclin, histone modifying drugs such as sodium butyrate, enzymatic inhibitors such as 5-azacytidine, anthracyclines such as doxorubicin, beta-lactams such as penicillin, anti-bacterials, chemotherapy agents, anti-virals, modulators from other organisms such as VP64, and drugs with insufficient bioavailability such as chemotherapeutics with deficient pharmacokinetics.

In some embodiments, the small molecule is an epigenetic modifying agent, for example such as those described in de Groote et al. Nuc. Acids Res. (2012):1-18. Exemplary small molecule epigenetic modifying agents are described, e.g., in Lu et al. J. Biomolecular Screening 17.5(2012):555-71, e.g., at Table 1 or 2, incorporated herein by reference. In some embodiments, an epigenetic modifying agent comprises vorinostat or romidepsin. In some embodiments, an epigenetic modifying agent comprises an inhibitor of class I, II, III, and/or IV histone deacetylase (HDAC). In some embodiments, an epigenetic modifying agent comprises an activator of SirTI. In some embodiments, an epigenetic modifying agent comprises Garcinol, Lys-CoA, C646, (+)-JQI, I-BET, BILI, MS120, DZNep, UNC0321, EPZ004777, AZ505, AMI-I, pyrazole amide 7b, benzo[d]imidazole 17b, acylated dapsone derivative (e.e.g, PRMTI), methylstat, 4,4'-dicarboxy-2,2'-bipyridine, SID 85736331, hydroxamate analog 8, tanylcypromie, bisguanidine and biguanide polyamine analogs, UNC669, Vidaza, decitabine, sodium phenyl butyrate (SDB), lipoic acid (LA), quercetin, valproic acid, hydralazine, bactrim, green tea extract (e.g., epigallocatechin gallate (EGCG)), curcumin, sulforphane and/or allicin/diallyl disulfide. In some embodiments, an epigenetic modifying agent inhibits DNA methylation, e.g., is an inhibitor of DNA methyltransferase (e.g., is 5-azacitidine and/or decitabine). In some embodiments, an epigenetic modifying agent modifies histone modification, e.g., histone acetylation, histone methylation, histone sumoylation, and/or histone phosphorylation. In some embodiments, the epigenetic modifying agent is an inhibitor of a histone deacetylase (e.g., is vorinostat and/or trichostatin A).

In some embodiments, the small molecule is a pharmaceutically active agent. In one embodiment, the small molecule is an inhibitor of a metabolic activity or component. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumour suppressers). One or a combination of molecules from the categories and examples described herein or from (Orme-Johnson 2007, Methods Cell Biol. 2007; 80:813-26) can be used. In one embodiment, the invention includes a composition comprising an antibiotic, anti-inflammatory drug, angiogenic or vasoactive agent, growth factor or chemotherapeutic agent.

Peptides or Proteins

In some embodiments, the composition or anellosome described herein may further comprise a peptide or protein. The peptide moieties may include, but are not limited to, a peptide ligand or antibody fragment (e.g., antibody fragment that binds a receptor such as an extracellular receptor), neuropeptide, hormone peptide, peptide drug, toxic peptide, viral or microbial peptide, synthetic peptide, and agonist or antagonist peptide.

Peptides moieties may be linear or branched. The peptide has a length from about 5 to about 200 amino acids, about 15 to about 150 amino acids, about 20 to about 125 amino acids, about 25 to about 100 amino acids, or any range therebetween.

Some examples of peptides include, but are not limited to, fluorescent tags or markers, antigens, antibodies, antibody fragments such as single domain antibodies, ligands and receptors such as glucagon-like peptide-1 (GLP-1), GLP-2 receptor 2, cholecystokinin B (CCKB) and somatostatin receptor, peptide therapeutics such as those that bind to specific cell surface receptors such as G protein-coupled receptors (GPCRs) or ion channels, synthetic or analog peptides from naturally-bioactive peptides, anti-microbial peptides, pore-forming peptides, tumor targeting or cytotoxic peptides, and degradation or self-destruction peptides such as an apoptosis-inducing peptide signal or photosensitizer peptide.

Peptides useful in the invention described herein also include small antigen-binding peptides, e.g., antigen binding antibody or antibody-like fragments, such as single chain antibodies, nanobodies (see, e.g., Steeland et al. 2016.

Nanobodies as therapeutics: big opportunities for small antibodies. Drug Discov Today: 21(7):1076-113). Such small antigen binding peptides may bind a cytosolic antigen, a nuclear antigen, an intra-organellar antigen.

In some embodiments, the composition or anellosome described herein includes a polypeptide linked to a ligand that is capable of targeting a specific location, tissue, or cell.

Oligonucleotide Aptamers

In some embodiments, the composition or anellosome described herein may further comprise an oligonucleotide aptamer. Aptamer moieties are oligonucleotide or peptide aptamers. Oligonucleotide aptamers are single-stranded DNA or RNA (ssDNA or ssRNA) molecules that can bind to pre-selected targets including proteins and peptides with high affinity and specificity.

Oligonucleotide aptamers are nucleic acid species that may be engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers provide discriminate molecular recognition, and can be produced by chemical synthesis. In addition, aptamers may possess desirable storage properties, and elicit little or no immunogenicity in therapeutic applications.

Both DNA and RNA aptamers can show robust binding affinities for various targets. For example, DNA and RNA aptamers have been selected for t lysozyme, thrombin, human immunodeficiency virus trans-acting responsive element (HIV TAR), (see en.wikipedia.org/wiki/Aptamer-cite_note-10), hemin, interferon γ, vascular endothelial growth factor (VEGF), prostate specific antigen (PSA), dopamine, and the non-classical oncogene, heat shock factor 1 (HSF1).

Peptide Aptamers

In some embodiments, the composition or anellosome described herein may further comprise a peptide aptamer. Peptide aptamers have one (or more) short variable peptide domains, including peptides having low molecular weight, 12-14 kDa. Peptide aptamers may be designed to specifically bind to and interfere with protein-protein interactions inside cells.

Peptide aptamers are artificial proteins selected or engineered to bind specific target molecules. These proteins include of one or more peptide loops of variable sequence. They are typically isolated from combinatorial libraries and often subsequently improved by directed mutation or rounds of variable region mutagenesis and selection. In vivo, peptide aptamers can bind cellular protein targets and exert biological effects, including interference with the normal protein interactions of their targeted molecules with other proteins. In particular, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene. Such experiments identify particular proteins bound by the aptamers, and protein interactions that the aptamers disrupt, to cause the phenotype. In addition, peptide aptamers derivatized with appropriate functional moieties can cause specific post-translational modification of their target proteins, or change the subcellular localization of the targets Peptide aptamers can also recognize targets in vitro. They have found use in lieu of antibodies in biosensors and used to detect active isoforms of proteins from populations containing both inactive and active protein forms. Derivatives known as tadpoles, in which peptide aptamer "heads" are covalently linked to unique sequence double-stranded DNA "tails", allow quantification of scarce target molecules in mixtures by PCR (using, for example, the quantitative real-time polymerase chain reaction) of their DNA tails.

Peptide aptamer selection can be made using different systems, but the most used is currently the yeast two-hybrid system. Peptide aptamers can also be selected from combinatorial peptide libraries constructed by phage display and other surface display technologies such as mRNA display, ribosome display, bacterial display and yeast display. These experimental procedures are also known as biopannings Among peptides obtained from biopannings, mimotopes can be considered as a kind of peptide aptamers. All the peptides panned from combinatorial peptide libraries have been stored in a special database with the name MimoDB.

Hosts

The invention is further directed to a host or host cell comprising a anellosome described herein. In some embodiments, the host or host cell is a plant, insect, bacteria, fungus, vertebrate, mammal (e.g., human), or other organism or cell. In certain embodiments, as confirmed herein, provided anellosomes infect a range of different host cells. Target host cells include cells of mesodermal, endodermal, or ectodermal origin. Target host cells include, e.g., epithelial cells, muscle cells, white blood cells (e.g., lymphocytes), kidney tissue cells, lung tissue cells.

In some embodiments, the anellosome is substantially non-immunogenic in the host. The anellosome or genetic element fails to produce an undesired substantial response by the host's immune system. Some immune responses include, but are not limited to, humoral immune responses (e.g., production of antigen-specific antibodies) and cell-mediated immune responses (e.g., lymphocyte proliferation).

In some embodiments, a host or a host cell is contacted with (e.g., infected with) a anellosome. In some embodiments, the host is a mammal, such as a human. The amount of the anellosome in the host can be measured at any time after administration. In certain embodiments, a time course of anellosome growth in a culture is determined.

In some embodiments, the anellosome, e.g., an anellosome as described herein, is heritable. In some embodiments, the anellosome is transmitted linearly in fluids and/or cells from mother to child. In some embodiments, daughter cells from an original host cell comprise the anellosome. In some embodiments, a mother transmits the anellosome to child with an efficiency of at least 25%, 50%, 60%, 70%, 80%, 85%, 90%, 95%, or 99%, or a transmission efficiency from host cell to daughter cell at least 25%, 50%, 60%, 70%, 80%, 85%, 90%, 95%, or 99%. In some embodiments, the anellosome in a host cell has a transmission efficiency during meiosis of at 25%, 50%, 60%, 70%, 80%, 85%, 90%, 95%, or 99%. In some embodiments, the anellosome in a host cell has a transmission efficiency during mitosis of at least 25%, 50%, 60%, 70%, 80%, 85%, 90%, 95%, or 99%. In some embodiments, the anellosome in a cell has a transmission efficiency between about 10%-20%, 20%-30%, 30%-40%, 40%-50%, 50%-60%, 60%-70%, 70%-75%, 75%-80%, 80%-85%, 85%-90%, 90%-95%, 95%-99%, or any percentage therebetween.

In some embodiments, the anellosome, e.g., anellosome replicates within the host cell. In one embodiment, the anellosome is capable of replicating in a mammalian cell, e.g., human cell.

While in some embodiments the anellosome replicates in the host cell, the anellosome does not integrate into the genome of the host, e.g., with the host's chromosomes. In some embodiments, the anellosome has a negligible recombination frequency, e.g., with the host's chromosomes. In some embodiments, the anellosome has a recombination frequency, e.g., less than about 1.0 cM/Mb, 0.9 cM/Mb, 0.8 cM/Mb, 0.7 cM/Mb, 0.6 cM/Mb, 0.5 cM/Mb, 0.4 cM/Mb, 0.3 cM/Mb, 0.2 cM/Mb, 0.1 cM/Mb, or less, e.g., with the host's chromosomes.

Methods of Use

The anellosomes and compositions comprising anellosomes described herein may be used in methods of treating a disease, disorder, or condition, e.g., in a subject (e.g., a mammalian subject, e.g., a human subject) in need thereof. Administration of a pharmaceutical composition described herein may be, for example, by way of parenteral (including intravenous, intratumoral, intraperitoneal, intramuscular, intracavity, and subcutaneous) administration. The anellosomes may be administered alone or formulated as a pharmaceutical composition.

The anellosomes may be administered in the form of a unit-dose composition, such as a unit dose parenteral composition. Such compositions are generally prepared by admixture and can be suitably adapted for parenteral administration. Such compositions may be, for example, in the form of injectable and infusable solutions or suspensions or suppositories or aerosols.

In some embodiments, administration of a anellosome or composition comprising same, e.g., as described herein, may result in delivery of a genetic element comprised by the anellosome to a target cell, e.g., in a subject.

An anellosome or composition thereof described herein, e.g., comprising an effector (e.g., an endogenous or exogenous effector), may be used to deliver the effector to a cell, tissue, or subject. In some embodiments, the anellosome or composition thereof is used to deliver the effector to bone marrow, blood, heart, GI or skin. Delivery of an effector by administration of a anellosome composition described herein may modulate (e.g., increase or decrease) expression levels of a noncoding RNA or polypeptide in the cell, tissue, or subject. Modulation of expression level in this fashion may result in alteration of a functional activity in the cell to which the effector is delivered. In some embodiments, the modulated functional activity may be enzymatic, structural, or regulatory in nature.

In some embodiments, the anellosome, or copies thereof, are detectable in a cell 24 hours (e.g., 1 day, 2 days, 3 days, 4 days, 5 days, 6 days, 1 week, 2 weeks, 3 weeks, 4 weeks, 30 days, or 1 month) after delivery into a cell. In embodiments, a anellosome or composition thereof mediates an effect on a target cell, and the effect lasts for at least 1, 2, 3, 4, 5, 6, or 7 days, 2, 3, or 4 weeks, or 1, 2, 3, 6, or 12 months. In some embodiments (e.g., wherein the anellosome or composition thereof comprises a genetic element encoding an exogenous protein), the effect lasts for less than 1, 2, 3, 4, 5, 6, or 7 days, 2, 3, or 4 weeks, or 1, 2, 3, 6, or 12 months.

Examples of diseases, disorders, and conditions that can be treated with the anellosome described herein, or a composition comprising the anellosome, include, without limitation-immune disorders, interferonopathies (e.g., Type I interferonopathies), infectious diseases, inflammatory disorders, autoimmune conditions, cancer (e.g., a solid tumor, e.g., lung cancer, non-small cell lung cancer, e.g., a tumor that expresses a gene responsive to mIR-625, e.g., caspase-3), and gastrointestinal disorders. In some embodiments, the anellosome modulates (e.g., increases or decreases) an activity or function in a cell with which the anellosome is contacted. In some embodiments, the anellosome modulates (e.g., increases or decreases) the level or activity of a molecule (e.g., a nucleic acid or a protein) in a cell with which the anellosome is contacted. In some embodiments, the anellosome decreases viability of a cell, e.g., a cancer cell, with which the anellosome is contacted, e.g., by at least about 10%, 20%, 30%, 40%, 50%, 60%, 70%, 80%, 90%, 95%, 99%, or more. In some embodiments, the anellosome comprises an effector, e.g., an miRNA, e.g., miR-625, that decreases viability of a cell, e.g., a cancer cell, with which the anellosome is contacted, e.g., by at least about 10%, 20%, 30%, 40%, 50%, 60%, 70%, 80%, 90%, 95%, 99%, or more. In some embodiments, the anellosome increases apoptosis of a cell, e.g., a cancer cell, e.g., by increasing caspase-3 activity, with which the anellosome is contacted, e.g., by at least about 10%, 20%, 30%, 40%, 50%, 60%, 70%, 80%, 90%, 95%, 99%, or more. In some embodiments, the anellosome comprises an effector, e.g., an miRNA, e.g., miR-625, that increases apoptosis of a cell, e.g., a cancer cell, e.g., by increasing caspase-3 activity, with which the anellosome is contacted, e.g., by at least about 10%, 20%, 30%, 40%, 50%, 60%, 70%, 80%, 90%, 95%, 99%, or more.

Methods of Production

Producing the Genetic Element

Methods of making the genetic element of the anellosome are described in, for example, Khudyakov & Fields, *Artificial DNA: Methods and Applications*, CRC Press (2002); in Zhao, *Synthetic Biology: Tools and Applications*, (First Edition), Academic Press (2013); and Egli & Herdewijn, *Chemistry and Biology of Artificial Nucleic Acids*, (First Edition), Wiley-VCH (2012).

In some embodiments, the genetic element may be designed using computer-aided design tools. The anellosome may be divided into smaller overlapping pieces (e.g., in the range of about 100 bp to about 10 kb segments or individual ORFs) that are easier to synthesize. These DNA segments are synthesized from a set of overlapping single-stranded oligonucleotides. The resulting overlapping synthons are then assembled into larger pieces of DNA, e.g., the anellosome. The segments or ORFs may be assembled into the anellosome, e.g., in vitro recombination or unique restriction sites at 5' and 3' ends to enable ligation.

The genetic element can alternatively be synthesized with a design algorithm that parses the anellosome into oligo-length fragments, creating optimal design conditions for synthesis that take into account the complexity of the sequence space. Oligos are then chemically synthesized on semiconductor-based, high-density chips, where over 200,000 individual oligos are synthesized per chip. The oligos are assembled with an assembly techniques, such as BioFab®, to build longer DNA segments from the smaller oligos. This is done in a parallel fashion, so hundreds to thousands of synthetic DNA segments are built at one time.

Each genetic element or segment of the genetic element may be sequence verified. In some embodiments, high-throughput sequencing of RNA or DNA can take place using AnyDot.chips (Genovoxx, Germany), which allows for the monitoring of biological processes (e.g., miRNA expression or allele variability (SNP detection). In particular, the AnyDot-chips allow for 10×-50× enhancement of nucleotide fluorescence signal detection. AnyDot.chips and methods for using them are described in part in International Publication Application Nos. WO 02088382, WO 03020968, WO 0303 1947, WO 2005044836, PCTEP 05105657, PCMEP 05105655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such systems involve sequencing a target nucleic acid molecule having a plurality of bases by the temporal addition of bases via a polymerization reaction that is measured on a molecule of nucleic acid, i.e., the activity of a nucleic acid polymerizing enzyme on the template nucleic acid molecule to be sequenced is followed in real time. The sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishably type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In some embodiments, shotgun sequencing is performed. In shotgun sequencing, DNA is broken up randomly into numerous small segments, which are sequenced using the chain termination method to obtain reads. Multiple overlapping reads for the target DNA are obtained by performing several rounds of this fragmentation and sequencing. Computer programs then use the overlapping ends of different reads to assemble them into a continuous sequence.

Producing the Anellosome

The genetic elements and vectors comprising the genetic elements prepared as described herein can be used in a variety of ways to express the anellosome in appropriate host cells. In some embodiments, the genetic element and vectors comprising the genetic element are transfected in appropriate host cells and the resulting RNA may direct the expression of the anellosome gene products, e.g., non-pathogenic protein and protein binding sequence, at high levels. Host cell systems which provide for high levels of expression include continuous cell lines that supply viral functions, such as cell lines superinfected with APV or MPV, respectively, cell lines engineered to complement APV or MPV functions, etc.

In some embodiments, the anellosome is produced as described in any of Examples 1, 2, 5, 6, or 15-17.

In some embodiments, the anellosome is cultivated in continuous animal cell lines in vitro. According to one embodiment of the invention, the cell lines may include porcine cell lines. The cell lines envisaged in the context of the present invention include immortalised porcine cell lines such as, but not limited to the porcine kidney epithelial cell lines PK-15 and SK, the monomyeloid cell line 3D4/31 and the testicular cell line ST. Also, other mammalian cells lines are included, such as CHO cells (Chinese hamster ovaries), MARC-145, MDBK, RK-13, EEL. Additionally or alternatively, particular embodiments of the methods of the invention make use of an animal cell line which is an epithelial cell line, i.e. a cell line of cells of epithelial lineage. Cell lines susceptible to infection with anellosomes include, but are not limited to cell lines of human or primate origin, such as human or primate kidney carcinoma cell lines.

In some embodiments, the genetic elements and vectors comprising the genetic elements are transfected into cell lines that express a viral polymerase protein in order to achieve expression of the anellosome. To this end, transformed cell lines that express an anellosome polymerase protein may be utilized as appropriate host cells. Host cells may be similarly engineered to provide other viral functions or additional functions.

To prepare the anellosome disclosed herein, a genetic element or vector comprising the genetic element disclosed herein may be used to transfect cells which provide anellosome proteins and functions required for replication and production. Alternatively, cells may be transfected with helper virus before, during, or after transfection by the genetic element or vector comprising the genetic element disclosed herein. In some embodiments, a helper virus may be useful to complement production of an incomplete viral particle. The helper virus may have a conditional growth defect, such as host range restriction or temperature sensitivity, which allows the subsequent selection of transfectant viruses. In some embodiments, a helper virus may provide one or more replication proteins utilized by the host cells to achieve expression of the anellosome. In some embodiments, the host cells may be transfected with vectors encoding viral proteins such as the one or more replication proteins. In some embodiments, a helper virus comprises an antiviral sensitivity.

The genetic element or vector comprising the genetic element disclosed herein can be replicated and produced into anellosome particles by any number of techniques known in the art, as described, e.g., in U.S. Pat. Nos. 4,650,764; 5,166,057; 5,854,037; European Patent Publication EP 0702085A1; U.S. patent application Ser. No. 09/152,845; International Patent Publications PCT WO97/12032; WO96/34625; European Patent Publication EP-A780475; WO 99/02657; WO 98/53078; WO 98/02530; WO 99/15672; WO 98/13501; WO 97/06270; and EPO 780 47SA1, each of which is incorporated by reference herein in its entirety.

The production of anellosome-containing cell cultures according to the present invention can be carried out in different scales, such as in flasks, roller bottles or bioreactors. The media used for the cultivation of the cells to be infected are known to the skilled person and can generally comprise the standard nutrients required for cell viability, but may also comprise additional nutrients dependent on the cell type. Optionally, the medium can be protein-free and/or serum-free. Depending on the cell type the cells can be cultured in suspension or on a substrate. In some embodiments, different media is used for growth of the host cells and for production of anellosomes.

The purification and isolation of anellosomes can be performed according to methods known by the skilled person in virus production and is described for example by Rinaldi, et al., DNA Vaccines: Methods and Protocols (Methods in Molecular Biology), 3rd ed. 2014, Humana Press.

In one aspect, the present invention includes a method for the in vitro replication and propagation of the anellosome as described herein, which may comprise the following steps: (a) transfecting a linearized genetic element into a cell line sensitive to anellosome infection; (b) harvesting the cells and isolating cells showing the presence of the genetic element; (c) culturing the cells obtained in step (b) for at least three days, such as at least one week or longer, depending on experimental conditions and gene expression; and (d) harvesting the cells of step (c).

In some embodiments, an anellosome may be introduced to a host cell line grown to a high cell density. In some embodiments, the anellosome may be harvested and/or purified by separation of solutes based on biophysical properties, e.g., ion exchange chromatography or tangential flow filtration, prior to formulation with a pharmaceutical excipient.

Administration/Delivery

The composition (e.g., a pharmaceutical composition comprising an anellosome as described herein) may be formulated to include a pharmaceutically acceptable excipient. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference).

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product.

In one aspect, the invention features a method of delivering an anellosome to a subject. The method includes administering a pharmaceutical composition comprising an anellosome as described herein to the subject. In some embodiments, the administered anellosome replicates in the subject (e.g., becomes a part of the virome of the subject).

The pharmaceutical composition may include wild-type or native viral elements and/or modified viral elements. The anellosome may include one or more of the sequences (e.g., nucleic acid sequences or nucleic acid sequences encoding amino acid sequences thereof) in any of Tables 1-18 or a sequence with at least about 60%, 65%, 70%, 75%, 80%, 85%, 90% 95%, 96%, 97%, 98% and 99% nucleotide sequence identity to any one of the nucleotide sequences or a sequence that is complementary to the sequence in any of Tables 1-18. The anellosome may comprise a nucleic acid molecule comprising a nucleic acid sequence with at least about 60%, 65%, 70%, 75%, 80%, 85%, 90% 95%, 96%, 97%, 98% and 99% sequence identity to one or more of the sequences in any of Tables 1, 3, 5, 7, 9, 11, 13, 15, 17, or 41. The anellosome may comprise a nucleic acid molecule encoding an amino acid sequence with at least about 60%, 65%, 70%, 75%, 80%, 85%, 90% 95%, 96%, 97%, 98% and 99% sequence identity to any one of the amino acid sequences in any of Tables 2, 4, 6, 8, 10, 12, 14, 16, or 18. The anellosome may comprise a polypeptide comprising an amino acid sequence with at least about 60%, 65%, 70%, 75%, 80%, 85%, 90% 95%, 96%, 97%, 98% and 99% sequence identity to any one of the amino acid sequences in any of Tables 2, 4, 6, 8, 10, 12, 14, 16, or 18. The anellosome may include one or more of the sequences in any of Tables 1, 3, 5, 7, 9, 11, 13, 15, 17, or 41, or a sequence with at least about 60%, 65%, 70%, 75%, 80%, 85%, 90% 95%, 96%, 97%, 98% and 99% nucleotide sequence identity to any one of the nucleotide sequences or a sequence that is complementary to the sequence in any of Tables 1, 3, 5, 7, 9, 11, 13, 15, 17, or 41.

In some embodiments, the anellosome is sufficient to increase (stimulate) endogenous gene and protein expression, e.g., at least about 5%, 10%, 15%, 20%, 25%, 30%, 35%, 40%, 45%, 50%, or more as compared to a reference, e.g., a healthy control. In certain embodiments, the anellosome is sufficient to decrease (inhibit) endogenous gene and protein expression, e.g., at least about 5%, 10%, 15%, 20%, 25%, 30%, 35%, 40%, 45%, 50%, or more as compared to a reference, e.g., a healthy control.

In some embodiments, the anellosome inhibits/enhances one or more viral properties, e.g., tropism, infectivity, immunosuppression/activation, in a host or host cell, e.g., at least about 5%, 10%, 15%, 20%, 25%, 30%, 35%, 40%, 45%, 50%, or more as compared to a reference, e.g., a healthy control.

In some embodiments, the subject is administered the pharmaceutical composition further comprising one or more viral strains that are not represented in the viral genetic information.

In some embodiments, the pharmaceutical composition comprising an anellosome described herein is administered in a dose and time sufficient to modulate a viral infection. Some non-limiting examples of viral infections include adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, Human enterovirus 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, Human papillomavirus 18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, and Zika Virus. In certain embodiments, the anellosome is sufficient to outcompete and/or displace a virus already present in the subject, e.g., at least about 5%, 10%, 15%, 20%, 25%, 30%, 35%, 40%, 45%, 50%, or more as compared to a reference. In certain embodiments, the anellosome is sufficient to compete with chronic or acute viral infection. In certain embodiments, the anellosome may be administered prophylactically to protect from viral infections (e.g. a provirotic). In some embodiments, the anellosome is in an amount sufficient to modulate (e.g., phenotype, virus levels, gene expression, compete with other viruses, disease state, etc. at least about 5%, 10%, 15%, 20%, 25%, 30%, 35%, 40%, 45%, 50%, or more).

All references and publications cited herein are hereby incorporated by reference.

The following examples are provided to further illustrate some embodiments of the present invention, but are not intended to limit the scope of the invention; it will be understood by their exemplary nature that other procedures, methodologies, or techniques known to those skilled in the art may alternatively be used.

EXAMPLES

Table of Contents

Example 1: Preparation of Anellosomes: Design and synthesis of a synthetic anellosome that inhibits interferon (IFN) expression
Example 2: Large-Scale Production of Anellosomes (Anellosome A and/or B): Production and propagation of anellosomes
Example 3: Effects of Anellosomes in vitro (Anellosome A): In vitro assessment of expression and effector function, e.g., expression of the miRNA, of the anellosome after cell infection
Example 4: Immunologic effects of Anellosomes (Anellosome A): in vivo effector function, e.g., expression of the miRNA, of the anellosome after administration
Example 5: Preparation of synthetic anellosomes: In vitro production of a synthetic anellosome
Example 6: Assembly and infection of anellosomes: In vitro production of infectious anellosomes using synthetic DNA sequences as described in Example 5
Example 7: Selectivity of anellosomes: Synthetic anellosomes produced in vitro infect cell lines of a variety of tissue origins
Example 8: Identification and use of protein binding sequences: putative protein-binding sites in the *Anellovirus* genome
Example 9: A minimal *Anellovirus* genome: characterization of the *Anellovirus* genome through deletions analysis
Example 10: Nucleotide insertions of various lengths into an *Anellovirus* genome: addition of DNA sequences of various lengths into an *Anellovirus* genome
Example 11: Exemplary cargo to be delivered: exemplary classes of nucleic acid and protein payloads in an anellosome
Example 12: Exemplary payload integration loci
Example 13: Defined categories of *Anellovirus* and conserved regions thereof
Example 14: Replication-deficient anellosomes and helper viruses
Example 15: Manufacturing process for replication-competent anellosomes
Example 16: Manufacturing process of replication-deficient anellosomes: recovery and scaling up of production of replication-deficient anellosomes
Example 17: Production of anellosomes using suspension cells: production of anellosomes in cells in suspension.
Example 18: Quantification of anellosome genome equivalents by qPCR: development of a hydrolysis probe-based quantitative PCR assay to quantify anellosomes
Example 19: Utilizing anellosomes to express an exogenous protein in mice: use of an anellosome to express a functional model protein in vivo
Example 20: Genome alignments to determine whether anellosome DNA integrated into host genomes
Example 21: Assessment of anellosome integration into a host genome
Example 22: Functional effects of an anellosome expressing an exogenous microRNA sequence: use of an anellosome to express a functional nucleic acid effector
Example 23: Preparation and production of anellosomes to express exogenous non-coding RNAs: use of anellosomes to express exogenous small non-coding RNAs
Example 24: Conservation in *Anellovirus* clades: identification of seven clades within the *Alphatorquevirus* genus
Example 25: Expression of an endogenous miRNA from an anellosome and deletion of the endogenous miRNA
Example 26: Localization of *Anellovirus* ORFs
Example 27: Characterization of regions required for anellosome development
Example 28: Anellosome delivery of exogenous proteins in vivo: This example demonstrates in vivo effector function (e.g. expression of proteins) of anellosomes after administration
Example 29: Identification of precursor miRNAs (pre-mIRs) in *Anelloviruses*: computational and experimental approaches to identify novel precursor miRNAs encoded by various *Anelloviruses*
Example 30: Determination of the endogenous target of *Anellovirus* pre-miRs: analysis to determine endogenous targets and potentially therapeutically relevant target pathways of pre-miRs encoded by various strains of *Anelloviruses*
Example 31: Making an anellosome encoding a native *Anellovirus* pre-miR: a process to package either the replicating or non-replicating form of anellosomes expressing native *Anellovirus* pre-miRs Example 32: Utilizing *Anellovirus* pre-miRs a tumor suppressor in an in vitro cell culture model: phenotypic effect of candidate pre-miRs identified as tumor suppressive from analysis, e.g., as described in Example 29

Example 33: Utilizing *Anellovirus* pre-miRs as tumor suppresors in vivo: in vivo experiments to confirm the tumor suppressive effect of a tumor suppressive *Anellovirus* pre-miRs and cancer cell lines from in vitro analysis, as described in Example 32

Example 34: Tandem copies of the *Anellovirus* genome

Example 35: In vitro circularized *Anellovirus* genomes: constructs comprising circular, double stranded Anelloviral genome DNA with minimal non-viral DNA Example 36: Modelling ORF1 and identification of conserved residues and domains: modelling of ORF1 proteins of Betatorqueviruses and defining putative domains Example 37: Production of anellosomes containing chimeric ORF1 with hypervariable domains from different Torque Teno Virus strains Example 38: Production of chimeric ORF1 containing non-TTV protein/peptides in place of hypervariable domains

Example 1: Preparation of Anellosomes

This example describes the design and synthesis of a synthetic anellosome that inhibits interferon (IFN) expression.

An anellosome (Anellosome A) is designed starting with 1) a DNA sequence for a capsid gene encoding a non-pathogenic packaging enclosure (Arch Virol (2007) 152: 1961-1975), Accession Number: A7XCE8.1 (ORF11_TTW3); 2) a DNA sequence coding for a microRNA that targets a host gene (e.g. IFN) (PLOS Pathogen (2013), 9(12), e1003818), Accession number: AJ620231.1; and 3) a DNA sequence (Journal of Virology (2003), 77(24), 13036-13041) that binds to a specific region in the capsid protein, (e.g., specific region of capsid having an Accession Number: Q99153.1).

Figure 2:
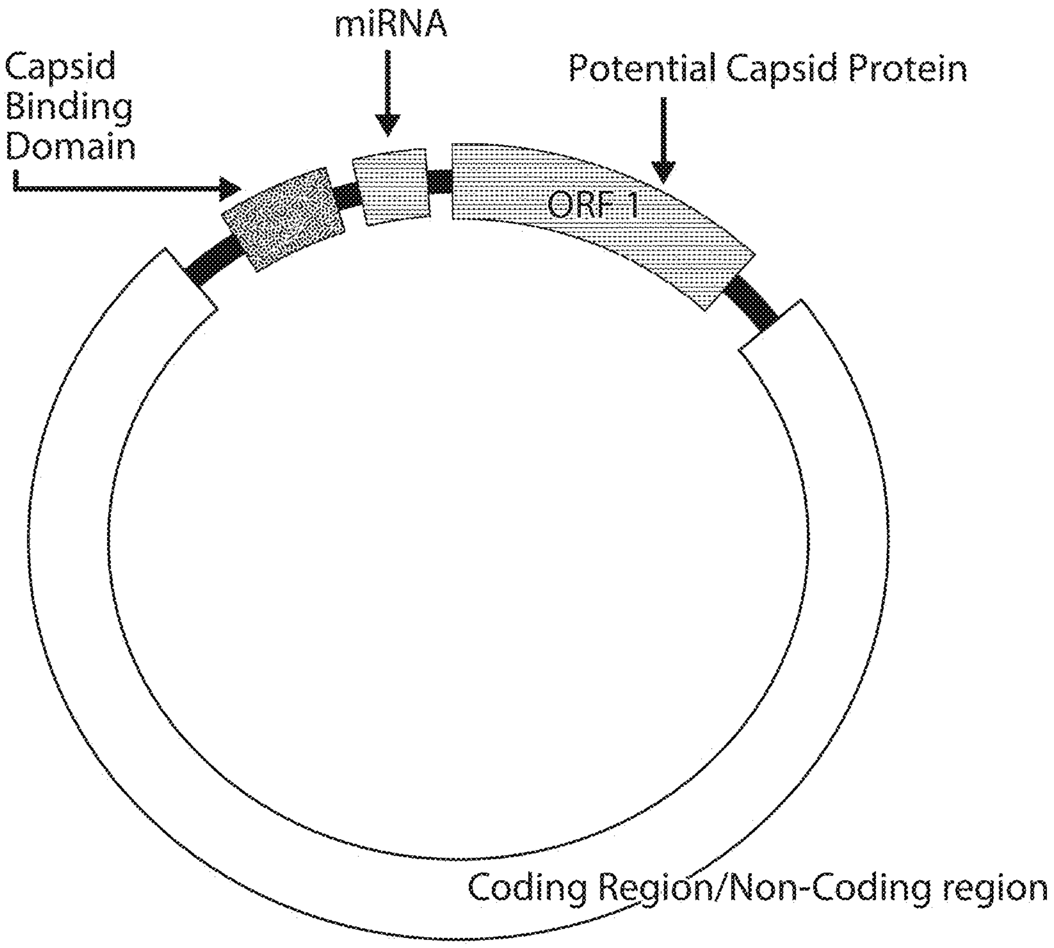
FIG. 2 is an illustration showing one embodiment of an anellosome.

To this sequence is added 1 kb non-coding DNA sequences (Anellosome B). The designed anellosome (FIG. 2) is chemically synthesized into 3 kb (total size), which is sequence verified.

The anellosome sequence is transfected into human embryonic kidney 293T cells (1 mg per $10^5$ cells on 12-well plates) with JetPEI reagent (PolyPlus-transfection, Illkirch, France) as recommended by the manufacturer. Controls transfections are included with vector alone or cells transfected with JetPEI alone and transfection efficiencies are optimized with a reporter plasmid encoding GFP. Fluorescence of control transfections is measured to ensure properly transfected cells. Transfected cultures are incubated overnight at 37° C. and 5% carbon dioxide.

After 18 hrs, the cells are washed three times with PBS before adding fresh medium. The supernatant is collected for ultracentrifugation and harvest of anellosomes as follows. The medium is cleared by centrifugation at 4,000×g for 30 min and then at 8,000×g for 15 min to remove cells and cell debris. The supernatant is then filtered through 0.45-μm-pore-size filters. Anellosomes are pelleted at 27,000 rpm for 1 hr through a 5% sucrose cushion (5 ml) and resuspended in 1× phosphate-buffered saline (PBS) plus 0.1% bacitracin in 1/100 of the original volume. The concentrated anellosomes are centrifuged through a 20 to 35% sucrose step gradient at 24,000 rpm for 2 hr. The anellosome band at the gradient junction is collected. The anellosomes are then diluted with 1×PBS and pelleted at 27,000 rpm for 1 hr. The anellosome pellets are resuspended in 1×PBS and further purified through a 20 to 35% continuous sucrose gradient.

Example 2: Large-Scale Production of Anellosomes (Anellosome A and/or B)

This example describes production and propagation of anellosomes.

Purified anellosomes as described in Example 1 are prepared for large-scale amplification in spinner flasks with producer A549 cells grown in suspension. A549 cells are maintained in F12K medium, 10% fetal bovine serum, 2 mM glutamine and antibiotics. A549 cells are infected with anellosomes at an anellosome load of $10^6$ anellosomes to produce ~$1\times10^7$ anellosome particles after an incubation at 37° C. and 5% carbon dioxide for 24 hrs. Cells are then washed three times with PBS and incubated with fresh medium for 6 hrs.

For anellosome purification, two ultracentrifugation steps based on cesium chloride gradients are performed followed by dialysis as follows (Bio-Protocol (2012) Bio101: e201). Cells are removed by centrifugation (6000×g for 10 min) and the supernatant is filtered through 0.8 and then 0.2 μm filters. The filtrate is concentrated by passage through filter membranes (100,000 mw) to a volume of 8 ml. The retentate is loaded into a cesium sulfate solution and centrifuged at 247,000×g for 20 h. Anellosome bands are removed, placed into 14,000 mw cutoff dialysis tubing, and dialyzed. A further concentration may be performed, if desired.

Example 3: Effects of Anellosomes In Vitro (Anellosome A)

This example describes in vitro assessment of expression and effector function, e.g., expression of the miRNA, of the anellosome after cell infection.

The effect of purified anellosomes as described in Example 1 is assessed in vitro through endogenous gene regulation (e.g. IFN signaling). HEK293T cells are co-transfected with dual luciferase plasmids (firefly luciferase with an interferon-stimulated response element (ISRE) based promoter and transfection control *Renilla* luciferase with constitutive promoter): Luciferase reporter mix (pcDNA3.1dsRluc to pISRE-Luc at 1:4 ratio (Clonetech)) (J Virol (2008), 82: 9823-9828).

Anellosomes are administered at multiplicity of infection of $10^7$ to HEK293T cells seeded in a 6-well plate (2 sets of triplicates-3 control wells and 3 experimental wells with Anellosome A).

After 48 hours, the media is replaced with new media with or without 100 u/ml of universal type I interferon (PBL, Piscataway, N.J.). Sixteen hours after IFN treatment, a dual-luciferase assay (J Virol (2008), 82: 9823-9828) is performed to determine IFN signaling. Firefly luciferase is normalized to *Renilla* luciferase expression to control for transfection differences. The fold induction of the ISRE ffLuc reporter is calculated by dividing the comparable experimental wells by the control wells and induction of each condition is compared relative to the negative control.

In an embodiment, a decreased luciferase signal in the anellosome treatment group compared to a control will indicate that the anellosomes decrease IFN production in the cells.

Example 4: Immunologic Effects of Anellosomes (Anellosome A)

This example describes in vivo effector function, e.g., expression of the miRNA, of the anellosome after administration.

Purified anellosomes prepared as described in Examples 1 and 2 are intravenously administered to healthy pigs at various doses using hundred-fold dilutions starting from $10^{14}$ genome equivalents per kilogram down to 0 genome equivalents per kilogram. In order to evaluate the effects on immune tolerance, pigs are injected daily for 3 days with the dosages of anellosomes specified above or vehicle control PBS and sacrificed after 3 days.

Spleen, bone marrow and lymph nodes are harvested. Single cell suspensions are prepared from each of the tissues and stained with extracellular markers for MHC-II, CD11c, and intracellular IFN. MHC+, CD11c+, IFN+ antigen presenting cells are analyzed via flow cytometry from each tissue, e.g., wherein a cell that is positive for a given one of the above-mentioned markers is a cell that exhibits higher fluorescence than 99% of cells in a negative control population that lack expression of the marker but is otherwise similar to the assay population of cells, under the same conditions.

In an embodiment, a decreased number of IFN+ cells in the anellosome treatment group compared to the control will indicate that the anellosomes decrease IFN production in cells after administration.

Example 5: Preparation of Synthetic Anellosomes

This example demonstrates in vitro production of a synthetic anellosome.

DNA sequences from LY1 and LY2 strains of TTMiniV (Eur Respir J. 2013 August; 42(2):470-9), between the EcoRV restriction enzyme sites, were cloned into a kanamycin vector (Integrated DNA Technologies). Anellosomes including DNA sequences from the LY1 and LY2 strains of TTMiniV are referred to as Anellosome 1 (Anello 1) and Anellosome 2 (Anello 2) respectively, in Examples 6 and 7 and in FIGS. 6A-10B. Cloned constructs were transformed into 10-Beta competent *E. coli.* (New England Biolabs Inc.), followed by plasmid purification (Qiagen) according to the manufacturer's protocol.

Figure 3:
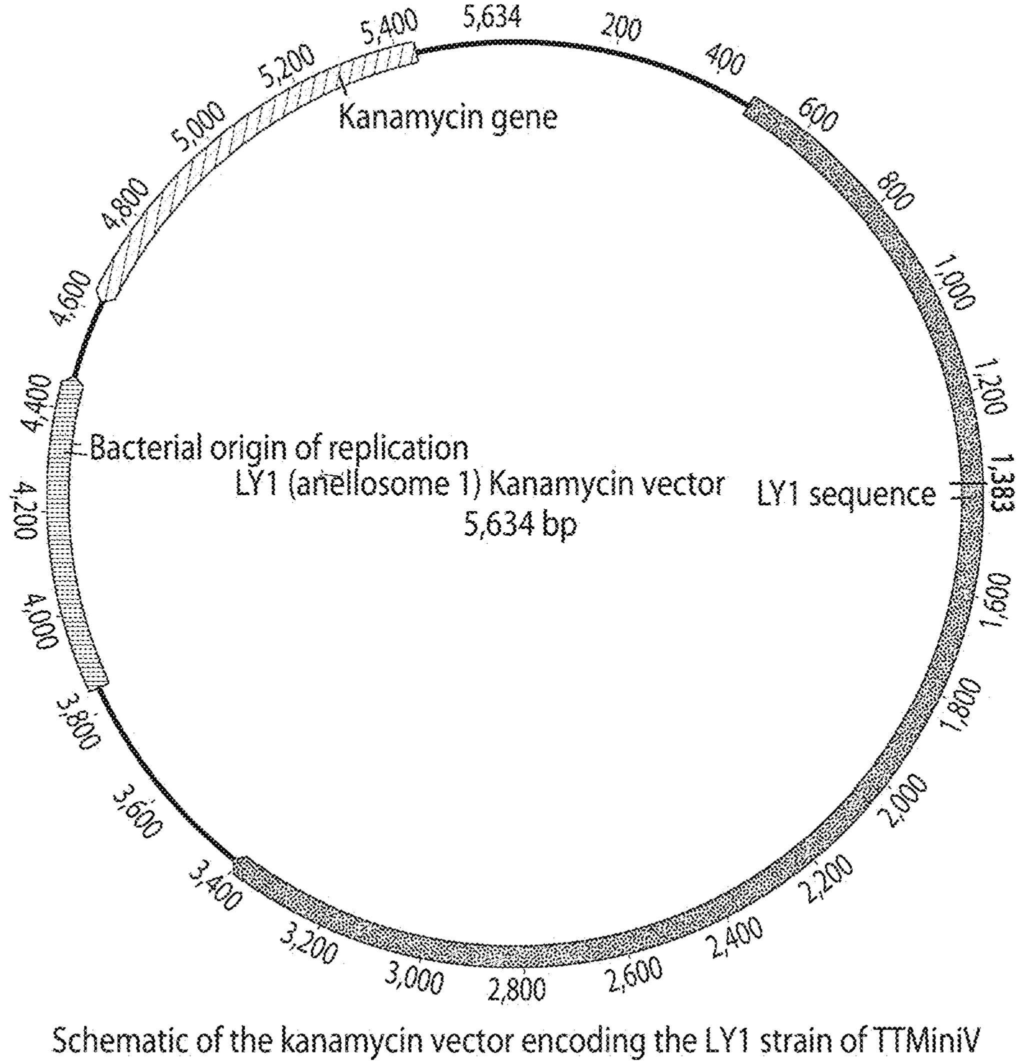
FIG. 3 depicts a schematic of a kanamycin vector encoding the LY1 strain of TTMiniV ("Anellosome 1").
Figure 4:
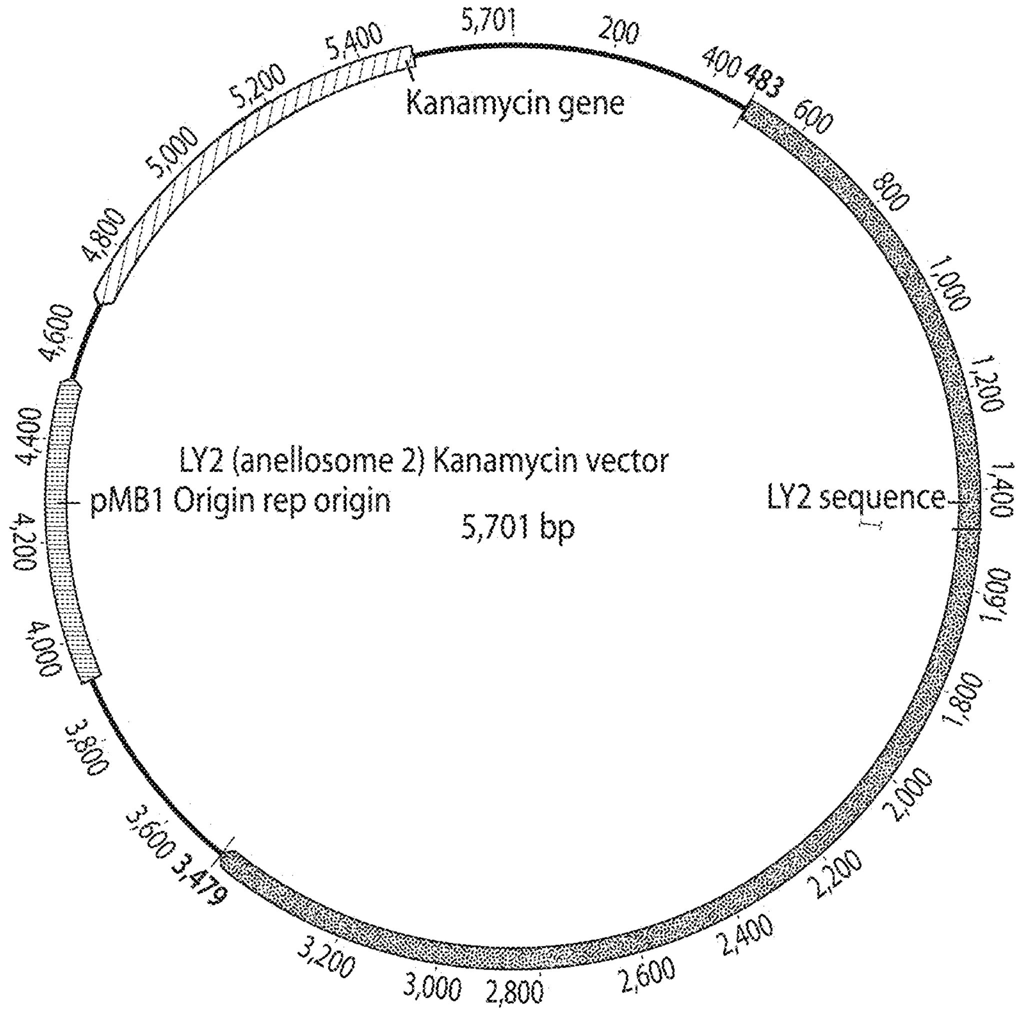
FIG. 4 depicts a schematic of a kanamycin vector encoding the LY2 strain of TTMiniV ("Anellosome 2").

DNA constructs (FIG. 3 and FIG. 4) were linearized with EcoRV restriction digest (New England Biolabs, Inc.) at 37 degree Celsius for 6 hours, followed by agarose gel electrophoresis, excision of a correctly size DNA band (2.9 kilobase pairs), and gel purification of DNA from excised agarose bands using a gel extraction kit (Qiagen) according to the manufacturer's protocol.

Example 6: Assembly and Infection of Anellosomes

This example demonstrates successful in vitro production of infectious anellosomes using synthetic DNA sequences as described in Example 5.

Figure 5:
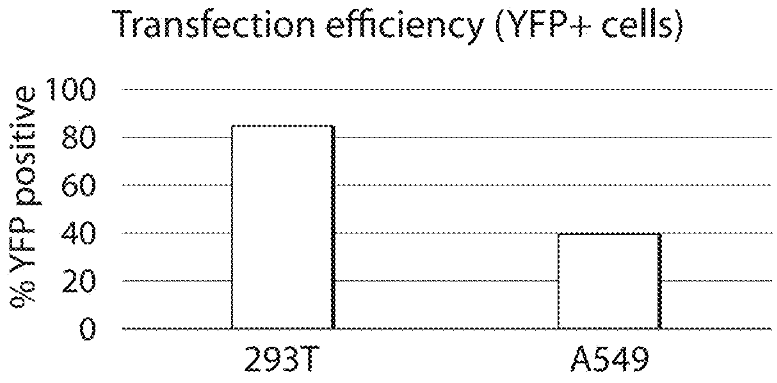
FIG. 5 depicts transfection efficiency of synthetic anellosomes in 293T and A549 cells.
Figure 6A:
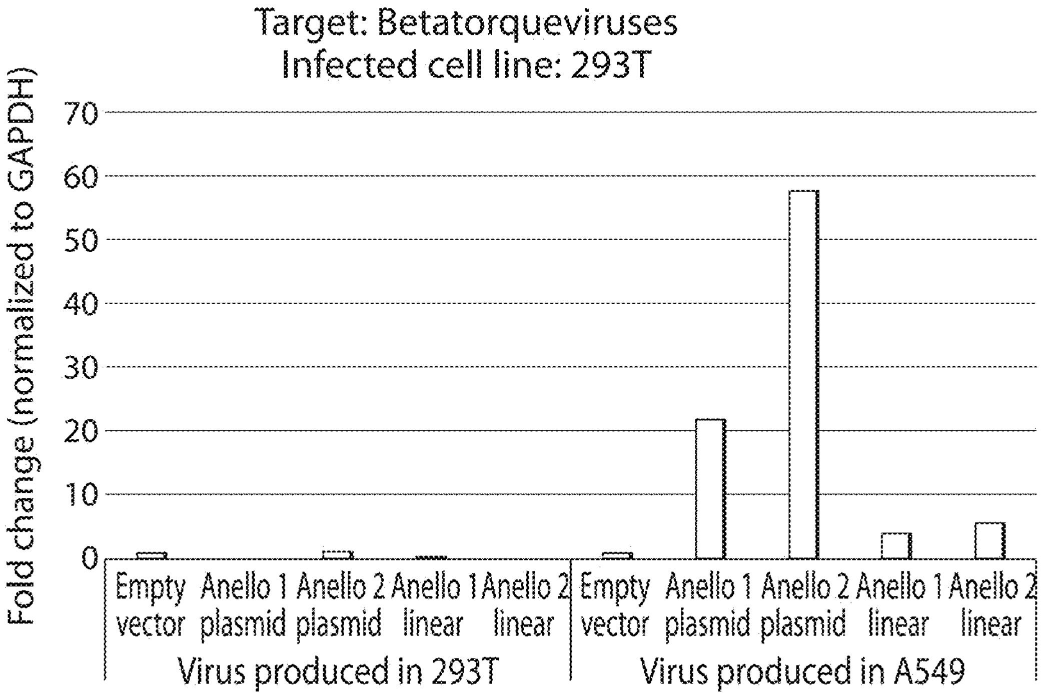
FIGS. 6A and 6B depict quantitative PCR results that illustrate successful infection of 293T cells by synthetic anellosomes.
Figure 6B:
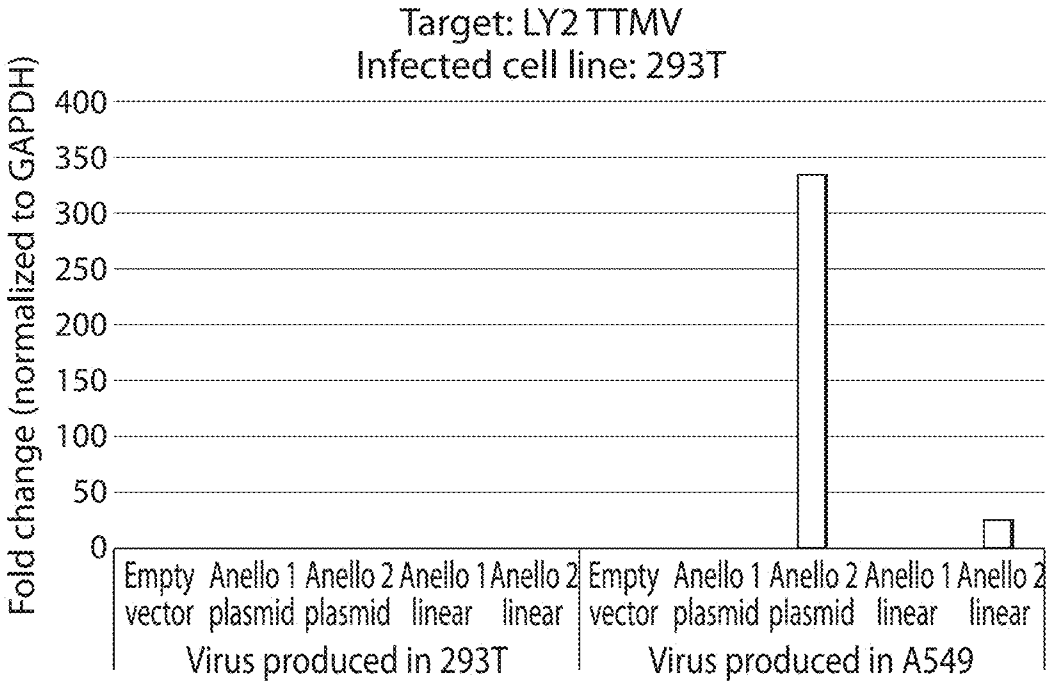
Figure 7A:
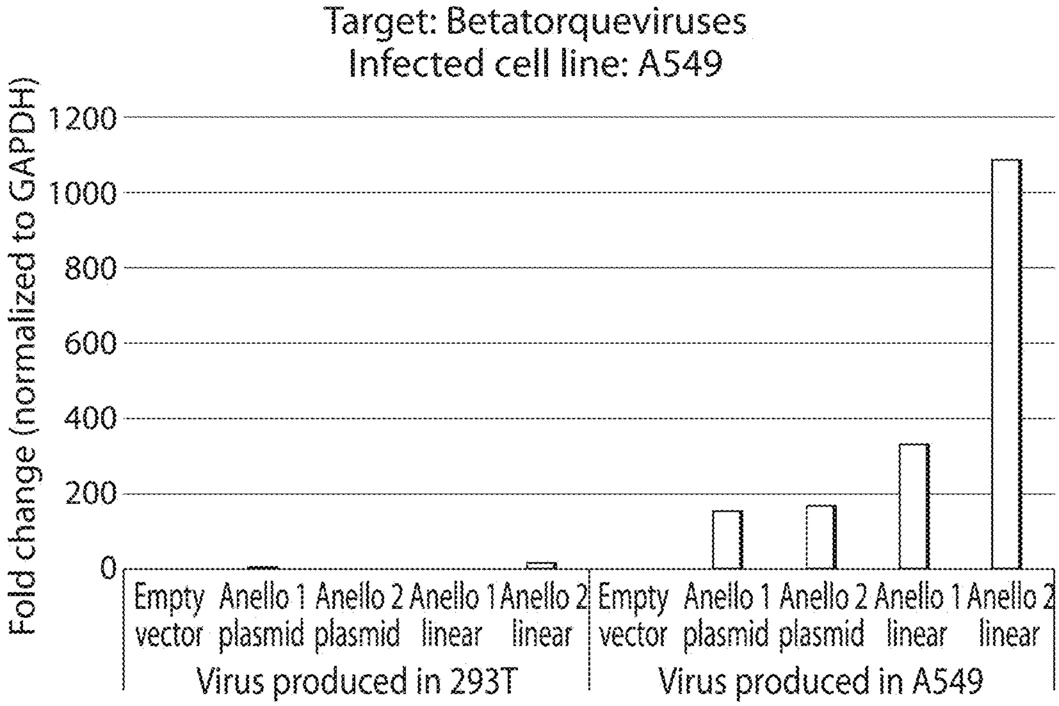
FIGS. 7A and 7B depict quantitative PCR results that illustrate successful infection of A549 cells by synthetic anellosomes.
Figure 7B:
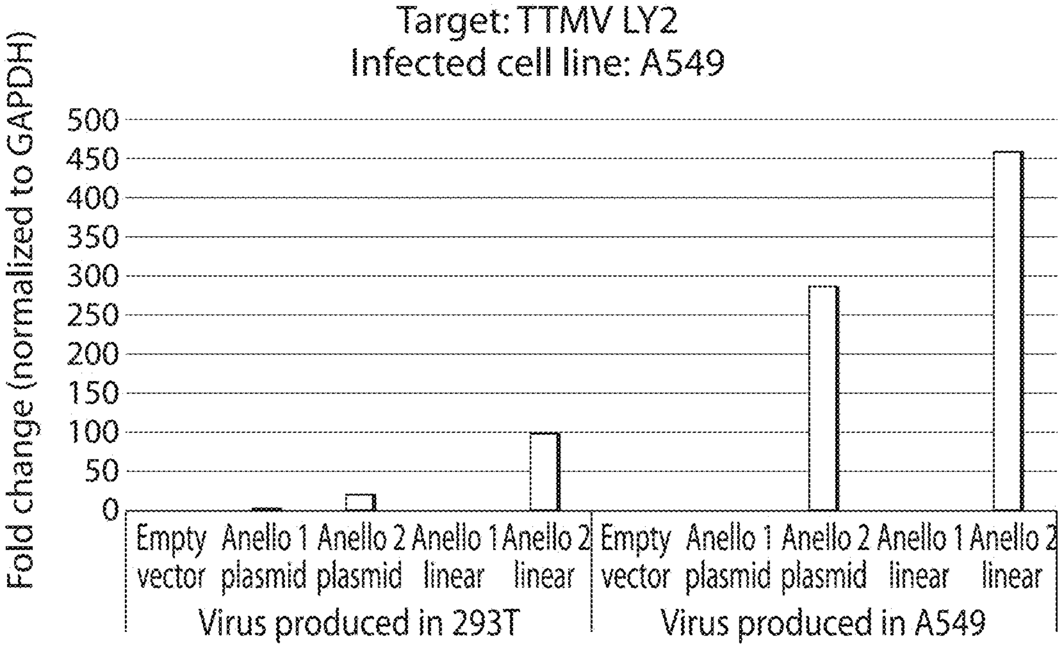
Figure 8A:
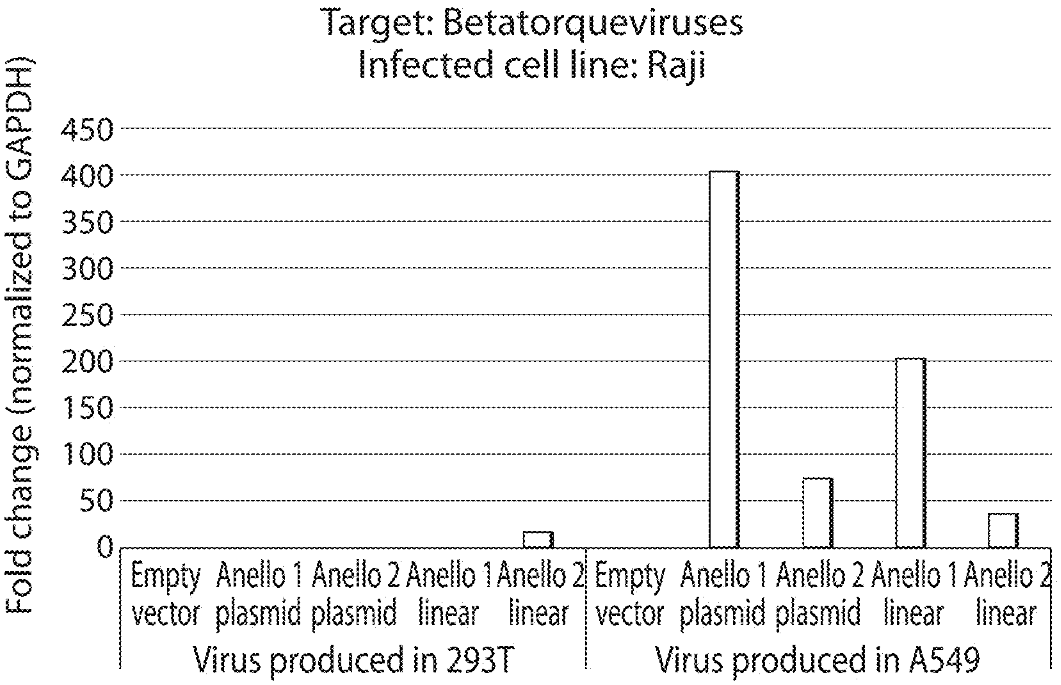
FIGS. 8A and 8B depict quantitative PCR results that illustrate successful infection of Raji cells by synthetic anellosomes.
Figure 8B:
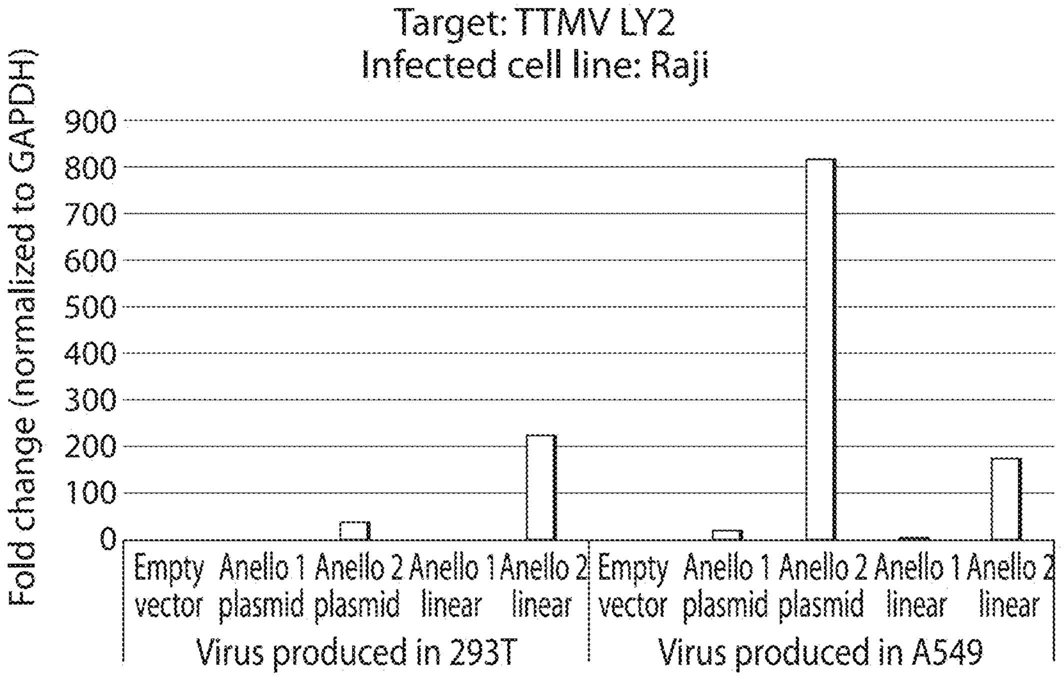
Figure 9A:
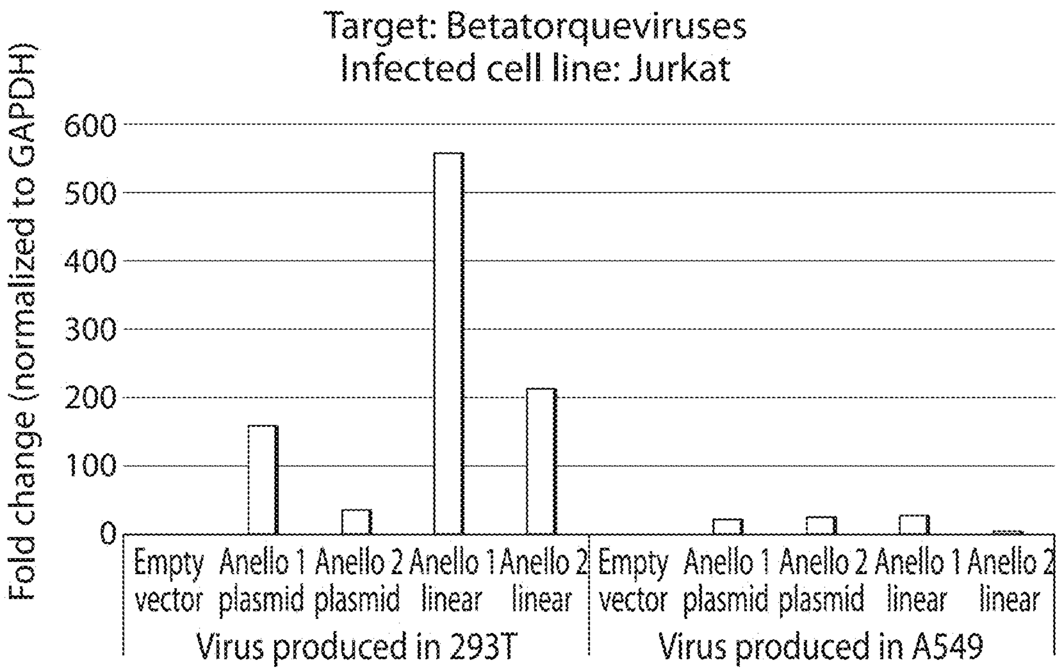
FIGS. 9A and 9B depict quantitative PCR results that illustrate successful infection of Jurkat cells by synthetic anellosomes.
Figure 9B:
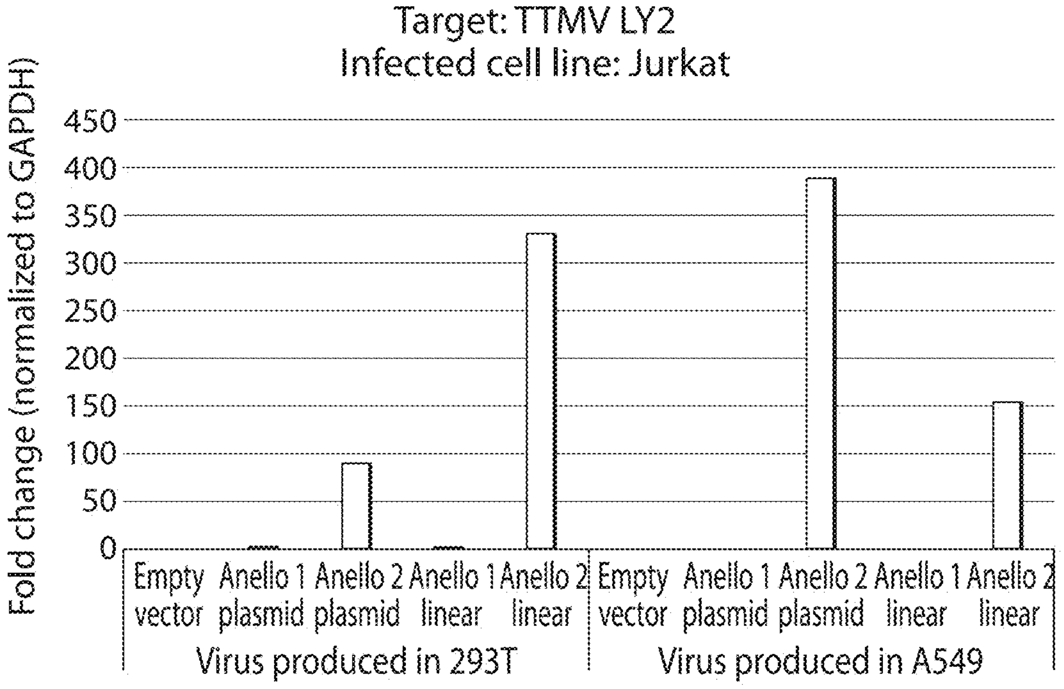
Figure 10A:
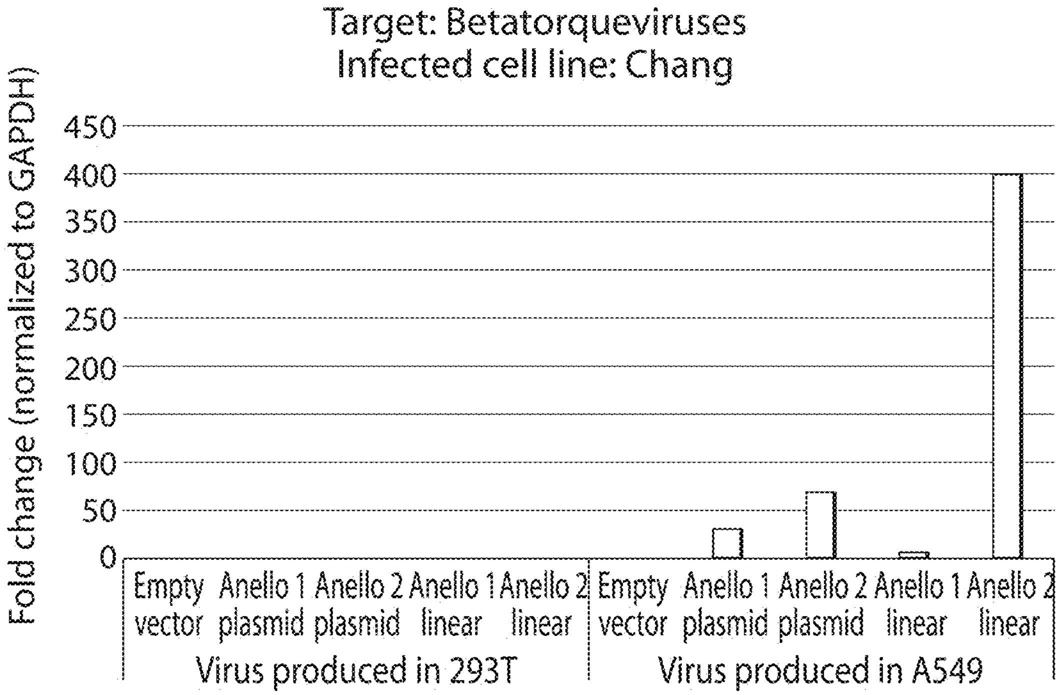
FIGS. 10A and 10B depict quantitative PCR results that illustrate successful infection of Chang cells by synthetic anellosomes.
Figure 10B:
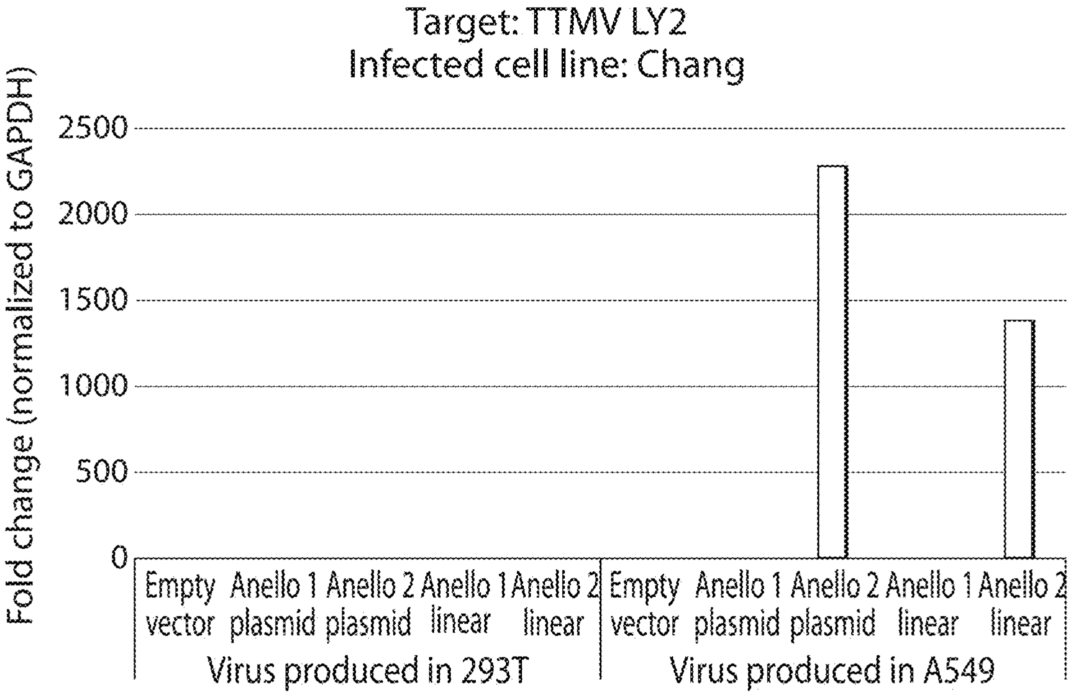

Anellosome DNA (obtained in Example 5) was transfected into either HEK293T cells (human embryonic kidney cell line) or A549 cells (human lung carcinoma cell line), either in an intact plasmid or in linearized form, with lipid transfection reagent (Thermo Fisher Scientific). 6 ug of plasmid or 1.5 ug of linearized DNA was used for transfection of 70% confluent cells in T25 flasks. Empty vector backbone lacking the viral sequences included in the anellosome was used as a negative control. Six hours post-transfection, cells were washed with PBS twice and were allowed to grow in fresh growth medium at 37 degrees Celsius and 5% carbon dioxide. DNA sequences encoding the human Ef1alpha promoter followed by YFP gene were synthesized from IDT. This DNA sequence was blunt end ligated into a cloning vector (Thermo Fisher Scientific). The resulting vector was used as a control to assess transfection efficiency. YFP was detected using a cell imaging system (Thermo Fisher Scientific) 72 hours post transfection. The transfection efficiencies of HEK293T and A549 cells were calculated as 85% and 40% respectively (FIG. 5).

Supernatants of 293T and A549 cells transfected with anellosomes were harvested 96 hours post transfection. The harvested supernatants were spun down at 2000 rpm for 10 minutes at 4 degrees Celsius to remove any cell debris. Each of the harvested supernatants was used to infect new 293T and A549 cells, respectively, that were 70% confluent in wells of 24 well plates. Supernatants were washed away after 24 hours of incubation at 37 degrees Celsius and 5% carbon dioxide, followed by two washes of PBS, and replacement with fresh growth medium. Following incubation of these cells at 37 degrees and 5% carbon dioxide for another 48 hours, cells were individually harvested for genomic DNA extraction. Genomic DNA from each of the samples was harvested using a genomic DNA extraction kit (Thermo Fisher Scientific), according to manufacturer's protocol.

To confirm the successful infection of 293T and A549 cells by anellosomes produced in vitro, 100 ng of genomic DNA harvested as described herein was used to perform quantitative polymerase chain reaction (qPCR) using primers specific for beta-torqueviruses or LY2 specific sequences. SYBR green reagent (Thermo Fisher Scientific) was used to perform qPCR, as per manufacturer's protocol. qPCR for primers specific to genomic DNA sequence of GAPDH was used for normalization. The sequences for all the primers used are listed in Table 42.

TABLE 42

| | Primer sequence (5' > 3') | |
|---|---|---|
| Target | Forward | Reverse |
| *Betatorque-viruses* | ATTCGAATGGCTGAGTTTATGC (SEQ ID NO: 690) | CCTTGACTACGGTGGTTTCAC (SEQ ID NO: 693) |
| LY2 TTMiniV strain | CACGAATTAGCCAAGACTGGGCAC (SEQ ID NO: 691) | TGCAGGCATTCGAGGGCTTGTT (SEQ ID NO: 694) |
| GAPDH | GCTCCCACTCCTGATTTCTG (SEQ ID NO: 692) | TTTAACCCCCTAGTCCCAGG (SEQ ID NO: 695) |

As shown in the qPCR results depicted in FIGS. 6A, 6B, 7A, and 7B, the anellosomes produced in vitro and as described in this example were infectious.

Example 7: Selectivity of Anellosomes

This example demonstrates the ability of synthetic anellosomes produced in vitro to infect cell lines of a variety of tissue origins.

Supernatants with the infectious TTMiniV anellosomes (described in Example 5) were incubated with 70% confluent 293T, A549, Jurkat (an acute T cell leukemia cell line), Raji (a Burkitt's lymphoma B cell line), and Chang (a liver carcinoma cell line) cell lines at 37 degrees and 5% carbon dioxide in wells of 24 well plates. Cells were washed with PBS twice, 24 hours post infection, followed by replacement with fresh growth medium. Cells were then incubated again at 37 degrees and 5% carbon dioxide for another 48 hours, followed by harvest for genomic DNA extraction. Genomic DNA from each of the samples was harvested using a genomic DNA extraction kit (Thermo Fisher Scientific), according to manufacturer's protocol.

To confirm successful infection of these cell lines by anellosomes produced in the previous Example, 100 ng of genomic DNA harvested as described herein was used to perform quantitative polymerase chain reaction (qPCR) using primers specific for beta-torqueviruses or LY2 specific sequences. SYBR green reagent (Thermo Fisher Scientific) was used to perform qPCR, as per manufacturer's protocol. qPCR for primers specific to genomic DNA sequence of GAPDH was used for normalization. The sequences for all the primers used are listed in Table 42.

As shown in the qPCR results depicted in FIGS. 6A-10B, not only were anellosomes produced in vitro infectious, they were able to infect a variety of cell lines, including examples of epithelial cells, lung tissue cells, liver cells, carcinoma cells, lymphocytes, lymphoblasts, T cells, B cells, and kidney cells. It was also observed that a synthetic anellosome was able to infect HepG2 cells, resulting in a greater than 100-fold increase relative to a control.

Example 8: Identification and Use of Protein Binding Sequences

This example describes putative protein-binding sites in the *Anellovirus* genome, which can be used for amplifying and packaging effectors, e.g., in an anellosome as described herein. In some instances, the protein-binding sites may be capable of binding to an exterior protein, such as a capsid protein.

Two conserved domains within the *Anellovirus* genome are putative origins of replication: the 5' UTR conserved domain (5CD) and the GC-rich domain (GCR) (de Villiers et al., Journal of Virology 2011; Okamoto et al., Virology 1999). In one example, in order to confirm whether these sequences act as DNA replication sites or as capsid packaging signals, deletions of each region are made in plasmids harboring TTMV-LY2. A539 cells are transfected with pTTMV-LY2A5CD or pTTMV-LY2ΔGCR. Transfected cells are incubated for four days, and then virus is isolated from supernatant and cell pellets. A549 cells are infected with virus, and after four days, virus is isolated from the supernatant and infected cell pellets. qPCR is performed to quantify viral genomes from the samples. Disruption of an origin of replication prevents viral replicase from amplifying viral DNA and results in reduced viral genomes isolated from transfected cell pellets compared to wild-type virus. A small amount of virus is still packaged and can be found in the transfected supernatant and infected cell pellets. In some embodiments, disruption of a packaging signal will prevent the viral DNA from being encapsulated by capsid proteins. Therefore, in embodiments, there will still be an amplification of viral genomes in the transfected cells, but no viral genomes are found in the supernatant or infected cell pellets.

In a further example, in order to characterize additional replication or packaging signals in the DNA, a series of deletions across the entire TTMV-LY2 genome is used. Deletions of 100 bp are made stepwise across the length of the sequence. Plasmids harboring TTMV-LY2 deletions are transfected into A549 and tested as described above. In some embodiments, deletions that disrupt viral amplification or packaging will contain potential cis-regulatory domains.

Replication and packaging signals can be incorporated into effector-encoding DNA sequences (e.g., in a genetic element in an anellosome) to induce amplification and encapsulation. This is done both in context of larger regions of the anellosome genome (i.e., inserting effectors into a specific site in the genome, or replacing viral ORFs with effectors, etc.), or by incorporating minimal cis signals into the effector DNA. In cases where the anellosome lacks trans replication or packaging factors (e.g., replicase and capsid proteins, etc.), the trans factors are supplied by helper genes. The helper genes express all of the proteins and RNAs sufficient to induce amplification and packaging, but lack their own packaging signals. The anellosome DNA is co-transfected with helper genes, resulting in amplification and packaging of the effector but not of the helper genes.

Example 9: A Minimal *Anellovirus* Genome

This Example describes deletions in the *Anellovirus* genome, both to help characterize the minimal genome sufficient for replicating virus and to insert effector payloads.

A 172-nucleotide (nt) deletion was made in the non-coding region (NCR) of TTV-tth8 downstream of the ORFs but upstream of the GC-rich region (nts 3436 to 3607). A random 56-nt sequence (TTTGTGACACAA-GATGGCCGACTTCCTTCCTCTTTAGTCTTCCC-CAAAGAAGACAA (SEQ ID NO: 696)) was inserted into the deletion. 2 μg of circular or linearized (by SmaI) pTTV-tth8(3436-3707::56nt), a DNA plasmid harboring the altered TTV-tth8, was transfected into HEK293 or A549 cells at 60% confluency in a 6 cm plate using lipofectamine 2000, in duplicate. Virus was isolated from cell pellets and supernatant 96 hours post transfection by freeze thaw, alternating three times between liquid nitrogen and 37° C. water bath. Virus from supernatant was used to re-infect cells (HEK293 cells infected by virus isolated from HEK293, and A549 cells infected by virus isolated from A549). 72 hours after infection, virus was isolated from cell pellets and supernatant by freeze thaw. qPCR was performed on all samples. As shown in Table 43 below, TTV-tth8 was observed in both the cell pellet and supernatant of infected cells, indicating successful virus production by pTTV-tth8(3436-3707::56nt). Therefore, TTV-tth8 is able to tolerate deletion of nts 3436 to 3707.

TABLE 43

TTV-tth8(3436-3707::56nt) infections in HEK293 and A549 result in viral amplification. Average genome equivalents from duplicate experiments compared to negative control cells with no plasmid or virus added.

| Genome Equivalents/Rx | | HEK293 P0 | HEK293 P1 | A549 P0 | A549 P1 | Negatives | |
|---|---|---|---|---|---|---|---|
| TTH8 | Sup | 2.45E+06 | 1.02E+03 | 1.87E+07 | 1.00E+04 | 293 Empty | 1.42E+02 |
| Linear | Cell | 2.52E+08 | 3.92E+05 | 2.89E+08 | 7.57E+05 | 293 Neg | 5.08E+02 |

TABLE 43-continued

TTV-tth8(3436-3707::56nt) infections in HEK293 and A549 result in viral amplification. Average genome equivalents from duplicate experiments compared to negative control cells with no plasmid or virus added.

| Genome Equivalents/Rx | | HEK293 P0 | HEK293 P1 | A549 P0 | A549 P1 | Negatives | |
|---|---|---|---|---|---|---|---|
| TTH8 | Sup | 1.69E+06 | 6.83E+02 | 5.07E+02 | 1.05E+04 | 549 Empty | 1.73E+01 |
| circular | Cell | 2.00E+08 | 3.75E+05 | 2.61E+08 | 8.36E+05 | 549 Neg | 2.08E+01 |

Figure 11A:
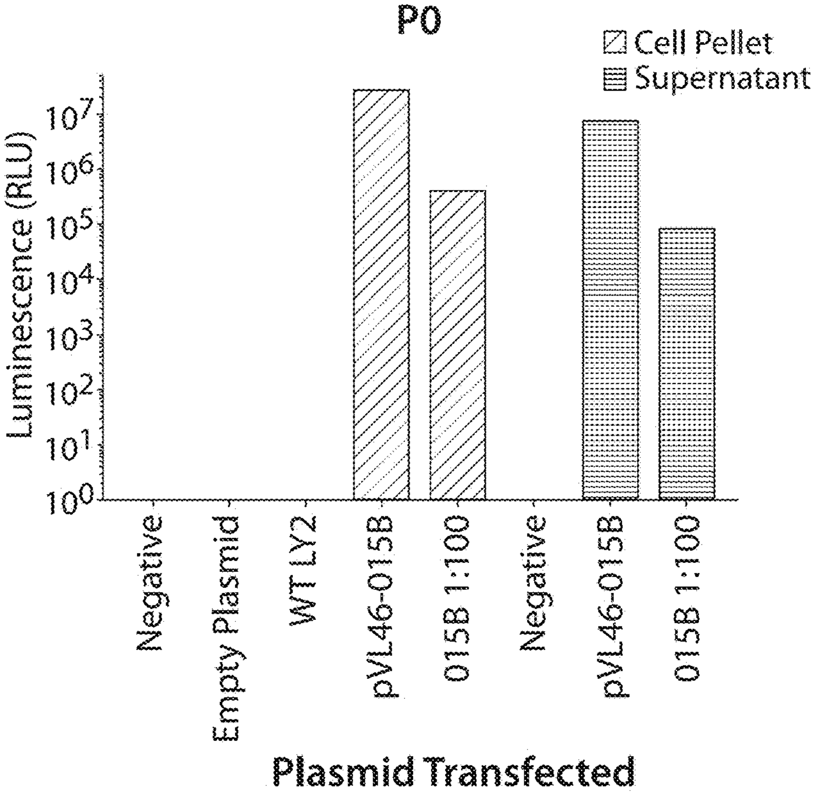
FIGS. 11A-11B are a series of graphs showing luciferase expression from cells transfected or infected with TTMV-LY2Δ574-1371,Δ1432-2210,2610::nLuc. Luminescence was observed in infected cells, indicating successful replication and packaging.
Figure 11B:
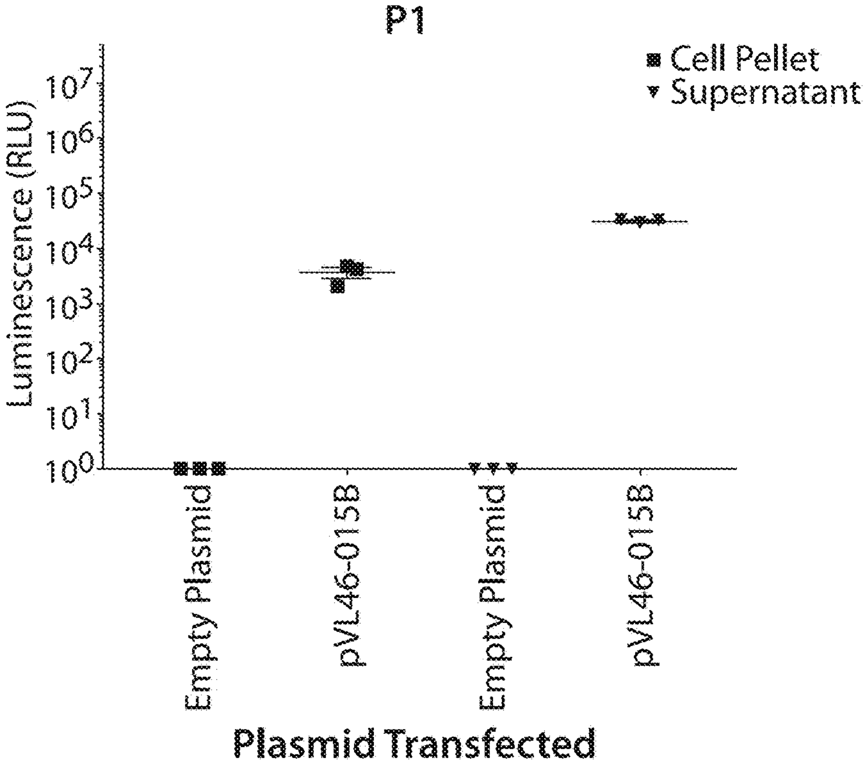

An engineered version of TTMV-LY2 was assembled, deleting nucleotides 574 to 1371 and 1432 to 2210 (1577 bp deletion) and inserting a 513 bp NanoLuc (nLuc) reporter ORF at the C-terminus of ORF1 (after nt 2609 in wild-type TTMV-LY2). Plasmids harboring the DNA sequence for the engineered TTMV-LY2 (pVL46-015B) were transfected into A549 cells, and then virus was isolated and used to infect new A549 cells, as described in Example 17. nLuc luminescence was detected in the cell pellets and supernatant of the infected cells, indicating viral replication (FIGS. 11A-11B). This demonstrates that TTMV-LY2 can tolerate at least a 1577 bp deletion in the ORF region.

To further characterize a minimal viral genome sufficient for replication, a series of deletions are made in the TTMV-LY2 DNA. A TTMV-LY2 with deletions of nts 574-1371 and 1432-2210 but no nLuc insertion is made and tested for viral replication as described previously. Further deletions are made to TTMV-LY2Δ574-1371,Δ1432-2210. Nts 1372-1431 are deleted to create TTMV-LY2Δ574-2210. Additionally, ORF3 sequence downstream of ORF1 is deleted (42610-2809). Finally, to test deletions in non-coding regions, a series of 100 bp deletions are made sequentially across the NCR. All deletion mutants are tested for viral replication as previously described. Deletions that result in successful viral production (indicating that the deleted region is not essential for viral replication) are combined to make variants of TTMV-LY2 with more deleted nucleotides. This strategy will provide a minimal virus sufficient for self-amplification. To identify the minimal virus that can be amplified with helpers, each of the deletion mutants that disrupted viral replication is tested alongside helper genes carrying trans replication and packaging elements. Deletions rescued by trans expression of replication elements indicate areas of the viral genome that can be deleted to form a minimal virus when helper genes are provided from a separate source.

Example 10: Nucleotide Insertions of Various Lengths into an *Anellovirus* Genome This example describes the addition of DNA sequences of various lengths into an *Anellovirus* genome, which can, in some instances, be used to generate an anellosome as described herein.

DNA sequences are cloned into plasmids harboring TTV-tth8 (GenBank accession number AJ620231.1) and TTMV-LY2 (GenBank accession number JX134045.1). Insertions are made in the noncoding regions (NCR) 3' of the open reading frames and 5' of the GC-rich region: after nucleotide 3588 in TTV-tth8, or nucleotide 2843 in TTMV-LY2.

Randomized DNA sequences of the following lengths are inserted into the NCRs of TTV-tth8 and TTMV-LY2: 100 base pairs (bp), 200 bp, 500 bp, 1000 bp, and 2000 bp. These sequences are designed to match the relative GC-content of each viral genome: approximately 50% GC for insertions into TTV-tth8, and approximately 38% GC for TTMV-LY2. In addition, several trans genes are inserted into the NCR. These include a miRNA driven by a U6 promoter (351 bp) and EGFP driven by a constitutive hEF1a promoter (2509 bp).

TTV-tth8 and TTMV-LY2 variants harboring various sized DNA inserts are transfected into mammalian cell lines, including HEK293 and A549, as previously described. Virus is isolated from the supernatant or cell pellets. Isolated virus is used to infect additional cells. Production of virus from the infected cells is monitored by quantitative PCR. In some embodiments, successful production of virus will indicate tolerance of insertions.

Example 11: Exemplary Cargo to be Delivered

This example describes exemplary classes of nucleic acid and protein payloads that may be delivered with an anellosome, e.g., an anellosome based on an *Anellovirus*, e.g., as described herein.

One example of a payload is mRNA for protein expression. A coding sequence of interest is transcribed from either a viral promoter native to the source virus (e.g., an *Anellovirus*) or from a promoter introduced with the payload as part of a trans gene. Alternatively, the mRNA is encoded within the open reading frames of the viral mRNAs, resulting in fusions between viral proteins and the protein of interest. Cleavage domains, for example, the 2A peptide or a proteinase target site, may be used to separate the protein of interest from the viral proteins when desired.

Non-coding RNAs (ncRNAs) are another example of a payload. These RNAs are generally transcribed using RNA polymerase III promoters, such as U6 or VA. Alternatively, an ncRNA is transcribed using RNA polymerase II, such as the native viral promoter or regulatable synthetic promoters. When expressed from RNA polymerase II promoters, the ncRNAs are encoded as part of the mRNA exon, introns, or as extra RNA transcribed downstream of the poly-A signal. ncRNAs are often encoded as part of a larger RNA molecule or are cleaved apart using ribozymes or endoribonucleases. ncRNAs that can be encoded as cargo in the genome of an anellosome include micro-RNA (miRNA), small-interfering RNAs (siRNA), short hairpin RNA (shRNA), antisense RNA, miRNA sponges, long-noncoding RNA (lncRNA), and guide RNA (gRNA).

DNA may be used as a functional element without requiring RNA transcription. For example, DNA may be used as a template for homologous recombination. In another example, a protein-binding DNA sequence may be used to drive packaging of proteins of interest into a capsid (e.g., in a proteinaceous exterior of an anellosome). For homologous recombination, regions of homology to human genomic DNA are encoded into the vector DNA to act as homology arms. Recombination can be driven by a targeted endonuclease (such as Cas9 with a gRNA, or a zinc-finger nuclease), which can be expressed either from the vector or from a separate source. Inside the cell, a single-stranded DNA genome is converted to double-stranded DNA, which then acts as a template for homologous recombination at the genomic DNA break site. For recruiting proteins of interest, a protein-binding sequence can be encoded in the anellosome DNA. A DNA-binding protein of interest, or a protein of interest fused to a DNA-binding protein (such as Ga14), binds to the anellosome DNA. When the anellosome DNA is encapsulated by the capsid proteins, the DNA-binding protein is encapsulated too, and can be delivered to cells with the anellosome.

Example 12: Exemplary Payload Integration Loci

This example describes exemplary loci in the genomes of TTV-tth8 (GenBank accession number AJ620231.1) and TTMV-LY2 (GenBank accession number JX134045) into which nucleic acid payloads can be inserted.

Several strategies can be employed for insertions into the open reading frame (ORF) regions of TTV-tth8 (nucleotides 336 to 3015) and TTMV-LY2 (nucleotides 424 to 2812). In one example, in order to tag viral proteins or create fusion proteins, a payload is inserted in frame within the specific ORF of interest. Alternatively, part or all of the ORF region is deleted, which may or may not disrupt viral protein function. The payload is then inserted into the deleted region. Additionally, a hyper-variable domain (HVD) in ORF1 of TTV-tth8 (between nucleotides 716 and 2362) or TTMV-LY2 (between nucleotides 724 and 2273) can be used as an insertion site.

Alternatively, payload insertions are made into regions of the vector comparable to the non-coding regions (NCRs) of TTV-tth8 or TTMV-LY2. In particular, insertions are made in the 5' NCR upstream of the TATA box, in the 5' untranslated region (UTR), in the 3' NCR downstream of the poly-A signal and upstream of the GC-rich region. Additionally, insertions are made into the miRNA region of TTV-tth8 (nucleotides 3429 to 3506). For the 5' NCR region, insertions are made upstream of the TATA box (between nucleotides 1 and 82 in TTV-tth8, and nucleotides 1 and 236 in TTMV-LY2). In some embodiments, trans genes are inserted in the reverse orientation to reduce promoter interference. For the 5' UTR, insertions are made downstream of the transcriptional start site (nucleotide 111 in TTV-tth8, and nucleotide 267 in TTMV-LY2) and upstream of the ORF2 start codon (nucleotide 336 in TTV-tth8, and nucleotide 421 in TTMV-LY2). 5' UTR insertions add or replace nucleotides in the 5' UTR. 3' NCR insertions are made upstream of the GC-rich region, in particular after nucleotide 3588 in TTV-tth8 or nucleotide 2843 in TTMV-LY2, as described in Example 10. The miRNA of TTV-tth8 is replaced by alternative natural or synthetic miRNA hairpins.

Example 13: Defined Categories of *Anellovirus* and Conserved Regions Thereof

Figure 11C:
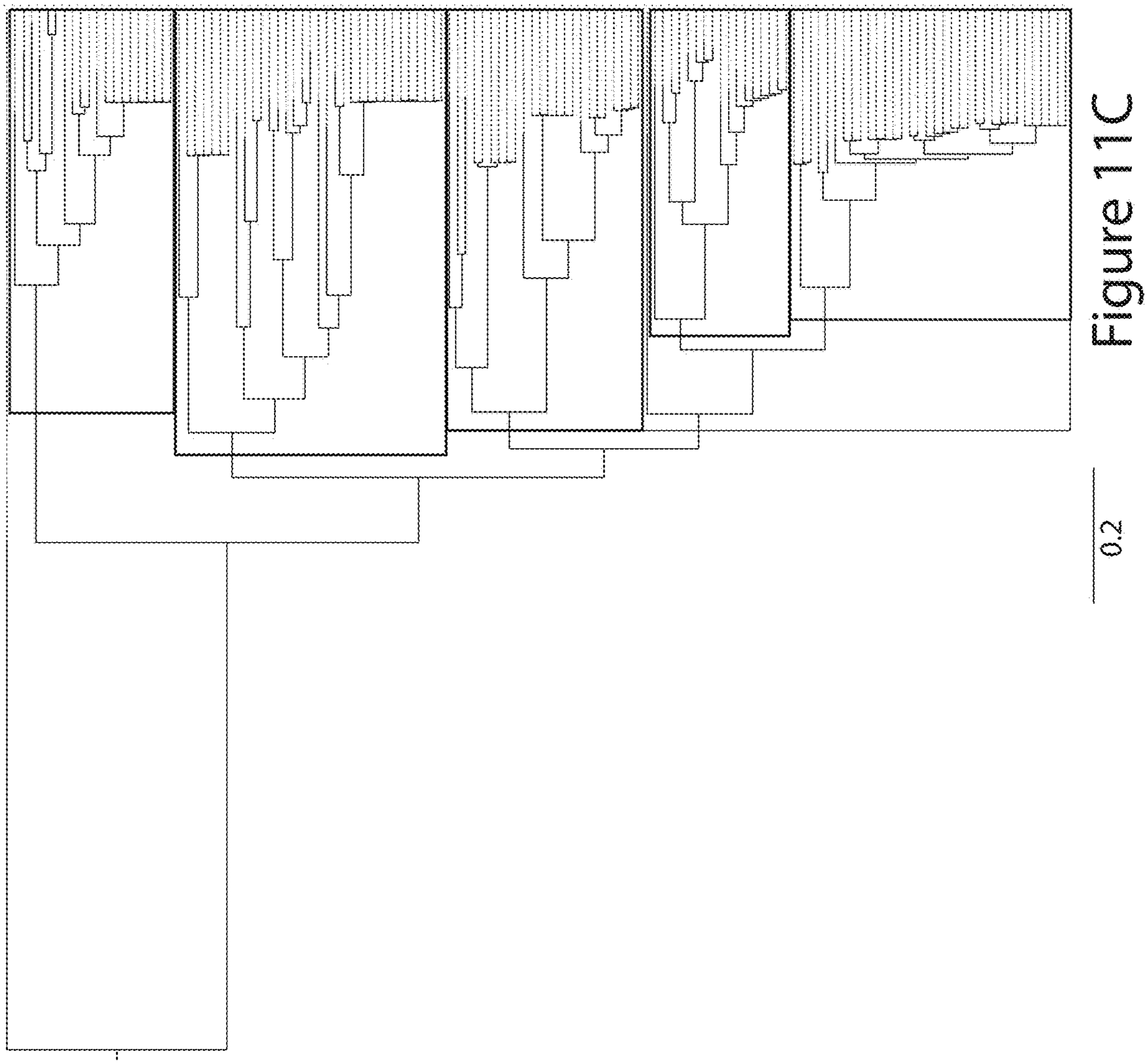
FIG. 11C is a diagram depicting the phylogenetic tree of *Alphatorquevirus* (Torque Teno Virus; TTV), with clades highlighted. At least 100 *Anellovirus* strains are represented. Exemplary sequences from several clades is provided herein, e.g., in Tables 1-18.

There are three genera of *Anellovirus* present in humans: *Alphatorquevirus* (Torque Teno Virus, TTV), *Betatorquevirus* (Torque Teno Midi Virus, TTMDV), and *Gammatorquevirus* (Torque Teno Mini Virus, TTMV). *Alphatorquevirus* includes at least five (e.g., seven) well-supported phylogenetic clades (FIG. 11C). It is contemplated that any of these *Anelloviruses* can be used as a source virus (e.g., a source of viral DNA sequences) for producing an anellosome as described herein.

Among these sequences, the highest conservation is found in the 5' UTR domain (about 75% conserved) and the GC-rich domain (greater than 100 base pairs, greater than 70% GC-content, about 70% conserved). Additional, a hypervariable domain (HVD) in the sequences has very low conservation (about 30% conserved). All *Anelloviruses* also contain a region in which all three reading frames are open.

Also provided herein are exemplary sequences of representative viruses from each of the TTV clades, and of TTMDV and TTMV, annotated with the conserved regions (see, e.g., Tables 1-18).

Example 14: Replication-Deficient Anellosomes and Helper Viruses

For replication and packaging of an anellosome, some elements can be provided in trans. These include proteins or non-coding RNAs that direct or support DNA replication or packaging. Trans elements can, in some instances, be provided from a source alternative to the anellosome, such as a helper virus, plasmid, or from the cellular genome.

Other elements are typically provided in cis. These elements can be, for example, sequences or structures in the anellosome DNA that act as origins of replication (e.g., to allow amplification of anellosome DNA) or packaging signals (e.g., to bind to proteins to load the genome into the capsid). Generally, a replication deficient virus or anellosome will be missing one or more of these elements, such that the DNA is unable to be packaged into an infectious virion or anellosome even if other elements are provided in trans.

Replication deficient viruses can be useful as helper viruses, e.g., for controlling replication of an anellosome (e.g., a replication-deficient or packaging-deficient anellosome) in the same cell. In some instances, the helper virus will lack cis replication or packaging elements, but express trans elements such as proteins and non-coding RNAs. Generally, the therapeutic anellosome would lack some or all of these trans elements and would therefore be unable to replicate on its own, but would retain the cis elements. When co-transfected/infected into cells, the replication-deficient helper virus would drive the amplification and packaging of the anellosome. The packaged particles collected would thus be comprised solely of therapeutic anellosome, without helper virus contamination.

To develop a replication deficient anellosome, conserved elements in the non-coding regions of *Anellovirus* will be removed. In particular, deletions of the conserved 5' UTR domain and the GC-rich domain will be tested, both separately and together. Both elements are contemplated to be important for viral replication or packaging. Additionally, deletion series will be performed across the entire non-coding region to identify previously unknown regions of interest.

Successful deletion of a replication element will result in reduction of anellosome DNA amplification within the cell, e.g., as measured by qPCR, but will support some infectious anellosome production, e.g., as monitored by assays on infected cells that can include any or all of qPCR, western blots, fluorescence assays, or luminescence assays. Successful deletion of a packaging element will not disrupt anellosome DNA amplification, so an increase in anellosome DNA will be observed in transfected cells by qPCR. However, the anellosome genomes will not be encapsulated, so no infectious anellosome production will be observed.

Example 15: Manufacturing Process for Replication-Competent Anellosomes

This example describes a method for recovery and scaling up of production of replication-competent anellosomes. Anellosomes are replication competent when they encode in their genome all the required genetic elements and ORFs necessary to replicate in cells. Since these anellosomes are not defective in their replication they do not need a complementing activity provided in trans. They might, however need helper activity, such as enhancers of transcriptions (e.g. sodium butyrate) or viral transcription factors (e.g. adenoviral E1, E2 E4, VA; HSV Vp16 and immediate early proteins).

In this example, double-stranded DNA encoding the full sequence of a synthetic anellosome either in its linear or circular form is introduced into 5E+05 adherent mammalian cells in a T75 flask by chemical transfection or into 5E+05 cells in suspension by electroporation. After an optimal period of time (e.g., 3-7 days post transfection), cells and supernatant are collected by scraping cells into the supernatant medium. A mild detergent, such as a biliary salt, is added to a final concentration of 0.5% and incubated at 37° C. for 30 minutes. Calcium and Magnesium Chloride is added to a final concentration of 0.5 mM and 2.5 mM, respectively. Endonuclease (e.g. DNAse I, Benzonase), is added and incubated at 25-37° C. for 0.5-4 hours. Anellosome suspension is centrifuged at 1000×g for 10 minutes at 4° C. The clarified supernatant is transferred to a new tube and diluted 1:1 with a cryoprotectant buffer (also known as stabilization buffer) and stored at −80° C. if desired. This produces passage 0 of the anellosome (P0). To bring the concentration of detergent below the safe limit to be used on cultured cells, this inoculum is diluted at least 100-fold or more in serum-free media (SFM) depending on the anellosome titer.

A fresh monolayer of mammalian cells in a T225 flask is overlaid with the minimum volume sufficient to cover the culture surface and incubated for 90 minutes at 37° C. and 5% carbon dioxide with gentle rocking. The mammalian cells used for this step may or may not be the same type of cells as used for the P0 recovery. After this incubation, the inoculum is replaced with 40 ml of serum-free, animal origin-free culture medium. Cells are incubated at 37° C. and 5% carbon dioxide for 3-7 days. 4 ml of a 10× solution of the same mild detergent previously utilized is added to achieve a final detergent concentration of 0.5%, and the mixture is then incubated at 37° C. for 30 minutes with gentle agitation. Endonuclease is added and incubated at 25-37° C. for 0.5-4 hours. The medium is then collected and centrifuged at 1000×g at 4° C. for 10 minutes. The clarified supernatant is mixed with 40 ml of stabilization buffer and stored at −80° C. This generates a seed stock, or passage 1 of anellosome (P1).

Figure 12:
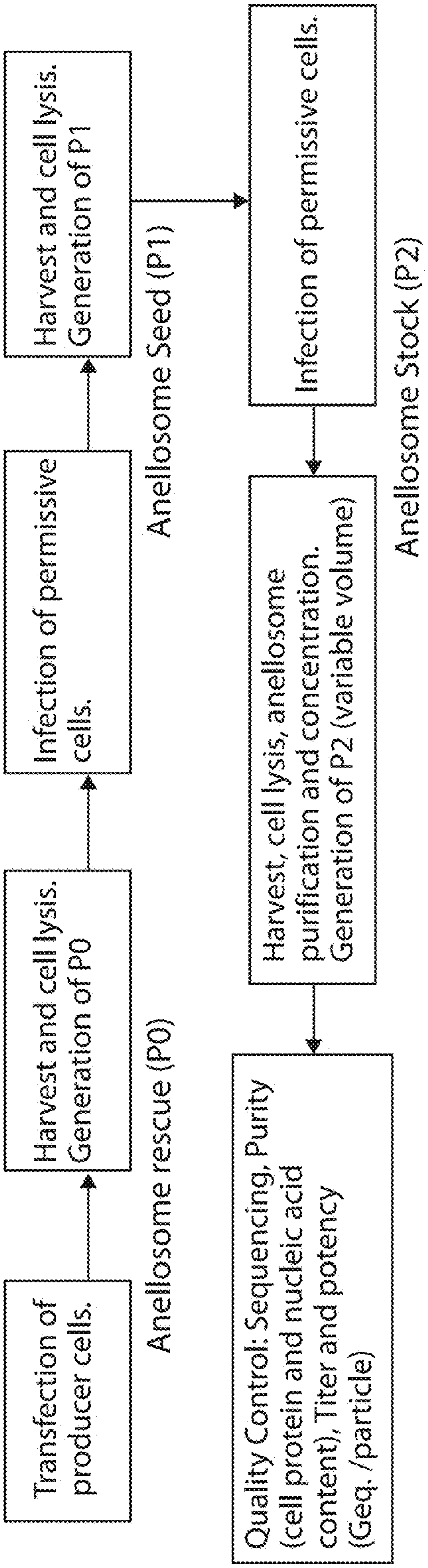
FIG. 12 is a schematic showing an exemplary workflow for production of anellosomes (e.g., replication-competent or replication-deficient anellosomes as described herein).

Depending on the titer of the stock, it is diluted no less than 100-fold in SFM and added to cells grown on multilayer flasks of the required size. Multiplicity of infection (MOI) and time of incubation is optimized at smaller scale to ensure maximal anellosome production. After harvest, anellosomes may then be purified and concentrated as needed. A schematic showing a workflow, e.g., as described in this example, is provided in FIG. 12.

Example 16: Manufacturing Process of Replication-Deficient Anellosomes

This example describes a method for recovery and scaling up of production of replication-deficient anellosomes.

Anellosomes can be rendered replication-deficient by deletion of one or more ORFs (e.g., ORF1, ORF1/1, ORF1/2, ORF2, ORF2/2, ORF2/3, and/or ORF2t/3) involved in replication. Replication-deficient anellosomes can be grown in a complementing cell line. Such cell line constitutively expresses components that promote anellosome growth but that are missing or nonfunctional in the genome of the anellosome.

In one example, the sequence(s) of any ORF(s) involved in anellosome propagation are cloned into a lentiviral expression system suitable for the generation of stable cell lines that encode a selection marker, and lentiviral vector is generated as described herein. A mammalian cell line capable of supporting anellosome propagation is infected with this lentiviral vector and subjected to selective pressure by the selection marker (e.g., puromycin or any other antibiotic) to select for cell populations that have stably integrated the cloned ORFs. Once this cell line is characterized and certified to complement the defect in the engineered anellosome, and hence to support growth and propagation of such anellosomes, it is expanded and banked in cryogenic storage. During expansion and maintenance of these cells, the selection antibiotic is added to the culture medium to maintain the selective pressure. Once anellosomes are introduced into these cells, the selection antibiotic may be withheld.

Once this cell line is established, growth and production of replication-deficient anellosomes is carried out, e.g., as described in Example 15.

Example 17: Production of Anellosomes Using Suspension Cells

This example describes the production of anellosomes in cells in suspension.

In this example, an A549 or 293T producer cell line that is adapted to grow in suspension conditions is grown in animal component-free and antibiotic-free suspension medium (Thermo Fisher Scientific) in WAVE bioreactor bags at 37 degrees and 5% carbon dioxide. These cells, seeded at $1\times10^6$ viable cells/mL, are transfected using lipofectamine 2000 (Thermo Fisher Scientific) under current good manufacturing practices (cGMP), with a plasmid comprising anellosome sequences, along with any complementing plasmids suitable or required to package the anellosome (e.g., in the case of a replication-deficient anellosome, e.g., as described in Example 16). The complementing plasmids can, in some instances, encode for viral proteins that have been deleted from the anellosome genome (e.g., an anellosome genome based on a viral genoe, e.g., an *Anellovirus* genome, e.g., as described herein) but are useful or required for replication and packaging of the anellosomes. Transfected cells are grown in the WAVE bioreactor bags and the supernatant is harvested at the following time points: 48, 72, and 96 hours post transfection. The supernatant is separated from the cell pellets for each sample using centrifugation. The packaged anellosome particles are then purified from the harvested supernatant and the lysed cell pellets using ion exchange chromatography.

The genome equivalents in the purified prep of the anellosomes can be determined, for example, by using a small aliquot of the purified prep to harvest the anellosome genome using a viral genome extraction kit (Qiagen), followed by qPCR using primers and probes targeted towards the anellosome DNA sequence, e.g., as described in Example 18.

The infectivity of the anellosomes in the purified prep can be quantified by making serial dilutions of the purified prep to infect new A549 cells. These cells are harvested 72 hours post transfection, followed by a qPCR assay on the genomic DNA using primers and probes that are specific to the anellosome DNA sequence.

Example 18: Quantification of Anellosome Genome Equivalents by qPCR

This example demonstrates the development of a hydrolysis probe-based quantitative PCR assay to quantify anellosomes. Sets of primers and probes were designed based on selected genome sequences of TTV (Accession No. AJ620231.1) and TTMV (Accession No. JX134045.1) using the software Geneious with a final user optimization. Primer sequences are shown in Table 44 below.

TABLE 44

Sequences of forward and reverse primers and hydrolysis probes used to quantify TTMV and TTV genome equivalents by quantitative PCR.

| | | SEQ ID NO: |
|---|---|---|
| TTMV | | |
| Forward Primer | 5'-GAAGCCCACCAAAAGCAATT-3' | 697 |
| Reverse Primer | 5'-AGTTCCCGTGTCTATAGTCGA-3' | 698 |
| Probe | 5'-ACTTCGTTACAGAGTCCAGGGG-3' | 699 |
| TTV | | |
| Forward Primer | 5'-AGCAACAGGTAATGGAGGAC-3' | 700 |
| Reverse Primer | 5'-TGGAAGCTGGGGTCTTTAAC-3' | 701 |
| Probe | 5'-TCTACCTTAGGTGCAAAGGGCC-3' | 702 |

Figure 13:
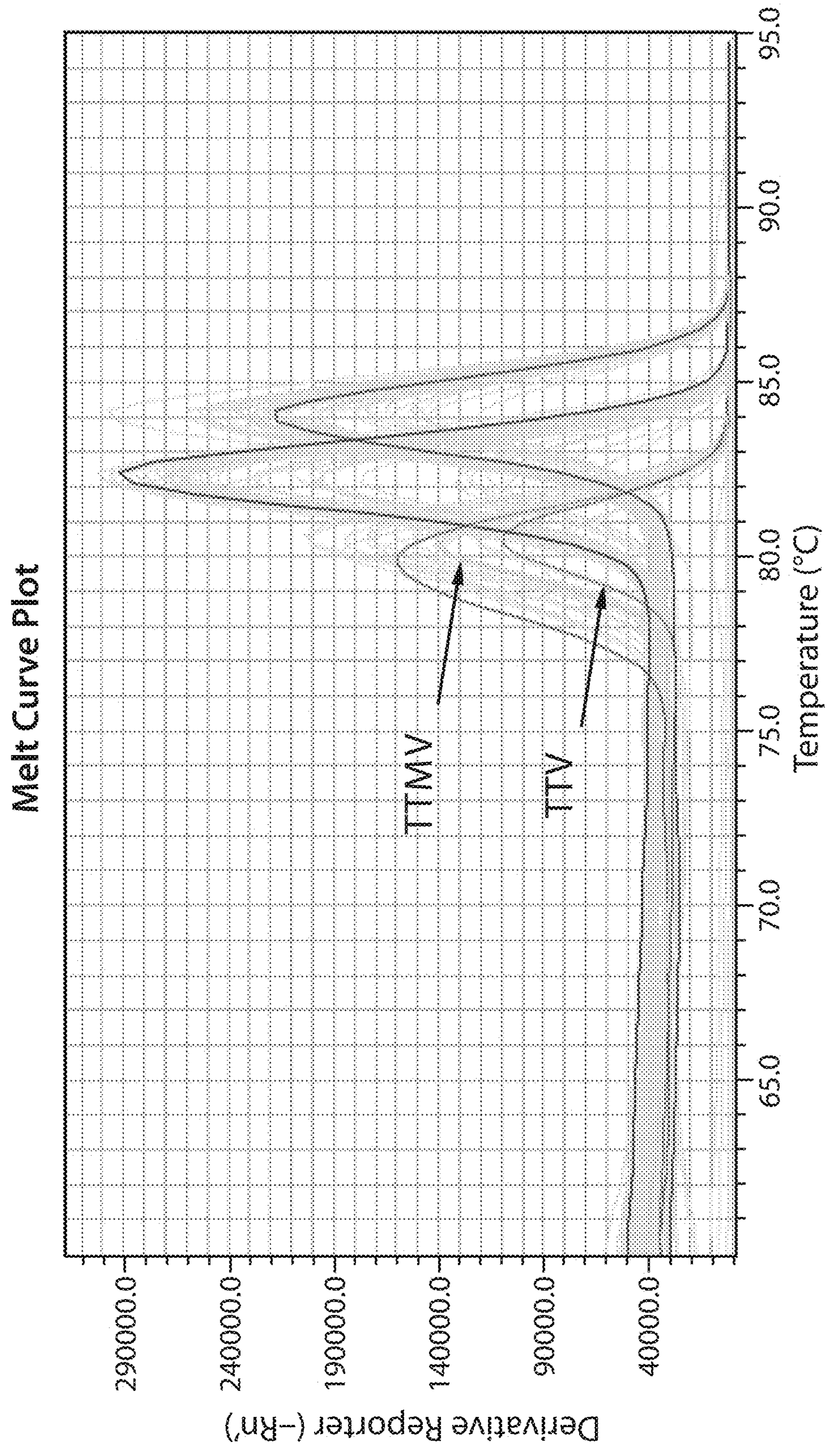
FIG. 13 is a graph showing primer specificity for primer sets designed for quantification of TTV and TTMV genomic equivalents. Quantitative PCR based on SYBR green chemistry shows one distinct peak for each of the amplification products using TTMV or TTV specific primer sets, as indicated, on plasmids encoding the respective genomes.

As a first step in the development process, qPCR is run using the TTV and TTMV primers with SYBR-green chemistry to check for primer specificity. FIG. 13 shows one distinct amplification peak for each primer pair.

Figure 14:
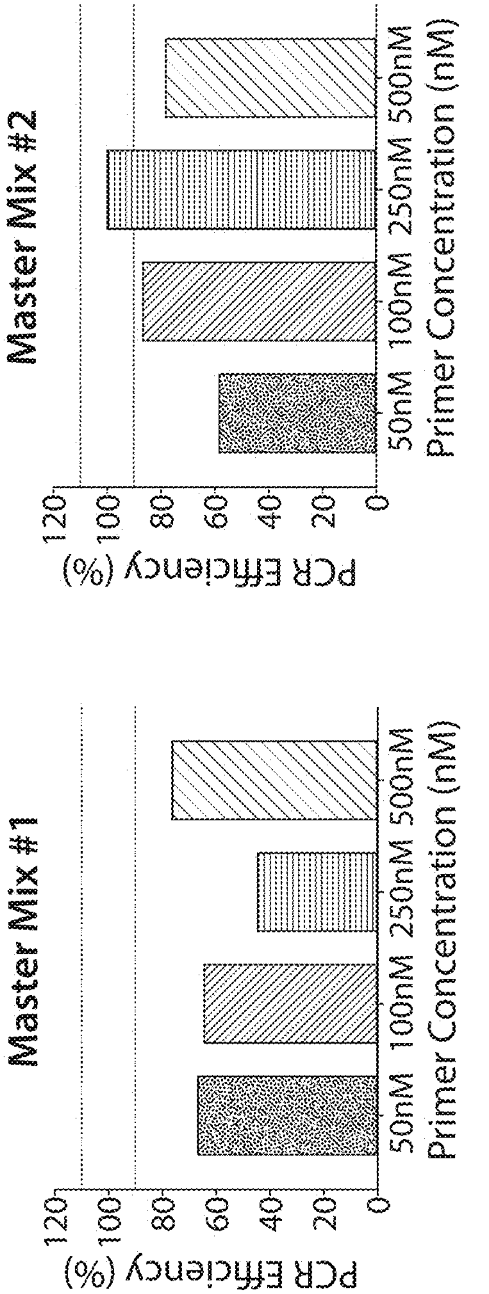
FIG. 14 is a series of graphs showing PCR efficiencies in the quantification of TTV genome equivalents by qPCR. Increasing concentrations of primers and a fixed concentration of hydrolysis probe (250 nM) were used with two different commercial qPCR master mixes. Efficiencies of 90-110% resulted in minimal error propagation during quantification.
Figure 15:
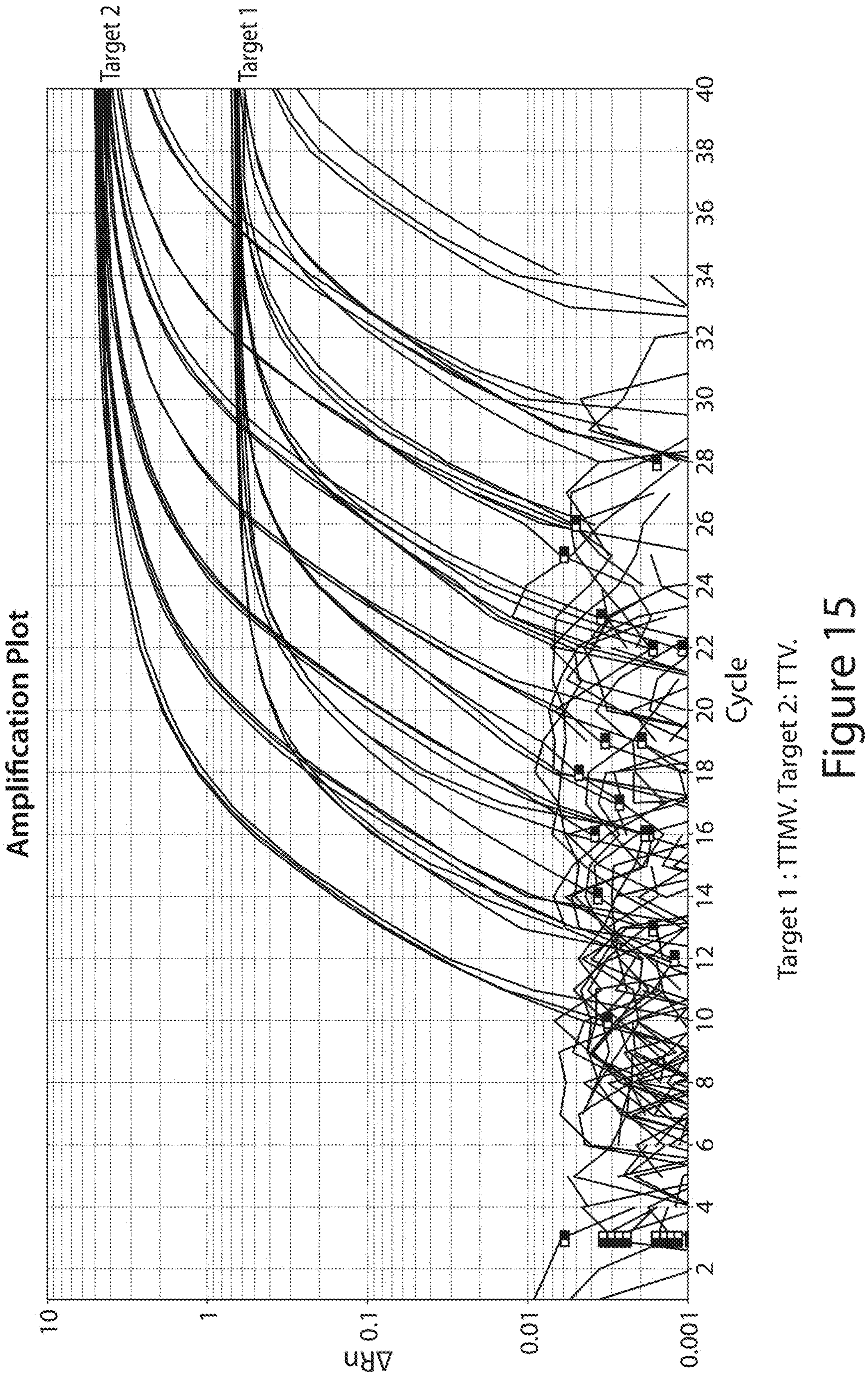
FIG. 15 is a graph showing an exemplary amplification plot for linear amplification of TTMV (Target 1) or TTV (Target 2) over a 7 log 10 of genome equivalent concentrations. Genome equivalents were quantified over 7 10-fold dilutions with high PCR efficiencies and linearity ($R^2$ TTMV: 0.996; $R^2$ TTV: 0.997).

Hydrolysis probes were ordered labeled with the fluorophore 6FAM at the 5' end and a minor groove binding, non-fluorescent quencher (MGBNFQ) at the 3' end. The PCR efficiency of the new primers and probes was then evaluated using two different commercial master mixes using purified plasmid DNA as component of a standard curve and increasing concentrations of primers. The standard curve was set up by using purified plasmids containing the target sequences for the different sets of primers-probes. Seven tenfold serial dilutions were performed to achieve a linear range over 7 logs and a lower limit of quantification of 15 copies per 20 ul reaction. Master mix #2 was capable of generating a PCR efficiency between 90-110%, values that are acceptable for quantitative PCR (FIG. 14). All primers for qPCR were ordered from IDT. Hydrolysis probes conjugated to the fluorophore 6FAM and a minor groove binding, non-fluorescent quencher (MGBNFQ) as well as all the qPCR master mixes were obtained from Thermo Fisher. An exemplary amplification plot is shown in FIG. 15.

Figure 16A:
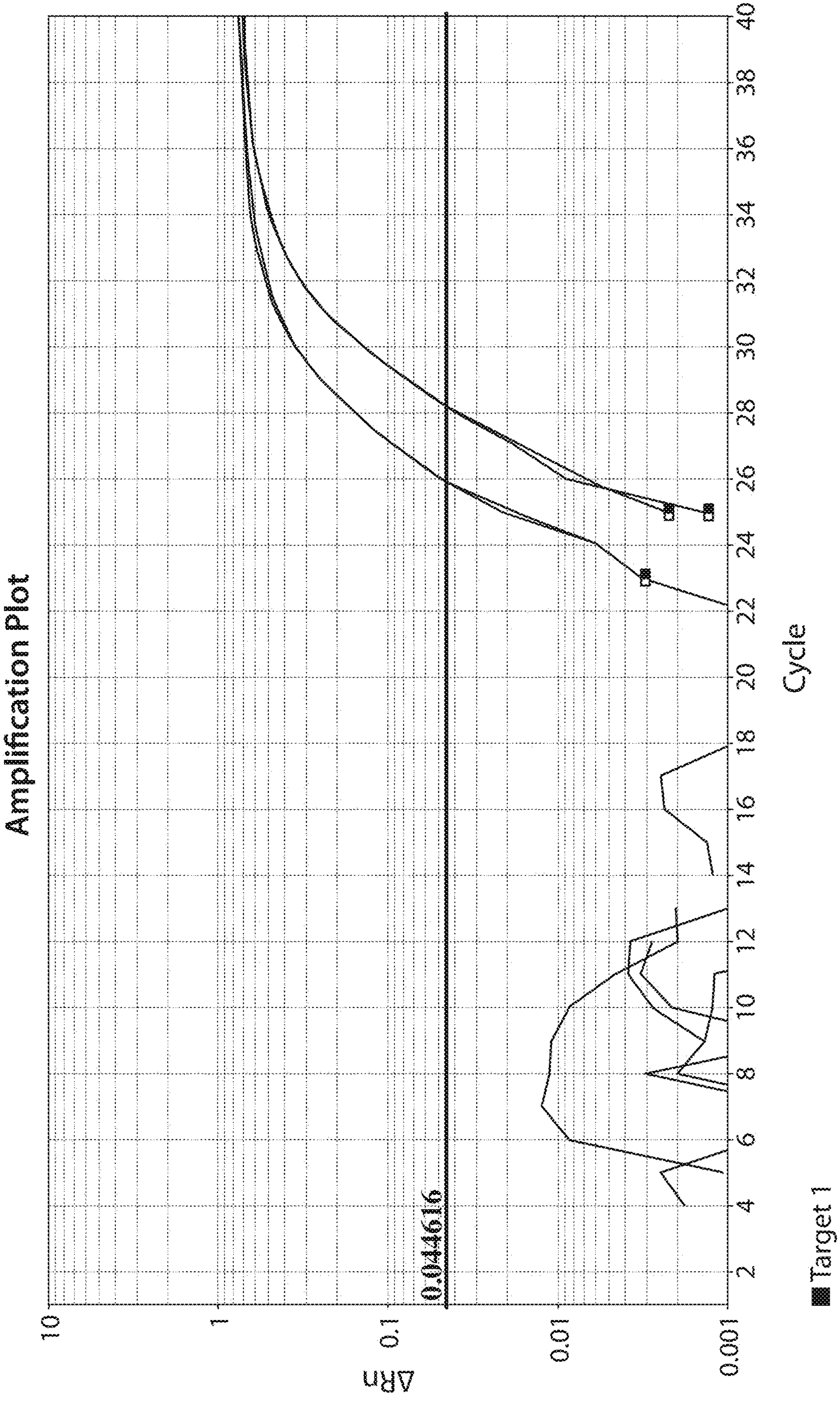
FIGS. 16A-16B are a series of graphs showing quantification of TTMV genome equivalents in an anellosome stock. (A) Amplification plot of two stocks, each diluted 1:10 and run in duplicate. (B) The same two samples as shown in panel A, here shown in the context of the linear range. Shown are the upper and lower limits in the two representative samples. PCR Efficiency: 99.58%, $R^2$: 0988.
Figure 16B:
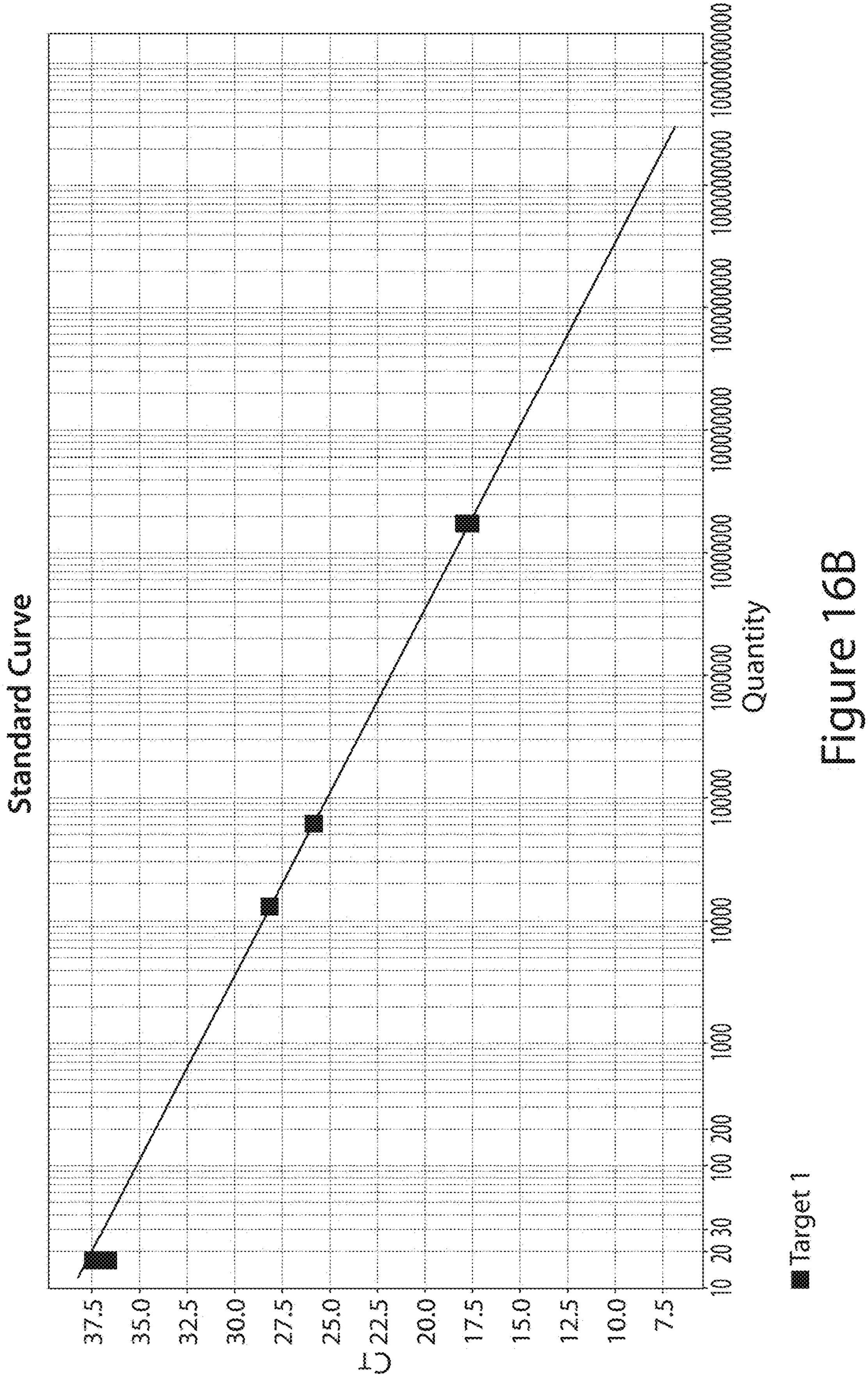

Using these primer-probe sets and reagents, the genome equivalent (GEq)/m1 in anellosome stocks was quantified. The linear range was between 1.5E+07-15 GEq per 20 ul reaction, which was then used to calculate the GEq/ml, as shown in FIGS. 16A-16B. Samples with higher concentrations than the linear range can be diluted as needed.

Example 19: Utilizing Anellosomes to Express an Exogenous Protein in Mice

This example describes the usage of an anellosome in which the Torque Teno Mini Virus (TTMV) genome is engineered to express the firefly luciferase protein in mice.

The plasmid encoding the DNA sequence of the engineered TTMV encoding the firefly-luciferase gene is introduced into A549 cells (human lung carcinoma cell line) by chemical transfection. 18 ug of plasmid DNA is used for transfection of 70% confluent cells in a 10 cm tissue culture plate. Empty vector backbone lacking the TTMV sequences is used as a negative control. Five hours post-transfection, cells are washed with PBS twice and are allowed to grow in fresh growth medium at 37° C. and 5% carbon dioxide.

Transfected A549 cells, along with their supernatant, are harvested 96 hours post transfection. Harvested material is treated with 0.5% deoxycholate (weight in volume) at 37° C. for 1 hour followed by endonuclease treatment. Anellosome particles are purified from this lysate using ion exchange chromatography. To determine anellosome concentration, a sample of the anellosome stock is run through a viral DNA purification kit and genome equivalents per ml are measured by qPCR using primers and probes targeted towards the anellosome DNA sequence.

A dose-range of genome equivalents of anellosomes in 1× phosphate-buffered saline is performed via a variety of routes of injection (e.g. intravenous, intraperitoneal, subcutaneous, intramuscular) in mice at 8-10 weeks of age. Ventral and dorsal bioluminescence imaging is performed on each animal at 3, 7, 10 and 15 days post injection. Imaging is performed by adding the luciferase substrate (Perkin-Elmer) to each animal intraperitoneally at indicated time points, according to the manufacturer's protocol, followed by intravital imaging.

Example 20: Genome Alignments to Determine Whether Anellosome DNA Integrated into Host Genomes This example describes the computational analysis performed to determine whether anellosome DNA can integrate into the host genome, by examining whether Torque Teno Virus (TTV) has integrated into the human genome.

The complete genomes of one representative TTV sequence from each of five exemplary *Alphatorquevirus* clades were aligned against the human genome sequence using the Basic Local Alignment Search Tool (BLAST) that finds regions of local similarity between sequences. The representative TTV sequences shown in Table 45 were analyzed:

TABLE 45

Representative TTV sequences

| TTV Clade | NCBI Accession No. |
|---|---|
| Clade A | AB064597.1 |
| Clade B | AB028669.1 |

TABLE 45-continued

| Representative TTV sequences | |
|---|---|
| TTV Clade | NCBI Accession No. |
| Clade C | AJ20231.1 |
| Clade D | AF122914.3 |
| Clade E | AF298585.1 |

Sequences from none of the aligned TTVs were found to have any significant similarity to the human genome, indicating that the TTVs have not integrated into the human genome.

Example 21: Assessment of Anellosome Integration into a Host Genome

In this example, A549 cells (human lung carcinoma cell line) and HEK293T cells (human embryonic kidney cell line) are infected with either anellosome particles or AAV particles at MOIs of 5, 10, 30 or 50. The cells are washed with PBS 5 hours post infection and replaced with fresh growth medium. The cells are then allowed to grow at 37 degrees and 5% carbon dioxide. Cells are harvested five days post infection and they are processed to harvest genomic DNA, using the genomic DNA extraction kit (Qiagen). Genomic DNA is also harvested from uninfected cells (negative control). Whole-genome sequencing libraries are prepared for these harvested DNAs, using the Nextera DNA library preparation kit (Illumina), according to manufacturers protocol. The DNA libraries are sequenced using the NextSeq 550 system (Illumina) according to manufacturer's protocol. Sequencing data is assembled to the reference genome and analyzed to look for junctions between anellosome or AAV genomes and host genome. In cases where junctions are detected they are verified in the original genomic DNA sample prior sequencing library preparation by PCR. Primers are designed to amplify the region containing and around the junctions. The frequency of integration of anellosomes into the host genome is determined by quantifying the number of junctions (representing integration events) and the total number of anellosome copies in the sample by qPCR. This ratio can be compared to that of AAV.

Example 22: Functional Effects of an Anellosome Expressing an Exogenous microRNA Sequence This example provides a successful demonstration of function of anellosomes expressing exogenous microRNA (miRNA) sequences.

Anellosome DNA sequences were generated that contained one of the following exogenous microRNA sequences in the 3' non-coding region (NCR):

1) miR-124
2) miR-518
3) miR-625
4) Non-targeting scramble miRNA (miR-scr)

Figure 17A:
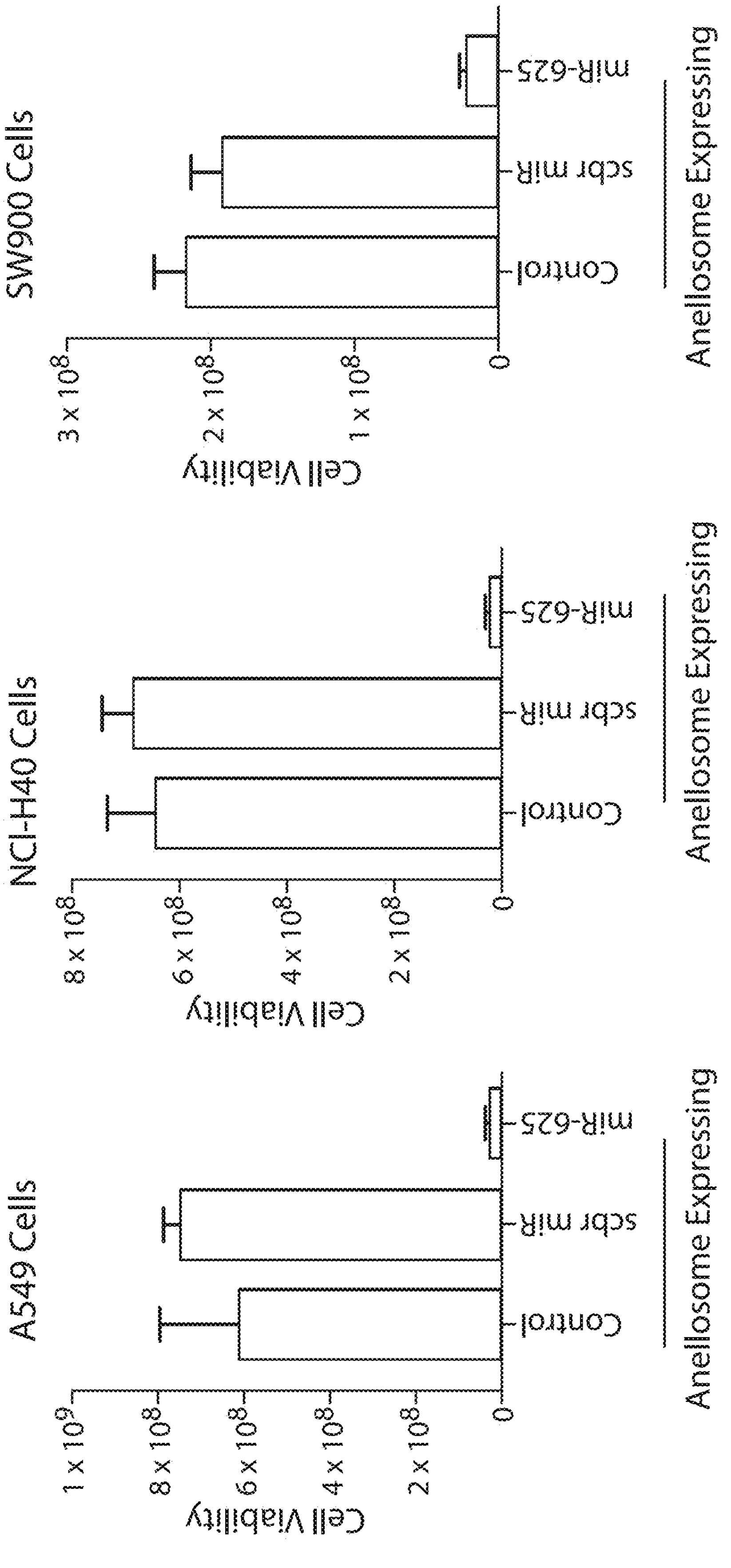
FIGS. 17A and 17B are a series of graphs showing the functional effects of a synthetic anellosome comprising an exogenous miRNA, miR-625. (A) Impact on cell viability of non-small cell lung cancer (NSCLC) cells when infected with anellosomes expressing miR-625 in three different NSCLC cell lines (A549 cells, NCI-H40 cells, and SW900 cells). (B) Impact of anellosomes expressing miR-625 on expression of a YFP reporter by HEK293T cells.

This was done by replacing the pre-miRNA sequence of the tth8-T1 miRNA of TTV-tth8 with the pre-miRNA sequences of the miRNAs mentioned above. Anellosome DNAs were then transfected into HEK293T cells seperately. Transfected 293T cells, along with the supernatants were harvested 96 hours post transfection. Harvested material was treated with 0.5% deoxycholate (weight in volume) at 37 degrees Celsius, followed by endonuclease treatment. This lysate containing the packaged anellosomes (P0 stock of anellosomes) were used to infect new 293T cells. These cells were harvested 96 hours, post infection. The harvested cells were then treated with 0.5% deoxycholate (weight in volume) at 37 degrees Celsius, followed by endonuclease treatment. This lysate was then dialyzed in the 10K molecular-weight cutoff dialysis cassettes in PBS at 4 degrees overnight to remove any deoxycholate. The titer of the anellosome was quantified in these dialyzed lysate (P1 stock of anellosome) using qPCR. P1 stock of anellosomes were then incubated with several KRAS mutant non-small cell lung cancer (NSCLC) cell lines (SW900, NCI-H460, and A549) for 3 days at a titer of 274 genome equivalents per cell. Cell viability was measured with an Alamar blue assay. As shown in FIG. 17A, anellosomes expressing an exogenous miR-625 significantly inhibited cancer cell line viability in all three NSCLC cell lines as compared to cells infected with control anellosomes expressing a scrambled non-targeted miRNA and uninfected cells.

Figure 17B:
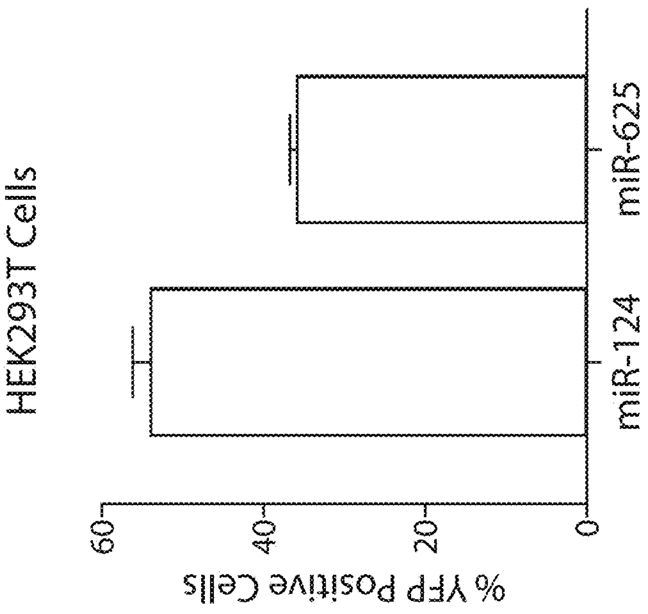

Additionally, a YFP-reporter assay was used to determine the downregulation of the target by anellosome miRNA by site specific binding to its target site. A YFP reporter that has a specific binding sequence for miR-625 was generated and transfected into HEK293T cells. 24 hours after transfection, these HEK293T cells were infected with anellosomes expressing either miR-625 or a non-specific miRNA (miR-124) at a titer of 2.4 genome equivalents per cell, and YFP fluorescence was then measured using flow cytometry. As shown in FIG. 17B, anellosomes expressing miR-625 significantly downregulated YFP expression, whereas anellosomes expressing the non-specific miRNA miR-124 did not affect YFP expression. These results show that the anellosome with miR-625 induced on-target downregulation of the YFP protein target.

Figure 17C:
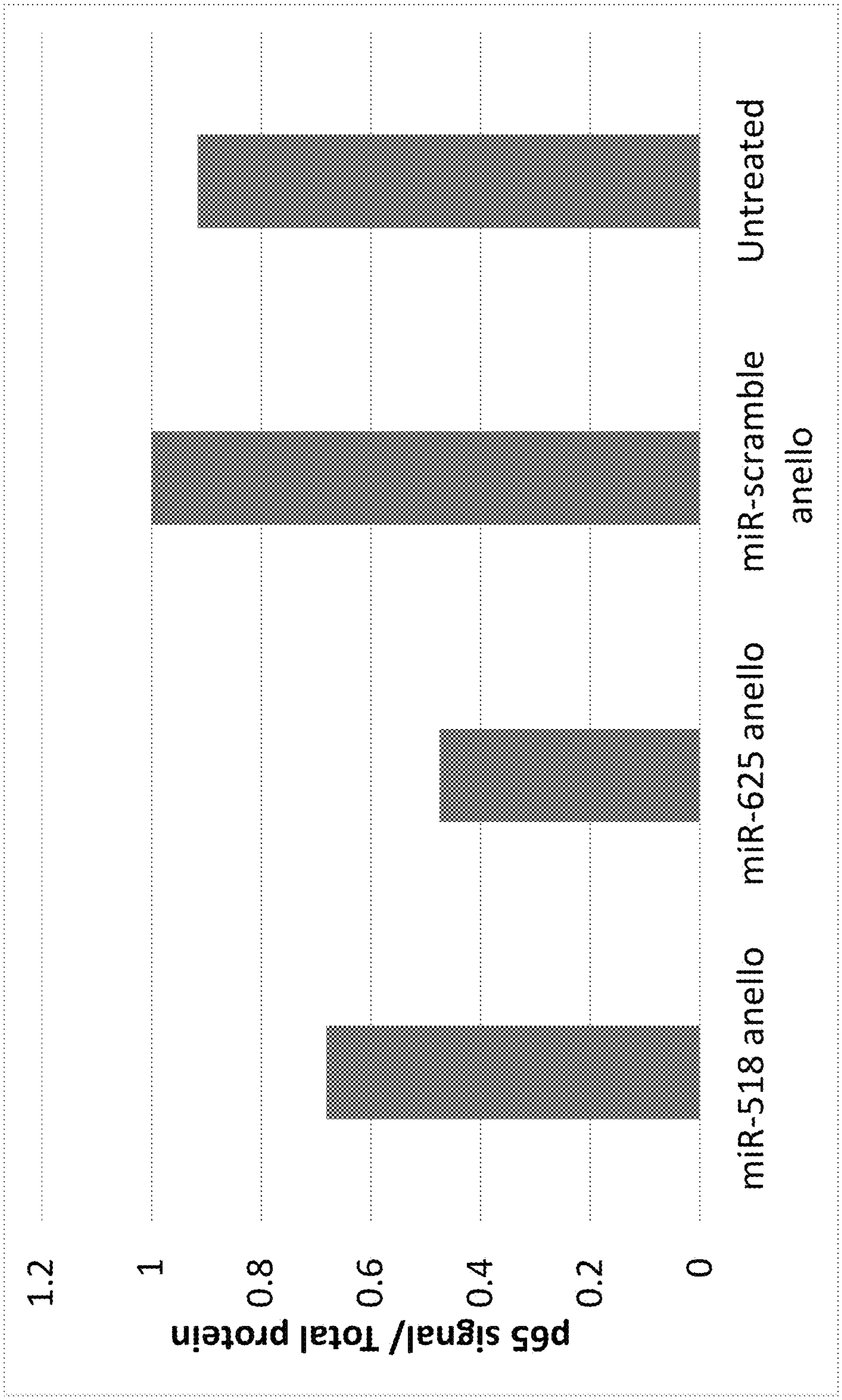
FIG. 17C is a graph showing quantification of p65 immunoblot analysis normalized to total protein for SW900 cells, either contacted with the indicated anellosomes or left untreated.

The ability of anellosomes expressing exogenous miRNAs to modulate host gene expression was also tested. SW-900 NSCLC cells were infected with anellosomes expressing either miR-518 or miR-625 or miR-scr at a dose of 10 genome equivalents per cell. Infected cells were harvested 72 hours post infection and total protein lysates were prepared Immunoblot analysis was performed on these protein lysates to determine the levels of p65 protein. The intensity of p65 protein signal was normalized to the total amount of protein on the membrane for each sample (FIG. 17C). A reduction in p65 levels was observed, indicating that anellosomes can modulate expression of a host gene.

Example 23: Preparation and Production of Anellosomes to Express Exogenous Non-Coding RNAs This example describes the synthesis and production of anellosomes to express exogenous small non-coding RNAs.

The DNA sequence from the tth8 strain of TTV (Jelcic et al, Journal of Virology, 2004) is synthesized and cloned into a vector containing the bacterial origin of replication and bacterial antibiotic resistance gene. In this vector, the DNA sequence encoding the TTV miRNA hairpin is replaced by a DNA sequence encoding an exogenous small non-coding RNA such as miRNA or shRNA. The engineered construct is then transformed into electro-competent bacteria, followed by plasmid isolation using a plasmid purification kit according to the manufacturer's protocols.

The anellosome DNA encoding the exogenous small non-coding RNAs is transfected into an eukaryotic producer cell line to produce anellosome particles. The supernatant of the transfected cells containing the anellosome particles is harvested at different time points post transfection. Anellosome particles, either from the filtered supernatant or after purification, are used for downstream applications, e.g., as described herein.

Example 24: Conservation in *Anellovirus* Clades

Figure 18:
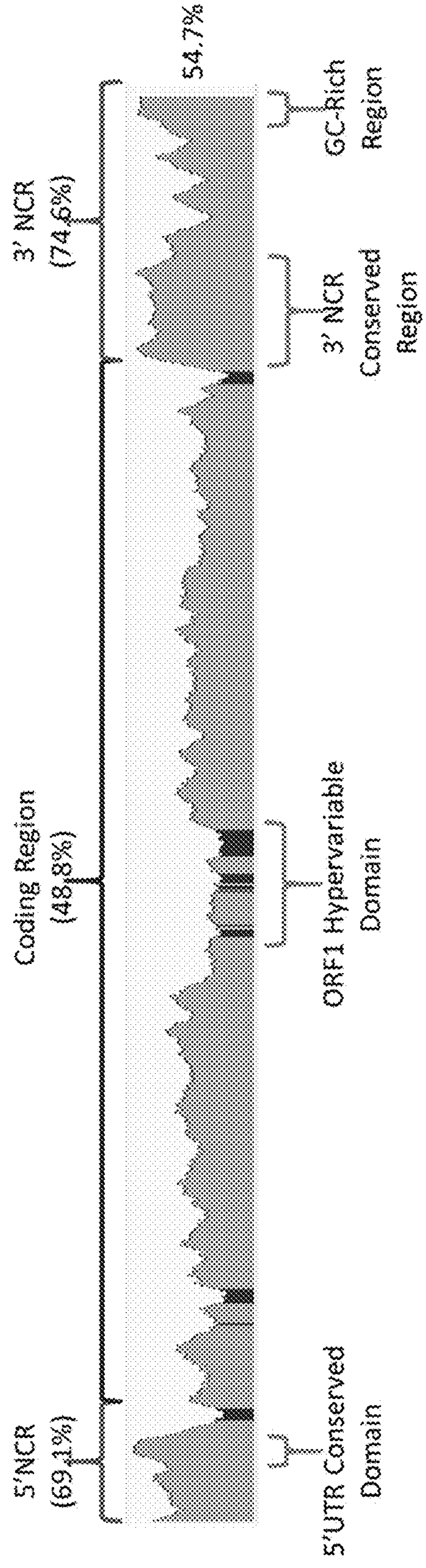
FIG. 18 is a diagram showing pairwise identity for alignments of representative sequences from each *Alphatorquevirus* Glade. DNA sequences for TTV-CT30F, TTV-P13-1, TTV-tth8, TTV-HD20a, TTV-16, TTV-TJN02, and TTV-HD16d were aligned. Pairwise percent identity across a 50-bp sliding window is shown along the length of the alignment. Brackets above indicate non-coding and coding regions with pairwise identities are indicated. Brackets below indicate regions of high or low sequence conservation.

This example describes the identification of seven clades within the *Alphatorquevirus* genus. Representative sequences between these clades showed 54.7% pairwise identity across the sequences (FIG. 18). The pairwise identity was lowest among the open reading frames (~48.8%), and higher in the non-coding regions (69.1% in the 5' NCR, 74.6% in the 3' NCR) (FIG. 18). This suggests that DNA sequences or structures in the non-coding regions play important roles in viral replication.

Figure 19:
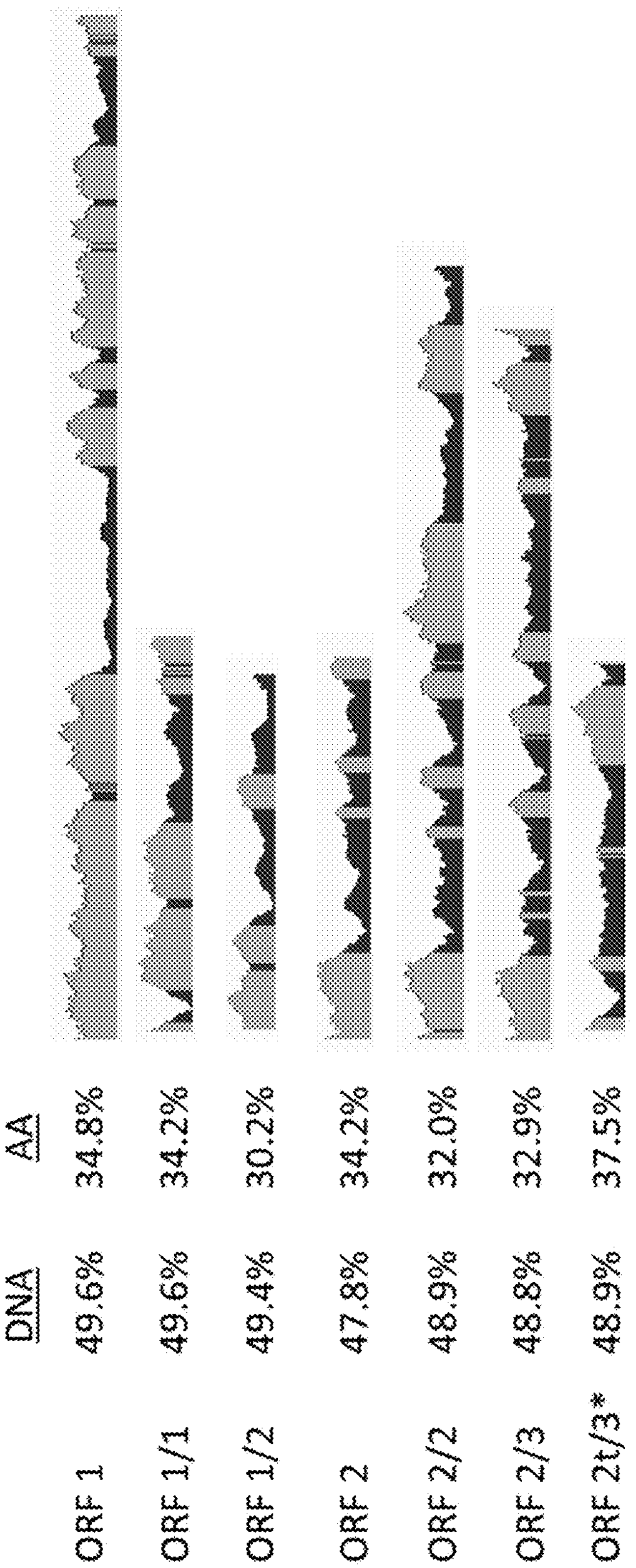
FIG. 19 is a diagram showing pairwise identity for amino acid alignments for putative proteins across the seven *Alphatorquevirus* clades Amino acid sequences for putative proteins from TTV-CT30F, TTV-P13-1, TTV-tth8, TTV-HD20a, TTV-16, TTV-TJN02, and TTV-HD16d were aligned. Pairwise percent identity across a 15-aa sliding window is shown along the length of each alignment. Pairwise identity for both open reading frame DNA sequence and protein amino acid sequence is indicated. (*) Putative ORF2t/3 amino acid sequences were aligned for TTV-CT30F, TTV-tth8, TTV-16, and TTV-TJN02.

The amino acid sequences of the putative proteins in *Alphatorquevirus* were also compared. The DNA sequences showed approximately 47-50% pairwise identity, while the amino acid sequences showed approximately 32-38% pairwise identity (FIG. 19). Interestingly, the representative sequences from the *Alphatorquevirus* clades are able to successfully replicate in vivo and are observed in the human population. This suggests that the amino acid sequences for *Anellovirus* proteins can vary widely while retaining functionalities such as replication and packaging.

Figure 21:
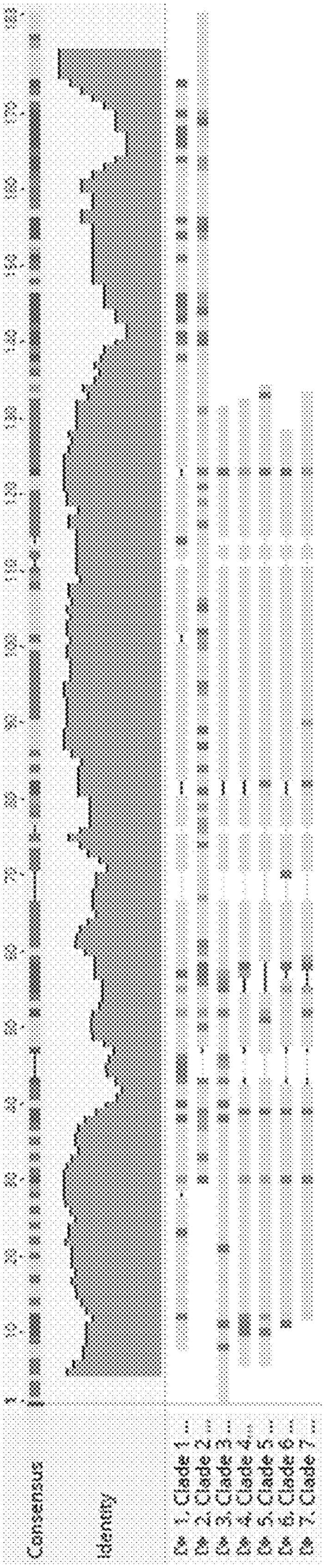
FIG. 21 is a diagram showing an alignment of the GC-rich domains from the seven *Alphatorquevirus* clades. Each *Anellovirus* has a region downstream of the ORFs with greater than 70% GC content. Shown is an alignment of the GC-rich regions from TTV-CT30F, TTV-P13-1, TTV-tth8, TTV-HD20a, TTV-16, TTV-TJN02, and TTV-HD16d. The regions vary in length, but where they do align they have 75.4% pairwise identity.

*Anelloviruses* were found to have regions of local high conservation in the non-coding regions. In the region downstream of the promoter is a 71-bp 5' UTR conserved domain that exhibited 95.2% pairwise identity across the seven *alphatorquevirus* clades (FIG. 20). Downstream of the open reading frames in the 3' non-coding region of *alphatorqueviruses*, there was a region with substantial pairwise identity between the representative sequences. Near the 3' end of this 3' conserved non-coding region is a highly conserved sequence. The *Anelloviruses* also included a GC-rich region having greater than 70% GC content, which exhibited 75.4% pairwise identity in areas where they align (FIG. 21).

Figure 22:
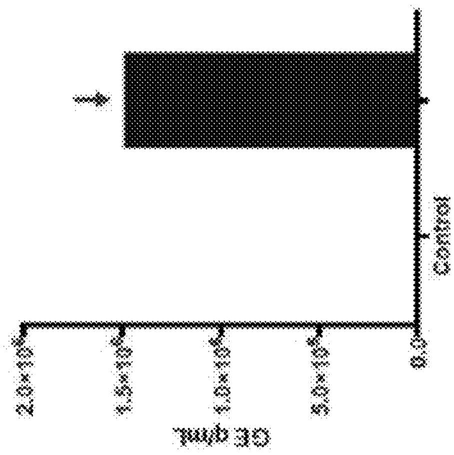
FIG. 22 is a diagram showing infection of Raji B cells with anellosomes encoding a miRNA targeting n-myc interacting protein (NMI). Shown is quantification of genome equivalents of anellosomes detected after infection of Raji B cells or control cells with NMI miRNA-encoding anellosomes.
Figure 23:
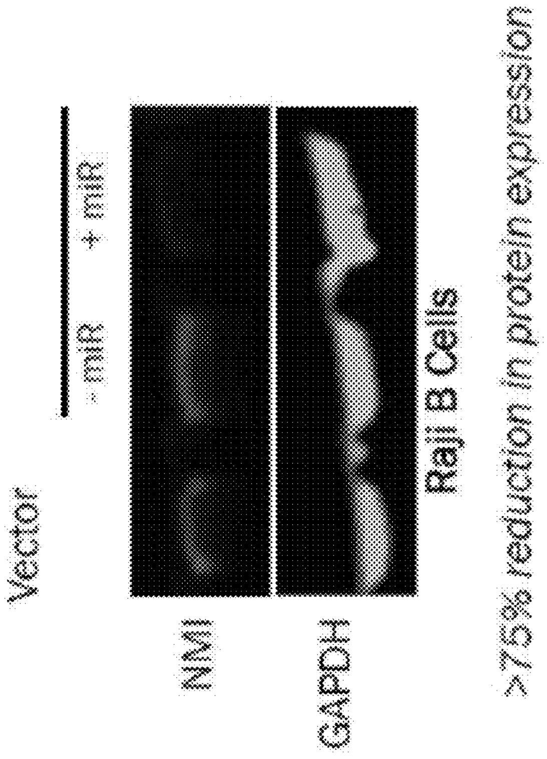
FIG. 23 is a diagram showing infection of Raji B cells with anellosomes encoding a miRNA targeting n-myc interacting protein (NMI). The Western blot shows that anellosomes encoding the miRNA against NMI reduced NMI protein expression in Raji B cells, whereas Raji B cells infected with anellosomes lacking the miRNA showed comparable NMI protein expression to controls.

Example 25: Expression of an Endogenous miRNA from an Anellosome and Deletion of the Endogenous miRNA In one example, anellosomes based on the TTV-tth8 strain were used to infect Raji B cells in culture. These anellosomes comprised a sequence encoding the endogenous payload of the TTV-tth8 *Anellovirus*, which is a miRNA targeting the mRNA encoding n-myc interacting protein (NMI). NMI operates downstream of the JAK/STAT pathway to regulate the transcription of various intracellular signals, including interferon-stimulated genes, proliferation and growth genes, and mediators of the inflammatory response. As shown in FIG. 22, anellosomes were able to successfully infect Raji B cells. Infection of cells with anellosomes comprising the miRNA against NMI resulted in successful knockdown of NMI compared to control cells infected with anellosomes lacking the miRNA against NMI (FIG. 23). Cells infected with anellosome comprising the miRNA against NMI showed a greater than 75% reduction in NMI protein levels compared to control cells. This example demonstrates that an anellosome with a native *Anellovirus* miRNA can knock down a target molecule in host cells.

Figure 24:
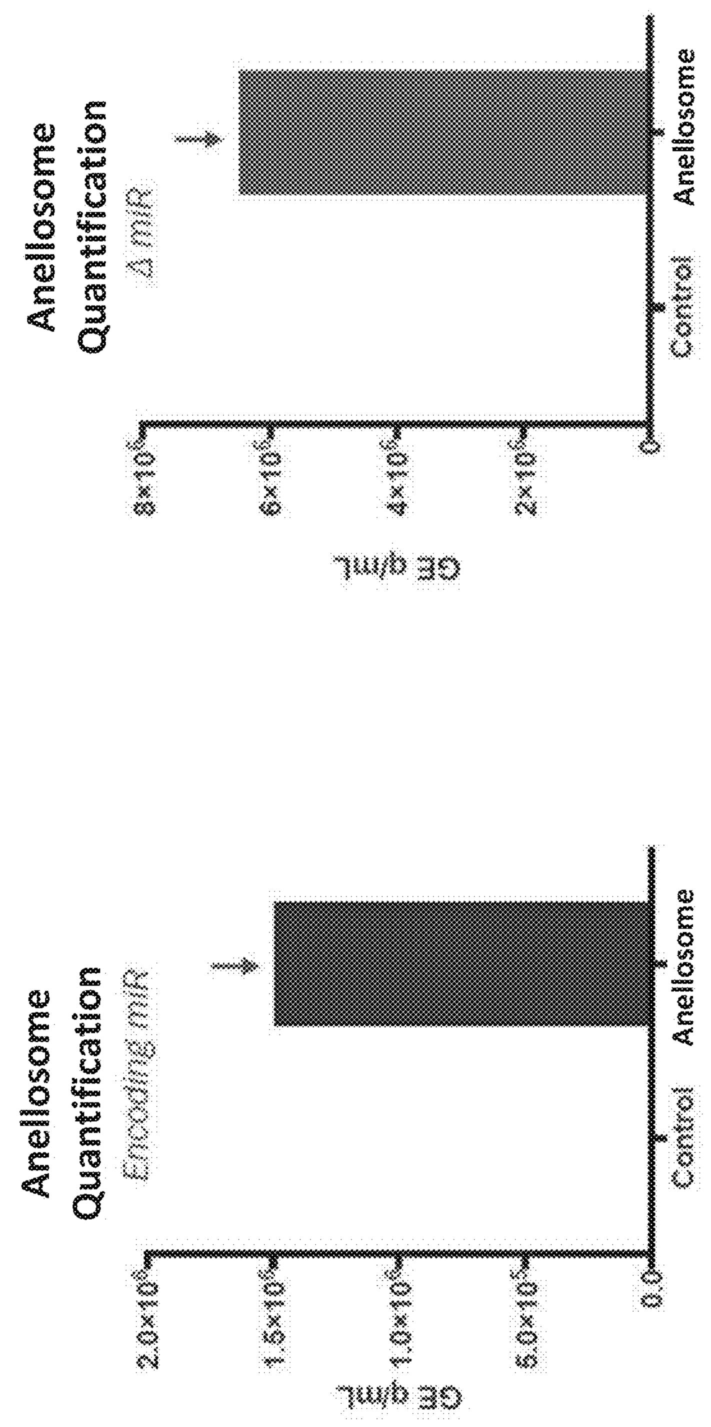
FIG. 24 is a series of graphs showing quantification of anellosome particles generated in host cells after infection with an anellosome comprising an endogenous miRNA-encoding sequence and a corresponding anellosome in which the endogenous miRNA-encoding sequence was deleted.

In another example, the endogenous miRNA of an *Anellovirus*-based anellosome was deleted. The resultant anellosome (A miR) was then used to infect host cells. Infection rate was compared to that of corresponding anellosomes in which the endogenous miRNA was retained. As shown in FIG. 24, anellosomes in which the endogenous miRNA were deleted were still able to infect cells at levels comparable to those observed for anellosomes in which the endogenous miRNA was still present. This example demonstrates that the endogenous miRNA of an *Anellovirus*-based anellosome can be mutated, or deleted entirely, and still generate infectious particles.

Example 26: Localization of *Anellovirus* ORFs

This Example describes novel functionality of various putative ORFs of *Anelloviruses*. In this example, putative open reading frame (ORF) sequences were designed downstream of a tagged protein (i.e. nanoLuciferase) at the N-terminus of each ORF. Each ORF-nLuc plasmid was introduced into 5E+05 adherent cells (Vero or HEK293T) in a 12-well plate by chemical transfection or into 5E+05 cells in suspension by electroporation. After an optimal period of time (e.g., 3-7 days post transfection), cells were fixed with 4% paraformaldehyde (ThermoFisher cat #28908) in PBS and permeabilized with 0.5% Triton X-100 and stained for nLuc with a rabbit polyclonal anti nLuc antibody (kind gift of Promega Corp.) followed by goat anti-rabbit Alexa488 (ThermoFisher cat #A-11008) conjugated secondary antibody. The nuclei were stained with DAPI (ThermoFisher Cat #D3571). The stained cells were visualized on a Zeiss AxioVert A1 with a 20× objective and a monochrome Axiocam 506 camera for tagged protein cellular localization.

Figure 25A:
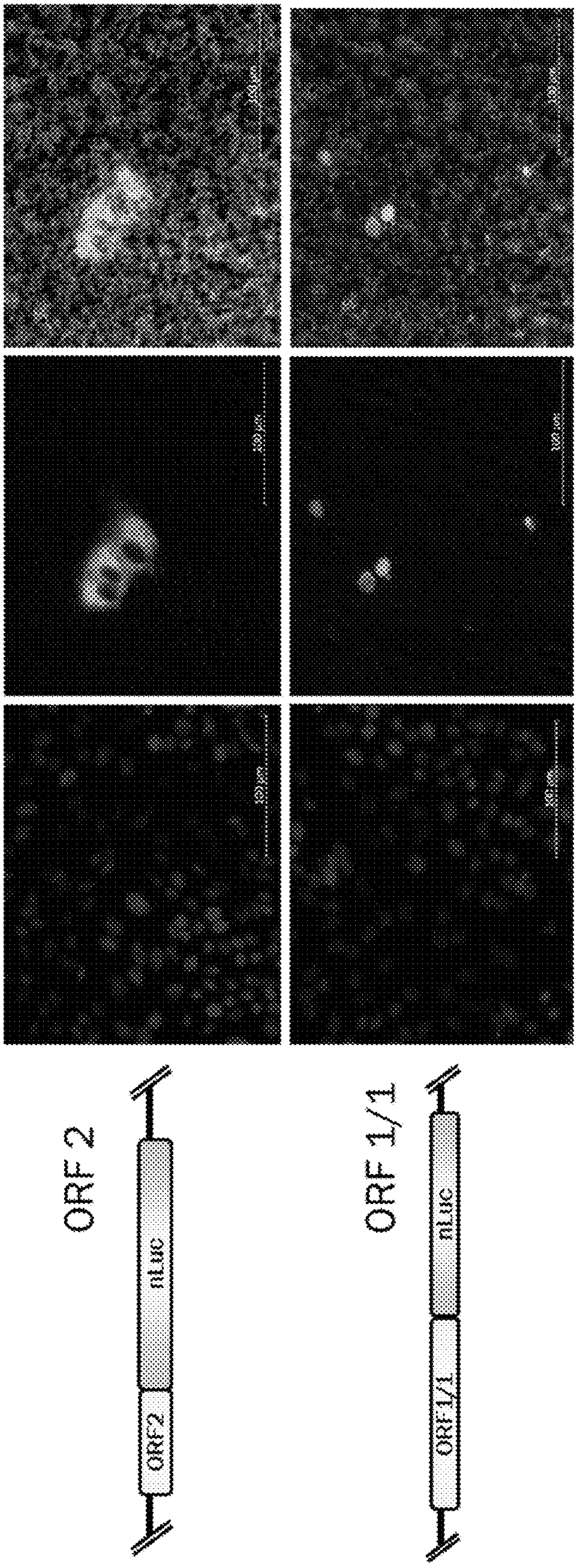
FIGS. 25A-25C are a series of diagrams showing intracellular localization of ORFs from TTMV-LY2 fused to nano-luciferase. (A) In Vero cells, ORF2 (top row) appeared to localize to the cytoplasm while ORF1/1 (bottom row) appeared to localize to the nucleus. (B) In HEK293 cells, ORF2 (top row) appeared to localize to the cytoplasm while ORF1/1 (bottom row) appeared to localize to the nucleus. (C) Localization patterns for ORF1/2 and ORF2/2 in cells.
Figure 25B:
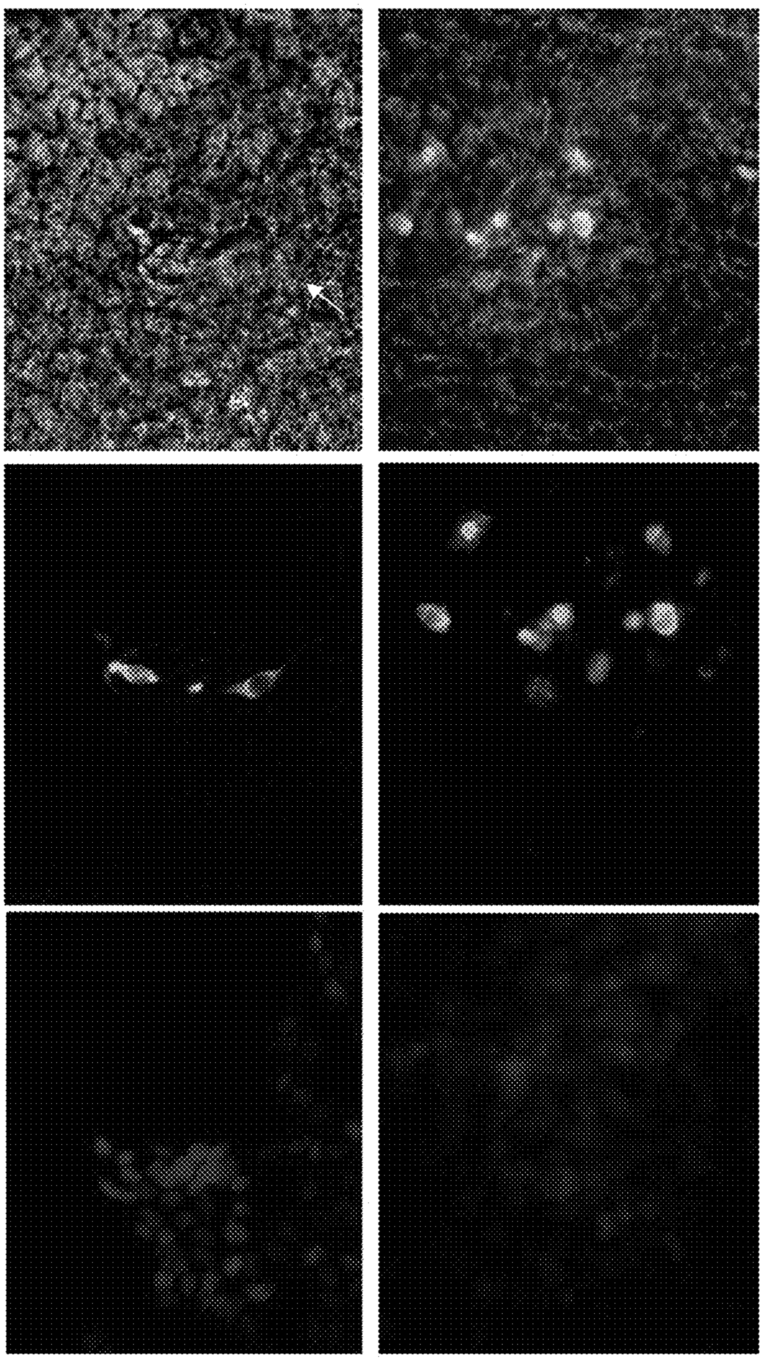
Figure 25C:
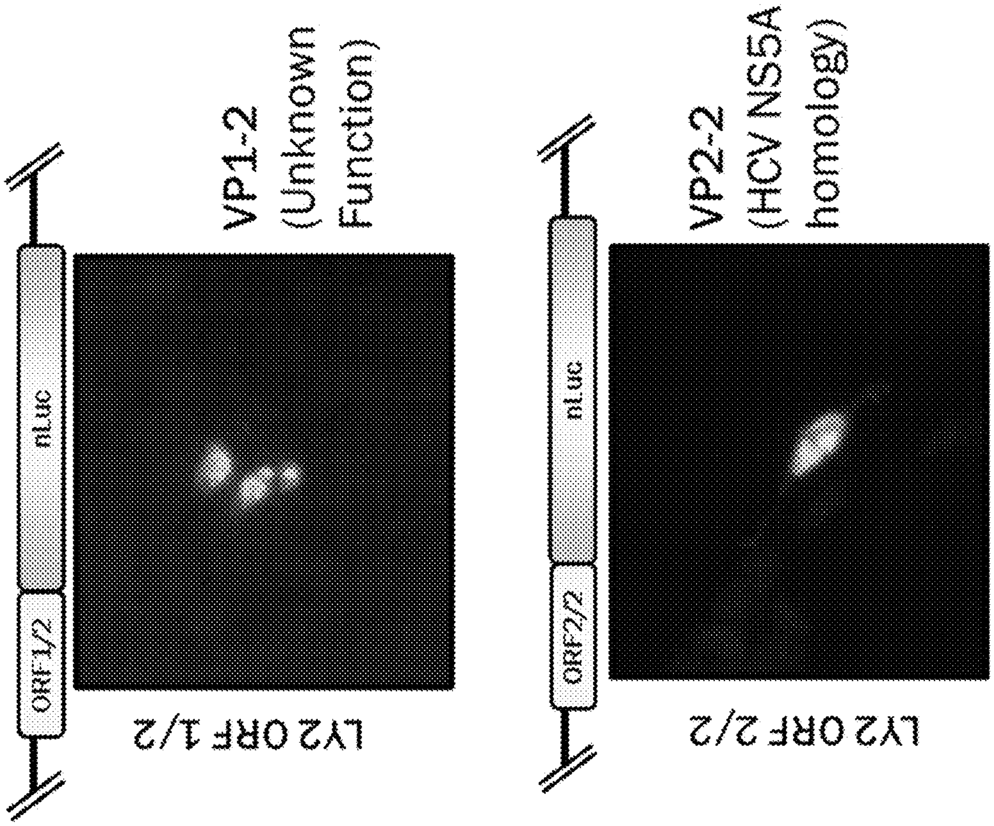

As shown in FIGS. 25A-25B, ORF2 was observed localized the cytoplasm and ORF1/1 was observed localized to the nucleus in both Vero cells and HEK293 cells. FIG. 25C shows the localization for ORF1/2 and ORF2/2.

Example 27: Characterization of Regions Required for Anellosome Development

Figure 26:
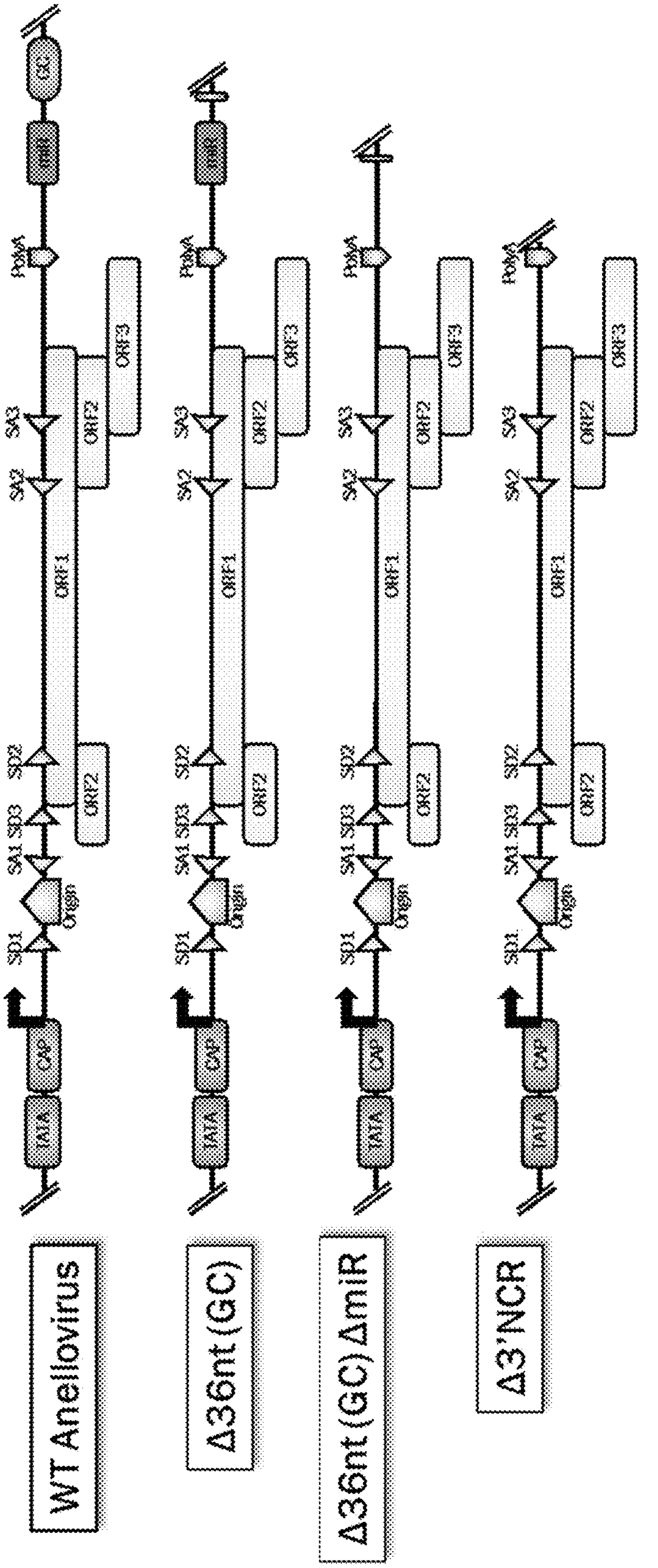
FIG. 26 is a series of diagrams showing sequential deletion controls in the 3' non-coding region (NCR) of TTV-tth8. The top row shows the structure of the wild-type TTV-tth8 *Anellovirus*. The second row shows TTV-tth8 with a deletion of 36 nucleotides in the GC-rich region of the 3' NCR (Δ36nt (GC)). The third row shows TTV-tth8 with the 36 nucleotide deletion and an additional deletion of the miRNA sequence, resulting in a total deletion of 78 nucleotides (Δ36nt (GC) ΔmiR) The fourth row shows TTV-tth8 with a deletion of 171 nucleotides from the 3' NCR, which includes both the 36 nucleotide deletion region and the miRNA sequence (43' NCR).
Figure 27A:
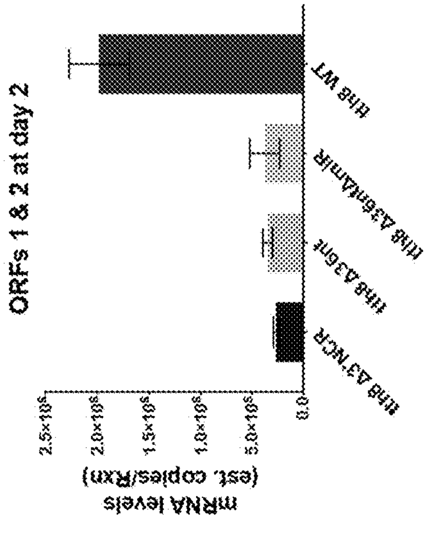
FIGS. 27A-27D are a series of diagrams showing that sequential deletions in the 3' NCR of TTV-tth8 have significant effects on *Anellovirus* ORF transcript levels. Shown are expression of ORF1 and ORF2 at day 2 (A), ORF1/1 and ORF2/2 at day 2 (B), ORF1/2 and ORF2/3 at day 2 (C), and ORF2t3 at day 2 (D).
Figure 27B:
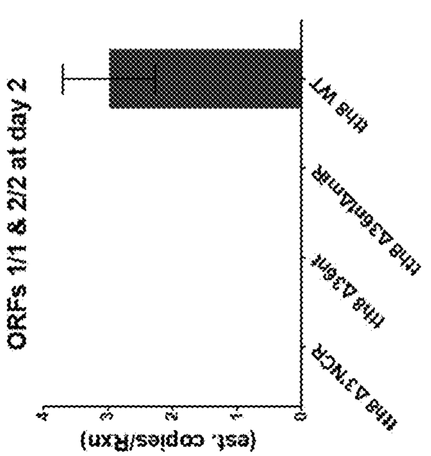
Figure 27C:
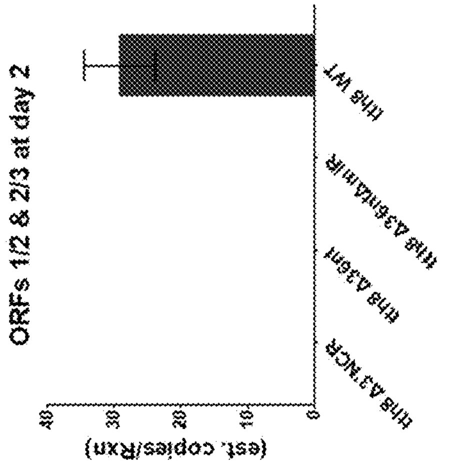
Figure 27D:
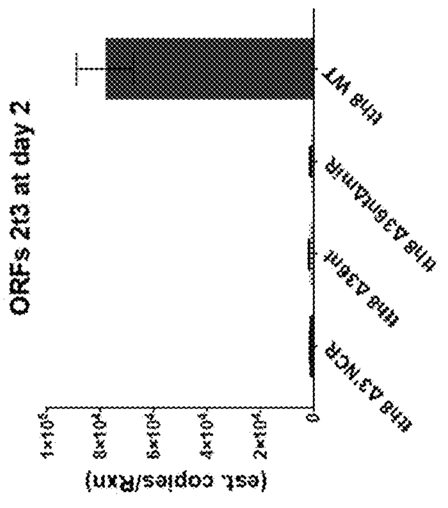

This Example describes deletions in the *Anellovirus* genome to help characterize the minimal genome sufficient for replicating virus and anellosome production. A series of deletions were made in the non-coding region (NCR) of TTV-tth8 downstream of the ORFs (nts 3016 to 3753). A 36-nucleotide (nt) sequence (CGCGCTGCGCGCGCCGCCCAGTAGGGGGAGC-CATGC (SEQ ID NO: 160)) was deleted from the GC region (labeled Δ36nt (GC)). Additionally, a 78-nt pre-microRNA sequence (CCGCCATCTTAAGTAGTT-GAGGCGGACGGTGGCGTGAGTTCAAAGGTCAC-CATCAGCCACA CCTACTCAAAATGGTGG (SEQ ID NO: 161)) was deleted from the 3' NCR (labeled Δ36nt (GC) AmiR) And lastly, an extra 171 nts in the 3'NCR of Δ36nt (GC) was deleted (CTTAAGTAGTT-GAGGCGGACGGTGGCGTGAGTTCAAAGGTCAC-CATCAGCCACACCTACTC AAAATGGTGGACAAT-TTCTTCCGGGTCAAAGGTTACAGCCGCCATGTTAAA ACACGTGACGT ATGACGTCACGGCCGCCAT-TTTGTGACACAAGATGGCCGACTTCCTTCC (SEQ ID NO: 162)) and labeled Δ3'NCR (FIG. 26). 2 μg of circular pTTV-tth8 (WT), pTTV-tth8(Δ36nt (GC)), pTTV-tth8 (Δ36nt (GC) AmiR), pTTV-tth8(Δ3'NCR) DNA plasmids harboring the altered 3'NCRs TTV-tth8 respectively described above, were transfected into HEK293 at 60% confluency in a 12-well plate using lipofectamine 2000, in triplicates. 48 hours after transfection, cell pellets were harvested and lysed to isolate mRNA transcripts (RNeasy, Qiagen cat #74104) and converted to cDNA (High-Capacity cDNA Reverse Transcription kit, ThermoFisher, cat

#4368814). qPCR was performed on all samples measuring viral transcripts expression with each deletion and normalized to the internal control mRNA of GAPDH.

As shown in FIGS. 27A-27D, all three of the deletion mutants significantly inhibited viral transcript expression in vitro. Therefore, the 3' NCR of TTV-tth8 is necessary for Curon production for expression of transgene.

The TTV strain tth8, GeneBank Accession No. AJ620231.1, was deposited as a full-genome sequence. In the GC-rich region, however, there is a stretch of 36 nucleotides annotated as generic Ns. This region is highly conserved among TTV strains and therefore might be important for the biology of these viruses. The DNA sequences of several hundred TTV strains were computationally aligned and used to generate a strong consensus sequence for those 36 nucleotides (CGCGCTGCGCGCGCCGCCCAGTAGGGGGAGCCATGC (SEQ ID NO: 160)). The TTV-tth8 genome sequence referred to herein as the "wild-type" sequence accordingly had this consensus sequence inserted in place of the stretch of 36 Ns listed in the publicly available TTV-tth8 sequence.

Example 28: Anellosome Delivery of Exogenous Proteins In Vivo

This example demonstrates in vivo effector function (e.g. expression of proteins) of anellosomes after administration.

Figure 28A:
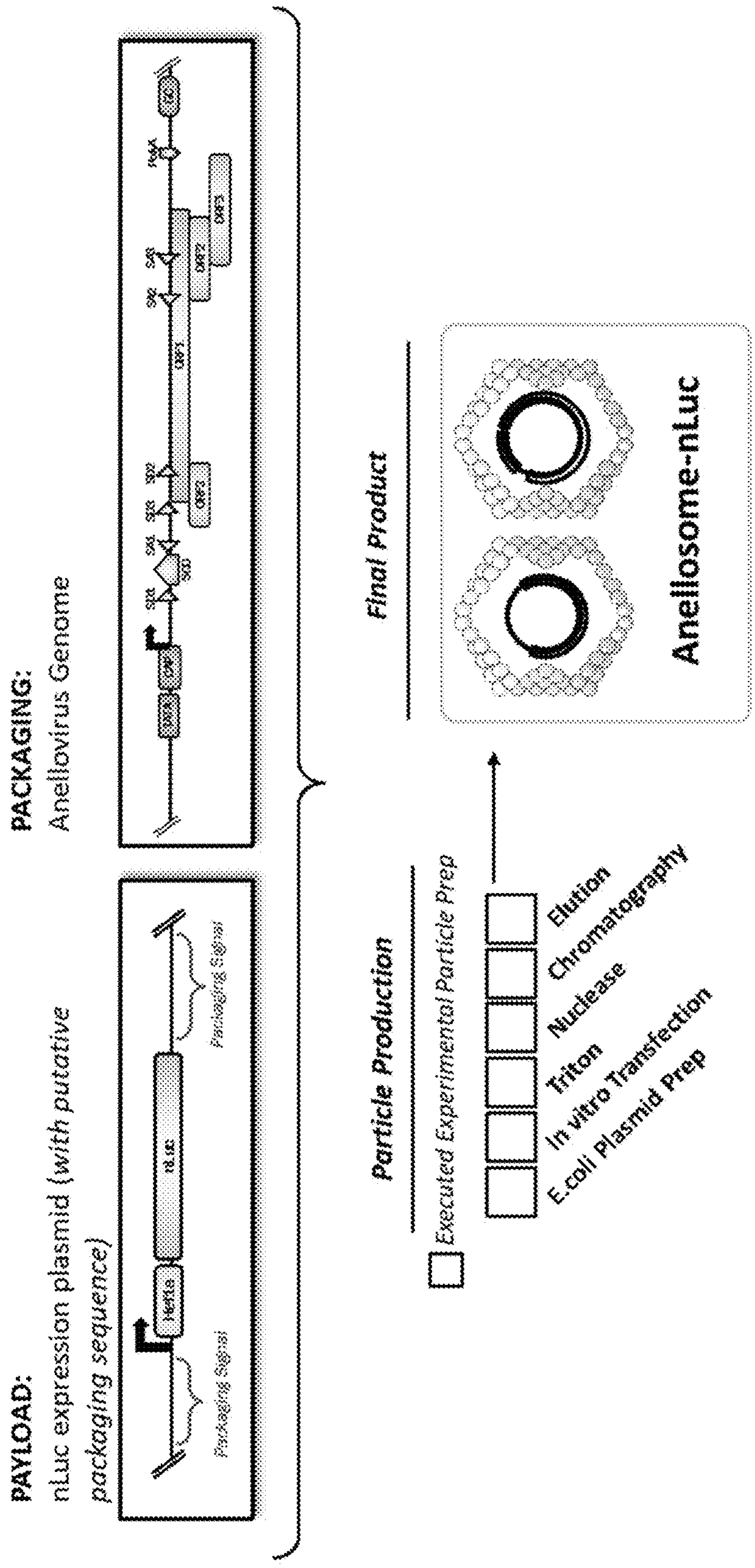
FIGS. 28A-28B are a series of diagrams showing constructs used to produce anellosomes expressing nano-luciferase (A) and a series of anellosome/plasmid combinations used to transfect cells (B)

Anellosomes comprising a transgene encoding nano-luciferase (FIG. 28A) were prepared.

Briefly, five constructs were produced: Construct A—TTMV-LY2 vector±Nanoluciferase; Construct B—Nanoluciferase protein and TTMV-LY2 ORFs; Construct C—Plasmids used in the production of TTMV-LY2 vector; Construct D—Plasmids used in the production of the Nanoluciferase protein and TTMV-LY2 ORFs; and Construct E—sterile PBS. Construct A and Construct B were produced in HEK-293T cells and purified via nuclease treatment, ultrafiltration/diafiltration, and sterile filtration. Construct C and Construct D were produced in *E. coli*, purified via MaxiPrep, and then diluted to a target copy number in PBS followed by sterile filtration. Construct E was produced by sterile filtration of PBS. HEK-293T cells were expanded to Passage 4 from thaw in DMEM+10% FBS on a three- and four-day passage schedule. On Passage 5, cells were seeded at approximately $5\times10^4$ cells/cm' for next day transfection. Cells were co-transfected with constructs using Lipofectamine 2000 one day post seeding. After transfection, cells were incubated to permit anellosome production and anellosomes were harvested.

Figure 28B:
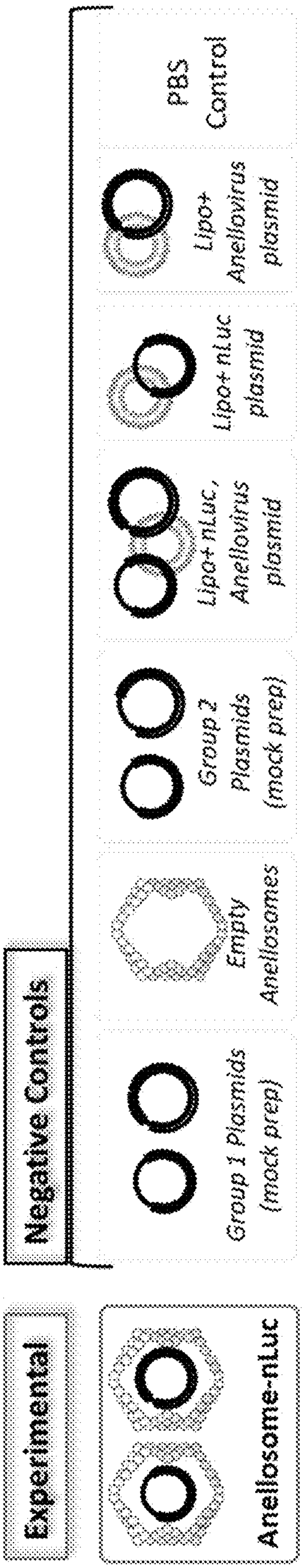

25 uL of anellosome preparation or appropriate controls (as shown in FIG. 28B) were administered to healthy mice intramuscularly. IVIS Spectrum in vivo imaging (PerkinElmer) was performed every day for each animal to visualize and measure luminescence of nano-luciferase protein. The luminescence signal and area were measured at each of days 0, 1, 2, 3, 4, 5, 6, 7, 8, and 9, with corresponding blood samples isolated at each of days 0, 2, 4, 6, and 8. Mice were sacrificed on day 9.

Figure 29A:
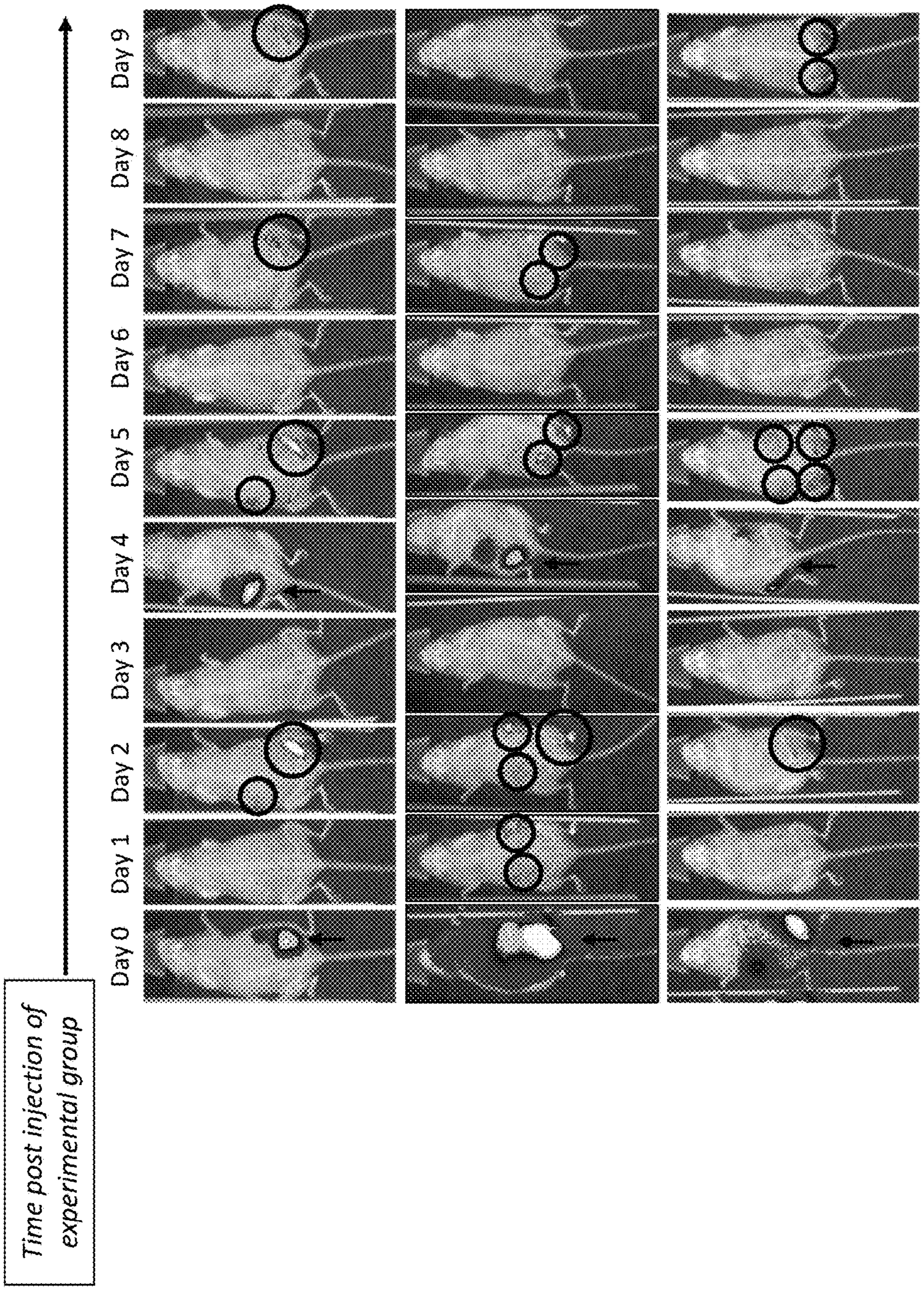
FIGS. 29A-29C are a series of diagrams showing nano-luciferase expression in mice injected with anellosomes. (A) Nano-luciferase expression in mice at days 0-9 after injection. (B) Nano-luciferase expression in mice injected with various anellosome/plasmid construct combinations, as indicated. (C) Quantification of nano-luciferase luminescence detected in mice after injection. Group A received a TTMV-LY2 vector±nano-luciferase. Group B received a nano-luciferase protein and TTMV-LY2 ORFs.
Figure 29B:
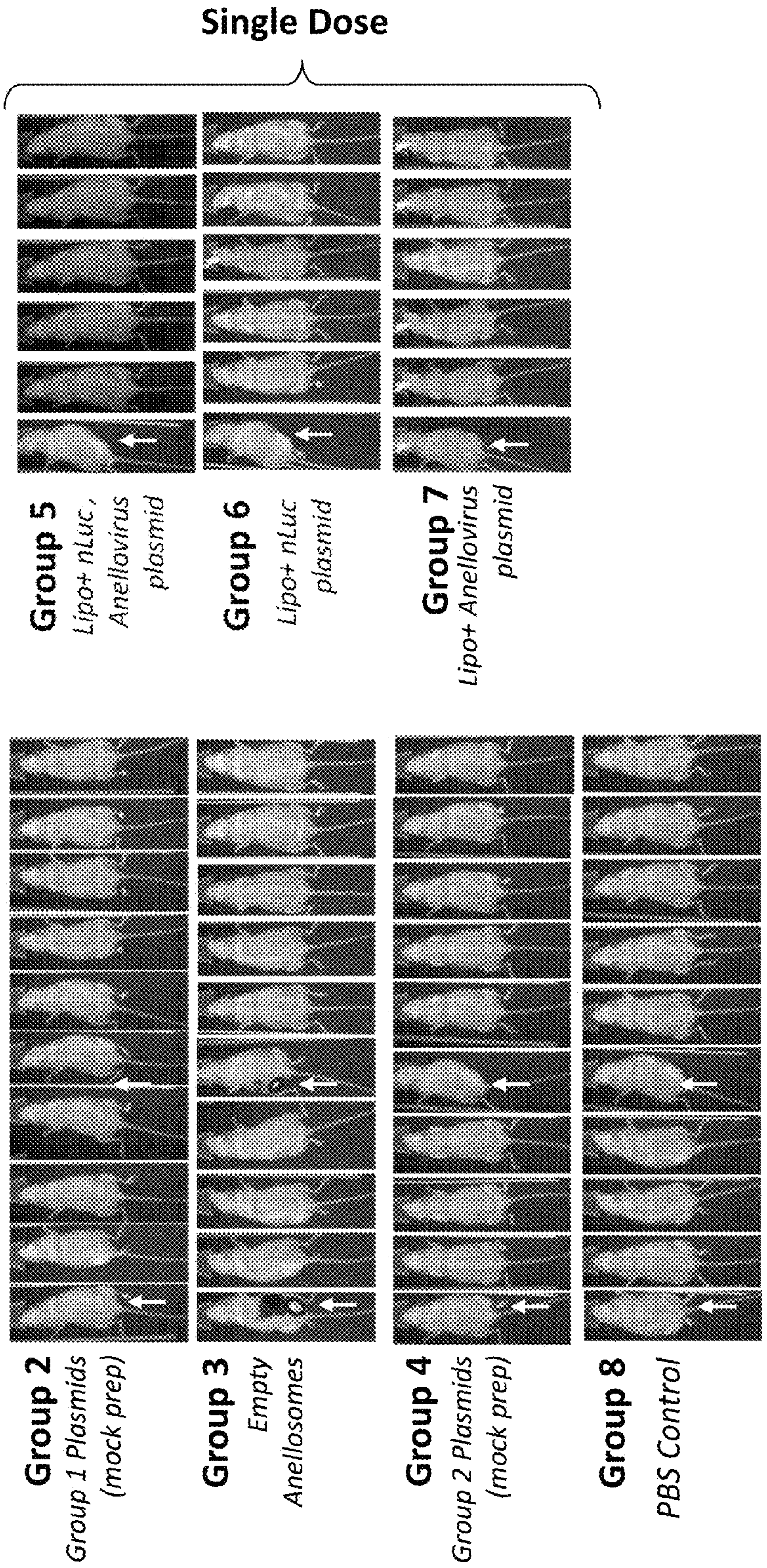
Figure 29C:
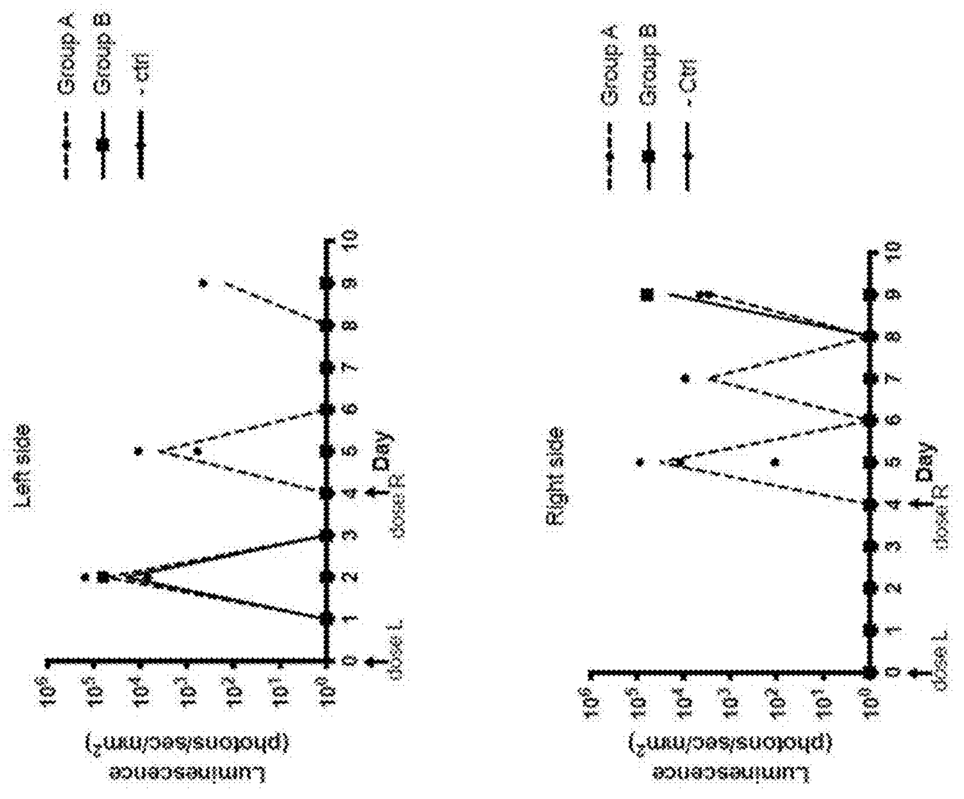

As shown in FIGS. 29A-29C, luminescent signal measured at days 2-9 demonstrated in vivo expression of nanoluciferase delivered via anellosome.

Example 29: Identification of Precursor miRNAs (Pre-mIRs) in *Anelloviruses*

This example describes various computational and experimental approaches to identify novel precursor miRNAs encoded by various *Anelloviruses*.

Computational Methods

Figure 29D:
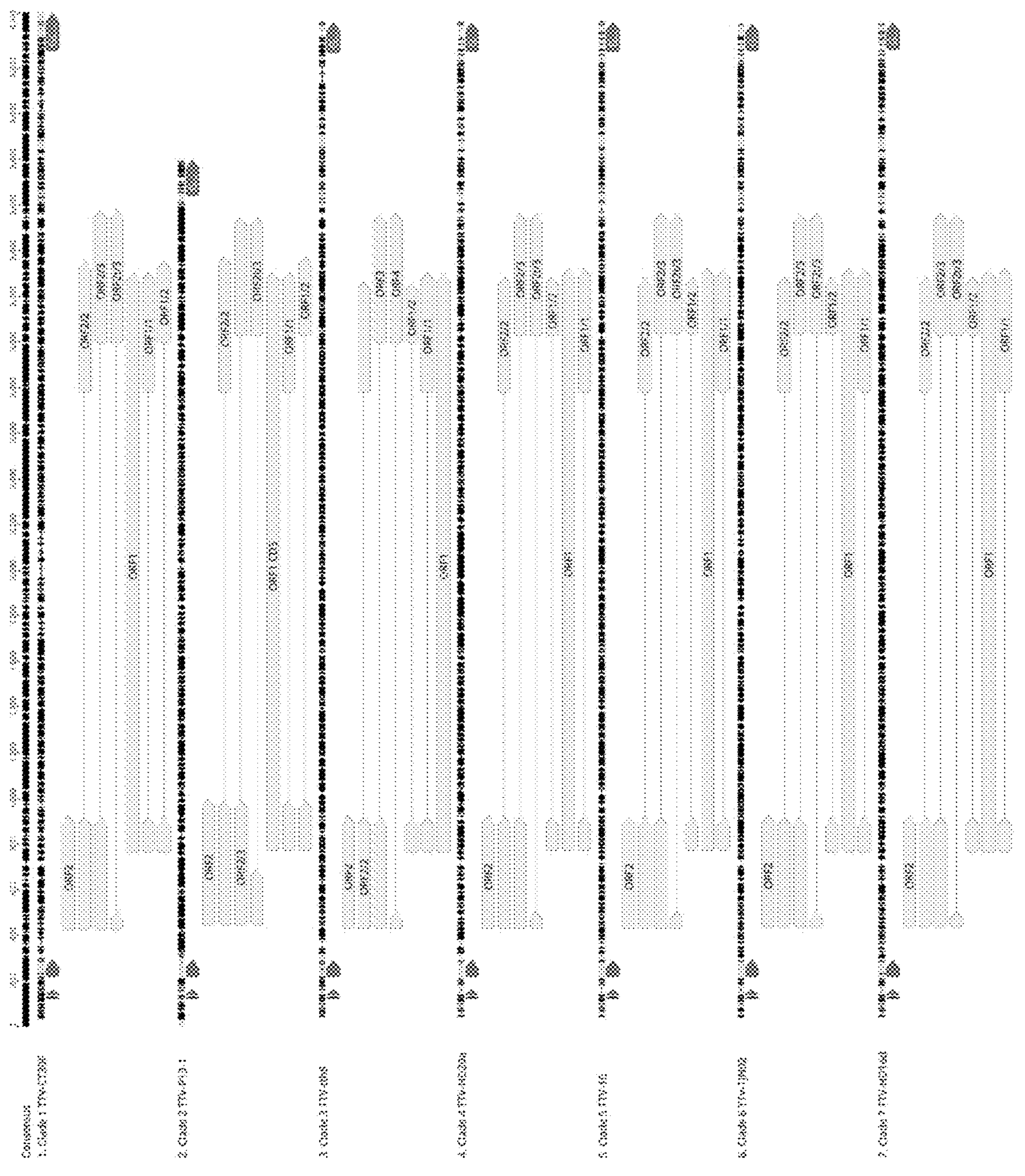
FIG. 29D is a schematic of the genomic organization of representative anellos from seven different *Alphatorquevirus* clades. Sequences for TTV-CT30F, TTV-P13-1, TTV-tth8, TTV-HD20a, TTV-16, TTV-TJN02, and TTV-HD16d were aligned, with key regions annotated. Putative open reading frames (ORFs) are represented in light gray, TATA boxes are represented in dark gray, and key putative regulatory regions are represented in medium gray, including the initiator element, the 5'UTR conserved domain, and the GC-rich region (e.g., as indicated).

*Anellovirus* strains are very diverse from each other at the level of nucleotide sequence. However, *Anellovirus* strains, especially the ones within the same Glade, can show significant similarity to each other in terms of genomic organization of various components such as promoter, GC rich region, non-coding region, and coding regions (see, e.g., FIG. 29D). Herein is described a method in which the pre-miR sequences of various *Anellovirus* strains (whose pre-miR sequences are unknown) are predicted by aligning with *Anellovirus* strains whose pre-miR sequences are already experimentally validated.

Briefly, various publicly available small RNA sequencing data sets for small RNAs from cell lines and various human samples are mined to discover novel pre-miR sequences encoded by various strains of *Anelloviruses*. Publicly available computational tools and algorithms that are based on structure prediction or machine-learning classification, such as the mFold program, miRANDA algorithm, miRScan, miRanalyzer, miRDeep (www.ncbi.nlm.nih.gov/pmc/articles/PMC1559940/, www.frontiersin.org/articles/10.3389/fbioe.2015.00007/full) are used to predict novel miRNAs encoded by various anellos. Northern blots with probes designed to specific miRNA sequences and/or RT-qPCR using primers specific to miRNAs are then used to confirm, validate and quantitate the expression of novel miRNAs.

Experimental Methods

In one example, high throughput small RNA sequencing is performed on human tissue or blood samples that are infected with anellos to discover novel *Anellovirus*-encoded pre-miRNAs. To perform this, RNA is harvested from homogenized human tissue samples or human blood samples Small RNA libraries are prepared and sequenced using Illumina kits and sequencing platforms. Sequencing reads are stored, aligned, and analyzed on BaseSpace Sequence Hub (Illumina).

In a second example, high throughput small RNA sequencing is performed on various cell lines treated with the following conditions to discover novel pre-miRNAs encoded by *Anelloviruses*: (a) cell lines infected with naturally occurring *Anelloviruses*, cell lines transfected with *Anellovirus* genomes synthesized in vitro, and (c) cell lines infected with *Anelloviruses* packaged in vitro using synthetic genomes. Northern blots with probes designed to specific miRNA sequences and/or RT-qPCR using primers specific to miRNAs are used to confirm, validate and quantitate the expression of novel miRNAs.

Example 30: Determination of the Endogenous Target of *Anellovirus* Pre-miRs

Figure 30:
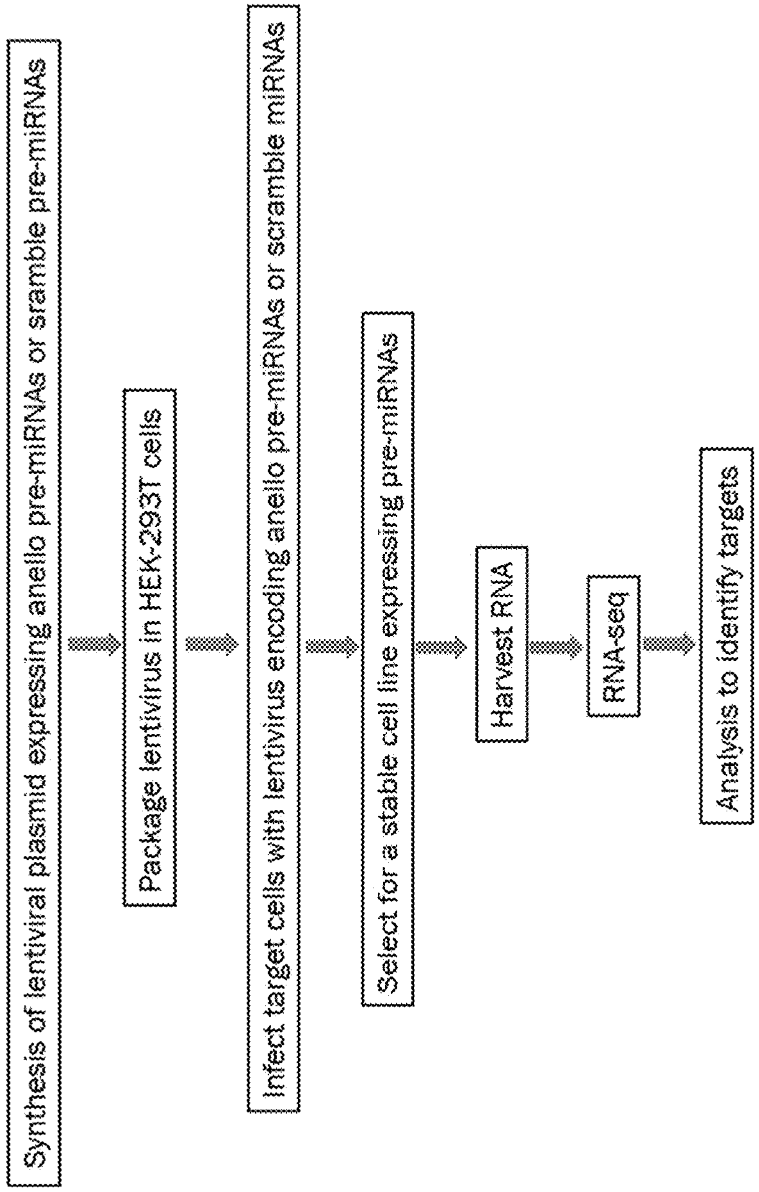
FIG. 30 is a schematic showing an exemplary workflow for determining the endogenous target of *Anellovirus* pre-miRNAs.

This example describes the analysis to determine endogenous targets and potentially therapeutically relevant target pathways of pre-miRs encoded by various strains of *Anelloviruses*. Computationally predicted and/or experimentally validated individual pre-miRNA sequences encoded by various *Anelloviruses* are cloned into a lentiviral vector, driven by a U6 promoter. A non-targeting scramble miRNA sequence, driven by a U6 promoter is also cloned in a similar way that is used as a control. The lentiviral plasmid is cloned such that when packaged, its genome will contain (i) a pre-miRNA sequence driven by a U6 promoter, (ii) a puromycin resistance gene driven by a SV40 promoter, and (iii) a Green Fluorescent Protein (GFP) gene driven by a CMV promoter. Each of these lentiviral plasmids are individually co-transfected into HEK-293T cells along with the lentiviral helper plasmids to package the virus. Six hours after transfection, the medium of the transfected cells is aspirated, washed with PBS once and replaced with fresh medium. This medium containing the lentivirus is harvested 72 hours post transfection. The medium is filtered through 0.4 um filter to remove any cells and then used to infect cell type of interest such as HeLa, Raji, and THP1, in triplicates. Cells containing the integrated lentiviral genomes are selected by treatment with puromycin that is initiated 3 days post infection. RNA is harvested from stably selected cell lines using the RNA extraction kits (Qiagen), followed by reverse transcription into cDNA using reverse transcriptase kit (Thermo Fisher Scientific). cDNA samples are processed to generate indexed short-read libraries. Uniquely indexed short read libraries are multiplexed to sequence to generate about 20 million reads per sample, using the Illumina sequencing platform. Sequencing reads are stored, aligned, and analyzed using the BaseSpace Sequence Hub (Illumina). Targets of each individual candidate pre-miR are determined by comparing expression of genes in cell lines expressing the candidate pre-miR compared to in cell lines expressing the scrambled pre-miR. Ingenuity Pathway analysis is performed to test whether the pre-miRNas target specific pathways, especially therapeutically relevant pathways. A schematic of the workflow described in this Example is shown in FIG. 30.

Example 31: Making an Anellosome Encoding a Native *Anellovirus* Pre-miR

This example describes a process to package either the replicating or non-replicating form of anellosomes expressing native *Anellovirus* pre-miRs.

The genome of the non-replicating form of the anellosome is synthesized containing the following components: (i) origin of replication, (ii) sequence encoding *Anellovirus* pre-miRNA, (iii) RNA polymerase III such as U6 or H1 driving the expression of pre-miRNA, and (iv) packaging signal. This genome is packaged by transfecting into a helper cell line that stably expresses all of the required proteins for viral packaging. The transfected cells are harvested 7 days post transfection and processed to make an anellosome preparation, as described herein. The genome equivalence titer of the anellosome preparation is determined by performing qPCR, as described herein. An appropriate dose of the anellosome preparation is then used for downstream applications.

The genome of the replicating form of the anellosome can be synthesized, for example, by generating the native *Anellovirus*, except that the expression of pre-miRNA sequence is manipulated using an exogenous promoter such as U6 or tissue specific promoters. The genome is packaged by transfecting into HEK-293T cells. The transfected cells are harvested 7 days post transfection and processed to make an anellosome preparation, as described herein. The genome equivalence titer of the anellosome preparation is determined by performing qPCR, as described herein. An appropriate dose of the anellosome preparation is used for downstream applications.

Example 32: Utilizing *Anellovirus* Pre-miRs a Tumor Suppressor in an In Vitro Cell Culture Model This example describes studies to confirm the phenotypic effect of candidate pre-miRs identified as tumor suppressive from analysis, e.g., as described in Example 29.

Candidate pre-miRNAs having a tumor suppressive effect are identified based on analysis as described in Example 29. Anellosome preparations of the replicating form of anellosomes encoding these candidate pre-miRNAs, as well as scrambled pre-miRNAs, are prepared as described in Example 31. Cancer cell lines from the NCI-60 cancer cell line panel are plated in 96 well plates. When 30% confluent, these cell lines are treated with anellosomes comprising the candidate pre-miRs or scrambled pre-miRs at a dosage of five genome equivalents per cell. The anellosome-containing medium is aspirated five hours after infection, followed by washing with PBS twice, and replacing with fresh medium. Alamar blue assay is performed on the treated cells three days after treatment to determine which of the pre-miRs inhibit the proliferation of the cancer cell lines.

Example 33: Utilizing *Anellovirus* Pre-miRs as Tumor Supppresors In Vivo

This example describes in vivo experiments to confirm the tumor suppressive effect for shortlisted candidate tumor suppressive *Anellovirus* pre-miRs and cancer cell lines from in vitro analysis, as described in Example 32.

Xenografts are generated by subcutaneously injecting cancer cell lines shortlisted from the analysis described in Example 32, along with Matrigel, into the flanks of athymic mice. Once the xenograft tumors become palpable, local tumor injection of $3 \times 10^6$ genome equivalents of anellosomes encoding tumor suppressive pre-miRNAs or scramble pre-miRNA is performed. Effect of anellosome injection on tumor growth is determined by routine tumor growth measurements for three weeks, tumor weight measurement of the xenograft tumor at the end of the experiment, as well as by BrdU incorporation assays.

Example 34: Tandem Copies of the *Anellovirus* Genome

Figure 31B:
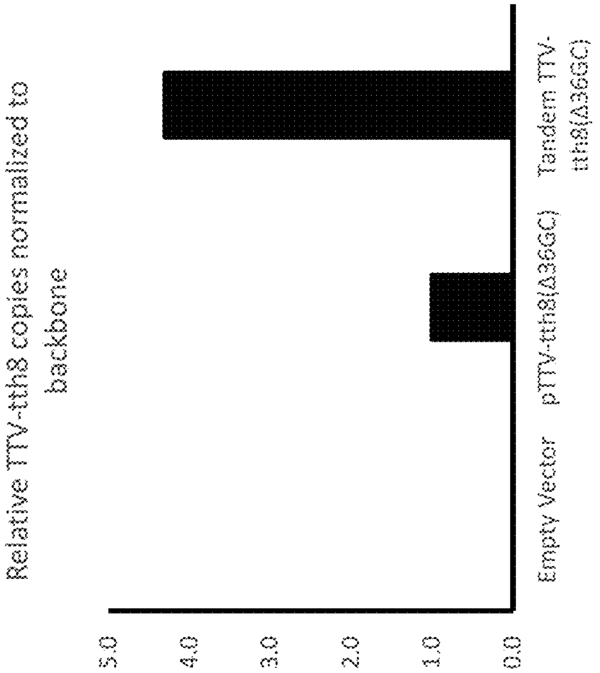
FIGS. 31A-31B are a series of diagrams showing that a tandem *Anellovirus* plasmid can increase *anellovirus* or anellosome production. (A) Plasmid map for an exemplary tandem *Anellovirus* plasmid. (B) Transfection of HEK293T cells with a tandem *Anellovirus* plasmid resulted in production of four times the number of viral genomes compared to single-copy harboring plasmids.
Figure 31A:
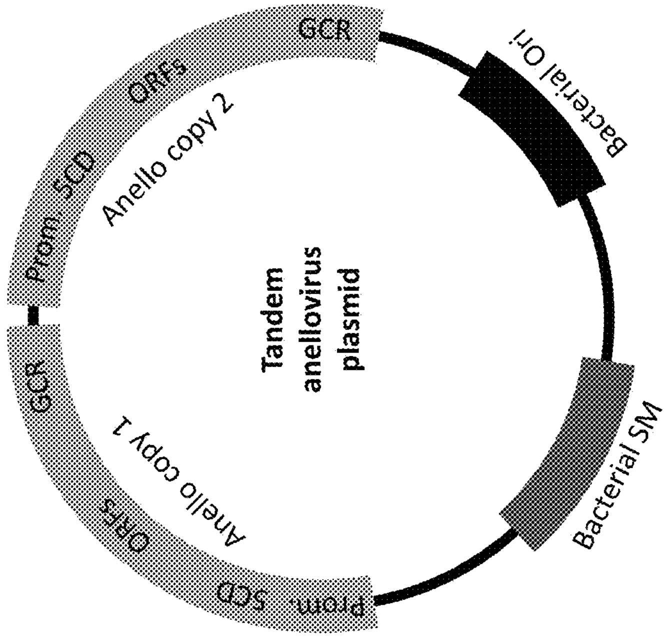

This example describes plasmid-based expression vectors harboring two copies of a single anelloviral genome, arranged in tandem such that the GC-rich region of the upstream genome is near the 5' region of the downstream genome (FIG. 31A).

*Anelloviruses* replicate via rolling circle, in which a replicase (Rep) protein binds to the genome at an origin of replication and initiates DNA synthesis around the circle. For *anellovirus* genomes contained in plasmid backbones, this requires either replication of the full plasmid length, which is longer than the native viral genome, or recombination of the plasmid resulting in a smaller circle comprising the genome with minimal backbone. Therefore, viral replication off of a plasmid can be inefficient. To improve viral genome replication efficiency, plasmids were engineered with tandem copies of TTV-tth8 and TTMV-LY2. These plasmids presented every possible circular permutation of the anelloviral genome: regardless of where the Rep protein binds, it will be able to drive replication of the viral genome from the upstream origin of replication to the downstream origin. A similar strategy has been used to produce porcine *Anelloviruses* (Huang et al., 2012, Journal of Virology 86 (11) 6042-6054).

Tandem TTV-tth8 was assembled by sequentially cloning copies of the genome into a plasmid backbone, leaving 12 bp of non-viral DNA between the two sequences. Several TTV-tth8 variants were assembled into tandem plasmids, including wild-type and TTV-tth8(Δ36GC) (i.e., a TTV-tth8 genome engineered to include the 36-nucleotide GC-rich sequence described herein), which is missing 36 base pairs from the GC-rich region. Tandem TTMV-LY2 was assembled via Golden-gate assembly, simultaneously incorporating two copies of the genome into a backbone and leaving no extra nucleotides between the genomes.

Plasmid harboring tandem copies of TTV-tth8(Δ36GC) was transfected into HEK239T cells. Cells were incubated for five days, then lysed using 0.1% Triton X-100 and treated with nucleases to digest DNA not protected by viral capsids. qPCR was then performed using Taqman probes for the TTV-tth8 genome sequence and the plasmid backbone. TTV-tth8 genome copies were normalized to backbone copies. As shown in FIG. 31B, tandem TTV-tth8 produced more than four times the number of viral genomes than single-copy harboring plasmids. When accounting for the doubled number of TTV-tth8 genome sequences, the tandem plasmid produced more than twice as many newly synthesized genome copies per transfected copy. These data demonstrated that engineering tandem Anelloviral genomes can increase viral genome replication and can be used as a strategy for increasing *Anellovirus* production.

Example 35: In Vitro Circularized *Anellovirus* Genomes

This example describes constructs comprising circular, double stranded Anelloviral genome DNA with minimal non-viral DNA. These circular viral genomes more closely match the double-stranded DNA intermediates found during wild-type *Anellovirus* replication, and therefore present a more optimal template for *Anellovirus* production.

In one example, plasmids harboring TTV-tth8 variants and TTMV-LY2 were digested with restriction endonucleases recognizing sites flanking the genomic DNA. The resulting linearized genomes were then ligated to form circular DNA. These ligation reactions were done with varying DNA concentrations to optimize the intramolecular ligations. The ligated circles were either directly transfected into mammalian cells, or further processed to remove non-circular genome DNA by digesting with restriction endonucleases to cleave the plasmid backbone and exonucleases to degrade linear DNA. For TTV-tth8, XmaI endonuclease was used to linearize the DNA; the ligated circle contained 53 bp of non-viral DNA between the GC-rich region and the 5' non-coding region. For TTMV-LY2, the type IIS restriction enzyme Esp3I was used, yielding a viral genomic DNA circle with no non-viral DNA. This protocol was adapted from previously published circularizations of TTV-tth8 (Kincaid et al., 2013, PLoS Pathogens 9(12): e1003818). To demonstrate the improvements in *Anellovirus* production, circularized TTV-tth8 and TTMV-LY2 were transfected into HEK293T cells. After 7 days of incubation, cells were lysed, and qPCR was performed to compare the levels of *anellovirus* genome between circularized and plasmid-based anelloviral genomes. Increased levels of Anelloviral genomes show that circularization of the viral DNA is a useful strategy for increasing *Anellovirus* production.

Figure 31C:
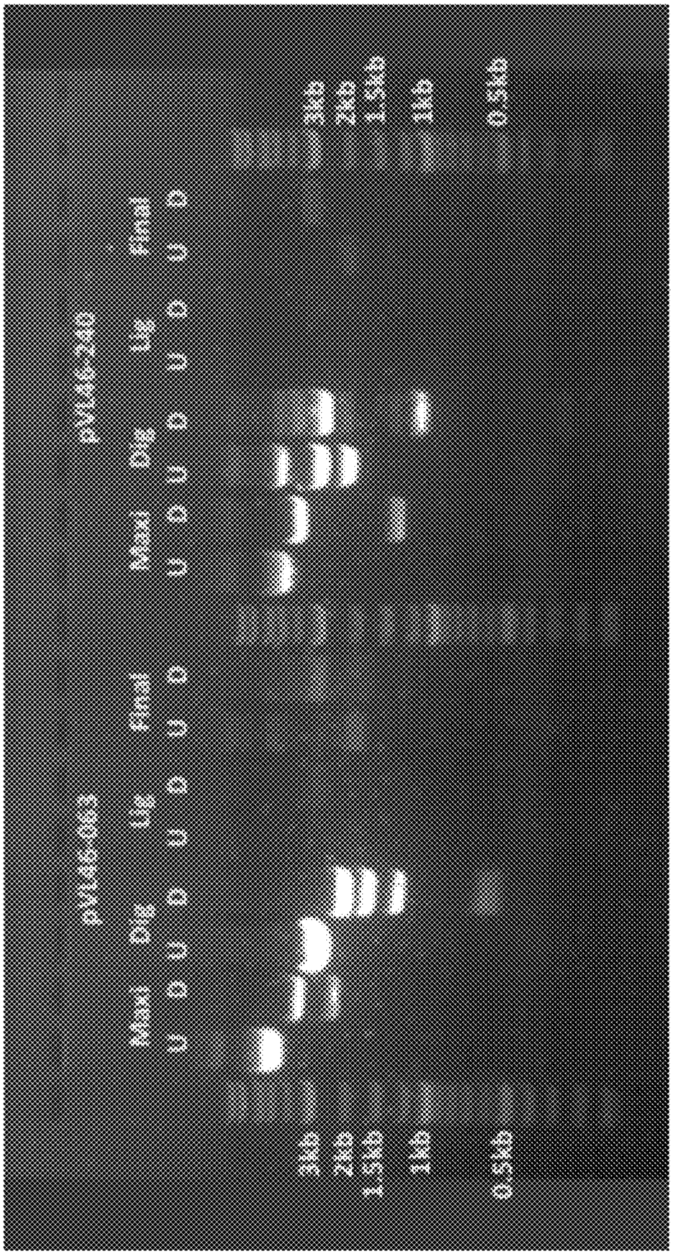
FIG. 31C is a gel electrophoresis image showing circularization of TTMV-LY2 plasmids pVL46-063 and pVL46-240.

In another example, TTMV-LY2 plasmid (pVL46-240) and TTMV-LY2-nLuc were linearized with Esp3I or EcoRV-HF, respectively. Digested plasmid was purified on 1% agarose gels prior to electroelution or Qiagen column purification and ligation with T4 DNA Ligase. Circularized DNA was concentrated on a 100 kDa UF/DF membrane before transfection. Circularization was confirmed by gel electrophoresis, as shown in FIG. 31C. T-225 flasks were seeded with HEK293T at $3\times10^4$ cells/$cm^2$ one day prior to lipofection with Lipofectamine 2000. Nine micrograms of circularized TTMV-LY2 DNA and 50 μg of circularized TTMV-LY2-nLuc were co-transfected one day post flask seeding. As a comparison, an additional T-225 flask was co-transfected with 50 μg of linearized TTMV-LY2 and 50 μg of linearized TTMV-LY2-nLuc.

Figure 31D:
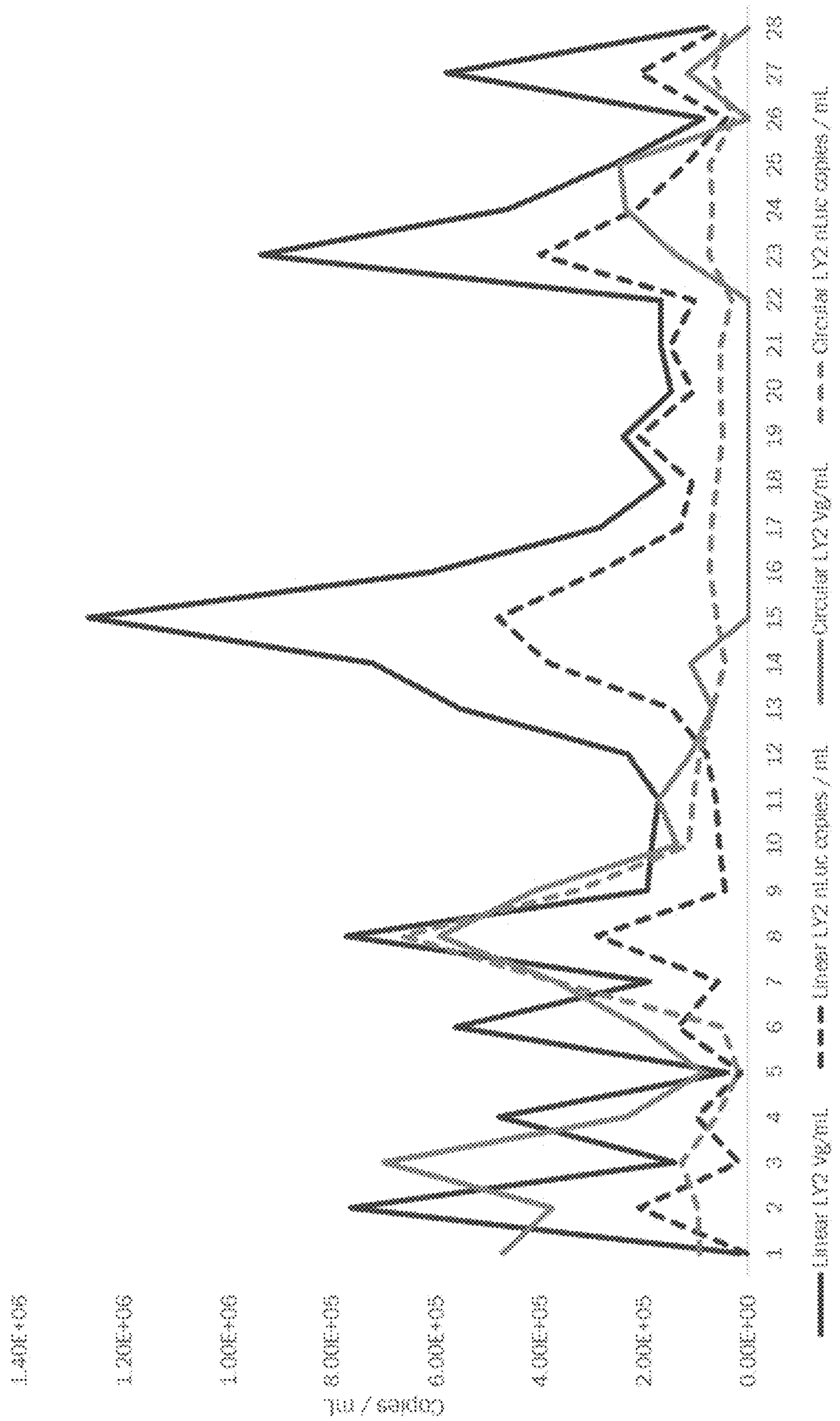
FIG. 31D is a chromatogram showing copy numbers for linear and circular TTMV-LY2 constructs, as determined by size exclusion chromatography (SEC).

Anellosome production proceeded for eight days prior to cell harvest in Triton X-100 harvest buffer. Harvested cells were nuclease treated prior to sodium chloride adjustment and 1.2 μm/0.45 μm normal flow filtration. Clarified harvest was concentrated and buffer exchanged into PBS on a 750 kDa MWCO mPES hollow fiber membrane. The TFF retentate was filtered with a 0.45 μm filter before loading on a Sephacryl S-500 HR SEC column pre-equilibrated in PBS. Anellosomes were processed across the SEC column at 30 cm/hr. Individual fractions were collected and assayed by qPCR for viral genome copy number and transgene copy number, as shown in FIG. 31D. Viral genomes and transgene copies were observed beginning at the void volume, Fraction 7, of the SEC chromatogram. A residual plasmid peak was observed at Fraction 15. Copy number for TTMV-LY2 genomes and TTMV-LY2-nLuc transgene were in good agreement for Anellosomes produced using circularized input DNA at Fraction 7-Fraction 10, indicating packaged Anellosomes containing nLuc transgene. SEC fractions were pooled and concentrated using a 100 kDa MWCO PVDF membrane and then 0.2 μm filtered prior to in vivo administration.

Circularization of input Anellosome DNA resulted a threefold increase in a percent recovery of nuclease protected genomes throughout the purification process when compared to linearized Anellosome DNA, indicating improved manufacturing efficiency using the circularized input Anellosome DNA as shown in Table 46.

TABLE 46

Purification Process Yields

| Step | Linearized TTMV-LY2 Total viral genome copies | Linearized TTMV-LY2 Total nLuc transgene genome copies | Circularized TTMV-LY2 Total viral genome copies | Circularized TTMV-LY2 Total nLuc transgene genome copies |
|---|---|---|---|---|
| Harvest pre-nuclease | 2.78E+12 | 2.17E+12 | 1.04E+11 | 4.39E+11 |
| Clarified Harvest | 9.96E+09 | 5.48E+09 | 6.55E+08 | 9.81E+08 |
| TFF | 1.01E+10 | 7.66E+09 | 2.58E+08 | 3.56E+08 |
| SEC | 3.18E+07 | 8.73E+06 | 9.16E+06 | 7.75E+06 |
| UF/DF | 8.82E+06 | 3.25E+06 | 1.78E+06 | 2.73E+06 |
| Sterile Filtration | 5.60E+06 | 2.64E+06 | 8.66E+05 | 1.63E+06 |
| Purification Process Yield (%) | 0.0002% | 0.0001% | 0.0006% | 0.0004% |

Example 36: Modelling ORF1 and Identification of Conserved Residues and Domains This example describes in silico modelling of ORF1 proteins of Betatorqueviruses and defining putative domains based upon structural motifs and amino acid conservation/similarity.

Figure 33:
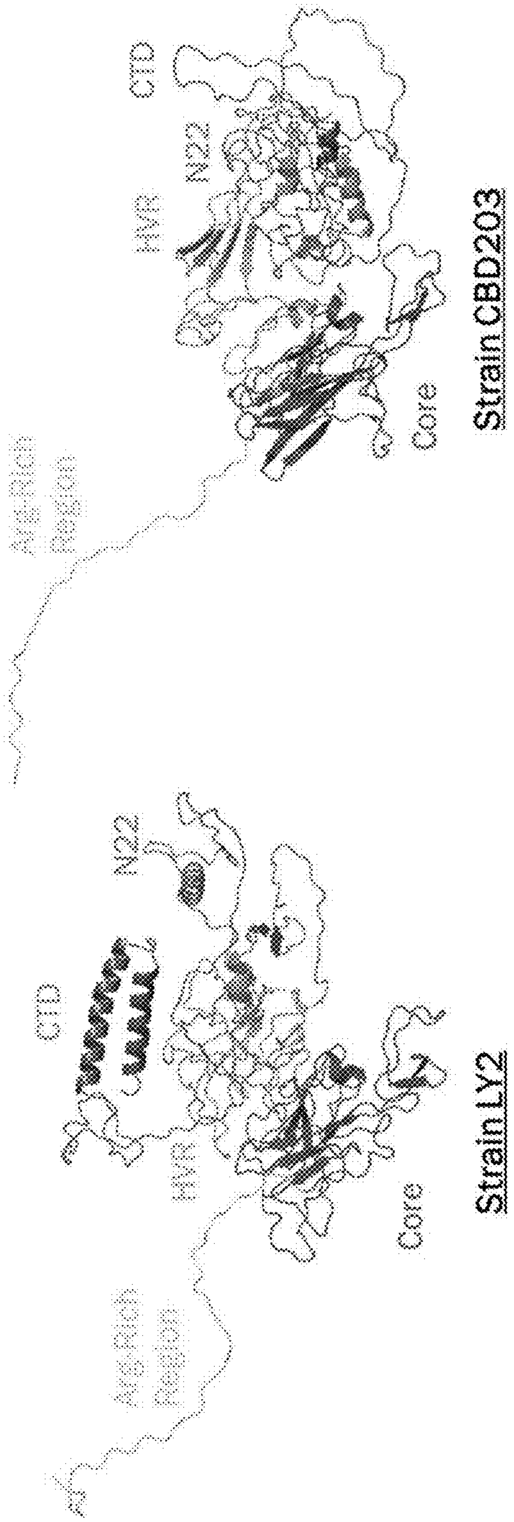
FIG. 33 is a series of diagrams showing ORF1 structures from *Anellovirus* strains LY2 and CBD203. Putative domains are labeled: arginine-rich region (arg-rich; yellow), core region comprising a jelly-roll domain (red), hypervariable region (HVR; cyan), N22 region (green), and C-terminal domain (CTD; gray).

The ORF1 protein is predicted to be the major capsid protein of *Anelloviruses*, based upon the presence of an arginine-rich region and the high presence of beta-sheets in secondary structure prediction using PSlpred (bioinf.cs.ucl.ac.uk/psipred/). RaptorX (raptorx.uchicago.edu/) was used for structure prediction and contact prediction for the sequences of eight Betatorqueviruses. *Betatorquevirus* ORF1 sequences were used as they are shorter (~650 amino acids) than *Alphatorqueviruses* (~750 amino acids) which fewer regions predicted to be unstructured. Five of the predicted structures contained elements of similarity which were used to identify putative domains of ORF1 (FIG. 33). ORF1 was divided into five regions—the arginine-rich region, the putative core (jelly-roll domain), the hypervariable region, the N22 region, and the C-terminal domain.

The structural model of the *Betatorquevirus* strain CBS203 was used to display the residues/structural regions that have some conservation among the *Betatorquevirus* family. To analyze conserved residues, 110 *Betatorquevirus* ORF1 sequences were aligned in Geneious using the ClustalW alignment algorithm. Residues were then assessed for conservation by percent identity and similarity using the BLOSUM62 matrix with a threshold of 1. Residues which possessed similarity of greater than 60% of all strains in the alignment were highlighted on the structural model (FIG. 34). In total, 26 residues (~4%) possessed amino acid similarity with 100% of aligned sequences. The 80% and 60% cut-offs contained 23.7% and 36.7% of total residues respectively.

Figure 35:
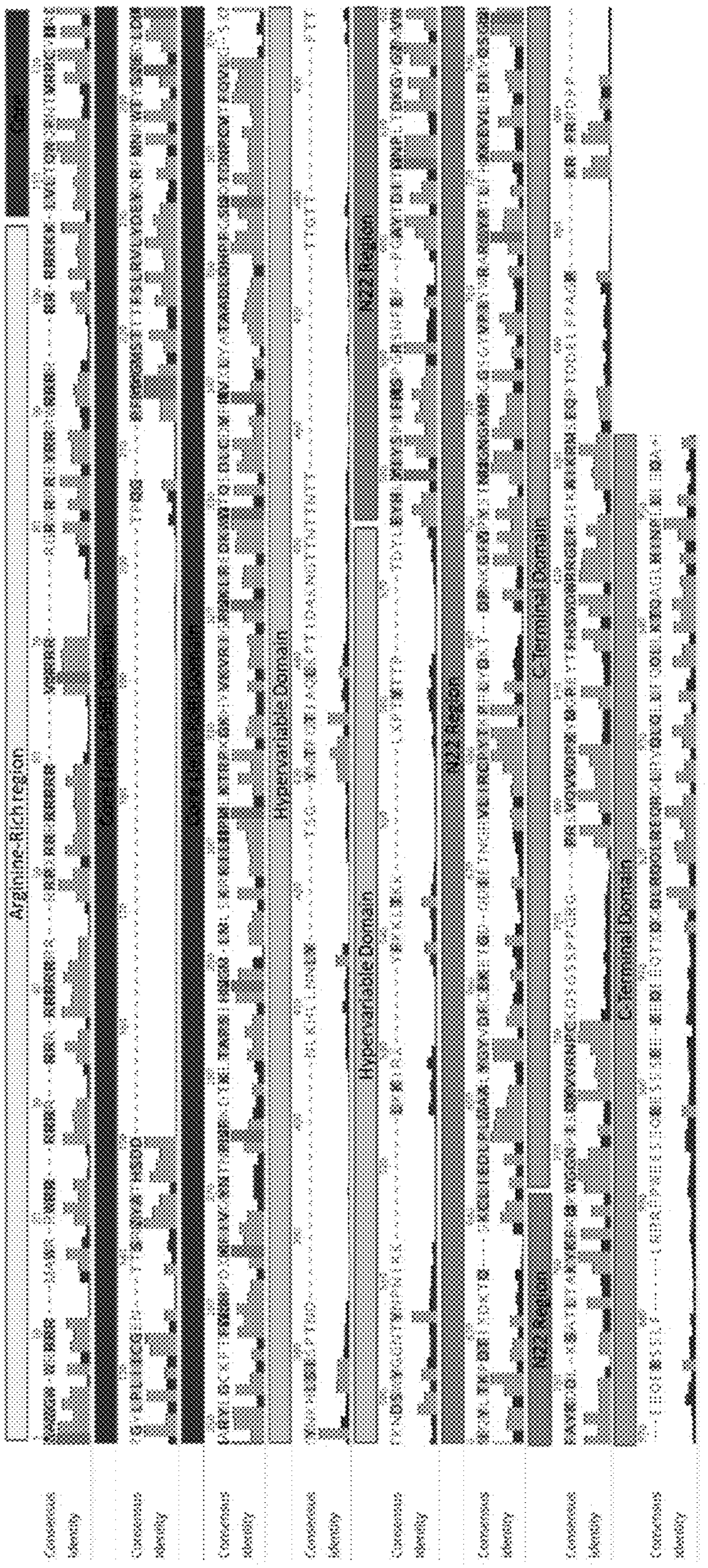

A similar alignment algorithm and similarity determination was conducted on 258 strains of *Alphatorqueviruses*. The similarity and identity were displayed in the consensus sequence from the alignment and putative domains were assigned based upon primary sequence alignment with the Betatorqueviruses (FIG. 35). *Alphatorqueviruses* possessed 29 residues (3.9%) which were 100% similar, remarkably consistent with the observation with Betatorqueviruses. Interestingly, *Alphatorqueviruses* possess a higher percentage of residues, when compared to Betatorqueviruses with at least 80% (30.9% of residues) or 60% (42.9% of residues) similarity.

Example 37: Production of Anellosomes Containing Chimeric ORF1 with Hypervariable Domains from Different Torque Teno Virus Strains This example describes domain swapping of hypervariable regions of ORF1 to produce chimeric anellosomes containing the ORF1 arginine-rich region, jelly-roll domain, N22, and C-terminal domain of one TTV strain, and the hypervariable domain from an ORF1 protein of a different TTV strain.

The full-length genome LY2 strain of *Betatorquevirus* has been cloned into expression vectors for expression in mammalian cells. This genome is mutated to remove the hypervariable domain of LY2 and replace it with the hypervariable domain of a distantly related Betatorqueviruses (FIG. 36). The plasmid containing the LY2 genome with the swapped hypervariable domain (pTTMV-LY2-HVRa-z) is then linearized and circularized using previously published methods (Kincaid et al., PLoS Pathogens 2013). HEK293T cells are transfected with the circularized genome and incubated for 5-7 days to allow anellosome production. After the incubation period anellosomes are purified from the supernatant and cell pellet of transfected cells by gradient ultracentrifugation.

To determine if the chimeric anellosomes are still infectious, the isolated viral particles are added to uninfected cells. The cells are incubated for 5-7 days to allow viral replication. After incubation the ability of the chimeric anellosomes to establish infection will be monitored by immunofluorescence, western blot, and qPCR. The structural integrity of the chimeric viruses is assessed by negative stain and cryo-electron microscopy. Chimeric anellosomes can further be tested for ability to infect cells in vivo. Establishment of the ability to produce functional chimeric anellosomes through hypervariable domain swapping could allow for engineering of viruses to alter tropism and potentially evade immune detection.

Example 38: Production of Chimeric ORF1 Containing Non-TTV Protein/Peptides in Place of Hypervariable Domains This example describes the replacement of the hypervariable regions of ORF1 with other proteins or peptides of interest to produce chimeric ORF1 protein containing the arginine-rich region, jelly-roll domain, N22, and C-terminal domain of one TTV strain, and a non-TTV protein/peptide in place of the hypervariable domain.

As shown in example B, the hypervariable domain of LY2 is deleted from the genome and a protein or peptide of interest may be inserted into this region (FIG. 37). Examples of types of sequences that could be introduced into this region include but are not limited to, affinity tags, single chain variable regions (scFv) of antibodies, and antigenic peptides. Mutated genomes in the plasmid (pTTMV-LY2-ΔHVR-POI) are linearized and circularized as described in example B. Circularized genomes are transfected into HEK293T cells and incubated for 5-7 days. Following incubation, the chimeric anellosomes containing the POI are purified from the supernatant and cell pellet via ultracentrifugation and/or affinity chromatography where appropriate.

The ability to produce functional chimeric anellosomes containing POIs is assessed using a variety of techniques. First, purified virus is added to uninfected cells to determine if chimeric anellosomes can replicate and/or deliver payload to naïve cells. Additionally, structural integrity of chimeric anellosomes is assessed using electron microscopy. For chimeric anellosomes that are functional in vitro, the ability of replicate/delivery payload in vivo is also assessed.

What is claimed is:

1. A method of delivering a therapeutic polypeptide or nucleic acid to a subject, comprising administering to the subject a pharmaceutical composition comprising an anellosome comprising:

(i) a proteinaceous exterior comprising an *Anellovirus* ORF1 polypeptide, and (ii) a genetic element encapsulated by the proteinaceous exterior; wherein the genetic element:

(a) comprises a promoter operably linked to a heterologous sequence encoding the therapeutic polypeptide or nucleic acid;

(b) comprises an *Anellovirus* 5' UTR;

(c) does not comprise any sequence encoding *Anellovirus* ORF1;

(d) does not comprise any sequence encoding *Anellovirus* ORF2; and (e) does not comprise any sequence encoding *Anellovirus* ORF3.

2. The method of claim 1, wherein the heterologous sequence encodes a therapeutic polypeptide.

3. The method of claim 1, wherein the heterologous sequence encodes a therapeutic nucleic acid.

4. The method of claim 1, wherein the therapeutic nucleic acid comprises a miRNA.

5. The method of claim 4, wherein the miRNA decreases the expression of a gene in the subject.

6. The method of claim 1, wherein the genetic element is circular.

7. The method of claim 1, wherein the genetic element is a single stranded DNA.

8. The method of claim 1, wherein the genetic element integrates into the genome of the subject at a frequency of less than 1%.

9. The method of claim 1, wherein the promoter element is not an *Anellovirus* promoter.

10. The method of claim 1, wherein the promoter element is an *Anellovirus* promoter.

11. The method of claim 1, wherein a population of at least 1000 of the anellosomes deliver at least 100 copies of the genetic element into one or more of cells of the subject.

12. The method of claim 1, wherein the anellosome directs the expression of the therapeutic polypeptide or nucleic acid in a cell of the subject.

13. The method of claim 1, wherein the *Anellovirus* ORF1 polypeptide in the proteinaceous exterior is the ORF1 of an *Alphatorquevirus*, a *Betatorquevirus*, or a *Gammatorquevirus*.

14. The method of claim 1, wherein the *Anellovirus* ORF1 polypeptide in the proteinaceous exterior is the ORF1 of an *Alphatorquevirus* clade 1, an *Alphatorquevirus* clade 2, an *Alphatorquevirus* clade 3, an *Alphatorquevirus* clade 4, an *Alphatorquevirus* clade 5, an *Alphatorquevirus* clade 6, or an *Alphatorquevirus* clade 7.

15. The method of claim 1, wherein the genetic element is between 3 kb to 4 kb in length.

16. The method of claim 1, wherein the anellosome is produced by introducing the genetic element into a host cell, under conditions suitable for enclosing the genetic element within the proteinaceous exterior in the host cell.

17. The method of claim 1, wherein the genetic element has a length less than 5 kb.

18. The method of claim 1, wherein the portions of the genetic element excluding the heterologous sequence have a combined size of less than 5 kb.

19. The method of claim 1, wherein the pharmaceutical composition comprises at least $10^4$ of the anellosomes.

20. The method of claim 1, wherein the heterologous sequence encodes a therapeutic polypeptide selected from an enzyme, growth factor, and cytokine.

21. The method of claim 1, wherein the genetic element comprises the nucleic acid sequence of SEQ ID NO: 105.

22. The method of claim 1, wherein the *Anellovirus* 5' UTR comprises a nucleic acid sequence having at least 95% sequence identity to a nucleic acid sequence selected from the group consisting of: nucleotides 177-247 of SEQ ID NO: 1, nucleotides 204-273 of SEQ ID NO: 9, nucleotides 170-240 of SEQ ID NO: 16, nucleotides 170-238 of SEQ ID NO: 24, nucleotides 170-240 of SEQ ID NO: 31, nucleotides 174-244 of SEQ ID NO: 39, nucleotides 170-240 of SEQ ID NO: 47, nucleotides 323-393 of SEQ ID NO: 54, and nucleotides 117-187 of SEQ ID NO: 61.

23. A method of delivering a therapeutic polypeptide or nucleic acid to a subject, comprising administering to the subject a pharmaceutical composition comprising an anellosome comprising:

(i) a proteinaceous exterior comprising an *Anellovirus* ORF1 polypeptide, and (ii) a genetic element encapsulated by the proteinaceous exterior; wherein the genetic element:

(a) comprises a promoter operably linked to a heterologous sequence encoding the therapeutic polypeptide or nucleic acid;

(b) comprises a nucleic acid sequence comprising at least 90% sequence identity to about 60 consecutive nucleotides of an *Anellovirus* 5' UTR;

(c) does not comprise any sequence encoding *Anellovirus* ORF1;

(d) does not comprise any sequence encoding *Anellovirus* ORF2; and (e) does not comprise any sequence encoding *Anellovirus* ORF3.

24. The method of claim 23, wherein the heterologous sequence encodes a therapeutic polypeptide.

25. The method of claim 23, wherein the heterologous sequence encodes a therapeutic nucleic acid.

26. The method of claim 23, wherein the therapeutic nucleic acid comprises a miRNA.

27. The method of claim 26, wherein the miRNA decreases the expression of a gene in the subject.

28. The method of claim 23, wherein the genetic element is circular.

29. The method of claim 23, wherein the genetic element is a single stranded DNA.

30. The method of claim 23, wherein the genetic element integrates into the genome of the subject at a frequency of less than 1%.

31. The method of claim 23, wherein the promoter element is not an *Anellovirus* promoter.

32. The method of claim 23, wherein the promoter element is an *Anellovirus* promoter.

33. The method of claim 23, wherein a population of at least 1000 of the anellosomes deliver at least 100 copies of the genetic element into one or more of cells of the subject.

34. The method of claim 23, wherein the anellosome directs the expression of the therapeutic polypeptide or nucleic acid in a cell of the subject.

35. The method of claim 23, wherein the *Anellovirus* ORF1 polypeptide in the proteinaceous exterior is the ORF1 of an *Alphatorquevirus*, a *Betatorquevirus*, or a *Gammatorquevirus.*

36. The method of claim 23, wherein the *Anellovirus* ORF1 polypeptide in the proteinaceous exterior is the ORF1 of an *Alphatorquevirus* clade 1, an Alphalorquevirus clade 2, an *Alphatorquevirus* clade 3, an *Alphatorquevirus* clade 4, an *Alphatorquevirus* clade 5, an *Alphatorquevirus* clade 6, or an *Alphatorquevirus* clade 7.

37. The method of claim 23, wherein the genetic element is between 3 kb to 4 kb in length.

38. The method of claim 23, wherein the anellosome is produced by introducing the genetic element into a host cell, under conditions suitable for enclosing the genetic element within the proteinaceous exterior in the host cell.

39. The method of claim 23, wherein the genetic element has a length less than 5 kb.

40. The method of claim 23, wherein the portions of the genetic element excluding the heterologous sequence have a combined size of less than 5 kb.

41. The method of claim 23, wherein the pharmaceutical composition comprises at least $10^4$ of the anellosomes.

42. The method of claim 23, wherein the heterologous sequence encodes a therapeutic polypeptide selected from an enzyme, growth factor, and cytokine.

43. A method of delivering a therapeutic polypeptide or nucleic acid to a subject, comprising administering to the subject a pharmaceutical composition comprising an anellosome comprising:

(i) a proteinaceous exterior comprising an *Anellovirus* ORF1 polypeptide, and (ii) a genetic element encapsulating the proteinaceous exterior; wherein the genetic element:

(a) comprises a promoter operably linked to a heterologous sequence encoding the therapeutic polypeptide or nucleic acid;

(b) comprises a nucleic acid sequence comprising at least 90% sequence identity to about 60 consecutive nucleotides of an *Anellovirus* 5' UTR;

(c) does not comprise any sequence encoding *Anellovirus* ORF1 or comprises a nucleic acid sequence encoding nonfunctional *Anellovirus* ORF1;

(d) does not comprise any sequence encoding *Anellovirus* ORF2 or comprises a nucleic acid sequence encoding nonfunctional *Anellovirus* ORF2; and (e) does not comprise any sequence encoding *Anellovirus* ORF3 or comprises a nucleic acid sequence encoding nonfunctional *Anellovirus* ORF3.

44. The method of claim 43, wherein the heterologous sequence encodes a therapeutic polypeptide.

45. The method of claim 43, wherein the heterologous sequence encodes a therapeutic nucleic acid.

46. The method of claim 43, wherein the therapeutic nucleic acid comprises a miRNA.

47. The method of claim 46, wherein the miRNA decreases the expression of a gene in the subject.

48. The method of claim 43, wherein the genetic element is circular.

49. The method of claim 43, wherein the genetic element is a single stranded DNA.

50. The method of claim 43, wherein the genetic element integrates into the genome of the subject at a frequency of less than 1%.

51. The method of claim 43, wherein the promoter element is not an *Anellovirus* promoter.

52. The method of claim 43, wherein the promoter element is an *Anellovirus* promoter.

53. The method of claim 43, wherein a population of at least 1000 of the anellosomes deliver at least 100 copies of the genetic element into one or more of cells of the subject.

54. The method of claim 43, wherein the anellosome directs the expression of the therapeutic polypeptide or nucleic acid in a cell of the subject.

55. The method of claim 43, wherein the *Anellovirus* ORF1 polypeptide in the proteinaceous exterior is the ORF1 of an *Alphatorquevirus*, a *Betatorquevirus*, or a *Gammatorquevirus.*

56. The method of claim 43, wherein the *Anellovirus* ORF1 polypeptide in the proteinaceous exterior is the ORF1 of an *Alphatorquevirus* clade 1, an *Alphatorquevirus* clade 2, an *Alphatorquevirus* clade 3, an *Alphatorquevirus* clade 4, an *Alphatorquevirus* clade 5, an *Alphatorquevirus* clade 6, or an *Alphatorquevirus* clade 7.

57. The method of claim 43, wherein the genetic element is between 3 kb to 4 kb in length.

58. The method of claim 43, wherein the anellosome is produced by introducing the genetic element into a host cell, under conditions suitable for enclosing the genetic element within the proteinaceous exterior in the host cell.

59. The method of claim 43, wherein the genetic element has a length less than 5 kb.

60. The method of claim 43, wherein the portions of the genetic element excluding the heterologous sequence have a combined size of less than 5 kb.

61. The method of claim 43, wherein the pharmaceutical composition comprises at least 104 of the anellosomes.

62. The method of claim 43, wherein the heterologous sequence encodes a therapeutic polypeptide selected from an enzyme, growth factor, and cytokine.

63. The method of claim 1, wherein the *Anellovirus* 5' UTR comprises a nucleic acid sequence having 100% sequence identity to a nucleic acid sequence selected from the group consisting of: nucleotides 177-247 of SEQ ID NO: 1, nucleotides 204-273 of SEQ ID NO: 9, nucleotides 170-240 of SEQ ID NO: 16, nucleotides 170-238 of SEQ ID NO: 24, nucleotides 170-240 of SEQ ID NO: 31, nucleotides 174-244 of SEQ ID NO: 39, nucleotides 170-240 of SEQ ID NO: 47, nucleotides 323-393 of SEQ ID NO: 54, and nucleotides 117-187 of SEQ ID NO: 61.

64. The method of claim 1, wherein the subject is a human subject.

65. The method of claim 23, wherein the subject is a human subject.

66. The method of claim 43, wherein the subject is a human subject.

* * * * *

SEQUENCE LISTING

```
<160> NUMBER OF SEQ ID NOS: 828

<210> SEQ ID NO 1
<211> LENGTH: 3570
<212> TYPE: DNA
<213> ORGANISM: Torque teno virus

<400> SEQUENCE: 1

attttgtgca gcccgccaat tctcgttcaa acaggccaat caggaggctc tacgtacact      60
```

tcctggggtg tgtcttcgaa gagtatataa gcagaggcgg tgacgaatgg tagagttttt 120
cctggcccgt ccgcggcgag agcgcgagcg gagcgagcga tcgagcgtcc cgtgggcggg 180
tgccgtaggt gagtttacac accgcagtca aggggcaatt cgggctcggg actggccggg 240
ctatgggcaa gattcttaaa aaattccccc gatccctctg tcgccaggac ataaaaacat 300
gccgtggaga ccgccggtgc atagtgtcca ggggcgagag gatcagtggt tcgcgagctt 360
ttttcacggc cacgcttcat tttgcggttg cggtgacgct gttggccatc ttaatagcat 420
tgctcctcgc tttcctcgcg ccggtccacc aaggccccct ccggggctag agcagcctaa 480
ccccccgcag cagggcccgg ccgggcccgg agggccgccc gccatcttgg cgctgccggc 540
tccgcccgcg gagcctgacg acccgcagcc acggcgtggt ggtggggacg gtggcgccgc 600
cgctggcgcc gcaggcgacc gtggagaccg agactacgac gaagaagagc tagacgagct 660
tttccgcgcc gccgccgaag acgatttgta agtaggagat ggcgccggcc ttacaggcgc 720
aggaggagac gcgggcgacg cagacgcaga cgcagacgca gacataagcc caccctagta 780
ctcagacagt ggcaacctga cgttatcaga cactgtaaga taacaggacg gatgcccctc 840
attatctgtg gaaaggggtc cacccagttc aactacatca cccacgcgga cgacatcacc 900
cccaggggag cctcctacgg gggcaacttc acaaacatga ctttctccct ggaggcaata 960
tacgaacagt ttctgtacca cagaaacagg tggtcagcct ccaaccacga cctcgaactc 1020
tgcagataca agggtaccac cctaaaactg tacaggcacc cagatgtaga ctacatagtc 1080
acctacagca gaacgggacc ctttgagatc agccacatga cctacctcag cactcacccc 1140
cttctcatgc tgctaaacaa acaccacata gtggtgccca gcctaaagac taagcccagg 1200
ggcagaaagg ccataaaagt cagaataaga ccccccaaac tcatgaacaa caagtggtac 1260
ttcaccagag acttctgtaa cataggcctc ttccagctct gggccacagg cttagaactc 1320
agaaacccct ggctcagaat gagcaccctg agcccctgca taggcttcaa tgtccttaaa 1380
aacagcattt acacaaacct cagcaaccta cctcagcaca gagaagacag acttaacatt 1440
attaacaaca cattacaccc acatgacata acaggaccaa acaataaaaa atggcagtac 1500
acatatacca aactcatggc ccccatttac tattcagcaa acagggccag cacctatgac 1560
ttactacgag agtatggcct ctacagtcca tactacctaa accccacaag gataaacctt 1620
gactggatga ccccctacac acacgtcagg tacaatccac tagtagacaa gggcttcgga 1680
aacagaatat acatacagtg gtgctcagag gcagatgtaa gctacaacag gactaaatcc 1740
aagtgtctct tacaagacat gcccctgttt ttcatgtgct atggctacat agactgggca 1800
attaaaaaca caggggtctc ctcactagcg agagacgcca gaatctgcat caggtgtccc 1860
tacacagagc cacagctggt gggctccaca gaagacatag ggttcgtacc catcacagag 1920
accttcatga ggggcgacat gccggtactt gcaccataca taccgttgag ctggttttgc 1980
aagtggtatc ccaacatagc tcaccagaag gaagtacttg aggcaatcat ttcctgcagc 2040
cccttcatgc cccgtgacca gggcatgaac ggttgggata ttacaatagg ttacaaaatg 2100
gacttcttat ggggcggttc ccctctcccc tcacagccaa tcgacgaccc ctgccagcag 2160
ggaacccacc cgattcccga ccccgataag caccctcgcc tcctacaagt gtcgaacccg 2220
aaactgctcg gaccgaggac agtgttccac aagtgggaca tcagacgtgg gcagtttagc 2280
aaaagaagta ttaaaagagt gtcagaatac tcatcggatg atgaatctct tgcgccaggt 2340
ctcccatcaa agcgaaacaa gctcgactcg gccttcagag gagaaaaccc agagcaaaaa 2400

```
gaatgctatt ctctcctcaa agcactcgag gaagaagaga ccccagaaga agaagaacca   2460

gcaccccaag aaaaagccca gaaagaggag ctactccacc agctccagct ccagagacgc   2520

caccagcgag tcctcagacg agggctcaag ctcgtcttta cagacatcct ccgactccgc   2580

cagggagtcc actggaaccc cgagctcaca tagagccccc accttacata ccagacctac   2640

tttttcccaa tactggtaaa aaaaaaaaat tctctccctt cgactgggaa acggaggccc   2700

agctagcagg gatattcaag cgtcctatgc gcttctatcc ctcagacacc cctcactacc   2760

cgtggttacc ccccaagcgc gatatcccga aaatatgtaa cataaacttc aaaataaagc   2820

tgcaagagtg agtgattcga ggccctcctc tgttcactta gcggtgtcta cctcttaaag   2880

tcaccaagca ctccgagcgt cagcgaggag tgcgaccctc caccaagggg caacttcctc   2940

ggggtccggc gctacgcgct tcgcgctgcg ccggacgcct cggacccccc cccgacccga   3000

atcgctcgcg cgattcggac ctgcggcctc ggggggggtc gggggcttta ctaaacagac   3060

tccgagttgc cactggactc aggagctgtg aatcagtaac gaaagtgagt ggggccagac   3120

ttcgccatag ggcctttaac ttggggtcgt ctgtcggtgg cttccgggtc cgcctgggcg   3180

ccgccatttt agctttagac gccattttag gccctcgcgg gcacccgtag gcgcgtttta   3240

atgacgtcac ggcagccatt ttgtcgtgac gtttgagaca cgtgatgggg gcgtgcctaa   3300

acccggaagc atccctggtc acgtgactct gacgtcacgg cggccatttt gtgctgtccg   3360

ccatcttgtg acttccttcc gctttttcaa aaaaaaagag gaagtatgac agtagcggcg   3420

ggggggcggc cgcgttcgcg cgccgcccac caggggggtgc tgcgcgcccc cccccgcgca   3480

tgcgcggggc ccccccccgg gggggctccg cccccccggc ccccccccgt gctaaaccca   3540

ccgcgcatgc gcgaccacgc ccccgccgcc                                    3570
```

```
<210> SEQ ID NO 2
<211> LENGTH: 130
<212> TYPE: PRT
<213> ORGANISM: Torque teno virus

<400> SEQUENCE: 2

Met Pro Trp Arg Pro Pro Val His Ser Val Gln Gly Arg Glu Asp Gln
1               5                   10                  15

Trp Phe Ala Ser Phe Phe His Gly His Ala Ser Phe Cys Gly Cys Gly
            20                  25                  30

Asp Ala Val Gly His Leu Asn Ser Ile Ala Pro Arg Phe Pro Arg Ala
        35                  40                  45

Gly Pro Pro Arg Pro Pro Pro Gly Leu Glu Gln Pro Asn Pro Pro Gln
    50                  55                  60

Gln Gly Pro Ala Gly Pro Gly Gly Pro Pro Ala Ile Leu Ala Leu Pro
65                  70                  75                  80

Ala Pro Pro Ala Glu Pro Asp Asp Pro Gln Pro Arg Arg Gly Gly Gly
                85                  90                  95

Asp Gly Gly Ala Ala Ala Gly Ala Ala Gly Asp Arg Gly Asp Arg Asp
            100                 105                 110

Tyr Asp Glu Glu Glu Leu Asp Glu Leu Phe Arg Ala Ala Ala Glu Asp
        115                 120                 125

Asp Leu
    130


<210> SEQ ID NO 3
<211> LENGTH: 303
<212> TYPE: PRT
```

<213> ORGANISM: Torque teno virus

<400> SEQUENCE: 3

```
Met Pro Trp Arg Pro Pro Val His Ser Val Gln Gly Arg Glu Asp Gln
1               5                   10                  15

Trp Phe Ala Ser Phe Phe His Gly His Ala Ser Phe Cys Gly Cys Gly
            20                  25                  30

Asp Ala Val Gly His Leu Asn Ser Ile Ala Pro Arg Phe Pro Arg Ala
        35                  40                  45

Gly Pro Pro Arg Pro Pro Pro Gly Leu Glu Gln Pro Asn Pro Pro Gln
    50                  55                  60

Gln Gly Pro Ala Gly Pro Gly Gly Pro Pro Ala Ile Leu Ala Leu Pro
65                  70                  75                  80

Ala Pro Pro Ala Glu Pro Asp Asp Pro Gln Pro Arg Arg Gly Gly Gly
                85                  90                  95

Asp Gly Gly Ala Ala Ala Gly Ala Ala Gly Asp Arg Gly Asp Arg Asp
            100                 105                 110

Tyr Asp Glu Glu Glu Leu Asp Glu Leu Phe Arg Ala Ala Ala Glu Asp
        115                 120                 125

Asp Phe Gln Ser Thr Thr Pro Ala Ser Arg Glu Pro Thr Arg Phe Pro
    130                 135                 140

Thr Pro Ile Ser Thr Leu Ala Ser Tyr Lys Cys Arg Thr Arg Asn Cys
145                 150                 155                 160

Ser Asp Arg Gly Gln Cys Ser Thr Ser Gly Thr Ser Asp Val Gly Ser
                165                 170                 175

Leu Ala Lys Glu Val Leu Lys Glu Cys Gln Asn Thr His Arg Met Met
            180                 185                 190

Asn Leu Leu Arg Gln Val Ser His Gln Ser Glu Thr Ser Ser Thr Arg
        195                 200                 205

Pro Ser Glu Glu Lys Thr Gln Ser Lys Lys Asn Ala Ile Leu Ser Ser
    210                 215                 220

Lys His Ser Arg Lys Lys Arg Pro Gln Lys Lys Lys Asn Gln His Pro
225                 230                 235                 240

Lys Lys Lys Pro Arg Lys Arg Ser Tyr Ser Thr Ser Ser Ser Ser Arg
                245                 250                 255

Asp Ala Thr Ser Glu Ser Ser Asp Glu Gly Ser Ser Ser Ser Leu Gln
            260                 265                 270

Thr Ser Ser Asp Ser Ala Arg Glu Ser Thr Gly Thr Pro Ser Ser His
        275                 280                 285

Arg Ala Pro Thr Leu His Thr Arg Pro Thr Phe Ser Gln Tyr Trp
    290                 295                 300
```

<210> SEQ ID NO 4
<211> LENGTH: 293
<212> TYPE: PRT
<213> ORGANISM: Torque teno virus

<400> SEQUENCE: 4

```
Met Pro Trp Arg Pro Pro Val His Ser Val Gln Gly Arg Glu Asp Gln
1               5                   10                  15

Trp Phe Ala Ser Phe Phe His Gly His Ala Ser Phe Cys Gly Cys Gly
            20                  25                  30

Asp Ala Val Gly His Leu Asn Ser Ile Ala Pro Arg Phe Pro Arg Ala
        35                  40                  45

Gly Pro Pro Arg Pro Pro Pro Gly Leu Glu Gln Pro Asn Pro Pro Gln
```

```
    50                  55                  60

Gln Gly Pro Ala Gly Pro Gly Gly Pro Pro Ala Ile Leu Ala Leu Pro
65                  70                  75                  80

Ala Pro Pro Ala Glu Pro Asp Asp Pro Gln Pro Arg Arg Gly Gly Gly
                85                  90                  95

Asp Gly Gly Ala Ala Ala Gly Ala Ala Gly Asp Arg Gly Asp Arg Asp
            100                 105                 110

Tyr Asp Glu Glu Glu Leu Asp Glu Leu Phe Arg Ala Ala Ala Glu Asp
        115                 120                 125

Asp Leu Ser Pro Ile Lys Ala Lys Gln Ala Arg Leu Gly Leu Gln Arg
    130                 135                 140

Arg Lys Pro Arg Ala Lys Arg Met Leu Phe Ser Pro Gln Ser Thr Arg
145                 150                 155                 160

Gly Arg Arg Asp Pro Arg Arg Arg Arg Thr Ser Thr Pro Arg Lys Ser
                165                 170                 175

Pro Glu Arg Gly Ala Thr Pro Pro Ala Pro Ala Pro Glu Thr Pro Pro
            180                 185                 190

Ala Ser Pro Gln Thr Arg Ala Gln Ala Arg Leu Tyr Arg His Pro Pro
        195                 200                 205

Thr Pro Pro Gly Ser Pro Leu Glu Pro Arg Ala His Ile Glu Pro Pro
    210                 215                 220

Pro Tyr Ile Pro Asp Leu Leu Phe Pro Asn Thr Gly Lys Lys Lys Lys
225                 230                 235                 240

Phe Ser Pro Phe Asp Trp Glu Thr Glu Ala Gln Leu Ala Gly Ile Phe
                245                 250                 255

Lys Arg Pro Met Arg Phe Tyr Pro Ser Asp Thr Pro His Tyr Pro Trp
            260                 265                 270

Leu Pro Pro Lys Arg Asp Ile Pro Lys Ile Cys Asn Ile Asn Phe Lys
        275                 280                 285

Ile Lys Leu Gln Glu
    290


<210> SEQ ID NO 5
<211> LENGTH: 180
<212> TYPE: PRT
<213> ORGANISM: Torque teno virus

<400> SEQUENCE: 5

Met Pro Trp Arg Pro Pro Val His Ser Val Gln Gly Arg Glu Asp Gln
1               5                   10                  15

Trp Ser Pro Ile Lys Ala Lys Gln Ala Arg Leu Gly Leu Gln Arg Arg
            20                  25                  30

Lys Pro Arg Ala Lys Arg Met Leu Phe Ser Pro Gln Ser Thr Arg Gly
        35                  40                  45

Arg Arg Asp Pro Arg Arg Arg Arg Thr Ser Thr Pro Arg Lys Ser Pro
    50                  55                  60

Glu Arg Gly Ala Thr Pro Pro Ala Pro Ala Pro Glu Thr Pro Pro Ala
65                  70                  75                  80

Ser Pro Gln Thr Arg Ala Gln Ala Arg Leu Tyr Arg His Pro Pro Thr
                85                  90                  95

Pro Pro Gly Ser Pro Leu Glu Pro Arg Ala His Ile Glu Pro Pro Pro
            100                 105                 110

Tyr Ile Pro Asp Leu Leu Phe Pro Asn Thr Gly Lys Lys Lys Lys Phe
        115                 120                 125
```

-continued

```
Ser Pro Phe Asp Trp Glu Thr Glu Ala Gln Leu Ala Gly Ile Phe Lys
    130                 135                 140

Arg Pro Met Arg Phe Tyr Pro Ser Asp Thr Pro His Tyr Pro Trp Leu
145                 150                 155                 160

Pro Pro Lys Arg Asp Ile Pro Lys Ile Cys Asn Ile Asn Phe Lys Ile
                165                 170                 175

Lys Leu Gln Glu
            180


<210> SEQ ID NO 6
<211> LENGTH: 680
<212> TYPE: PRT
<213> ORGANISM: Torque teno virus

<400> SEQUENCE: 6

Thr Ala Trp Trp Trp Gly Arg Trp Arg Arg Arg Trp Arg Arg Arg Arg
1               5                   10                  15

Pro Trp Arg Pro Arg Leu Arg Arg Arg Arg Ala Arg Arg Ala Phe Pro
            20                  25                  30

Arg Arg Arg Arg Arg Arg Phe Val Ser Arg Arg Trp Arg Arg Pro Tyr
        35                  40                  45

Arg Arg Arg Arg Arg Arg Gly Arg Arg Arg Arg Arg Arg Arg Arg Arg
    50                  55                  60

His Lys Pro Thr Leu Val Leu Arg Gln Trp Gln Pro Asp Val Ile Arg
65                  70                  75                  80

His Cys Lys Ile Thr Gly Arg Met Pro Leu Ile Ile Cys Gly Lys Gly
                85                  90                  95

Ser Thr Gln Phe Asn Tyr Ile Thr His Ala Asp Asp Ile Thr Pro Arg
            100                 105                 110

Gly Ala Ser Tyr Gly Gly Asn Phe Thr Asn Met Thr Phe Ser Leu Glu
        115                 120                 125

Ala Ile Tyr Glu Gln Phe Leu Tyr His Arg Asn Arg Trp Ser Ala Ser
    130                 135                 140

Asn His Asp Leu Glu Leu Cys Arg Tyr Lys Gly Thr Thr Leu Lys Leu
145                 150                 155                 160

Tyr Arg His Pro Asp Val Asp Tyr Ile Val Thr Tyr Ser Arg Thr Gly
                165                 170                 175

Pro Phe Glu Ile Ser His Met Thr Tyr Leu Ser Thr His Pro Leu Leu
            180                 185                 190

Met Leu Leu Asn Lys His His Ile Val Val Pro Ser Leu Lys Thr Lys
        195                 200                 205

Pro Arg Gly Arg Lys Ala Ile Lys Val Arg Ile Arg Pro Pro Lys Leu
    210                 215                 220

Met Asn Asn Lys Trp Tyr Phe Thr Arg Asp Phe Cys Asn Ile Gly Leu
225                 230                 235                 240

Phe Gln Leu Trp Ala Thr Gly Leu Glu Leu Arg Asn Pro Trp Leu Arg
                245                 250                 255

Met Ser Thr Leu Ser Pro Cys Ile Gly Phe Asn Val Leu Lys Asn Ser
            260                 265                 270

Ile Tyr Thr Asn Leu Ser Asn Leu Pro Gln His Arg Glu Asp Arg Leu
        275                 280                 285

Asn Ile Ile Asn Asn Thr Leu His Pro His Asp Ile Thr Gly Pro Asn
    290                 295                 300

Asn Lys Lys Trp Gln Tyr Thr Tyr Thr Lys Leu Met Ala Pro Ile Tyr
305                 310                 315                 320
```

```
Tyr Ser Ala Asn Arg Ala Ser Thr Tyr Asp Leu Leu Arg Glu Tyr Gly
                325                 330                 335

Leu Tyr Ser Pro Tyr Tyr Leu Asn Pro Thr Arg Ile Asn Leu Asp Trp
            340                 345                 350

Met Thr Pro Tyr Thr His Val Arg Tyr Asn Pro Leu Val Asp Lys Gly
        355                 360                 365

Phe Gly Asn Arg Ile Tyr Ile Gln Trp Cys Ser Glu Ala Asp Val Ser
    370                 375                 380

Tyr Asn Arg Thr Lys Ser Lys Cys Leu Leu Gln Asp Met Pro Leu Phe
385                 390                 395                 400

Phe Met Cys Tyr Gly Tyr Ile Asp Trp Ala Ile Lys Asn Thr Gly Val
                405                 410                 415

Ser Ser Leu Ala Arg Asp Ala Arg Ile Cys Ile Arg Cys Pro Tyr Thr
            420                 425                 430

Glu Pro Gln Leu Val Gly Ser Thr Glu Asp Ile Gly Phe Val Pro Ile
        435                 440                 445

Thr Glu Thr Phe Met Arg Gly Asp Met Pro Val Leu Ala Pro Tyr Ile
    450                 455                 460

Pro Leu Ser Trp Phe Cys Lys Trp Tyr Pro Asn Ile Ala His Gln Lys
465                 470                 475                 480

Glu Val Leu Glu Ala Ile Ile Ser Cys Ser Pro Phe Met Pro Arg Asp
                485                 490                 495

Gln Gly Met Asn Gly Trp Asp Ile Thr Ile Gly Tyr Lys Met Asp Phe
            500                 505                 510

Leu Trp Gly Gly Ser Pro Leu Pro Ser Gln Pro Ile Asp Asp Pro Cys
        515                 520                 525

Gln Gln Gly Thr His Pro Ile Pro Asp Pro Asp Lys His Pro Arg Leu
    530                 535                 540

Leu Gln Val Ser Asn Pro Lys Leu Leu Gly Pro Arg Thr Val Phe His
545                 550                 555                 560

Lys Trp Asp Ile Arg Arg Gly Gln Phe Ser Lys Arg Ser Ile Lys Arg
                565                 570                 575

Val Ser Glu Tyr Ser Ser Asp Asp Glu Ser Leu Ala Pro Gly Leu Pro
            580                 585                 590

Ser Lys Arg Asn Lys Leu Asp Ser Ala Phe Arg Gly Glu Asn Pro Glu
        595                 600                 605

Gln Lys Glu Cys Tyr Ser Leu Leu Lys Ala Leu Glu Glu Glu Glu Thr
    610                 615                 620

Pro Glu Glu Glu Glu Pro Ala Pro Gln Glu Lys Ala Gln Lys Glu Glu
625                 630                 635                 640

Leu Leu His Gln Leu Gln Leu Gln Arg Arg His Gln Arg Val Leu Arg
                645                 650                 655

Arg Gly Leu Lys Leu Val Phe Thr Asp Ile Leu Arg Leu Arg Gln Gly
            660                 665                 670

Val His Trp Asn Pro Glu Leu Thr
        675                 680


<210> SEQ ID NO 7
<211> LENGTH: 197
<212> TYPE: PRT
<213> ORGANISM: Torque teno virus

<400> SEQUENCE: 7

Thr Ala Trp Trp Trp Gly Arg Trp Arg Arg Arg Trp Arg Arg Arg Arg
```

-continued

```
1               5                   10                  15

Pro Trp Arg Pro Arg Leu Arg Arg Arg Arg Ala Arg Arg Ala Phe Pro
            20                  25                  30

Arg Arg Arg Arg Arg Arg Phe Pro Ile Asp Asp Pro Cys Gln Gln Gly
        35                  40                  45

Thr His Pro Ile Pro Asp Pro Asp Lys His Pro Arg Leu Leu Gln Val
    50                  55                  60

Ser Asn Pro Lys Leu Leu Gly Pro Arg Thr Val Phe His Lys Trp Asp
65                  70                  75                  80

Ile Arg Arg Gly Gln Phe Ser Lys Arg Ser Ile Lys Arg Val Ser Glu
                85                  90                  95

Tyr Ser Ser Asp Asp Glu Ser Leu Ala Pro Gly Leu Pro Ser Lys Arg
            100                 105                 110

Asn Lys Leu Asp Ser Ala Phe Arg Gly Glu Asn Pro Glu Gln Lys Glu
        115                 120                 125

Cys Tyr Ser Leu Leu Lys Ala Leu Glu Glu Glu Glu Thr Pro Glu Glu
    130                 135                 140

Glu Glu Pro Ala Pro Gln Glu Lys Ala Gln Lys Glu Glu Leu Leu His
145                 150                 155                 160

Gln Leu Gln Leu Gln Arg Arg His Gln Arg Val Leu Arg Arg Gly Leu
                165                 170                 175

Lys Leu Val Phe Thr Asp Ile Leu Arg Leu Arg Gln Gly Val His Trp
            180                 185                 190

Asn Pro Glu Leu Thr
        195


<210> SEQ ID NO 8
<211> LENGTH: 145
<212> TYPE: PRT
<213> ORGANISM: Torque teno virus

<400> SEQUENCE: 8

Thr Ala Trp Trp Trp Gly Arg Trp Arg Arg Arg Trp Arg Arg Arg Arg
1               5                   10                  15

Pro Trp Arg Pro Arg Leu Arg Arg Arg Arg Ala Arg Arg Ala Phe Pro
            20                  25                  30

Arg Arg Arg Arg Arg Arg Phe Val Ser His Gln Ser Glu Thr Ser Ser
        35                  40                  45

Thr Arg Pro Ser Glu Glu Lys Thr Gln Ser Lys Lys Asn Ala Ile Leu
    50                  55                  60

Ser Ser Lys His Ser Arg Lys Lys Arg Pro Gln Lys Lys Lys Asn Gln
65                  70                  75                  80

His Pro Lys Lys Lys Pro Arg Lys Arg Ser Tyr Ser Thr Ser Ser Ser
                85                  90                  95

Ser Arg Asp Ala Thr Ser Glu Ser Ser Asp Glu Gly Ser Ser Ser Ser
            100                 105                 110

Leu Gln Thr Ser Ser Asp Ser Ala Arg Glu Ser Thr Gly Thr Pro Ser
        115                 120                 125

Ser His Arg Ala Pro Thr Leu His Thr Arg Pro Thr Phe Ser Gln Tyr
    130                 135                 140

Trp
145


<210> SEQ ID NO 9
<211> LENGTH: 3451
```

<212> TYPE: DNA
<213> ORGANISM: Torque teno virus

<400> SEQUENCE: 9
aattttgcta aacagactcc gaggtgctct tggacactga gtgggcgtac agcaacgaaa 60
gtgagtgggg ccagacttcg ccataaggcc tttatcttcg ggtctacatc ataatataaa 120
gatgtgcact tccgaatggc tgagtttttc acgccattcc gcagcggtgg agcagcgcag 180
ccacgacccc cgcgtcccga gggcgggtgc cggaggtgag tttacacacc gcagtcaagg 240
ggcaattcgg gctcgggact ggccgggccc gggcaaggct cttaaagcga aaccatgttc 300
ctcggcaggc cctaccgcca cagaaagcgg caccaggccg gcaagaaagg gccactgcca 360
ctgccaaatc tgcaacctgc acaggagaaa cgggctggtg gtccgtcctt gatggcctcc 420
ggacgcaggg gatggatgcc cccggacctg acggtccagg agagggagga tgcctggtgg 480
accagcttct gcgctagcca ccgcagcttt tgtagctgcg acgatcctgt gggccatatt 540
aatactctcg cccgcgataa tagtcctctg gcccagactc ctactacaac ttcaggccag 600
gggccgccgc cgccgcctac gcctccgcgg acgccggggc cgcgccctgg gtctgctccg 660
gaccaggggg gaaggatcag ggcctcctgg acctaccccc tagcccccgg aggtcccggt 720
agcacgccat ggcctactgg tggggccgga gacgccggtg gcgccgctgg aggaggcgcc 780
ggcgtcctct ccgccgccgc cggcggtggc ggagaaggcg acgctggccc agaaggcgcc 840
ggtggaggcg aaggagacga cgtgcgagac ctgctcgccg ctatcgaagg agacgtgggc 900
gcagacgggt aaggagacgc cgtcgccccc agaaactagt actgactcag tggaatcccc 960
agactgtgag aaagtgtgtt attagggggt ttctgcccct gttcttctgc ggacaggggg 1020
cctaccacag aaactttaca gaccactatg acgatgtgtt ccccaaggga cccagcggag 1080
gtgggcacgg gagcatggtg ttcaacctgt cctttctgta ccaagagttt aagaagcacc 1140
acaataagtg gtcgcgcagc aacctggact ttgacttagt gagatacaag ggcacagtga 1200
taaagctgta cagacaccag gactttgact acatagtgtg gataagcagg acccctccct 1260
tccaggagag cctgctcaca gtaatgaccc accagcccag cgtcatgctg caggcaaaaa 1320
agtgcataat agtaaagagc tacaggaccc acccgggggg caaaccctat gtaactgcaa 1380
aagttaggcc ccccagactc ctaactgaca agtggtactt ccagtcagac ttctgcaacg 1440
ttccgctttt tagcctacag tttgcccttg cggaactgcg gtttccgatc tgctcaccac 1500
aaactgacac caattgcatt aacttcctgg tgttagatga catctactac aagtttctag 1560
ataataagcc taaacagagt tcagacccta atgacgaaaa cagaataaaa ttctggcacg 1620
gcctatggtc cactatgaga tatttaaaca ccacctacat aaacacactg tttccaggca 1680
cagacagtct agtggccgcc aaagatactg acaatagtgt aaataaatac cccagcacag 1740
ccactaaaca gccctacaaa gacagtcagt acatgcaaaa tatatggaat acatcaaaaa 1800
tacatgcctt atatacgtgg gtagcagaga caaactacaa aagactgcag gcctactaca 1860
cacagaccta cggaggctac cagagacaat ttttcacagg aaaacagtac tgggactaca 1920
gagtaggcat gtttagtcca gccttcctga gtcccagcag actaaatccc cagaacccag 1980
gggcatacac agaggtctcc tacaacccct ggacagacga gggcacgggc aacgtagtgt 2040
gcctgcagta tctgactaaa gagacctcag actacaaacc aggtggtggg agcaagttct 2100
gcatagaagg tgtgcctcta tgggcagcgc tggtgggata cgtagacatg tgtaaaaaag 2160
agggcaagga cccgggcatc agactaaact gtctcctgtt agtcaagtgt ccctatacaa 2220

-continued

```
agcctcagct gtatgacaaa aaaaaccccg agaaactgtt tgtaccttac tcctataact   2280
ttgggcacgg caagatgccg gggggagaca aatacatacc catagagttc aaagacaggt   2340
ggtacccctg cctgctccac caagaggagt ggatagagga cattgtcagg tcgggaccct   2400
tcgttccaaa agacatgccc agcagcgtca cctgcatgat gaggtacagc tctcttttta   2460
actggggcgg taatataatc caagaacagg ccgtggaaga cccctgtaag aaaggcacct   2520
tcgtcgttcc cggaaccagt ggcatcgctc gcatactaca agtcagcaac ccggccaagc   2580
agacccccac gacaacctgg cactcgtggg actggagacg atccctcttt acagagacgg   2640
gtcttaaaag aatgcgcgaa caacaaccat atgatgaact gtcttatacg ggccctaaaa   2700
agccaaaact gtcccttccc gcagggcccg ccgtccccgg tgccgccgtc gcctcctcct   2760
ggtgggaaac aaaacaggtc acctcgccag acgtcagcga gacggagacc gaagcagaag   2820
cccaccaaga ggaagagacg gagccggagg agggagtcca gctccagcag ctgtgggagc   2880
agcaactcct gcaaaagcga cagctgggag tcgtgttcca gcaactcctc cgactcagac   2940
agggggcgga gatccacccg ggcctcgtat aattcctggg ccccagaacc cgtacctgct   3000
tttcccggag caggcccctc caaaagtgcc tatttttgac ccctttggtc agaaaacaga   3060
gctagagctg tgcggctgct tcgacaggcc gcccaggaac aaccccctacg accacccctt   3120
ctacccctgg ctgcccaaag agcctccctc ctactaccag ggctacaaag tgtctttcaa   3180
actagggttc cacccagaca agcatgtgtg aaccccgcca ataaaccact gctgctacac   3240
tgattcttag gccgtgggag tctcactggt cggtgtctac ctcttaaggt cactaagcac   3300
tccgagcgtt agcgaggagt gcgaccctac cccctgggcc cacttcttcg gagccgcgcg   3360
ctacgccttc ggctgcgcgc ggcacctcag acccccgctc gtgctgacac gcttgcgcgt   3420
gtcagaccac ttcgggctcg cgggggtcgg g                                  3451
```

```
<210> SEQ ID NO 10
<211> LENGTH: 166
<212> TYPE: PRT
<213> ORGANISM: Torque teno virus

<400> SEQUENCE: 10

Met Ala Ser Gly Arg Arg Gly Trp Met Pro Pro Asp Leu Thr Val Gln
1               5                   10                  15

Glu Arg Glu Asp Ala Trp Trp Thr Ser Phe Cys Ala Ser His Arg Ser
            20                  25                  30

Phe Cys Ser Cys Asp Asp Pro Val Gly His Ile Asn Thr Leu Ala Arg
        35                  40                  45

Asp Asn Ser Pro Leu Ala Gln Thr Pro Thr Thr Thr Ser Gly Gln Gly
    50                  55                  60

Pro Pro Pro Pro Pro Thr Pro Pro Arg Thr Pro Gly Pro Arg Pro Gly
65                  70                  75                  80

Ser Ala Pro Asp Gln Gly Gly Arg Ile Arg Ala Ser Trp Thr Tyr Pro
                85                  90                  95

Leu Ala Pro Gly Gly Pro Gly Ser Thr Pro Trp Pro Thr Gly Gly Ala
            100                 105                 110

Gly Asp Ala Gly Gly Ala Ala Gly Gly Gly Ala Gly Val Leu Ser Ala
        115                 120                 125

Ala Ala Gly Gly Gly Gly Glu Gly Asp Ala Gly Pro Glu Gly Ala Gly
    130                 135                 140

Gly Gly Glu Gly Asp Asp Val Arg Asp Leu Leu Ala Ala Ile Glu Gly
145                 150                 155                 160
```

Asp Val Gly Ala Asp Gly
165

<210> SEQ ID NO 11
<211> LENGTH: 348
<212> TYPE: PRT
<213> ORGANISM: Torque teno virus

<400> SEQUENCE: 11

Met Ala Ser Gly Arg Arg Gly Trp Met Pro Pro Asp Leu Thr Val Gln
1 5 10 15

Glu Arg Glu Asp Ala Trp Trp Thr Ser Phe Cys Ala Ser His Arg Ser
20 25 30

Phe Cys Ser Cys Asp Asp Pro Val Gly His Ile Asn Thr Leu Ala Arg
35 40 45

Asp Asn Ser Pro Leu Ala Gln Thr Pro Thr Thr Thr Ser Gly Gln Gly
50 55 60

Pro Pro Pro Pro Pro Thr Pro Pro Arg Thr Pro Gly Pro Arg Pro Gly
65 70 75 80

Ser Ala Pro Asp Gln Gly Gly Arg Ile Arg Ala Ser Trp Thr Tyr Pro
85 90 95

Leu Ala Pro Gly Gly Pro Gly Ser Thr Pro Trp Pro Thr Gly Gly Ala
100 105 110

Gly Asp Ala Gly Gly Ala Ala Gly Gly Gly Ala Gly Val Leu Ser Ala
115 120 125

Ala Ala Gly Gly Gly Gly Glu Gly Asp Ala Gly Pro Glu Gly Ala Gly
130 135 140

Gly Gly Glu Gly Asp Asp Val Arg Asp Leu Leu Ala Ala Ile Glu Gly
145 150 155 160

Asp Val Gly Ala Asp Gly Pro Trp Lys Thr Pro Val Arg Lys Ala Pro
165 170 175

Ser Ser Phe Pro Glu Pro Val Ala Ser Leu Ala Tyr Tyr Lys Ser Ala
180 185 190

Thr Arg Pro Ser Arg Pro Pro Arg Gln Pro Gly Thr Arg Gly Thr Gly
195 200 205

Asp Asp Pro Ser Leu Gln Arg Arg Val Leu Lys Glu Cys Ala Asn Asn
210 215 220

Asn His Met Met Asn Cys Leu Ile Arg Ala Leu Lys Ser Gln Asn Cys
225 230 235 240

Pro Phe Pro Gln Gly Pro Pro Ser Pro Val Pro Pro Ser Pro Pro Pro
245 250 255

Gly Gly Lys Gln Asn Arg Ser Pro Arg Gln Thr Ser Ala Arg Arg Arg
260 265 270

Pro Lys Gln Lys Pro Thr Lys Arg Lys Arg Arg Ser Arg Arg Arg Glu
275 280 285

Ser Ser Ser Ser Ser Cys Gly Ser Ser Asn Ser Cys Lys Ser Asp Ser
290 295 300

Trp Glu Ser Cys Ser Ser Asn Ser Ser Asp Ser Asp Arg Gly Arg Arg
305 310 315 320

Ser Thr Arg Ala Ser Tyr Asn Ser Trp Ala Pro Glu Pro Val Pro Ala
325 330 335

Phe Pro Gly Ala Gly Pro Ser Lys Ser Ala Tyr Phe
340 345

<210> SEQ ID NO 12
<211> LENGTH: 327
<212> TYPE: PRT
<213> ORGANISM: Torque teno virus

<400> SEQUENCE: 12

```
Met Ala Ser Gly Arg Arg Gly Trp Met Pro Pro Asp Leu Thr Val Gln
1               5                   10                  15

Glu Arg Glu Asp Ala Trp Trp Thr Ser Phe Cys Ala Ser His Arg Ser
            20                  25                  30

Phe Cys Ser Cys Asp Asp Pro Val Gly His Ile Asn Thr Leu Ala Arg
        35                  40                  45

Asp Asn Ser Pro Leu Ala Gln Thr Pro Thr Thr Thr Ser Gly Gln Gly
    50                  55                  60

Pro Pro Pro Pro Pro Thr Pro Pro Arg Thr Pro Gly Pro Arg Pro Gly
65                  70                  75                  80

Ser Ala Pro Asp Gln Gly Gly Arg Ile Arg Ala Ser Trp Thr Tyr Pro
                85                  90                  95

Leu Ala Pro Gly Gly Pro Gly Ser Thr Pro Trp Pro Thr Gly Gly Ala
            100                 105                 110

Gly Asp Ala Gly Gly Ala Ala Gly Gly Gly Ala Gly Val Leu Ser Ala
        115                 120                 125

Ala Ala Gly Gly Gly Gly Glu Gly Asp Ala Gly Pro Glu Gly Ala Gly
    130                 135                 140

Gly Gly Glu Gly Asp Asp Val Arg Asp Leu Leu Ala Ala Ile Glu Gly
145                 150                 155                 160

Asp Val Gly Ala Asp Gly Ala Arg Arg Pro Arg Cys Arg Arg Arg Leu
                165                 170                 175

Leu Leu Val Gly Asn Lys Thr Gly His Leu Ala Arg Arg Gln Arg Asp
            180                 185                 190

Gly Asp Arg Ser Arg Ser Pro Pro Arg Gly Arg Asp Gly Ala Gly Gly
        195                 200                 205

Gly Ser Pro Ala Pro Ala Ala Val Gly Ala Ala Thr Pro Ala Lys Ala
    210                 215                 220

Thr Ala Gly Ser Arg Val Pro Ala Thr Pro Pro Thr Gln Thr Gly Gly
225                 230                 235                 240

Gly Asp Pro Pro Gly Pro Arg Ile Ile Pro Gly Pro Gln Asn Pro Tyr
                245                 250                 255

Leu Leu Phe Pro Glu Gln Ala Pro Pro Lys Val Pro Ile Phe Asp Pro
            260                 265                 270

Phe Gly Gln Lys Thr Glu Leu Glu Leu Cys Gly Cys Phe Asp Arg Pro
        275                 280                 285

Pro Arg Asn Asn Pro Tyr Asp His Pro Phe Tyr Pro Trp Leu Pro Lys
    290                 295                 300

Glu Pro Pro Ser Tyr Tyr Gln Gly Tyr Lys Val Ser Phe Lys Leu Gly
305                 310                 315                 320

Phe His Pro Asp Lys His Val
                325
```

<210> SEQ ID NO 13
<211> LENGTH: 747
<212> TYPE: PRT
<213> ORGANISM: Torque teno virus

<400> SEQUENCE: 13

```
Met Ala Tyr Trp Trp Gly Arg Arg Arg Arg Trp Arg Arg Trp Arg Arg
```

-continued

```
1               5                   10                  15

Arg Arg Arg Pro Leu Arg Arg Arg Arg Arg Trp Arg Arg Arg Arg Arg
            20                  25                  30

Trp Pro Arg Arg Arg Arg Trp Arg Arg Arg Arg Arg Arg Ala Arg Pro
        35                  40                  45

Ala Arg Arg Tyr Arg Arg Arg Arg Gly Arg Arg Arg Val Arg Arg Arg
    50                  55                  60

Arg Arg Pro Gln Lys Leu Val Leu Thr Gln Trp Asn Pro Gln Thr Val
65                  70                  75                  80

Arg Lys Cys Val Ile Arg Gly Phe Leu Pro Leu Phe Phe Cys Gly Gln
                85                  90                  95

Gly Ala Tyr His Arg Asn Phe Thr Asp His Tyr Asp Asp Val Phe Pro
            100                 105                 110

Lys Gly Pro Ser Gly Gly Gly His Gly Ser Met Val Phe Asn Leu Ser
        115                 120                 125

Phe Leu Tyr Gln Glu Phe Lys Lys His His Asn Lys Trp Ser Arg Ser
    130                 135                 140

Asn Leu Asp Phe Asp Leu Val Arg Tyr Lys Gly Thr Val Ile Lys Leu
145                 150                 155                 160

Tyr Arg His Gln Asp Phe Asp Tyr Ile Val Trp Ile Ser Arg Thr Pro
                165                 170                 175

Pro Phe Gln Glu Ser Leu Leu Thr Val Met Thr His Gln Pro Ser Val
            180                 185                 190

Met Leu Gln Ala Lys Lys Cys Ile Ile Val Lys Ser Tyr Arg Thr His
        195                 200                 205

Pro Gly Gly Lys Pro Tyr Val Thr Ala Lys Val Arg Pro Pro Arg Leu
    210                 215                 220

Leu Thr Asp Lys Trp Tyr Phe Gln Ser Asp Phe Cys Asn Val Pro Leu
225                 230                 235                 240

Phe Ser Leu Gln Phe Ala Leu Ala Glu Leu Arg Phe Pro Ile Cys Ser
                245                 250                 255

Pro Gln Thr Asp Thr Asn Cys Ile Asn Phe Leu Val Leu Asp Asp Ile
            260                 265                 270

Tyr Tyr Lys Phe Leu Asp Asn Lys Pro Lys Gln Ser Ser Asp Pro Asn
        275                 280                 285

Asp Glu Asn Arg Ile Lys Phe Trp His Gly Leu Trp Ser Thr Met Arg
    290                 295                 300

Tyr Leu Asn Thr Thr Tyr Ile Asn Thr Leu Phe Pro Gly Thr Asp Ser
305                 310                 315                 320

Leu Val Ala Ala Lys Asp Thr Asp Asn Ser Val Asn Lys Tyr Pro Ser
                325                 330                 335

Thr Ala Thr Lys Gln Pro Tyr Lys Asp Ser Gln Tyr Met Gln Asn Ile
            340                 345                 350

Trp Asn Thr Ser Lys Ile His Ala Leu Tyr Thr Trp Val Ala Glu Thr
        355                 360                 365

Asn Tyr Lys Arg Leu Gln Ala Tyr Tyr Thr Gln Thr Tyr Gly Gly Tyr
    370                 375                 380

Gln Arg Gln Phe Phe Thr Gly Lys Gln Tyr Trp Asp Tyr Arg Val Gly
385                 390                 395                 400

Met Phe Ser Pro Ala Phe Leu Ser Pro Ser Arg Leu Asn Pro Gln Asn
                405                 410                 415

Pro Gly Ala Tyr Thr Glu Val Ser Tyr Asn Pro Trp Thr Asp Glu Gly
            420                 425                 430
```

-continued

```
Thr Gly Asn Val Val Cys Leu Gln Tyr Leu Thr Lys Glu Thr Ser Asp
        435                 440                 445

Tyr Lys Pro Gly Gly Gly Ser Lys Phe Cys Ile Glu Gly Val Pro Leu
    450                 455                 460

Trp Ala Ala Leu Val Gly Tyr Val Asp Met Cys Lys Lys Glu Gly Lys
465                 470                 475                 480

Asp Pro Gly Ile Arg Leu Asn Cys Leu Leu Leu Val Lys Cys Pro Tyr
                485                 490                 495

Thr Lys Pro Gln Leu Tyr Asp Lys Lys Asn Pro Glu Lys Leu Phe Val
            500                 505                 510

Pro Tyr Ser Tyr Asn Phe Gly His Gly Lys Met Pro Gly Gly Asp Lys
        515                 520                 525

Tyr Ile Pro Ile Glu Phe Lys Asp Arg Trp Tyr Pro Cys Leu Leu His
    530                 535                 540

Gln Glu Glu Trp Ile Glu Asp Ile Val Arg Ser Gly Pro Phe Val Pro
545                 550                 555                 560

Lys Asp Met Pro Ser Ser Val Thr Cys Met Met Arg Tyr Ser Ser Leu
                565                 570                 575

Phe Asn Trp Gly Gly Asn Ile Ile Gln Glu Gln Ala Val Glu Asp Pro
            580                 585                 590

Cys Lys Lys Gly Thr Phe Val Val Pro Gly Thr Ser Gly Ile Ala Arg
        595                 600                 605

Ile Leu Gln Val Ser Asn Pro Ala Lys Gln Thr Pro Thr Thr Thr Trp
    610                 615                 620

His Ser Trp Asp Trp Arg Arg Ser Leu Phe Thr Glu Thr Gly Leu Lys
625                 630                 635                 640

Arg Met Arg Glu Gln Gln Pro Tyr Asp Glu Leu Ser Tyr Thr Gly Pro
                645                 650                 655

Lys Lys Pro Lys Leu Ser Leu Pro Ala Gly Pro Ala Val Pro Gly Ala
            660                 665                 670

Ala Val Ala Ser Ser Trp Trp Glu Thr Lys Gln Val Thr Ser Pro Asp
        675                 680                 685

Val Ser Glu Thr Glu Thr Glu Ala Glu Ala His Gln Glu Glu Glu Thr
    690                 695                 700

Glu Pro Glu Glu Gly Val Gln Leu Gln Gln Leu Trp Glu Gln Gln Leu
705                 710                 715                 720

Leu Gln Lys Arg Gln Leu Gly Val Val Phe Gln Gln Leu Leu Arg Leu
                725                 730                 735

Arg Gln Gly Ala Glu Ile His Pro Gly Leu Val
            740                 745
```

<210> SEQ ID NO 14
<211> LENGTH: 220
<212> TYPE: PRT
<213> ORGANISM: Torque teno virus

<400> SEQUENCE: 14

```
Met Ala Tyr Trp Trp Gly Arg Arg Arg Arg Trp Arg Arg Trp Arg Arg
1               5                   10                  15

Arg Arg Arg Pro Leu Arg Arg Arg Arg Arg Trp Arg Arg Arg Arg Arg
            20                  25                  30

Trp Pro Arg Arg Arg Arg Trp Arg Arg Arg Arg Arg Arg Ala Arg Pro
        35                  40                  45

Ala Arg Arg Tyr Arg Arg Arg Arg Gly Arg Arg Arg Ala Val Glu Asp
```

```
    50                  55                  60

Pro Cys Lys Lys Gly Thr Phe Val Val Pro Gly Thr Ser Gly Ile Ala
65                  70                  75                  80

Arg Ile Leu Gln Val Ser Asn Pro Ala Lys Gln Thr Pro Thr Thr Thr
                85                  90                  95

Trp His Ser Trp Asp Trp Arg Arg Ser Leu Phe Thr Glu Thr Gly Leu
            100                 105                 110

Lys Arg Met Arg Glu Gln Gln Pro Tyr Asp Glu Leu Ser Tyr Thr Gly
        115                 120                 125

Pro Lys Lys Pro Lys Leu Ser Leu Pro Ala Gly Pro Ala Val Pro Gly
    130                 135                 140

Ala Ala Val Ala Ser Ser Trp Trp Glu Thr Lys Gln Val Thr Ser Pro
145                 150                 155                 160

Asp Val Ser Glu Thr Glu Thr Glu Ala Glu Ala His Gln Glu Glu Glu
                165                 170                 175

Thr Glu Pro Glu Glu Gly Val Gln Leu Gln Gln Leu Trp Glu Gln Gln
            180                 185                 190

Leu Leu Gln Lys Arg Gln Leu Gly Val Val Phe Gln Gln Leu Leu Arg
        195                 200                 205

Leu Arg Gln Gly Ala Glu Ile His Pro Gly Leu Val
    210                 215                 220


<210> SEQ ID NO 15
<211> LENGTH: 164
<212> TYPE: PRT
<213> ORGANISM: Torque teno virus

<400> SEQUENCE: 15

Met Ala Tyr Trp Trp Gly Arg Arg Arg Arg Trp Arg Arg Trp Arg Arg
1               5                   10                  15

Arg Arg Arg Pro Leu Arg Arg Arg Arg Arg Trp Arg Arg Arg Arg Arg
            20                  25                  30

Trp Pro Arg Arg Arg Arg Trp Arg Arg Arg Arg Arg Arg Ala Arg Pro
        35                  40                  45

Ala Arg Arg Tyr Arg Arg Arg Arg Gly Arg Arg Arg Gly Pro Pro Ser
    50                  55                  60

Pro Val Pro Pro Ser Pro Pro Pro Gly Gly Lys Gln Asn Arg Ser Pro
65                  70                  75                  80

Arg Gln Thr Ser Ala Arg Arg Arg Pro Lys Gln Lys Pro Thr Lys Arg
                85                  90                  95

Lys Arg Arg Ser Arg Arg Arg Glu Ser Ser Ser Ser Ser Cys Gly Ser
            100                 105                 110

Ser Asn Ser Cys Lys Ser Asp Ser Trp Glu Ser Cys Ser Ser Asn Ser
        115                 120                 125

Ser Asp Ser Asp Arg Gly Arg Arg Ser Thr Arg Ala Ser Tyr Asn Ser
    130                 135                 140

Trp Ala Pro Glu Pro Val Pro Ala Phe Pro Gly Ala Gly Pro Ser Lys
145                 150                 155                 160

Ser Ala Tyr Phe


<210> SEQ ID NO 16
<211> LENGTH: 3753
<212> TYPE: DNA
<213> ORGANISM: Torque teno virus

<400> SEQUENCE: 16
```

-continued

```
tgctacgtca ctaacccacg tgtcctctac aggccaatcg cagtctatgt cgtgcacttc     60
ctgggcatgg tctacataat tatataaatg cttgcacttc cgaatggctg agtttttgct    120
gcccgtccgc ggagaggagc cacggcaggg gatccgaacg tcctgagggc gggtgccgga    180
ggtgagttta cacaccgaag tcaaggggca attcgggctc aggactggcc gggctttggg    240
caaggctctt aaaaatgcac ttttctcgaa taagcagaaa gaaaaggaaa gtgctactgc    300
tttgcgtgcc agcagctaag aaaaaaccaa ctgctatgag cttctggaaa cctccggtac    360
acaatgtcac ggggatccaa cgcatgtggt atgagtcctt tcaccgtggc cacgcttctt    420
tttgtggttg tgggaatcct atacttcaca ttactgcact tgctgaaaca tatggccatc    480
caacaggccc gagaccttct gggccaccgg gagtagaccc caaccccccac atccgtagag    540
ccaggcctgc cccggccgct ccggagccct cacaggttga ttcgagacca gccctgacat    600
ggcatgggga tggtggaagc gacggaggcg ctggtggttc cggaagcggt ggacccgtgg    660
cagacttcgc agacgatggc ctcgatcagc tcgtcgccgc cctagacgac gaagagtaag    720
gaggcgcaga cggtggagga gggggagacg aaaaacaagg acttacagac gcaggagacg    780
ctttagacgc aggggacgaa aagcaaaact tataataaaa ctgtggcaac ctgcagtaat    840
taaaagatgc agaataaagg gatacatacc actgattata agtgggaacg gtacctttgc    900
cacaaacttt accagtcaca taaatgacag aataatgaaa ggccccttcg ggggaggaca    960
cagcactatg aggttcagcc tctacatttt gtttgaggag cacctcagac acatgaactt   1020
ctggaccaga agcaacgata acctagagct aaccagatac ttgggggctt cagtaaaaat   1080
atacaggcac ccagaccaag actttatagt aatatacaac agaagaaccc ctctaggagg   1140
caacatctac acagcaccct ctctacaccc aggcaatgcc attttagcaa aacacaaaat   1200
attagtacca agtttacaga caagaccaaa gggtagaaaa gcaattagac taagaatagc   1260
accccccaca ctctttacag acaagtggta ctttcaaaag gacatagccg acctcaccct   1320
tttcaacatc atggcagttg aggctgactt gcggtttccg ttctgctcac cacaaactga   1380
caacacttgc atcagcttcc aggtccttag ttccgtttac aacaactacc tcagtattaa   1440
tacctttaat aatgacaact cagactcaaa gttaaaagaa tttttaaata aagcatttcc   1500
aacaacaggc acaaaaggaa caagtttaaa tgcactaaat acatttagaa cagaaggatg   1560
cataagtcac ccacaactaa aaaaaccaaa cccacaaata aacaaaccat tagagtcaca   1620
atactttgca cctttagatg ccctctgggg agaccccata tactataatg atctaaatga   1680
aaacaaaagt ttgaacgata tcattgagaa aatactaata aaaaacatga ttacatacca   1740
tgcaaaacta agagaatttc caaattcata ccaaggaaac aaggcctttt gccacctaac   1800
aggcatatac agcccaccat acctaaacca aggcagaata tctccagaaa tatttggact   1860
gtacacagaa ataatttaca acccttacac agacaaagga actggaaaca aagtatggat   1920
ggacccacta actaaagaga acaacatata taaagaagga cagagcaaat gcctactgac   1980
tgacatgccc ctatggactt tactttttgg atatacagac tggtgtaaaa aggacactaa   2040
taactgggac ttaccactaa actacagact agtactaata tgcccttata cctttccaaa   2100
attgtacaat gaaaaagtaa aagactatgg gtacatcccg tactcctaca aattcggagc   2160
gggtcagatg ccagacggca gcaactacat accctttcag tttagagcaa agtggtaccc   2220
cacagtacta caccagcaac aggtaatgga ggacataagc aggagcgggc cctttgcacc   2280
taaggtagaa aaaccaagca ctcagctggt aatgaagtac tgttttaact ttaactgggg   2340
```

-continued

```
cggtaaccct atcattgaac agattgttaa agaccccagc ttccagccca cctatgaaat   2400

acccggtacc ggtaacatcc ctagaagaat acaagtcatc gacccgcggg tcctgggacc   2460

gcactactcg ttccggtcat gggacatgcg cagacacaca tttagcagag caagtattaa   2520

gagagtgtca gaacaacaag aaacttctga ccttgtattc tcaggcccaa aaaagcctcg   2580

ggtcgacatc ccaaaacaag aaacccaaga agaaagctca cattcactcc aaagagaatc   2640

gagaccgtgg gagaccgagg aagaaagcga gacagaagcc ctctcgcaag agagccaaga   2700

ggtccccttc caacagcagt tgcagcagca gtaccaagag cagctcaagc tcagacaggg   2760

aatcaaagtc ctcttcgagc agctcataag gacccaacaa ggggtccatg taaacccatg   2820

cctacggtag gtcccaggca gtggctgttt ccagagagaa agccagcccc agctcctagc   2880

agtggagact gggccatgga gtttctcgca gcaaaaatat ttgataggcc agttagaagc   2940

aaccttaaag ataccccta ctacccatat gttaaaaacc aatacaatgt ctactttgac   3000

cttaaatttg aataaacagc agcttcaaac ttgcaaggcc gtgggagttt cactggtcgg   3060

tgtctacctc taaaggtcac taagcactcc gagcgtaagc gaggagtgcg accctccccc   3120

ctggaacaac ttcttcggag tccggcgcta cgccttcggc tgcgccggac acctcagacc   3180

ccccctccac ccgaaacgct tgcgcgtttc ggaccttcgg cgtcgggggg gtcgggagct   3240

ttattaaacg gactccgaag tgctcttgga cactgagggg gtgaacagca acgaaagtga   3300

gtggggccag acttcgccat aaggccttta tcttcttgcc atttgtcagt gtccggggtc   3360

gccataggct tcgggctcgt ttttaggcct tccggactac aaaaatcgcc attttggtga   3420

cgtcacggcc gccatcttaa gtagttgagg cggacggtgg cgtgagttca aaggtcacca   3480

tcagccacac ctactcaaaa tggtggacaa tttcttccgg gtcaaaggtt acagccgcca   3540

tgttaaaaca cgtgacgtat gacgtcacgg ccgccatttt gtgacacaag atggccgact   3600

tccttcctct ttttcaaaaa aaagcggaag tgccgccgcg gcggcggggg gcggcgcgct   3660

gcgcgcgccg cccagtaggg ggagccatgc gccccccccc gcgcatgcgc ggggcccccc   3720

cccgcggggg gctccgcccc ccggcccccc ccg                                3753
```

```
<210> SEQ ID NO 17
<211> LENGTH: 127
<212> TYPE: PRT
<213> ORGANISM: Torque teno virus

<400> SEQUENCE: 17

Met Ser Phe Trp Lys Pro Pro Val His Asn Val Thr Gly Ile Gln Arg
1               5                   10                  15

Met Trp Tyr Glu Ser Phe His Arg Gly His Ala Ser Phe Cys Gly Cys
            20                  25                  30

Gly Asn Pro Ile Leu His Ile Thr Ala Leu Ala Glu Thr Tyr Gly His
        35                  40                  45

Pro Thr Gly Pro Arg Pro Ser Gly Pro Pro Gly Val Asp Pro Asn Pro
    50                  55                  60

His Ile Arg Arg Ala Arg Pro Ala Pro Ala Ala Pro Glu Pro Ser Gln
65                  70                  75                  80

Val Asp Ser Arg Pro Ala Leu Thr Trp His Gly Asp Gly Gly Ser Asp
                85                  90                  95

Gly Gly Ala Gly Gly Ser Gly Ser Gly Gly Pro Val Ala Asp Phe Ala
            100                 105                 110

Asp Asp Gly Leu Asp Gln Leu Val Ala Ala Leu Asp Asp Glu Glu
        115                 120                 125
```

<210> SEQ ID NO 18
<211> LENGTH: 268
<212> TYPE: PRT
<213> ORGANISM: Torque teno virus

<400> SEQUENCE: 18

```
Met Ser Phe Trp Lys Pro Pro Val His Asn Val Thr Gly Ile Gln Arg
1               5                   10                  15

Met Trp Tyr Glu Ser Phe His Arg Gly His Ala Ser Phe Cys Gly Cys
            20                  25                  30

Gly Asn Pro Ile Leu His Ile Thr Ala Leu Ala Glu Thr Tyr Gly His
        35                  40                  45

Pro Thr Gly Pro Arg Pro Ser Gly Pro Pro Gly Val Asp Pro Asn Pro
    50                  55                  60

His Ile Arg Arg Ala Arg Pro Ala Pro Ala Ala Pro Glu Pro Ser Gln
65                  70                  75                  80

Val Asp Ser Arg Pro Ala Leu Thr Trp His Gly Asp Gly Gly Ser Asp
                85                  90                  95

Gly Gly Ala Gly Gly Ser Gly Ser Gly Gly Pro Val Ala Asp Phe Ala
            100                 105                 110

Asp Asp Gly Leu Asp Gln Leu Val Ala Ala Leu Asp Asp Glu Glu Leu
        115                 120                 125

Leu Lys Thr Pro Ala Ser Ser Pro Pro Met Lys Tyr Pro Val Pro Val
    130                 135                 140

Thr Ser Leu Glu Glu Tyr Lys Ser Ser Thr Arg Gly Ser Trp Asp Arg
145                 150                 155                 160

Thr Thr Arg Ser Gly His Gly Thr Cys Ala Asp Thr His Leu Ala Glu
                165                 170                 175

Gln Val Leu Arg Glu Cys Gln Asn Asn Lys Lys Leu Leu Thr Leu Tyr
            180                 185                 190

Ser Gln Ala Gln Lys Ser Leu Gly Ser Thr Ser Gln Asn Lys Lys Pro
        195                 200                 205

Lys Lys Lys Ala His Ile His Ser Lys Glu Asn Arg Asp Arg Gly Arg
    210                 215                 220

Pro Arg Lys Lys Ala Arg Gln Lys Pro Ser Arg Lys Arg Ala Lys Arg
225                 230                 235                 240

Ser Pro Ser Asn Ser Ser Cys Ser Ser Ser Thr Lys Ser Ser Ser Ser
                245                 250                 255

Ser Asp Arg Glu Ser Lys Ser Ser Ser Ser Ser Ser
            260                 265
```

<210> SEQ ID NO 19
<211> LENGTH: 276
<212> TYPE: PRT
<213> ORGANISM: Torque teno virus

<400> SEQUENCE: 19

```
Met Ser Phe Trp Lys Pro Pro Val His Asn Val Thr Gly Ile Gln Arg
1               5                   10                  15

Met Trp Tyr Glu Ser Phe His Arg Gly His Ala Ser Phe Cys Gly Cys
            20                  25                  30

Gly Asn Pro Ile Leu His Ile Thr Ala Leu Ala Glu Thr Tyr Gly His
        35                  40                  45

Pro Thr Gly Pro Arg Pro Ser Gly Pro Pro Gly Val Asp Pro Asn Pro
    50                  55                  60
```

His Ile Arg Arg Ala Arg Pro Ala Pro Ala Ala Pro Glu Pro Ser Gln
65 70 75 80

Val Asp Ser Arg Pro Ala Leu Thr Trp His Gly Asp Gly Gly Ser Asp
85 90 95

Gly Gly Ala Gly Gly Ser Gly Ser Gly Gly Pro Val Ala Asp Phe Ala
100 105 110

Asp Asp Gly Leu Asp Gln Leu Val Ala Ala Leu Asp Asp Glu Glu Pro
115 120 125

Lys Lys Ala Ser Gly Arg His Pro Lys Thr Arg Asn Pro Arg Arg Lys
130 135 140

Leu Thr Phe Thr Pro Lys Arg Ile Glu Thr Val Gly Asp Arg Gly Arg
145 150 155 160

Lys Arg Asp Arg Ser Pro Leu Ala Arg Glu Pro Arg Gly Pro Leu Pro
165 170 175

Thr Ala Val Ala Ala Ala Val Pro Arg Ala Ala Gln Ala Gln Thr Gly
180 185 190

Asn Gln Ser Pro Leu Arg Ala Ala His Lys Asp Pro Thr Arg Gly Pro
195 200 205

Cys Lys Pro Met Pro Thr Val Gly Pro Arg Gln Trp Leu Phe Pro Glu
210 215 220

Arg Lys Pro Ala Pro Ala Pro Ser Ser Gly Asp Trp Ala Met Glu Phe
225 230 235 240

Leu Ala Ala Lys Ile Phe Asp Arg Pro Val Arg Ser Asn Leu Lys Asp
245 250 255

Thr Pro Tyr Tyr Pro Tyr Val Lys Asn Gln Tyr Asn Val Tyr Phe Asp
260 265 270

Leu Lys Phe Glu
275

<210> SEQ ID NO 20
<211> LENGTH: 167
<212> TYPE: PRT
<213> ORGANISM: Torque teno virus

<400> SEQUENCE: 20

Met Ser Phe Trp Lys Pro Pro Val His Asn Val Thr Gly Ile Gln Arg
1 5 10 15

Met Trp Pro Lys Lys Ala Ser Gly Arg His Pro Lys Thr Arg Asn Pro
20 25 30

Arg Arg Lys Leu Thr Phe Thr Pro Lys Arg Ile Glu Thr Val Gly Asp
35 40 45

Arg Gly Arg Lys Arg Asp Arg Ser Pro Leu Ala Arg Glu Pro Arg Gly
50 55 60

Pro Leu Pro Thr Ala Val Ala Ala Ala Val Pro Arg Ala Ala Gln Ala
65 70 75 80

Gln Thr Gly Asn Gln Ser Pro Leu Arg Ala Ala His Lys Asp Pro Thr
85 90 95

Arg Gly Pro Cys Lys Pro Met Pro Thr Val Gly Pro Arg Gln Trp Leu
100 105 110

Phe Pro Glu Arg Lys Pro Ala Pro Ala Pro Ser Ser Gly Asp Trp Ala
115 120 125

Met Glu Phe Leu Ala Ala Lys Ile Phe Asp Arg Pro Val Arg Ser Asn
130 135 140

Leu Lys Asp Thr Pro Tyr Tyr Pro Tyr Val Lys Asn Gln Tyr Asn Val

```
145                 150                 155                 160

Tyr Phe Asp Leu Lys Phe Glu
                165


<210> SEQ ID NO 21
<211> LENGTH: 743
<212> TYPE: PRT
<213> ORGANISM: Torque teno virus

<400> SEQUENCE: 21

Met Ala Trp Gly Trp Trp Lys Arg Arg Arg Arg Trp Trp Phe Arg Lys
1               5                   10                  15

Arg Trp Thr Arg Gly Arg Leu Arg Arg Arg Trp Pro Arg Ser Ala Arg
            20                  25                  30

Arg Arg Pro Arg Arg Arg Arg Val Arg Arg Arg Arg Arg Trp Arg Arg
        35                  40                  45

Gly Arg Arg Lys Thr Arg Thr Tyr Arg Arg Arg Arg Arg Phe Arg Arg
    50                  55                  60

Arg Gly Arg Lys Ala Lys Leu Ile Ile Lys Leu Trp Gln Pro Ala Val
65                  70                  75                  80

Ile Lys Arg Cys Arg Ile Lys Gly Tyr Ile Pro Leu Ile Ile Ser Gly
                85                  90                  95

Asn Gly Thr Phe Ala Thr Asn Phe Thr Ser His Ile Asn Asp Arg Ile
            100                 105                 110

Met Lys Gly Pro Phe Gly Gly Gly His Ser Thr Met Arg Phe Ser Leu
        115                 120                 125

Tyr Ile Leu Phe Glu Glu His Leu Arg His Met Asn Phe Trp Thr Arg
    130                 135                 140

Ser Asn Asp Asn Leu Glu Leu Thr Arg Tyr Leu Gly Ala Ser Val Lys
145                 150                 155                 160

Ile Tyr Arg His Pro Asp Gln Asp Phe Ile Val Ile Tyr Asn Arg Arg
                165                 170                 175

Thr Pro Leu Gly Gly Asn Ile Tyr Thr Ala Pro Ser Leu His Pro Gly
            180                 185                 190

Asn Ala Ile Leu Ala Lys His Lys Ile Leu Val Pro Ser Leu Gln Thr
        195                 200                 205

Arg Pro Lys Gly Arg Lys Ala Ile Arg Leu Arg Ile Ala Pro Pro Thr
    210                 215                 220

Leu Phe Thr Asp Lys Trp Tyr Phe Gln Lys Asp Ile Ala Asp Leu Thr
225                 230                 235                 240

Leu Phe Asn Ile Met Ala Val Glu Ala Asp Leu Arg Phe Pro Phe Cys
                245                 250                 255

Ser Pro Gln Thr Asp Asn Thr Cys Ile Ser Phe Gln Val Leu Ser Ser
            260                 265                 270

Val Tyr Asn Asn Tyr Leu Ser Ile Asn Thr Phe Asn Asn Asp Asn Ser
        275                 280                 285

Asp Ser Lys Leu Lys Glu Phe Leu Asn Lys Ala Phe Pro Thr Thr Gly
    290                 295                 300

Thr Lys Gly Thr Ser Leu Asn Ala Leu Asn Thr Phe Arg Thr Glu Gly
305                 310                 315                 320

Cys Ile Ser His Pro Gln Leu Lys Lys Pro Asn Pro Gln Ile Asn Lys
                325                 330                 335

Pro Leu Glu Ser Gln Tyr Phe Ala Pro Leu Asp Ala Leu Trp Gly Asp
            340                 345                 350
```

```
Pro Ile Tyr Tyr Asn Asp Leu Asn Glu Asn Lys Ser Leu Asn Asp Ile
        355                 360                 365

Ile Glu Lys Ile Leu Ile Lys Asn Met Ile Thr Tyr His Ala Lys Leu
    370                 375                 380

Arg Glu Phe Pro Asn Ser Tyr Gln Gly Asn Lys Ala Phe Cys His Leu
385                 390                 395                 400

Thr Gly Ile Tyr Ser Pro Pro Tyr Leu Asn Gln Gly Arg Ile Ser Pro
                405                 410                 415

Glu Ile Phe Gly Leu Tyr Thr Glu Ile Ile Tyr Asn Pro Tyr Thr Asp
            420                 425                 430

Lys Gly Thr Gly Asn Lys Val Trp Met Asp Pro Leu Thr Lys Glu Asn
        435                 440                 445

Asn Ile Tyr Lys Glu Gly Gln Ser Lys Cys Leu Leu Thr Asp Met Pro
    450                 455                 460

Leu Trp Thr Leu Leu Phe Gly Tyr Thr Asp Trp Cys Lys Lys Asp Thr
465                 470                 475                 480

Asn Asn Trp Asp Leu Pro Leu Asn Tyr Arg Leu Val Leu Ile Cys Pro
                485                 490                 495

Tyr Thr Phe Pro Lys Leu Tyr Asn Glu Lys Val Lys Asp Tyr Gly Tyr
            500                 505                 510

Ile Pro Tyr Ser Tyr Lys Phe Gly Ala Gly Gln Met Pro Asp Gly Ser
        515                 520                 525

Asn Tyr Ile Pro Phe Gln Phe Arg Ala Lys Trp Tyr Pro Thr Val Leu
    530                 535                 540

His Gln Gln Gln Val Met Glu Asp Ile Ser Arg Ser Gly Pro Phe Ala
545                 550                 555                 560

Pro Lys Val Glu Lys Pro Ser Thr Gln Leu Val Met Lys Tyr Cys Phe
                565                 570                 575

Asn Phe Asn Trp Gly Gly Asn Pro Ile Ile Glu Gln Ile Val Lys Asp
            580                 585                 590

Pro Ser Phe Gln Pro Thr Tyr Glu Ile Pro Gly Thr Gly Asn Ile Pro
        595                 600                 605

Arg Arg Ile Gln Val Ile Asp Pro Arg Val Leu Gly Pro His Tyr Ser
    610                 615                 620

Phe Arg Ser Trp Asp Met Arg Arg His Thr Phe Ser Arg Ala Ser Ile
625                 630                 635                 640

Lys Arg Val Ser Glu Gln Gln Glu Thr Ser Asp Leu Val Phe Ser Gly
                645                 650                 655

Pro Lys Lys Pro Arg Val Asp Ile Pro Lys Gln Glu Thr Gln Glu Glu
            660                 665                 670

Ser Ser His Ser Leu Gln Arg Glu Ser Arg Pro Trp Glu Thr Glu Glu
        675                 680                 685

Glu Ser Glu Thr Glu Ala Leu Ser Gln Glu Ser Gln Glu Val Pro Phe
    690                 695                 700

Gln Gln Gln Leu Gln Gln Gln Tyr Gln Glu Gln Leu Lys Leu Arg Gln
705                 710                 715                 720

Gly Ile Lys Val Leu Phe Glu Gln Leu Ile Arg Thr Gln Gln Gly Val
                725                 730                 735

His Val Asn Pro Cys Leu Arg
            740
```

<210> SEQ ID NO 22
<211> LENGTH: 194
<212> TYPE: PRT

<213> ORGANISM: Torque teno virus

<400> SEQUENCE: 22

```
Met Ala Trp Gly Trp Trp Lys Arg Arg Arg Arg Trp Trp Phe Arg Lys
1               5                   10                  15

Arg Trp Thr Arg Gly Arg Leu Arg Arg Arg Trp Pro Arg Ser Ala Arg
            20                  25                  30

Arg Arg Pro Arg Arg Arg Arg Ile Val Lys Asp Pro Ser Phe Gln Pro
        35                  40                  45

Thr Tyr Glu Ile Pro Gly Thr Gly Asn Ile Pro Arg Arg Ile Gln Val
    50                  55                  60

Ile Asp Pro Arg Val Leu Gly Pro His Tyr Ser Phe Arg Ser Trp Asp
65                  70                  75                  80

Met Arg Arg His Thr Phe Ser Arg Ala Ser Ile Lys Arg Val Ser Glu
                85                  90                  95

Gln Gln Glu Thr Ser Asp Leu Val Phe Ser Gly Pro Lys Lys Pro Arg
            100                 105                 110

Val Asp Ile Pro Lys Gln Glu Thr Gln Glu Glu Ser Ser His Ser Leu
        115                 120                 125

Gln Arg Glu Ser Arg Pro Trp Glu Thr Glu Glu Glu Ser Glu Thr Glu
    130                 135                 140

Ala Leu Ser Gln Glu Ser Gln Glu Val Pro Phe Gln Gln Gln Leu Gln
145                 150                 155                 160

Gln Gln Tyr Gln Glu Gln Leu Lys Leu Arg Gln Gly Ile Lys Val Leu
                165                 170                 175

Phe Glu Gln Leu Ile Arg Thr Gln Gln Gly Val His Val Asn Pro Cys
            180                 185                 190

Leu Arg
```

<210> SEQ ID NO 23
<211> LENGTH: 113
<212> TYPE: PRT
<213> ORGANISM: Torque teno virus

<400> SEQUENCE: 23

```
Met Ala Trp Gly Trp Trp Lys Arg Arg Arg Arg Trp Trp Phe Arg Lys
1               5                   10                  15

Arg Trp Thr Arg Gly Arg Leu Arg Arg Arg Trp Pro Arg Ser Ala Arg
            20                  25                  30

Arg Arg Pro Arg Arg Arg Arg Ala Gln Lys Ser Leu Gly Ser Thr Ser
        35                  40                  45

Gln Asn Lys Lys Pro Lys Lys Lys Ala His Ile His Ser Lys Glu Asn
    50                  55                  60

Arg Asp Arg Gly Arg Pro Arg Lys Lys Ala Arg Gln Lys Pro Ser Arg
65                  70                  75                  80

Lys Arg Ala Lys Arg Ser Pro Ser Asn Ser Ser Cys Ser Ser Ser Thr
                85                  90                  95

Lys Ser Ser Ser Ser Ser Asp Arg Glu Ser Lys Ser Ser Ser Ser Ser
            100                 105                 110

Ser
```

<210> SEQ ID NO 24
<211> LENGTH: 3878
<212> TYPE: DNA
<213> ORGANISM: Torque teno virus

<400> SEQUENCE: 24

```
aaatacgtca ctaaccacgt gactcccaca ggccaaccac agtctatgtc gtgcacttcc     60
tgggcatggt ctacgtgata atataaagcg gtgcacttcc gaatggctga gttttccacg    120
cccgtccgca gcgagatcgc gacgtaggag cgatcgagcg tcccgagggc gggtgccgga    180
ggtgagttta cacaccgcag tcaaggggca attcgggctc gggaggccgg gccatgggca    240
aggctcttaa aaagctatgt ttctcggtaa aatctacagg aagaaaagga aactgcttct    300
gcaggctgtg cgtgctccgc agacgccatc ttccatgagc cgctgctggt gtccccctcg    360
gggtgatgtc tcctcccgcg agtctcgatg gtacgaggcg gttcgaggaa gccacgatgc    420
tttttgtggc tgtagtgatc ctattcttca tctttctcgt ctggctgcac gttttaacca    480
tcagggacct ccgacgcccc ccacggacga ccgtgcgccg cagaataccc cagtgagacg    540
cctgctgcct ctccccagct accccggcga gggtccccag gctagatggc ctggtgggga    600
tggaggcgcc gctggtggcg accgaagaga aggtggagat ggcggcgcgc gcgccgccga    660
agacgagtac cagcccgaag acctagacga gcttttcggc gctatcgaac aagaacagta    720
aggaggaggc gaagggggag gcggaggggc taccggcgcc gttacagact gagacgctat    780
gccagacgca ggttccgacg caaaaagata gtactgactc agtggaaccc ccagactacc    840
agaaaatgta taataagggg catgatgcca gtactgtggg ccggcatggg tacggggggc    900
agaaactatg cagtgaggtc agatgactat gtggtgaaca aagggttcgg gggctccttc    960
gccacggaga ccttctccct gaaggttctc tatgaccagt ttcaaagggg cttcaacagg   1020
tggtcccaca ctaacgagga cctagacctg gcccgctaca ggggctgcag gtggactttt   1080
tacagacata aagacacaga ctttatagtg tactttacaa acaatcctcc catgaagacc   1140
aaccagttct ccgcgcccct gacgaccccc ggcatgctca tgcgcagtaa atacaaagtc   1200
ctcattccca gcttccagac cagacccaag ggtcgcaaaa cagtaaccgt taaaataaga   1260
ccccccaaac tatttcaaga caagtggtac acccagcagg acctgtgttc agttcctctt   1320
gtccaactga acgtgaccgc agctgatttc acacatccgt tcggctcacc actaactgaa   1380
actccttgcg tagagttcca ggtgctgggt gacttgtaca atacatgtct caatatcgac   1440
cttccgcaat ttagtgaatt aggagaaata actagtgcct actcaaaacc aaactcaaat   1500
aacctaaaag aattatacaa agaattgttc acaaaagcca catcaggaca ctactggcag   1560
acattcataa ccaacagcat ggtcagagca cacatagatg cagacaaagc taaagaagca   1620
caaagagcat ccaccacacc ctcatacaac aatgacccct tccccacaat acctgttaaa   1680
tcagagtttg cacagtggaa aaagaaattc acagacacta gagacagccc ctttcttttt   1740
gccacttacc atcccgaagc tataaaagac acaattatga aatgagagaa gaacaacttt   1800
aagctagaga caggacccaa tgacaagtat ggagactaca cagcacagta ccaaggaaac   1860
acacacatgc tagactacta ccttggcttt tacagcccca tattcctctc agatggaagg   1920
tctaacgtag aattcttcac tgcctacaga gacatagtat acaatccctt cttagacaag   1980
gcccagggca acatggtgtg gtttcagtac cacacaaaga cagacaacaa gtttaaaaaa   2040
ccagagtgcc actgggaaat caaagacatg cccctgtggg ccctcctaaa cggatatgta   2100
gactacttag agactcaaat acagtatggt gacctcagta aagaagggaa agtcctcatc   2160
aggtgtccct acaccaagcc agcactagta gaccccagag acgacactgc aggatatgta   2220
gtctacaaca gaaactttgg cagaggcaag tggatagacg gagggggcta catccccctg   2280
cacgagagga caaaatggta cgtgatgctc agataccaga cggacgtctt ccatgacata   2340
```

```
gtgacctgtg ggccctggca gtacagagac gacaacaaaa acagccagct agtggccaaa   2400

taccgcttca gctttatatg gggaggtaac actgtccact ctcaggtcat cagaaacccg   2460

tgcaaagaca accaagtatc cggtccccgt cgacagccta gggatataca agtcgttgac   2520

ccgcaacgca tcacgccgcc gtgggtcctc cacagcttcg accagcgaag aggcctcttt   2580

actgaaacag ctctcaggcg cctgctccag gaaccactac ctggcgagta tgctgttagc   2640

accctcagga cacccctcct ctttctaccc tcagaatacc agcgagaaga cggcgctgca   2700

gaaagcgcct caggttcacc ggccaaaaga ccccgtatct ggtcagaaga gagtcagacg   2760

gagacgatct cctcggagga gaacccggcg gagacgacga gggagctcct ccagcgaaag   2820

ctccgagagc agcgagcact ccagttccaa ctccagcact tcgcggtcca actcgccaag   2880

acccaggcga atctccacgt aaaccccctg ttatctttcc cgcaatgaat aaggtctttc   2940

tgtttccccc agagggtccc aagcccatcc tgggcaaaga ggcctggcag gacgagtacg   3000

agacctgcag ggtctggaac agacctgcca gaacccacca cacagacacc cccttctatc   3060

cctgggcccc ccacaagttc catgtaagct tcaaacttgg cttccaataa aattactagg   3120

ccgtggaact ctcactggtc ggtgtctacc tcttaaggtc actaagcact ccgagcgtca   3180

gcgaggagtg cgaccctcta ccctggtgca acgccctcgg cggccgcgcg ctacgccttc   3240

ggctgcgcgc ggcacctcgg acccccgctc gtgctgacgc gctcgcgcgc gtcagaccac   3300

ttcgggctcg cgggggtcgg gaattttgct aaacagactc cgagttgcca ttggacactg   3360

tagctgtgaa tcagtaacga aagtgagtgg ggccagactt cgccataggg cctttatctt   3420

cttgccattg gtccgtgtag gggtcgccca taggcttcga cctccctttt aggccttccg   3480

gactacaaaa atggcggatt cagtgacgtc acggccgcca ttttaagtag gtgccgtcca   3540

ggactgcagt tccgggtcag agtgcatcct cggcggaacc tgcacaaaat ggcggtcaat   3600

atcttccggg tcaaaggtca cacctacgtc ataagtcacg tgactgggtc ctgctacgtc   3660

atatgcggaa gtaggccccg ccacgtgact cgtcacgtgg gcgctgcgtc acggcggcca   3720

ttttgtatca caaaatggcg gacttccttc ctctttttta aaaataacgg cccagcggcg   3780

gcgcgcgcgc ttcgcgcgcg cgccgggggg ctccgccccc ccccgcgcat gcgcggggcc   3840

ccccccgcg gggggctccg ccccccggtc cccccccg                            3878
```

```
<210> SEQ ID NO 25
<211> LENGTH: 128
<212> TYPE: PRT
<213> ORGANISM: Torque teno virus

<400> SEQUENCE: 25

Met Ser Arg Cys Trp Cys Pro Pro Arg Gly Asp Val Ser Ser Arg Glu
1               5                   10                  15

Ser Arg Trp Tyr Glu Ala Val Arg Gly Ser His Asp Ala Phe Cys Gly
            20                  25                  30

Cys Ser Asp Pro Ile Leu His Leu Ser Arg Leu Ala Ala Arg Phe Asn
        35                  40                  45

His Gln Gly Pro Pro Thr Pro Pro Thr Asp Asp Arg Ala Pro Gln Asn
    50                  55                  60

Thr Pro Val Arg Arg Leu Leu Pro Leu Pro Ser Tyr Pro Gly Glu Gly
65                  70                  75                  80

Pro Gln Ala Arg Trp Pro Gly Gly Asp Gly Gly Ala Ala Gly Gly Asp
                85                  90                  95
```

```
Arg Arg Glu Gly Gly Asp Gly Gly Ala Arg Ala Ala Glu Asp Glu Tyr
            100                 105                 110

Gln Pro Glu Asp Leu Asp Glu Leu Phe Gly Ala Ile Glu Gln Glu Gln
        115                 120                 125


<210> SEQ ID NO 26
<211> LENGTH: 279
<212> TYPE: PRT
<213> ORGANISM: Torque teno virus

<400> SEQUENCE: 26

Met Ser Arg Cys Trp Cys Pro Pro Arg Gly Asp Val Ser Ser Arg Glu
1               5                   10                  15

Ser Arg Trp Tyr Glu Ala Val Arg Gly Ser His Asp Ala Phe Cys Gly
            20                  25                  30

Cys Ser Asp Pro Ile Leu His Leu Ser Arg Leu Ala Ala Arg Phe Asn
        35                  40                  45

His Gln Gly Pro Pro Thr Pro Pro Thr Asp Asp Arg Ala Pro Gln Asn
    50                  55                  60

Thr Pro Val Arg Arg Leu Leu Pro Leu Pro Ser Tyr Pro Gly Glu Gly
65                  70                  75                  80

Pro Gln Ala Arg Trp Pro Gly Gly Asp Gly Gly Ala Ala Gly Gly Asp
                85                  90                  95

Arg Arg Glu Gly Gly Asp Gly Gly Ala Arg Ala Ala Glu Asp Glu Tyr
            100                 105                 110

Gln Pro Glu Asp Leu Asp Glu Leu Phe Gly Ala Ile Glu Gln Glu Gln
        115                 120                 125

Ser Ser Glu Thr Arg Ala Lys Thr Thr Lys Tyr Pro Val Pro Val Asp
    130                 135                 140

Ser Leu Gly Ile Tyr Lys Ser Leu Thr Arg Asn Ala Ser Arg Arg Arg
145                 150                 155                 160

Gly Ser Ser Thr Ala Ser Thr Ser Glu Glu Ala Ser Leu Leu Lys Gln
                165                 170                 175

Leu Ser Gly Ala Cys Ser Arg Asn His Tyr Leu Ala Ser Met Leu Leu
            180                 185                 190

Ala Pro Ser Gly His Pro Ser Ser Phe Tyr Pro Gln Asn Thr Ser Glu
        195                 200                 205

Lys Thr Ala Leu Gln Lys Ala Pro Gln Val His Arg Pro Lys Asp Pro
    210                 215                 220

Val Ser Gly Gln Lys Arg Val Arg Arg Arg Arg Ser Pro Arg Arg Arg
225                 230                 235                 240

Thr Arg Arg Arg Arg Arg Gly Ser Ser Ser Ser Glu Ser Ser Glu Ser
                245                 250                 255

Ser Glu His Ser Ser Ser Asn Ser Ser Thr Ser Arg Ser Asn Ser Pro
            260                 265                 270

Arg Pro Arg Arg Ile Ser Thr
        275


<210> SEQ ID NO 27
<211> LENGTH: 272
<212> TYPE: PRT
<213> ORGANISM: Torque teno virus

<400> SEQUENCE: 27

Met Ser Arg Cys Trp Cys Pro Pro Arg Gly Asp Val Ser Ser Arg Glu
1               5                   10                  15
```

```
Ser Arg Trp Tyr Glu Ala Val Arg Gly Ser His Asp Ala Phe Cys Gly
            20                  25                  30

Cys Ser Asp Pro Ile Leu His Leu Ser Arg Leu Ala Ala Arg Phe Asn
        35                  40                  45

His Gln Gly Pro Pro Thr Pro Pro Thr Asp Asp Arg Ala Pro Gln Asn
    50                  55                  60

Thr Pro Val Arg Arg Leu Leu Pro Leu Pro Ser Tyr Pro Gly Glu Gly
65                  70                  75                  80

Pro Gln Ala Arg Trp Pro Gly Gly Asp Gly Gly Ala Ala Gly Gly Asp
                85                  90                  95

Arg Arg Glu Gly Gly Asp Gly Gly Ala Arg Ala Ala Glu Asp Glu Tyr
            100                 105                 110

Gln Pro Glu Asp Leu Asp Glu Leu Phe Gly Ala Ile Glu Gln Glu Gln
        115                 120                 125

Ile Pro Ala Arg Arg Arg Arg Cys Arg Lys Arg Leu Arg Phe Thr Gly
    130                 135                 140

Gln Lys Thr Pro Tyr Leu Val Arg Arg Glu Ser Asp Gly Asp Asp Leu
145                 150                 155                 160

Leu Gly Gly Glu Pro Gly Gly Asp Asp Glu Gly Ala Pro Pro Ala Lys
                165                 170                 175

Ala Pro Arg Ala Ala Ser Thr Pro Val Pro Thr Pro Ala Leu Arg Gly
            180                 185                 190

Pro Thr Arg Gln Asp Pro Gly Glu Ser Pro Arg Lys Pro Pro Val Ile
        195                 200                 205

Phe Pro Ala Met Asn Lys Val Phe Leu Phe Pro Pro Glu Gly Pro Lys
    210                 215                 220

Pro Ile Leu Gly Lys Glu Ala Trp Gln Asp Glu Tyr Glu Thr Cys Arg
225                 230                 235                 240

Val Trp Asn Arg Pro Ala Arg Thr His His Thr Asp Thr Pro Phe Tyr
                245                 250                 255

Pro Trp Ala Pro His Lys Phe His Val Ser Phe Lys Leu Gly Phe Gln
            260                 265                 270


<210> SEQ ID NO 28
<211> LENGTH: 780
<212> TYPE: PRT
<213> ORGANISM: Torque teno virus

<400> SEQUENCE: 28

Met Ala Trp Trp Gly Trp Arg Arg Arg Trp Trp Arg Pro Lys Arg Arg
1               5                   10                  15

Trp Arg Trp Arg Arg Ala Arg Arg Arg Arg Arg Val Pro Ala Arg Arg
            20                  25                  30

Pro Arg Arg Ala Phe Arg Arg Tyr Arg Thr Arg Thr Val Arg Arg Arg
        35                  40                  45

Arg Arg Gly Arg Arg Arg Gly Tyr Arg Arg Arg Tyr Arg Leu Arg Arg
    50                  55                  60

Tyr Ala Arg Arg Arg Phe Arg Arg Lys Lys Ile Val Leu Thr Gln Trp
65                  70                  75                  80

Asn Pro Gln Thr Thr Arg Lys Cys Ile Ile Arg Gly Met Met Pro Val
                85                  90                  95

Leu Trp Ala Gly Met Gly Thr Gly Gly Arg Asn Tyr Ala Val Arg Ser
            100                 105                 110

Asp Asp Tyr Val Val Asn Lys Gly Phe Gly Gly Ser Phe Ala Thr Glu
        115                 120                 125
```

```
Thr Phe Ser Leu Lys Val Leu Tyr Asp Gln Phe Gln Arg Gly Phe Asn
    130                 135                 140

Arg Trp Ser His Thr Asn Glu Asp Leu Asp Leu Ala Arg Tyr Arg Gly
145                 150                 155                 160

Cys Arg Trp Thr Phe Tyr Arg His Lys Asp Thr Asp Phe Ile Val Tyr
                165                 170                 175

Phe Thr Asn Asn Pro Pro Met Lys Thr Asn Gln Phe Ser Ala Pro Leu
            180                 185                 190

Thr Thr Pro Gly Met Leu Met Arg Ser Lys Tyr Lys Val Leu Ile Pro
        195                 200                 205

Ser Phe Gln Thr Arg Pro Lys Gly Arg Lys Thr Val Thr Val Lys Ile
    210                 215                 220

Arg Pro Pro Lys Leu Phe Gln Asp Lys Trp Tyr Thr Gln Gln Asp Leu
225                 230                 235                 240

Cys Ser Val Pro Leu Val Gln Leu Asn Val Thr Ala Ala Asp Phe Thr
                245                 250                 255

His Pro Phe Gly Ser Pro Leu Thr Glu Thr Pro Cys Val Glu Phe Gln
            260                 265                 270

Val Leu Gly Asp Leu Tyr Asn Thr Cys Leu Asn Ile Asp Leu Pro Gln
        275                 280                 285

Phe Ser Glu Leu Gly Glu Ile Thr Ser Ala Tyr Ser Lys Pro Asn Ser
    290                 295                 300

Asn Asn Leu Lys Glu Leu Tyr Lys Glu Leu Phe Thr Lys Ala Thr Ser
305                 310                 315                 320

Gly His Tyr Trp Gln Thr Phe Ile Thr Asn Ser Met Val Arg Ala His
                325                 330                 335

Ile Asp Ala Asp Lys Ala Lys Glu Ala Gln Arg Ala Ser Thr Thr Pro
            340                 345                 350

Ser Tyr Asn Asn Asp Pro Phe Pro Thr Ile Pro Val Lys Ser Glu Phe
        355                 360                 365

Ala Gln Trp Lys Lys Lys Phe Thr Asp Thr Arg Asp Ser Pro Phe Leu
    370                 375                 380

Phe Ala Thr Tyr His Pro Glu Ala Ile Lys Asp Thr Ile Met Lys Met
385                 390                 395                 400

Arg Glu Asn Asn Phe Lys Leu Glu Thr Gly Pro Asn Asp Lys Tyr Gly
                405                 410                 415

Asp Tyr Thr Ala Gln Tyr Gln Gly Asn Thr His Met Leu Asp Tyr Tyr
            420                 425                 430

Leu Gly Phe Tyr Ser Pro Ile Phe Leu Ser Asp Gly Arg Ser Asn Val
        435                 440                 445

Glu Phe Phe Thr Ala Tyr Arg Asp Ile Val Tyr Asn Pro Phe Leu Asp
    450                 455                 460

Lys Ala Gln Gly Asn Met Val Trp Phe Gln Tyr His Thr Lys Thr Asp
465                 470                 475                 480

Asn Lys Phe Lys Lys Pro Glu Cys His Trp Glu Ile Lys Asp Met Pro
                485                 490                 495

Leu Trp Ala Leu Leu Asn Gly Tyr Val Asp Tyr Leu Glu Thr Gln Ile
            500                 505                 510

Gln Tyr Gly Asp Leu Ser Lys Glu Gly Lys Val Leu Ile Arg Cys Pro
        515                 520                 525

Tyr Thr Lys Pro Ala Leu Val Asp Pro Arg Asp Asp Thr Ala Gly Tyr
    530                 535                 540
```

-continued

```
Val Val Tyr Asn Arg Asn Phe Gly Arg Gly Lys Trp Ile Asp Gly Gly
545                 550                 555                 560

Gly Tyr Ile Pro Leu His Glu Arg Thr Lys Trp Tyr Val Met Leu Arg
                565                 570                 575

Tyr Gln Thr Asp Val Phe His Asp Ile Val Thr Cys Gly Pro Trp Gln
            580                 585                 590

Tyr Arg Asp Asp Asn Lys Asn Ser Gln Leu Val Ala Lys Tyr Arg Phe
        595                 600                 605

Ser Phe Ile Trp Gly Gly Asn Thr Val His Ser Gln Val Ile Arg Asn
    610                 615                 620

Pro Cys Lys Asp Asn Gln Val Ser Gly Pro Arg Arg Gln Pro Arg Asp
625                 630                 635                 640

Ile Gln Val Val Asp Pro Gln Arg Ile Thr Pro Pro Trp Val Leu His
                645                 650                 655

Ser Phe Asp Gln Arg Arg Gly Leu Phe Thr Glu Thr Ala Leu Arg Arg
            660                 665                 670

Leu Leu Gln Glu Pro Leu Pro Gly Glu Tyr Ala Val Ser Thr Leu Arg
        675                 680                 685

Thr Pro Leu Leu Phe Leu Pro Ser Glu Tyr Gln Arg Glu Asp Gly Ala
    690                 695                 700

Ala Glu Ser Ala Ser Gly Ser Pro Ala Lys Arg Pro Arg Ile Trp Ser
705                 710                 715                 720

Glu Glu Ser Gln Thr Glu Thr Ile Ser Ser Glu Glu Asn Pro Ala Glu
                725                 730                 735

Thr Thr Arg Glu Leu Leu Gln Arg Lys Leu Arg Glu Gln Arg Ala Leu
            740                 745                 750

Gln Phe Gln Leu Gln His Phe Ala Val Gln Leu Ala Lys Thr Gln Ala
        755                 760                 765

Asn Leu His Val Asn Pro Leu Leu Ser Phe Pro Gln
    770                 775                 780


<210> SEQ ID NO 29
<211> LENGTH: 204
<212> TYPE: PRT
<213> ORGANISM: Torque teno virus

<400> SEQUENCE: 29

Met Ala Trp Trp Gly Trp Arg Arg Arg Trp Trp Arg Pro Lys Arg Arg
1               5                   10                  15

Trp Arg Trp Arg Arg Ala Arg Arg Arg Arg Arg Val Pro Ala Arg Arg
            20                  25                  30

Pro Arg Arg Ala Phe Arg Arg Tyr Arg Thr Arg Thr Val Ile Arg Asn
        35                  40                  45

Pro Cys Lys Asp Asn Gln Val Ser Gly Pro Arg Arg Gln Pro Arg Asp
    50                  55                  60

Ile Gln Val Val Asp Pro Gln Arg Ile Thr Pro Pro Trp Val Leu His
65                  70                  75                  80

Ser Phe Asp Gln Arg Arg Gly Leu Phe Thr Glu Thr Ala Leu Arg Arg
                85                  90                  95

Leu Leu Gln Glu Pro Leu Pro Gly Glu Tyr Ala Val Ser Thr Leu Arg
            100                 105                 110

Thr Pro Leu Leu Phe Leu Pro Ser Glu Tyr Gln Arg Glu Asp Gly Ala
        115                 120                 125

Ala Glu Ser Ala Ser Gly Ser Pro Ala Lys Arg Pro Arg Ile Trp Ser
    130                 135                 140
```

```
Glu Glu Ser Gln Thr Glu Thr Ile Ser Ser Glu Glu Asn Pro Ala Glu
145                 150                 155                 160

Thr Thr Arg Glu Leu Leu Gln Arg Lys Leu Arg Glu Gln Arg Ala Leu
                165                 170                 175

Gln Phe Gln Leu Gln His Phe Ala Val Gln Leu Ala Lys Thr Gln Ala
            180                 185                 190

Asn Leu His Val Asn Pro Leu Leu Ser Phe Pro Gln
        195                 200


<210> SEQ ID NO 30
<211> LENGTH: 119
<212> TYPE: PRT
<213> ORGANISM: Torque teno virus

<400> SEQUENCE: 30

Met Ala Trp Trp Gly Trp Arg Arg Arg Trp Trp Arg Pro Lys Arg Arg
1               5                   10                  15

Trp Arg Trp Arg Arg Ala Arg Arg Arg Arg Arg Val Pro Ala Arg Arg
            20                  25                  30

Pro Arg Arg Ala Phe Arg Arg Tyr Arg Thr Arg Thr Asn Thr Ser Glu
        35                  40                  45

Lys Thr Ala Leu Gln Lys Ala Pro Gln Val His Arg Pro Lys Asp Pro
    50                  55                  60

Val Ser Gly Gln Lys Arg Val Arg Arg Arg Arg Ser Pro Arg Arg Arg
65                  70                  75                  80

Thr Arg Arg Arg Arg Arg Gly Ser Ser Ser Ser Glu Ser Ser Glu Ser
                85                  90                  95

Ser Glu His Ser Ser Ser Asn Ser Ser Thr Ser Arg Ser Asn Ser Pro
            100                 105                 110

Arg Pro Arg Arg Ile Ser Thr
        115


<210> SEQ ID NO 31
<211> LENGTH: 3818
<212> TYPE: DNA
<213> ORGANISM: Torque teno virus

<400> SEQUENCE: 31

aagtccgcca ctaaccacgt gactcccgca ggccaaccca gtactatgtc gtccacttcc      60

tgggacgagt ctacgtcctg atataagtaa gtgcacttcc gaatggctga gttttccacg     120

cccgtccgca gcgagaacgc cacggagggg agtccgcgcg tcccgagggc gggtgccgga     180

ggtgagttta cacaccgcag tcaaggggca attcgggctc gggactggcc gggccccggg     240

caaggctctt aaaaaatgca ctttcgcaga gtgcgagcga aaaggaaact gctactgcaa     300

gctgtgcgag ctccaccgaa ggcacctgcc atgagcttca ccacacctac tattaatgcc     360

gggatccgag agcagcaatg gttcgagtcc acccttagat cccaccactc gttctgtggc     420

tgtggtgatc ccgtgcttca ttttactaac cttgctactc gctttaacta tctgcctgct     480

acctcttcgc ctctggaccc tcccggccca gcgccgcgag gccgcccggc gctccgccgc     540

ctcccggcac tcccttcagc cccgcgacc ccttctagag aactagcatg gcctactggt      600

tcagaaggtg gggctggagg ccgaggcgcc ggtggagaag gtggcgccgc cgtcgaagga     660

gactaccgag aagaagaact agacgagctg ttcgcggcct tggaagaaga cgcaaaccaa     720

gggtaaggag gcgccgcaga actcgcagac gtacctacag acgggggtgg agacgcagga     780
```

-continued

```
ggtacataag acgggggcga cgcaaaaaga aactcatact gactcagtgg aacccggcaa    840
tagttaagag gtgcaacatt aagggcggac ttccaataat tatatgcgga gagcccaggg    900
cagcctttaa ctatggctac cacatggagg actacactcc tcaacctttc cccttcggag    960
ggggaatgag cacagtgact ttctctctga aagccttgta tgaccagtac ctaaaacacc   1020
aaaacaggtg gactttctca aacgaccagc tagacctcgc cagatacagg ggctgtaaac   1080
taaggttcta cagaagcccc gtctgtgact ttatagtaca ctacaaccta atacctccac   1140
taaaaatgaa ccagttcaca agtcccaaca cgcacccggg actactcatg ctcagcaaac   1200
acaagataat aattcccagc tttcaaacaa gacctggggg cagacgcttt gttaaaataa   1260
gacttaatcc ccccaaacta tttgaagaca agtggtacac tcagcaagac ctgtgcaagg   1320
ttccgctcgt tagtattaca gcaactgcgg ctgacttgcg gtatccgttc tgctcaccac   1380
aaacgaacaa cccttgcacc accttccagg tactgcgcaa gaactacaat acagttatag   1440
gaacttccgt aaaagaccaa gagtccacac aagactttga aaattggctt tataaaacag   1500
actcacacta tcaaacattt gccacagagg ctcaactagg cagaattcct gcatttaatc   1560
ctgatggcac taaaaacact aaacagcagt cgtggcaaga taactggagc aaaaaaaatt   1620
caccatggac aggtaactca ggtacatacc cacaaacaac cagtgaaatg tacaaaattc   1680
catatgacag taacttcggc tttcccacat acagagccca aaaagactac attttagaaa   1740
gaagacagtg caactttaac tatgaagtta ataatccagt tagcaaaaaa gtatggccac   1800
aacctagtac aacaacaccc acagtagact actatgaata ccactgtgga tggttcagca   1860
acatattcat aggccccaac agatacaacc tacagtttca aacagcatat gtagacacca   1920
catacaaccc actaatggac aagggcaaag gcaacaaaat atggtttcaa tatctgtcta   1980
aaaagggcac agactacaat gaaaaacaat gctactgcac cctagaagac atgcccctat   2040
gggcaatatg ctttggatac actgactatg tagagactca actaggaccc aatgtggacc   2100
atgaaacagc aggcttaata attatgatct gtccatacac tcaaccacct atgtatgaca   2160
aaaacagacc taactgggga tacgtagtct atgacacaaa ctttggcaat ggaaaaatgc   2220
cctcaggaag tggccaagtc ccagtatact ggcaatgccg atggaggccc atgctgtggt   2280
tccaacaaca agtactcaat gacatctcaa agactggacc gtacgcctac agagacgaat   2340
ataaaaatgt acaactgact ctctactaca actttatttt taactggggg ggcgacatgt   2400
attacccaca ggtcgttaaa aacccctgtg gagactccgg aatcgttccc ggttccggta   2460
gattcactcg agaagtacaa gtcgttagcc cgctttccat gggaccggcc tacatcttcc   2520
actacttcga ctccagacgc gggttcttta gtgaaaaagc tcttaaaaga atgcaacaac   2580
aacaagaatt tgatgaatct tttacattca aacctaagag acccaaactt tctacagcag   2640
ccgcagaaat cctccagctc gaagaagact cgacttcagg ggaaggaaaa tcgccactac   2700
agcaagaaga gaaagaagtc gaagtcctcc aaacgccgac agtacagctc cagctccagc   2760
gaaacatcca ggagcagctc gcaatcaagc agcagctcca attcctcttg ctccaactcc   2820
tcaaaaccca atccaatttg catttaaacc cacaattttt aagcccttca taaaatatga   2880
catgtttggg gaccccttc ctcaccccc aacagccgaa gagtgggaaa cagagtacca   2940
gtgctgtaag gcctttaaca gaccacctag aaccaaccta aaagacaccc ccttctaccc   3000
ctgggtacct aaacctaaac ctcaattccg tgtatctttt aaacttggtt ttcaataaac   3060
aaggccgtgg gagtttcact tgtcggtgtc aacctcttaa ggtcactaag cactccgagc   3120
gtaagcgagg agtgcgaccc tccccctgg ggcaactccc tcgaagtccg gcgctacgcg   3180
```

```
cttcgcgctg cgccggacat ctcggacccc ccctccaccc gaaacgcttg cgcgtttcgg   3240

accttcggcg tcgggggggt cgggggcttt actaaacaga ctccgaggtg ccattggaca   3300

ctgaggggat gaacagcaac gaaagtgagt ggggccagac ttcgccataa ggcctttatc   3360

ttcttgccat ttgtcagtat agagggtcgc cataggcttc ggcctccatt ttaacctcta   3420

aaaactacca aaatggccgt tccagtgacg tcacagccgc cattttaagt agctgacgtc   3480

aaggattgac gtgaaggtta aaggtcatcc tcggcggaag ctacacaaaa tggtggacaa   3540

catcttccgg gtcaaaggtc gtgcacacgt cataagtcac gtggtgggga cccgctgtaa   3600

cccggaagta ggccccgtca cgtgatttgt cacgtgtgta cacgtcacaa ccgccatttt   3660

gttttacaaa atggctgact tccttcctct tttttaaaaa aaacggccgt gcggcggcgc   3720

gcgcgcttcg cgcgcgcgcc gggggctgcc gccccccccc gcgcatgcgc gcggggcccc   3780

cccccgcggg gggctccgcc ccccggcccc cccccccg                           3818


<210> SEQ ID NO 32
<211> LENGTH: 131
<212> TYPE: PRT
<213> ORGANISM: Torque teno virus

<400> SEQUENCE: 32

Met Ser Phe Thr Thr Pro Thr Ile Asn Ala Gly Ile Arg Glu Gln Gln
1               5                   10                  15

Trp Phe Glu Ser Thr Leu Arg Ser His His Ser Phe Cys Gly Cys Gly
            20                  25                  30

Asp Pro Val Leu His Phe Thr Asn Leu Ala Thr Arg Phe Asn Tyr Leu
        35                  40                  45

Pro Ala Thr Ser Ser Pro Leu Asp Pro Pro Gly Pro Ala Pro Arg Gly
    50                  55                  60

Arg Pro Ala Leu Arg Arg Leu Pro Ala Leu Pro Ser Ala Pro Ala Thr
65                  70                  75                  80

Pro Ser Arg Glu Leu Ala Trp Pro Thr Gly Ser Glu Gly Gly Ala Gly
                85                  90                  95

Gly Arg Gly Ala Gly Gly Glu Gly Gly Ala Ala Val Glu Gly Asp Tyr
            100                 105                 110

Arg Glu Glu Glu Leu Asp Glu Leu Phe Ala Ala Leu Glu Glu Asp Ala
        115                 120                 125

Asn Gln Gly
    130


<210> SEQ ID NO 33
<211> LENGTH: 275
<212> TYPE: PRT
<213> ORGANISM: Torque teno virus

<400> SEQUENCE: 33

Met Ser Phe Thr Thr Pro Thr Ile Asn Ala Gly Ile Arg Glu Gln Gln
1               5                   10                  15

Trp Phe Glu Ser Thr Leu Arg Ser His His Ser Phe Cys Gly Cys Gly
            20                  25                  30

Asp Pro Val Leu His Phe Thr Asn Leu Ala Thr Arg Phe Asn Tyr Leu
        35                  40                  45

Pro Ala Thr Ser Ser Pro Leu Asp Pro Pro Gly Pro Ala Pro Arg Gly
    50                  55                  60

Arg Pro Ala Leu Arg Arg Leu Pro Ala Leu Pro Ser Ala Pro Ala Thr
```

65 70 75 80

Pro Ser Arg Glu Leu Ala Trp Pro Thr Gly Ser Glu Gly Gly Ala Gly
85 90 95

Gly Arg Gly Ala Gly Gly Glu Gly Gly Ala Ala Val Glu Gly Asp Tyr
100 105 110

Arg Glu Glu Glu Leu Asp Glu Leu Phe Ala Ala Leu Glu Glu Asp Ala
115 120 125

Asn Gln Gly Ser Leu Lys Thr Pro Val Glu Thr Pro Glu Ser Phe Pro
130 135 140

Val Pro Val Asp Ser Leu Glu Lys Tyr Lys Ser Leu Ala Arg Phe Pro
145 150 155 160

Trp Asp Arg Pro Thr Ser Ser Thr Thr Ser Thr Pro Asp Ala Gly Ser
165 170 175

Leu Val Lys Lys Leu Leu Lys Glu Cys Asn Asn Asn Lys Asn Leu Met
180 185 190

Asn Leu Leu His Ser Asn Leu Arg Asp Pro Asn Phe Leu Gln Gln Pro
195 200 205

Gln Lys Ser Ser Ser Ser Lys Lys Thr Arg Leu Gln Gly Lys Glu Asn
210 215 220

Arg His Tyr Ser Lys Lys Arg Lys Lys Ser Lys Ser Ser Lys Arg Arg
225 230 235 240

Gln Tyr Ser Ser Ser Ser Ser Glu Thr Ser Arg Ser Ser Ser Gln Ser
245 250 255

Ser Ser Ser Ser Asn Ser Ser Cys Ser Asn Ser Ser Lys Pro Asn Pro
260 265 270

Ile Cys Ile
275

<210> SEQ ID NO 34
<211> LENGTH: 270
<212> TYPE: PRT
<213> ORGANISM: Torque teno virus

<400> SEQUENCE: 34

Met Ser Phe Thr Thr Pro Thr Ile Asn Ala Gly Ile Arg Glu Gln Gln
1 5 10 15

Trp Phe Glu Ser Thr Leu Arg Ser His His Ser Phe Cys Gly Cys Gly
20 25 30

Asp Pro Val Leu His Phe Thr Asn Leu Ala Thr Arg Phe Asn Tyr Leu
35 40 45

Pro Ala Thr Ser Ser Pro Leu Asp Pro Pro Gly Pro Ala Pro Arg Gly
50 55 60

Arg Pro Ala Leu Arg Arg Leu Pro Ala Leu Pro Ser Ala Pro Ala Thr
65 70 75 80

Pro Ser Arg Glu Leu Ala Trp Pro Thr Gly Ser Glu Gly Gly Ala Gly
85 90 95

Gly Arg Gly Ala Gly Gly Glu Gly Gly Ala Ala Val Glu Gly Asp Tyr
100 105 110

Arg Glu Glu Glu Leu Asp Glu Leu Phe Ala Ala Leu Glu Glu Asp Ala
115 120 125

Asn Gln Gly Ser Arg Arg Asn Pro Pro Ala Arg Arg Arg Leu Asp Phe
130 135 140

Arg Gly Arg Lys Ile Ala Thr Thr Ala Arg Arg Glu Arg Ser Arg Ser
145 150 155 160

```
Pro Pro Asn Ala Asp Ser Thr Ala Pro Ala Pro Ala Lys His Pro Gly
                165                 170                 175

Ala Ala Arg Asn Gln Ala Ala Ala Pro Ile Pro Leu Ala Pro Thr Pro
            180                 185                 190

Gln Asn Pro Ile Gln Phe Ala Phe Lys Pro Thr Ile Phe Lys Pro Phe
        195                 200                 205

Ile Lys Tyr Asp Met Phe Gly Asp Pro Leu Pro His Pro Pro Thr Ala
    210                 215                 220

Glu Glu Trp Glu Thr Glu Tyr Gln Cys Cys Lys Ala Phe Asn Arg Pro
225                 230                 235                 240

Pro Arg Thr Asn Leu Lys Asp Thr Pro Phe Tyr Pro Trp Val Pro Lys
                245                 250                 255

Pro Lys Pro Gln Phe Arg Val Ser Phe Lys Leu Gly Phe Gln
            260                 265                 270


<210> SEQ ID NO 35
<211> LENGTH: 156
<212> TYPE: PRT
<213> ORGANISM: Torque teno virus

<400> SEQUENCE: 35

Met Ser Phe Thr Thr Pro Thr Ile Asn Ala Gly Ile Arg Glu Gln Gln
1               5                   10                  15

Cys Ser Arg Arg Asn Pro Pro Ala Arg Arg Arg Leu Asp Phe Arg Gly
            20                  25                  30

Arg Lys Ile Ala Thr Thr Ala Arg Arg Glu Arg Ser Arg Ser Pro Pro
        35                  40                  45

Asn Ala Asp Ser Thr Ala Pro Ala Pro Ala Lys His Pro Gly Ala Ala
    50                  55                  60

Arg Asn Gln Ala Ala Ala Pro Ile Pro Leu Ala Pro Thr Pro Gln Asn
65                  70                  75                  80

Pro Ile Gln Phe Ala Phe Lys Pro Thr Ile Phe Lys Pro Phe Ile Lys
                85                  90                  95

Tyr Asp Met Phe Gly Asp Pro Leu Pro His Pro Pro Thr Ala Glu Glu
            100                 105                 110

Trp Glu Thr Glu Tyr Gln Cys Cys Lys Ala Phe Asn Arg Pro Pro Arg
        115                 120                 125

Thr Asn Leu Lys Asp Thr Pro Phe Tyr Pro Trp Val Pro Lys Pro Lys
    130                 135                 140

Pro Gln Phe Arg Val Ser Phe Lys Leu Gly Phe Gln
145                 150                 155


<210> SEQ ID NO 36
<211> LENGTH: 761
<212> TYPE: PRT
<213> ORGANISM: Torque teno virus

<400> SEQUENCE: 36

Met Ala Tyr Trp Phe Arg Arg Trp Gly Trp Arg Pro Arg Arg Arg Trp
1               5                   10                  15

Arg Arg Trp Arg Arg Arg Arg Arg Arg Leu Pro Arg Arg Arg Thr Arg
            20                  25                  30

Arg Ala Val Arg Gly Leu Gly Arg Arg Arg Lys Pro Arg Val Arg Arg
        35                  40                  45

Arg Arg Arg Thr Arg Arg Arg Thr Tyr Arg Arg Gly Trp Arg Arg Arg
    50                  55                  60
```

-continued

```
Arg Tyr Ile Arg Arg Gly Arg Arg Lys Lys Lys Leu Ile Leu Thr Gln
65                  70                  75                  80

Trp Asn Pro Ala Ile Val Lys Arg Cys Asn Ile Lys Gly Gly Leu Pro
                85                  90                  95

Ile Ile Ile Cys Gly Glu Pro Arg Ala Ala Phe Asn Tyr Gly Tyr His
            100                 105                 110

Met Glu Asp Tyr Thr Pro Gln Pro Phe Pro Phe Gly Gly Gly Met Ser
        115                 120                 125

Thr Val Thr Phe Ser Leu Lys Ala Leu Tyr Asp Gln Tyr Leu Lys His
    130                 135                 140

Gln Asn Arg Trp Thr Phe Ser Asn Asp Gln Leu Asp Leu Ala Arg Tyr
145                 150                 155                 160

Arg Gly Cys Lys Leu Arg Phe Tyr Arg Ser Pro Val Cys Asp Phe Ile
                165                 170                 175

Val His Tyr Asn Leu Ile Pro Pro Leu Lys Met Asn Gln Phe Thr Ser
            180                 185                 190

Pro Asn Thr His Pro Gly Leu Leu Met Leu Ser Lys His Lys Ile Ile
        195                 200                 205

Ile Pro Ser Phe Gln Thr Arg Pro Gly Gly Arg Arg Phe Val Lys Ile
    210                 215                 220

Arg Leu Asn Pro Pro Lys Leu Phe Glu Asp Lys Trp Tyr Thr Gln Gln
225                 230                 235                 240

Asp Leu Cys Lys Val Pro Leu Val Ser Ile Thr Ala Thr Ala Ala Asp
                245                 250                 255

Leu Arg Tyr Pro Phe Cys Ser Pro Gln Thr Asn Asn Pro Cys Thr Thr
            260                 265                 270

Phe Gln Val Leu Arg Lys Asn Tyr Asn Thr Val Ile Gly Thr Ser Val
        275                 280                 285

Lys Asp Gln Glu Ser Thr Gln Asp Phe Glu Asn Trp Leu Tyr Lys Thr
    290                 295                 300

Asp Ser His Tyr Gln Thr Phe Ala Thr Glu Ala Gln Leu Gly Arg Ile
305                 310                 315                 320

Pro Ala Phe Asn Pro Asp Gly Thr Lys Asn Thr Lys Gln Gln Ser Trp
                325                 330                 335

Gln Asp Asn Trp Ser Lys Lys Asn Ser Pro Trp Thr Gly Asn Ser Gly
            340                 345                 350

Thr Tyr Pro Gln Thr Thr Ser Glu Met Tyr Lys Ile Pro Tyr Asp Ser
        355                 360                 365

Asn Phe Gly Phe Pro Thr Tyr Arg Ala Gln Lys Asp Tyr Ile Leu Glu
    370                 375                 380

Arg Arg Gln Cys Asn Phe Asn Tyr Glu Val Asn Asn Pro Val Ser Lys
385                 390                 395                 400

Lys Val Trp Pro Gln Pro Ser Thr Thr Thr Pro Thr Val Asp Tyr Tyr
                405                 410                 415

Glu Tyr His Cys Gly Trp Phe Ser Asn Ile Phe Ile Gly Pro Asn Arg
            420                 425                 430

Tyr Asn Leu Gln Phe Gln Thr Ala Tyr Val Asp Thr Thr Tyr Asn Pro
        435                 440                 445

Leu Met Asp Lys Gly Lys Gly Asn Lys Ile Trp Phe Gln Tyr Leu Ser
    450                 455                 460

Lys Lys Gly Thr Asp Tyr Asn Glu Lys Gln Cys Tyr Cys Thr Leu Glu
465                 470                 475                 480

Asp Met Pro Leu Trp Ala Ile Cys Phe Gly Tyr Thr Asp Tyr Val Glu
```

```
                485                 490                 495

Thr Gln Leu Gly Pro Asn Val Asp His Glu Thr Ala Gly Leu Ile Ile
            500                 505                 510

Met Ile Cys Pro Tyr Thr Gln Pro Pro Met Tyr Asp Lys Asn Arg Pro
        515                 520                 525

Asn Trp Gly Tyr Val Val Tyr Asp Thr Asn Phe Gly Asn Gly Lys Met
    530                 535                 540

Pro Ser Gly Ser Gly Gln Val Pro Val Tyr Trp Gln Cys Arg Trp Arg
545                 550                 555                 560

Pro Met Leu Trp Phe Gln Gln Gln Val Leu Asn Asp Ile Ser Lys Thr
                565                 570                 575

Gly Pro Tyr Ala Tyr Arg Asp Glu Tyr Lys Asn Val Gln Leu Thr Leu
            580                 585                 590

Tyr Tyr Asn Phe Ile Phe Asn Trp Gly Gly Asp Met Tyr Tyr Pro Gln
        595                 600                 605

Val Val Lys Asn Pro Cys Gly Asp Ser Gly Ile Val Pro Gly Ser Gly
    610                 615                 620

Arg Phe Thr Arg Glu Val Gln Val Val Ser Pro Leu Ser Met Gly Pro
625                 630                 635                 640

Ala Tyr Ile Phe His Tyr Phe Asp Ser Arg Arg Gly Phe Phe Ser Glu
                645                 650                 655

Lys Ala Leu Lys Arg Met Gln Gln Gln Gln Glu Phe Asp Glu Ser Phe
            660                 665                 670

Thr Phe Lys Pro Lys Arg Pro Lys Leu Ser Thr Ala Ala Ala Glu Ile
        675                 680                 685

Leu Gln Leu Glu Glu Asp Ser Thr Ser Gly Glu Gly Lys Ser Pro Leu
    690                 695                 700

Gln Gln Glu Glu Lys Glu Val Glu Val Leu Gln Thr Pro Thr Val Gln
705                 710                 715                 720

Leu Gln Leu Gln Arg Asn Ile Gln Glu Gln Leu Ala Ile Lys Gln Gln
                725                 730                 735

Leu Gln Phe Leu Leu Leu Gln Leu Leu Lys Thr Gln Ser Asn Leu His
            740                 745                 750

Leu Asn Pro Gln Phe Leu Ser Pro Ser
        755                 760


<210> SEQ ID NO 37
<211> LENGTH: 198
<212> TYPE: PRT
<213> ORGANISM: Torque teno virus

<400> SEQUENCE: 37

Met Ala Tyr Trp Phe Arg Arg Trp Gly Trp Arg Pro Arg Arg Arg Trp
1               5                   10                  15

Arg Arg Trp Arg Arg Arg Arg Arg Arg Leu Pro Arg Arg Arg Thr Arg
            20                  25                  30

Arg Ala Val Arg Gly Leu Gly Arg Arg Arg Lys Pro Arg Val Val Lys
        35                  40                  45

Asn Pro Cys Gly Asp Ser Gly Ile Val Pro Gly Ser Gly Arg Phe Thr
    50                  55                  60

Arg Glu Val Gln Val Val Ser Pro Leu Ser Met Gly Pro Ala Tyr Ile
65                  70                  75                  80

Phe His Tyr Phe Asp Ser Arg Arg Gly Phe Phe Ser Glu Lys Ala Leu
                85                  90                  95
```

```
Lys Arg Met Gln Gln Gln Gln Glu Phe Asp Glu Ser Phe Thr Phe Lys
            100                 105                 110

Pro Lys Arg Pro Lys Leu Ser Thr Ala Ala Ala Glu Ile Leu Gln Leu
        115                 120                 125

Glu Glu Asp Ser Thr Ser Gly Glu Gly Lys Ser Pro Leu Gln Gln Glu
    130                 135                 140

Glu Lys Glu Val Glu Val Leu Gln Thr Pro Thr Val Gln Leu Gln Leu
145                 150                 155                 160

Gln Arg Asn Ile Gln Glu Gln Leu Ala Ile Lys Gln Gln Leu Gln Phe
                165                 170                 175

Leu Leu Leu Gln Leu Leu Lys Thr Gln Ser Asn Leu His Leu Asn Pro
            180                 185                 190

Gln Phe Leu Ser Pro Ser
        195


<210> SEQ ID NO 38
<211> LENGTH: 114
<212> TYPE: PRT
<213> ORGANISM: Torque teno virus

<400> SEQUENCE: 38

Met Ala Tyr Trp Phe Arg Arg Trp Gly Trp Arg Pro Arg Arg Arg Trp
1               5                   10                  15

Arg Arg Trp Arg Arg Arg Arg Arg Arg Leu Pro Arg Arg Arg Thr Arg
            20                  25                  30

Arg Ala Val Arg Gly Leu Gly Arg Arg Arg Lys Pro Arg Gln Pro Gln
        35                  40                  45

Lys Ser Ser Ser Ser Lys Lys Thr Arg Leu Gln Gly Lys Glu Asn Arg
    50                  55                  60

His Tyr Ser Lys Lys Arg Lys Lys Ser Lys Ser Ser Lys Arg Arg Gln
65                  70                  75                  80

Tyr Ser Ser Ser Ser Ser Glu Thr Ser Arg Ser Ser Ser Gln Ser Ser
                85                  90                  95

Ser Ser Ser Asn Ser Ser Cys Ser Asn Ser Ser Lys Pro Asn Pro Ile
            100                 105                 110

Cys Ile


<210> SEQ ID NO 39
<211> LENGTH: 3794
<212> TYPE: DNA
<213> ORGANISM: Torque teno virus

<400> SEQUENCE: 39

cccgaagtcc gtcactaacc acgtgactcc tgtcgcccaa tcagagtgta tgtcgtgcat      60

ttcctgggca tggtctacat cctgatataa ctaagtgcac ttccgaatgg ctgagttttc     120

cacgcccgtc cgcagcgagg gagcgacgga ggagctcccg agcgtcccga gggcgggtgc     180

cggaggtgag tttacacacc gcagtcaagg ggcaattcgg gctcgggact ggccgggcta     240

tgggcaaggc tcttagggtc ttcattctta atatgtttct tggcagagtt taccgccaca     300

agaaaaggaa agtgctactg tccacactgc gagctccaca ggcgtctcgc agggctatga     360

gttggcgacc cccggtacac gatgcacccg gcatcgagcg caattggtac gaggcctgtt     420

tcagagccca cgctggagct tgtggctgtg gcaattttat tatgcacctt aatcttttgg     480

ctgggcgtta tggttttact ccggggtcag cgccgccagg tggtcctcct ccgggcaccc     540

cgcagataag gagagccagg cctagtcccg ccgcaccaga gcagcccgct gccctaccat     600
```

```
ggcatgggga tggtggagat ggcggcgccg ctggcccgcc agacgctgga ggagacgccg    660
tcgccggcgc cccgtacgga gaacaagagc tcgccgacct gctcgacgct atagaagacg    720
acgaacagta agaaccaggc gaaggcggtg ggggcgcaga cggtacagac ggggctggag    780
acgcaggact tatgtgagaa aggggcgaca cagaaaaaag aaaaagagac tgatactgag    840
acagtggcaa ccagccacaa gacgcagatg taccataact gggtacctgc ccatagtgtt    900
ctgcggccac actaggggca ataaaaacta tgcactacac tctgacgact acacccccca    960
aggacaacca tttggagggg ctctaagcac tacctcattc tctttaaaag tactatttga   1020
ccagcatcag agaggactaa acaagtggtc ttttccaaac gaccaactag acctcgccag   1080
atatagaggc tgcaaattta tattttatag aacaaaacaa actgactggg tgggccagta   1140
tgacatatca gaaccctaca agctagacaa atacagctgc cccaactatc accctggaaa   1200
catgattaag gcaaagcaca aatttttaat accaagctat gacactaatc ctagaggcag   1260
acaaaaaatt atagttaaaa ttcccccccc agacctcttt gtagacaagt ggtacactca   1320
agaggatctg tgttccgtta atcttgtgtc acttgcggtt tctgcggctt cctttctcca   1380
cccattcggc tcaccacaaa ctgacaaccc ttgctacacc ttccaggtgt tgaaagagtt   1440
ctactatcag gcaataggct tctctgcaag cacacaagca atgacatcag tattagacac   1500
gctatacaca caaaacagtt attgggaatc taatctaact cagttttatg tacttaatgc   1560
aaaaaaaggc agtgatacaa cacagccttt aactagcaat atgccaactc gtgaagagtt   1620
tatggcaaaa aaaaatacca attacaactg gtatacatac aaggccgcgt cagtaaaaaa   1680
taaactacat caaatgagac aaacctattt tgaggagtta acctctaagg ggccacaaac   1740
aacaaaaagt gaggaaggct acagtcagca ctggaccacc ccctccacaa acgcctacga   1800
atatcactta ggaatgttta gtgcaatatt tctagcccca gacaggccag tacctagatt   1860
tccatgcgcc taccaagatg taacttacaa ccccttaatg gacaaagggg tgggaaacca   1920
catttggttt cagtacaaca caaaggcaga cactcagcta atagtcacag gagggtcctg   1980
caaagcacac atacaagaca taccactgtg ggcggccttc tatggataca gtgactttat   2040
agagtcagaa ctaggcccct ttgtagatgc agagacggta ggcttagtgt gtgtaatatg   2100
cccttataca aaacccccca tgtacaacaa gacaaacccc gccatgggct acgtgttcta   2160
tgacagaaac tttggtgacg gaaaatggac tgacggacgg ggcaaaatag agccctactg   2220
gcaagttagg tggaggcccg aaatgctttt ccaagaaact gtaatggcag acctagttca   2280
gactgggccc tttagctaca aagacgaact taaaaacagc accctagtgt gcaagtacaa   2340
attctatttc acctggggag gtaacatgat gttccaacag acgatcaaaa acccgtgcaa   2400
gacggacgga caacccaccg actccagtag acaccctaga ggaatacaag tggcggaccc   2460
ggaacaaatg ggaccccgct gggtgttcca ctcctttgac tggcgaaggg gctatcttag   2520
cgagaaagct ctcaaacgcc tgcaagaaaa acctcttgac tatgacgaat attttacaca   2580
accaaaaaga cctagaatct ttcctccaac agaatcagca gagggagagt tccgagagcc   2640
cgaaaaaggc tcgtattcag aggaagaaag gtcgcaagcc tctgccgaag agcagacgca   2700
ggaggcgaca gtactcctcc tcaagcgacg actcagagag caacagcagc tccagcagca   2760
gctccaattc ctcacccgag aaatgttcaa aacgcaagcg ggtctccacc taaaccctat   2820
gttattaaac cagcgataaa ccaagtgtac ctgtttccag agagggcccc aaaacccccct   2880
cctagcagcc aagactggca gcaggagtac gaggcctgcg cagcctggga caggccccct   2940
```

```
agatacaatc tgtcctctcc tcctttctac cccagctgcc cttcaaaatt ctgtgtaaaa   3000

ttcagccttg gctttaaata aatggcaact ttactgtgca aggccgtggg agtttcactg   3060

gtcggtgtct acctctaaag gtcactaagc actccgagcg ttagcgagga gtgcgaccct   3120

tccccctgac tcaacttctt cggagccgcg cgctacgcct tcggctgcgc gcggcacctc   3180

agacccccgc tcgtgctgac acgctcgcgc gtgtcagacc acttcgggct cgcgggggtc   3240

gggaattttg ctaaacagac tccgagttgc tcttggacac tgagggggca tatcagtaac   3300

gaaagtgagt ggggccagac ttcgccataa ggcctttatc ttcttgccat tggatagtat   3360

cgagggttgc cataggcttc gacctccatt ttaggccttc cggactacaa aaatggccgt   3420

tttagtgacg tcacggccgc cattttaagt aaggcggaag cagctcggcg tacacaaaat   3480

ggcggcggag cacttccggc ttgcccaaaa tggtgggcaa cttcttccgg gtcaaaggtc   3540

acagctacgt cacaagtcac gtggggaggg ttggcgttta acccggaagc caatcctctt   3600

acgtggcctg tcacgtgact tgtacgtcac gaccaccatt ttgttttaca aaatggccga   3660

cttccttcct ctttttaaa aataacggtt cggcggcggc gcgcgcgcta cgcgcgcgcg   3720

ccggggggct gccgcccccc ccccgcgcat gcgcggggcc cccccccgcg gggggctccg   3780

ccccccggcc cccc                                                      3794
```

<210> SEQ ID NO 40
<211> LENGTH: 124
<212> TYPE: PRT
<213> ORGANISM: Torque teno virus

<400> SEQUENCE: 40

```
Met Ser Trp Arg Pro Pro Val His Asp Ala Pro Gly Ile Glu Arg Asn
1               5                   10                  15

Trp Tyr Glu Ala Cys Phe Arg Ala His Ala Gly Ala Cys Gly Cys Gly
            20                  25                  30

Asn Phe Ile Met His Leu Asn Leu Leu Ala Gly Arg Tyr Gly Phe Thr
        35                  40                  45

Pro Gly Ser Ala Pro Pro Gly Gly Pro Pro Pro Gly Thr Pro Gln Ile
    50                  55                  60

Arg Arg Ala Arg Pro Ser Pro Ala Ala Pro Glu Gln Pro Ala Ala Leu
65                  70                  75                  80

Pro Trp His Gly Asp Gly Gly Asp Gly Gly Ala Ala Gly Pro Pro Asp
                85                  90                  95

Ala Gly Gly Asp Ala Val Ala Gly Ala Pro Tyr Gly Glu Gln Glu Leu
            100                 105                 110

Ala Asp Leu Leu Asp Ala Ile Glu Asp Asp Glu Gln
        115                 120
```

<210> SEQ ID NO 41
<211> LENGTH: 267
<212> TYPE: PRT
<213> ORGANISM: Torque teno virus

<400> SEQUENCE: 41

```
Met Ser Trp Arg Pro Pro Val His Asp Ala Pro Gly Ile Glu Arg Asn
1               5                   10                  15

Trp Tyr Glu Ala Cys Phe Arg Ala His Ala Gly Ala Cys Gly Cys Gly
            20                  25                  30

Asn Phe Ile Met His Leu Asn Leu Leu Ala Gly Arg Tyr Gly Phe Thr
        35                  40                  45
```

```
Pro Gly Ser Ala Pro Pro Gly Gly Pro Pro Pro Gly Thr Pro Gln Ile
    50                  55                  60

Arg Arg Ala Arg Pro Ser Pro Ala Ala Pro Glu Gln Pro Ala Ala Leu
65                  70                  75                  80

Pro Trp His Gly Asp Gly Gly Asp Gly Gly Ala Ala Gly Pro Pro Asp
                85                  90                  95

Ala Gly Gly Asp Ala Val Ala Gly Ala Pro Tyr Gly Glu Gln Glu Leu
            100                 105                 110

Ala Asp Leu Leu Asp Ala Ile Glu Asp Asp Glu Gln Arg Ser Lys Thr
        115                 120                 125

Arg Ala Arg Arg Thr Asp Asn Pro Pro Thr Pro Val Asp Thr Leu Glu
    130                 135                 140

Glu Tyr Lys Trp Arg Thr Arg Asn Lys Trp Asp Pro Ala Gly Cys Ser
145                 150                 155                 160

Thr Pro Leu Thr Gly Glu Gly Ala Ile Leu Ala Arg Lys Leu Ser Asn
                165                 170                 175

Ala Cys Lys Lys Asn Leu Leu Thr Met Thr Asn Ile Leu His Asn Gln
            180                 185                 190

Lys Asp Leu Glu Ser Phe Leu Gln Gln Asn Gln Gln Arg Glu Ser Ser
        195                 200                 205

Glu Ser Pro Lys Lys Ala Arg Ile Gln Arg Lys Lys Gly Arg Lys Pro
    210                 215                 220

Leu Pro Lys Ser Arg Arg Arg Arg Arg Gln Tyr Ser Ser Ser Ser Asp
225                 230                 235                 240

Asp Ser Glu Ser Asn Ser Ser Ser Ser Ser Ser Ser Asn Ser Ser Pro
                245                 250                 255

Glu Lys Cys Ser Lys Arg Lys Arg Val Ser Thr
            260                 265


<210> SEQ ID NO 42
<211> LENGTH: 257
<212> TYPE: PRT
<213> ORGANISM: Torque teno virus

<400> SEQUENCE: 42

Met Ser Trp Arg Pro Pro Val His Asp Ala Pro Gly Ile Glu Arg Asn
1               5                   10                  15

Trp Tyr Glu Ala Cys Phe Arg Ala His Ala Gly Ala Cys Gly Cys Gly
            20                  25                  30

Asn Phe Ile Met His Leu Asn Leu Leu Ala Gly Arg Tyr Gly Phe Thr
        35                  40                  45

Pro Gly Ser Ala Pro Pro Gly Gly Pro Pro Pro Gly Thr Pro Gln Ile
    50                  55                  60

Arg Arg Ala Arg Pro Ser Pro Ala Ala Pro Glu Gln Pro Ala Ala Leu
65                  70                  75                  80

Pro Trp His Gly Asp Gly Gly Asp Gly Gly Ala Ala Gly Pro Pro Asp
                85                  90                  95

Ala Gly Gly Asp Ala Val Ala Gly Ala Pro Tyr Gly Glu Gln Glu Leu
            100                 105                 110

Ala Asp Leu Leu Asp Ala Ile Glu Asp Asp Glu His Arg Gly Arg Val
        115                 120                 125

Pro Arg Ala Arg Lys Arg Leu Val Phe Arg Gly Arg Lys Val Ala Ser
    130                 135                 140

Leu Cys Arg Arg Ala Asp Ala Gly Gly Asp Ser Thr Pro Pro Gln Ala
145                 150                 155                 160
```

Thr Thr Gln Arg Ala Thr Ala Ala Pro Ala Ala Ala Pro Ile Pro His
165 170 175

Pro Arg Asn Val Gln Asn Ala Ser Gly Ser Pro Pro Lys Pro Tyr Val
180 185 190

Ile Lys Pro Ala Ile Asn Gln Val Tyr Leu Phe Pro Glu Arg Ala Pro
195 200 205

Lys Pro Pro Pro Ser Ser Gln Asp Trp Gln Gln Glu Tyr Glu Ala Cys
210 215 220

Ala Ala Trp Asp Arg Pro Pro Arg Tyr Asn Leu Ser Ser Pro Pro Phe
225 230 235 240

Tyr Pro Ser Cys Pro Ser Lys Phe Cys Val Lys Phe Ser Leu Gly Phe
245 250 255

Lys

<210> SEQ ID NO 43
<211> LENGTH: 150
<212> TYPE: PRT
<213> ORGANISM: Torque teno virus

<400> SEQUENCE: 43

Met Ser Trp Arg Pro Pro Val His Asp Ala Pro Gly Ile Glu Arg Asn
1 5 10 15

Cys Arg Gly Arg Val Pro Arg Ala Arg Lys Arg Leu Val Phe Arg Gly
20 25 30

Arg Lys Val Ala Ser Leu Cys Arg Arg Ala Asp Ala Gly Gly Asp Ser
35 40 45

Thr Pro Pro Gln Ala Thr Thr Gln Arg Ala Thr Ala Ala Pro Ala Ala
50 55 60

Ala Pro Ile Pro His Pro Arg Asn Val Gln Asn Ala Ser Gly Ser Pro
65 70 75 80

Pro Lys Pro Tyr Val Ile Lys Pro Ala Ile Asn Gln Val Tyr Leu Phe
85 90 95

Pro Glu Arg Ala Pro Lys Pro Pro Pro Ser Ser Gln Asp Trp Gln Gln
100 105 110

Glu Tyr Glu Ala Cys Ala Ala Trp Asp Arg Pro Pro Arg Tyr Asn Leu
115 120 125

Ser Ser Pro Pro Phe Tyr Pro Ser Cys Pro Ser Lys Phe Cys Val Lys
130 135 140

Phe Ser Leu Gly Phe Lys
145 150

<210> SEQ ID NO 44
<211> LENGTH: 746
<212> TYPE: PRT
<213> ORGANISM: Torque teno virus

<400> SEQUENCE: 44

Met Ala Trp Gly Trp Trp Arg Trp Arg Arg Arg Trp Pro Ala Arg Arg
1 5 10 15

Trp Arg Arg Arg Arg Arg Arg Arg Pro Val Arg Arg Thr Arg Ala Arg
20 25 30

Arg Pro Ala Arg Arg Tyr Arg Arg Arg Arg Thr Val Arg Thr Arg Arg
35 40 45

Arg Arg Trp Gly Arg Arg Arg Tyr Arg Arg Gly Trp Arg Arg Arg Thr
50 55 60

-continued

```
Tyr Val Arg Lys Gly Arg His Arg Lys Lys Lys Lys Arg Leu Ile Leu
65                  70                  75                  80

Arg Gln Trp Gln Pro Ala Thr Arg Arg Arg Cys Thr Ile Thr Gly Tyr
                85                  90                  95

Leu Pro Ile Val Phe Cys Gly His Thr Arg Gly Asn Lys Asn Tyr Ala
            100                 105                 110

Leu His Ser Asp Asp Tyr Thr Pro Gln Gly Gln Pro Phe Gly Gly Ala
        115                 120                 125

Leu Ser Thr Thr Ser Phe Ser Leu Lys Val Leu Phe Asp Gln His Gln
    130                 135                 140

Arg Gly Leu Asn Lys Trp Ser Phe Pro Asn Asp Gln Leu Asp Leu Ala
145                 150                 155                 160

Arg Tyr Arg Gly Cys Lys Phe Ile Phe Tyr Arg Thr Lys Gln Thr Asp
                165                 170                 175

Trp Val Gly Gln Tyr Asp Ile Ser Glu Pro Tyr Lys Leu Asp Lys Tyr
            180                 185                 190

Ser Cys Pro Asn Tyr His Pro Gly Asn Met Ile Lys Ala Lys His Lys
        195                 200                 205

Phe Leu Ile Pro Ser Tyr Asp Thr Asn Pro Arg Gly Arg Gln Lys Ile
    210                 215                 220

Ile Val Lys Ile Pro Pro Pro Asp Leu Phe Val Asp Lys Trp Tyr Thr
225                 230                 235                 240

Gln Glu Asp Leu Cys Ser Val Asn Leu Val Ser Leu Ala Val Ser Ala
                245                 250                 255

Ala Ser Phe Leu His Pro Phe Gly Ser Pro Gln Thr Asp Asn Pro Cys
            260                 265                 270

Tyr Thr Phe Gln Val Leu Lys Glu Phe Tyr Tyr Gln Ala Ile Gly Phe
        275                 280                 285

Ser Ala Ser Thr Gln Ala Met Thr Ser Val Leu Asp Thr Leu Tyr Thr
    290                 295                 300

Gln Asn Ser Tyr Trp Glu Ser Asn Leu Thr Gln Phe Tyr Val Leu Asn
305                 310                 315                 320

Ala Lys Lys Gly Ser Asp Thr Thr Gln Pro Leu Thr Ser Asn Met Pro
                325                 330                 335

Thr Arg Glu Glu Phe Met Ala Lys Lys Asn Thr Asn Tyr Asn Trp Tyr
            340                 345                 350

Thr Tyr Lys Ala Ala Ser Val Lys Asn Lys Leu His Gln Met Arg Gln
        355                 360                 365

Thr Tyr Phe Glu Glu Leu Thr Ser Lys Gly Pro Gln Thr Thr Lys Ser
    370                 375                 380

Glu Glu Gly Tyr Ser Gln His Trp Thr Thr Pro Ser Thr Asn Ala Tyr
385                 390                 395                 400

Glu Tyr His Leu Gly Met Phe Ser Ala Ile Phe Leu Ala Pro Asp Arg
                405                 410                 415

Pro Val Pro Arg Phe Pro Cys Ala Tyr Gln Asp Val Thr Tyr Asn Pro
            420                 425                 430

Leu Met Asp Lys Gly Val Gly Asn His Ile Trp Phe Gln Tyr Asn Thr
        435                 440                 445

Lys Ala Asp Thr Gln Leu Ile Val Thr Gly Gly Ser Cys Lys Ala His
    450                 455                 460

Ile Gln Asp Ile Pro Leu Trp Ala Ala Phe Tyr Gly Tyr Ser Asp Phe
465                 470                 475                 480

Ile Glu Ser Glu Leu Gly Pro Phe Val Asp Ala Glu Thr Val Gly Leu
```

```
                485                 490                 495

Val Cys Val Ile Cys Pro Tyr Thr Lys Pro Pro Met Tyr Asn Lys Thr
            500                 505                 510

Asn Pro Ala Met Gly Tyr Val Phe Tyr Asp Arg Asn Phe Gly Asp Gly
        515                 520                 525

Lys Trp Thr Asp Gly Arg Gly Lys Ile Glu Pro Tyr Trp Gln Val Arg
    530                 535                 540

Trp Arg Pro Glu Met Leu Phe Gln Glu Thr Val Met Ala Asp Leu Val
545                 550                 555                 560

Gln Thr Gly Pro Phe Ser Tyr Lys Asp Glu Leu Lys Asn Ser Thr Leu
                565                 570                 575

Val Cys Lys Tyr Lys Phe Tyr Phe Thr Trp Gly Gly Asn Met Met Phe
            580                 585                 590

Gln Gln Thr Ile Lys Asn Pro Cys Lys Thr Asp Gly Gln Pro Thr Asp
        595                 600                 605

Ser Ser Arg His Pro Arg Gly Ile Gln Val Ala Asp Pro Glu Gln Met
    610                 615                 620

Gly Pro Arg Trp Val Phe His Ser Phe Asp Trp Arg Arg Gly Tyr Leu
625                 630                 635                 640

Ser Glu Lys Ala Leu Lys Arg Leu Gln Glu Lys Pro Leu Asp Tyr Asp
                645                 650                 655

Glu Tyr Phe Thr Gln Pro Lys Arg Pro Arg Ile Phe Pro Pro Thr Glu
            660                 665                 670

Ser Ala Glu Gly Glu Phe Arg Glu Pro Glu Lys Gly Ser Tyr Ser Glu
        675                 680                 685

Glu Glu Arg Ser Gln Ala Ser Ala Glu Glu Gln Thr Gln Glu Ala Thr
    690                 695                 700

Val Leu Leu Leu Lys Arg Arg Leu Arg Glu Gln Gln Gln Leu Gln Gln
705                 710                 715                 720

Gln Leu Gln Phe Leu Thr Arg Glu Met Phe Lys Thr Gln Ala Gly Leu
                725                 730                 735

His Leu Asn Pro Met Leu Leu Asn Gln Arg
            740                 745


<210> SEQ ID NO 45
<211> LENGTH: 195
<212> TYPE: PRT
<213> ORGANISM: Torque teno virus

<400> SEQUENCE: 45

Met Ala Trp Gly Trp Trp Arg Trp Arg Arg Arg Trp Pro Ala Arg Arg
1               5                   10                  15

Trp Arg Arg Arg Arg Arg Arg Arg Pro Val Arg Arg Thr Arg Ala Arg
            20                  25                  30

Arg Pro Ala Arg Arg Tyr Arg Arg Arg Arg Thr Thr Ile Lys Asn Pro
        35                  40                  45

Cys Lys Thr Asp Gly Gln Pro Thr Asp Ser Ser Arg His Pro Arg Gly
    50                  55                  60

Ile Gln Val Ala Asp Pro Glu Gln Met Gly Pro Arg Trp Val Phe His
65                  70                  75                  80

Ser Phe Asp Trp Arg Arg Gly Tyr Leu Ser Glu Lys Ala Leu Lys Arg
                85                  90                  95

Leu Gln Glu Lys Pro Leu Asp Tyr Asp Glu Tyr Phe Thr Gln Pro Lys
            100                 105                 110
```

-continued

```
Arg Pro Arg Ile Phe Pro Pro Thr Glu Ser Ala Glu Gly Glu Phe Arg
        115                 120                 125

Glu Pro Glu Lys Gly Ser Tyr Ser Glu Glu Glu Arg Ser Gln Ala Ser
    130                 135                 140

Ala Glu Glu Gln Thr Gln Glu Ala Thr Val Leu Leu Leu Lys Arg Arg
145                 150                 155                 160

Leu Arg Glu Gln Gln Gln Leu Gln Gln Gln Leu Gln Phe Leu Thr Arg
                165                 170                 175

Glu Met Phe Lys Thr Gln Ala Gly Leu His Leu Asn Pro Met Leu Leu
            180                 185                 190

Asn Gln Arg
        195


<210> SEQ ID NO 46
<211> LENGTH: 107
<212> TYPE: PRT
<213> ORGANISM: Torque teno virus

<400> SEQUENCE: 46

Met Ala Trp Gly Trp Trp Arg Trp Arg Arg Arg Trp Pro Ala Arg Arg
1               5                   10                  15

Trp Arg Arg Arg Arg Arg Arg Arg Pro Val Arg Arg Thr Arg Ala Arg
            20                  25                  30

Arg Pro Ala Arg Arg Tyr Arg Arg Arg Arg Thr Gln Arg Glu Ser Ser
        35                  40                  45

Glu Ser Pro Lys Lys Ala Arg Ile Gln Arg Lys Lys Gly Arg Lys Pro
    50                  55                  60

Leu Pro Lys Ser Arg Arg Arg Arg Arg Gln Tyr Ser Ser Ser Ser Asp
65                  70                  75                  80

Asp Ser Glu Ser Asn Ser Ser Ser Ser Ser Ser Ser Asn Ser Ser Pro
                85                  90                  95

Glu Lys Cys Ser Lys Arg Lys Arg Val Ser Thr
            100                 105


<210> SEQ ID NO 47
<211> LENGTH: 3866
<212> TYPE: DNA
<213> ORGANISM: Torque teno virus

<400> SEQUENCE: 47

aagtccgtca ctaaccacgt gactcccgca ggccaatcag agtctatgtc gtgcacttcc      60

tgggcatggt ctacgttctc atataactaa ctgcacttcc gaatggctga gttttccacg     120

cccgtccgca gcggcagcac cacggagggt gatccccgcg tcccgagggc gggtgccgaa     180

ggtgagttta cacaccgcag tcaaggggca attcgggctc gggactggcc gggctatggg     240

caaggctctt agggctttca ttgttaaaaa tgtttctcgg caggccttac aggagaaaga     300

aaagggcgct gtcactgcct ggcgtgcgag ctgcacaggc gaaacaacct ggtgatatga     360

gctggagccg tccagtacat aatgccgccg ggatcgaaag gcagtggttc gaatccacct     420

ttagatccca cgctagttgc tgtggctgcg gcaattttgt taatcatatt aatgtactgg     480

ctgctcgcta cggctttact ggggggccga cgccgccagg tggtcctggg ccgcgtccac     540

aactgaggcc cgcgcttccc gcgccggacc ccgacccccca ggcgcccaac cgtgagccat     600

ggcgtggagc tggtggtggc aacgatggag aaggcgccgc tggaaaccca ggaggcgccg     660

ctggagacgt ctacgatgga gaagacctag acgcgctgtt cgccgccgtc gtcgaggacg     720
```

-continued

```
tagagtaagg aggcggaggt gggcgcgtag acgggggcga cgcagacggt acgccaccag    780
acgaaagaga cgttataggg gtcgccgctt taaaaagaaa ctagtactga ctcagtggca    840
ccctaatacc atgagacgct gcttaatcaa gggcatagtc cccctggtaa tatgcggcca    900
caccaggtgg aactacaact acgccctcca tagcaaggac tacacagagg agggtcgcta    960
ccctcacggg ggggccctca gcaccactac gtggtccctt aaggtgctgt atgacgagca   1020
cctcaaacac cacgacttct ggggctatcc caacaaccag ctagacctgg ccaggtacaa   1080
gggggccaag ttcaccttct acagacacaa aaagactgac tttataatat tctttaacag   1140
aaagcctccc tttaagctaa acaagtacag ctgtgcctcc tatcacccag gcatgctgat   1200
gcagcagaga cacaagatcc tgctacccag ctacgaaact aaacccaagg gcaggccaaa   1260
gataacagtt agaataaagc cccccactct gttagaggac aagtggtaca cccagcagga   1320
cctgtgcgac gttaacctgt tgcaacttgt ggtcactgcg gctgactttc gacatccact   1380
ctgctcacca caaacgaaca ctccaaccac aaccttccag gtgttgaaag acatctatta   1440
tgacactatg agcatatctg aacccacaga ctcctacact agtgttaaca ataaaagtac   1500
aacacaaact tttactaact actcaaacac cttagaaaac attctgtaca cacgagcctc   1560
ctactggaac tcgttccacg ccactgaata cctaaacccc aacatcatat acaaaaacgg   1620
tgaaaaacta ttcaaagaac atgaagactt aataacctgg atgacccaaa ctaacaatac   1680
cgggtttcta actaaaaaca acacagcttt tggcaacaac agctacaggc ccaatgcaga   1740
caaaattaaa aaagccagaa agacatactg gaacgcccta ataggcacca acgacctggc   1800
cactaatata ggccaggcca gagcagaaag gttcgagtac cacctaggct ggtactcccc   1860
catatttctc agcagacaca ggagcaacat gaactttgcc agggcctacc aagacgtcac   1920
atacaacccc aactgtgaca ggggagttaa caacagggtg tgggttcagc ctctaactaa   1980
acccaccaca gagttcgacg agaaaaggtg taagtgcgta gtgcagcacc tgcctctgtg   2040
ggcggctctg tactgctacc aagactttgt agaggaggag ctggggtcct cctcagagat   2100
attaaattca tgcctactgg tattacagtg cccttacacc tttcccccaa tgtatgacaa   2160
aaagctacca gacaagggat tcgtgtttta tgactccctt tttggagacg gcaaaatgtc   2220
tgacggacgc ggacaggtgg acattttctg gcaacagcga tggtaccctc gcttagccac   2280
tcagatgcaa gtcatgcacg acatcaccat gacgggcccc ttctcctacc gagacgagct   2340
agttagcacc caactgactg ccaagtacac ctttgacttt atgtggggcg gaaatatgat   2400
ctccacacag atcatcaaga acccctgcaa agacagtgga ctggaacccg cctaccccgg   2460
tagacagcgt cgcgacttac aaattgttga cccatactcc atgggccccc aattctcgtt   2520
ccacaactgg gactacagac atggcctttt tggccaagac gctatcgaca gagtgtctaa   2580
acaaccaaaa gatgatgcag actatcctaa cccatacaaa aggcctagat attttccacc   2640
cacagaccaa gccgcccaag agcaagaaaa agacttcagt ttcctcaaaa cagcaccgtc   2700
gaactcagaa gagagcgatc aagaagtcct ccaagaaacg caagtactcc gattccagcc   2760
agagcagcac aagcaactcc acctgcagct cgcagagcgg cagcgaatcg gagagcaact   2820
ccgataccta ctccaacaga tgttcaaaac tcaggccaat ctccacctaa acccatatac   2880
atttacccag ctgtaaagca ggtgtttatg tttgaccccc cgggccctaa ggctatctcg   2940
ggcgccaagg cctgggagga cgagttcctc accgcaaaag tgtggaaccg cccggtacgc   3000
aagtactact cagacacccc ctactacccc tgggccccca aaccccagta ctctgtcagt   3060
ttcaaactcg gctggaaata aaaaaagcct gctccactgt actaggccgt gggagtttca   3120
```

```
ctcgtcggtg tctacctctt aaggtcacca agcactccga gcgtcagcga ggagtgcgac   3180

ccttgggggt gggtgcaacg ccctcggcgg ccgcgcgcta cgccttcggc tgcgcgcggc   3240

acctcggacc cccgctcgtg ctgacgcgct tgcgcgcgtc agaccacttc gggctcgcgg   3300

gggtcggaaa ttttgctaaa cagactccga gttgccattg gacactggag ccgtgaatca   3360

gtaacgaaag tgagtggggc cagacttcgc cataaggcct ttatcttttt gccatttgtc   3420

cgtggggaag ggtcgctgca agcgcggacc ccgttttcac cccttccgga ctacaaaaat   3480

agcgcattag tgacgtcacg gccgccattt taagtaaggc ggaagcaact ccactttctc   3540

acaaaatggc ggcggagcac ttccggcttg cccaaaatgg ccgccaaaaa catccgggtc   3600

aaagttcgcc gctacgtcat aagtcacgtg actggggagg tacttaaaca cggaagtatc   3660

ctcaaccacg taactggtca cgtggtgcgc acgtcacggc aaccattttg ttttacaaaa   3720

tggcgcattt ccttcctctt ttttaaaaat taaccgttgg cggcggcgcg cgcgctacgc   3780

gcgcgcgccg gggagctctg cccccccccg cgcatgcgcg cgggtccccc ccccgcgggg   3840

ggctccgccc cccggtcccc cccccg                                       3866
```

<210> SEQ ID NO 48
<211> LENGTH: 123
<212> TYPE: PRT
<213> ORGANISM: Torque teno virus

<400> SEQUENCE: 48

```
Met Ser Trp Ser Arg Pro Val His Asn Ala Ala Gly Ile Glu Arg Gln
1               5                   10                  15

Trp Phe Glu Ser Thr Phe Arg Ser His Ala Ser Cys Cys Gly Cys Gly
            20                  25                  30

Asn Phe Val Asn His Ile Asn Val Leu Ala Ala Arg Tyr Gly Phe Thr
        35                  40                  45

Gly Gly Pro Thr Pro Pro Gly Gly Pro Gly Pro Arg Pro Gln Leu Arg
    50                  55                  60

Pro Ala Leu Pro Ala Pro Asp Pro Asp Pro Gln Ala Pro Asn Arg Glu
65                  70                  75                  80

Pro Trp Arg Gly Ala Gly Gly Gly Asn Asp Gly Glu Gly Ala Ala Gly
                85                  90                  95

Asn Pro Gly Gly Ala Ala Gly Asp Val Tyr Asp Gly Glu Asp Leu Asp
            100                 105                 110

Ala Leu Phe Ala Ala Val Val Glu Asp Val Glu
        115                 120
```

<210> SEQ ID NO 49
<211> LENGTH: 275
<212> TYPE: PRT
<213> ORGANISM: Torque teno virus

<400> SEQUENCE: 49

```
Met Ser Trp Ser Arg Pro Val His Asn Ala Ala Gly Ile Glu Arg Gln
1               5                   10                  15

Trp Phe Glu Ser Thr Phe Arg Ser His Ala Ser Cys Cys Gly Cys Gly
            20                  25                  30

Asn Phe Val Asn His Ile Asn Val Leu Ala Ala Arg Tyr Gly Phe Thr
        35                  40                  45

Gly Gly Pro Thr Pro Pro Gly Gly Pro Gly Pro Arg Pro Gln Leu Arg
    50                  55                  60
```

Pro Ala Leu Pro Ala Pro Asp Pro Asp Pro Gln Ala Pro Asn Arg Glu
65 70 75 80

Pro Trp Arg Gly Ala Gly Gly Gly Asn Asp Gly Glu Gly Ala Ala Gly
85 90 95

Asn Pro Gly Gly Ala Ala Gly Asp Val Tyr Asp Gly Glu Asp Leu Asp
100 105 110

Ala Leu Phe Ala Ala Val Val Glu Asp Val Glu Ser Ser Arg Thr Pro
115 120 125

Ala Lys Thr Val Asp Trp Asn Pro Pro Thr Pro Val Asp Ser Val Ala
130 135 140

Thr Tyr Lys Leu Leu Thr His Thr Pro Trp Ala Pro Asn Ser Arg Ser
145 150 155 160

Thr Thr Gly Thr Thr Asp Met Ala Phe Leu Ala Lys Thr Leu Ser Thr
165 170 175

Glu Cys Leu Asn Asn Gln Lys Met Met Gln Thr Ile Leu Thr His Thr
180 185 190

Lys Gly Leu Asp Ile Phe His Pro Gln Thr Lys Pro Pro Lys Ser Lys
195 200 205

Lys Lys Thr Ser Val Ser Ser Lys Gln His Arg Arg Thr Gln Lys Arg
210 215 220

Ala Ile Lys Lys Ser Ser Lys Lys Arg Lys Tyr Ser Asp Ser Ser Gln
225 230 235 240

Ser Ser Thr Ser Asn Ser Thr Cys Ser Ser Gln Ser Gly Ser Glu Ser
245 250 255

Glu Ser Asn Ser Asp Thr Tyr Ser Asn Arg Cys Ser Lys Leu Arg Pro
260 265 270

Ile Ser Thr
275

<210> SEQ ID NO 50
<211> LENGTH: 267
<212> TYPE: PRT
<213> ORGANISM: Torque teno virus

<400> SEQUENCE: 50

Met Ser Trp Ser Arg Pro Val His Asn Ala Ala Gly Ile Glu Arg Gln
1 5 10 15

Trp Phe Glu Ser Thr Phe Arg Ser His Ala Ser Cys Cys Gly Cys Gly
20 25 30

Asn Phe Val Asn His Ile Asn Val Leu Ala Ala Arg Tyr Gly Phe Thr
35 40 45

Gly Gly Pro Thr Pro Pro Gly Gly Pro Gly Pro Arg Pro Gln Leu Arg
50 55 60

Pro Ala Leu Pro Ala Pro Asp Pro Asp Pro Gln Ala Pro Asn Arg Glu
65 70 75 80

Pro Trp Arg Gly Ala Gly Gly Gly Asn Asp Gly Glu Gly Ala Ala Gly
85 90 95

Asn Pro Gly Gly Ala Ala Gly Asp Val Tyr Asp Gly Glu Asp Leu Asp
100 105 110

Ala Leu Phe Ala Ala Val Val Glu Asp Val Glu Pro Ser Arg Pro Arg
115 120 125

Ala Arg Lys Arg Leu Gln Phe Pro Gln Asn Ser Thr Val Glu Leu Arg
130 135 140

Arg Glu Arg Ser Arg Ser Pro Pro Arg Asn Ala Ser Thr Pro Ile Pro
145 150 155 160

```
Ala Arg Ala Ala Gln Ala Thr Pro Pro Ala Ala Arg Arg Ala Ala Ala
                165                 170                 175

Asn Arg Arg Ala Thr Pro Ile Pro Thr Pro Thr Asp Val Gln Asn Ser
            180                 185                 190

Gly Gln Ser Pro Pro Lys Pro Ile Tyr Ile Tyr Pro Ala Val Lys Gln
        195                 200                 205

Val Phe Met Phe Asp Pro Pro Gly Pro Lys Ala Ile Ser Gly Ala Lys
    210                 215                 220

Ala Trp Glu Asp Glu Phe Leu Thr Ala Lys Val Trp Asn Arg Pro Val
225                 230                 235                 240

Arg Lys Tyr Tyr Ser Asp Thr Pro Tyr Tyr Pro Trp Ala Pro Lys Pro
                245                 250                 255

Gln Tyr Ser Val Ser Phe Lys Leu Gly Trp Lys
            260                 265


<210> SEQ ID NO 51
<211> LENGTH: 765
<212> TYPE: PRT
<213> ORGANISM: Torque teno virus

<400> SEQUENCE: 51

Met Ala Trp Ser Trp Trp Trp Gln Arg Trp Arg Arg Arg Arg Trp Lys
1               5                   10                  15

Pro Arg Arg Arg Arg Trp Arg Arg Leu Arg Trp Arg Arg Pro Arg Arg
            20                  25                  30

Ala Val Arg Arg Arg Arg Arg Gly Arg Arg Val Arg Arg Arg Arg Trp
        35                  40                  45

Ala Arg Arg Arg Gly Arg Arg Arg Arg Tyr Ala Thr Arg Arg Lys Arg
    50                  55                  60

Arg Tyr Arg Gly Arg Arg Phe Lys Lys Lys Leu Val Leu Thr Gln Trp
65                  70                  75                  80

His Pro Asn Thr Met Arg Arg Cys Leu Ile Lys Gly Ile Val Pro Leu
                85                  90                  95

Val Ile Cys Gly His Thr Arg Trp Asn Tyr Asn Tyr Ala Leu His Ser
            100                 105                 110

Lys Asp Tyr Thr Glu Glu Gly Arg Tyr Pro His Gly Gly Ala Leu Ser
        115                 120                 125

Thr Thr Thr Trp Ser Leu Lys Val Leu Tyr Asp Glu His Leu Lys His
    130                 135                 140

His Asp Phe Trp Gly Tyr Pro Asn Asn Gln Leu Asp Leu Ala Arg Tyr
145                 150                 155                 160

Lys Gly Ala Lys Phe Thr Phe Tyr Arg His Lys Lys Thr Asp Phe Ile
                165                 170                 175

Ile Phe Phe Asn Arg Lys Pro Pro Phe Lys Leu Asn Lys Tyr Ser Cys
            180                 185                 190

Ala Ser Tyr His Pro Gly Met Leu Met Gln Gln Arg His Lys Ile Leu
        195                 200                 205

Leu Pro Ser Tyr Glu Thr Lys Pro Lys Gly Arg Pro Lys Ile Thr Val
    210                 215                 220

Arg Ile Lys Pro Pro Thr Leu Leu Glu Asp Lys Trp Tyr Thr Gln Gln
225                 230                 235                 240

Asp Leu Cys Asp Val Asn Leu Leu Gln Leu Val Val Thr Ala Ala Asp
                245                 250                 255

Phe Arg His Pro Leu Cys Ser Pro Gln Thr Asn Thr Pro Thr Thr Thr
```

```
            260                 265                 270

Phe Gln Val Leu Lys Asp Ile Tyr Tyr Asp Thr Met Ser Ile Ser Glu
        275                 280                 285

Pro Thr Asp Ser Tyr Thr Ser Val Asn Asn Lys Ser Thr Thr Gln Thr
    290                 295                 300

Phe Thr Asn Tyr Ser Asn Thr Leu Glu Asn Ile Leu Tyr Thr Arg Ala
305                 310                 315                 320

Ser Tyr Trp Asn Ser Phe His Ala Thr Glu Tyr Leu Asn Pro Asn Ile
                325                 330                 335

Ile Tyr Lys Asn Gly Glu Lys Leu Phe Lys Glu His Glu Asp Leu Ile
            340                 345                 350

Thr Trp Met Thr Gln Thr Asn Asn Thr Gly Phe Leu Thr Lys Asn Asn
        355                 360                 365

Thr Ala Phe Gly Asn Asn Ser Tyr Arg Pro Asn Ala Asp Lys Ile Lys
    370                 375                 380

Lys Ala Arg Lys Thr Tyr Trp Asn Ala Leu Ile Gly Thr Asn Asp Leu
385                 390                 395                 400

Ala Thr Asn Ile Gly Gln Ala Arg Ala Glu Arg Phe Glu Tyr His Leu
                405                 410                 415

Gly Trp Tyr Ser Pro Ile Phe Leu Ser Arg His Arg Ser Asn Met Asn
            420                 425                 430

Phe Ala Arg Ala Tyr Gln Asp Val Thr Tyr Asn Pro Asn Cys Asp Arg
        435                 440                 445

Gly Val Asn Asn Arg Val Trp Val Gln Pro Leu Thr Lys Pro Thr Thr
    450                 455                 460

Glu Phe Asp Glu Lys Arg Cys Lys Cys Val Val Gln His Leu Pro Leu
465                 470                 475                 480

Trp Ala Ala Leu Tyr Cys Tyr Gln Asp Phe Val Glu Glu Glu Leu Gly
                485                 490                 495

Ser Ser Ser Glu Ile Leu Asn Ser Cys Leu Leu Val Leu Gln Cys Pro
            500                 505                 510

Tyr Thr Phe Pro Pro Met Tyr Asp Lys Lys Leu Pro Asp Lys Gly Phe
        515                 520                 525

Val Phe Tyr Asp Ser Leu Phe Gly Asp Gly Lys Met Ser Asp Gly Arg
    530                 535                 540

Gly Gln Val Asp Ile Phe Trp Gln Gln Arg Trp Tyr Pro Arg Leu Ala
545                 550                 555                 560

Thr Gln Met Gln Val Met His Asp Ile Thr Met Thr Gly Pro Phe Ser
                565                 570                 575

Tyr Arg Asp Glu Leu Val Ser Thr Gln Leu Thr Ala Lys Tyr Thr Phe
            580                 585                 590

Asp Phe Met Trp Gly Gly Asn Met Ile Ser Thr Gln Ile Ile Lys Asn
        595                 600                 605

Pro Cys Lys Asp Ser Gly Leu Glu Pro Ala Tyr Pro Gly Arg Gln Arg
    610                 615                 620

Arg Asp Leu Gln Ile Val Asp Pro Tyr Ser Met Gly Pro Gln Phe Ser
625                 630                 635                 640

Phe His Asn Trp Asp Tyr Arg His Gly Leu Phe Gly Gln Asp Ala Ile
                645                 650                 655

Asp Arg Val Ser Lys Gln Pro Lys Asp Asp Ala Asp Tyr Pro Asn Pro
            660                 665                 670

Tyr Lys Arg Pro Arg Tyr Phe Pro Pro Thr Asp Gln Ala Ala Gln Glu
        675                 680                 685
```

```
Gln Glu Lys Asp Phe Ser Phe Leu Lys Thr Ala Pro Ser Asn Ser Glu
    690                 695                 700

Glu Ser Asp Gln Glu Val Leu Gln Glu Thr Gln Val Leu Arg Phe Gln
705                 710                 715                 720

Pro Glu Gln His Lys Gln Leu His Leu Gln Leu Ala Glu Arg Gln Arg
                725                 730                 735

Ile Gly Glu Gln Leu Arg Tyr Leu Leu Gln Gln Met Phe Lys Thr Gln
            740                 745                 750

Ala Asn Leu His Leu Asn Pro Tyr Thr Phe Thr Gln Leu
        755                 760                 765


<210> SEQ ID NO 52
<211> LENGTH: 203
<212> TYPE: PRT
<213> ORGANISM: Torque teno virus

<400> SEQUENCE: 52

Met Ala Trp Ser Trp Trp Trp Gln Arg Trp Arg Arg Arg Arg Trp Lys
1               5                   10                  15

Pro Arg Arg Arg Arg Trp Arg Arg Leu Arg Trp Arg Arg Pro Arg Arg
            20                  25                  30

Ala Val Arg Arg Arg Arg Arg Gly Arg Arg Ile Ile Lys Asn Pro Cys
        35                  40                  45

Lys Asp Ser Gly Leu Glu Pro Ala Tyr Pro Gly Arg Gln Arg Arg Asp
    50                  55                  60

Leu Gln Ile Val Asp Pro Tyr Ser Met Gly Pro Gln Phe Ser Phe His
65                  70                  75                  80

Asn Trp Asp Tyr Arg His Gly Leu Phe Gly Gln Asp Ala Ile Asp Arg
                85                  90                  95

Val Ser Lys Gln Pro Lys Asp Asp Ala Asp Tyr Pro Asn Pro Tyr Lys
            100                 105                 110

Arg Pro Arg Tyr Phe Pro Pro Thr Asp Gln Ala Ala Gln Glu Gln Glu
        115                 120                 125

Lys Asp Phe Ser Phe Leu Lys Thr Ala Pro Ser Asn Ser Glu Glu Ser
    130                 135                 140

Asp Gln Glu Val Leu Gln Glu Thr Gln Val Leu Arg Phe Gln Pro Glu
145                 150                 155                 160

Gln His Lys Gln Leu His Leu Gln Leu Ala Glu Arg Gln Arg Ile Gly
                165                 170                 175

Glu Gln Leu Arg Tyr Leu Leu Gln Gln Met Phe Lys Thr Gln Ala Asn
            180                 185                 190

Leu His Leu Asn Pro Tyr Thr Phe Thr Gln Leu
        195                 200


<210> SEQ ID NO 53
<211> LENGTH: 116
<212> TYPE: PRT
<213> ORGANISM: Torque teno virus

<400> SEQUENCE: 53

Met Ala Trp Ser Trp Trp Trp Gln Arg Trp Arg Arg Arg Arg Trp Lys
1               5                   10                  15

Pro Arg Arg Arg Arg Trp Arg Arg Leu Arg Trp Arg Arg Pro Arg Arg
            20                  25                  30

Ala Val Arg Arg Arg Arg Arg Gly Arg Arg Thr Lys Pro Pro Lys Ser
        35                  40                  45
```

```
Lys Lys Lys Thr Ser Val Ser Ser Lys Gln His Arg Arg Thr Gln Lys
    50                  55                  60

Arg Ala Ile Lys Lys Ser Ser Lys Lys Arg Lys Tyr Ser Asp Ser Ser
65                  70                  75                  80

Gln Ser Ser Thr Ser Asn Ser Thr Cys Ser Ser Gln Ser Gly Ser Glu
                85                  90                  95

Ser Glu Ser Asn Ser Asp Thr Tyr Ser Asn Arg Cys Ser Lys Leu Arg
            100                 105                 110

Pro Ile Ser Thr
        115


<210> SEQ ID NO 54
<211> LENGTH: 2979
<212> TYPE: DNA
<213> ORGANISM: TTV-like mini virus

<400> SEQUENCE: 54

taataaatat tcaacaggaa aaccacctaa tttaaattgc cgaccacaaa ccgtcactta      60

gttccccttt ttgcaacaac ttctgctttt ttccaactgc cggaaaacca cataatttgc     120

atggctaacc acaaactgat atgctaatta acttccacaa aacaacttcc ccttttaaaa     180

ccacacctac aaattaatta ttaaacacag tcacatcctg ggaggtacta ccacactata     240

ataccaagtg cacttccgaa tggctgagtt tatgccgcta gacggagaac gcatcagtta     300

ctgactgcgg actgaacttg ggcgggtgcc gaaggtgagt gaaaccaccg aagtcaaggg     360

gcaattcggg ctagttcagt ctagcggaac gggcaagaaa cttaaaatta ttttattttt     420

cagatgagcg actgctttaa accaacatgc tacaacaaca aaacaaagca aactcactgg     480

attaataacc tgcatttaac ccacgacctg atctgcttct gcccaacacc aactagacac     540

ttattactag ctttagcaga acaacaagaa acaattgaag tgtctaaaca agaaaaagaa     600

aaaataacaa gatgccttat tactacagaa gaagacggta caactacaga cgtcctagat     660

ggtatggacg aggttggatt agacgccctt ttcgcagaag atttcgaaga aaaagaaggg     720

taagacctac ttatactact attcctctaa agcaatggca accgccatat aaaagaacat     780

gctatataaa aggacaagac tgtttaatat actatagcaa cttaagactg ggaatgaata     840

gtacaatgta tgaaaaaagt attgtacctg tacattggcc gggagggggt tctttttctg     900

taagcatgtt aactttagat gccttgtatg atatacataa actttgtaga aactggtgga     960

catccacaaa ccaagactta ccactagtaa gatataaagg atgcaaaata acattttatc    1020

aaagcacatt tacagactac atagtaagaa tacatacaga actaccagct aacagtaaca    1080

aactaacata cccaaacaca catccactaa tgatgatgat gtctaagtac aaacacatta    1140

tacctagtag acaaacaaga agaaaaaaga aaccatacac aaaaatattt gtaaaaccac    1200

ctccgcaatt tgaaaacaaa tggtactttg ctacagacct ctacaaaatt ccattactac    1260

aaatacactg cacagcatgc aacttacaaa acccatttgt aaaaccagac aaattatcaa    1320

acaatgttac attatggtca ctaaacacca taagcataca aaatagaaac atgtcagtgg    1380

atcaaggaca atcatggcca tttaaaatac taggaacaca aagcttttat ttttactttt    1440

acaccggagc aaacctacca ggtgacacaa cacaaatacc agtagcagac ctattaccac    1500

taacaaaccc aagaataaac agaccaggac aatcactaaa tgaggcaaaa attacagacc    1560

atattacttt cacagaatac aaaaacaaat ttacaaatta ttggggtaac ccatttaata    1620

aacacattca agaacaccta gatatgatac tatactcact aaaaagtcca gaagcaataa    1680
```

aaaacgaatg gacaacagaa aacatgaaat ggaaccaatt aaacaatgca ggaacaatgg 1740
cattaacacc atttaacgag ccaatattca cacaaataca atataaccca gatagagaca 1800
caggagaaga cactcaatta tacctactct ctaacgctac aggaacagga tgggacccac 1860
caggaattcc agaattaata ctagaaggat ttccactatg gttaatatat tggggatttg 1920
cagactttca aaaaaaccta aaaaaagtaa caaacataga cacaaattac atgttagtag 1980
caaaaacaaa atttacacaa aaacctggca cattctactt agtaatacta aatgacacct 2040
ttgtagaagg caatagccca tatgaaaaac aacctttacc tgaagacaac attaaatggt 2100
acccacaagt acaataccaa ttagaagcac aaaacaaact actacaaact gggccattta 2160
caccaaacat acaaggacaa ctatcagaca atatatcaat gttttataaa ttttacttta 2220
aatggggagg aagcccacca aaagcaatta atgttgaaaa tcctgcccac cagattcaat 2280
atcccatacc ccgtaacgag catgaaacaa cttcgttaca gagtccaggg gaagccccag 2340
aatccatctt atactccttc gactatagac acgggaacta cacaacaaca gctttgtcac 2400
gaattagcca agactgggca cttaaagaca ctgtttctaa aattacagag ccagatcgac 2460
agcaactgct caaacaagcc ctcgaatgcc tgcaaatctc ggaagaaacg caggagaaaa 2520
aagaaaaaga agtacagcag ctcatcagca acctcagaca gcagcagcag ctgtacagag 2580
agcgaataat atcattatta aaggaccaat aacttttaac tgtgtaaaaa aggtgaaatt 2640
gtttgatgat aaaccaaaaa accgtagatt tacacctgag gaatttgaaa ctgagttaca 2700
aatagcaaaa tggttaaaga gacccccaag atcctttgta aatgatcctc ccttttaccc 2760
atggttacca cctgaacctg ttgtaaactt taagcttaat tttactgaat aaaggccagc 2820
attaattcac ttaaggagtc tgtttattta agttaaacct taataaacgg tcaccgcctc 2880
cctaatacgc aggcgcagaa agggggctcc gcccccttta acccccaggg ggctccgccc 2940
cctgaaaccc ccaagggggc tacgccccct tacaccccc 2979

<210> SEQ ID NO 55
<211> LENGTH: 99
<212> TYPE: PRT
<213> ORGANISM: TTV-like mini virus

<400> SEQUENCE: 55

Met Ser Asp Cys Phe Lys Pro Thr Cys Tyr Asn Asn Lys Thr Lys Gln
1 5 10 15

Thr His Trp Ile Asn Asn Leu His Leu Thr His Asp Leu Ile Cys Phe
20 25 30

Cys Pro Thr Pro Thr Arg His Leu Leu Leu Ala Leu Ala Glu Gln Gln
35 40 45

Glu Thr Ile Glu Val Ser Lys Gln Glu Lys Glu Lys Ile Thr Arg Cys
50 55 60

Leu Ile Thr Thr Glu Glu Asp Gly Thr Thr Thr Asp Val Leu Asp Gly
65 70 75 80

Met Asp Glu Val Gly Leu Asp Ala Leu Phe Ala Glu Asp Phe Glu Glu
85 90 95

Lys Glu Gly

<210> SEQ ID NO 56
<211> LENGTH: 203
<212> TYPE: PRT
<213> ORGANISM: TTV-like mini virus

<400> SEQUENCE: 56

```
Met Ser Asp Cys Phe Lys Pro Thr Cys Tyr Asn Asn Lys Thr Lys Gln
1               5                   10                  15

Thr His Trp Ile Asn Asn Leu His Leu Thr His Asp Leu Ile Cys Phe
            20                  25                  30

Cys Pro Thr Pro Thr Arg His Leu Leu Leu Ala Leu Ala Glu Gln Gln
        35                  40                  45

Glu Thr Ile Glu Val Ser Lys Gln Glu Lys Glu Lys Ile Thr Arg Cys
    50                  55                  60

Leu Ile Thr Thr Glu Glu Asp Gly Thr Thr Thr Asp Val Leu Asp Gly
65                  70                  75                  80

Met Asp Glu Val Gly Leu Asp Ala Leu Phe Ala Glu Asp Phe Glu Glu
                85                  90                  95

Lys Glu Gly Phe Asn Ile Pro Tyr Pro Val Thr Ser Met Lys Gln Leu
            100                 105                 110

Arg Tyr Arg Val Gln Gly Lys Pro Gln Asn Pro Ser Tyr Thr Pro Ser
        115                 120                 125

Thr Ile Asp Thr Gly Thr Thr Gln Gln Gln Leu Cys His Glu Leu Ala
    130                 135                 140

Lys Thr Gly His Leu Lys Thr Leu Phe Leu Lys Leu Gln Ser Gln Ile
145                 150                 155                 160

Asp Ser Asn Cys Ser Asn Lys Pro Ser Asn Ala Cys Lys Ser Arg Lys
                165                 170                 175

Lys Arg Arg Arg Lys Lys Lys Lys Lys Tyr Ser Ser Ser Ser Ala Thr
            180                 185                 190

Ser Asp Ser Ser Ser Ser Cys Thr Glu Ser Glu
        195                 200
```

<210> SEQ ID NO 57
<211> LENGTH: 219
<212> TYPE: PRT
<213> ORGANISM: TTV-like mini virus

<400> SEQUENCE: 57

```
Met Ser Asp Cys Phe Lys Pro Thr Cys Tyr Asn Asn Lys Thr Lys Gln
1               5                   10                  15

Thr His Trp Ile Asn Asn Leu His Leu Thr His Asp Leu Ile Cys Phe
            20                  25                  30

Cys Pro Thr Pro Thr Arg His Leu Leu Leu Ala Leu Ala Glu Gln Gln
        35                  40                  45

Glu Thr Ile Glu Val Ser Lys Gln Glu Lys Glu Lys Ile Thr Arg Cys
    50                  55                  60

Leu Ile Thr Thr Glu Glu Asp Gly Thr Thr Thr Asp Val Leu Asp Gly
65                  70                  75                  80

Met Asp Glu Val Gly Leu Asp Ala Leu Phe Ala Glu Asp Phe Glu Glu
                85                  90                  95

Lys Glu Gly Ala Arg Ser Thr Ala Thr Ala Gln Thr Ser Pro Arg Met
            100                 105                 110

Pro Ala Asn Leu Gly Arg Asn Ala Gly Glu Lys Arg Lys Arg Ser Thr
        115                 120                 125

Ala Ala His Gln Gln Pro Gln Thr Ala Ala Ala Ala Val Gln Arg Ala
    130                 135                 140

Asn Asn Ile Ile Ile Lys Gly Pro Ile Thr Phe Asn Cys Val Lys Lys
145                 150                 155                 160
```

```
Val Lys Leu Phe Asp Asp Lys Pro Lys Asn Arg Arg Phe Thr Pro Glu
                165                 170                 175

Glu Phe Glu Thr Glu Leu Gln Ile Ala Lys Trp Leu Lys Arg Pro Pro
            180                 185                 190

Arg Ser Phe Val Asn Asp Pro Pro Phe Tyr Pro Trp Leu Pro Pro Glu
        195                 200                 205

Pro Val Val Asn Phe Lys Leu Asn Phe Thr Glu
    210                 215
```

<210> SEQ ID NO 58
<211> LENGTH: 666
<212> TYPE: PRT
<213> ORGANISM: TTV-like mini virus

<400> SEQUENCE: 58

```
Met Pro Tyr Tyr Tyr Arg Arg Arg Arg Tyr Asn Tyr Arg Arg Pro Arg
1               5                   10                  15

Trp Tyr Gly Arg Gly Trp Ile Arg Arg Pro Phe Arg Arg Arg Phe Arg
            20                  25                  30

Arg Lys Arg Arg Val Arg Pro Thr Tyr Thr Thr Ile Pro Leu Lys Gln
        35                  40                  45

Trp Gln Pro Pro Tyr Lys Arg Thr Cys Tyr Ile Lys Gly Gln Asp Cys
    50                  55                  60

Leu Ile Tyr Tyr Ser Asn Leu Arg Leu Gly Met Asn Ser Thr Met Tyr
65                  70                  75                  80

Glu Lys Ser Ile Val Pro Val His Trp Pro Gly Gly Gly Ser Phe Ser
                85                  90                  95

Val Ser Met Leu Thr Leu Asp Ala Leu Tyr Asp Ile His Lys Leu Cys
            100                 105                 110

Arg Asn Trp Trp Thr Ser Thr Asn Gln Asp Leu Pro Leu Val Arg Tyr
        115                 120                 125

Lys Gly Cys Lys Ile Thr Phe Tyr Gln Ser Thr Phe Thr Asp Tyr Ile
    130                 135                 140

Val Arg Ile His Thr Glu Leu Pro Ala Asn Ser Asn Lys Leu Thr Tyr
145                 150                 155                 160

Pro Asn Thr His Pro Leu Met Met Met Met Ser Lys Tyr Lys His Ile
                165                 170                 175

Ile Pro Ser Arg Gln Thr Arg Arg Lys Lys Lys Pro Tyr Thr Lys Ile
            180                 185                 190

Phe Val Lys Pro Pro Pro Gln Phe Glu Asn Lys Trp Tyr Phe Ala Thr
        195                 200                 205

Asp Leu Tyr Lys Ile Pro Leu Leu Gln Ile His Cys Thr Ala Cys Asn
    210                 215                 220

Leu Gln Asn Pro Phe Val Lys Pro Asp Lys Leu Ser Asn Asn Val Thr
225                 230                 235                 240

Leu Trp Ser Leu Asn Thr Ile Ser Ile Gln Asn Arg Asn Met Ser Val
                245                 250                 255

Asp Gln Gly Gln Ser Trp Pro Phe Lys Ile Leu Gly Thr Gln Ser Phe
            260                 265                 270

Tyr Phe Tyr Phe Tyr Thr Gly Ala Asn Leu Pro Gly Asp Thr Thr Gln
        275                 280                 285

Ile Pro Val Ala Asp Leu Leu Pro Leu Thr Asn Pro Arg Ile Asn Arg
    290                 295                 300

Pro Gly Gln Ser Leu Asn Glu Ala Lys Ile Thr Asp His Ile Thr Phe
305                 310                 315                 320
```

Thr Glu Tyr Lys Asn Lys Phe Thr Asn Tyr Trp Gly Asn Pro Phe Asn
325 330 335

Lys His Ile Gln Glu His Leu Asp Met Ile Leu Tyr Ser Leu Lys Ser
340 345 350

Pro Glu Ala Ile Lys Asn Glu Trp Thr Thr Glu Asn Met Lys Trp Asn
355 360 365

Gln Leu Asn Asn Ala Gly Thr Met Ala Leu Thr Pro Phe Asn Glu Pro
370 375 380

Ile Phe Thr Gln Ile Gln Tyr Asn Pro Asp Arg Asp Thr Gly Glu Asp
385 390 395 400

Thr Gln Leu Tyr Leu Leu Ser Asn Ala Thr Gly Thr Gly Trp Asp Pro
405 410 415

Pro Gly Ile Pro Glu Leu Ile Leu Glu Gly Phe Pro Leu Trp Leu Ile
420 425 430

Tyr Trp Gly Phe Ala Asp Phe Gln Lys Asn Leu Lys Lys Val Thr Asn
435 440 445

Ile Asp Thr Asn Tyr Met Leu Val Ala Lys Thr Lys Phe Thr Gln Lys
450 455 460

Pro Gly Thr Phe Tyr Leu Val Ile Leu Asn Asp Thr Phe Val Glu Gly
465 470 475 480

Asn Ser Pro Tyr Glu Lys Gln Pro Leu Pro Glu Asp Asn Ile Lys Trp
485 490 495

Tyr Pro Gln Val Gln Tyr Gln Leu Glu Ala Gln Asn Lys Leu Leu Gln
500 505 510

Thr Gly Pro Phe Thr Pro Asn Ile Gln Gly Gln Leu Ser Asp Asn Ile
515 520 525

Ser Met Phe Tyr Lys Phe Tyr Phe Lys Trp Gly Gly Ser Pro Pro Lys
530 535 540

Ala Ile Asn Val Glu Asn Pro Ala His Gln Ile Gln Tyr Pro Ile Pro
545 550 555 560

Arg Asn Glu His Glu Thr Thr Ser Leu Gln Ser Pro Gly Glu Ala Pro
565 570 575

Glu Ser Ile Leu Tyr Ser Phe Asp Tyr Arg His Gly Asn Tyr Thr Thr
580 585 590

Thr Ala Leu Ser Arg Ile Ser Gln Asp Trp Ala Leu Lys Asp Thr Val
595 600 605

Ser Lys Ile Thr Glu Pro Asp Arg Gln Gln Leu Leu Lys Gln Ala Leu
610 615 620

Glu Cys Leu Gln Ile Ser Glu Glu Thr Gln Glu Lys Lys Glu Lys Glu
625 630 635 640

Val Gln Gln Leu Ile Ser Asn Leu Arg Gln Gln Gln Gln Leu Tyr Arg
645 650 655

Glu Arg Ile Ile Ser Leu Leu Lys Asp Gln
660 665

<210> SEQ ID NO 59
<211> LENGTH: 148
<212> TYPE: PRT
<213> ORGANISM: TTV-like mini virus

<400> SEQUENCE: 59

Met Pro Tyr Tyr Tyr Arg Arg Arg Arg Tyr Asn Tyr Arg Arg Pro Arg
1 5 10 15

Trp Tyr Gly Arg Gly Trp Ile Arg Arg Pro Phe Arg Arg Arg Phe Arg

```
            20                  25                  30

Arg Lys Arg Arg Ile Gln Tyr Pro Ile Pro Arg Asn Glu His Glu Thr
        35                  40                  45

Thr Ser Leu Gln Ser Pro Gly Glu Ala Pro Glu Ser Ile Leu Tyr Ser
    50                  55                  60

Phe Asp Tyr Arg His Gly Asn Tyr Thr Thr Thr Ala Leu Ser Arg Ile
65                  70                  75                  80

Ser Gln Asp Trp Ala Leu Lys Asp Thr Val Ser Lys Ile Thr Glu Pro
                85                  90                  95

Asp Arg Gln Gln Leu Leu Lys Gln Ala Leu Glu Cys Leu Gln Ile Ser
            100                 105                 110

Glu Glu Thr Gln Glu Lys Lys Glu Lys Glu Val Gln Gln Leu Ile Ser
        115                 120                 125

Asn Leu Arg Gln Gln Gln Gln Leu Tyr Arg Glu Arg Ile Ile Ser Leu
    130                 135                 140

Leu Lys Asp Gln
145


<210> SEQ ID NO 60
<211> LENGTH: 82
<212> TYPE: PRT
<213> ORGANISM: TTV-like mini virus

<400> SEQUENCE: 60

Met Pro Tyr Tyr Tyr Arg Arg Arg Arg Tyr Asn Tyr Arg Arg Pro Arg
1               5                   10                  15

Trp Tyr Gly Arg Gly Trp Ile Arg Arg Pro Phe Arg Arg Arg Phe Arg
            20                  25                  30

Arg Lys Arg Arg Ser Gln Ile Asp Ser Asn Cys Ser Asn Lys Pro Ser
        35                  40                  45

Asn Ala Cys Lys Ser Arg Lys Lys Arg Arg Arg Lys Lys Lys Lys Lys
    50                  55                  60

Tyr Ser Ser Ser Ser Ala Thr Ser Asp Ser Ser Ser Ser Cys Thr Glu
65                  70                  75                  80

Ser Glu


<210> SEQ ID NO 61
<211> LENGTH: 3242
<212> TYPE: DNA
<213> ORGANISM: Torque teno midi virus 1

<400> SEQUENCE: 61

aggtggagac tcttaagcta tataaccaag tggggtggcg aatggctgag tttaccccgc      60

tagacggtgc agggaccgga tcgagcgcag cgaggaggtc cccggctgcc cgtgggcggg     120

agcccgaggt gagtgaaacc accgaggtct aggggcaatt cgggctaggg cagtctagcg     180

gaacgggcaa gaaacttaaa aatatttctt ttacagatgc aaaacctatc agccaaagac     240

ttctacaaac catgcagata caactgtgaa actaaaaacc aaatgtggat gtctggcatt     300

gctgactccc atgacagttg gtgtgactgt gatactcctt ttgctcacct cctggctagt     360

atttttcctc ctggtcacac agatcgcaca cgaaccatcc aagaaatact taccagagat     420

tttaggaaaa catgcctttc tggtggggcc gacgcaacaa attctggtat ggccgaaact     480

atagaagaaa aaagagaaga tttccaaaaa gaagaaaaag aagattttac agaagaacaa     540

aatatagaag acctgctcgc cgccgtcgca gacgcagaag gaaggtaaga agaaaaaaaa     600
```

```
aaactcttat agtaagacaa tggcagccag actctattgt actctgtaaa attaaagggt    660
atgactctat aatatgggga gctgaaggca cacagtttca atgttctaca catgaaatgt    720
atgaatatac aagacaaaag taccctgggg gaggaggatt tggtgtacaa ctttacagct    780
tagagtattt gtatgaccaa tggaaactta gaaataatat atggactaaa acaaatcaac    840
tcaaagattt gtgtagatac ttaaaatgtg ttatgacctt ttacagacac caacacatag    900
attttgtaat tgtatatgaa agacaacccc catttgaaat agataaacta acatacatga    960
aatatcatcc atatatgtta ttacaaagaa agcataaaat aattttacct agtcaaacaa   1020
ctaatcctag aggtaaatta aaaaaaaaga aaactattaa acctcccaaa caaatgctca   1080
gcaaatggtt ttttcaacaa caatttgcta aatatgatct actacttatt gctgcagcag   1140
catgtagttt aagataccct agaataggct gctgcaatga aaatagaatg ataaccttat   1200
actgtttaaa tactaaattt tatcaagata cagaatgggg aactacaaaa caggcccccc   1260
actactttaa accatatgca acaattaata aatccatgat atttgtctct aactatggag   1320
gtaaaaaaac agaatataac ataggccaat ggatagaaac agatatacct ggagaaggta   1380
atctagcaag atactacaga tcaataagta aagaaggagg ttacttttca cctaaaatac   1440
tgcaagcata tcaaacaaaa gtaaagtctg tagactacaa acctttacca attgttttag   1500
gtagatataa cccagcaata gatgatggaa aaggcaacaa aatttactta caaactataa   1560
tgaatggcca ttggggccta cctcaaaaaa caccagatta tataatagaa gaggtccctc   1620
tttggctagg cttctgggga tactataact acttaaaaca aacaagaact gaagctatat   1680
ttccactaca catgtttgta gtgcaaagca aatacattca aacacaacaa acagaaacac   1740
ctaacaattt ttgggcattt atagacaaca gctttataca gggcaaaaac ccatgggact   1800
cagttattac ttactcagaa caaaagctat ggtttcctac agttgcatgg caactaaaaa   1860
ccataaatgc tatttgtgaa agtggaccat atgtacctaa actagacaat caaacatata   1920
gtacctggga actagcaact cattactcat ttcactttaa atggggtggt ccacagatat   1980
cagaccaacc agttgaagac ccaggaaaca aaaacaaata tgatgtgccc gatacaatca   2040
aagaagcatt acaaattgtt aacccagcaa aaaacattgc tgccacgatg ttccatgact   2100
gggactacag acggggttgc attacatcaa cagctattaa aagaatgcaa caaaacctcc   2160
caactgattc atctctcgaa tctgattcag actcagaacc agcacccaag aaaaaaagac   2220
tactaccagt cctccacgac ccacaaaaga aaacggaaaa gatcaaccaa tgtctcctct   2280
ctctctgcga agaaagtaca tgccaggagc aggaaacgga ggaaaacatc ctcaagctca   2340
tccagcagca gcagcagcag cagcagaaac tcaagcacaa cctcttagta ctaatcaagg   2400
acttaaaagt gaaacaaaga ttattacaac tacaaacggg ggtactagaa taacccttac   2460
cagatttaaa ccaggatttg agcaagaaac tgaaaaagag ttagcacaag catttaacag   2520
accccctaga ctgttcaaag aagataaacc cttttacccc tggctaccca gatttacacc   2580
ccttgtaaac tttcacctta attttaaagg ctaggcctac actgctcact tagtggtgta   2640
tgtttattaa agtttgcacc ccagaaaaat tgtaaaataa aaaaaaaaaa aaaaaataaa   2700
aaattgcaaa aattcggcgc tcgcgcgcgc tgcgcgcgcg agcgccgtca cgcgccggcg   2760
ctcgcgcgcc gcgcgtatgt gctaacacac cacgcaccta gattggggtg cgcgcgtagc   2820
gcgcgcaccc caatgcgccc cgccctcgtt ccgacccgct tgcgcgggtc ggaccacttc   2880
gggctcgggg gggcgcgcct gcggcgctta tttactaaac agactccgag tcgccattgg   2940
gcccccccta agctccgccc ccctcatgaa tattcataaa ggaaaccaca aaattagaat   3000
```

-continued

```
tgccgaccac aaactgccat atgctaatta gttccccttt tacacagtaa aaaggggaag   3060

tggggggca gagccccccc acaccccccg cgggggggc agagcccccc ccgcaccccc   3120

cctacgtcac aggccacgcc cccgccgcca tcttgggtgc ggcagggcgg ggactaaaat   3180

ggcgggaccc aatcatttta tactttcact ttccaattaa aacccgccac gtcacacaaa   3240

ag                                                                 3242
```

```
<210> SEQ ID NO 62
<211> LENGTH: 101
<212> TYPE: PRT
<213> ORGANISM: Torque teno midi virus 1

<400> SEQUENCE: 62

Met Trp Met Ser Gly Ile Ala Asp Ser His Asp Ser Trp Cys Asp Cys
1               5                   10                  15

Asp Thr Pro Phe Ala His Leu Leu Ala Ser Ile Phe Pro Pro Gly His
            20                  25                  30

Thr Asp Arg Thr Arg Thr Ile Gln Glu Ile Leu Thr Arg Asp Phe Arg
        35                  40                  45

Lys Thr Cys Leu Ser Gly Gly Ala Asp Ala Thr Asn Ser Gly Met Ala
    50                  55                  60

Glu Thr Ile Glu Glu Lys Arg Glu Asp Phe Gln Lys Glu Glu Lys Glu
65                  70                  75                  80

Asp Phe Thr Glu Glu Gln Asn Ile Glu Asp Leu Leu Ala Ala Val Ala
                85                  90                  95

Asp Ala Glu Gly Arg
            100


<210> SEQ ID NO 63
<211> LENGTH: 237
<212> TYPE: PRT
<213> ORGANISM: Torque teno midi virus 1

<400> SEQUENCE: 63

Met Trp Met Ser Gly Ile Ala Asp Ser His Asp Ser Trp Cys Asp Cys
1               5                   10                  15

Asp Thr Pro Phe Ala His Leu Leu Ala Ser Ile Phe Pro Pro Gly His
            20                  25                  30

Thr Asp Arg Thr Arg Thr Ile Gln Glu Ile Leu Thr Arg Asp Phe Arg
        35                  40                  45

Lys Thr Cys Leu Ser Gly Gly Ala Asp Ala Thr Asn Ser Gly Met Ala
    50                  55                  60

Glu Thr Ile Glu Glu Lys Arg Glu Asp Phe Gln Lys Glu Glu Lys Glu
65                  70                  75                  80

Asp Phe Thr Glu Glu Gln Asn Ile Glu Asp Leu Leu Ala Ala Val Ala
                85                  90                  95

Asp Ala Glu Gly Arg Tyr Gln Thr Asn Gln Leu Lys Thr Gln Glu Thr
            100                 105                 110

Lys Thr Asn Met Met Cys Pro Ile Gln Ser Lys Lys His Tyr Lys Leu
        115                 120                 125

Leu Thr Gln Gln Lys Thr Leu Leu Pro Arg Cys Ser Met Thr Gly Thr
    130                 135                 140

Thr Asp Gly Val Ala Leu His Gln Gln Leu Leu Lys Glu Cys Asn Lys
145                 150                 155                 160

Thr Ser Gln Leu Ile His Leu Ser Asn Leu Ile Gln Thr Gln Asn Gln
```

```
                165                 170                 175

His Pro Arg Lys Lys Asp Tyr Tyr Gln Ser Ser Thr Thr His Lys Arg
            180                 185                 190

Lys Arg Lys Arg Ser Thr Asn Val Ser Ser Leu Ser Ala Lys Lys Val
        195                 200                 205

His Ala Arg Ser Arg Lys Arg Arg Lys Thr Ser Ser Ser Ser Ser Ser
    210                 215                 220

Ser Ser Ser Ser Ser Ser Arg Asn Ser Ser Thr Thr Ser
225                 230                 235


<210> SEQ ID NO 64
<211> LENGTH: 239
<212> TYPE: PRT
<213> ORGANISM: Torque teno midi virus 1

<400> SEQUENCE: 64

Met Trp Met Ser Gly Ile Ala Asp Ser His Asp Ser Trp Cys Asp Cys
1               5                   10                  15

Asp Thr Pro Phe Ala His Leu Leu Ala Ser Ile Phe Pro Pro Gly His
            20                  25                  30

Thr Asp Arg Thr Arg Thr Ile Gln Glu Ile Leu Thr Arg Asp Phe Arg
        35                  40                  45

Lys Thr Cys Leu Ser Gly Gly Ala Asp Ala Thr Asn Ser Gly Met Ala
    50                  55                  60

Glu Thr Ile Glu Glu Lys Arg Glu Asp Phe Gln Lys Glu Glu Lys Glu
65                  70                  75                  80

Asp Phe Thr Glu Glu Gln Asn Ile Glu Asp Leu Leu Ala Ala Val Ala
                85                  90                  95

Asp Ala Glu Gly Arg Thr Ser Thr Gln Glu Lys Lys Thr Thr Thr Ser
            100                 105                 110

Pro Pro Arg Pro Thr Lys Glu Asn Gly Lys Asp Gln Pro Met Ser Pro
        115                 120                 125

Leu Ser Leu Arg Arg Lys Tyr Met Pro Gly Ala Gly Asn Gly Gly Lys
    130                 135                 140

His Pro Gln Ala His Pro Ala Ala Ala Ala Ala Ala Ala Glu Thr Gln
145                 150                 155                 160

Ala Gln Pro Leu Ser Thr Asn Gln Gly Leu Lys Ser Glu Thr Lys Ile
                165                 170                 175

Ile Thr Thr Thr Asn Gly Gly Thr Arg Ile Thr Leu Thr Arg Phe Lys
            180                 185                 190

Pro Gly Phe Glu Gln Glu Thr Glu Lys Glu Leu Ala Gln Ala Phe Asn
        195                 200                 205

Arg Pro Pro Arg Leu Phe Lys Glu Asp Lys Pro Phe Tyr Pro Trp Leu
    210                 215                 220

Pro Arg Phe Thr Pro Leu Val Asn Phe His Leu Asn Phe Lys Gly
225                 230                 235


<210> SEQ ID NO 65
<211> LENGTH: 673
<212> TYPE: PRT
<213> ORGANISM: Torque teno midi virus 1

<400> SEQUENCE: 65

Met Pro Phe Trp Trp Gly Arg Arg Asn Lys Phe Trp Tyr Gly Arg Asn
1               5                   10                  15

Tyr Arg Arg Lys Lys Arg Arg Phe Pro Lys Arg Arg Lys Arg Arg Phe
```

```
            20                  25                  30

Tyr Arg Arg Thr Lys Tyr Arg Arg Pro Ala Arg Arg Arg Arg Arg Arg
        35                  40                  45

Arg Arg Lys Val Arg Arg Lys Lys Lys Thr Leu Ile Val Arg Gln Trp
    50                  55                  60

Gln Pro Asp Ser Ile Val Leu Cys Lys Ile Lys Gly Tyr Asp Ser Ile
65                  70                  75                  80

Ile Trp Gly Ala Glu Gly Thr Gln Phe Gln Cys Ser Thr His Glu Met
                85                  90                  95

Tyr Glu Tyr Thr Arg Gln Lys Tyr Pro Gly Gly Gly Gly Phe Gly Val
            100                 105                 110

Gln Leu Tyr Ser Leu Glu Tyr Leu Tyr Asp Gln Trp Lys Leu Arg Asn
        115                 120                 125

Asn Ile Trp Thr Lys Thr Asn Gln Leu Lys Asp Leu Cys Arg Tyr Leu
    130                 135                 140

Lys Cys Val Met Thr Phe Tyr Arg His Gln His Ile Asp Phe Val Ile
145                 150                 155                 160

Val Tyr Glu Arg Gln Pro Pro Phe Glu Ile Asp Lys Leu Thr Tyr Met
                165                 170                 175

Lys Tyr His Pro Tyr Met Leu Leu Gln Arg Lys His Lys Ile Ile Leu
            180                 185                 190

Pro Ser Gln Thr Thr Asn Pro Arg Gly Lys Leu Lys Lys Lys Lys Thr
        195                 200                 205

Ile Lys Pro Pro Lys Gln Met Leu Ser Lys Trp Phe Phe Gln Gln Gln
    210                 215                 220

Phe Ala Lys Tyr Asp Leu Leu Leu Ile Ala Ala Ala Ala Cys Ser Leu
225                 230                 235                 240

Arg Tyr Pro Arg Ile Gly Cys Cys Asn Glu Asn Arg Met Ile Thr Leu
                245                 250                 255

Tyr Cys Leu Asn Thr Lys Phe Tyr Gln Asp Thr Glu Trp Gly Thr Thr
            260                 265                 270

Lys Gln Ala Pro His Tyr Phe Lys Pro Tyr Ala Thr Ile Asn Lys Ser
        275                 280                 285

Met Ile Phe Val Ser Asn Tyr Gly Gly Lys Lys Thr Glu Tyr Asn Ile
    290                 295                 300

Gly Gln Trp Ile Glu Thr Asp Ile Pro Gly Glu Gly Asn Leu Ala Arg
305                 310                 315                 320

Tyr Tyr Arg Ser Ile Ser Lys Glu Gly Gly Tyr Phe Ser Pro Lys Ile
                325                 330                 335

Leu Gln Ala Tyr Gln Thr Lys Val Lys Ser Val Asp Tyr Lys Pro Leu
            340                 345                 350

Pro Ile Val Leu Gly Arg Tyr Asn Pro Ala Ile Asp Asp Gly Lys Gly
        355                 360                 365

Asn Lys Ile Tyr Leu Gln Thr Ile Met Asn Gly His Trp Gly Leu Pro
    370                 375                 380

Gln Lys Thr Pro Asp Tyr Ile Ile Glu Glu Val Pro Leu Trp Leu Gly
385                 390                 395                 400

Phe Trp Gly Tyr Tyr Asn Tyr Leu Lys Gln Thr Arg Thr Glu Ala Ile
                405                 410                 415

Phe Pro Leu His Met Phe Val Val Gln Ser Lys Tyr Ile Gln Thr Gln
            420                 425                 430

Gln Thr Glu Thr Pro Asn Asn Phe Trp Ala Phe Ile Asp Asn Ser Phe
        435                 440                 445
```

```
Ile Gln Gly Lys Asn Pro Trp Asp Ser Val Ile Thr Tyr Ser Glu Gln
    450                 455                 460

Lys Leu Trp Phe Pro Thr Val Ala Trp Gln Leu Lys Thr Ile Asn Ala
465                 470                 475                 480

Ile Cys Glu Ser Gly Pro Tyr Val Pro Lys Leu Asp Asn Gln Thr Tyr
                485                 490                 495

Ser Thr Trp Glu Leu Ala Thr His Tyr Ser Phe His Phe Lys Trp Gly
            500                 505                 510

Gly Pro Gln Ile Ser Asp Gln Pro Val Glu Asp Pro Gly Asn Lys Asn
        515                 520                 525

Lys Tyr Asp Val Pro Asp Thr Ile Lys Glu Ala Leu Gln Ile Val Asn
    530                 535                 540

Pro Ala Lys Asn Ile Ala Ala Thr Met Phe His Asp Trp Asp Tyr Arg
545                 550                 555                 560

Arg Gly Cys Ile Thr Ser Thr Ala Ile Lys Arg Met Gln Gln Asn Leu
                565                 570                 575

Pro Thr Asp Ser Ser Leu Glu Ser Asp Ser Asp Ser Glu Pro Ala Pro
            580                 585                 590

Lys Lys Lys Arg Leu Leu Pro Val Leu His Asp Pro Gln Lys Lys Thr
        595                 600                 605

Glu Lys Ile Asn Gln Cys Leu Leu Ser Leu Cys Glu Glu Ser Thr Cys
    610                 615                 620

Gln Glu Gln Glu Thr Glu Glu Asn Ile Leu Lys Leu Ile Gln Gln Gln
625                 630                 635                 640

Gln Gln Gln Gln Gln Lys Leu Lys His Asn Leu Leu Val Leu Ile Lys
                645                 650                 655

Asp Leu Lys Val Lys Gln Arg Leu Leu Gln Leu Gln Thr Gly Val Leu
            660                 665                 670

Glu


<210> SEQ ID NO 66
<211> LENGTH: 209
<212> TYPE: PRT
<213> ORGANISM: Torque teno midi virus 1

<400> SEQUENCE: 66

Met Pro Phe Trp Trp Gly Arg Arg Asn Lys Phe Trp Tyr Gly Arg Asn
1               5                   10                  15

Tyr Arg Arg Lys Lys Arg Arg Phe Pro Lys Arg Arg Lys Arg Arg Phe
            20                  25                  30

Tyr Arg Arg Thr Lys Tyr Arg Arg Pro Ala Arg Arg Arg Arg Arg Arg
        35                  40                  45

Arg Arg Lys Ile Ser Asp Gln Pro Val Glu Asp Pro Gly Asn Lys Asn
    50                  55                  60

Lys Tyr Asp Val Pro Asp Thr Ile Lys Glu Ala Leu Gln Ile Val Asn
65                  70                  75                  80

Pro Ala Lys Asn Ile Ala Ala Thr Met Phe His Asp Trp Asp Tyr Arg
                85                  90                  95

Arg Gly Cys Ile Thr Ser Thr Ala Ile Lys Arg Met Gln Gln Asn Leu
            100                 105                 110

Pro Thr Asp Ser Ser Leu Glu Ser Asp Ser Asp Ser Glu Pro Ala Pro
        115                 120                 125

Lys Lys Lys Arg Leu Leu Pro Val Leu His Asp Pro Gln Lys Lys Thr
    130                 135                 140
```

```
Glu Lys Ile Asn Gln Cys Leu Leu Ser Leu Cys Glu Glu Ser Thr Cys
145                 150                 155                 160

Gln Glu Gln Glu Thr Glu Glu Asn Ile Leu Lys Leu Ile Gln Gln Gln
                165                 170                 175

Gln Gln Gln Gln Gln Lys Leu Lys His Asn Leu Leu Val Leu Ile Lys
            180                 185                 190

Asp Leu Lys Val Lys Gln Arg Leu Leu Gln Leu Gln Thr Gly Val Leu
        195                 200                 205

Glu


<210> SEQ ID NO 67
<211> LENGTH: 209
<212> TYPE: PRT
<213> ORGANISM: Torque teno midi virus 1

<400> SEQUENCE: 67

Met Pro Phe Trp Trp Gly Arg Arg Asn Lys Phe Trp Tyr Gly Arg Asn
1               5                   10                  15

Tyr Arg Arg Lys Lys Arg Arg Phe Pro Lys Arg Arg Lys Arg Arg Phe
            20                  25                  30

Tyr Arg Arg Thr Lys Tyr Arg Arg Pro Ala Arg Arg Arg Arg Arg Arg
        35                  40                  45

Arg Arg Lys Ile Ser Asp Gln Pro Val Glu Asp Pro Gly Asn Lys Asn
    50                  55                  60

Lys Tyr Asp Val Pro Asp Thr Ile Lys Glu Ala Leu Gln Ile Val Asn
65                  70                  75                  80

Pro Ala Lys Asn Ile Ala Ala Thr Met Phe His Asp Trp Asp Tyr Arg
                85                  90                  95

Arg Gly Cys Ile Thr Ser Thr Ala Ile Lys Arg Met Gln Gln Asn Leu
            100                 105                 110

Pro Thr Asp Ser Ser Leu Glu Ser Asp Ser Asp Ser Glu Pro Ala Pro
        115                 120                 125

Lys Lys Lys Arg Leu Leu Pro Val Leu His Asp Pro Gln Lys Lys Thr
    130                 135                 140

Glu Lys Ile Asn Gln Cys Leu Leu Ser Leu Cys Glu Glu Ser Thr Cys
145                 150                 155                 160

Gln Glu Gln Glu Thr Glu Glu Asn Ile Leu Lys Leu Ile Gln Gln Gln
                165                 170                 175

Gln Gln Gln Gln Gln Lys Leu Lys His Asn Leu Leu Val Leu Ile Lys
            180                 185                 190

Asp Leu Lys Val Lys Gln Arg Leu Leu Gln Leu Gln Thr Gly Val Leu
        195                 200                 205

Glu


<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (9)..(10)
```

<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (24)..(24)
<223> OTHER INFORMATION: Any amino acid

<400> SEQUENCE: 68

```
Leu Ile Xaa Arg Gln Trp Gln Pro Xaa Xaa Ile Arg Arg Cys Xaa Ile
1               5                   10                  15

Xaa Gly Tyr Xaa Pro Leu Ile Xaa Cys
            20                  25
```

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 69

```
Asn Tyr Xaa Xaa His Xaa Asp
1               5
```

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(5)
<223> OTHER INFORMATION: Any amino acid

<400> SEQUENCE: 70

```
Phe Ser Leu Xaa Xaa Leu Tyr Asp Glx
1               5
```

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:

<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 71

Asn Xaa Trp Thr Xaa Ser Asn Xaa Asp Leu Asp Leu Cys Arg Tyr Xaa
1 5 10 15

Gly Cys

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid

<400> SEQUENCE: 72

Thr Xaa Pro Ser Xaa His Pro Gly Xaa Met Xaa Leu Xaa Lys His Lys
1 5 10 15

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 73

Ile Pro Ser Leu Xaa Thr Arg Pro Xaa Gly
1 5 10

<210> SEQ ID NO 74
<211> LENGTH: 18
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 74

Arg Ile Xaa Pro Pro Xaa Leu Phe Xaa Asp Lys Trp Tyr Phe Gln Xaa
1               5                   10                  15

Asp Leu

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 75

Leu Leu Xaa Ile Xaa Ala Thr Ala
1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 76

Leu Xaa Xaa Pro Phe Xaa Ser Pro Xaa Thr Asp
1               5                   10

<210> SEQ ID NO 77
<211> LENGTH: 14

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 77

Tyr Asn Pro Xaa Xaa Asp Lys Gly Xaa Gly Asn Xaa Ile Trp
1 5 10

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Any amino acid

<400> SEQUENCE: 78

Cys Pro Tyr Thr Glx Pro Xaa Leu
1 5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 79

Xaa Phe Gly Xaa Gly Xaa Met Pro
1 5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 80

His Gln Xaa Glu Val Xaa Glu Xaa
1               5

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 81

Lys Tyr Xaa Phe Xaa Phe Xaa Trp Gly Gly Asn Pro
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 82

His Ser Trp Asp Xaa Arg Arg Gly
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 83

Ala Ile Lys Arg Xaa Gln Gln
1               5

<210> SEQ ID NO 84
<211> LENGTH: 8

<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 84

Xaa Gln Glx Gln Xaa Xaa Leu Arg
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (6)..(7)
<223> OTHER INFORMATION: Any amino acid

<400> SEQUENCE: 85

Pro Arg Xaa Xaa Gln Xaa Xaa Asp Pro
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Any amino acid

<400> SEQUENCE: 86

His Ser Trp Asp Xaa Arg Arg Gly
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Any amino acid

<400> SEQUENCE: 87

Ala Ile Lys Arg Xaa Gln Gln 1 5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(5)
<223> OTHER INFORMATION: Any amino acid

<400> SEQUENCE: 88

Gln Glx Gln Xaa Xaa Leu Arg
1 5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Any amino acid

<400> SEQUENCE: 89

Lys Xaa Lys Arg Arg Arg Arg
1 5

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 90

Pro Ile Xaa Ser Leu Xaa Xaa Tyr Lys Xaa Xaa Thr Arg
1 5 10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (10)..(10)

<223> OTHER INFORMATION: Any amino acid

<400> SEQUENCE: 91

Leu Ala Xaa Gln Leu Leu Lys Glu Cys Xaa Lys Asn
1 5 10

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Any amino acid

<400> SEQUENCE: 92

His Leu Asn Xaa Leu Ala
1 5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Asp Arg Pro Pro Arg
1 5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 94

Asp Xaa Pro Phe Tyr Pro Trp Xaa Pro
1 5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 95

Val Xaa Phe Lys Leu Xaa Phe
1 5

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 96

Trp Xaa Pro Pro Val His Asx Val Xaa Gly Ile Glu Arg Xaa Trp
1 5 10 15

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (6)..(6)
<223> OTHER INFORMATION: Any amino acid

<400> SEQUENCE: 97

Ala Lys Arg Lys Leu Xaa
1 5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 98

Pro Ser Ser Xaa Asp Trp Xaa Xaa Glu Tyr
1 5 10

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Asp Arg Pro Pro Arg
1 5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Pro Phe Tyr Pro Trp
1 5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 101

Asn Val Xaa Phe Lys Leu Xaa Phe
1 5

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Leu or Ile
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (9)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (22)..(22)
<223> OTHER INFORMATION: Leu or Ile

<400> SEQUENCE: 102

```
Xaa Xaa Xaa Xaa Xaa Trp Gln Pro Xaa Xaa Xaa Xaa Xaa Cys Xaa Ile
1               5                   10                  15

Xaa Gly Xaa Xaa Xaa Xaa Trp Gln Pro
            20                  25


<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid

<400> SEQUENCE: 103

Asn Xaa Trp Xaa Xaa Xaa Asn Xaa Xaa Xaa Xaa Leu Xaa Arg Tyr
1               5                   10                  15


<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 104

Tyr Asn Pro Xaa Xaa Asp Xaa Gly
1               5


<210> SEQ ID NO 105
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105

cgggtgccgk aggtgagttt acacaccgma gtcaaggggc aattcgggct crggactggc     60

cgggcyhtgg g                                                           71


<210> SEQ ID NO 106
<211> LENGTH: 71
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 106
cgggtgccgg aggtgagttt acacaccgca gtcaaggggc aattcgggct cgggactggc 60
cgggctwtgg g 71

<210> SEQ ID NO 107
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
cgggtgccgt aggtgagttt acacaccgca gtcaaggggc aattcgggct cgggactggc 60
cgggctatgg g 71

<210> SEQ ID NO 108
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
cgggtgccgg aggtgagttt acacaccgca gtcaaggggc aattcgggct cgggactggc 60
cgggccctgg g 71

<210> SEQ ID NO 109
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
cgggtgccgg aggtgagttt acacaccgca gtcaaggggc aattcgggct cgggactggc 60
cgggctttgg g 71

<210> SEQ ID NO 110
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
cgggtgccgg aggtgagttt acacaccgca gtcaaggggc aattcgggct cgggactggc 60
cgggctatgg g 71

<210> SEQ ID NO 111
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
cgggtgccgg aggtgagttt acacaccgaa gtcaaggggc aattcgggct caggactggc 60
cgggctttgg g 71

<210> SEQ ID NO 112
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
cgggtgccgg aggtgagttt acacaccgca gtcaaggggc aattcgggct cgggactggc 60
cgggcyhtgg g 71

<210> SEQ ID NO 113
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
cgggtgccgt aggtgagttt acacaccgca gtcaaggggc aattcgggct cgggactggc 60
cgggctatgg g 71

<210> SEQ ID NO 114
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
cgggtgccgg aggtgagttt acacaccgca gtcaaggggc aattcgggct cgggactggc 60
cgggcccggg 70

<210> SEQ ID NO 115
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
cgggtgccgg aggtgagttt acacaccgaa gtcaaggggc aattcgggct caggactggc 60
cgggctttgg g 71

<210> SEQ ID NO 116
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
cgggtgccgg aggtgagttt acacaccgca gtcaaggggc aattcgggct cgggaggccg 60
ggccatggg 69

<210> SEQ ID NO 117
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
cgggtgccgg aggtgagttt acacaccgca gtcaaggggc aattcgggct cgggactggc 60
cgggccccgg g 71

<210> SEQ ID NO 118
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
cgggtgccgg aggtgagttt acacaccgca gtcaaggggc aattcgggct cgggactggc 60
cgggctatgg g 71

<210> SEQ ID NO 119
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
cgggtgccga aggtgagttt acacaccgca gtcaaggggc aattcgggct cgggactggc 60
cgggctatgg g 71

<210> SEQ ID NO 120
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (10)..(10)
<223> OTHER INFORMATION: g, c, or absent
<220> FEATURE:
<221> NAME/KEY: modified_base
<222> LOCATION: (12)..(12)
<223> OTHER INFORMATION: c or absent
<220> FEATURE:
<221> NAME/KEY: modified_base
<222> LOCATION: (30)..(30)
<223> OTHER INFORMATION: g or absent
<220> FEATURE:
<221> NAME/KEY: modified_base
<222> LOCATION: (31)..(31)
<223> OTHER INFORMATION: c or absent
<220> FEATURE:
<221> NAME/KEY: modified_base
<222> LOCATION: (32)..(32)
<223> OTHER INFORMATION: c or absent
<220> FEATURE:
<221> NAME/KEY: modified_base
<222> LOCATION: (34)..(34)
<223> OTHER INFORMATION: g, a, or absent
<220> FEATURE:
<221> NAME/KEY: modified_base
<222> LOCATION: (43)..(43)
<223> OTHER INFORMATION: a, g, t, or absent
<220> FEATURE:
<221> NAME/KEY: modified_base
<222> LOCATION: (44)..(44)
<223> OTHER INFORMATION: g, c, or absent
<220> FEATURE:
<221> NAME/KEY: modified_base
<222> LOCATION: (45)..(45)
<223> OTHER INFORMATION: g, c, or absent
<220> FEATURE:
<221> NAME/KEY: modified_base
<222> LOCATION: (46)..(46)
<223> OTHER INFORMATION: c, a, or absent
<220> FEATURE:
<221> NAME/KEY: modified_base
<222> LOCATION: (52)..(52)
<223> OTHER INFORMATION: g, t, or absent
<220> FEATURE:
<221> NAME/KEY: modified_base
<222> LOCATION: (53)..(53)
<223> OTHER INFORMATION: c or absent
<220> FEATURE:
<221> NAME/KEY: modified_base
<222> LOCATION: (54)..(54)
<223> OTHER INFORMATION: g, c, or absent
<220> FEATURE:
<221> NAME/KEY: modified_base
<222> LOCATION: (70)..(70)
<223> OTHER INFORMATION: g or absent
<220> FEATURE:
<221> NAME/KEY: modified_base
<222> LOCATION: (71)..(71)
<223> OTHER INFORMATION: c or absent
<220> FEATURE:
<221> NAME/KEY: modified_base
<222> LOCATION: (89)..(89)
<223> OTHER INFORMATION: c, t, or absent
<220> FEATURE:
<221> NAME/KEY: modified_base
<222> LOCATION: (90)..(90)
<223> OTHER INFORMATION: g, c, a, or absent
<220> FEATURE:
<221> NAME/KEY: modified_base
<222> LOCATION: (103)..(103)
<223> OTHER INFORMATION: c or absent

<400> SEQUENCE: 120
cggcggsggn gnsscgcgct dcgcgcgcsn nncnsyrggg grnnnnmwgc snnncccccc 60
cscgcgcatn ngcrcgggkc cccccccnn sggggggctc cgncccccg gcccccc 117

<210> SEQ ID NO 121
<211> LENGTH: 169
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (40)..(42)
<223> OTHER INFORMATION: a, c, t, g, unknown or other
<220> FEATURE:
<221> NAME/KEY: modified_base
<222> LOCATION: (53)..(56)
<223> OTHER INFORMATION: a, c, t, g, unknown or other
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (64)..(64)
<223> OTHER INFORMATION: a, c, t, g, unknown or other
<220> FEATURE:
<221> NAME/KEY: modified_base
<222> LOCATION: (97)..(98)
<223> OTHER INFORMATION: a, c, t, g, unknown or other

<400> SEQUENCE: 121
gccgccgcgg cggcggsggn gnsgcgcgct dcgcgcgcsn nncrccrggg ggnnnncwgc 60
sncncccccc cccgcgcatg cgcgggkccc ccccccnncg gggggctccg ccccccggcc 120
cccccccgtg ctaaacccac cgcgcatgcg cgaccacgcc cccgccgcc 169

<210> SEQ ID NO 122
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (40)..(42)
<223> OTHER INFORMATION: a, c, t, g, unknown or other
<220> FEATURE:
<221> NAME/KEY: modified_base
<222> LOCATION: (53)..(56)
<223> OTHER INFORMATION: a, c, t, g, unknown or other
<220> FEATURE:
<221> NAME/KEY: modified_base
<222> LOCATION: (62)..(62)
<223> OTHER INFORMATION: a, c, t, g, unknown or other
<220> FEATURE:
<221> NAME/KEY: modified_base
<222> LOCATION: (64)..(64)
<223> OTHER INFORMATION: a, c, t, g, unknown or other

<400> SEQUENCE: 122
gccgccgcgg cggcggsggn gnsgcgcgct dcgcgcgcsn nncrccrggg ggnnnncwgc 60 sncnccccccc cccgcgcat 79

<210> SEQ ID NO 123
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (18)..(19)
<223> OTHER INFORMATION: a, c, t, g, unknown or other

<400> SEQUENCE: 123
gcgcgggkcc cccccccnnc gggggctcc g 31

<210> SEQ ID NO 124

<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
ccccccggcc cccccccgtg ctaaacccac cgcgcatgcg cgaccacgcc cccgccgcc 59

<210> SEQ ID NO 125
<211> LENGTH: 156
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125
gcggcggggg ggcggccgcg ttcgcgcgcc gcccaccagg gggtgctgcg cgcccccccc 60
cgcgcatgcg cggggccccc ccccgggggg gctccgcccc cccggccccc ccccgtgcta 120
aacccaccgc gcatgcgcga ccacgccccc gccgcc 156

<210> SEQ ID NO 126
<211> LENGTH: 7
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126 gcggcgg 7

<210> SEQ ID NO 127
<211> LENGTH: 7
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127 gggggcg 7

<210> SEQ ID NO 128
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128 gccgcg 6

<210> SEQ ID NO 129
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
ttcgcgcgcc gcccaccagg gggtg 25

<210> SEQ ID NO 130
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130 ctgcg 5

<210> SEQ ID NO 131
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
cgcccccccc cgcgcat 17

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132
gcgcggggcc ccccccc 17

<210> SEQ ID NO 133
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133 ggggggctc cgcccccccg gccccccccc gtgctaaacc caccgcgcat gcgcgaccac 60
gcccccgccg cc 72

<210> SEQ ID NO 134
<211> LENGTH: 115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134
cggcggcggc ggcgcgcgcg ctgcgcgcgc gcgccggggg ggcgccagcg cccccccccc 60
cgcgcatgca cgggtccccc cccccacggg gggctccgcc ccccggcccc ccccc 115

<210> SEQ ID NO 135
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
cggcggcggc ggcg 14

<210> SEQ ID NO 136
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 136
cgcgcgctgc gcgcgcg 17

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 137
cgccgggggg gcgccagcg 19

<210> SEQ ID NO 138
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 138
cccccccccc cgcgcat 17

<210> SEQ ID NO 139
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 139
gcacgggtcc cccccccac gggggctcc g 31

<210> SEQ ID NO 140
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
ccccccggcc ccccccc 17

<210> SEQ ID NO 141
<211> LENGTH: 121
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 141
ccgtcggcgg gggggccgcg cgctgcgcgc gcggcccccg ggggaggcac agcctccccc 60
ccccgcgcgc atgcgcgcgg gtcccccccc ctccgggggg ctccgccccc cggccccccc 120
c 121

<210> SEQ ID NO 142
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
ccgtcggcgg gggggccgcg cgctgcgcgc gcggccc 37

<210> SEQ ID NO 143
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
ccgggggagg cacagcctcc cccccccgcg cgcatgcgcg cgggtccccc cccctccggg 60
gggctccgcc ccccggcccc cccc 84

<210> SEQ ID NO 144
<211> LENGTH: 104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 144
cggcggcggc gcgcgcgcta cgcgcgcgcg ccgggggggct gccgcccccc ccccgcgcat 60
gcgcggggcc cccccccgcg gggggctccg ccccccggcc cccc 104

<210> SEQ ID NO 145
<211> LENGTH: 11
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
cggcggcggc g 11

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
cgcgcgctac gcgcgcg 17

<210> SEQ ID NO 147
<211> LENGTH: 10

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
cgccgggggg 10

<210> SEQ ID NO 148
<211> LENGTH: 7
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148 ctgccgc 7

<210> SEQ ID NO 149
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149
cccccccccg cgcat 15

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
gcgcggggcc ccccccc 17

<210> SEQ ID NO 151
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
gcggggggct ccg 13

<210> SEQ ID NO 152
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
ccccccggcc cccc 14

<210> SEQ ID NO 153
<211> LENGTH: 122
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 153
gccgccgcgg cggcgggggg cggcgcgctg cgcgcgccgc ccagtagggg gagccatgcg     60
cccccccccg cgcatgcgcg gggccccccc ccgcgggggg ctccgccccc cggccccccc    120
cg                                                                   122

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gccgccgcgg cggcggggg                                                  19

<210> SEQ ID NO 155
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gcggcgcgct gcgcgcgccg cccagtaggg ggagccatgc g                         41

<210> SEQ ID NO 156
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cccccccccg cgcat                                                      15

<210> SEQ ID NO 157
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gcgcggggcc ccccccc                                                    17

<210> SEQ ID NO 158
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gcggggggct ccg                                                        13

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
ccccccggcc cccccg 17

<210> SEQ ID NO 160
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 160
cgcgctgcgc gcgccgccca gtagggggag ccatgc 36

<210> SEQ ID NO 161
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
ccgccatctt aagtagttga ggcggacggt ggcgtgagtt caaaggtcac catcagccac 60
acctactcaa aatggtgg 78

<210> SEQ ID NO 162
<211> LENGTH: 172
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162
cttaagtagt tgaggcggac ggtggcgtga gttcaaaggt caccatcagc cacacctact 60
caaaatggtg gacaatttct tccgggtcaa aggttacagc cgccatgtta aaacacgtga 120
cgtatgacgt cacggccgcc attttgtgac acaagatggc cgacttcctt cc 172

<210> SEQ ID NO 163
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
cgcgctgcgc gcgccgccca gtagggggag ccatgc 36

<210> SEQ ID NO 164
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
gcgctdcgcg cgcgcgccgg ggggctgcgc cccccc 36

<210> SEQ ID NO 165
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 165
gcgcttcgcg cgccgcccac tagggggcgt tgcgcg 36

<210> SEQ ID NO 166
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
gcgctgcgcg cgccgcccag tagggggcgc aatgcg 36

<210> SEQ ID NO 167
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
gcgctgcgcg cgcggccccc gggggaggca ttgcct 36

<210> SEQ ID NO 168
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
gcgctgcgcg cgcgcgccgg gggggcgcca gcgccc 36

<210> SEQ ID NO 169
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 169
gcgcttcgcg cgcgcgccgg ggggctccgc cccccc 36

<210> SEQ ID NO 170
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 170
gcgcttcgcg cgcgcgccgg ggggctgcgc cccccc 36

<210> SEQ ID NO 171
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
gcgctacgcg cgcgcgccgg ggggctgcgc cccccc 36

<210> SEQ ID NO 172
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
gcgctacgcg cgcgcgccgg ggggctctgc cccccc 36

<210> SEQ ID NO 173
<211> LENGTH: 680
<212> TYPE: PRT
<213> ORGANISM: Torque teno virus

<400> SEQUENCE: 173

```
Thr Ala Trp Trp Trp Gly Arg Trp Arg Arg Arg Trp Arg Arg Arg Arg
1               5                   10                  15

Pro Trp Arg Pro Arg Leu Arg Arg Arg Arg Ala Arg Arg Ala Phe Pro
            20                  25                  30

Arg Arg Arg Arg Arg Arg Phe Val Ser Arg Arg Trp Arg Arg Pro Tyr
        35                  40                  45

Arg Arg Arg Arg Arg Arg Gly Arg Arg Arg Arg Arg Arg Arg Arg Arg
    50                  55                  60

His Lys Pro Thr Leu Val Leu Arg Gln Trp Gln Pro Asp Val Ile Arg
65                  70                  75                  80

His Cys Lys Ile Thr Gly Arg Met Pro Leu Ile Ile Cys Gly Lys Gly
                85                  90                  95

Ser Thr Gln Phe Asn Tyr Ile Thr His Ala Asp Asp Ile Thr Pro Arg
            100                 105                 110

Gly Ala Ser Tyr Gly Gly Asn Phe Thr Asn Met Thr Phe Ser Leu Glu
        115                 120                 125

Ala Ile Tyr Glu Gln Phe Leu Tyr His Arg Asn Arg Trp Ser Ala Ser
    130                 135                 140

Asn His Asp Leu Glu Leu Cys Arg Tyr Lys Gly Thr Thr Leu Lys Leu
145                 150                 155                 160

Tyr Arg His Pro Asp Val Asp Tyr Ile Val Thr Tyr Ser Arg Thr Gly
                165                 170                 175

Pro Phe Glu Ile Ser His Met Thr Tyr Leu Ser Thr His Pro Leu Leu
            180                 185                 190

Met Leu Leu Asn Lys His His Ile Val Val Pro Ser Leu Lys Thr Lys
        195                 200                 205

Pro Arg Gly Arg Lys Ala Ile Lys Val Arg Ile Arg Pro Pro Lys Leu
    210                 215                 220
```

-continued

```
Met Asn Asn Lys Trp Tyr Phe Thr Arg Asp Phe Cys Asn Ile Gly Leu
225                 230                 235                 240

Phe Gln Leu Trp Ala Thr Gly Leu Glu Leu Arg Asn Pro Trp Leu Arg
                245                 250                 255

Met Ser Thr Leu Ser Pro Cys Ile Gly Phe Asn Val Leu Lys Asn Ser
            260                 265                 270

Ile Tyr Thr Asn Leu Ser Asn Leu Pro Gln His Arg Glu Asp Arg Leu
        275                 280                 285

Asn Ile Ile Asn Asn Thr Leu His Pro His Asp Ile Thr Gly Pro Asn
    290                 295                 300

Asn Lys Lys Trp Gln Tyr Thr Tyr Thr Lys Leu Met Ala Pro Ile Tyr
305                 310                 315                 320

Tyr Ser Ala Asn Arg Ala Ser Thr Tyr Asp Leu Leu Arg Glu Tyr Gly
                325                 330                 335

Leu Tyr Ser Pro Tyr Tyr Leu Asn Pro Thr Arg Ile Asn Leu Asp Trp
            340                 345                 350

Met Thr Pro Tyr Thr His Val Arg Tyr Asn Pro Leu Val Asp Lys Gly
        355                 360                 365

Phe Gly Asn Arg Ile Tyr Ile Gln Trp Cys Ser Glu Ala Asp Val Ser
    370                 375                 380

Tyr Asn Arg Thr Lys Ser Lys Cys Leu Leu Gln Asp Met Pro Leu Phe
385                 390                 395                 400

Phe Met Cys Tyr Gly Tyr Ile Asp Trp Ala Ile Lys Asn Thr Gly Val
                405                 410                 415

Ser Ser Leu Ala Arg Asp Ala Arg Ile Cys Ile Arg Cys Pro Tyr Thr
            420                 425                 430

Glu Pro Gln Leu Val Gly Ser Thr Glu Asp Ile Gly Phe Val Pro Ile
        435                 440                 445

Thr Glu Thr Phe Met Arg Gly Asp Met Pro Val Leu Ala Pro Tyr Ile
    450                 455                 460

Pro Leu Ser Trp Phe Cys Lys Trp Tyr Pro Asn Ile Ala His Gln Lys
465                 470                 475                 480

Glu Val Leu Glu Ala Ile Ile Ser Cys Ser Pro Phe Met Pro Arg Asp
                485                 490                 495

Gln Gly Met Asn Gly Trp Asp Ile Thr Ile Gly Tyr Lys Met Asp Phe
            500                 505                 510

Leu Trp Gly Gly Ser Pro Leu Pro Ser Gln Pro Ile Asp Asp Pro Cys
        515                 520                 525

Gln Gln Gly Thr His Pro Ile Pro Asp Pro Asp Lys His Pro Arg Leu
    530                 535                 540

Leu Gln Val Ser Asn Pro Lys Leu Leu Gly Pro Arg Thr Val Phe His
545                 550                 555                 560

Lys Trp Asp Ile Arg Arg Gly Gln Phe Ser Lys Arg Ser Ile Lys Arg
                565                 570                 575

Val Ser Glu Tyr Ser Ser Asp Asp Glu Ser Leu Ala Pro Gly Leu Pro
            580                 585                 590

Ser Lys Arg Asn Lys Leu Asp Ser Ala Phe Arg Gly Glu Asn Pro Glu
        595                 600                 605

Gln Lys Glu Cys Tyr Ser Leu Leu Lys Ala Leu Glu Glu Glu Glu Thr
    610                 615                 620

Pro Glu Glu Glu Glu Pro Ala Pro Gln Glu Lys Ala Gln Lys Glu Glu
625                 630                 635                 640

Leu Leu His Gln Leu Gln Leu Gln Arg Arg His Gln Arg Val Leu Arg
```

```
                645                 650                 655

Arg Gly Leu Lys Leu Val Phe Thr Asp Ile Leu Arg Leu Arg Gln Gly
            660                 665                 670

Val His Trp Asn Pro Glu Leu Thr
        675                 680


<210> SEQ ID NO 174
<211> LENGTH: 66
<212> TYPE: PRT
<213> ORGANISM: Torque teno virus

<400> SEQUENCE: 174

Thr Ala Trp Trp Trp Gly Arg Trp Arg Arg Arg Trp Arg Arg Arg Arg
1               5                   10                  15

Pro Trp Arg Pro Arg Leu Arg Arg Arg Arg Ala Arg Arg Ala Phe Pro
            20                  25                  30

Arg Arg Arg Arg Arg Arg Phe Val Ser Arg Arg Trp Arg Arg Pro Tyr
        35                  40                  45

Arg Arg Arg Arg Arg Arg Gly Arg Arg Arg Arg Arg Arg Arg Arg Arg
    50                  55                  60

His Lys
65


<210> SEQ ID NO 175
<211> LENGTH: 211
<212> TYPE: PRT
<213> ORGANISM: Torque teno virus

<400> SEQUENCE: 175

Pro Thr Leu Val Leu Arg Gln Trp Gln Pro Asp Val Ile Arg His Cys
1               5                   10                  15

Lys Ile Thr Gly Arg Met Pro Leu Ile Ile Cys Gly Lys Gly Ser Thr
            20                  25                  30

Gln Phe Asn Tyr Ile Thr His Ala Asp Asp Ile Thr Pro Arg Gly Ala
        35                  40                  45

Ser Tyr Gly Gly Asn Phe Thr Asn Met Thr Phe Ser Leu Glu Ala Ile
    50                  55                  60

Tyr Glu Gln Phe Leu Tyr His Arg Asn Arg Trp Ser Ala Ser Asn His
65                  70                  75                  80

Asp Leu Glu Leu Cys Arg Tyr Lys Gly Thr Thr Leu Lys Leu Tyr Arg
                85                  90                  95

His Pro Asp Val Asp Tyr Ile Val Thr Tyr Ser Arg Thr Gly Pro Phe
            100                 105                 110

Glu Ile Ser His Met Thr Tyr Leu Ser Thr His Pro Leu Leu Met Leu
        115                 120                 125

Leu Asn Lys His His Ile Val Val Pro Ser Leu Lys Thr Lys Pro Arg
    130                 135                 140

Gly Arg Lys Ala Ile Lys Val Arg Ile Arg Pro Pro Lys Leu Met Asn
145                 150                 155                 160

Asn Lys Trp Tyr Phe Thr Arg Asp Phe Cys Asn Ile Gly Leu Phe Gln
                165                 170                 175

Leu Trp Ala Thr Gly Leu Glu Leu Arg Asn Pro Trp Leu Arg Met Ser
            180                 185                 190

Thr Leu Ser Pro Cys Ile Gly Phe Asn Val Leu Lys Asn Ser Ile Tyr
        195                 200                 205

Thr Asn Leu
```

210

<210> SEQ ID NO 176
<211> LENGTH: 70
<212> TYPE: PRT
<213> ORGANISM: Torque teno virus

<400> SEQUENCE: 176

Ser Asn Leu Pro Gln His Arg Glu Asp Arg Leu Asn Ile Ile Asn Asn
1               5                   10                  15

Thr Leu His Pro His Asp Ile Thr Gly Pro Asn Asn Lys Lys Trp Gln
            20                  25                  30

Tyr Thr Tyr Thr Lys Leu Met Ala Pro Ile Tyr Tyr Ser Ala Asn Arg
        35                  40                  45

Ala Ser Thr Tyr Asp Leu Leu Arg Glu Tyr Gly Leu Tyr Ser Pro Tyr
    50                  55                  60

Tyr Leu Asn Pro Thr Arg
65                  70

<210> SEQ ID NO 177
<211> LENGTH: 166
<212> TYPE: PRT
<213> ORGANISM: Torque teno virus

<400> SEQUENCE: 177

Ile Asn Leu Asp Trp Met Thr Pro Tyr Thr His Val Arg Tyr Asn Pro
1               5                   10                  15

Leu Val Asp Lys Gly Phe Gly Asn Arg Ile Tyr Ile Gln Trp Cys Ser
            20                  25                  30

Glu Ala Asp Val Ser Tyr Asn Arg Thr Lys Ser Lys Cys Leu Leu Gln
        35                  40                  45

Asp Met Pro Leu Phe Phe Met Cys Tyr Gly Tyr Ile Asp Trp Ala Ile
    50                  55                  60

Lys Asn Thr Gly Val Ser Ser Leu Ala Arg Asp Ala Arg Ile Cys Ile
65                  70                  75                  80

Arg Cys Pro Tyr Thr Glu Pro Gln Leu Val Gly Ser Thr Glu Asp Ile
                85                  90                  95

Gly Phe Val Pro Ile Thr Glu Thr Phe Met Arg Gly Asp Met Pro Val
            100                 105                 110

Leu Ala Pro Tyr Ile Pro Leu Ser Trp Phe Cys Lys Trp Tyr Pro Asn
        115                 120                 125

Ile Ala His Gln Lys Glu Val Leu Glu Ala Ile Ile Ser Cys Ser Pro
    130                 135                 140

Phe Met Pro Arg Asp Gln Gly Met Asn Gly Trp Asp Ile Thr Ile Gly
145                 150                 155                 160

Tyr Lys Met Asp Phe Leu
                165

<210> SEQ ID NO 178
<211> LENGTH: 167
<212> TYPE: PRT
<213> ORGANISM: Torque teno virus

<400> SEQUENCE: 178

Trp Gly Gly Ser Pro Leu Pro Ser Gln Pro Ile Asp Asp Pro Cys Gln
1               5                   10                  15

Gln Gly Thr His Pro Ile Pro Asp Pro Asp Lys His Pro Arg Leu Leu
            20                  25                  30

-continued

Gln Val Ser Asn Pro Lys Leu Leu Gly Pro Arg Thr Val Phe His Lys
35 40 45

Trp Asp Ile Arg Arg Gly Gln Phe Ser Lys Arg Ser Ile Lys Arg Val
50 55 60

Ser Glu Tyr Ser Ser Asp Asp Glu Ser Leu Ala Pro Gly Leu Pro Ser
65 70 75 80

Lys Arg Asn Lys Leu Asp Ser Ala Phe Arg Gly Glu Asn Pro Glu Gln
85 90 95

Lys Glu Cys Tyr Ser Leu Leu Lys Ala Leu Glu Glu Glu Glu Thr Pro
100 105 110

Glu Glu Glu Glu Pro Ala Pro Gln Glu Lys Ala Gln Lys Glu Glu Leu
115 120 125

Leu His Gln Leu Gln Leu Gln Arg Arg His Gln Arg Val Leu Arg Arg
130 135 140

Gly Leu Lys Leu Val Phe Thr Asp Ile Leu Arg Leu Arg Gln Gly Val
145 150 155 160

His Trp Asn Pro Glu Leu Thr
165

<210> SEQ ID NO 179
<211> LENGTH: 747
<212> TYPE: PRT
<213> ORGANISM: Torque teno virus

<400> SEQUENCE: 179

Met Ala Tyr Trp Trp Gly Arg Arg Arg Arg Trp Arg Arg Trp Arg Arg
1 5 10 15

Arg Arg Arg Pro Leu Arg Arg Arg Arg Arg Trp Arg Arg Arg Arg Arg
20 25 30

Trp Pro Arg Arg Arg Arg Trp Arg Arg Arg Arg Arg Arg Ala Arg Pro
35 40 45

Ala Arg Arg Tyr Arg Arg Arg Arg Gly Arg Arg Arg Val Arg Arg Arg
50 55 60

Arg Arg Pro Gln Lys Leu Val Leu Thr Gln Trp Asn Pro Gln Thr Val
65 70 75 80

Arg Lys Cys Val Ile Arg Gly Phe Leu Pro Leu Phe Phe Cys Gly Gln
85 90 95

Gly Ala Tyr His Arg Asn Phe Thr Asp His Tyr Asp Asp Val Phe Pro
100 105 110

Lys Gly Pro Ser Gly Gly Gly His Gly Ser Met Val Phe Asn Leu Ser
115 120 125

Phe Leu Tyr Gln Glu Phe Lys Lys His His Asn Lys Trp Ser Arg Ser
130 135 140

Asn Leu Asp Phe Asp Leu Val Arg Tyr Lys Gly Thr Val Ile Lys Leu
145 150 155 160

Tyr Arg His Gln Asp Phe Asp Tyr Ile Val Trp Ile Ser Arg Thr Pro
165 170 175

Pro Phe Gln Glu Ser Leu Leu Thr Val Met Thr His Gln Pro Ser Val
180 185 190

Met Leu Gln Ala Lys Lys Cys Ile Ile Val Lys Ser Tyr Arg Thr His
195 200 205

Pro Gly Gly Lys Pro Tyr Val Thr Ala Lys Val Arg Pro Pro Arg Leu
210 215 220

Leu Thr Asp Lys Trp Tyr Phe Gln Ser Asp Phe Cys Asn Val Pro Leu

-continued

```
225                 230                 235                 240

Phe Ser Leu Gln Phe Ala Leu Ala Glu Leu Arg Phe Pro Ile Cys Ser
                245                 250                 255

Pro Gln Thr Asp Thr Asn Cys Ile Asn Phe Leu Val Leu Asp Asp Ile
            260                 265                 270

Tyr Tyr Lys Phe Leu Asp Asn Lys Pro Lys Gln Ser Ser Asp Pro Asn
        275                 280                 285

Asp Glu Asn Arg Ile Lys Phe Trp His Gly Leu Trp Ser Thr Met Arg
    290                 295                 300

Tyr Leu Asn Thr Thr Tyr Ile Asn Thr Leu Phe Pro Gly Thr Asp Ser
305                 310                 315                 320

Leu Val Ala Ala Lys Asp Thr Asp Asn Ser Val Asn Lys Tyr Pro Ser
                325                 330                 335

Thr Ala Thr Lys Gln Pro Tyr Lys Asp Ser Gln Tyr Met Gln Asn Ile
            340                 345                 350

Trp Asn Thr Ser Lys Ile His Ala Leu Tyr Thr Trp Val Ala Glu Thr
        355                 360                 365

Asn Tyr Lys Arg Leu Gln Ala Tyr Tyr Thr Gln Thr Tyr Gly Gly Tyr
    370                 375                 380

Gln Arg Gln Phe Phe Thr Gly Lys Gln Tyr Trp Asp Tyr Arg Val Gly
385                 390                 395                 400

Met Phe Ser Pro Ala Phe Leu Ser Pro Ser Arg Leu Asn Pro Gln Asn
                405                 410                 415

Pro Gly Ala Tyr Thr Glu Val Ser Tyr Asn Pro Trp Thr Asp Glu Gly
            420                 425                 430

Thr Gly Asn Val Val Cys Leu Gln Tyr Leu Thr Lys Glu Thr Ser Asp
        435                 440                 445

Tyr Lys Pro Gly Gly Gly Ser Lys Phe Cys Ile Glu Gly Val Pro Leu
    450                 455                 460

Trp Ala Ala Leu Val Gly Tyr Val Asp Met Cys Lys Lys Glu Gly Lys
465                 470                 475                 480

Asp Pro Gly Ile Arg Leu Asn Cys Leu Leu Leu Val Lys Cys Pro Tyr
                485                 490                 495

Thr Lys Pro Gln Leu Tyr Asp Lys Lys Asn Pro Glu Lys Leu Phe Val
            500                 505                 510

Pro Tyr Ser Tyr Asn Phe Gly His Gly Lys Met Pro Gly Gly Asp Lys
        515                 520                 525

Tyr Ile Pro Ile Glu Phe Lys Asp Arg Trp Tyr Pro Cys Leu Leu His
    530                 535                 540

Gln Glu Glu Trp Ile Glu Asp Ile Val Arg Ser Gly Pro Phe Val Pro
545                 550                 555                 560

Lys Asp Met Pro Ser Ser Val Thr Cys Met Met Arg Tyr Ser Ser Leu
                565                 570                 575

Phe Asn Trp Gly Gly Asn Ile Ile Gln Glu Gln Ala Val Glu Asp Pro
            580                 585                 590

Cys Lys Lys Gly Thr Phe Val Val Pro Gly Thr Ser Gly Ile Ala Arg
        595                 600                 605

Ile Leu Gln Val Ser Asn Pro Ala Lys Gln Thr Pro Thr Thr Thr Trp
    610                 615                 620

His Ser Trp Asp Trp Arg Arg Ser Leu Phe Thr Glu Thr Gly Leu Lys
625                 630                 635                 640

Arg Met Arg Glu Gln Gln Pro Tyr Asp Glu Leu Ser Tyr Thr Gly Pro
                645                 650                 655
```

Lys Lys Pro Lys Leu Ser Leu Pro Ala Gly Pro Ala Val Pro Gly Ala
660 665 670

Ala Val Ala Ser Ser Trp Trp Glu Thr Lys Gln Val Thr Ser Pro Asp
675 680 685

Val Ser Glu Thr Glu Thr Glu Ala Glu Ala His Gln Glu Glu Glu Thr
690 695 700

Glu Pro Glu Glu Gly Val Gln Leu Gln Gln Leu Trp Glu Gln Gln Leu
705 710 715 720

Leu Gln Lys Arg Gln Leu Gly Val Val Phe Gln Gln Leu Leu Arg Leu
725 730 735

Arg Gln Gly Ala Glu Ile His Pro Gly Leu Val
740 745

<210> SEQ ID NO 180
<211> LENGTH: 69
<212> TYPE: PRT
<213> ORGANISM: Torque teno virus

<400> SEQUENCE: 180

Met Ala Tyr Trp Trp Gly Arg Arg Arg Arg Trp Arg Arg Trp Arg Arg
1 5 10 15

Arg Arg Arg Pro Leu Arg Arg Arg Arg Arg Trp Arg Arg Arg Arg Arg
20 25 30

Trp Pro Arg Arg Arg Arg Trp Arg Arg Arg Arg Arg Arg Ala Arg Pro
35 40 45

Ala Arg Arg Tyr Arg Arg Arg Arg Gly Arg Arg Arg Val Arg Arg Arg
50 55 60

Arg Arg Pro Gln Lys
65

<210> SEQ ID NO 181
<211> LENGTH: 210
<212> TYPE: PRT
<213> ORGANISM: Torque teno virus

<400> SEQUENCE: 181

Leu Val Leu Thr Gln Trp Asn Pro Gln Thr Val Arg Lys Cys Val Ile
1 5 10 15

Arg Gly Phe Leu Pro Leu Phe Phe Cys Gly Gln Gly Ala Tyr His Arg
20 25 30

Asn Phe Thr Asp His Tyr Asp Asp Val Phe Pro Lys Gly Pro Ser Gly
35 40 45

Gly Gly His Gly Ser Met Val Phe Asn Leu Ser Phe Leu Tyr Gln Glu
50 55 60

Phe Lys Lys His His Asn Lys Trp Ser Arg Ser Asn Leu Asp Phe Asp
65 70 75 80

Leu Val Arg Tyr Lys Gly Thr Val Ile Lys Leu Tyr Arg His Gln Asp
85 90 95

Phe Asp Tyr Ile Val Trp Ile Ser Arg Thr Pro Pro Phe Gln Glu Ser
100 105 110

Leu Leu Thr Val Met Thr His Gln Pro Ser Val Met Leu Gln Ala Lys
115 120 125

Lys Cys Ile Ile Val Lys Ser Tyr Arg Thr His Pro Gly Gly Lys Pro
130 135 140

Tyr Val Thr Ala Lys Val Arg Pro Pro Arg Leu Leu Thr Asp Lys Trp
145 150 155 160

```
Tyr Phe Gln Ser Asp Phe Cys Asn Val Pro Leu Phe Ser Leu Gln Phe
                165                 170                 175

Ala Leu Ala Glu Leu Arg Phe Pro Ile Cys Ser Pro Gln Thr Asp Thr
            180                 185                 190

Asn Cys Ile Asn Phe Leu Val Leu Asp Asp Ile Tyr Tyr Lys Phe Leu
        195                 200                 205

Asp Asn
    210
```

<210> SEQ ID NO 182
<211> LENGTH: 132
<212> TYPE: PRT
<213> ORGANISM: Torque teno virus

<400> SEQUENCE: 182

```
Lys Pro Lys Gln Ser Ser Asp Pro Asn Asp Glu Asn Arg Ile Lys Phe
1               5                   10                  15

Trp His Gly Leu Trp Ser Thr Met Arg Tyr Leu Asn Thr Thr Tyr Ile
            20                  25                  30

Asn Thr Leu Phe Pro Gly Thr Asp Ser Leu Val Ala Ala Lys Asp Thr
        35                  40                  45

Asp Asn Ser Val Asn Lys Tyr Pro Ser Thr Ala Thr Lys Gln Pro Tyr
    50                  55                  60

Lys Asp Ser Gln Tyr Met Gln Asn Ile Trp Asn Thr Ser Lys Ile His
65                  70                  75                  80

Ala Leu Tyr Thr Trp Val Ala Glu Thr Asn Tyr Lys Arg Leu Gln Ala
                85                  90                  95

Tyr Tyr Thr Gln Thr Tyr Gly Gly Tyr Gln Arg Gln Phe Phe Thr Gly
            100                 105                 110

Lys Gln Tyr Trp Asp Tyr Arg Val Gly Met Phe Ser Pro Ala Phe Leu
        115                 120                 125

Ser Pro Ser Arg
    130
```

<210> SEQ ID NO 183
<211> LENGTH: 167
<212> TYPE: PRT
<213> ORGANISM: Torque teno virus

<400> SEQUENCE: 183

```
Leu Asn Pro Gln Asn Pro Gly Ala Tyr Thr Glu Val Ser Tyr Asn Pro
1               5                   10                  15

Trp Thr Asp Glu Gly Thr Gly Asn Val Val Cys Leu Gln Tyr Leu Thr
            20                  25                  30

Lys Glu Thr Ser Asp Tyr Lys Pro Gly Gly Gly Ser Lys Phe Cys Ile
        35                  40                  45

Glu Gly Val Pro Leu Trp Ala Ala Leu Val Gly Tyr Val Asp Met Cys
    50                  55                  60

Lys Lys Glu Gly Lys Asp Pro Gly Ile Arg Leu Asn Cys Leu Leu Leu
65                  70                  75                  80

Val Lys Cys Pro Tyr Thr Lys Pro Gln Leu Tyr Asp Lys Lys Asn Pro
                85                  90                  95

Glu Lys Leu Phe Val Pro Tyr Ser Tyr Asn Phe Gly His Gly Lys Met
            100                 105                 110

Pro Gly Gly Asp Lys Tyr Ile Pro Ile Glu Phe Lys Asp Arg Trp Tyr
        115                 120                 125
```

Pro Cys Leu Leu His Gln Glu Glu Trp Ile Glu Asp Ile Val Arg Ser
    130                 135                 140

Gly Pro Phe Val Pro Lys Asp Met Pro Ser Ser Val Thr Cys Met Met
145                 150                 155                 160

Arg Tyr Ser Ser Leu Phe Asn
                165

<210> SEQ ID NO 184
<211> LENGTH: 169
<212> TYPE: PRT
<213> ORGANISM: Torque teno virus

<400> SEQUENCE: 184

Trp Gly Gly Asn Ile Ile Gln Glu Gln Ala Val Glu Asp Pro Cys Lys
1               5                   10                  15

Lys Gly Thr Phe Val Val Pro Gly Thr Ser Gly Ile Ala Arg Ile Leu
            20                  25                  30

Gln Val Ser Asn Pro Ala Lys Gln Thr Pro Thr Thr Thr Trp His Ser
        35                  40                  45

Trp Asp Trp Arg Arg Ser Leu Phe Thr Glu Thr Gly Leu Lys Arg Met
    50                  55                  60

Arg Glu Gln Gln Pro Tyr Asp Glu Leu Ser Tyr Thr Gly Pro Lys Lys
65                  70                  75                  80

Pro Lys Leu Ser Leu Pro Ala Gly Pro Ala Val Pro Gly Ala Ala Val
                85                  90                  95

Ala Ser Ser Trp Trp Glu Thr Lys Gln Val Thr Ser Pro Asp Val Ser
            100                 105                 110

Glu Thr Glu Thr Glu Ala Glu Ala His Gln Glu Glu Glu Thr Glu Pro
        115                 120                 125

Glu Glu Gly Val Gln Leu Gln Gln Leu Trp Glu Gln Gln Leu Leu Gln
    130                 135                 140

Lys Arg Gln Leu Gly Val Val Phe Gln Gln Leu Leu Arg Leu Arg Gln
145                 150                 155                 160

Gly Ala Glu Ile His Pro Gly Leu Val
                165

<210> SEQ ID NO 185
<211> LENGTH: 743
<212> TYPE: PRT
<213> ORGANISM: Torque teno virus

<400> SEQUENCE: 185

Met Ala Trp Gly Trp Trp Lys Arg Arg Arg Arg Trp Trp Phe Arg Lys
1               5                   10                  15

Arg Trp Thr Arg Gly Arg Leu Arg Arg Arg Trp Pro Arg Ser Ala Arg
            20                  25                  30

Arg Arg Pro Arg Arg Arg Arg Val Arg Arg Arg Arg Arg Trp Arg Arg
        35                  40                  45

Gly Arg Arg Lys Thr Arg Thr Tyr Arg Arg Arg Arg Arg Phe Arg Arg
    50                  55                  60

Arg Gly Arg Lys Ala Lys Leu Ile Ile Lys Leu Trp Gln Pro Ala Val
65                  70                  75                  80

Ile Lys Arg Cys Arg Ile Lys Gly Tyr Ile Pro Leu Ile Ile Ser Gly
                85                  90                  95

Asn Gly Thr Phe Ala Thr Asn Phe Thr Ser His Ile Asn Asp Arg Ile
            100                 105                 110

```
Met Lys Gly Pro Phe Gly Gly Gly His Ser Thr Met Arg Phe Ser Leu
        115                 120                 125

Tyr Ile Leu Phe Glu Glu His Leu Arg His Met Asn Phe Trp Thr Arg
    130                 135                 140

Ser Asn Asp Asn Leu Glu Leu Thr Arg Tyr Leu Gly Ala Ser Val Lys
145                 150                 155                 160

Ile Tyr Arg His Pro Asp Gln Asp Phe Ile Val Ile Tyr Asn Arg Arg
                165                 170                 175

Thr Pro Leu Gly Gly Asn Ile Tyr Thr Ala Pro Ser Leu His Pro Gly
            180                 185                 190

Asn Ala Ile Leu Ala Lys His Lys Ile Leu Val Pro Ser Leu Gln Thr
        195                 200                 205

Arg Pro Lys Gly Arg Lys Ala Ile Arg Leu Arg Ile Ala Pro Pro Thr
    210                 215                 220

Leu Phe Thr Asp Lys Trp Tyr Phe Gln Lys Asp Ile Ala Asp Leu Thr
225                 230                 235                 240

Leu Phe Asn Ile Met Ala Val Glu Ala Asp Leu Arg Phe Pro Phe Cys
                245                 250                 255

Ser Pro Gln Thr Asp Asn Thr Cys Ile Ser Phe Gln Val Leu Ser Ser
            260                 265                 270

Val Tyr Asn Asn Tyr Leu Ser Ile Asn Thr Phe Asn Asn Asp Asn Ser
        275                 280                 285

Asp Ser Lys Leu Lys Glu Phe Leu Asn Lys Ala Phe Pro Thr Thr Gly
    290                 295                 300

Thr Lys Gly Thr Ser Leu Asn Ala Leu Asn Thr Phe Arg Thr Glu Gly
305                 310                 315                 320

Cys Ile Ser His Pro Gln Leu Lys Lys Pro Asn Pro Gln Ile Asn Lys
                325                 330                 335

Pro Leu Glu Ser Gln Tyr Phe Ala Pro Leu Asp Ala Leu Trp Gly Asp
            340                 345                 350

Pro Ile Tyr Tyr Asn Asp Leu Asn Glu Asn Lys Ser Leu Asn Asp Ile
        355                 360                 365

Ile Glu Lys Ile Leu Ile Lys Asn Met Ile Thr Tyr His Ala Lys Leu
    370                 375                 380

Arg Glu Phe Pro Asn Ser Tyr Gln Gly Asn Lys Ala Phe Cys His Leu
385                 390                 395                 400

Thr Gly Ile Tyr Ser Pro Pro Tyr Leu Asn Gln Gly Arg Ile Ser Pro
                405                 410                 415

Glu Ile Phe Gly Leu Tyr Thr Glu Ile Ile Tyr Asn Pro Tyr Thr Asp
            420                 425                 430

Lys Gly Thr Gly Asn Lys Val Trp Met Asp Pro Leu Thr Lys Glu Asn
        435                 440                 445

Asn Ile Tyr Lys Glu Gly Gln Ser Lys Cys Leu Leu Thr Asp Met Pro
    450                 455                 460

Leu Trp Thr Leu Leu Phe Gly Tyr Thr Asp Trp Cys Lys Lys Asp Thr
465                 470                 475                 480

Asn Asn Trp Asp Leu Pro Leu Asn Tyr Arg Leu Val Leu Ile Cys Pro
                485                 490                 495

Tyr Thr Phe Pro Lys Leu Tyr Asn Glu Lys Val Lys Asp Tyr Gly Tyr
            500                 505                 510

Ile Pro Tyr Ser Tyr Lys Phe Gly Ala Gly Gln Met Pro Asp Gly Ser
        515                 520                 525
```

```
Asn Tyr Ile Pro Phe Gln Phe Arg Ala Lys Trp Tyr Pro Thr Val Leu
    530                 535                 540

His Gln Gln Gln Val Met Glu Asp Ile Ser Arg Ser Gly Pro Phe Ala
545                 550                 555                 560

Pro Lys Val Glu Lys Pro Ser Thr Gln Leu Val Met Lys Tyr Cys Phe
                565                 570                 575

Asn Phe Asn Trp Gly Gly Asn Pro Ile Ile Glu Gln Ile Val Lys Asp
            580                 585                 590

Pro Ser Phe Gln Pro Thr Tyr Glu Ile Pro Gly Thr Gly Asn Ile Pro
        595                 600                 605

Arg Arg Ile Gln Val Ile Asp Pro Arg Val Leu Gly Pro His Tyr Ser
    610                 615                 620

Phe Arg Ser Trp Asp Met Arg Arg His Thr Phe Ser Arg Ala Ser Ile
625                 630                 635                 640

Lys Arg Val Ser Glu Gln Gln Glu Thr Ser Asp Leu Val Phe Ser Gly
                645                 650                 655

Pro Lys Lys Pro Arg Val Asp Ile Pro Lys Gln Glu Thr Gln Glu Glu
            660                 665                 670

Ser Ser His Ser Leu Gln Arg Glu Ser Arg Pro Trp Glu Thr Glu Glu
        675                 680                 685

Glu Ser Glu Thr Glu Ala Leu Ser Gln Glu Ser Gln Glu Val Pro Phe
    690                 695                 700

Gln Gln Gln Leu Gln Gln Gln Tyr Gln Glu Gln Leu Lys Leu Arg Gln
705                 710                 715                 720

Gly Ile Lys Val Leu Phe Glu Gln Leu Ile Arg Thr Gln Gln Gly Val
                725                 730                 735

His Val Asn Pro Cys Leu Arg
            740
```

<210> SEQ ID NO 186
<211> LENGTH: 68
<212> TYPE: PRT
<213> ORGANISM: Torque teno virus

<400> SEQUENCE: 186

```
Met Ala Trp Gly Trp Trp Lys Arg Arg Arg Arg Trp Trp Phe Arg Lys
1               5                   10                  15

Arg Trp Thr Arg Gly Arg Leu Arg Arg Arg Trp Pro Arg Ser Ala Arg
            20                  25                  30

Arg Arg Pro Arg Arg Arg Arg Val Arg Arg Arg Arg Arg Trp Arg Arg
        35                  40                  45

Gly Arg Arg Lys Thr Arg Thr Tyr Arg Arg Arg Arg Arg Phe Arg Arg
    50                  55                  60

Arg Gly Arg Lys
65
```

<210> SEQ ID NO 187
<211> LENGTH: 212
<212> TYPE: PRT
<213> ORGANISM: Torque teno virus

<400> SEQUENCE: 187

```
Ala Lys Leu Ile Ile Lys Leu Trp Gln Pro Ala Val Ile Lys Arg Cys
1               5                   10                  15

Arg Ile Lys Gly Tyr Ile Pro Leu Ile Ile Ser Gly Asn Gly Thr Phe
            20                  25                  30
```

```
Ala Thr Asn Phe Thr Ser His Ile Asn Asp Arg Ile Met Lys Gly Pro
        35                  40                  45

Phe Gly Gly Gly His Ser Thr Met Arg Phe Ser Leu Tyr Ile Leu Phe
    50                  55                  60

Glu Glu His Leu Arg His Met Asn Phe Trp Thr Arg Ser Asn Asp Asn
65                  70                  75                  80

Leu Glu Leu Thr Arg Tyr Leu Gly Ala Ser Val Lys Ile Tyr Arg His
                85                  90                  95

Pro Asp Gln Asp Phe Ile Val Ile Tyr Asn Arg Arg Thr Pro Leu Gly
            100                 105                 110

Gly Asn Ile Tyr Thr Ala Pro Ser Leu His Pro Gly Asn Ala Ile Leu
        115                 120                 125

Ala Lys His Lys Ile Leu Val Pro Ser Leu Gln Thr Arg Pro Lys Gly
    130                 135                 140

Arg Lys Ala Ile Arg Leu Arg Ile Ala Pro Pro Thr Leu Phe Thr Asp
145                 150                 155                 160

Lys Trp Tyr Phe Gln Lys Asp Ile Ala Asp Leu Thr Leu Phe Asn Ile
                165                 170                 175

Met Ala Val Glu Ala Asp Leu Arg Phe Pro Phe Cys Ser Pro Gln Thr
            180                 185                 190

Asp Asn Thr Cys Ile Ser Phe Gln Val Leu Ser Ser Val Tyr Asn Asn
        195                 200                 205

Tyr Leu Ser Ile
    210
```

<210> SEQ ID NO 188
<211> LENGTH: 133
<212> TYPE: PRT
<213> ORGANISM: Torque teno virus

<400> SEQUENCE: 188

```
Asn Thr Phe Asn Asn Asp Asn Ser Asp Ser Lys Leu Lys Glu Phe Leu
1               5                   10                  15

Asn Lys Ala Phe Pro Thr Thr Gly Thr Lys Gly Thr Ser Leu Asn Ala
            20                  25                  30

Leu Asn Thr Phe Arg Thr Glu Gly Cys Ile Ser His Pro Gln Leu Lys
        35                  40                  45

Lys Pro Asn Pro Gln Ile Asn Lys Pro Leu Glu Ser Gln Tyr Phe Ala
    50                  55                  60

Pro Leu Asp Ala Leu Trp Gly Asp Pro Ile Tyr Tyr Asn Asp Leu Asn
65                  70                  75                  80

Glu Asn Lys Ser Leu Asn Asp Ile Ile Glu Lys Ile Leu Ile Lys Asn
                85                  90                  95

Met Ile Thr Tyr His Ala Lys Leu Arg Glu Phe Pro Asn Ser Tyr Gln
            100                 105                 110

Gly Asn Lys Ala Phe Cys His Leu Thr Gly Ile Tyr Ser Pro Pro Tyr
        115                 120                 125

Leu Asn Gln Gly Arg
    130
```

<210> SEQ ID NO 189
<211> LENGTH: 166
<212> TYPE: PRT
<213> ORGANISM: Torque teno virus

<400> SEQUENCE: 189

-continued

```
Ile Ser Pro Glu Ile Phe Gly Leu Tyr Thr Glu Ile Ile Tyr Asn Pro
1               5                   10                  15

Tyr Thr Asp Lys Gly Thr Gly Asn Lys Val Trp Met Asp Pro Leu Thr
            20                  25                  30

Lys Glu Asn Asn Ile Tyr Lys Glu Gly Gln Ser Lys Cys Leu Leu Thr
        35                  40                  45

Asp Met Pro Leu Trp Thr Leu Leu Phe Gly Tyr Thr Asp Trp Cys Lys
    50                  55                  60

Lys Asp Thr Asn Asn Trp Asp Leu Pro Leu Asn Tyr Arg Leu Val Leu
65                  70                  75                  80

Ile Cys Pro Tyr Thr Phe Pro Lys Leu Tyr Asn Glu Lys Val Lys Asp
                85                  90                  95

Tyr Gly Tyr Ile Pro Tyr Ser Tyr Lys Phe Gly Ala Gly Gln Met Pro
            100                 105                 110

Asp Gly Ser Asn Tyr Ile Pro Phe Gln Phe Arg Ala Lys Trp Tyr Pro
        115                 120                 125

Thr Val Leu His Gln Gln Gln Val Met Glu Asp Ile Ser Arg Ser Gly
    130                 135                 140

Pro Phe Ala Pro Lys Val Glu Lys Pro Ser Thr Gln Leu Val Met Lys
145                 150                 155                 160

Tyr Cys Phe Asn Phe Asn
                165
```

<210> SEQ ID NO 190
<211> LENGTH: 164
<212> TYPE: PRT
<213> ORGANISM: Torque teno virus

<400> SEQUENCE: 190

```
Trp Gly Gly Asn Pro Ile Ile Glu Gln Ile Val Lys Asp Pro Ser Phe
1               5                   10                  15

Gln Pro Thr Tyr Glu Ile Pro Gly Thr Gly Asn Ile Pro Arg Arg Ile
            20                  25                  30

Gln Val Ile Asp Pro Arg Val Leu Gly Pro His Tyr Ser Phe Arg Ser
        35                  40                  45

Trp Asp Met Arg Arg His Thr Phe Ser Arg Ala Ser Ile Lys Arg Val
    50                  55                  60

Ser Glu Gln Gln Glu Thr Ser Asp Leu Val Phe Ser Gly Pro Lys Lys
65                  70                  75                  80

Pro Arg Val Asp Ile Pro Lys Gln Glu Thr Gln Glu Glu Ser Ser His
                85                  90                  95

Ser Leu Gln Arg Glu Ser Arg Pro Trp Glu Thr Glu Glu Glu Ser Glu
            100                 105                 110

Thr Glu Ala Leu Ser Gln Glu Ser Gln Glu Val Pro Phe Gln Gln Gln
        115                 120                 125

Leu Gln Gln Gln Tyr Gln Glu Gln Leu Lys Leu Arg Gln Gly Ile Lys
    130                 135                 140

Val Leu Phe Glu Gln Leu Ile Arg Thr Gln Gln Gly Val His Val Asn
145                 150                 155                 160

Pro Cys Leu Arg
```

<210> SEQ ID NO 191
<211> LENGTH: 780
<212> TYPE: PRT
<213> ORGANISM: Torque teno virus

<400> SEQUENCE: 191

```
Met Ala Trp Trp Gly Trp Arg Arg Arg Trp Trp Arg Pro Lys Arg Arg
1               5                   10                  15

Trp Arg Trp Arg Arg Ala Arg Arg Arg Arg Arg Val Pro Ala Arg Arg
            20                  25                  30

Pro Arg Arg Ala Phe Arg Arg Tyr Arg Thr Arg Thr Val Arg Arg Arg
        35                  40                  45

Arg Arg Gly Arg Arg Arg Gly Tyr Arg Arg Arg Tyr Arg Leu Arg Arg
    50                  55                  60

Tyr Ala Arg Arg Arg Phe Arg Arg Lys Lys Ile Val Leu Thr Gln Trp
65                  70                  75                  80

Asn Pro Gln Thr Thr Arg Lys Cys Ile Ile Arg Gly Met Met Pro Val
                85                  90                  95

Leu Trp Ala Gly Met Gly Thr Gly Gly Arg Asn Tyr Ala Val Arg Ser
            100                 105                 110

Asp Asp Tyr Val Val Asn Lys Gly Phe Gly Gly Ser Phe Ala Thr Glu
        115                 120                 125

Thr Phe Ser Leu Lys Val Leu Tyr Asp Gln Phe Gln Arg Gly Phe Asn
    130                 135                 140

Arg Trp Ser His Thr Asn Glu Asp Leu Asp Leu Ala Arg Tyr Arg Gly
145                 150                 155                 160

Cys Arg Trp Thr Phe Tyr Arg His Lys Asp Thr Asp Phe Ile Val Tyr
                165                 170                 175

Phe Thr Asn Asn Pro Pro Met Lys Thr Asn Gln Phe Ser Ala Pro Leu
            180                 185                 190

Thr Thr Pro Gly Met Leu Met Arg Ser Lys Tyr Lys Val Leu Ile Pro
        195                 200                 205

Ser Phe Gln Thr Arg Pro Lys Gly Arg Lys Thr Val Thr Val Lys Ile
    210                 215                 220

Arg Pro Pro Lys Leu Phe Gln Asp Lys Trp Tyr Thr Gln Gln Asp Leu
225                 230                 235                 240

Cys Ser Val Pro Leu Val Gln Leu Asn Val Thr Ala Ala Asp Phe Thr
                245                 250                 255

His Pro Phe Gly Ser Pro Leu Thr Glu Thr Pro Cys Val Glu Phe Gln
            260                 265                 270

Val Leu Gly Asp Leu Tyr Asn Thr Cys Leu Asn Ile Asp Leu Pro Gln
        275                 280                 285

Phe Ser Glu Leu Gly Glu Ile Thr Ser Ala Tyr Ser Lys Pro Asn Ser
    290                 295                 300

Asn Asn Leu Lys Glu Leu Tyr Lys Glu Leu Phe Thr Lys Ala Thr Ser
305                 310                 315                 320

Gly His Tyr Trp Gln Thr Phe Ile Thr Asn Ser Met Val Arg Ala His
                325                 330                 335

Ile Asp Ala Asp Lys Ala Lys Glu Ala Gln Arg Ala Ser Thr Thr Pro
            340                 345                 350

Ser Tyr Asn Asn Asp Pro Phe Pro Thr Ile Pro Val Lys Ser Glu Phe
        355                 360                 365

Ala Gln Trp Lys Lys Lys Phe Thr Asp Thr Arg Asp Ser Pro Phe Leu
    370                 375                 380

Phe Ala Thr Tyr His Pro Glu Ala Ile Lys Asp Thr Ile Met Lys Met
385                 390                 395                 400

Arg Glu Asn Asn Phe Lys Leu Glu Thr Gly Pro Asn Asp Lys Tyr Gly
                405                 410                 415
```

```
Asp Tyr Thr Ala Gln Tyr Gln Gly Asn Thr His Met Leu Asp Tyr Tyr
            420                 425                 430

Leu Gly Phe Tyr Ser Pro Ile Phe Leu Ser Asp Gly Arg Ser Asn Val
        435                 440                 445

Glu Phe Phe Thr Ala Tyr Arg Asp Ile Val Tyr Asn Pro Phe Leu Asp
    450                 455                 460

Lys Ala Gln Gly Asn Met Val Trp Phe Gln Tyr His Thr Lys Thr Asp
465                 470                 475                 480

Asn Lys Phe Lys Lys Pro Glu Cys His Trp Glu Ile Lys Asp Met Pro
                485                 490                 495

Leu Trp Ala Leu Leu Asn Gly Tyr Val Asp Tyr Leu Glu Thr Gln Ile
            500                 505                 510

Gln Tyr Gly Asp Leu Ser Lys Glu Gly Lys Val Leu Ile Arg Cys Pro
        515                 520                 525

Tyr Thr Lys Pro Ala Leu Val Asp Pro Arg Asp Asp Thr Ala Gly Tyr
    530                 535                 540

Val Val Tyr Asn Arg Asn Phe Gly Arg Gly Lys Trp Ile Asp Gly Gly
545                 550                 555                 560

Gly Tyr Ile Pro Leu His Glu Arg Thr Lys Trp Tyr Val Met Leu Arg
                565                 570                 575

Tyr Gln Thr Asp Val Phe His Asp Ile Val Thr Cys Gly Pro Trp Gln
            580                 585                 590

Tyr Arg Asp Asp Asn Lys Asn Ser Gln Leu Val Ala Lys Tyr Arg Phe
        595                 600                 605

Ser Phe Ile Trp Gly Gly Asn Thr Val His Ser Gln Val Ile Arg Asn
    610                 615                 620

Pro Cys Lys Asp Asn Gln Val Ser Gly Pro Arg Arg Gln Pro Arg Asp
625                 630                 635                 640

Ile Gln Val Val Asp Pro Gln Arg Ile Thr Pro Pro Trp Val Leu His
                645                 650                 655

Ser Phe Asp Gln Arg Arg Gly Leu Phe Thr Glu Thr Ala Leu Arg Arg
            660                 665                 670

Leu Leu Gln Glu Pro Leu Pro Gly Glu Tyr Ala Val Ser Thr Leu Arg
        675                 680                 685

Thr Pro Leu Leu Phe Leu Pro Ser Glu Tyr Gln Arg Glu Asp Gly Ala
    690                 695                 700

Ala Glu Ser Ala Ser Gly Ser Pro Ala Lys Arg Pro Arg Ile Trp Ser
705                 710                 715                 720

Glu Glu Ser Gln Thr Glu Thr Ile Ser Ser Glu Glu Asn Pro Ala Glu
                725                 730                 735

Thr Thr Arg Glu Leu Leu Gln Arg Lys Leu Arg Glu Gln Arg Ala Leu
            740                 745                 750

Gln Phe Gln Leu Gln His Phe Ala Val Gln Leu Ala Lys Thr Gln Ala
        755                 760                 765

Asn Leu His Val Asn Pro Leu Leu Ser Phe Pro Gln
    770                 775                 780
```

<210> SEQ ID NO 192
<211> LENGTH: 74
<212> TYPE: PRT
<213> ORGANISM: Torque teno virus

<400> SEQUENCE: 192

```
Met Ala Trp Trp Gly Trp Arg Arg Arg Trp Trp Arg Pro Lys Arg Arg
```

1 5 10 15

Trp Arg Trp Arg Arg Ala Arg Arg Arg Arg Arg Val Pro Ala Arg Arg
20 25 30

Pro Arg Arg Ala Phe Arg Arg Tyr Arg Thr Arg Thr Val Arg Arg Arg
35 40 45

Arg Arg Gly Arg Arg Arg Gly Tyr Arg Arg Arg Tyr Arg Leu Arg Arg
50 55 60

Tyr Ala Arg Arg Arg Phe Arg Arg Lys Lys
65 70

<210> SEQ ID NO 193
<211> LENGTH: 210
<212> TYPE: PRT
<213> ORGANISM: Torque teno virus

<400> SEQUENCE: 193

Ile Val Leu Thr Gln Trp Asn Pro Gln Thr Thr Arg Lys Cys Ile Ile
1 5 10 15

Arg Gly Met Met Pro Val Leu Trp Ala Gly Met Gly Thr Gly Gly Arg
20 25 30

Asn Tyr Ala Val Arg Ser Asp Asp Tyr Val Val Asn Lys Gly Phe Gly
35 40 45

Gly Ser Phe Ala Thr Glu Thr Phe Ser Leu Lys Val Leu Tyr Asp Gln
50 55 60

Phe Gln Arg Gly Phe Asn Arg Trp Ser His Thr Asn Glu Asp Leu Asp
65 70 75 80

Leu Ala Arg Tyr Arg Gly Cys Arg Trp Thr Phe Tyr Arg His Lys Asp
85 90 95

Thr Asp Phe Ile Val Tyr Phe Thr Asn Asn Pro Pro Met Lys Thr Asn
100 105 110

Gln Phe Ser Ala Pro Leu Thr Thr Pro Gly Met Leu Met Arg Ser Lys
115 120 125

Tyr Lys Val Leu Ile Pro Ser Phe Gln Thr Arg Pro Lys Gly Arg Lys
130 135 140

Thr Val Thr Val Lys Ile Arg Pro Pro Lys Leu Phe Gln Asp Lys Trp
145 150 155 160

Tyr Thr Gln Gln Asp Leu Cys Ser Val Pro Leu Val Gln Leu Asn Val
165 170 175

Thr Ala Ala Asp Phe Thr His Pro Phe Gly Ser Pro Leu Thr Glu Thr
180 185 190

Pro Cys Val Glu Phe Gln Val Leu Gly Asp Leu Tyr Asn Thr Cys Leu
195 200 205

Asn Ile
210

<210> SEQ ID NO 194
<211> LENGTH: 161
<212> TYPE: PRT
<213> ORGANISM: Torque teno virus

<400> SEQUENCE: 194

Asp Leu Pro Gln Phe Ser Glu Leu Gly Glu Ile Thr Ser Ala Tyr Ser
1 5 10 15

Lys Pro Asn Ser Asn Asn Leu Lys Glu Leu Tyr Lys Glu Leu Phe Thr
20 25 30

Lys Ala Thr Ser Gly His Tyr Trp Gln Thr Phe Ile Thr Asn Ser Met

```
        35                  40                  45

Val Arg Ala His Ile Asp Ala Asp Lys Ala Lys Glu Ala Gln Arg Ala
    50                  55                  60

Ser Thr Thr Pro Ser Tyr Asn Asn Asp Pro Phe Pro Thr Ile Pro Val
65                  70                  75                  80

Lys Ser Glu Phe Ala Gln Trp Lys Lys Lys Phe Thr Asp Thr Arg Asp
                85                  90                  95

Ser Pro Phe Leu Phe Ala Thr Tyr His Pro Glu Ala Ile Lys Asp Thr
            100                 105                 110

Ile Met Lys Met Arg Glu Asn Asn Phe Lys Leu Glu Thr Gly Pro Asn
        115                 120                 125

Asp Lys Tyr Gly Asp Tyr Thr Ala Gln Tyr Gln Gly Asn Thr His Met
    130                 135                 140

Leu Asp Tyr Tyr Leu Gly Phe Tyr Ser Pro Ile Phe Leu Ser Asp Gly
145                 150                 155                 160

Arg


<210> SEQ ID NO 195
<211> LENGTH: 166
<212> TYPE: PRT
<213> ORGANISM: Torque teno virus

<400> SEQUENCE: 195

Ser Asn Val Glu Phe Phe Thr Ala Tyr Arg Asp Ile Val Tyr Asn Pro
1               5                   10                  15

Phe Leu Asp Lys Ala Gln Gly Asn Met Val Trp Phe Gln Tyr His Thr
            20                  25                  30

Lys Thr Asp Asn Lys Phe Lys Lys Pro Glu Cys His Trp Glu Ile Lys
        35                  40                  45

Asp Met Pro Leu Trp Ala Leu Leu Asn Gly Tyr Val Asp Tyr Leu Glu
    50                  55                  60

Thr Gln Ile Gln Tyr Gly Asp Leu Ser Lys Glu Gly Lys Val Leu Ile
65                  70                  75                  80

Arg Cys Pro Tyr Thr Lys Pro Ala Leu Val Asp Pro Arg Asp Asp Thr
                85                  90                  95

Ala Gly Tyr Val Val Tyr Asn Arg Asn Phe Gly Arg Gly Lys Trp Ile
            100                 105                 110

Asp Gly Gly Gly Tyr Ile Pro Leu His Glu Arg Thr Lys Trp Tyr Val
        115                 120                 125

Met Leu Arg Tyr Gln Thr Asp Val Phe His Asp Ile Val Thr Cys Gly
    130                 135                 140

Pro Trp Gln Tyr Arg Asp Asp Asn Lys Asn Ser Gln Leu Val Ala Lys
145                 150                 155                 160

Tyr Arg Phe Ser Phe Ile
                165


<210> SEQ ID NO 196
<211> LENGTH: 169
<212> TYPE: PRT
<213> ORGANISM: Torque teno virus

<400> SEQUENCE: 196

Trp Gly Gly Asn Thr Val His Ser Gln Val Ile Arg Asn Pro Cys Lys
1               5                   10                  15

Asp Asn Gln Val Ser Gly Pro Arg Arg Gln Pro Arg Asp Ile Gln Val
            20                  25                  30
```

```
Val Asp Pro Gln Arg Ile Thr Pro Pro Trp Val Leu His Ser Phe Asp
        35                  40                  45

Gln Arg Arg Gly Leu Phe Thr Glu Thr Ala Leu Arg Arg Leu Leu Gln
    50                  55                  60

Glu Pro Leu Pro Gly Glu Tyr Ala Val Ser Thr Leu Arg Thr Pro Leu
65                  70                  75                  80

Leu Phe Leu Pro Ser Glu Tyr Gln Arg Glu Asp Gly Ala Ala Glu Ser
                85                  90                  95

Ala Ser Gly Ser Pro Ala Lys Arg Pro Arg Ile Trp Ser Glu Glu Ser
            100                 105                 110

Gln Thr Glu Thr Ile Ser Ser Glu Glu Asn Pro Ala Glu Thr Thr Arg
        115                 120                 125

Glu Leu Leu Gln Arg Lys Leu Arg Glu Gln Arg Ala Leu Gln Phe Gln
    130                 135                 140

Leu Gln His Phe Ala Val Gln Leu Ala Lys Thr Gln Ala Asn Leu His
145                 150                 155                 160

Val Asn Pro Leu Leu Ser Phe Pro Gln
                165


<210> SEQ ID NO 197
<211> LENGTH: 761
<212> TYPE: PRT
<213> ORGANISM: Torque teno virus

<400> SEQUENCE: 197

Met Ala Tyr Trp Phe Arg Arg Trp Gly Trp Arg Pro Arg Arg Arg Trp
1               5                   10                  15

Arg Arg Trp Arg Arg Arg Arg Arg Arg Leu Pro Arg Arg Arg Thr Arg
            20                  25                  30

Arg Ala Val Arg Gly Leu Gly Arg Arg Arg Lys Pro Arg Val Arg Arg
        35                  40                  45

Arg Arg Arg Thr Arg Arg Arg Thr Tyr Arg Arg Gly Trp Arg Arg Arg
    50                  55                  60

Arg Tyr Ile Arg Arg Gly Arg Arg Lys Lys Lys Leu Ile Leu Thr Gln
65                  70                  75                  80

Trp Asn Pro Ala Ile Val Lys Arg Cys Asn Ile Lys Gly Gly Leu Pro
                85                  90                  95

Ile Ile Ile Cys Gly Glu Pro Arg Ala Ala Phe Asn Tyr Gly Tyr His
            100                 105                 110

Met Glu Asp Tyr Thr Pro Gln Pro Phe Pro Phe Gly Gly Gly Met Ser
        115                 120                 125

Thr Val Thr Phe Ser Leu Lys Ala Leu Tyr Asp Gln Tyr Leu Lys His
    130                 135                 140

Gln Asn Arg Trp Thr Phe Ser Asn Asp Gln Leu Asp Leu Ala Arg Tyr
145                 150                 155                 160

Arg Gly Cys Lys Leu Arg Phe Tyr Arg Ser Pro Val Cys Asp Phe Ile
                165                 170                 175

Val His Tyr Asn Leu Ile Pro Pro Leu Lys Met Asn Gln Phe Thr Ser
            180                 185                 190

Pro Asn Thr His Pro Gly Leu Leu Met Leu Ser Lys His Lys Ile Ile
        195                 200                 205

Ile Pro Ser Phe Gln Thr Arg Pro Gly Gly Arg Arg Phe Val Lys Ile
    210                 215                 220

Arg Leu Asn Pro Pro Lys Leu Phe Glu Asp Lys Trp Tyr Thr Gln Gln
```

```
225                 230                 235                 240

Asp Leu Cys Lys Val Pro Leu Val Ser Ile Thr Ala Thr Ala Ala Asp
                245                 250                 255

Leu Arg Tyr Pro Phe Cys Ser Pro Gln Thr Asn Asn Pro Cys Thr Thr
            260                 265                 270

Phe Gln Val Leu Arg Lys Asn Tyr Asn Thr Val Ile Gly Thr Ser Val
        275                 280                 285

Lys Asp Gln Glu Ser Thr Gln Asp Phe Glu Asn Trp Leu Tyr Lys Thr
    290                 295                 300

Asp Ser His Tyr Gln Thr Phe Ala Thr Glu Ala Gln Leu Gly Arg Ile
305                 310                 315                 320

Pro Ala Phe Asn Pro Asp Gly Thr Lys Asn Thr Lys Gln Gln Ser Trp
                325                 330                 335

Gln Asp Asn Trp Ser Lys Lys Asn Ser Pro Trp Thr Gly Asn Ser Gly
            340                 345                 350

Thr Tyr Pro Gln Thr Thr Ser Glu Met Tyr Lys Ile Pro Tyr Asp Ser
        355                 360                 365

Asn Phe Gly Phe Pro Thr Tyr Arg Ala Gln Lys Asp Tyr Ile Leu Glu
    370                 375                 380

Arg Arg Gln Cys Asn Phe Asn Tyr Glu Val Asn Asn Pro Val Ser Lys
385                 390                 395                 400

Lys Val Trp Pro Gln Pro Ser Thr Thr Thr Pro Thr Val Asp Tyr Tyr
                405                 410                 415

Glu Tyr His Cys Gly Trp Phe Ser Asn Ile Phe Ile Gly Pro Asn Arg
            420                 425                 430

Tyr Asn Leu Gln Phe Gln Thr Ala Tyr Val Asp Thr Thr Tyr Asn Pro
        435                 440                 445

Leu Met Asp Lys Gly Lys Gly Asn Lys Ile Trp Phe Gln Tyr Leu Ser
    450                 455                 460

Lys Lys Gly Thr Asp Tyr Asn Glu Lys Gln Cys Tyr Cys Thr Leu Glu
465                 470                 475                 480

Asp Met Pro Leu Trp Ala Ile Cys Phe Gly Tyr Thr Asp Tyr Val Glu
                485                 490                 495

Thr Gln Leu Gly Pro Asn Val Asp His Glu Thr Ala Gly Leu Ile Ile
            500                 505                 510

Met Ile Cys Pro Tyr Thr Gln Pro Pro Met Tyr Asp Lys Asn Arg Pro
        515                 520                 525

Asn Trp Gly Tyr Val Val Tyr Asp Thr Asn Phe Gly Asn Gly Lys Met
    530                 535                 540

Pro Ser Gly Ser Gly Gln Val Pro Val Tyr Trp Gln Cys Arg Trp Arg
545                 550                 555                 560

Pro Met Leu Trp Phe Gln Gln Gln Val Leu Asn Asp Ile Ser Lys Thr
                565                 570                 575

Gly Pro Tyr Ala Tyr Arg Asp Glu Tyr Lys Asn Val Gln Leu Thr Leu
            580                 585                 590

Tyr Tyr Asn Phe Ile Phe Asn Trp Gly Gly Asp Met Tyr Tyr Pro Gln
        595                 600                 605

Val Val Lys Asn Pro Cys Gly Asp Ser Gly Ile Val Pro Gly Ser Gly
    610                 615                 620

Arg Phe Thr Arg Glu Val Gln Val Val Ser Pro Leu Ser Met Gly Pro
625                 630                 635                 640

Ala Tyr Ile Phe His Tyr Phe Asp Ser Arg Arg Gly Phe Phe Ser Glu
                645                 650                 655
```

```
Lys Ala Leu Lys Arg Met Gln Gln Gln Gln Glu Phe Asp Glu Ser Phe
            660                 665                 670

Thr Phe Lys Pro Lys Arg Pro Lys Leu Ser Thr Ala Ala Ala Glu Ile
        675                 680                 685

Leu Gln Leu Glu Glu Asp Ser Thr Ser Gly Glu Gly Lys Ser Pro Leu
    690                 695                 700

Gln Gln Glu Glu Lys Glu Val Glu Val Leu Gln Thr Pro Thr Val Gln
705                 710                 715                 720

Leu Gln Leu Gln Arg Asn Ile Gln Glu Gln Leu Ala Ile Lys Gln Gln
                725                 730                 735

Leu Gln Phe Leu Leu Leu Gln Leu Leu Lys Thr Gln Ser Asn Leu His
            740                 745                 750

Leu Asn Pro Gln Phe Leu Ser Pro Ser
        755                 760


<210> SEQ ID NO 198
<211> LENGTH: 75
<212> TYPE: PRT
<213> ORGANISM: Torque teno virus

<400> SEQUENCE: 198

Met Ala Tyr Trp Phe Arg Arg Trp Gly Trp Arg Pro Arg Arg Arg Trp
1               5                   10                  15

Arg Arg Trp Arg Arg Arg Arg Arg Arg Leu Pro Arg Arg Arg Thr Arg
            20                  25                  30

Arg Ala Val Arg Gly Leu Gly Arg Arg Arg Lys Pro Arg Val Arg Arg
        35                  40                  45

Arg Arg Arg Thr Arg Arg Arg Thr Tyr Arg Arg Gly Trp Arg Arg Arg
    50                  55                  60

Arg Tyr Ile Arg Arg Gly Arg Arg Lys Lys Lys
65                  70                  75


<210> SEQ ID NO 199
<211> LENGTH: 209
<212> TYPE: PRT
<213> ORGANISM: Torque teno virus

<400> SEQUENCE: 199

Leu Ile Leu Thr Gln Trp Asn Pro Ala Ile Val Lys Arg Cys Asn Ile
1               5                   10                  15

Lys Gly Gly Leu Pro Ile Ile Ile Cys Gly Glu Pro Arg Ala Ala Phe
            20                  25                  30

Asn Tyr Gly Tyr His Met Glu Asp Tyr Thr Pro Gln Pro Phe Pro Phe
        35                  40                  45

Gly Gly Gly Met Ser Thr Val Thr Phe Ser Leu Lys Ala Leu Tyr Asp
    50                  55                  60

Gln Tyr Leu Lys His Gln Asn Arg Trp Thr Phe Ser Asn Asp Gln Leu
65                  70                  75                  80

Asp Leu Ala Arg Tyr Arg Gly Cys Lys Leu Arg Phe Tyr Arg Ser Pro
                85                  90                  95

Val Cys Asp Phe Ile Val His Tyr Asn Leu Ile Pro Pro Leu Lys Met
            100                 105                 110

Asn Gln Phe Thr Ser Pro Asn Thr His Pro Gly Leu Leu Met Leu Ser
        115                 120                 125

Lys His Lys Ile Ile Ile Pro Ser Phe Gln Thr Arg Pro Gly Gly Arg
    130                 135                 140
```

```
Arg Phe Val Lys Ile Arg Leu Asn Pro Pro Lys Leu Phe Glu Asp Lys
145                 150                 155                 160

Trp Tyr Thr Gln Gln Asp Leu Cys Lys Val Pro Leu Val Ser Ile Thr
                165                 170                 175

Ala Thr Ala Ala Asp Leu Arg Tyr Pro Phe Cys Ser Pro Gln Thr Asn
            180                 185                 190

Asn Pro Cys Thr Thr Phe Gln Val Leu Arg Lys Asn Tyr Asn Thr Val
        195                 200                 205

Ile


<210> SEQ ID NO 200
<211> LENGTH: 148
<212> TYPE: PRT
<213> ORGANISM: Torque teno virus

<400> SEQUENCE: 200

Gly Thr Ser Val Lys Asp Gln Glu Ser Thr Gln Asp Phe Glu Asn Trp
1               5                   10                  15

Leu Tyr Lys Thr Asp Ser His Tyr Gln Thr Phe Ala Thr Glu Ala Gln
            20                  25                  30

Leu Gly Arg Ile Pro Ala Phe Asn Pro Asp Gly Thr Lys Asn Thr Lys
        35                  40                  45

Gln Gln Ser Trp Gln Asp Asn Trp Ser Lys Lys Asn Ser Pro Trp Thr
    50                  55                  60

Gly Asn Ser Gly Thr Tyr Pro Gln Thr Thr Ser Glu Met Tyr Lys Ile
65                  70                  75                  80

Pro Tyr Asp Ser Asn Phe Gly Phe Pro Thr Tyr Arg Ala Gln Lys Asp
                85                  90                  95

Tyr Ile Leu Glu Arg Arg Gln Cys Asn Phe Asn Tyr Glu Val Asn Asn
            100                 105                 110

Pro Val Ser Lys Lys Val Trp Pro Gln Pro Ser Thr Thr Thr Pro Thr
        115                 120                 125

Val Asp Tyr Tyr Glu Tyr His Cys Gly Trp Phe Ser Asn Ile Phe Ile
    130                 135                 140

Gly Pro Asn Arg
145


<210> SEQ ID NO 201
<211> LENGTH: 167
<212> TYPE: PRT
<213> ORGANISM: Torque teno virus

<400> SEQUENCE: 201

Tyr Asn Leu Gln Phe Gln Thr Ala Tyr Val Asp Thr Thr Tyr Asn Pro
1               5                   10                  15

Leu Met Asp Lys Gly Lys Gly Asn Lys Ile Trp Phe Gln Tyr Leu Ser
            20                  25                  30

Lys Lys Gly Thr Asp Tyr Asn Glu Lys Gln Cys Tyr Cys Thr Leu Glu
        35                  40                  45

Asp Met Pro Leu Trp Ala Ile Cys Phe Gly Tyr Thr Asp Tyr Val Glu
    50                  55                  60

Thr Gln Leu Gly Pro Asn Val Asp His Glu Thr Ala Gly Leu Ile Ile
65                  70                  75                  80

Met Ile Cys Pro Tyr Thr Gln Pro Pro Met Tyr Asp Lys Asn Arg Pro
                85                  90                  95
```

```
Asn Trp Gly Tyr Val Val Tyr Asp Thr Asn Phe Gly Asn Gly Lys Met
            100                 105                 110

Pro Ser Gly Ser Gly Gln Val Pro Val Tyr Trp Gln Cys Arg Trp Arg
        115                 120                 125

Pro Met Leu Trp Phe Gln Gln Gln Val Leu Asn Asp Ile Ser Lys Thr
    130                 135                 140

Gly Pro Tyr Ala Tyr Arg Asp Glu Tyr Lys Asn Val Gln Leu Thr Leu
145                 150                 155                 160

Tyr Tyr Asn Phe Ile Phe Asn
                165


<210> SEQ ID NO 202
<211> LENGTH: 162
<212> TYPE: PRT
<213> ORGANISM: Torque teno virus

<400> SEQUENCE: 202

Trp Gly Gly Asp Met Tyr Tyr Pro Gln Val Val Lys Asn Pro Cys Gly
1               5                   10                  15

Asp Ser Gly Ile Val Pro Gly Ser Gly Arg Phe Thr Arg Glu Val Gln
            20                  25                  30

Val Val Ser Pro Leu Ser Met Gly Pro Ala Tyr Ile Phe His Tyr Phe
        35                  40                  45

Asp Ser Arg Arg Gly Phe Phe Ser Glu Lys Ala Leu Lys Arg Met Gln
    50                  55                  60

Gln Gln Gln Glu Phe Asp Glu Ser Phe Thr Phe Lys Pro Lys Arg Pro
65                  70                  75                  80

Lys Leu Ser Thr Ala Ala Ala Glu Ile Leu Gln Leu Glu Glu Asp Ser
                85                  90                  95

Thr Ser Gly Glu Gly Lys Ser Pro Leu Gln Gln Glu Glu Lys Glu Val
            100                 105                 110

Glu Val Leu Gln Thr Pro Thr Val Gln Leu Gln Leu Gln Arg Asn Ile
        115                 120                 125

Gln Glu Gln Leu Ala Ile Lys Gln Gln Leu Gln Phe Leu Leu Leu Gln
    130                 135                 140

Leu Leu Lys Thr Gln Ser Asn Leu His Leu Asn Pro Gln Phe Leu Ser
145                 150                 155                 160

Pro Ser


<210> SEQ ID NO 203
<211> LENGTH: 746
<212> TYPE: PRT
<213> ORGANISM: Torque teno virus

<400> SEQUENCE: 203

Met Ala Trp Gly Trp Trp Arg Trp Arg Arg Arg Trp Pro Ala Arg Arg
1               5                   10                  15

Trp Arg Arg Arg Arg Arg Arg Arg Pro Val Arg Arg Thr Arg Ala Arg
            20                  25                  30

Arg Pro Ala Arg Arg Tyr Arg Arg Arg Arg Thr Val Arg Thr Arg Arg
        35                  40                  45

Arg Arg Trp Gly Arg Arg Arg Tyr Arg Arg Gly Trp Arg Arg Arg Thr
    50                  55                  60

Tyr Val Arg Lys Gly Arg His Arg Lys Lys Lys Lys Arg Leu Ile Leu
65                  70                  75                  80

Arg Gln Trp Gln Pro Ala Thr Arg Arg Arg Cys Thr Ile Thr Gly Tyr
```

```
                85                  90                  95

Leu Pro Ile Val Phe Cys Gly His Thr Arg Gly Asn Lys Asn Tyr Ala
            100                 105                 110

Leu His Ser Asp Asp Tyr Thr Pro Gln Gly Gln Pro Phe Gly Gly Ala
        115                 120                 125

Leu Ser Thr Thr Ser Phe Ser Leu Lys Val Leu Phe Asp Gln His Gln
    130                 135                 140

Arg Gly Leu Asn Lys Trp Ser Phe Pro Asn Asp Gln Leu Asp Leu Ala
145                 150                 155                 160

Arg Tyr Arg Gly Cys Lys Phe Ile Phe Tyr Arg Thr Lys Gln Thr Asp
                165                 170                 175

Trp Val Gly Gln Tyr Asp Ile Ser Glu Pro Tyr Lys Leu Asp Lys Tyr
            180                 185                 190

Ser Cys Pro Asn Tyr His Pro Gly Asn Met Ile Lys Ala Lys His Lys
        195                 200                 205

Phe Leu Ile Pro Ser Tyr Asp Thr Asn Pro Arg Gly Arg Gln Lys Ile
    210                 215                 220

Ile Val Lys Ile Pro Pro Pro Asp Leu Phe Val Asp Lys Trp Tyr Thr
225                 230                 235                 240

Gln Glu Asp Leu Cys Ser Val Asn Leu Val Ser Leu Ala Val Ser Ala
                245                 250                 255

Ala Ser Phe Leu His Pro Phe Gly Ser Pro Gln Thr Asp Asn Pro Cys
            260                 265                 270

Tyr Thr Phe Gln Val Leu Lys Glu Phe Tyr Tyr Gln Ala Ile Gly Phe
        275                 280                 285

Ser Ala Ser Thr Gln Ala Met Thr Ser Val Leu Asp Thr Leu Tyr Thr
    290                 295                 300

Gln Asn Ser Tyr Trp Glu Ser Asn Leu Thr Gln Phe Tyr Val Leu Asn
305                 310                 315                 320

Ala Lys Lys Gly Ser Asp Thr Thr Gln Pro Leu Thr Ser Asn Met Pro
                325                 330                 335

Thr Arg Glu Glu Phe Met Ala Lys Lys Asn Thr Asn Tyr Asn Trp Tyr
            340                 345                 350

Thr Tyr Lys Ala Ala Ser Val Lys Asn Lys Leu His Gln Met Arg Gln
        355                 360                 365

Thr Tyr Phe Glu Glu Leu Thr Ser Lys Gly Pro Gln Thr Thr Lys Ser
    370                 375                 380

Glu Glu Gly Tyr Ser Gln His Trp Thr Thr Pro Ser Thr Asn Ala Tyr
385                 390                 395                 400

Glu Tyr His Leu Gly Met Phe Ser Ala Ile Phe Leu Ala Pro Asp Arg
                405                 410                 415

Pro Val Pro Arg Phe Pro Cys Ala Tyr Gln Asp Val Thr Tyr Asn Pro
            420                 425                 430

Leu Met Asp Lys Gly Val Gly Asn His Ile Trp Phe Gln Tyr Asn Thr
        435                 440                 445

Lys Ala Asp Thr Gln Leu Ile Val Thr Gly Gly Ser Cys Lys Ala His
    450                 455                 460

Ile Gln Asp Ile Pro Leu Trp Ala Ala Phe Tyr Gly Tyr Ser Asp Phe
465                 470                 475                 480

Ile Glu Ser Glu Leu Gly Pro Phe Val Asp Ala Glu Thr Val Gly Leu
                485                 490                 495

Val Cys Val Ile Cys Pro Tyr Thr Lys Pro Pro Met Tyr Asn Lys Thr
            500                 505                 510
```

```
Asn Pro Ala Met Gly Tyr Val Phe Tyr Asp Arg Asn Phe Gly Asp Gly
        515                 520                 525

Lys Trp Thr Asp Gly Arg Gly Lys Ile Glu Pro Tyr Trp Gln Val Arg
    530                 535                 540

Trp Arg Pro Glu Met Leu Phe Gln Glu Thr Val Met Ala Asp Leu Val
545                 550                 555                 560

Gln Thr Gly Pro Phe Ser Tyr Lys Asp Glu Leu Lys Asn Ser Thr Leu
                565                 570                 575

Val Cys Lys Tyr Lys Phe Tyr Phe Thr Trp Gly Gly Asn Met Met Phe
            580                 585                 590

Gln Gln Thr Ile Lys Asn Pro Cys Lys Thr Asp Gly Gln Pro Thr Asp
        595                 600                 605

Ser Ser Arg His Pro Arg Gly Ile Gln Val Ala Asp Pro Glu Gln Met
    610                 615                 620

Gly Pro Arg Trp Val Phe His Ser Phe Asp Trp Arg Arg Gly Tyr Leu
625                 630                 635                 640

Ser Glu Lys Ala Leu Lys Arg Leu Gln Glu Lys Pro Leu Asp Tyr Asp
                645                 650                 655

Glu Tyr Phe Thr Gln Pro Lys Arg Pro Arg Ile Phe Pro Pro Thr Glu
            660                 665                 670

Ser Ala Glu Gly Glu Phe Arg Glu Pro Glu Lys Gly Ser Tyr Ser Glu
        675                 680                 685

Glu Glu Arg Ser Gln Ala Ser Ala Glu Glu Gln Thr Gln Glu Ala Thr
    690                 695                 700

Val Leu Leu Leu Lys Arg Arg Leu Arg Glu Gln Gln Gln Leu Gln Gln
705                 710                 715                 720

Gln Leu Gln Phe Leu Thr Arg Glu Met Phe Lys Thr Gln Ala Gly Leu
                725                 730                 735

His Leu Asn Pro Met Leu Leu Asn Gln Arg
            740                 745
```

<210> SEQ ID NO 204
<211> LENGTH: 77
<212> TYPE: PRT
<213> ORGANISM: Torque teno virus

<400> SEQUENCE: 204

```
Met Ala Trp Gly Trp Trp Arg Trp Arg Arg Arg Trp Pro Ala Arg Arg
1               5                   10                  15

Trp Arg Arg Arg Arg Arg Arg Arg Pro Val Arg Arg Thr Arg Ala Arg
            20                  25                  30

Arg Pro Ala Arg Arg Tyr Arg Arg Arg Arg Thr Val Arg Thr Arg Arg
        35                  40                  45

Arg Arg Trp Gly Arg Arg Arg Tyr Arg Arg Gly Trp Arg Arg Arg Thr
    50                  55                  60

Tyr Val Arg Lys Gly Arg His Arg Lys Lys Lys Lys Arg
65                  70                  75
```

<210> SEQ ID NO 205
<211> LENGTH: 209
<212> TYPE: PRT
<213> ORGANISM: Torque teno virus

<400> SEQUENCE: 205

```
Leu Ile Leu Arg Gln Trp Gln Pro Ala Thr Arg Arg Arg Cys Thr Ile
1               5                   10                  15
```

```
Thr Gly Tyr Leu Pro Ile Val Phe Cys Gly His Thr Arg Gly Asn Lys
            20                  25                  30

Asn Tyr Ala Leu His Ser Asp Asp Tyr Thr Pro Gln Gly Gln Pro Phe
        35                  40                  45

Gly Gly Ala Leu Ser Thr Thr Ser Phe Ser Leu Lys Val Leu Phe Asp
    50                  55                  60

Gln His Gln Arg Gly Leu Asn Lys Trp Ser Phe Pro Asn Asp Gln Leu
65                  70                  75                  80

Asp Leu Ala Arg Tyr Arg Gly Cys Lys Phe Ile Phe Tyr Arg Thr Lys
                85                  90                  95

Gln Thr Asp Trp Val Gly Gln Tyr Asp Ile Ser Glu Pro Tyr Lys Leu
            100                 105                 110

Asp Lys Tyr Ser Cys Pro Asn Tyr His Pro Gly Asn Met Ile Lys Ala
        115                 120                 125

Lys His Lys Phe Leu Ile Pro Ser Tyr Asp Thr Asn Pro Arg Gly Arg
    130                 135                 140

Gln Lys Ile Ile Val Lys Ile Pro Pro Pro Asp Leu Phe Val Asp Lys
145                 150                 155                 160

Trp Tyr Thr Gln Glu Asp Leu Cys Ser Val Asn Leu Val Ser Leu Ala
                165                 170                 175

Val Ser Ala Ala Ser Phe Leu His Pro Phe Gly Ser Pro Gln Thr Asp
            180                 185                 190

Asn Pro Cys Tyr Thr Phe Gln Val Leu Lys Glu Phe Tyr Tyr Gln Ala
        195                 200                 205

Ile
```

<210> SEQ ID NO 206
<211> LENGTH: 130
<212> TYPE: PRT
<213> ORGANISM: Torque teno virus

<400> SEQUENCE: 206

```
Gly Phe Ser Ala Ser Thr Gln Ala Met Thr Ser Val Leu Asp Thr Leu
1               5                   10                  15

Tyr Thr Gln Asn Ser Tyr Trp Glu Ser Asn Leu Thr Gln Phe Tyr Val
            20                  25                  30

Leu Asn Ala Lys Lys Gly Ser Asp Thr Thr Gln Pro Leu Thr Ser Asn
        35                  40                  45

Met Pro Thr Arg Glu Glu Phe Met Ala Lys Lys Asn Thr Asn Tyr Asn
    50                  55                  60

Trp Tyr Thr Tyr Lys Ala Ala Ser Val Lys Asn Lys Leu His Gln Met
65                  70                  75                  80

Arg Gln Thr Tyr Phe Glu Glu Leu Thr Ser Lys Gly Pro Gln Thr Thr
                85                  90                  95

Lys Ser Glu Glu Gly Tyr Ser Gln His Trp Thr Thr Pro Ser Thr Asn
            100                 105                 110

Ala Tyr Glu Tyr His Leu Gly Met Phe Ser Ala Ile Phe Leu Ala Pro
        115                 120                 125

Asp Arg
    130
```

<210> SEQ ID NO 207
<211> LENGTH: 169
<212> TYPE: PRT
<213> ORGANISM: Torque teno virus

<400> SEQUENCE: 207

Pro Val Pro Arg Phe Pro Cys Ala Tyr Gln Asp Val Thr Tyr Asn Pro
1 5 10 15

Leu Met Asp Lys Gly Val Gly Asn His Ile Trp Phe Gln Tyr Asn Thr
20 25 30

Lys Ala Asp Thr Gln Leu Ile Val Thr Gly Gly Ser Cys Lys Ala His
35 40 45

Ile Gln Asp Ile Pro Leu Trp Ala Ala Phe Tyr Gly Tyr Ser Asp Phe
50 55 60

Ile Glu Ser Glu Leu Gly Pro Phe Val Asp Ala Glu Thr Val Gly Leu
65 70 75 80

Val Cys Val Ile Cys Pro Tyr Thr Lys Pro Pro Met Tyr Asn Lys Thr
85 90 95

Asn Pro Ala Met Gly Tyr Val Phe Tyr Asp Arg Asn Phe Gly Asp Gly
100 105 110

Lys Trp Thr Asp Gly Arg Gly Lys Ile Glu Pro Tyr Trp Gln Val Arg
115 120 125

Trp Arg Pro Glu Met Leu Phe Gln Glu Thr Val Met Ala Asp Leu Val
130 135 140

Gln Thr Gly Pro Phe Ser Tyr Lys Asp Glu Leu Lys Asn Ser Thr Leu
145 150 155 160

Val Cys Lys Tyr Lys Phe Tyr Phe Thr
165

<210> SEQ ID NO 208
<211> LENGTH: 161
<212> TYPE: PRT
<213> ORGANISM: Torque teno virus

<400> SEQUENCE: 208

Trp Gly Gly Asn Met Met Phe Gln Gln Thr Ile Lys Asn Pro Cys Lys
1 5 10 15

Thr Asp Gly Gln Pro Thr Asp Ser Ser Arg His Pro Arg Gly Ile Gln
20 25 30

Val Ala Asp Pro Glu Gln Met Gly Pro Arg Trp Val Phe His Ser Phe
35 40 45

Asp Trp Arg Arg Gly Tyr Leu Ser Glu Lys Ala Leu Lys Arg Leu Gln
50 55 60

Glu Lys Pro Leu Asp Tyr Asp Glu Tyr Phe Thr Gln Pro Lys Arg Pro
65 70 75 80

Arg Ile Phe Pro Pro Thr Glu Ser Ala Glu Gly Glu Phe Arg Glu Pro
85 90 95

Glu Lys Gly Ser Tyr Ser Glu Glu Glu Arg Ser Gln Ala Ser Ala Glu
100 105 110

Glu Gln Thr Gln Glu Ala Thr Val Leu Leu Leu Lys Arg Arg Leu Arg
115 120 125

Glu Gln Gln Gln Leu Gln Gln Gln Leu Gln Phe Leu Thr Arg Glu Met
130 135 140

Phe Lys Thr Gln Ala Gly Leu His Leu Asn Pro Met Leu Leu Asn Gln
145 150 155 160

Arg

<210> SEQ ID NO 209
<211> LENGTH: 765

<212> TYPE: PRT
<213> ORGANISM: Torque teno virus

<400> SEQUENCE: 209

Met Ala Trp Ser Trp Trp Trp Gln Arg Trp Arg Arg Arg Arg Trp Lys
1 5 10 15

Pro Arg Arg Arg Arg Trp Arg Arg Leu Arg Trp Arg Arg Pro Arg Arg
20 25 30

Ala Val Arg Arg Arg Arg Arg Gly Arg Arg Val Arg Arg Arg Arg Trp
35 40 45

Ala Arg Arg Arg Gly Arg Arg Arg Arg Tyr Ala Thr Arg Arg Lys Arg
50 55 60

Arg Tyr Arg Gly Arg Arg Phe Lys Lys Lys Leu Val Leu Thr Gln Trp
65 70 75 80

His Pro Asn Thr Met Arg Arg Cys Leu Ile Lys Gly Ile Val Pro Leu
85 90 95

Val Ile Cys Gly His Thr Arg Trp Asn Tyr Asn Tyr Ala Leu His Ser
100 105 110

Lys Asp Tyr Thr Glu Glu Gly Arg Tyr Pro His Gly Gly Ala Leu Ser
115 120 125

Thr Thr Thr Trp Ser Leu Lys Val Leu Tyr Asp Glu His Leu Lys His
130 135 140

His Asp Phe Trp Gly Tyr Pro Asn Asn Gln Leu Asp Leu Ala Arg Tyr
145 150 155 160

Lys Gly Ala Lys Phe Thr Phe Tyr Arg His Lys Lys Thr Asp Phe Ile
165 170 175

Ile Phe Phe Asn Arg Lys Pro Pro Phe Lys Leu Asn Lys Tyr Ser Cys
180 185 190

Ala Ser Tyr His Pro Gly Met Leu Met Gln Gln Arg His Lys Ile Leu
195 200 205

Leu Pro Ser Tyr Glu Thr Lys Pro Lys Gly Arg Pro Lys Ile Thr Val
210 215 220

Arg Ile Lys Pro Pro Thr Leu Leu Glu Asp Lys Trp Tyr Thr Gln Gln
225 230 235 240

Asp Leu Cys Asp Val Asn Leu Leu Gln Leu Val Val Thr Ala Ala Asp
245 250 255

Phe Arg His Pro Leu Cys Ser Pro Gln Thr Asn Thr Pro Thr Thr Thr
260 265 270

Phe Gln Val Leu Lys Asp Ile Tyr Tyr Asp Thr Met Ser Ile Ser Glu
275 280 285

Pro Thr Asp Ser Tyr Thr Ser Val Asn Asn Lys Ser Thr Thr Gln Thr
290 295 300

Phe Thr Asn Tyr Ser Asn Thr Leu Glu Asn Ile Leu Tyr Thr Arg Ala
305 310 315 320

Ser Tyr Trp Asn Ser Phe His Ala Thr Glu Tyr Leu Asn Pro Asn Ile
325 330 335

Ile Tyr Lys Asn Gly Glu Lys Leu Phe Lys Glu His Glu Asp Leu Ile
340 345 350

Thr Trp Met Thr Gln Thr Asn Asn Thr Gly Phe Leu Thr Lys Asn Asn
355 360 365

Thr Ala Phe Gly Asn Asn Ser Tyr Arg Pro Asn Ala Asp Lys Ile Lys
370 375 380

Lys Ala Arg Lys Thr Tyr Trp Asn Ala Leu Ile Gly Thr Asn Asp Leu
385 390 395 400

```
Ala Thr Asn Ile Gly Gln Ala Arg Ala Glu Arg Phe Glu Tyr His Leu
                405                 410                 415

Gly Trp Tyr Ser Pro Ile Phe Leu Ser Arg His Arg Ser Asn Met Asn
            420                 425                 430

Phe Ala Arg Ala Tyr Gln Asp Val Thr Tyr Asn Pro Asn Cys Asp Arg
        435                 440                 445

Gly Val Asn Asn Arg Val Trp Val Gln Pro Leu Thr Lys Pro Thr Thr
    450                 455                 460

Glu Phe Asp Glu Lys Arg Cys Lys Cys Val Val Gln His Leu Pro Leu
465                 470                 475                 480

Trp Ala Ala Leu Tyr Cys Tyr Gln Asp Phe Val Glu Glu Glu Leu Gly
                485                 490                 495

Ser Ser Ser Glu Ile Leu Asn Ser Cys Leu Leu Val Leu Gln Cys Pro
            500                 505                 510

Tyr Thr Phe Pro Pro Met Tyr Asp Lys Lys Leu Pro Asp Lys Gly Phe
        515                 520                 525

Val Phe Tyr Asp Ser Leu Phe Gly Asp Gly Lys Met Ser Asp Gly Arg
    530                 535                 540

Gly Gln Val Asp Ile Phe Trp Gln Gln Arg Trp Tyr Pro Arg Leu Ala
545                 550                 555                 560

Thr Gln Met Gln Val Met His Asp Ile Thr Met Thr Gly Pro Phe Ser
                565                 570                 575

Tyr Arg Asp Glu Leu Val Ser Thr Gln Leu Thr Ala Lys Tyr Thr Phe
            580                 585                 590

Asp Phe Met Trp Gly Gly Asn Met Ile Ser Thr Gln Ile Ile Lys Asn
        595                 600                 605

Pro Cys Lys Asp Ser Gly Leu Glu Pro Ala Tyr Pro Gly Arg Gln Arg
    610                 615                 620

Arg Asp Leu Gln Ile Val Asp Pro Tyr Ser Met Gly Pro Gln Phe Ser
625                 630                 635                 640

Phe His Asn Trp Asp Tyr Arg His Gly Leu Phe Gly Gln Asp Ala Ile
                645                 650                 655

Asp Arg Val Ser Lys Gln Pro Lys Asp Asp Ala Asp Tyr Pro Asn Pro
            660                 665                 670

Tyr Lys Arg Pro Arg Tyr Phe Pro Pro Thr Asp Gln Ala Ala Gln Glu
        675                 680                 685

Gln Glu Lys Asp Phe Ser Phe Leu Lys Thr Ala Pro Ser Asn Ser Glu
    690                 695                 700

Glu Ser Asp Gln Glu Val Leu Gln Glu Thr Gln Val Leu Arg Phe Gln
705                 710                 715                 720

Pro Glu Gln His Lys Gln Leu His Leu Gln Leu Ala Glu Arg Gln Arg
                725                 730                 735

Ile Gly Glu Gln Leu Arg Tyr Leu Leu Gln Gln Met Phe Lys Thr Gln
            740                 745                 750

Ala Asn Leu His Leu Asn Pro Tyr Thr Phe Thr Gln Leu
        755                 760                 765
```

<210> SEQ ID NO 210
<211> LENGTH: 74
<212> TYPE: PRT
<213> ORGANISM: Torque teno virus

<400> SEQUENCE: 210

```
Met Ala Trp Ser Trp Trp Trp Gln Arg Trp Arg Arg Arg Arg Trp Lys
```

```
1               5                   10                  15

Pro Arg Arg Arg Arg Trp Arg Arg Leu Arg Trp Arg Arg Pro Arg Arg
            20                  25                  30

Ala Val Arg Arg Arg Arg Arg Gly Arg Arg Val Arg Arg Arg Arg Trp
        35                  40                  45

Ala Arg Arg Arg Gly Arg Arg Arg Arg Tyr Ala Thr Arg Arg Lys Arg
    50                  55                  60

Arg Tyr Arg Gly Arg Arg Phe Lys Lys Lys
65                  70
```

<210> SEQ ID NO 211
<211> LENGTH: 212
<212> TYPE: PRT
<213> ORGANISM: Torque teno virus

<400> SEQUENCE: 211

```
Leu Val Leu Thr Gln Trp His Pro Asn Thr Met Arg Arg Cys Leu Ile
1               5                   10                  15

Lys Gly Ile Val Pro Leu Val Ile Cys Gly His Thr Arg Trp Asn Tyr
            20                  25                  30

Asn Tyr Ala Leu His Ser Lys Asp Tyr Thr Glu Glu Gly Arg Tyr Pro
        35                  40                  45

His Gly Gly Ala Leu Ser Thr Thr Thr Trp Ser Leu Lys Val Leu Tyr
    50                  55                  60

Asp Glu His Leu Lys His His Asp Phe Trp Gly Tyr Pro Asn Asn Gln
65                  70                  75                  80

Leu Asp Leu Ala Arg Tyr Lys Gly Ala Lys Phe Thr Phe Tyr Arg His
                85                  90                  95

Lys Lys Thr Asp Phe Ile Ile Phe Phe Asn Arg Lys Pro Pro Phe Lys
            100                 105                 110

Leu Asn Lys Tyr Ser Cys Ala Ser Tyr His Pro Gly Met Leu Met Gln
        115                 120                 125

Gln Arg His Lys Ile Leu Leu Pro Ser Tyr Glu Thr Lys Pro Lys Gly
    130                 135                 140

Arg Pro Lys Ile Thr Val Arg Ile Lys Pro Pro Thr Leu Leu Glu Asp
145                 150                 155                 160

Lys Trp Tyr Thr Gln Gln Asp Leu Cys Asp Val Asn Leu Leu Gln Leu
                165                 170                 175

Val Val Thr Ala Ala Asp Phe Arg His Pro Leu Cys Ser Pro Gln Thr
            180                 185                 190

Asn Thr Pro Thr Thr Thr Phe Gln Val Leu Lys Asp Ile Tyr Tyr Asp
        195                 200                 205

Thr Met Ser Ile
    210
```

<210> SEQ ID NO 212
<211> LENGTH: 142
<212> TYPE: PRT
<213> ORGANISM: Torque teno virus

<400> SEQUENCE: 212

```
Ser Glu Pro Thr Asp Ser Tyr Thr Ser Val Asn Asn Lys Ser Thr Thr
1               5                   10                  15

Gln Thr Phe Thr Asn Tyr Ser Asn Thr Leu Glu Asn Ile Leu Tyr Thr
            20                  25                  30

Arg Ala Ser Tyr Trp Asn Ser Phe His Ala Thr Glu Tyr Leu Asn Pro
```

35 40 45

Asn Ile Ile Tyr Lys Asn Gly Glu Lys Leu Phe Lys Glu His Glu Asp
50 55 60

Leu Ile Thr Trp Met Thr Gln Thr Asn Asn Thr Gly Phe Leu Thr Lys
65 70 75 80

Asn Asn Thr Ala Phe Gly Asn Asn Ser Tyr Arg Pro Asn Ala Asp Lys
85 90 95

Ile Lys Lys Ala Arg Lys Thr Tyr Trp Asn Ala Leu Ile Gly Thr Asn
100 105 110

Asp Leu Ala Thr Asn Ile Gly Gln Ala Arg Ala Glu Arg Phe Glu Tyr
115 120 125

His Leu Gly Trp Tyr Ser Pro Ile Phe Leu Ser Arg His Arg
130 135 140

<210> SEQ ID NO 213
<211> LENGTH: 167
<212> TYPE: PRT
<213> ORGANISM: Torque teno virus

<400> SEQUENCE: 213

Ser Asn Met Asn Phe Ala Arg Ala Tyr Gln Asp Val Thr Tyr Asn Pro
1 5 10 15

Asn Cys Asp Arg Gly Val Asn Asn Arg Val Trp Val Gln Pro Leu Thr
20 25 30

Lys Pro Thr Thr Glu Phe Asp Glu Lys Arg Cys Lys Cys Val Val Gln
35 40 45

His Leu Pro Leu Trp Ala Ala Leu Tyr Cys Tyr Gln Asp Phe Val Glu
50 55 60

Glu Glu Leu Gly Ser Ser Ser Glu Ile Leu Asn Ser Cys Leu Leu Val
65 70 75 80

Leu Gln Cys Pro Tyr Thr Phe Pro Pro Met Tyr Asp Lys Lys Leu Pro
85 90 95

Asp Lys Gly Phe Val Phe Tyr Asp Ser Leu Phe Gly Asp Gly Lys Met
100 105 110

Ser Asp Gly Arg Gly Gln Val Asp Ile Phe Trp Gln Gln Arg Trp Tyr
115 120 125

Pro Arg Leu Ala Thr Gln Met Gln Val Met His Asp Ile Thr Met Thr
130 135 140

Gly Pro Phe Ser Tyr Arg Asp Glu Leu Val Ser Thr Gln Leu Thr Ala
145 150 155 160

Lys Tyr Thr Phe Asp Phe Met
165

<210> SEQ ID NO 214
<211> LENGTH: 170
<212> TYPE: PRT
<213> ORGANISM: Torque teno virus

<400> SEQUENCE: 214

Trp Gly Gly Asn Met Ile Ser Thr Gln Ile Ile Lys Asn Pro Cys Lys
1 5 10 15

Asp Ser Gly Leu Glu Pro Ala Tyr Pro Gly Arg Gln Arg Arg Asp Leu
20 25 30

Gln Ile Val Asp Pro Tyr Ser Met Gly Pro Gln Phe Ser Phe His Asn
35 40 45

Trp Asp Tyr Arg His Gly Leu Phe Gly Gln Asp Ala Ile Asp Arg Val

```
    50                  55                  60

Ser Lys Gln Pro Lys Asp Asp Ala Asp Tyr Pro Asn Pro Tyr Lys Arg
65                  70                  75                  80

Pro Arg Tyr Phe Pro Pro Thr Asp Gln Ala Ala Gln Glu Gln Glu Lys
                85                  90                  95

Asp Phe Ser Phe Leu Lys Thr Ala Pro Ser Asn Ser Glu Glu Ser Asp
            100                 105                 110

Gln Glu Val Leu Gln Glu Thr Gln Val Leu Arg Phe Gln Pro Glu Gln
        115                 120                 125

His Lys Gln Leu His Leu Gln Leu Ala Glu Arg Gln Arg Ile Gly Glu
    130                 135                 140

Gln Leu Arg Tyr Leu Leu Gln Gln Met Phe Lys Thr Gln Ala Asn Leu
145                 150                 155                 160

His Leu Asn Pro Tyr Thr Phe Thr Gln Leu
                165                 170


<210> SEQ ID NO 215
<211> LENGTH: 666
<212> TYPE: PRT
<213> ORGANISM: TTV-like mini virus

<400> SEQUENCE: 215

Met Pro Tyr Tyr Tyr Arg Arg Arg Arg Tyr Asn Tyr Arg Arg Pro Arg
1               5                   10                  15

Trp Tyr Gly Arg Gly Trp Ile Arg Arg Pro Phe Arg Arg Arg Phe Arg
            20                  25                  30

Arg Lys Arg Arg Val Arg Pro Thr Tyr Thr Thr Ile Pro Leu Lys Gln
        35                  40                  45

Trp Gln Pro Pro Tyr Lys Arg Thr Cys Tyr Ile Lys Gly Gln Asp Cys
    50                  55                  60

Leu Ile Tyr Tyr Ser Asn Leu Arg Leu Gly Met Asn Ser Thr Met Tyr
65                  70                  75                  80

Glu Lys Ser Ile Val Pro Val His Trp Pro Gly Gly Gly Ser Phe Ser
                85                  90                  95

Val Ser Met Leu Thr Leu Asp Ala Leu Tyr Asp Ile His Lys Leu Cys
            100                 105                 110

Arg Asn Trp Trp Thr Ser Thr Asn Gln Asp Leu Pro Leu Val Arg Tyr
        115                 120                 125

Lys Gly Cys Lys Ile Thr Phe Tyr Gln Ser Thr Phe Thr Asp Tyr Ile
    130                 135                 140

Val Arg Ile His Thr Glu Leu Pro Ala Asn Ser Asn Lys Leu Thr Tyr
145                 150                 155                 160

Pro Asn Thr His Pro Leu Met Met Met Met Ser Lys Tyr Lys His Ile
                165                 170                 175

Ile Pro Ser Arg Gln Thr Arg Arg Lys Lys Lys Pro Tyr Thr Lys Ile
            180                 185                 190

Phe Val Lys Pro Pro Pro Gln Phe Glu Asn Lys Trp Tyr Phe Ala Thr
        195                 200                 205

Asp Leu Tyr Lys Ile Pro Leu Leu Gln Ile His Cys Thr Ala Cys Asn
    210                 215                 220

Leu Gln Asn Pro Phe Val Lys Pro Asp Lys Leu Ser Asn Asn Val Thr
225                 230                 235                 240

Leu Trp Ser Leu Asn Thr Ile Ser Ile Gln Asn Arg Asn Met Ser Val
                245                 250                 255
```

```
Asp Gln Gly Gln Ser Trp Pro Phe Lys Ile Leu Gly Thr Gln Ser Phe
            260                 265                 270

Tyr Phe Tyr Phe Tyr Thr Gly Ala Asn Leu Pro Gly Asp Thr Thr Gln
        275                 280                 285

Ile Pro Val Ala Asp Leu Leu Pro Leu Thr Asn Pro Arg Ile Asn Arg
    290                 295                 300

Pro Gly Gln Ser Leu Asn Glu Ala Lys Ile Thr Asp His Ile Thr Phe
305                 310                 315                 320

Thr Glu Tyr Lys Asn Lys Phe Thr Asn Tyr Trp Gly Asn Pro Phe Asn
                325                 330                 335

Lys His Ile Gln Glu His Leu Asp Met Ile Leu Tyr Ser Leu Lys Ser
            340                 345                 350

Pro Glu Ala Ile Lys Asn Glu Trp Thr Thr Glu Asn Met Lys Trp Asn
        355                 360                 365

Gln Leu Asn Asn Ala Gly Thr Met Ala Leu Thr Pro Phe Asn Glu Pro
    370                 375                 380

Ile Phe Thr Gln Ile Gln Tyr Asn Pro Asp Arg Asp Thr Gly Glu Asp
385                 390                 395                 400

Thr Gln Leu Tyr Leu Leu Ser Asn Ala Thr Gly Thr Gly Trp Asp Pro
                405                 410                 415

Pro Gly Ile Pro Glu Leu Ile Leu Glu Gly Phe Pro Leu Trp Leu Ile
            420                 425                 430

Tyr Trp Gly Phe Ala Asp Phe Gln Lys Asn Leu Lys Lys Val Thr Asn
        435                 440                 445

Ile Asp Thr Asn Tyr Met Leu Val Ala Lys Thr Lys Phe Thr Gln Lys
    450                 455                 460

Pro Gly Thr Phe Tyr Leu Val Ile Leu Asn Asp Thr Phe Val Glu Gly
465                 470                 475                 480

Asn Ser Pro Tyr Glu Lys Gln Pro Leu Pro Glu Asp Asn Ile Lys Trp
                485                 490                 495

Tyr Pro Gln Val Gln Tyr Gln Leu Glu Ala Gln Asn Lys Leu Leu Gln
            500                 505                 510

Thr Gly Pro Phe Thr Pro Asn Ile Gln Gly Gln Leu Ser Asp Asn Ile
        515                 520                 525

Ser Met Phe Tyr Lys Phe Tyr Phe Lys Trp Gly Gly Ser Pro Pro Lys
    530                 535                 540

Ala Ile Asn Val Glu Asn Pro Ala His Gln Ile Gln Tyr Pro Ile Pro
545                 550                 555                 560

Arg Asn Glu His Glu Thr Thr Ser Leu Gln Ser Pro Gly Glu Ala Pro
                565                 570                 575

Glu Ser Ile Leu Tyr Ser Phe Asp Tyr Arg His Gly Asn Tyr Thr Thr
            580                 585                 590

Thr Ala Leu Ser Arg Ile Ser Gln Asp Trp Ala Leu Lys Asp Thr Val
        595                 600                 605

Ser Lys Ile Thr Glu Pro Asp Arg Gln Gln Leu Leu Lys Gln Ala Leu
    610                 615                 620

Glu Cys Leu Gln Ile Ser Glu Glu Thr Gln Glu Lys Lys Glu Lys Glu
625                 630                 635                 640

Val Gln Gln Leu Ile Ser Asn Leu Arg Gln Gln Gln Gln Leu Tyr Arg
                645                 650                 655

Glu Arg Ile Ile Ser Leu Leu Lys Asp Gln
            660                 665
```

<210> SEQ ID NO 216
<211> LENGTH: 38
<212> TYPE: PRT
<213> ORGANISM: TTV-like mini virus

<400> SEQUENCE: 216

Met Pro Tyr Tyr Tyr Arg Arg Arg Arg Tyr Asn Tyr Arg Arg Pro Arg
1 5 10 15

Trp Tyr Gly Arg Gly Trp Ile Arg Arg Pro Phe Arg Arg Arg Phe Arg
20 25 30

Arg Lys Arg Arg Val Arg
35

<210> SEQ ID NO 217
<211> LENGTH: 208
<212> TYPE: PRT
<213> ORGANISM: TTV-like mini virus

<400> SEQUENCE: 217

Pro Thr Tyr Thr Thr Ile Pro Leu Lys Gln Trp Gln Pro Pro Tyr Lys
1 5 10 15

Arg Thr Cys Tyr Ile Lys Gly Gln Asp Cys Leu Ile Tyr Tyr Ser Asn
20 25 30

Leu Arg Leu Gly Met Asn Ser Thr Met Tyr Glu Lys Ser Ile Val Pro
35 40 45

Val His Trp Pro Gly Gly Gly Ser Phe Ser Val Ser Met Leu Thr Leu
50 55 60

Asp Ala Leu Tyr Asp Ile His Lys Leu Cys Arg Asn Trp Trp Thr Ser
65 70 75 80

Thr Asn Gln Asp Leu Pro Leu Val Arg Tyr Lys Gly Cys Lys Ile Thr
85 90 95

Phe Tyr Gln Ser Thr Phe Thr Asp Tyr Ile Val Arg Ile His Thr Glu
100 105 110

Leu Pro Ala Asn Ser Asn Lys Leu Thr Tyr Pro Asn Thr His Pro Leu
115 120 125

Met Met Met Met Ser Lys Tyr Lys His Ile Ile Pro Ser Arg Gln Thr
130 135 140

Arg Arg Lys Lys Lys Pro Tyr Thr Lys Ile Phe Val Lys Pro Pro Pro
145 150 155 160

Gln Phe Glu Asn Lys Trp Tyr Phe Ala Thr Asp Leu Tyr Lys Ile Pro
165 170 175

Leu Leu Gln Ile His Cys Thr Ala Cys Asn Leu Gln Asn Pro Phe Val
180 185 190

Lys Pro Asp Lys Leu Ser Asn Asn Val Thr Leu Trp Ser Leu Asn Thr
195 200 205

<210> SEQ ID NO 218
<211> LENGTH: 128
<212> TYPE: PRT
<213> ORGANISM: TTV-like mini virus

<400> SEQUENCE: 218

Ile Ser Ile Gln Asn Arg Asn Met Ser Val Asp Gln Gly Gln Ser Trp
1 5 10 15

Pro Phe Lys Ile Leu Gly Thr Gln Ser Phe Tyr Phe Tyr Phe Tyr Thr
20 25 30

Gly Ala Asn Leu Pro Gly Asp Thr Thr Gln Ile Pro Val Ala Asp Leu
35 40 45

```
Leu Pro Leu Thr Asn Pro Arg Ile Asn Arg Pro Gly Gln Ser Leu Asn
    50                  55                  60

Glu Ala Lys Ile Thr Asp His Ile Thr Phe Thr Glu Tyr Lys Asn Lys
65                  70                  75                  80

Phe Thr Asn Tyr Trp Gly Asn Pro Phe Asn Lys His Ile Gln Glu His
                85                  90                  95

Leu Asp Met Ile Leu Tyr Ser Leu Lys Ser Pro Glu Ala Ile Lys Asn
            100                 105                 110

Glu Trp Thr Thr Glu Asn Met Lys Trp Asn Gln Leu Asn Asn Ala Gly
        115                 120                 125


<210> SEQ ID NO 219
<211> LENGTH: 163
<212> TYPE: PRT
<213> ORGANISM: TTV-like mini virus

<400> SEQUENCE: 219

Thr Met Ala Leu Thr Pro Phe Asn Glu Pro Ile Phe Thr Gln Ile Gln
1               5                   10                  15

Tyr Asn Pro Asp Arg Asp Thr Gly Glu Asp Thr Gln Leu Tyr Leu Leu
            20                  25                  30

Ser Asn Ala Thr Gly Thr Gly Trp Asp Pro Pro Gly Ile Pro Glu Leu
        35                  40                  45

Ile Leu Glu Gly Phe Pro Leu Trp Leu Ile Tyr Trp Gly Phe Ala Asp
    50                  55                  60

Phe Gln Lys Asn Leu Lys Lys Val Thr Asn Ile Asp Thr Asn Tyr Met
65                  70                  75                  80

Leu Val Ala Lys Thr Lys Phe Thr Gln Lys Pro Gly Thr Phe Tyr Leu
                85                  90                  95

Val Ile Leu Asn Asp Thr Phe Val Glu Gly Asn Ser Pro Tyr Glu Lys
            100                 105                 110

Gln Pro Leu Pro Glu Asp Asn Ile Lys Trp Tyr Pro Gln Val Gln Tyr
        115                 120                 125

Gln Leu Glu Ala Gln Asn Lys Leu Leu Gln Thr Gly Pro Phe Thr Pro
    130                 135                 140

Asn Ile Gln Gly Gln Leu Ser Asp Asn Ile Ser Met Phe Tyr Lys Phe
145                 150                 155                 160

Tyr Phe Lys


<210> SEQ ID NO 220
<211> LENGTH: 129
<212> TYPE: PRT
<213> ORGANISM: TTV-like mini virus

<400> SEQUENCE: 220

Trp Gly Gly Ser Pro Pro Lys Ala Ile Asn Val Glu Asn Pro Ala His
1               5                   10                  15

Gln Ile Gln Tyr Pro Ile Pro Arg Asn Glu His Glu Thr Thr Ser Leu
            20                  25                  30

Gln Ser Pro Gly Glu Ala Pro Glu Ser Ile Leu Tyr Ser Phe Asp Tyr
        35                  40                  45

Arg His Gly Asn Tyr Thr Thr Thr Ala Leu Ser Arg Ile Ser Gln Asp
    50                  55                  60

Trp Ala Leu Lys Asp Thr Val Ser Lys Ile Thr Glu Pro Asp Arg Gln
65                  70                  75                  80
```

-continued

```
Gln Leu Leu Lys Gln Ala Leu Glu Cys Leu Gln Ile Ser Glu Glu Thr
                85                  90                  95

Gln Glu Lys Lys Glu Lys Glu Val Gln Gln Leu Ile Ser Asn Leu Arg
            100                 105                 110

Gln Gln Gln Gln Leu Tyr Arg Glu Arg Ile Ile Ser Leu Leu Lys Asp
        115                 120                 125

Gln


<210> SEQ ID NO 221
<211> LENGTH: 673
<212> TYPE: PRT
<213> ORGANISM: Torque teno midi virus 1

<400> SEQUENCE: 221

Met Pro Phe Trp Trp Gly Arg Arg Asn Lys Phe Trp Tyr Gly Arg Asn
1               5                   10                  15

Tyr Arg Arg Lys Lys Arg Arg Phe Pro Lys Arg Arg Lys Arg Arg Phe
            20                  25                  30

Tyr Arg Arg Thr Lys Tyr Arg Arg Pro Ala Arg Arg Arg Arg Arg Arg
        35                  40                  45

Arg Arg Lys Val Arg Arg Lys Lys Lys Thr Leu Ile Val Arg Gln Trp
    50                  55                  60

Gln Pro Asp Ser Ile Val Leu Cys Lys Ile Lys Gly Tyr Asp Ser Ile
65                  70                  75                  80

Ile Trp Gly Ala Glu Gly Thr Gln Phe Gln Cys Ser Thr His Glu Met
                85                  90                  95

Tyr Glu Tyr Thr Arg Gln Lys Tyr Pro Gly Gly Gly Gly Phe Gly Val
            100                 105                 110

Gln Leu Tyr Ser Leu Glu Tyr Leu Tyr Asp Gln Trp Lys Leu Arg Asn
        115                 120                 125

Asn Ile Trp Thr Lys Thr Asn Gln Leu Lys Asp Leu Cys Arg Tyr Leu
    130                 135                 140

Lys Cys Val Met Thr Phe Tyr Arg His Gln His Ile Asp Phe Val Ile
145                 150                 155                 160

Val Tyr Glu Arg Gln Pro Pro Phe Glu Ile Asp Lys Leu Thr Tyr Met
                165                 170                 175

Lys Tyr His Pro Tyr Met Leu Leu Gln Arg Lys His Lys Ile Ile Leu
            180                 185                 190

Pro Ser Gln Thr Thr Asn Pro Arg Gly Lys Leu Lys Lys Lys Lys Thr
        195                 200                 205

Ile Lys Pro Pro Lys Gln Met Leu Ser Lys Trp Phe Phe Gln Gln Gln
    210                 215                 220

Phe Ala Lys Tyr Asp Leu Leu Leu Ile Ala Ala Ala Ala Cys Ser Leu
225                 230                 235                 240

Arg Tyr Pro Arg Ile Gly Cys Cys Asn Glu Asn Arg Met Ile Thr Leu
                245                 250                 255

Tyr Cys Leu Asn Thr Lys Phe Tyr Gln Asp Thr Glu Trp Gly Thr Thr
            260                 265                 270

Lys Gln Ala Pro His Tyr Phe Lys Pro Tyr Ala Thr Ile Asn Lys Ser
        275                 280                 285

Met Ile Phe Val Ser Asn Tyr Gly Gly Lys Lys Thr Glu Tyr Asn Ile
    290                 295                 300

Gly Gln Trp Ile Glu Thr Asp Ile Pro Gly Glu Gly Asn Leu Ala Arg
305                 310                 315                 320
```

```
Tyr Tyr Arg Ser Ile Ser Lys Glu Gly Gly Tyr Phe Ser Pro Lys Ile
                325                 330                 335

Leu Gln Ala Tyr Gln Thr Lys Val Lys Ser Val Asp Tyr Lys Pro Leu
            340                 345                 350

Pro Ile Val Leu Gly Arg Tyr Asn Pro Ala Ile Asp Asp Gly Lys Gly
        355                 360                 365

Asn Lys Ile Tyr Leu Gln Thr Ile Met Asn Gly His Trp Gly Leu Pro
    370                 375                 380

Gln Lys Thr Pro Asp Tyr Ile Ile Glu Glu Val Pro Leu Trp Leu Gly
385                 390                 395                 400

Phe Trp Gly Tyr Tyr Asn Tyr Leu Lys Gln Thr Arg Thr Glu Ala Ile
                405                 410                 415

Phe Pro Leu His Met Phe Val Val Gln Ser Lys Tyr Ile Gln Thr Gln
            420                 425                 430

Gln Thr Glu Thr Pro Asn Asn Phe Trp Ala Phe Ile Asp Asn Ser Phe
        435                 440                 445

Ile Gln Gly Lys Asn Pro Trp Asp Ser Val Ile Thr Tyr Ser Glu Gln
    450                 455                 460

Lys Leu Trp Phe Pro Thr Val Ala Trp Gln Leu Lys Thr Ile Asn Ala
465                 470                 475                 480

Ile Cys Glu Ser Gly Pro Tyr Val Pro Lys Leu Asp Asn Gln Thr Tyr
                485                 490                 495

Ser Thr Trp Glu Leu Ala Thr His Tyr Ser Phe His Phe Lys Trp Gly
            500                 505                 510

Gly Pro Gln Ile Ser Asp Gln Pro Val Glu Asp Pro Gly Asn Lys Asn
        515                 520                 525

Lys Tyr Asp Val Pro Asp Thr Ile Lys Glu Ala Leu Gln Ile Val Asn
    530                 535                 540

Pro Ala Lys Asn Ile Ala Ala Thr Met Phe His Asp Trp Asp Tyr Arg
545                 550                 555                 560

Arg Gly Cys Ile Thr Ser Thr Ala Ile Lys Arg Met Gln Gln Asn Leu
                565                 570                 575

Pro Thr Asp Ser Ser Leu Glu Ser Asp Ser Asp Ser Glu Pro Ala Pro
            580                 585                 590

Lys Lys Lys Arg Leu Leu Pro Val Leu His Asp Pro Gln Lys Lys Thr
        595                 600                 605

Glu Lys Ile Asn Gln Cys Leu Leu Ser Leu Cys Glu Glu Ser Thr Cys
    610                 615                 620

Gln Glu Gln Glu Thr Glu Glu Asn Ile Leu Lys Leu Ile Gln Gln Gln
625                 630                 635                 640

Gln Gln Gln Gln Gln Lys Leu Lys His Asn Leu Leu Val Leu Ile Lys
                645                 650                 655

Asp Leu Lys Val Lys Gln Arg Leu Leu Gln Leu Gln Thr Gly Val Leu
            660                 665                 670

Glu
```

<210> SEQ ID NO 222
<211> LENGTH: 57
<212> TYPE: PRT
<213> ORGANISM: Torque teno midi virus 1

<400> SEQUENCE: 222

```
Met Pro Phe Trp Trp Gly Arg Arg Asn Lys Phe Trp Tyr Gly Arg Asn
1               5                   10                  15
```

```
Tyr Arg Arg Lys Lys Arg Arg Phe Pro Lys Arg Arg Lys Arg Arg Phe
            20                  25                  30

Tyr Arg Arg Thr Lys Tyr Arg Arg Pro Ala Arg Arg Arg Arg Arg Arg
        35                  40                  45

Arg Arg Lys Val Arg Arg Lys Lys Lys
    50                  55


<210> SEQ ID NO 223
<211> LENGTH: 202
<212> TYPE: PRT
<213> ORGANISM: Torque teno midi virus 1

<400> SEQUENCE: 223

Thr Leu Ile Val Arg Gln Trp Gln Pro Asp Ser Ile Val Leu Cys Lys
1               5                   10                  15

Ile Lys Gly Tyr Asp Ser Ile Ile Trp Gly Ala Glu Gly Thr Gln Phe
            20                  25                  30

Gln Cys Ser Thr His Glu Met Tyr Glu Tyr Thr Arg Gln Lys Tyr Pro
        35                  40                  45

Gly Gly Gly Gly Phe Gly Val Gln Leu Tyr Ser Leu Glu Tyr Leu Tyr
    50                  55                  60

Asp Gln Trp Lys Leu Arg Asn Asn Ile Trp Thr Lys Thr Asn Gln Leu
65                  70                  75                  80

Lys Asp Leu Cys Arg Tyr Leu Lys Cys Val Met Thr Phe Tyr Arg His
                85                  90                  95

Gln His Ile Asp Phe Val Ile Val Tyr Glu Arg Gln Pro Pro Phe Glu
            100                 105                 110

Ile Asp Lys Leu Thr Tyr Met Lys Tyr His Pro Tyr Met Leu Leu Gln
        115                 120                 125

Arg Lys His Lys Ile Ile Leu Pro Ser Gln Thr Thr Asn Pro Arg Gly
    130                 135                 140

Lys Leu Lys Lys Lys Lys Thr Ile Lys Pro Pro Lys Gln Met Leu Ser
145                 150                 155                 160

Lys Trp Phe Phe Gln Gln Gln Phe Ala Lys Tyr Asp Leu Leu Leu Ile
                165                 170                 175

Ala Ala Ala Ala Cys Ser Leu Arg Tyr Pro Arg Ile Gly Cys Cys Asn
            180                 185                 190

Glu Asn Arg Met Ile Thr Leu Tyr Cys Leu
        195                 200


<210> SEQ ID NO 224
<211> LENGTH: 92
<212> TYPE: PRT
<213> ORGANISM: Torque teno midi virus 1

<400> SEQUENCE: 224

Asn Thr Lys Phe Tyr Gln Asp Thr Glu Trp Gly Thr Thr Lys Gln Ala
1               5                   10                  15

Pro His Tyr Phe Lys Pro Tyr Ala Thr Ile Asn Lys Ser Met Ile Phe
            20                  25                  30

Val Ser Asn Tyr Gly Gly Lys Lys Thr Glu Tyr Asn Ile Gly Gln Trp
        35                  40                  45

Ile Glu Thr Asp Ile Pro Gly Glu Gly Asn Leu Ala Arg Tyr Tyr Arg
    50                  55                  60

Ser Ile Ser Lys Glu Gly Gly Tyr Phe Ser Pro Lys Ile Leu Gln Ala
65                  70                  75                  80
```

Tyr Gln Thr Lys Val Lys Ser Val Asp Tyr Lys Pro
85 90

<210> SEQ ID NO 225
<211> LENGTH: 159
<212> TYPE: PRT
<213> ORGANISM: Torque teno midi virus 1

<400> SEQUENCE: 225

Leu Pro Ile Val Leu Gly Arg Tyr Asn Pro Ala Ile Asp Asp Gly Lys
1 5 10 15

Gly Asn Lys Ile Tyr Leu Gln Thr Ile Met Asn Gly His Trp Gly Leu
20 25 30

Pro Gln Lys Thr Pro Asp Tyr Ile Ile Glu Glu Val Pro Leu Trp Leu
35 40 45

Gly Phe Trp Gly Tyr Tyr Asn Tyr Leu Lys Gln Thr Arg Thr Glu Ala
50 55 60

Ile Phe Pro Leu His Met Phe Val Val Gln Ser Lys Tyr Ile Gln Thr
65 70 75 80

Gln Gln Thr Glu Thr Pro Asn Asn Phe Trp Ala Phe Ile Asp Asn Ser
85 90 95

Phe Ile Gln Gly Lys Asn Pro Trp Asp Ser Val Ile Thr Tyr Ser Glu
100 105 110

Gln Lys Leu Trp Phe Pro Thr Val Ala Trp Gln Leu Lys Thr Ile Asn
115 120 125

Ala Ile Cys Glu Ser Gly Pro Tyr Val Pro Lys Leu Asp Asn Gln Thr
130 135 140

Tyr Ser Thr Trp Glu Leu Ala Thr His Tyr Ser Phe His Phe Lys
145 150 155

<210> SEQ ID NO 226
<211> LENGTH: 163
<212> TYPE: PRT
<213> ORGANISM: Torque teno midi virus 1

<400> SEQUENCE: 226

Trp Gly Gly Pro Gln Ile Ser Asp Gln Pro Val Glu Asp Pro Gly Asn
1 5 10 15

Lys Asn Lys Tyr Asp Val Pro Asp Thr Ile Lys Glu Ala Leu Gln Ile
20 25 30

Val Asn Pro Ala Lys Asn Ile Ala Ala Thr Met Phe His Asp Trp Asp
35 40 45

Tyr Arg Arg Gly Cys Ile Thr Ser Thr Ala Ile Lys Arg Met Gln Gln
50 55 60

Asn Leu Pro Thr Asp Ser Ser Leu Glu Ser Asp Ser Asp Ser Glu Pro
65 70 75 80

Ala Pro Lys Lys Lys Arg Leu Leu Pro Val Leu His Asp Pro Gln Lys
85 90 95

Lys Thr Glu Lys Ile Asn Gln Cys Leu Leu Ser Leu Cys Glu Glu Ser
100 105 110

Thr Cys Gln Glu Gln Glu Thr Glu Glu Asn Ile Leu Lys Leu Ile Gln
115 120 125

Gln Gln Gln Gln Gln Gln Gln Lys Leu Lys His Asn Leu Leu Val Leu
130 135 140

Ile Lys Asp Leu Lys Val Lys Gln Arg Leu Leu Gln Leu Gln Thr Gly
145 150 155 160

Val Leu Glu

<210> SEQ ID NO 227
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (29)..(31)
<223> OTHER INFORMATION: Any amino acid
<220> FEATURE:
<221> NAME/KEY: MISC_FEATURE
<222> LOCATION: (29)..(31)
<223> OTHER INFORMATION: This region may encompass 0-3 residues
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (125)..(129)
<223> OTHER INFORMATION: Any amino acid
<220> FEATURE:
<221> NAME/KEY: MISC_FEATURE
<222> LOCATION: (125)..(129)
<223> OTHER INFORMATION: This region may encompass 1-5 residues
<220> FEATURE:
<221> NAME/KEY: MOD_RES
<222> LOCATION: (181)..(181)
<223> OTHER INFORMATION: Any amino acid
<220> FEATURE:
<221> NAME/KEY: MOD_RES
<222> LOCATION: (211)..(211)
<223> OTHER INFORMATION: Any amino acid

<400> SEQUENCE: 227

Leu Val Leu Thr Gln Trp Gln Pro Asn Thr Val Arg Arg Cys Tyr Ile
1 5 10 15

Arg Gly Tyr Leu Pro Leu Ile Ile Cys Gly Glu Asn Xaa Xaa Xaa Thr
20 25 30

Thr Ser Arg Asn Tyr Ala Thr His Ser Asp Asp Thr Ile Gln Lys Gly
35 40 45

Pro Phe Gly Gly Gly Met Ser Thr Thr Thr Phe Ser Leu Arg Val Leu
50 55 60

Tyr Asp Glu Tyr Gln Arg Phe Met Asn Arg Trp Thr Tyr Ser Asn Glu
65 70 75 80

Asp Leu Asp Leu Ala Arg Tyr Leu Gly Cys Lys Phe Thr Phe Tyr Arg
85 90 95

His Pro Asp Xaa Asp Phe Ile Val Gln Tyr Asn Thr Asn Pro Pro Phe
100 105 110

Lys Asp Thr Lys Leu Thr Ala Pro Ser Ile His Pro Xaa Xaa Xaa Xaa
115 120 125

Xaa Gly Met Leu Met Leu Ser Lys Arg Lys Ile Leu Ile Pro Ser Leu
130 135 140

Lys Thr Arg Pro Lys Gly Lys His Tyr Val Lys Val Arg Ile Gly Pro
145 150 155 160

Pro Lys Leu Phe Glu Asp Lys Trp Tyr Thr Gln Ser Asp Leu Cys Asp
165 170 175

Val Pro Leu Val Xaa Leu Tyr Ala Thr Ala Ala Asp Leu Gln His Pro
180 185 190

Phe Gly Ser Pro Gln Thr Asp Asn Pro Cys Val Thr Phe Gln Val Leu
195 200 205

```
Gly Ser Xaa Tyr Asn Lys His Leu Ser Ile Ser Pro
    210                 215                 220


<210> SEQ ID NO 228
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (44)..(46)
<223> OTHER INFORMATION: Any amino acid
<220> FEATURE:
<221> NAME/KEY: MISC_FEATURE
<222> LOCATION: (44)..(46)
<223> OTHER INFORMATION: This region may encompass 0-3 residues
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (98)..(101)
<223> OTHER INFORMATION: Any amino acid
<220> FEATURE:
<221> NAME/KEY: MISC_FEATURE
<222> LOCATION: (98)..(101)
<223> OTHER INFORMATION: This region may encompass 0-4 residues

<400> SEQUENCE: 228

Ser Asn Phe Glu Phe Pro Gly Ala Tyr Thr Asp Ile Thr Tyr Asn Pro
1               5                   10                  15

Leu Thr Asp Lys Gly Val Gly Asn Met Val Trp Ile Gln Tyr Leu Thr
            20                  25                  30

Lys Pro Asp Thr Ile Xaa Asp Lys Thr Gln Ser Xaa Xaa Xaa Lys Cys
        35                  40                  45

Leu Ile Glu Asp Leu Pro Leu Trp Ala Ala Leu Tyr Gly Tyr Val Asp
    50                  55                  60

Phe Cys Glu Lys Glu Thr Gly Asp Ser Ala Ile Ile Xaa Asn Xaa Gly
65                  70                  75                  80

Arg Val Leu Ile Arg Cys Pro Tyr Thr Lys Pro Pro Leu Tyr Asp Lys
                85                  90                  95

Thr Xaa Xaa Xaa Xaa Asn Lys Gly Phe Val Pro Tyr Ser Thr Asn Phe
            100                 105                 110

Gly Asn Gly Lys Met Pro Gly Gly Ser Gly Tyr Val Pro Ile Tyr Trp
        115                 120                 125

Arg Ala Arg Trp Tyr Pro Thr Leu Phe His Gln Lys Glu Val Leu Glu
    130                 135                 140

Asp Ile Val Gln Ser Gly Pro Phe Ala Tyr Lys Asp Glu Lys Pro Ser
145                 150                 155                 160

Thr Gln Leu Val Met Lys Tyr Cys Phe Asn Phe Asn
                165                 170


<210> SEQ ID NO 229
<211> LENGTH: 258
```

<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (20)..(22)
<223> OTHER INFORMATION: Any amino acid
<220> FEATURE:
<221> NAME/KEY: MISC_FEATURE
<222> LOCATION: (20)..(22)
<223> OTHER INFORMATION: This region may encompass 0-3 residues
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (91)..(91)
<223> OTHER INFORMATION: Any amino acid
<220> FEATURE:
<221> NAME/KEY: MOD_RES
<222> LOCATION: (95)..(98)
<223> OTHER INFORMATION: Any amino acid
<220> FEATURE:
<221> NAME/KEY: MISC_FEATURE
<222> LOCATION: (95)..(98)
<223> OTHER INFORMATION: This region may encompass 1-4 residues
<220> FEATURE:
<221> NAME/KEY: MOD_RES
<222> LOCATION: (107)..(120)
<223> OTHER INFORMATION: Any amino acid
<220> FEATURE:
<221> NAME/KEY: MISC_FEATURE
<222> LOCATION: (107)..(120)
<223> OTHER INFORMATION: This region may encompass 2-14 residues
<220> FEATURE:
<221> NAME/KEY: MOD_RES
<222> LOCATION: (129)..(129)
<223> OTHER INFORMATION: Any amino acid
<220> FEATURE:
<221> NAME/KEY: MOD_RES
<222> LOCATION: (139)..(168)
<223> OTHER INFORMATION: Any amino acid
<220> FEATURE:
<221> NAME/KEY: MISC_FEATURE
<222> LOCATION: (139)..(168)
<223> OTHER INFORMATION: This region may encompass 0-30 residues
<220> FEATURE:
<221> NAME/KEY: MOD_RES
<222> LOCATION: (201)..(204)
<223> OTHER INFORMATION: Any amino acid
<220> FEATURE:
<221> NAME/KEY: MISC_FEATURE
<222> LOCATION: (201)..(204)
<223> OTHER INFORMATION: This region may encompass 0-4 residues
<220> FEATURE:
<221> NAME/KEY: MOD_RES
<222> LOCATION: (219)..(258)
<223> OTHER INFORMATION: Any amino acid
<220> FEATURE:
<221> NAME/KEY: MISC_FEATURE
<222> LOCATION: (219)..(258)
<223> OTHER INFORMATION: This region may encompass 0-40 residues

<400> SEQUENCE: 229

```
Trp Gly Gly Asn Pro Ile Ser Gln Gln Val Val Arg Asn Pro Cys Lys
1               5                   10                  15
```

```
Asp Ser Gly Xaa Xaa Xaa Ser Gly Xaa Gly Arg Gln Pro Arg Ser Val
            20                  25                  30

Gln Val Val Asp Pro Lys Tyr Met Gly Pro Glu Tyr Thr Phe His Ser
        35                  40                  45

Trp Asp Trp Arg Arg Gly Leu Phe Gly Glu Lys Ala Ile Lys Arg Met
    50                  55                  60

Ser Glu Gln Pro Thr Asp Asp Glu Ile Phe Thr Gly Gly Xaa Pro Lys
65                  70                  75                  80

Arg Pro Arg Arg Asp Pro Pro Thr Xaa Gln Xaa Pro Glu Glu Xaa Xaa
                85                  90                  95

Xaa Xaa Gln Lys Glu Ser Ser Ser Phe Arg Xaa Xaa Xaa Xaa Xaa Xaa
            100                 105                 110

Xaa Xaa Xaa Xaa Xaa Xaa Xaa Xaa Pro Trp Glu Ser Ser Ser Gln Glu
        115                 120                 125

Xaa Glu Ser Glu Ser Gln Glu Glu Glu Glu Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Glu Gln Thr Val Gln Gln Gln Leu
                165                 170                 175

Arg Gln Gln Leu Arg Glu Gln Arg Arg Leu Arg Val Gln Leu Gln Leu
            180                 185                 190

Leu Phe Gln Gln Leu Leu Lys Thr Xaa Xaa Xaa Xaa Gln Ala Gly Leu
        195                 200                 205

His Ile Asn Pro Leu Leu Leu Ser Gln Ala Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa
```

```
<210> SEQ ID NO 230
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (138)..(141)
<223> OTHER INFORMATION: Any amino acid
<220> FEATURE:
<221> NAME/KEY: MISC_FEATURE
<222> LOCATION: (138)..(141)
<223> OTHER INFORMATION: This region may encompass 1-4 residues
<220> FEATURE:
<221> NAME/KEY: MOD_RES
<222> LOCATION: (179)..(179)
<223> OTHER INFORMATION: Any amino acid

<400> SEQUENCE: 230

Leu Lys Gln Trp Gln Pro Ser Thr Ile Arg Lys Cys Lys Ile Lys Gly
1               5                   10                  15

Tyr Leu Pro Leu Phe Gln Cys Gly Lys Gly Arg Ile Ser Asn Asn Tyr
            20                  25                  30
```

```
Thr Gln Tyr Lys Glu Ser Ile Val Pro His His Glu Pro Gly Gly Gly
        35                  40                  45

Gly Trp Ser Ile Gln Gln Phe Thr Leu Gly Ala Leu Tyr Glu Glu His
    50                  55                  60

Leu Lys Leu Arg Asn Trp Trp Thr Lys Ser Asn Asp Gly Leu Pro Leu
65                  70                  75                  80

Val Arg Tyr Leu Gly Cys Thr Ile Lys Leu Tyr Arg Ser Glu Asp Thr
                85                  90                  95

Asp Tyr Ile Val Thr Tyr Gln Arg Cys Tyr Pro Met Thr Ala Thr Lys
            100                 105                 110

Leu Thr Tyr Leu Ser Thr Gln Pro Ser Arg Met Leu Met Asn Lys His
        115                 120                 125

Lys Ile Ile Val Pro Ser Lys Xaa Thr Xaa Xaa Xaa Xaa Asn Lys Lys
    130                 135                 140

Lys Lys Pro Tyr Lys Lys Ile Phe Ile Lys Pro Pro Ser Gln Met Gln
145                 150                 155                 160

Asn Lys Trp Tyr Phe Gln Gln Asp Ile Ala Asn Thr Pro Leu Leu Gln
                165                 170                 175

Leu Thr Xaa Thr Ala Cys Ser Leu Asp Arg Met Tyr Leu Ser Ser Asp
            180                 185                 190

Ser Ile Ser Asn Asn Ile Thr Phe Thr Ser Leu Asn Thr Asn Phe Phe
        195                 200                 205

Gln Asn Pro Asn Phe Gln
    210
```

<210> SEQ ID NO 231
<211> LENGTH: 187
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(10)
<223> OTHER INFORMATION: Any amino acid
<220> FEATURE:
<221> NAME/KEY: MISC_FEATURE
<222> LOCATION: (1)..(10)
<223> OTHER INFORMATION: This region may encompass 4-10 residues
<220> FEATURE:
<221> NAME/KEY: MOD_RES
<222> LOCATION: (38)..(45)
<223> OTHER INFORMATION: Any amino acid
<220> FEATURE:
<221> NAME/KEY: MISC_FEATURE
<222> LOCATION: (38)..(45)
<223> OTHER INFORMATION: This region may encompass 1-8 residues
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (100)..(102)
<223> OTHER INFORMATION: Any amino acid
<220> FEATURE:
<221> NAME/KEY: MISC_FEATURE
<222> LOCATION: (100)..(102)
<223> OTHER INFORMATION: This region may encompass 1-3 residues
<220> FEATURE:
<221> NAME/KEY: MOD_RES
<222> LOCATION: (112)..(112)
<223> OTHER INFORMATION: Any amino acid
<220> FEATURE:
<221> NAME/KEY: MOD_RES
<222> LOCATION: (114)..(115)
<223> OTHER INFORMATION: Any amino acid
<220> FEATURE:
<221> NAME/KEY: MISC_FEATURE
<222> LOCATION: (114)..(115)
<223> OTHER INFORMATION: This region may encompass 0-2 residues
<220> FEATURE:
<221> NAME/KEY: MOD_RES
<222> LOCATION: (124)..(139)
<223> OTHER INFORMATION: Any amino acid
<220> FEATURE:
<221> NAME/KEY: MISC_FEATURE
<222> LOCATION: (124)..(139)
<223> OTHER INFORMATION: This region may encompass 3-16 residues
<220> FEATURE:
<221> NAME/KEY: MOD_RES
<222> LOCATION: (154)..(154)
<223> OTHER INFORMATION: Any amino acid

<400> SEQUENCE: 231

```
Xaa Xaa Xaa Xaa Xaa Xaa Xaa Xaa Xaa Xaa Thr Pro Leu Tyr Phe Glu
1               5                   10                  15

Cys Arg Tyr Asn Pro Phe Lys Asp Lys Gly Thr Gly Asn Lys Val Tyr
            20                  25                  30

Leu Val Ser Asn Asn Xaa Xaa Xaa Xaa Xaa Xaa Xaa Xaa Thr Gly Trp
        35                  40                  45

Asp Pro Pro Thr Asp Pro Asp Leu Ile Ile Glu Gly Phe Pro Leu Trp
    50                  55                  60

Leu Leu Leu Trp Gly Trp Leu Asp Trp Gln Lys Lys Leu Gly Lys Ile
65                  70                  75                  80

Gln Asn Ile Asp Thr Asp Tyr Ile Leu Val Ile Gln Ser Xaa Tyr Tyr
                85                  90                  95

Ile Pro Pro Xaa Xaa Xaa Lys Leu Pro Tyr Tyr Val Pro Leu Asp Xaa
            100                 105                 110

Asp Xaa Xaa Phe Leu His Gly Arg Ser Pro Tyr Xaa Xaa Xaa Xaa Xaa
        115                 120                 125

Xaa Xaa Xaa Xaa Xaa Xaa Xaa Xaa Xaa Xaa Xaa Pro Ser Asp Lys Gln
    130                 135                 140

His Trp His Pro Lys Val Arg Phe Gln Xaa Glu Thr Ile Asn Asn Ile
145                 150                 155                 160

Ala Leu Thr Gly Pro Gly Thr Pro Lys Leu Pro Asn Gln Lys Ser Ile
                165                 170                 175

Gln Ala His Met Lys Tyr Lys Phe Tyr Phe Lys
            180                 185
```

<210> SEQ ID NO 232
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (77)..(78)
<223> OTHER INFORMATION: Any amino acid
<220> FEATURE:
<221> NAME/KEY: MOD_RES
<222> LOCATION: (86)..(87)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (102)..(106)
<223> OTHER INFORMATION: Any amino acid
<220> FEATURE:
<221> NAME/KEY: MISC_FEATURE
<222> LOCATION: (102)..(106)
<223> OTHER INFORMATION: This region may encompass 0-5 residues
<220> FEATURE:
<221> NAME/KEY: MOD_RES
<222> LOCATION: (125)..(125)
<223> OTHER INFORMATION: Any amino acid
<220> FEATURE:
<221> NAME/KEY: MOD_RES
<222> LOCATION: (135)..(135)
<223> OTHER INFORMATION: Any amino acid
<220> FEATURE:
<221> NAME/KEY: MOD_RES
<222> LOCATION: (138)..(163)
<223> OTHER INFORMATION: Any amino acid
<220> FEATURE:
<221> NAME/KEY: MISC_FEATURE
<222> LOCATION: (138)..(163)
<223> OTHER INFORMATION: This region may encompass 0-26 residues

<400> SEQUENCE: 232

```
Trp Gly Gly Cys Pro Ala Pro Met Glu Thr Ile Thr Asp Pro Cys Lys
1               5                   10                  15

Gln Pro Lys Tyr Pro Ile Pro Asn Asn Leu Leu Gln Thr Thr Ser Leu
            20                  25                  30

Gln Xaa Pro Thr Thr Pro Ile Glu Thr Tyr Leu Tyr Lys Phe Asp Glu
        35                  40                  45

Arg Arg Gly Leu Leu Thr Lys Lys Ala Ala Lys Arg Ile Lys Lys Asp
    50                  55                  60

Xaa Thr Thr Glu Thr Thr Leu Phe Thr Asp Thr Gly Xaa Xaa Thr Ser
65                  70                  75                  80

Thr Thr Leu Pro Thr Xaa Xaa Gln Thr Glu Thr Thr Gln Glu Glu Xaa
                85                  90                  95

Thr Ser Glu Glu Glu Xaa Xaa Xaa Xaa Xaa Glu Thr Leu Leu Gln Gln
            100                 105                 110

Leu Gln Gln Leu Arg Arg Lys Gln Lys Gln Leu Arg Xaa Arg Ile Leu
        115                 120                 125

Gln Leu Leu Gln Leu Leu Xaa Leu Leu Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa
```

<210> SEQ ID NO 233
<211> LENGTH: 203
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (104)..(104)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (120)..(121)
<223> OTHER INFORMATION: Any amino acid
<220> FEATURE:
<221> NAME/KEY: MOD_RES
<222> LOCATION: (125)..(125)
<223> OTHER INFORMATION: Any amino acid
<220> FEATURE:
<221> NAME/KEY: MOD_RES
<222> LOCATION: (170)..(170)
<223> OTHER INFORMATION: Any amino acid

<400> SEQUENCE: 233

```
Thr Ile Pro Leu Lys Gln Trp Gln Pro Glu Ser Ile Arg Lys Cys Lys
1               5                   10                  15

Ile Lys Gly Tyr Gly Thr Leu Val Leu Gly Ala Glu Gly Arg Gln Phe
            20                  25                  30

Tyr Cys Tyr Thr Asn Glu Lys Asp Glu Tyr Thr Pro Pro Lys Ala Pro
        35                  40                  45

Gly Gly Gly Gly Phe Gly Val Glu Leu Phe Ser Leu Glu Tyr Leu Tyr
    50                  55                  60

Glu Gln Trp Lys Ala Arg Asn Asn Ile Trp Thr Lys Ser Asn Xaa Tyr
65                  70                  75                  80

Lys Asp Leu Cys Arg Tyr Thr Gly Cys Lys Ile Thr Phe Tyr Arg His
                85                  90                  95

Pro Thr Thr Asp Phe Ile Val Xaa Tyr Ser Arg Gln Pro Pro Phe Glu
            100                 105                 110

Ile Asp Lys Xaa Thr Tyr Met Xaa Xaa His Pro Gln Xaa Leu Leu Leu
        115                 120                 125

Arg Lys His Lys Lys Ile Ile Leu Ser Lys Ala Thr Asn Pro Lys Gly
    130                 135                 140

Lys Leu Lys Lys Lys Ile Lys Ile Lys Pro Pro Lys Gln Met Leu Asn
145                 150                 155                 160

Lys Trp Phe Phe Gln Lys Gln Phe Ala Xaa Tyr Gly Leu Val Gln Leu
                165                 170                 175

Gln Ala Ala Ala Cys Asx Leu Arg Tyr Pro Arg Leu Gly Cys Cys Asn
            180                 185                 190

Glu Asn Arg Leu Ile Thr Leu Tyr Tyr Leu Asn
        195                 200
```

<210> SEQ ID NO 234
<211> LENGTH: 162
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (23)..(23)

<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (58)..(58)
<223> OTHER INFORMATION: Leu or Ile
<220> FEATURE:
<221> NAME/KEY: MOD_RES
<222> LOCATION: (84)..(84)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (105)..(105)
<223> OTHER INFORMATION: Any amino acid
<220> FEATURE:
<221> NAME/KEY: MOD_RES
<222> LOCATION: (111)..(111)
<223> OTHER INFORMATION: Leu or Ile
<220> FEATURE:
<221> NAME/KEY: MOD_RES
<222> LOCATION: (113)..(113)
<223> OTHER INFORMATION: Any amino acid
<220> FEATURE:
<221> NAME/KEY: MOD_RES
<222> LOCATION: (154)..(154)
<223> OTHER INFORMATION: Any amino acid
<220> FEATURE:
<221> NAME/KEY: MOD_RES
<222> LOCATION: (156)..(156)
<223> OTHER INFORMATION: Any amino acid

<400> SEQUENCE: 234

```
Leu Pro Ile Val Val Ala Arg Tyr Asn Pro Ala Xaa Asp Thr Gly Lys
1               5                   10                  15

Gly Asn Lys Xaa Trp Leu Xaa Ser Thr Leu Asn Gly Ser Xaa Trp Ala
            20                  25                  30

Pro Pro Thr Thr Asp Lys Asp Leu Ile Ile Glu Gly Leu Pro Leu Trp
        35                  40                  45

Leu Ala Leu Tyr Gly Tyr Trp Ser Tyr Xaa Lys Lys Val Lys Lys Asp
    50                  55                  60

Lys Gly Ile Leu Gln Ser His Met Phe Val Val Lys Ser Pro Ala Ile
65                  70                  75                  80

Gln Pro Leu Xaa Thr Ala Thr Thr Gln Xaa Thr Phe Tyr Pro Xaa Ile
                85                  90                  95

Asp Asn Ser Phe Ile Gln Gly Lys Xaa Pro Tyr Asp Glu Pro Xaa Thr
            100                 105                 110

Xaa Asn Gln Lys Lys Leu Trp Tyr Pro Thr Leu Glu His Gln Gln Glu
        115                 120                 125

Thr Ile Asn Ala Ile Val Glu Ser Gly Pro Tyr Val Pro Lys Leu Asp
    130                 135                 140

Asn Gln Lys Asn Ser Thr Trp Glu Leu Xaa Tyr Xaa Tyr Thr Phe Tyr
145                 150                 155                 160

Phe Lys
```

<210> SEQ ID NO 235
<211> LENGTH: 177

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (81)..(82)
<223> OTHER INFORMATION: Any amino acid
<220> FEATURE:
<221> NAME/KEY: MISC_FEATURE
<222> LOCATION: (81)..(82)
<223> OTHER INFORMATION: This region may encompass 0-2 residues
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (119)..(124)
<223> OTHER INFORMATION: Any amino acid
<220> FEATURE:
<221> NAME/KEY: MISC_FEATURE
<222> LOCATION: (119)..(124)
<223> OTHER INFORMATION: This region may encompass 1-6 residues
<220> FEATURE:
<221> NAME/KEY: MOD_RES
<222> LOCATION: (168)..(177)
<223> OTHER INFORMATION: Any amino acid
<220> FEATURE:
<221> NAME/KEY: MISC_FEATURE
<222> LOCATION: (168)..(177)
<223> OTHER INFORMATION: This region may encompass 1-10 residues

<400> SEQUENCE: 235

Trp Gly Gly Pro Gln Ile Pro Asp Gln Pro Val Glu Asp Pro Lys Xaa
1               5                   10                  15

Gln Gly Thr Tyr Pro Val Pro Asp Thr Xaa Gln Gln Thr Ile Gln Ile
            20                  25                  30

Xaa Asn Pro Leu Lys Gln Lys Pro Glu Thr Met Phe His Asp Trp Asp
        35                  40                  45

Tyr Arg Arg Gly Ile Ile Thr Ser Thr Ala Leu Lys Arg Met Gln Glu
    50                  55                  60

Asn Leu Glu Thr Asp Ser Ser Phe Xaa Ser Asp Ser Glu Glu Thr Pro
65                  70                  75                  80

Xaa Xaa Lys Lys Lys Lys Arg Leu Thr Xaa Glu Leu Pro Xaa Pro Gln
                85                  90                  95

Glu Glu Thr Glu Glu Ile Gln Ser Cys Leu Leu Ser Leu Cys Glu Glu
            100                 105                 110

Ser Thr Cys Gln Glu Glu Xaa Xaa Xaa Xaa Xaa Xaa Glu Asn Leu Gln
        115                 120                 125
```

-continued

```
Gln Leu Ile His Gln Gln Gln Gln Gln Gln Gln Gln Leu Lys His Asn
    130                 135                 140

Ile Leu Lys Leu Leu Ser Asp Leu Lys Glx Lys Gln Arg Leu Leu Gln
145                 150                 155                 160

Leu Gln Thr Gly Ile Leu Glu Xaa Xaa Xaa Xaa Xaa Xaa Xaa Xaa Xaa
                165                 170                 175

Xaa
```

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

-continued

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 300
gccauuuuaa guagcugacg ucaaggauug acguaaaggu uaaaggucau ccucggcgga 60
agcuacacaa aauggu 76

<210> SEQ ID NO 301
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 301
gcguacguca caagucacgu ggaggggacc cgcuguaacc cggaaguagg ccccgucacg 60
ugacuuacca cgugugua 78

<210> SEQ ID NO 302
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 302
gccauuuuaa guagcugacg ucaaggauug acgugaaggu uaaaggucau ccucggcgga 60
agcuacacaa aauggug 77

<210> SEQ ID NO 303
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 303
gcacacguca uaagucacgu ggugggggacc cgcuguaacc cggaaguagg ccccgucacg 60
ugauuuguca cgugugua 78

<210> SEQ ID NO 304
<211> LENGTH: 66
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 304
cuuccggguc auaggucaca ccuacgucac aagucacgug gggaggguug gcguauagcc 60
cggaag 66

<210> SEQ ID NO 305
<211> LENGTH: 68
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 305
gccggggggc ugccgccccc cccggggaaa gggggggggcc ccccccgggg gggggguuugc 60 cccccggc 68

<210> SEQ ID NO 306
<211> LENGTH: 78

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 306
auacgucauc agucacgugg gggaaggcgu gccuaaaccc ggaagcaucc ucguccacgu 60
gacugugacg ugugugc 78

<210> SEQ ID NO 307
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 307
cauuuuaagu aaggcggaag cagcucggcg uacacaaaau ggcggcggag cacuuccggc 60
uugcccaaaa ugg 73

<210> SEQ ID NO 308
<211> LENGTH: 71
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 308
gucacaaguc acguggggag gguuggcguu uaacccggaa gccaauccuc uuacguggcc 60
ugucacguga c 71

<210> SEQ ID NO 309
<211> LENGTH: 70
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 309
cgaccgcguc ccgaaggcgg guacccgagg ugaguuuaca caccgagguu aagggccaau 60
ucgggcuugg 70

<210> SEQ ID NO 310
<211> LENGTH: 59
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 310
cgcgguaucg uagccgacgc ggaccccguu uucggggccc ccgcggggcu cucggcgcg 59

<210> SEQ ID NO 311
<211> LENGTH: 78
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 311
cgccauuuug ugauacgcgc guccccuccc ggcuuccgua caacgucagg cggggcgugg 60
ccguaucaga aaauggcg 78

<210> SEQ ID NO 312
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 312
gcuacgucau aagucacgug acugggcagg uacuaaaccc ggaaguaucc ucggucacgu 60
ggccugucac guaguug 77

<210> SEQ ID NO 313
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 313
ggcusugacg ucaaagucac gugggraggg uggcguuaaa cccggaaguc auccucguca 60
cgugaccuga cgucacagcc 80

<210> SEQ ID NO 314
<211> LENGTH: 66
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 314
gcccguccgc ggcgagagcg cgagcgaagc gagcgaucga gcgucccgug ggcgggugcc 60
gaaggu 66

<210> SEQ ID NO 315
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 315
gguugugacg ucaaagucac guggggaggg cggcguuaaa cccggaaguc auccucguca 60
cgugaccuga cgucacggcc 80

<210> SEQ ID NO 316
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 316
gcccguccgc ggcgagagcg cgagcgaagc gagcgaucga gcgucccgug ggcgggugcc 60
guaggug 67

<210> SEQ ID NO 317
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 317
gcccguccgc ggcgagagcg cgagcgaagc gagcgaucga gcgucccgug ggcgggugcc 60
guaggug 67

<210> SEQ ID NO 318
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 318
ggcugugacg ucaaagucac guggggaggg cggcguuaaa cccggaaguc auccucguca 60
cgugaccuga cgucacggcc 80

<210> SEQ ID NO 319
<211> LENGTH: 79
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 319
agaccacgug guaagucacg ugggggcagc ugcuguaaac ccggaaguag cugacccgcg 60
ugacugguca cgugaccug 79

<210> SEQ ID NO 320
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
cgccauuuua uaauacgcgc guccccuccc ggcuuccgua cuacgucagg cggggcgugg 60
ccguauuaga aaauggug 78

<210> SEQ ID NO 321
<211> LENGTH: 72
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 321
uaaguaaggc ggaaccaggc ugucacccug ugucaaaggu caagggacag ccuuccggcu 60
ugcacaaaau gg 72

<210> SEQ ID NO 322

<211> LENGTH: 78
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 322
ugccuacguc auaagucacg uggggacggc ugcuguaaac acggaaguag cugacccgcg 60
ugacuuguca cgugagca 78

<210> SEQ ID NO 323
<211> LENGTH: 72
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 323
uuguguaagg cggaacaggc ugacaccccg ugucaaaggu caggggucag ccuccgcuuu 60
gcaccaaaug gu 72

<210> SEQ ID NO 324
<211> LENGTH: 79
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 324
uaccuacguc auaagucacg ugggaagagc ugcugugaac cuggaaguag cugacccgcg 60
uggcuuguca cgugagugc 79

<210> SEQ ID NO 325
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325
uuuuccuggc ccguccgcgg cgagagcgcg agcgaagcga gcgaucgggc gucccgaggg 60
cgggugccgg aggug 75

<210> SEQ ID NO 326
<211> LENGTH: 68
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326
aaagugagug gggccagacu ucgccauagg gccuuuaacu uccgggugcg ucugggggcc 60
gccauuuu 68

<210> SEQ ID NO 327
<211> LENGTH: 73
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 327
gugacguuac ucucacguga ugggggcgug cucuaacccg gaagcauccu cgaccacgug     60
acugugacgu cac                                                        73

<210> SEQ ID NO 328
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
agcgucuacu acguacacuu ccuggggugu guccugccac uguauauaaa ccagaggggu     60
gacgaauggu agagu                                                      75

<210> SEQ ID NO 329
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
gugacgucaa agucacgugg ugacggccau uuuaacccgg aaguggcugu ugucacguga     60
cuugacguca cgg                                                        73

<210> SEQ ID NO 330
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
gcuuuagacg ccauuuuagg cccucgcggg cacccguagg cgcguuuuaa ugacgucacg     60
gc                                                                    62

<210> SEQ ID NO 331
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
cacccguagg cgcguuuuaa ugacgucacg gcagccauuu ugucgugacg uuugagacac     60 gugaugggggg cgu                                                       73

<210> SEQ ID NO 332
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
gucgugacgu uugagacacg ugaugggggc gugccuaaac ccggaagcau cccuggucac 60
gugacucuga cgucacggcg 80

<210> SEQ ID NO 333
<211> LENGTH: 77
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 333
cgaaagugag uggggccaga cuucgccaua aggccuuuaa cuuccgggug cgugugggggg 60 ccgccauuuu agcuucg 77

<210> SEQ ID NO 334
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 334
cugugacguc aaagucacgu ggggagggcg gcguguaacc cggaagucau ccucgucacg 60
ugaccugacg ucacgg 76

<210> SEQ ID NO 335
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 335
cuguccgcca ucuugugacu uccuuccgcu uuuucaaaaa aaaagaggaa guaugacgua 60
gcggcggggg ggc 73

<210> SEQ ID NO 336
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 336
gguagaguuu uuuccgcccg uccgcagcga ggacgcgagc gcagcgagcg gccgagcgac 60
ccguggg 67

<210> SEQ ID NO 337
<211> LENGTH: 80
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 337
gcugugacgu uucagucacg uggggaggga acgccuaaac ccggaagcgu cccuggucac 60
gugauuguga cgucacggcc 80

<210> SEQ ID NO 338
<211> LENGTH: 63
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 338
ccgccauuuu gugacuuccu uccgcuuuuu caaaaaaaaa gaggaagugu gacguagcgg 60
cgg 63

<210> SEQ ID NO 339
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 339
gacugugacg ucaaagucac guggggaggg cggcguguaa cccggaaguc auccucguca 60
cgugaccuga cgucacgg 78

<210> SEQ ID NO 340
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 340
cuguccgcca ucuugugacu uccuuccgcu uuuucaaaaa aaaagaggaa guaugacgug 60
gcggcggggg ggc 73

<210> SEQ ID NO 341
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 341
gguugugacg ucaaagucac guggggaggg cggcguguaa cccggaaguc auccucguca 60
cgugaccuga cgucacggcc 80

<210> SEQ ID NO 342
<211> LENGTH: 65
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 342
cccgccaucu ugugacuucc uuccgcuuuu ucaaaaaaaa agaggaagug ugacguagcg 60
gcggg 65

<210> SEQ ID NO 343
<211> LENGTH: 67

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 343
gcccguccgc ggcgagagcg cgagcgaagc gagcgaucga gcgucccgug ggcgggugcc 60
guaggug 67

<210> SEQ ID NO 344
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 344
gacugugacg ucaaagucac guggggagga gggcguguaa cccggaaguc auccucguca 60
cgugaccuga cgucacgg 78

<210> SEQ ID NO 345
<211> LENGTH: 62
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 345
ucgcgucuua gugacgucac ggcagccauc uugguccuga cgucacuguc acguggggag 60
gg 62

<210> SEQ ID NO 346
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 346
ugacgucacu gucacguggg gagggaacac gugaacccgg aagugucccu ggucacguga 60
caugacguca cggccg 76

<210> SEQ ID NO 347
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 347
cgccauuuua aguaagcaug gcgggcggug augucaaaug uuaaagguca cagccgguca 60
ugcuugcaca aaauggcg 78

<210> SEQ ID NO 348
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 348
cgccauuuua aguaagcaug gcgggcggug acgugcaaug ucaaagguca cagccuguca    60
ugcuugcaca aaauggcg                                                 78

<210> SEQ ID NO 349
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ccaucuuaag uaguugaggc ggacgguggc gucgguucaa aggucaccau cagccacacc    60
uacucaaaau gg                                                       72

<210> SEQ ID NO 350
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
gccugucaug cuugcacaaa auggcggacu uccgcuuccg ggucgccgcc auauuugguc    60
acgugac                                                             67

<210> SEQ ID NO 351
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
gccauuuuaa guagcugacg ucaaggauug acguaaaggu uaaaggucau ccucggcgga    60
agcuacacaa aauggu                                                   76

<210> SEQ ID NO 352
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
gccauuuuaa guagcugacg ucaaggauug acguaaaggu uaaaggucau ccucggcgga    60
agcuacacaa aauggu                                                   76

<210> SEQ ID NO 353
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
gcauacguca caagucacgu gggggggacc cgcuguaacc cggaaguagg ccccgucacg 60
ugacuuacca cgugugua 78

<210> SEQ ID NO 354
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 354
gccauuuuaa guagcugacg ucaaggauug acgugaaggu uaaaggucau ccucggcgga 60
agcuacacaa aauggu 76

<210> SEQ ID NO 355
<211> LENGTH: 78
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 355
gcacacguca uaagucacgu ggugggggacc cgcuguaacc cggaaguagg ccccgucacg 60
ugauuuguca cgugugua 78

<210> SEQ ID NO 356
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 356
gccauuuuaa gucagcucug gggaggcgug acuuccaguu caaaggucau ccucaccaua 60
acuggcacaa aauggc 76

<210> SEQ ID NO 357
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 357
gccauuuuaa guagcugacg ucaaggauug acguaaaggu uaaaggucau ccucggcgga 60
agcuacacaa aauggu 76

<210> SEQ ID NO 358
<211> LENGTH: 78
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 358
gcauacguca caagucacgu ggaggggaca cgcuguaacc cggaaguagg ccccgucacg 60
ugacuuacca cgugugua 78

<210> SEQ ID NO 359
<211> LENGTH: 79
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 359
gcgccauguu aaguggcugu cgccgaggau ugacgucaca guucaaaggu cauccucgac 60
gguaaccgca aacauggcg 79

<210> SEQ ID NO 360
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 360
caugcgucau aagucacaug acaggggucc acuuaaacac ggaaguaggc cccgacaugu 60
gacucgucac gugugu 76

<210> SEQ ID NO 361
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 361
uggcagcacu uccgaauggc ugaguuuucc acgcccgucc gcggagaggg agccacggag 60
gugaucccga acg 73

<210> SEQ ID NO 362
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 362
gccauuuuaa gucagcgcug gggaggcaug acuguaaguu caaaggucau ccucaccgga 60
acugacacaa aauggccg 78

<210> SEQ ID NO 363
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 363
gccaucuuaa guggcugucg ccgaggauug acgucacagu ucaaagguca uccucggcgg 60
uaaccgcaaa gauggcgguc 80

<210> SEQ ID NO 364
<211> LENGTH: 76
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 364
auacgucaua agucacaugu cuaggggucc acuuaaacac ggaaguaggc cccgacaugu     60
gacucgucac gugugu                                                     76

<210> SEQ ID NO 365
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
ccauuuuaag uaaggcggaa gcagcugucc cuguaacaaa auggcggcga cagccuuccg     60
cuuugcacaa aauggag                                                    77

<210> SEQ ID NO 366
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
gccaucuuaa guggcugucg cugaggauug acgucacagu ucaaagguca uccucggcgg     60
uaaccgcaaa gauggcgguc                                                 80

<210> SEQ ID NO 367
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
cauacgucau aagucacaug acaggagucc acuuaaacac ggaaguaggc cccgacaugu     60
gacucgucac gugugu                                                     76

<210> SEQ ID NO 368
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
cgccaucuua aguggcuguc gccgaggauu ggcgucacag uucaaagguc auccucggcg     60
guaaccgcaa agauggcggu                                                 80

<210> SEQ ID NO 369
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
cauacgucau aagucacaug acaggggucc acuuaaacac ggaaguaggc cccgacaugu 60
gacucgucac gugugu 76

<210> SEQ ID NO 370
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 370
gcauacguca caagucacgu gggggggacc cgcuguaacc cggaaguagg ccccgucacg 60
ugacuuacca cguggugu 78

<210> SEQ ID NO 371
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 371
ccgccauuuu aggcuguugc cgggcguuug acuuccgugu uaaaggucaa acacccagcg 60
acaccaaaaa auggccg 77

<210> SEQ ID NO 372
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 372
cuacgucaua agucacguga cagggagggg cgacaaaccc ggaagucauc cucgcccacg 60
ugacuuacca cguggug 77

<210> SEQ ID NO 373
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 373
gccauuuuaa guaggugacg uccaggacug acguaaaguu caaaggucau ccucggcgga 60
accuauacaa aauggcg 77

<210> SEQ ID NO 374
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 374
cuacgucaua agucacgugg ggacggcugu acuuaaacac ggaaguaggc cccgucacgu 60
gauuuaccac guggug 76

<210> SEQ ID NO 375
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 375
gccauuuuaa guaaggcgga agagcucuag cuauacaaaa uggcggcgga gcacuuccgc 60
uuugcccaaa aug 73

<210> SEQ ID NO 376
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 376
gccauuuuaa guagcugacg ucaaggauug acguagaggu uaaaggucau ccucggcgga 60
agcuacacaa aauggug 77

<210> SEQ ID NO 377
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
gcauacguca caagucacgu gggggggacc cgcuguaacc cggaaguagg ccccgucacg 60
ugacuuacca cgugugua 78

<210> SEQ ID NO 378
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 378
ggcgccauuu uaaguaagca uggcgggcgg cgacgucaca ugucaaaggu caccgcacuu 60
ccgugcuugc acaaaauggc 80

<210> SEQ ID NO 379
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 379
ugcuacguca ucgagacacg uggugccagc agcuguaaac ccggaagucg cugacacacg 60
ugucuuguca cgu 73

<210> SEQ ID NO 380
<211> LENGTH: 78
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 380
gccauuuuaa guaagcaccg ccuagggaug acguauaagu ucaaagguca uccucagccg 60
gaacuuacac aaaauggu 78

<210> SEQ ID NO 381
<211> LENGTH: 72
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 381
acgucauaug ucacgugggg aggcccugcu gcgcaaacgc ggaaguaggc cccgucacgu 60
gucauaccac gu 72

<210> SEQ ID NO 382
<211> LENGTH: 77
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 382
ccauuuuaag uaaggcggaa gcagcuccac uuucucacaa aauggcggcg gggcacuucc 60
ggcuugccca aaauggc 77

<210> SEQ ID NO 383
<211> LENGTH: 72
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383
ccauuuuaag uaaggcggaa guuucuccac uauacaaaau ggcggcggag cacuuccggc 60
uugcccaaaa ug 72

<210> SEQ ID NO 384
<211> LENGTH: 72
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 384
ccaucuuaag uaguugaggc ggacgguggc gugaguucaa aggucaccau cagccacacc 60
uacucaaaau gg 72

<210> SEQ ID NO 385
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 385
cgccaucuua aguaguugag gcggacggug gcgugaguuc aaaggucacc aucagccaca 60
ccuacucaaa auggug 76

<210> SEQ ID NO 386
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 386
uuucggaccu ucggcgucgg gggggucggg ggcuuuacua aacagacucc gagaugccau 60
uggacacuga ggg 73

<210> SEQ ID NO 387
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 387
ccauuuuaag uaggugccgu ccagcacugc uguuccgggu uaaagggcau ccucggcgga 60
accuauacaa aauggc 76

<210> SEQ ID NO 388
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 388
cuacgucauc gaugacgugg ggaggcguac uaugaaacgc ggaaguaggc cccgcuacgu 60
caucaucacg ugg 73

<210> SEQ ID NO 389
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 389
ccauuuuaag uaaggcggaa gagcugcucu auauacaaaa uggcggagga gcacuuccgg 60
cuugcccaaa aug 73

<210> SEQ ID NO 390
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 390
ugccuacgua acaagucacg uggggagggu uggcguauaa cccggaaguc aauccuccca 60
cguggccugu cacgu 75

<210> SEQ ID NO 391
<211> LENGTH: 72
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 391
uaaguaaggc ggaaccaggc ugucaccccg ugucaaaggu caggggucag ccuuccgcuu 60
uacacaaaau gg 72

<210> SEQ ID NO 392
<211> LENGTH: 72
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 392
uaaguaaggc ggaaccaggc ugucaccccg ugucaaaggu caggggucag ccuuccgcuu 60
uacacaaaau gg 72

<210> SEQ ID NO 393
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 393
gcagccauuu uaagucagcu ucggggaggg ucacgcaaag uucaaagguc auccucaccg 60
gaacugguac aaaauggccg 80

<210> SEQ ID NO 394
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 394
ugcuacguca uaagugacgu agcugguguc ugcuguaaac acggaaguag gccccgccac 60
gucacuuguc acgu 74

<210> SEQ ID NO 395
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 395
aguagcugac gucaaggauu gac 23

<210> SEQ ID NO 396
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
caagucacgu ggaggggacc cg 22

<210> SEQ ID NO 397
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
aaguagcuga cgucaaggau ugacg 25

<210> SEQ ID NO 398
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
auaagucacg uggugggac ccg 23

<210> SEQ ID NO 399
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
uggggagggu uggcguauag cccgga 26

<210> SEQ ID NO 400
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400 cccccccgg gggggguuu gccc 24

<210> SEQ ID NO 401
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
aucagucacg ugggggaagg cgugc 25

<210> SEQ ID NO 402
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 402
aaguaaggcg gaagcagcuc gg 22

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 403
agucacgugg ggaggguugg c 21

<210> SEQ ID NO 404
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 404
cccgaaggcg gguacccgag gu 22

<210> SEQ ID NO 405
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 405
uaucguagcc gacgcggacc ccg 23

<210> SEQ ID NO 406
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 406
auuuugugau acgcgcgucc ccuccc 26

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 407
aagucacgug acugggcagg u 21

<210> SEQ ID NO 408

<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 408
ugacgucaaa gucacguggg ragggu 26

<210> SEQ ID NO 409
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 409
gaucgagcgu cccgugggcg ggu 23

<210> SEQ ID NO 410
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 410
ugacgucaaa gucacguggg gagggcgg 28

<210> SEQ ID NO 411
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 411
gaucgagcgu cccgugggcg ggu 23

<210> SEQ ID NO 412
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 412
gaucgagcgu cccgugggcg ggu 23

<210> SEQ ID NO 413
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 413
ugacgucaaa gucacguggg gagggcgg 28

<210> SEQ ID NO 414
<211> LENGTH: 26

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 414
acgugguaag ucacgugggg gcagcu 26

<210> SEQ ID NO 415
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 415
auuuuauaau acgcgcgucc ccucc 25

<210> SEQ ID NO 416
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 416
aagggacagc cuuccggcuu gc 22

<210> SEQ ID NO 417
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 417
cauaagucac guggggacgg cugcu 25

<210> SEQ ID NO 418
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 418
uaaggcggaa caggcugaca cccc 24

<210> SEQ ID NO 419
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 419
uacgucauaa gucacguggg aagagcug 28

<210> SEQ ID NO 420
<211> LENGTH: 22
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 420
ucgggcgucc cgagggcggg ug 22

<210> SEQ ID NO 421
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 421
aaagugagug gggccagacu ucgcc 25

<210> SEQ ID NO 422
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 422
cucucacgug augggggcgu gc 22

<210> SEQ ID NO 423
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 423
ucuacuacgu acacuuccug gggugugu 28

<210> SEQ ID NO 424
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 424
uggcuguugu cacgugacuu ga 22

<210> SEQ ID NO 425
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 425
agacgccauu uuaggcccuc gcgg 24

<210> SEQ ID NO 426
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 426
ugucgugacg uuugagacac gugau 25

<210> SEQ ID NO 427
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 427
ugacguuuga gacacgugau gggggcgugc 30

<210> SEQ ID NO 428
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 428
agugaguggg gccagacuuc gc 22

<210> SEQ ID NO 429
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 429
ugugacguca aagucacgug gggagggcgg 30

<210> SEQ ID NO 430
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 430
aaaagaggaa guaugacgua gcggcgg 27

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 431
agcgagcggc cgagcgaccc g 21

<210> SEQ ID NO 432
<211> LENGTH: 24
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 432
uucagucacg uggggaggga acgc 24

<210> SEQ ID NO 433
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
aaaagaggaa gugugacgua gcgg 24

<210> SEQ ID NO 434
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ugugacguca aagucacgug gggagggcgg 30

<210> SEQ ID NO 435
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
aaaagaggaa guaugacgug gcgg 24

<210> SEQ ID NO 436
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
ugacgucaaa gucacguggg gagggcgg 28

<210> SEQ ID NO 437
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
aaaaaagagg aagugugacg uagcggcgg 29

<210> SEQ ID NO 438
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 438
gaucgagcgu cccgugggcg ggu 23

<210> SEQ ID NO 439
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 439
ugugacguca aagucacgug gggaggaggg 30

<210> SEQ ID NO 440
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 440
uugguccuga cgucacuguc a 21

<210> SEQ ID NO 441
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 441
cgucacuguc acguggggag ggaacac 27

<210> SEQ ID NO 442
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 442
uaaguaagca uggcgggcgg ugau 24

<210> SEQ ID NO 443
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 443
aaguaagcau ggcgggcggu ga 22

<210> SEQ ID NO 444
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 444
uaaguaguug aggcggacgg uggc 24

<210> SEQ ID NO 445
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 445
ucaugcuugc acaaaauggc ggacuuccg 29

<210> SEQ ID NO 446
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 446
aguagcugac gucaaggauu gac 23

<210> SEQ ID NO 447
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 447
aguagcugac gucaaggauu gac 23

<210> SEQ ID NO 448
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 448
acaagucacg ugggggggac ccg 23

<210> SEQ ID NO 449
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 449
aaguagcuga cgucaaggau ugacg 25

<210> SEQ ID NO 450
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 450
auaagucacg uggugggac ccg 23

<210> SEQ ID NO 451
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 451
aagucagcuc uggggaggcg ugacuu 26

<210> SEQ ID NO 452
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 452
aguagcugac gucaaggauu gac 23

<210> SEQ ID NO 453
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 453
caagucacgu ggaggggaca cg 22

<210> SEQ ID NO 454
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 454
uguuaagugg cugucgccga ggauuga 27

<210> SEQ ID NO 455
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 455
uaagucacau gacagggguc ca 22

<210> SEQ ID NO 456
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 456
cggagaggga gccacggagg ug 22

<210> SEQ ID NO 457
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 457
aagucagcgc uggggaggca uga 23

<210> SEQ ID NO 458
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 458
ucuuaagugg cugucgccga ggauugac 28

<210> SEQ ID NO 459
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 459
aagucacaug ucuagggguc cacu 24

<210> SEQ ID NO 460
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 460
aaguaaggcg gaagcagcug ucc 23

<210> SEQ ID NO 461
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 461
aucuuaagug gcugucgcug aggauugac 29

<210> SEQ ID NO 462
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 462
uaagucacau gacaggaguc cacu 24

<210> SEQ ID NO 463
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 463
aaguggcugu cgccgaggau ug 22

<210> SEQ ID NO 464
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 464
uaagucacau gacaggguc ca 22

<210> SEQ ID NO 465
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 465
acaagucacg ugggggggac ccg 23

<210> SEQ ID NO 466
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 466
auuuuaggcu guugccgggc guuugacu 28

<210> SEQ ID NO 467
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 467
auaagucacg ugacagggag ggg 23

<210> SEQ ID NO 468
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 468
aaguagguga cguccaggac u 21

<210> SEQ ID NO 469
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 469
cauaagucac guggggacgg cugu 24

<210> SEQ ID NO 470
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 470
uaaguaaggc ggaagagcuc uagcua 26

<210> SEQ ID NO 471
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 471
aguagcugac gucaaggauu gac 23

<210> SEQ ID NO 472
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 472
acaagucacg ugggggggac ccg 23

<210> SEQ ID NO 473
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 473
uaaguaagca uggcgggcgg cgac 24

<210> SEQ ID NO 474
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 474
aucgagacac guggugccag cagcu 25

<210> SEQ ID NO 475
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 475
ucauccucag ccggaacuua cacaaaaugg 30

<210> SEQ ID NO 476
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 476
auaugucacg uggggaggcc cugcug 26

<210> SEQ ID NO 477
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 477
aaguaaggcg gaagcagcuc cacuuu 26

<210> SEQ ID NO 478
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 478
aaguaaggcg gaaguuucuc cacu 24

<210> SEQ ID NO 479
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 479
uaaguaguug aggcggacgg uggc 24

<210> SEQ ID NO 480
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 480
uaaguaguug aggcggacgg ugg 23

<210> SEQ ID NO 481
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 481
gaccuucggc gucgggggg ucggggg 27

<210> SEQ ID NO 482
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 482
auccucggcg gaaccuaua 19

<210> SEQ ID NO 483
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 483
aucgaugacg uggggaggcg uacuau 26

<210> SEQ ID NO 484
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 484
uggcggagga gcacuuccgg cuug 24

<210> SEQ ID NO 485
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 485
aacaagucac guggggaggg uuggc 25

<210> SEQ ID NO 486
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 486
aggggucagc cuuccgcuuu a 21

<210> SEQ ID NO 487

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 487
aggggucagc cuuccgcuuu a 21

<210> SEQ ID NO 488
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 488
uaagucagcu ucggggaggg ucac 24

<210> SEQ ID NO 489
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 489
ucauaaguga cguagcuggu gucugcu 27

<210> SEQ ID NO 490
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 490
cauccucggc ggaagcuaca caa 23

<210> SEQ ID NO 491
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 491
ggccccguca cgugacuuac cac 23

<210> SEQ ID NO 492
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 492
ucauccucgg cggaagcuac acaa 24

<210> SEQ ID NO 493
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 493
ggccccguca cgugauuugu cac 23

<210> SEQ ID NO 494
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 494
ccgggucaua ggucacaccu acgucac 27

<210> SEQ ID NO 495
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 495
ggcugccgcc ccccccgggg aaaggggg 28

<210> SEQ ID NO 496
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 496
auccucgucc acgugacugu ga 22

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 497
gagcacuucc ggcuugccca a 21

<210> SEQ ID NO 498
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 498
caauccucuu acguggccug 20

<210> SEQ ID NO 499
<211> LENGTH: 24
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 499
cgagguuaag ggccaauucg ggcu 24

<210> SEQ ID NO 500
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 500
gggcccccgc ggggcucucg gcg 23

<210> SEQ ID NO 501
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 501
gcggggcgug gccguaucag aaaaugg 27

<210> SEQ ID NO 502
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 502
ccucggucac guggccugu 19

<210> SEQ ID NO 503
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 503
ccucgucacg ugaccugacg ucacag 26

<210> SEQ ID NO 504
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 504
ccguccgcgg cgagagcgcg agcga 25

<210> SEQ ID NO 505
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 505
auccucguca cgugaccuga cgucacg 27

<210> SEQ ID NO 506
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 506
ccguccgcgg cgagagcgcg agcga 25

<210> SEQ ID NO 507
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 507
ccguccgcgg cgagagcgcg agcga 25

<210> SEQ ID NO 508
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 508
auccucguca cgugaccuga cgucacg 27

<210> SEQ ID NO 509
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 509
cugacccgcg ugacugguca cguga 25

<210> SEQ ID NO 510
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 510
cggggcgugg ccguauuaga aaaugg 26

<210> SEQ ID NO 511
<211> LENGTH: 29
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 511
aguaaggcgg aaccaggcug ucacccugu 29

<210> SEQ ID NO 512
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
uagcugaccc gcgugacuug ucac 24

<210> SEQ ID NO 513
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
ggucagccuc cgcuuugca 19

<210> SEQ ID NO 514
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
gcugacccgc guggcuuguc acgugagu 28

<210> SEQ ID NO 515
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
ggcccguccg cggcgagagc gcgag 25

<210> SEQ ID NO 516
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
uccgggugcg ucugggggcc gccauuu 27

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 517
auccucgacc acgugacugu g 21

<210> SEQ ID NO 518
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 518
auaaaccaga ggggugacga augguagagu 30

<210> SEQ ID NO 519
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 519
caaagucacg uggugacggc cau 23

<210> SEQ ID NO 520
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 520
guaggcgcgu uuuaaugacg ucacgg 26

<210> SEQ ID NO 521
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 521
uaggcgcguu uuaaugacgu cacggcag 28

<210> SEQ ID NO 522
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 522
aucccugguc acgugacucu gacgucacg 29

<210> SEQ ID NO 523
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 523
gcgugugggg gccgccauuu uagcuu 26

<210> SEQ ID NO 524
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 524
ucauccucgu cacgugaccu gacgucacg 29

<210> SEQ ID NO 525
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 525
cgccaucuug ugacuuccuu ccgcuuuuu 29

<210> SEQ ID NO 526
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 526
uagaguuuuu uccgcccguc cg 22

<210> SEQ ID NO 527
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 527
gucccugguc acgugauugu gac 23

<210> SEQ ID NO 528
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 528
cauuuuguga cuuccuuccg cuuuuu 26

<210> SEQ ID NO 529
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 529
ucauccucgu cacgugaccu gacgucacg 29

<210> SEQ ID NO 530
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 530
ccgccaucuu gugacuuccu uccgcuuuuu 30

<210> SEQ ID NO 531
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 531
auccucguca cgugaccuga cgucacg 27

<210> SEQ ID NO 532
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 532
cgccaucuug ugacuuccuu ccgcuuuuuc 30

<210> SEQ ID NO 533
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 533
ccguccgcgg cgagagcgcg agcga 25

<210> SEQ ID NO 534
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 534
ucauccucgu cacgugaccu gacgucacg 29

<210> SEQ ID NO 535
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 535
cuuagugacg ucacggcagc cau 23

<210> SEQ ID NO 536
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 536
gucccugguc acgugacaug acguc 25

<210> SEQ ID NO 537
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 537
cacagccggu caugcuugca caaa 24

<210> SEQ ID NO 538
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 538
acagccuguc augcuugcac aa 22

<210> SEQ ID NO 539
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 539
caccaucagc cacaccuacu caaa 24

<210> SEQ ID NO 540
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 540
cgggucgccg ccauauuugg ucacguga 28

<210> SEQ ID NO 541
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 541
cauccucggc ggaagcuaca caa 23

<210> SEQ ID NO 542
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 542
cauccucggc ggaagcuaca caa 23

<210> SEQ ID NO 543
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 543
ggccccguca cgugacuuac cac 23

<210> SEQ ID NO 544
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 544
ucauccucgg cggaagcuac acaa 24

<210> SEQ ID NO 545
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 545
ggccccguca cgugauuugu cac 23

<210> SEQ ID NO 546
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 546
gucauccuca ccauaacugg cacaa 25

<210> SEQ ID NO 547
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 547
cauccucggc ggaagcuaca caa 23

<210> SEQ ID NO 548
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 548
ggccccguca cgugacuuac cac 23

<210> SEQ ID NO 549
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 549
auccucgacg guaaccgcaa acaug 25

<210> SEQ ID NO 550
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 550
ggccccgaca ugugacucgu c 21

<210> SEQ ID NO 551
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 551
agcacuuccg aauggcugag uuuucca 27

<210> SEQ ID NO 552
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 552
auccucaccg gaacugacac aa 22

<210> SEQ ID NO 553
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 553
cauccucggc gguaaccgca aagaug 26

<210> SEQ ID NO 554
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 554
uaggccccga caugugacuc gu 22

<210> SEQ ID NO 555
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 555
acagccuucc gcuuugcaca a 21

<210> SEQ ID NO 556
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 556
cauccucggc gguaaccgca aagaugg 27

<210> SEQ ID NO 557
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 557
uaggccccga caugugacuc guc 23

<210> SEQ ID NO 558
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 558
uccucggcgg uaaccgcaaa 20

<210> SEQ ID NO 559
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 559
ggccccgaca ugugacucgu c 21

<210> SEQ ID NO 560
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 560
ggccccguca cgugacuuac cac 23

<210> SEQ ID NO 561
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 561
ucaaacaccc agcgacacca aaaaaugg 28

<210> SEQ ID NO 562
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 562
ccucgcccac gugacuuacc ac 22

<210> SEQ ID NO 563
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 563
ccucggcgga accuauacaa 20

<210> SEQ ID NO 564
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564
gccccgucac gugauuuacc ac 22

<210> SEQ ID NO 565
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 565
gcggcggagc acuuccgcuu ugcccaaa 28

<210> SEQ ID NO 566

-continued

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 566
cauccucggc ggaagcuaca caa 23

<210> SEQ ID NO 567
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 567
ggccccguca cgugacuuac cac 23

<210> SEQ ID NO 568
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 568
caccgcacuu ccgugcuugc acaaa 25

<210> SEQ ID NO 569
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 569
ucgcugacac acgugucuug ucac 24

<210> SEQ ID NO 570
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 570
cauuuuaagu aagcaccgcc uagggaugac 30

<210> SEQ ID NO 571
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 571
guaggccccg ucacguguca uaccac 26

<210> SEQ ID NO 572
<211> LENGTH: 25

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 572
ggcggggcac uuccggcuug cccaa 25

<210> SEQ ID NO 573
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 573
cggcggagca cuuccggcuu gcccaa 26

<210> SEQ ID NO 574
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 574
caccaucagc cacaccuacu caaa 24

<210> SEQ ID NO 575
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 575
accaucagcc acaccuacuc aaa 23

<210> SEQ ID NO 576
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 576
gacuccgaga ugccauugga cacugagg 28

<210> SEQ ID NO 577
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 577
aguaggugcc guccagca 18

<210> SEQ ID NO 578
<211> LENGTH: 27
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 578
aaguaggccc cgcuacguca ucaucac 27

<210> SEQ ID NO 579
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 579
aaggcggaag agcugcucua uau 23

<210> SEQ ID NO 580
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 580
caauccuccc acguggccug ucac 24

<210> SEQ ID NO 581
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 581
aaggcggaac caggcuguca ccccgu 26

<210> SEQ ID NO 582
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 582
aaggcggaac caggcuguca ccccgu 26

<210> SEQ ID NO 583
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 583
cauccucacc ggaacuggua caaa 24

<210> SEQ ID NO 584
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
uaggccccgc cacgucacuu gucacg 26

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 690
attcgaatgg ctgagtttat gc 22

<210> SEQ ID NO 691
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 691
cacgaattag ccaagactgg gcac 24

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 692
gctcccactc ctgatttctg 20

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 693
ccttgactac ggtggtttca c 21

<210> SEQ ID NO 694
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 694
tgcaggcatt cgagggcttg tt 22

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 695
tttaaccccc tagtcccagg 20

<210> SEQ ID NO 696
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 696
tttgtgacac aagatggccg acttccttcc tctttagtct tccccaaaga agacaa 56

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 697
gaagcccacc aaaagcaatt 20

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 698
agttcccgtg tctatagtcg a 21

<210> SEQ ID NO 699
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 699
acttcgttac agagtccagg gg 22

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 700
agcaacaggt aatggaggac 20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 701
tggaagctgg ggtctttaac 20

<210> SEQ ID NO 702
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 702
tctaccttag gtgcaaaggg cc 22

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761

<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768
<400> SEQUENCE: 768
000

<210> SEQ ID NO 769
<400> SEQUENCE: 769
000

<210> SEQ ID NO 770
<400> SEQUENCE: 770
000

<210> SEQ ID NO 771
<400> SEQUENCE: 771
000

<210> SEQ ID NO 772
<400> SEQUENCE: 772
000

<210> SEQ ID NO 773
<400> SEQUENCE: 773
000

<210> SEQ ID NO 774
<400> SEQUENCE: 774
000

<210> SEQ ID NO 775
<400> SEQUENCE: 775
000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801
<211> LENGTH: 156
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 801
gcggcggggg ggcggccgcg ttcgcgcgcc gcccaccagg gggtgctgcg cgcccccccc 60
cgcgcatgcg cggggccccc ccccgggggg gctccgcccc cccggccccc ccccgtgcta 120
aacccaccgc gcatgcgcga ccacgccccc gccgcc 156

<210> SEQ ID NO 802
<211> LENGTH: 150
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 802
ccgagcgtta gcgaggagtg cgaccctacc ccctgggccc acttcttcgg agccgcgcgc 60
tacgccttcg gctgcgcgcg gcacctcaga cccccgctcg tgctgacacg cttgcgcgtg 120
tcagaccact tcgggctcgc gggggtcggg 150

<210> SEQ ID NO 803
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 803
gccgccgcgg cggcgggggg cggcgcgctg cgcgcgccgc ccagtagggg gagccatgcg 60
cccccccccg cgcatgcgcg gggccccccc ccgcgggggg ctccgccccc cggccccccc 120
cg 122

<210> SEQ ID NO 804
<211> LENGTH: 111
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 804
cggcccagcg gcggcgcgcg cgcttcgcgc gcgcgccggg gggctccgcc cccccccgcg 60
catgcgcggg gccccccccc gcggggggct ccgccccccg gtcccccccc g 111

<210> SEQ ID NO 805
<211> LENGTH: 115
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 805
cggccgtgcg gcggcgcgcg cgcttcgcgc gcgcgccggg ggctgccgcc cccccccgcg 60
catgcgcgcg gggccccccc ccgcgggggg ctccgccccc cggccccccc ccccg 115

<210> SEQ ID NO 806
<211> LENGTH: 104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 806
cggcggcggc gcgcgcgcta cgcgcgcgcg ccggggggct gccgcccccc ccccgcgcat 60
gcgcggggcc cccccccgcg gggggctccg ccccccggcc cccc 104

<210> SEQ ID NO 807
<211> LENGTH: 108
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 807
ggcggcggcg cgcgcgctac gcgcgcgcgc cggggagctc tgcccccccc cgcgcatgcg 60
cgcgggtccc ccccccgcgg ggggctccgc cccccggtcc cccccccg 108

<210> SEQ ID NO 808
<211> LENGTH: 37
<212> TYPE: PRT
<213> ORGANISM: Unknown
<220> FEATURE:
<223> OTHER INFORMATION: Description of Unknown:
Arginine-rich region

<400> SEQUENCE: 808

Thr Val Val Arg Arg Arg Gly Arg Ser Pro Arg Arg Arg Thr Pro Ser
1 5 10 15

Pro Arg Arg Arg Arg Ser Gln Ser Pro Arg Arg Arg Arg Ser Gln Ser
20 25 30

Arg Glu Ser Gln Cys
35

<210> SEQ ID NO 809
<211> LENGTH: 27
<212> TYPE: PRT
<213> ORGANISM: Unknown
<220> FEATURE:
<223> OTHER INFORMATION: Description of Unknown:
Arginine-rich region

<400> SEQUENCE: 809

Arg Arg Arg Tyr Ala Arg Pro Tyr Arg Arg Arg His Ile Arg Arg Tyr
1               5                   10                  15

Arg Arg Arg Arg Arg His Phe Arg Arg Arg Arg
            20                  25

<210> SEQ ID NO 810
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
cgggtgccgg aggtgagttt acacaccgca gtcaaggggc aattcgggct cgggactggc     60
cgggcymtgg g                                                          71

<210> SEQ ID NO 811
<211> LENGTH: 71
<212> TYPE: DNA
<213> ORGANISM: Unknown
<220> FEATURE:
<223> OTHER INFORMATION: Description of Unknown:
      Alphatorquevirus clade sequence

<400> SEQUENCE: 811
cgggtgccgt aggtgagttt acacaccgca gtcaaggggc aattcgggct cgggactggc     60
cgggctatgg g                                                          71

<210> SEQ ID NO 812
<211> LENGTH: 70
<212> TYPE: DNA
<213> ORGANISM: Unknown
<220> FEATURE:
<223> OTHER INFORMATION: Description of Unknown:
      Alphatorquevirus clade sequence

<400> SEQUENCE: 812
cgggtgccgg aggtgagttt acacaccgca gtcaaggggc aattcgggct cgggactggc     60
cgggcccggg                                                            70

<210> SEQ ID NO 813
<211> LENGTH: 71
<212> TYPE: DNA
<213> ORGANISM: Unknown
<220> FEATURE:
<223> OTHER INFORMATION: Description of Unknown:
      Alphatorquevirus clade sequence

<400> SEQUENCE: 813
cgggtgccgg aggtgagttt acacaccgaa gtcaaggggc aattcgggct caggactggc     60
cgggctttgg g                                                          71

<210> SEQ ID NO 814
<211> LENGTH: 69
<212> TYPE: DNA
<213> ORGANISM: Unknown
<220> FEATURE:
<223> OTHER INFORMATION: Description of Unknown:
      Alphatorquevirus clade sequence

<400> SEQUENCE: 814 cggtgccgg aggtgagttt acacaccgca gtcaaggggc aattcgggct cgggaggccg 60
ggccatggg 69

<210> SEQ ID NO 815
<211> LENGTH: 71
<212> TYPE: DNA
<213> ORGANISM: Unknown
<220> FEATURE:
<223> OTHER INFORMATION: Description of Unknown:
Alphatorquevirus clade sequence

<400> SEQUENCE: 815
cgggtgccgg aggtgagttt acacaccgca gtcaaggggc aattcgggct cgggactggc 60
cgggccccgg g 71

<210> SEQ ID NO 816
<211> LENGTH: 71
<212> TYPE: DNA
<213> ORGANISM: Unknown
<220> FEATURE:
<223> OTHER INFORMATION: Description of Unknown:
Alphatorquevirus clade sequence

<400> SEQUENCE: 816
cgggtgccgg aggtgagttt acacaccgca gtcaaggggc aattcgggct cgggactggc 60
cgggctatgg g 71

<210> SEQ ID NO 817
<211> LENGTH: 71
<212> TYPE: DNA
<213> ORGANISM: Unknown
<220> FEATURE:
<223> OTHER INFORMATION: Description of Unknown:
Alphatorquevirus clade sequence

<400> SEQUENCE: 817
cgggtgccga aggtgagttt acacaccgca gtcaaggggc aattcgggct cgggactggc 60
cgggctatgg g 71

<210> SEQ ID NO 818
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 818
gcgctkcgcg cgcgcgccgg ggggctgcgc cccccc 36

<210> SEQ ID NO 819
<211> LENGTH: 36
<212> TYPE: DNA
<213> ORGANISM: Torque teno virus

<400> SEQUENCE: 819
gcgcttcgcg cgccgcccac tagggggcgt tgcgcg 36

<210> SEQ ID NO 820
<211> LENGTH: 36
<212> TYPE: DNA
<213> ORGANISM: Torque teno virus

<400> SEQUENCE: 820
gcgctgcgcg cgccgcccag tagggggcgc aatgcg 36

<210> SEQ ID NO 821
<211> LENGTH: 36
<212> TYPE: DNA
<213> ORGANISM: Torque teno virus

<400> SEQUENCE: 821
gcgctgcgcg cgcggccccc gggggaggca ttgcct 36

<210> SEQ ID NO 822
<211> LENGTH: 36
<212> TYPE: DNA
<213> ORGANISM: Torque teno virus

<400> SEQUENCE: 822
gcgctgcgcg cgcgcgccgg gggggcgcca gcgccc 36

<210> SEQ ID NO 823
<211> LENGTH: 36
<212> TYPE: DNA
<213> ORGANISM: Torque teno virus

<400> SEQUENCE: 823
gcgcttcgcg cgcgcgccgg ggggctccgc cccccc 36

<210> SEQ ID NO 824
<211> LENGTH: 36
<212> TYPE: DNA
<213> ORGANISM: Anelloviridae sp.

<400> SEQUENCE: 824
gcgcttcgcg cgcgcgccgg ggggctccgc cccccc 36

<210> SEQ ID NO 825
<211> LENGTH: 36
<212> TYPE: DNA
<213> ORGANISM: Torque teno virus

<400> SEQUENCE: 825
gcgcttcgcg cgcgcgccgg ggggctgcgc cccccc 36

<210> SEQ ID NO 826
<211> LENGTH: 36
<212> TYPE: DNA
<213> ORGANISM: Torque teno virus

<400> SEQUENCE: 826
gcgctacgcg cgcgcgccgg ggggctgcgc cccccc 36

<210> SEQ ID NO 827
<211> LENGTH: 36
<212> TYPE: DNA
<213> ORGANISM: Torque teno virus

<400> SEQUENCE: 827
gcgctacgcg cgcgcgccgg ggggctctgc cccccc 36

<210> SEQ ID NO 828
<211> LENGTH: 724
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (170)..(170)
<223> OTHER INFORMATION: Any amino acid
<220> FEATURE:
<221> NAME/KEY: MOD_RES
<222> LOCATION: (246)..(246)
<223> OTHER INFORMATION: Any amino acid
<220> FEATURE:
<221> NAME/KEY: MOD_RES
<222> LOCATION: (276)..(276)
<223> OTHER INFORMATION: Any amino acid
<220> FEATURE:
<221> NAME/KEY: MOD_RES
<222> LOCATION: (360)..(360)
<223> OTHER INFORMATION: Any amino acid
<220> FEATURE:
<221> NAME/KEY: MOD_RES
<222> LOCATION: (370)..(370)
<223> OTHER INFORMATION: Any amino acid
<220> FEATURE:
<221> NAME/KEY: MOD_RES
<222> LOCATION: (434)..(434)
<223> OTHER INFORMATION: Any amino acid
<220> FEATURE:
<221> NAME/KEY: MOD_RES
<222> LOCATION: (682)..(682)
<223> OTHER INFORMATION: Any amino acid

<400> SEQUENCE: 828

Met Ala Trp Gly Trp Trp Arg Arg Arg Arg Met Ala Trp Arg Arg Trp
1               5                   10                  15

Arg Arg Arg Arg Arg Arg Arg Arg Arg Arg Arg Arg Arg Arg Arg Arg
            20                  25                  30

Arg Arg Pro Xaa Arg Arg Arg Arg Arg Arg Arg Arg Val Arg Arg Arg
        35                  40                  45

Arg Arg Gly Arg Trp Arg Arg Arg Arg Tyr Arg Arg Arg Trp Arg Arg
    50                  55                  60

Arg Arg Arg Arg Arg Arg Arg Lys Lys Leu Val Leu Thr Gln Trp Gln
65                  70                  75                  80

Pro Asn Thr Val Arg Arg Cys Tyr Ile Arg Arg Gly Tyr Leu Pro Leu
                85                  90                  95

Ile Ile Cys Gly Glu Asn Thr Thr Ser Arg Asn Tyr Ala Thr His Ser
            100                 105                 110

Asp Asp Thr Pro Gln Gly Pro Phe Gly Gly Gly Met Ser Thr Thr Thr
        115                 120                 125

Phe Ser Leu Arg Val Leu Tyr Asp Glu Tyr Gln Arg Phe Met Asn Arg
    130                 135                 140

Trp Thr Tyr Ser Asn Glu Asp Leu Asp Leu Ala Arg Tyr Leu Gly Cys
145                 150                 155                 160

Lys Phe Thr Phe Tyr Arg His Pro Asp Xaa Asp Phe Ile Val Gln Tyr
                165                 170                 175

Asn Thr Asn Pro Pro Phe Lys Asp Thr Lys Leu Thr Ala Pro Ser Ile
            180                 185                 190

His Pro Gly Met Leu Met Leu Ser Lys Arg Lys Ile Leu Ile Pro Ser
        195                 200                 205

Leu Lys Thr Arg Pro Lys Gly Lys His Tyr Val Lys Val Arg Ile Gly
    210                 215                 220
```

-continued

```
Pro Pro Lys Leu Phe Glu Asp Lys Trp Tyr Thr Gln Ser Asp Leu Cys
225                 230                 235                 240

Asp Val Pro Leu Val Xaa Leu Tyr Ala Thr Ala Ala Asp Leu Gln His
                245                 250                 255

Pro Phe Gly Ser Pro Gln Thr Asp Asn Pro Cys Val Thr Phe Gln Val
            260                 265                 270

Leu Gly Ser Xaa Tyr Asn Lys His Leu Ser Ile Ser Pro Thr Asn Asp
        275                 280                 285

Asn Leu Lys His Leu Leu Asn Asn Leu Tyr Thr Ser Gly Tyr Asn Thr
    290                 295                 300

Phe Gln Thr Ile Ala Gln Leu Lys Pro Thr Ile Asp Ala Lys Asn Gly
305                 310                 315                 320

Thr Thr Asn Thr Thr Asn Thr Thr Thr Thr Gly Thr Thr Phe Thr Thr
                325                 330                 335

Thr Lys Asn Asp Ser Trp Tyr Gly Gly Asn Thr Tyr Asn Pro Asn Ile
            340                 345                 350

Lys Lys Leu Lys Lys Ile Arg Xaa Tyr Phe Lys Lys Leu Thr Lys Lys
        355                 360                 365

Leu Xaa Pro Thr Tyr Thr Thr Pro Thr Asp Tyr Leu Glu Tyr His Leu
    370                 375                 380

Gly Ile Tyr Ser Pro Ile Phe Ile Ser Pro Gly Arg Ser Asn Phe Glu
385                 390                 395                 400

Phe Pro Gly Ala Tyr Thr Asp Ile Thr Tyr Asn Pro Leu Thr Asp Lys
                405                 410                 415

Gly Val Gly Asn Met Val Trp Ile Gln Tyr Leu Thr Lys Pro Asp Thr
            420                 425                 430

Ile Xaa Asp Lys Thr Gln Ser Lys Cys Leu Ile Glu Asp Leu Pro Leu
        435                 440                 445

Met Ala Ala Leu Tyr Gly Tyr Val Asp Phe Cys Glu Lys Glu Thr Gly
    450                 455                 460

Asp Gln Asp Ile Glu Thr Asn Gly Arg Val Leu Ile Arg Cys Pro Tyr
465                 470                 475                 480

Thr Lys Pro Pro Leu Tyr Asp Lys Thr Asp Pro Asn Lys Gly Phe Val
                485                 490                 495

Pro Tyr Ser Thr Asn Ile Gly Asn Gly Lys Met Pro Gly Gly Ser Gly
            500                 505                 510

Tyr Val Pro Ile Tyr Trp Arg Ala Arg Met Tyr Pro Thr Leu Phe His
        515                 520                 525

Gln Lys Glu Val Leu Glu Asp Ile Val Gln Ser Gly Pro Phe Ala Tyr
    530                 535                 540

Lys Asp Asp Leu Lys Ser Ala Thr Leu Thr Ala Lys Tyr Lys Phe Lys
545                 550                 555                 560

Phe Lys Trp Gly Gly Asn Pro Ile Ser Gln Gln Val Val Arg Asn Pro
                565                 570                 575

Cys Lys Asp Ser Gly Ser Ser Pro Pro Gly Arg Gly Pro Arg Ser Val
            580                 585                 590

Gln Val Val Asp Pro Lys Tyr Met Gly Pro Glu Tyr Thr Phe His Ser
        595                 600                 605

Trp Asp Trp Arg Arg Gly Leu Phe Gly Glu Lys Ala Ile Lys Arg Met
    610                 615                 620

Ser Glu Gln Pro Thr Asp Asp Glu Leu Phe Pro Ala Gly Pro Lys Arg
625                 630                 635                 640

Pro Arg Arg Asp Pro Pro Glu Glu Gln Glu Glu Ser Ser Leu Phe Leu
```

-continued

```
            645                 650                 655

Arg Arg Arg Pro Pro Trp Glu Glu Ser Ser Gln Glu Glu Ser Ser Ser
            660                 665                 670

Glu Glu Glu Glu Gln Glu Glu Gln Thr Xaa Gln Gln Gln Leu Arg Gln
        675                 680                 685

Gln Leu Arg Glu Gln Arg Gln Leu Arg Val Gln Leu Gln Leu Leu Phe
    690                 695                 700

Gln Gln Leu Leu Lys Thr Gln Ala Gly Leu His Ile Asn Pro Leu Leu
705                 710                 715                 720

Leu Ser Gln Ala
```

UNITED STATES PATENT AND TRADEMARK OFFICE
CERTIFICATE OF CORRECTION

PATENT NO. : 11,166,996 B2
APPLICATION NO. : 16/448589
DATED : November 9, 2021
INVENTOR(S) : Weinstein et al.

Page 1 of 1

It is certified that error appears in the above-identified patent and that said Letters Patent is hereby corrected as shown below:

In the Claims

At Column 673, Claim number 36, Line number 32, please delete "The method of claim 23, wherein the *Anellovirus* ORF1 polypeptide in the proteinaceous exterior is the ORF1 of an *Alphatorquevirus* clade 1, an Alphalorquevirus clade 2, an *Alphatorquevirus* clade 3, an *Alphatorquevirus* clade 4, an *Alphatorquevirus* clade 5, an *Alphatorquevirus* clade 6, or an Alphatorquevirus clade 7." and insert -- The method of claim 23, wherein the *Anellovirus* ORF1 polypeptide in the proteinaceous exterior is the ORF1 of an *Alphatorquevirus* clade 1, an *Alphatorquevirus* clade 2, an *Alphatorquevirus* clade 3, an *Alphatorquevirus* clade 4, an *Alphatorquevirus* clade 5, an *Alphatorquevirus* clade 6, or an Alphatorquevirus clade 7. --

At Column 674, Claim number 61, Line number 56, please delete "The method of claim 43, wherein the pharmaceutical composition comprises at least 104 of the anellosomes." and insert -- The method of claim 43, wherein the pharmaceutical composition comprises at least $10^4$ of the anellosomes. --

Signed and Sealed this
Second Day of August, 2022

Katherine Kelly Vidal
*Director of the United States Patent and Trademark Office*